(12) United States Patent
Brunton et al.

(10) Patent No.: US 8,273,747 B2
(45) Date of Patent: Sep. 25, 2012

(54) SMALL ORGANIC MOLECULE REGULATORS OF CELL PROLIFERATION

(75) Inventors: Shirley Ann Brunton, Berkshire (GB); Oivin M. Guicherit, San Diego, CA (US); Lawrence I. Kruse, Claremont, NH (US)

(73) Assignee: Curis, Inc., Cambridge, MA (US)

( * ) Notice: Subject to any disclaimer, the term of this patent is extended or adjusted under 35 U.S.C. 154(b) by 1069 days.

(21) Appl. No.: 11/982,709

(22) Filed: Nov. 2, 2007

(65) Prior Publication Data

US 2008/0193423 A1 Aug. 14, 2008

Related U.S. Application Data

(60) Provisional application No. 60/856,780, filed on Nov. 2, 2006, provisional application No. 60/961,445, filed on Jul. 20, 2007.

(51) Int. Cl.
*A61K 31/497* (2006.01)
*A61K 31/506* (2006.01)
*C07D 239/84* (2006.01)
*C07D 409/08* (2006.01)

(52) U.S. Cl. ............... 514/252.1; 514/275; 544/297; 544/405

(58) Field of Classification Search .............. 514/469, 514/252.1, 275; 549/435; 544/297, 405
See application file for complete search history.

(56) References Cited

U.S. PATENT DOCUMENTS

| 5,571,834 | A | 11/1996 | Casagrande et al. |
|---|---|---|---|
| 5,756,502 | A | 5/1998 | Padia |
| 5,869,665 | A | 2/1999 | Padia |
| 6,022,708 | A | 2/2000 | de Sauvage et al. |
| 6,613,798 | B1 | 9/2003 | Porter |
| 6,683,108 | B1 | 1/2004 | Baxter et al. |
| 6,683,192 | B2 | 1/2004 | Baxter et al. |
| 7,115,653 | B2 | 10/2006 | Baxter et al. |

FOREIGN PATENT DOCUMENTS

| WO | WO-95/18856 | 7/1995 |
|---|---|---|
| WO | WO-95/19169 | 7/1995 |
| WO | WO-99/20298 | 4/1999 |
| WO | WO-99/28343 | 6/1999 |
| WO | WO-99/41281 | 8/1999 |
| WO | WO-00/27422 | 5/2000 |
| WO | WO-00/41545 | 7/2000 |
| WO | WO-01/16114 | 3/2001 |
| WO | WO-01/19800 | 3/2001 |
| WO | WO-01/30768 | 5/2001 |
| WO | WO-01/74344 | 10/2001 |
| WO | WO-03/027234 | 4/2003 |
| WO | WO 2007/089669 | 8/2007 |
| WO | WO2008/057469 | 5/2008 |

OTHER PUBLICATIONS

International Preliminary Report on Patentability dated May 14, 2009 from PCT/US2007/023228.
International Preliminary Report on Patentability dated May 14, 2009 from PCT/US2007/023229.
International Preliminary Report on Patentability dated May 14, 2009 from PCT/US2007/023297.
Chen, J. et al., "Small molecule modulation of Smoothened activity", PNAS, vol. 99, No. 2, 14071-14076 (2002).
Database Beilstein, Beilstein Institute for Organic Chemistry, Frankfurt-Main, DE, Database Accession No. BRN: 10357365; from Collins et al. *Bioorg. Med. Chem.*, 2006, 14, 1255-1273.
Database Beilstein, Beilstein Institute for Organic Chemistry, Frankfurt-Main, DE, Database Accession No. Reaction ID 10213600; from Collins et al. *Bioorg. Med. Chem.*, 2006, 14, 1255-1273.
Database Beilstein, Beilstein Institute for Organic Chemistry, Frankfurt-Main, DE, Database Accession No. BRN 5964753; from *Bull. Acad. Sci. USSR Div. Chem. Sci.*, 1998, 37, 715-718.
Epstein, D., et al., "Antagonizing cAMP-dependent protein kinase A in the dorsal CNS activates a conserved Sonic hedgehog signaling pathway", Development, 122, 2885-2894 (1996).
First Declaration of Jeffrey T. Finer, Jun. 30, 2006.
Second Declaration of Jeffrey T. Finer, Jun. 30, 2006.
Franco, P., et al., "Functional association of retinoic acid and *hedgehog* signaling *Xenopus* primary neurogenesis", Development, 126, 4257-4265 (1999).
Frank-Kamenetsky, M., et al., "Small-molecule modulators of Hedgehog signaling: identification and characterization of Smoothened agonists and antagonists", Journal of Biology, 1:10 (2002).
Gaffield, W., et al., "A looking Glass Perspective: Thalidomide and Cyclopamine", Cellular and Molecular Biology 45 (5), 579-588 (1999).
Hammerschmidt, M. et al., "Protein kinase A is a common negative regulator of Hedgehog signaling in the vertebrate embryo", Genes & Development 10:647-658 (1996).
Hammerschmidt, M., "The world according to *hedgehog*", Reviews, Trend in Genetics, vol. 13, No. 1, 14-21 (1997).
Thornber, C.W., "Isosterism and Molecular Modification in Drug Design", Chem. Soc. Rev., 563-580 (1979).
Masdeu, C. et al., "Identification and characterization of Hedgehog modulator properties after functional coupling of Smoothened to $G_{15}$", Biochemical and Biophysical Research Communications, 349, 2006, 471-479.
King, R., "Roughing up Smoothened chemical modulators of Hedgehog signaling", Databasse accession No. 2003:93485, Database CA Chemical Abstracts Service, Abstract and Journal of Biology, 1(2), 2002.
International Search Report from PCT/US2007/023228 dated Mar. 25, 2008.

*Primary Examiner* — Taofiq A Solola
(74) *Attorney, Agent, or Firm* — Pabst Patent Group LLP

(57) ABSTRACT

The present invention makes available methods and reagents for modulating proliferation or differentiation in a cell or tissue comprising contacting the cell with a compound. In certain embodiments, the methods and reagents may be employed to correct or inhibit an aberrant or unwanted growth state, e.g., by antagonizing a normal patched pathway or agonizing smoothened or hedgehog activity.

31 Claims, 1 Drawing Sheet

SMALL ORGANIC MOLECULE REGULATORS OF CELL PROLIFERATION

RELATED APPLICATIONS

This application claims the benefit of U.S. Provisional Patent Application Nos. 60/856,780, filed Nov. 2, 2006 and 60/961,445, filed Jul. 20, 2007, which applications are hereby incorporated by reference in their entirety.

BACKGROUND OF THE INVENTION

Members of the Hedgehog family of signaling molecules mediate many important short- and long-range patterning processes during invertebrate and vertebrate development. Genetic and functional studies demonstrate that patched is part of the hedgehog signaling cascade, an evolutionarily conserved pathway that regulates expression of a number of downstream genes. In addition to embryonic development and patterning, hedgehog signalling has been implicated in wound healing, hair growth, nerve repair, angiogenesis, and other processes in adult organisms. Accordingly, methods and compositions for modulating differentiation or proliferation of cells, particularly using small molecules that are simpler to administer than a peptide, would be useful.

SUMMARY OF THE INVENTION

The present invention makes available methods and compositions for modulating differentiation or proliferation of a cell. Compounds which may be useful in such methods and compositions are described herein and include those represented by general formulas I-V.

Compounds of the present invention may be used in in vivo methods, e.g., for treating a disease or condition in an animal or patient, and in in vitro methods, e.g., for culturing cells (e.g., as a component of the culture medium), including stem or progenitor cells, such as to promote proliferation, survival, and/or differentiation of the cultured cells.

DETAILED DESCRIPTION OF THE INVENTION

I. Overview

Figure 1A:
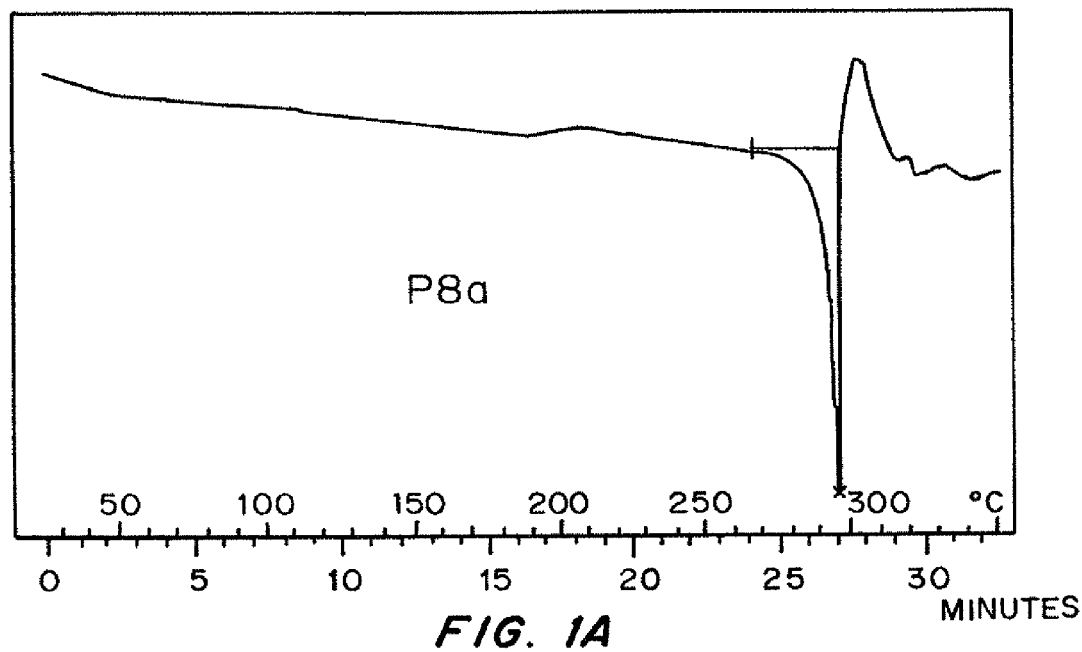
FIG. 1 shows a differential scanning calorimetry plot of heat flow versus temperature and time.

The present invention relates to the discovery that signal transduction pathways regulated by hedgehog (hh), patched, gli and/or smoothened may be modulated, at least in part, by small molecules. While not wishing to be bound by any particular theory, the activation of a patched-smoothened pathway through alteration of cell-surface associations (such as complexes) may be the mechanism by which these agents act. The hedgehog pathway is believed to be negatively regulated by an interaction between patched and smoothened that is disrupted by the binding of hedgehog to patched. While not wishing to be bound by any theory, the ability of these agents to activate the hedgehog pathway may be due to the ability of such molecules to interact with or bind to smoothened, to otherwise disrupt the interaction between smoothened and patched, or at least to promote the ability of those proteins to activate a hedgehog, patched, and/or smoothened-mediated signal transduction pathway. This mode of action, e.g., modulation of a smoothened-dependent pathway is distinguished from compounds which modulate the hedgehog pathway by directly activating the cAMP pathway, e.g., by binding to or interacting with PKA, adenylate cyclase, cAMP phosphodiesterase, etc.

Certain compounds disclosed herein may modulate hedgehog activity in the absence of hedgehog protein itself, e.g., the compounds may mimic the activity of hedgehog, rather than merely supplement or increase the activity of hedgehog protein, e.g., by promoting hedgehog binding to patched. These compounds may be referred to as hedgehog-independent agonists and alone may mimic the phenotype or effect resulting from hedgehog treatment. Certain other compounds of the present invention may enhance the activity of hedgehog protein, and require the presence or addition of hedgehog protein to observe the phenotype or effect resulting from hedgehog induction. Such hedgehog-dependent agonists may be used in therapeutic preparations or treatments which include hedgehog protein, or may be used to increase the activity of hedgehog protein naturally produced by the cells or tissue to be treated with the agonist. The present compounds disclosed herein may induce dissociation of a patched-smoothened complex or disrupt interactions between patched and smoothened, such as by binding to patched or to smoothened, thereby activating the hedgehog pathway. In certain embodiments, the compositions and methods of the present invention employ a compound which acts on one or more components of the extracellular membrane of a target cell.

Accordingly, in some embodiments, the present invention provides a method for agonizing the hedgehog pathway in a cell, comprising contacting the cell with one or more of the present compounds or compositions.

In certain embodiments, the present compounds may be useful in inducing hedgehog-dependent transcriptional regulation, such as expression of the gli1 or patched genes. Such compounds may thus induce or increase the hedgehog-dependent pathway activation resulting from, for example, increased levels of hedgehog protein. In certain embodiments, the present compounds have the ability of increasing gli-1 expression levels in human cells.

It is, therefore, specifically contemplated that these small molecules which modulate aspects of hedgehog, patched, or smoothened signal transduction activity will likewise be capable of promoting proliferation (or other biological consequences) in cells having a functional patched-smoothened pathway. Activation of the hedgehog pathway by a hedgehog agonist, for example a compound as described herein, may be quantified, for example, by detecting the increase in patched or gli-1 transcription in the presence of the agonist relative to a control in the absence of agonist. For example, an increase of at least about 5%, at least about 10%, at least about 20%, or even at least about 50% may be indicative of hedgehog pathway activation by a test compound. In certain embodiments, a compound which may be useful in the present invention, such as described above, may have an $EC_{50}$ for inducing or augmenting one or more hedgehog activities (such as upregulation of patched or gli expression) of less than about 1000 nM, less than about 100 nM, less than about 10 nM, or even less than about 1 nM. The coding sequences for exemplary human Gli genes include, for example, the Gli-1 gene sequence of GenBank accession X07384 and the Gli-2 gene sequence of GenBank accession AB007298. See also Kinzler et al. Nature 1988, 332, 371. The level of gli or patched expression may be determined, for example, by measuring the level of mRNA (transcription) or the level of protein (translation).

Thus, the methods of the present invention may include the use of small molecules which antagonize patched inhibition of hedgehog signalling, such as by activating smoothened or downstream components of the signal pathway, in the regulation of repair and/or functional performance of a wide range of cells, tissues and organs. For instance, the present invention may have therapeutic and cosmetic applications ranging from regulation of neural tissues, bone and cartilage formation and repair, regulation of spermatogenesis, regulation of smooth muscle, regulation of lung, liver, urogenital organs (e.g., bladder), and other organs arising from the primitive gut, regulation of hematopoietic function, regulation of skin and/or hair growth, etc. Moreover, the present invention may be performed on cells which are provided in culture (in vitro), or on cells in a whole animal (in vivo). See, for example, PCT publications WO 95/18856 and WO 96/17924 (the specifications of which are expressly incorporated by reference herein).

In one embodiment, the present invention may be used to treat epithelial cells. In general, an epithelial cell may be contacted with an amount of a present compound to induce epithelial tissue growth and/or formation. The present invention may be carried out on epithelial cells which may be either dispersed in culture or a part of an intact tissue or organ. Moreover, the method may be performed on cells which are provided in culture (in vitro), or on cells in a whole animal (in vivo).

The compounds of the present invention may be used as part of regimens in the treatment of disorders of, or surgical or cosmetic repair of, such epithelial tissues as skin and skin organs; corneal, lens and other ocular tissue; mucosal membranes; and periodontal epithelium. The methods and compositions disclosed herein provide for the treatment or prevention of a variety of damaged epithelial and mucosal tissues. For instance, the present invention may be used to control wound healing processes, as for example may be desirable in connection with any surgery involving epithelial tissue, such as from dermatological or periodontal surgeries. Exemplary surgical repair for which these compounds may be useful include severe burn and skin regeneration, skin grafts, pressure sores, dermal ulcers, fissures, post surgery scar reduction, and ulcerative colitis.

In another aspect of the present invention, the present compounds may be used to effect the growth of hair, as for example in the treatment or prevention of alopecia whereby hair growth is potentiated.

In another aspect, the present invention may provide pharmaceutical preparations comprising, as an active ingredient, a compound such as described herein, formulated in an amount sufficient to promote, in vivo, proliferation or other biological consequences.

The present invention may be effective for both human and animal subjects. Animal subjects to which the present invention may be applicable extend to both domestic animals and livestock, raised either as pets or for commercial purposes. Examples may include apes, monkeys, chimpanzees, dogs, cats, cattle, horses, sheep, hogs, and goats.

II. Definitions

For convenience, certain terms employed in the specification, examples, and appended claims are collected here. These definitions should be read in light of the remainder of the disclosure and understood as by a person of skill in the art.

The phrase "aberrant modification or mutation" of a gene refers to such genetic lesions as, for example, deletions, substitution or addition of nucleotides to a gene, as well as gross chromosomal rearrangements of the gene and/or abnormal methylation of the gene. Likewise, mis-expression of a gene refers to aberrant levels of transcription of the gene relative to those levels in a normal cell under similar conditions, as well as non-wild-type splicing of mRNA transcribed from the gene.

The term "active" as used herein means biologically, therapeutically or pharmacologically active.

An "adjuvant", as the term is used herein, is a compound that has little or no therapeutic value on its own, but increases the effectiveness of a therapeutic agent. Exemplary adjuvants may include radiosensitizers, transfection-enhancing agents (such as chloroquine and analogs thereof), chemotactic agents and chemoattractants, peptides that modulate cell adhesion and/or cell mobility, cell permeabilizing agents, inhibitors of multidrug resistance and/or efflux pumps, etc.

"Angiogenesis" refers to any alteration of an existing vascular bed or the formation of new vasculature which benefits tissue perfusion. This may include the formation of new vessels by sprouting of endothelial cells from existing blood vessels or the remodeling of existing vessels to alter size, maturity, direction or flow properties to improve blood perfusion of tissue.

"Burn wounds" refer to cases where large surface areas of skin have been removed or lost from an individual due to heat and/or chemical agents.

The phrase "controlled release" or "sustained release" refers to the use of systems that allow for the controlled or tunable delivery of one or more of the present compounds or compositions over time. For example, in certain instances, the present compounds or compositions are used in conjunction with a controlled release system that delivers an effective amount (such as an approximately continuous amount, an increasing amount, or a decreasing amount) of the compound(s) over a certain period of time, for example, over a period of at least about 4, 8, 12, 24, 48, or 72 hours, over a period of at least about 1, 2, 3, 4, or 5 days, over a period of at least about 1, 2, or 3 weeks, or over a period of at least about 1, 2, 3, 4, 5, or 6 months. Such controlled release systems may be used in conjunction with medical devices, such as stents and catheters, to provide medical devices which offer controlled release of the present compounds and/or compositions. By way of example, some suitable controlled release systems include hydrogels, polymers, meshes, and others demonstrated in the art.

The "corium" or "dermis" refers to the layer of the skin deep to the epidermis, consisting of a dense bed of vascular connective tissue, and containing the nerves and terminal organs of sensation. The hair roots, and sebaceous and sweat glands are structures of the epidermis which are deeply embedded in the dermis.

"Dental tissue" refers to tissue in the mouth which is similar to epithelial tissue, for example gum tissue. The compounds of the present invention may be useful for treating periodontal disease.

"Dermal skin ulcers" refer to lesions on the skin caused by superficial loss of tissue, usually with inflammation. Dermal skin ulcers which may be treated by the present invention include decubitus ulcers, diabetic ulcers, venous stasis ulcers and arterial ulcers. Decubitus wounds refer to chronic ulcers that result from pressure applied to areas of the skin for extended periods of time. Wounds of this type are often called bedsores or pressure sores. Venous stasis ulcers result from the stagnation of blood or other fluids from defective veins. Arterial ulcers refer to necrotic skin in the area around arteries having poor blood flow.

As used herein, the term "$EC_{50}$" means the concentration of a drug that produces 50% of its maximum response or effect.

The term "$ED_{50}$" means the dose of a drug which produces 50% of its maximum response or effect.

An "effective amount" of, e.g., a present compound refers to an amount of the compound in a preparation which, when applied as part of a desired dosage regimen brings about a desired effect, e.g., a change in the rate of cell proliferation and/or the state of differentiation of a cell and/or rate of survival of a cell according to clinically acceptable standards for the disorder to be treated or the cosmetic purpose.

The terms "epithelia", "epithelial" and "epithelium" refer to the cellular covering of internal and external body surfaces (cutaneous, mucous and serous), including the glands and other structures derived therefrom, e.g., corneal, esophageal, epidermal, and hair follicle epithelial cells. Other exemplary epithelial tissue includes: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium may also refer to transitional epithelium, like that which is characteristically found lining hollow organs that are subject to great mechanical change due to contraction and distention, e.g., tissue which represents a transition between stratified squamous and columnar epithelium.

The term "epithelialization" refers to healing by the growth of epithelial tissue over a denuded surface.

The term "epidermal gland" refers to an aggregation of cells associated with the epidermis and specialized to secrete or excrete materials not related to their ordinary metabolic needs. For example, "sebaceous glands" are holocrine glands in the corium that secrete an oily substance and sebum. The term "sweat glands" refers to glands that secrete sweat, situated in the corium or subcutaneous tissue, opening by a duct on the body surface.

The term "epidermis" refers to the outermost and nonvascular layer of the skin, derived from the embryonic ectoderm, varying in thickness from about 0.07 to about 1.4 mm. On the palmar and plantar surfaces it comprises, from within outward, five layers: basal layer composed of columnar cells arranged perpendicularly; prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, cornified non-nucleated cells. In the epidermis of the general body surface, the clear layer is usually absent.

"Excisional wounds" include tears, abrasions, cuts, punctures or lacerations in the epithelial layer of the skin and may extend into the dermal layer and even into subcutaneous fat and beyond. Excisional wounds may result from surgical procedures or from accidental penetration of the skin.

The "growth state" of a cell refers to the rate of proliferation of the cell and/or the state of differentiation of the cell. An "altered growth state" refers to a growth state characterized by an abnormal rate of proliferation, e.g., a cell exhibiting an increased or decreased rate of proliferation relative to a normal cell.

The term "hair" refers to a threadlike structure, especially the specialized epidermal structure composed of keratin and developing from a papilla sunk in the corium, produced only by mammals and characteristic of that group of animals. Also, "hair" may refer to the aggregate of such hairs. A "hair follicle" refers to one of the tubular-invaginations of the epidermis enclosing the hairs, and from which the hairs grow. "Hair follicle epithelial cells" refers to epithelial cells which surround the dermal papilla in the hair follicle, e.g., stem cells, outer root sheath cells, matrix cells, and inner root sheath cells. Such cells may be normal non-malignant cells, or transformed/immortalized cells.

The term "hedgehog agonist" refers to an agent which potentiates or recapitulates the bioactivity of hedgehog, such as to activate transcription of target genes. Preferred compounds may be used to mimic or enhance the activity or effect of hedgehog protein in a smoothened-dependent manner. The term 'hedgehog agonist' as used herein refers not only to any agent that may act by directly activating the normal function of the hedgehog protein, but also to any agent that activates the hedgehog signalling pathway, and thus inhibits the function of patched. In preferred embodiments, one or more of the present compounds is a hedgehog agonist.

The term "hedgehog loss-of-function" refers to an aberrant modification or mutation of a patched gene, hedgehog gene, or smoothened gene, or a decrease (or loss) in the level of expression of such A gene, which results in a phenotype which resembles contacting a cell with a hedgehog inhibitor, e.g., aberrant inhibition of a hedgehog pathway. The loss-of-function may include an increase in the ability of the patched gene product to regulate the level of expression of Ci genes, e.g., Gli1, Gli2, and Gli3. The term 'hedgehog loss-of-function' is also used herein to refer to any similar cellular phenotype (e.g., exhibiting reduced proliferation) which occurs due to an alteration anywhere in the hedgehog signal transduction pathway, including, but not limited to, a modification or mutation of hedgehog itself. For example, a cell with an abnormally low proliferation rate due to inactivation of the hedgehog signalling pathway would have a 'hedgehog loss-of-function' phenotype, even if hedgehog is not mutated in that cell.

The term "$IC_{50}$" means the dose of a drug that inhibits a biological activity by 50%.

"Internal epithelial tissue" refers to tissue inside the body which has characteristics similar to the epidermal layer in the skin. Examples include the lining of the intestine. The compounds of the present invention may be useful for promoting the healing of certain internal wounds, for example wounds resulting from surgery.

The term "$LD_{50}$" means the dose of a drug which is lethal in about 50% of test subjects.

The term "nail" refers to the horny cutaneous plate on the dorsal surface of the distal end of a finger or toe.

The term "neuroprotective", as used herein, for example, in the case of cerebral ischemia, refers to A the ability to diminish infarct volume relative to that which would occur in the absence of treatment with one or more of the present compounds or compositions. That is, a neuroprotective therapy is intended to maintain or rescue damaged nerve cells, preventing or reducing the occurrence of their death. As such, the present compounds and compositions may be used in various neuroprotective methods. A method which is "neuroprotective", for example, in the case of dopaminergic and GABAergic cells, results in diminished loss of cells of those phenotype relative to that which would occur in the absence of treatment with a present compound or composition. In one instance, such a treatment comprises a present compound or composition in combination with a neurotrophic factor.

The term "patched gain-of-function" refers to an aberrant modification or mutation of a patched gene, or an increased level of expression of the gene, which results in a phenotype which resembles contacting a cell with a hedgehog inhibitor, e.g., aberrant deactivation of a hedgehog pathway. The gain-of-function may include an increase of the ability of the patched gene product to regulate the level of expression of Ci genes, e.g., Gli1, Gli2 and Gli3.

A "patient," "subject," or "host" to be treated by the present invention may mean either a human or non-human animal, such as primates, mammals, and vertebrates. Some suitable examples of non-human animals may include apes, monkeys, chimpanzees, dogs, cats, horses, cows, goats, sheep, donkeys, burros, pigs, ferrets, gerbils, hamsters, and rabbits. In certain instances, the patient may be a domestic pet for a human, for example, a dog, cat, rabbit, hamster, etc.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use. Each carrier must be "acceptable" in the sense of being compatible with other ingredients of the formulation and not injurious to the patient.

Some examples of materials which may serve as pharmaceutically acceptable carriers include (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" is art-recognized, and includes relatively non-toxic, inorganic and organic acid addition salts of compositions, including without limitation, analgesic agents, therapeutic agents, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, *J. Pharm. Sci.* 66: 1-19 (1977).

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

The phrase "pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

"Physiological conditions" describe the conditions inside an organism, i.e., in vivo. Physiological conditions include the acidic and basic environments of body cavities and organs, enzymatic cleavage, metabolism, and other biological processes, and preferably refer to physiological conditions in a vertebrate, such as a mammal.

The term "physiological pH," as used herein, refers to a pH that is about 7.4 at the standard physiological temperature of 37.4° C. The term "non-physiological pH," as used herein, refers to a pH that is less than or greater than "physiological pH," preferably between about 4 and 7.3, or greater than 7.5 and less than about 12. The term "neutral pH," as used herein, refers to a pH of about 7. In preferred embodiments, physiological pH refers to pH 7.4, and non-physiological pH refers to pH between about 6 and 7. The term "acidic pH" refers to a pH that is below pH 7, preferably below about pH 6, or even below about pH 4.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population. As such, preventing includes the reduction of severity of a disease, condition, or symptoms thereof, which in some instances may include the complete eradication of the disease, condition, or symptoms thereof and in other instances may not include complete eradication.

The term "prodrug" is intended to encompass compounds which, under physiological conditions, are converted into the therapeutically active agents of the present invention. A common method for making a prodrug is to include selected moieties which are hydrolyzed under physiological conditions to reveal the desired molecule. In other embodiments, the prodrug is converted by an enzymatic activity of the host animal.

As used herein, "proliferating" and "proliferation" refer to cells undergoing mitosis.

The term "prophylactic" or "therapeutic" treatment is art-recognized and includes administration to the host of one or more of the present compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic, (i.e., it is intended to diminish, ameliorate, or stabilize the existing unwanted condition or side effects thereof).

The phrase "protecting group" or "protective group" as used herein means a temporary substituent that protects a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

The phrase "and salts and solvates thereof" as used herein means that compounds of the present invention may exist in one or a mixture of salts and solvate forms. For example a compound of the present invention may be substantially pure in one particular salt or solvate form or else may be mixtures of two or more salt or solvate forms.

The term "skin" refers to the outer protective covering of the body, consisting of the corium and the epidermis, and is understood to include sweat and sebaceous glands, as well as hair follicle structures. Throughout the present application, the adjective "cutaneous" may be used, and should be understood to refer generally to attributes of the skin, as appropriate to the context in which they are used.

The term "small molecule" refers to a compound having a molecular weight less than about 2500 amu, preferably less than about 2000 amu, even more preferably less than about 1500 amu, still more preferably less than about 1000 amu, or most preferably less than about 750 amu.

The term "smoothened loss-of-function" refers to an aberrant modification or mutation of a smoothened gene, or a decreased level of expression of the gene, which results in a phenotype which resembles contacting a cell with a hedgehog inhibitor, e.g., aberrant deactivation of a hedgehog pathway. While not wishing to be bound by any particular theory, it is noted that patched may not signal directly into the cell, but rather interact with smoothened, another membrane-bound protein located downstream of patched in hedgehog signaling (Marigo et al., (1996) *Nature* 384: 177-179). The gene smoothened is a segment-polarity gene required for the correct patterning of every segment in *Drosophila* (Alcedo et al., (1996) *Cell* 86: 221-232). Human homologs of smoothened have been identified. See, for example, Stone et al. (1996) *Nature* 384:129-134, and GenBank accession U84401. The smoothened gene encodes an integral membrane protein with characteristics of heterotrimeric G-protein-coupled receptors; i.e., 7-transmembrane regions. This protein shows homology to the *Drosophila* Frizzled (Fz) protein, a member of the wingless pathway. It was originally thought that smoothened encodes a receptor of the hedgehog signal. However, this suggestion was subsequently disproved, as evidence for patched being the hedgehog receptor was obtained. Cells that express smoothened fail to bind hedgehog, indicating that smoothened does not interact directly with hedgehog (Nusse, (1996) *Nature* 384: 119-120). Rather, the binding of Sonic hedgehog (Shh) to its receptor, patched, is thought to prevent normal inhibition by patched of smoothened, a seven-span transmembrane protein.

The phrases "systemic administration," "administered systemically," "peripheral administration" and "administered peripherally" are art-recognized, and include the administration of a present composition, therapeutic or other material at a site remote from the disease being treated. Administration of an agent directly into, onto, or in the vicinity of a lesion of the disease being treated, even if the agent is subsequently distributed systemically, may be termed "local" or "topical" or "regional" administration, other than directly into the central nervous system, e.g., by subcutaneous administration, such that it enters the patient's system and, thus, is subject to metabolism and other like processes.

The term "therapeutic index" refers to the therapeutic index of a drug defined as $LD_{50}/ED_{50}$.

The term "treating" is art-recognized and includes preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain. For example, treating includes bringing at least one symptom of a disease or condition to a tolerable level. Treating may further include acute, chronic, and/or maintenance treatments, for example, acute, chronic, and/or maintenance therapeutic or prophylactic treatments.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The terms "alkenyl" and "alkynyl" refer to unsaturated aliphatic groups analogous in length and possible substitution to the alkyls described below, but that contain at least one double or triple bond respectively.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain. The term "alkylamino", as used herein, refers to an amino group substituted with at least one alkyl group.

The term "alkylthio", as used herein, refers to a thiol group substituted with an alkyl group and may be represented by the general formula alkyl-S—.

The term "amide" or "amido," as used herein, refers to a group

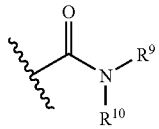

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that may be represented by

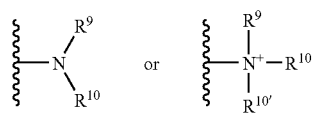

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "amino-protecting group" as used herein refers to a derivative of the groups commonly employed to block or protect an amino group while reactions are carried out on other functional groups on the compound. Examples of such protecting groups include carbamates, amides, alkyl and aryl groups, imines, as well as many N-heteroatom derivatives which may be removed to regenerate the desired amine group. Preferred amino protecting groups are Boc, Fmoc and Cbz. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino" refers to an amino group substituted with one of the above amino-protecting groups.

The term "aminoalkyl", as used herein, refers to an alkyl group substituted with an amino group.

The term "amidine" denotes the group —C(NH)—NHR wherein R is H or alkyl or aralkyl. A preferred amidine is the group —C(NH)—NH$_2$.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings may be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

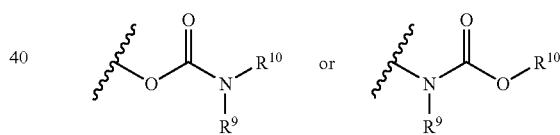

wherein $R^9$ and $R^{10}$ independently represent hydrogen or a hydrocarbyl group.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group —OCO$_2$—.

The term "carboxy", as used herein, refers to a group represented by the formula —CO$_2$H.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl such as t-butyl or t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and may be removed at the appropriate point without disrupting the remainder of the molecule. Preferred carboxylic acid protecting groups are the alkyl (e.g., methyl, ethyl, t-butyl), allyl, benzyl and p-nitrobenzyl groups. Similar carboxy-protecting groups used in the cephalosporin, penicillin and peptide arts may also be used to protect a carboxy group substituents. Further examples of these groups are found in T. W. Greene and P. G. M. Wuts, "Protective Groups in Organic Synthesis", $2^{nd}$ ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy" refers to a carboxy group substituted with one of the above carboxy-protecting groups.

The term "carbonyl" is art-recognized and includes such moieties as may be represented by the general formula:

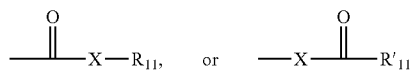

wherein X is a bond or represents an oxygen or a sulfur, and $R_{11}$ represents a hydrogen, an alkyl, an alkenyl, $-(CH_2)_m-R_8$ or a pharmaceutically acceptable salt, $R'_{11}$ represents a hydrogen, an alkyl, an alkenyl or $-(CH_2)_m-R_8$, where m and $R_8$ are as defined above. Where X is an oxygen and $R_{11}$ or $R'_{11}$ is not hydrogen, the formula represents an "ester". Where X is an oxygen, and $R_1$, is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R_{11}'$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "electron donating group" refers to chemical groups which donate electron density to the atom or group of atoms to which the electron donating group is attached. The donation of electron density includes donation both by inductive and by delocalization/resonance effects. Examples of electron donating groups attached to aromatic rings include alkyl, alkenyl, and alkynyl groups, and heteroatoms with electron lone pairs capable of delocalization.

The term "electron withdrawing group" refers to chemical groups which withdraw electron density from the atom or group of atoms to which electron withdrawing group is attached. The withdrawal of electron density includes withdrawal both by inductive and by delocalization/resonance effects. Examples of electron withdrawing groups attached to aromatic rings include halogens, azides, carbonyl containing groups such as acyl groups, cyano groups, and imine containing groups.

The term "ester", as used herein, refers to a group $-C(O)OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The term "guanidine" denotes the group —NH—C(NH)—NHR wherein R is H or alkyl or aralkyl. A particular guanidine group is —NH—C(NH)—NH$_2$.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings may be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings may be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "hydroxy-protecting group" as used herein refers to a derivative of the hydroxy group commonly employed to block or protect the hydroxy group while reactions are carried out on other functional groups on the compound. Examples of such protecting groups include tetrahydropyranyl, benzoyl, acetyl, carbamoyl, benzyl, and silyl (e.g., TBS, TBDPS) groups. Further examples of these groups are found in T. W. Greene and P. G. M. Wuts, "Protective Groups in Organic Synthesis", 2$^{nd}$ ed., John Wiley & Sons, Inc., New York, N.Y., 1991, chapters 2-3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected hydroxy" refers to a hydroxy group substituted with one of the above hydroxy-protecting groups.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle may be substituted or unsubstituted. In certain embodiments, each ring of the polycycle contains from 3 to 10 atoms in the ring, preferably from 5 to 7.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents may include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate.

The term "sulfate" is art-recognized and refers to the group —OSO$_3$H, or a pharmaceutically acceptable salt thereof.

The term "sulfonamide" is art-recognized and refers to the group represented by the general formulae

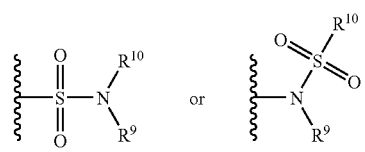

wherein R$^9$ and R$^{10}$ independently represents hydrogen or hydrocarbyl.

The term "sulfoxide" is art-recognized and refers to the group -S(O)—.

The term "sulfonate" is art-recognized and refers to the group SO$_3$H, or a pharmaceutically acceptable salt thereof.

The term "sulfone" is art-recognized and refers to the group —S(O)$_2$—.

The term "thioalkyl", as used herein, refers to an alkyl group substituted with a thiol group.

The term "thioester", as used herein, refers to a group —C(O)SR$^9$ or —SC(O)R$^9$ wherein R$^9$ represents a hydrocarbyl.

The term "thioether", as used herein, is equivalent to an ether, wherein the oxygen is replaced with a sulfur.

The term "urea" is art-recognized and may be represented by the general formula

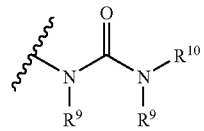

wherein R$^9$ and R$^{10}$ independently represent hydrogen or a hydrocarbyl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the present invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., the ability to activate hedgehog signaling), wherein one or more simple variations of substituents are made which do not adversely affect the efficacy of the compound. In general, the compounds of the present invention may be prepared by the methods illustrated in general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which may be substituted or unsubstituted.

III. Exemplary Compounds of the Invention.

As described in further detail below, it is contemplated that the present invention may be carried out using a variety of different small molecules which may be readily identified, for example, by such drug screening assays as described herein and in WO03/027234 and WO01/74344, which are incorporated by reference herein. For example, compounds that may be useful in the present invention include compounds represented by general formula (I):

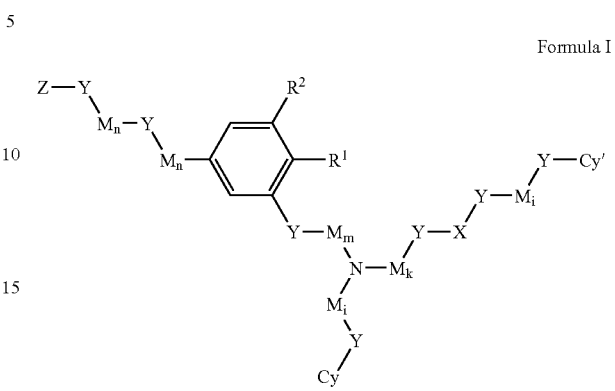

Formula I wherein, as valence and stability permit,

Z is absent or represents a substituted or unsubstituted aryl, carbocyclyl, or heteroaryl ring, or a lower alkyl, nitro, cyano, azido or halogen substituent;

Y, independently for each occurrence, is absent or represents —N(R)—, —O—, —S—, or —Se—, provided that if Z is not a ring, then Y attached to Z is absent;

X is selected from —C(=O)—, —C(=S)—, —S(O)$_2$—, —S(O)—, and a methylene group optionally substituted with 1-2 lower alkyl groups;

M represents, independently for each occurrence, a substituted or unsubstituted methylene group or two M taken together represent substituted or unsubstituted ethene or ethyne;

$R^1$ and $R^2$ are, independently, H, halogen, hydroxyl, lower alkyl, or lower alkoxy, provided that at least one of $R^1$ and $R^2$ is not H;

R represents H or substituted or unsubstituted alkyl;

Cy represents a substituted or unsubstituted aryl, heterocyclyl, heteroaryl, or cycloalkyl, including polycyclic groups, wherein Cy includes or is substituted with a primary, secondary, or tertiary amine other than $N(M_m)(M_i)(M_k)$;

Cy' represents a substituted or unsubstituted aryl, heterocyclyl, heteroaryl, or cycloalkyl, including polycyclic groups;

i represents, independently for each occurrence, an integer from 0 to 5;

k represents an integer from 0 to 3;

m represents an integer from 0 to 3; and n represents, independently for each occurrence, an integer from 0 to 5.

In certain embodiments, M represents, independently for each occurrence, a substituted or unsubstituted methylene group, such as —CH$_2$—, —CHF—, —CHOH—, —CH(Me)-, C(=O)—, etc.

In certain embodiments, $R^1$ represents lower alkyl, e.g., Me, Et, or Pr. In other embodiments, $R^1$ represents hydroxyl or lower alkoxy, such as methoxy, or ethoxy, particularly methoxy. In some embodiments, $R^1$ or $R^2$ represents halogen, for example, fluoro. In some embodiments, $R^2$ is H and $R^1$ is not H.

In certain embodiments, Cy represents a substituted or unsubstituted non-aromatic carbocyclic, such as cycloalkyl, or heterocyclic ring, such as heterocyclyl, i.e., including at least one sp$^3$ hybridized atom, and preferably a plurality of sp$^3$ hybridized atoms. In certain embodiments, Cy includes an amine within the atoms of the ring or on a substituent of the ring, e.g., Cy is piperidyl, pyrrolidyl, piperazyl, etc., and/or bears an amino substituent. An amine within the atoms of the ring may be in a 1,2; 1,3; 1,5; or preferably 1,4 position relative to Y. For example, Cy may be piperidine, wherein the amine in the piperidine ring is in a 1,4 position relative to Y. In certain embodiments, Cy is a 5- to 7-membered ring. In certain embodiments, Cy is a 5- to 7-membered cycloalkyl ring, for example, a 6-membered ring, such as cyclohexyl. In certain embodiments, Cy is attached directly to N. In certain embodiments Cy is a six-membered ring, such as cyclohexyl, attached directly to N and bears a primary, secondary or tertiary amino substituent represented by —N(R$^a$)$_2$, wherein R$^a$ represents, independently for each occurrence, H; substituted or unsubstituted alkynyl, alkenyl, or alkyl; or two R$^a$ taken together may form a 4- to 8-membered ring. The amino substituent of Cy may be at the 4 position of the ring relative to Y, and the Y group of Cy and amino substituents may be disposed trans on the ring. In certain embodiments, one or more R$^a$ in N(R$^a$)$_2$ is H and/or lower alkyl, i.e., N(R$^a$)$_2$ is NH$_2$, NH(lower alkyl), or N(lower alkyl)$_2$. In specific embodiments, N(R$^a$)$_2$ is NH$_2$ while in other embodiments it is NH(lower alkyl) such as a methylamino group.

In certain embodiments, Cy' is a substituted or unsubstituted aryl or heteroaryl. In certain embodiments, Cy' is attached directly to X. In certain embodiments, Cy' is a substituted or unsubstituted bicyclic or heteroaryl ring. In certain embodiments, Cy' is both bicyclic and heteroaryl, such as benzothiophene, benzofuran, benzopyrrole, benzopyridine, etc. In particular embodiments, Cy' is a benzothiophene, such as a 3-halo-benzo[b]thien-2-yl, for example a 3-chloro-benzo[b]thien-2-yl or a 3-fluoro-benzo[b]thien-2-yl, or a 3-methyl-benzo[b]thien-2-yl. In embodiments of Cy' that comprise a benzo ring, the benzo ring may be substituted with from 1-4 substituents such as halogen, nitro, cyano, methyl (e.g., including halomethyl, such as CHCl$_2$ and CF$_3$), and ethyl (e.g., including haloethyl, such as CH$_2$CCl$_3$, C$_2$F$_5$, etc.), preferably with halogen and methyl (e.g., including halomethyl, such as CHCl$_2$ and CF$_3$). In certain such embodiments, Cy' represents a 3-chloro-benzo[b]thien-2-yl, 3-fluoro-benzo[b]thien-2-yl, or 3-methyl-benzo[b]thien-2-yl, wherein the benzo ring is substituted with fluoro at the 4-position (peri to the 3-substituent on the thienyl ring) and, optionally, at the 7-position ('peri' to the S of the thienyl ring). Alternatively, the benzo ring may be unsubstituted. In certain embodiments, the benzo ring is selected from:

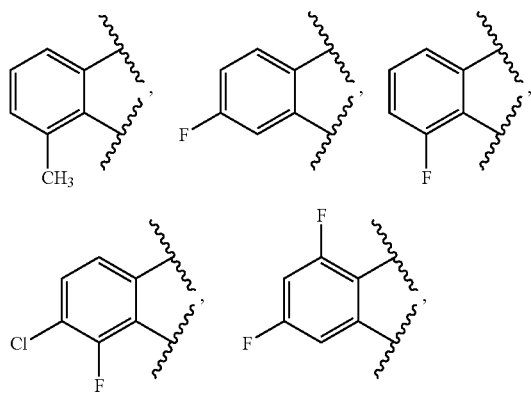

-continued

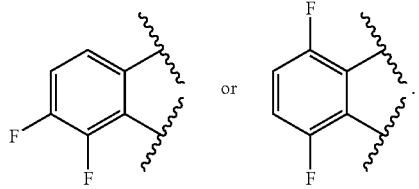

In yet further embodiments, Cy' is selected from:

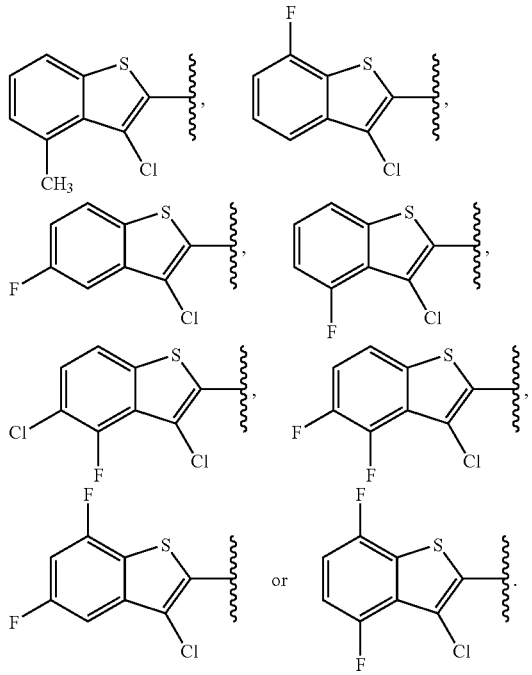

In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system.

In certain embodiments, Z represents an aryl or heteroaryl ring, e.g., unsubstituted or substituted with one or more groups including heteroatoms such as O, N, and S. In certain embodiments, Z represents a phenyl ring. In certain embodiments, Z represents a heteroaryl ring, e.g., a pyrrole, pyrazole, imidazole, pyridine, pyrimidine, pyrazine, pyridazine, triazine, tetrazine, furan, thiophene, thiazole, isothiazole, thiadiazole, oxazole, isoxazole, or oxadiazole ring. Z may be attached to the rest of the molecule at any position on its ring; for example, if Z is a pyridine ring, Z may be attached at the 2, 3, or 4 position relative to the nitrogen of the pyridine ring. In certain embodiments, R$^1$ and the chain containing Z are attached to the phenyl ring in a para (i.e., 1,4) relationship.

In certain embodiments, substituents on Z are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$ OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above, wherein p and n, individually for each occurrence, represent integers from 0 to 10, preferably from 0 to 5.

In certain embodiments, Z is substituted with one or more groups selected from halogen, lower alkyl, —CN, azido, —NR$^x$R$^x$, —NR$^x$—C(O)—R$^x$, —C(O)—NR$^x$R$^x$, —C(O)—R$^x$, NSO$_2$R$^x$, —SO$_2$R$^x$, —(C(R$^x$)$_2$)$_n$—OR$^x$, —(C(R$^x$)$_2$)$_n$—NR$^x$R$^x$; wherein R$^x$ is, independently for each occurrence, H or lower alkyl; and n is an integer from 0-2.

In certain embodiments, Z is substituted with one or more electron withdrawing groups. For example, sometimes Z is substituted with one or more groups selected from halogen, —CN, azido, —CO$_2$$_0$R$^x$, —C(O)—NR$^x$R$^x$, and —C(O)—R$^x$.

In certain embodiments, X is selected from —C(=O)—, —C(=S)—, and —S(O$_2$)—. In other embodiments, X represents a methylene group optionally substituted with 1-2 lower alkyl groups.

In certain embodiments, Y is absent from all positions, e.g., it is a direct bond if between two groups. In embodiments wherein Y is present in a position, i preferably represents an integer from 1-2 in an adjacent M$_i$ if i=0 would result in two occurrences of Y being attached directly, or an occurrence of Y being attached directly to N. In certain embodiments, Y, independently for each occurrence, represents —N(R)—, —O—, or —S—.

In certain embodiments, i is 0, k is 0, and m is 1.

In certain embodiments, the N in N(M$_m$)(M$_i$)(M$_k$) is bonded to exactly three carbon atoms.

In certain embodiments, Z is a substituted or unsubstituted aryl or heteroaryl ring; R$^a$ is methyl; R$^1$ is halogen, such as fluoro or chloro, methoxy, or ethoxy; and R$^2$ is H. In some embodiments, R$^1$ is methoxy. In other embodiments, R$^1$ is fluoro. In some instances, R$^1$ is ethoxy. In some instances, Z is not a substituted or unsubstituted pyridine N-oxide ring or a pyridine ring substituted with one or more halogens. In certain embodiments, Z is substituted with one or more electron withdrawing groups.

In certain embodiments, Z is a substituted or unsubstituted aryl or heteroaryl ring; R$^a$ is H or methyl; R$^1$ is H; and R$^2$ is halogen, such as fluoro or chloro, hydroxyl, methyl, ethyl, methoxy, or ethoxy. In some embodiments, R$^2$ is methoxy. In certain embodiments, R$^a$ is methyl. In certain embodiments, Z is substituted with one or more electron withdrawing groups.

In certain embodiments, Z is a substituted or unsubstituted aryl or heteroaryl ring; R$^a$ is H or methyl; R$^1$ is hydroxyl, methyl, or ethyl; and R$^2$ is H, halogen, such as fluoro or chloro, hydroxyl, methyl, ethyl, methoxy, or ethoxy. In certain embodiments, R$^1$ is methyl. In certain embodiments, R$^2$ is H. In certain embodiments, R$^1$ is hydroxyl. In certain embodiments, R$^1$ is methyl. In certain embodiments, R$^1$ is ethyl. In some embodiments, one or both of R$^1$ or R$^2$ is hydroxyl; for example, sometimes R$^1$ is hydroxyl. In certain embodiments, Z is substituted with one or more electron withdrawing groups.

In certain embodiments, Z is a substituted or unsubstituted pyridine N-oxide ring; R$^a$ is H or methyl; and R$^1$ and R$^2$ are, independently, H, halogen, such as fluoro or chloro, hydroxyl, methyl, ethyl, methoxy, or ethoxy, provided that at least one of R$^1$ and R$^2$ is not H. In certain embodiments, one or both of R$^1$ or R$^2$ is methoxy; for example, sometimes R$^1$ is methoxy, sometimes R$^2$ is methoxy, and sometimes both R$^1$ and R$^2$ are methoxy. In certain embodiments, one or both of R$^1$ or R$^2$ is fluoro; for example, sometimes R$^1$ is fluoro, sometimes R$^2$ is fluoro, and sometimes both R$^1$ and R$^2$ are fluoro. In certain embodiments, R$^2$ is H. In certain embodiments, R$^1$ is hydroxyl. In certain embodiments, R$^1$ is methyl. In certain embodiments, R$^1$ is ethyl. In some embodiments, one or both of R$^1$ or R$^2$ is hydroxyl; for example, sometimes R$^1$ is hydroxyl. In certain embodiments, Z is substituted with one or more electron withdrawing groups.

In certain embodiments, Z is a pyridine ring substituted with one or more halogens, such as fluoro and/or chloro, and optionally further substituted; R$^a$ is H or methyl; and R$^1$ and R$^2$ are, independently, H, halogen, such as fluoro or chloro, hydroxyl, methyl, ethyl, methoxy, or ethoxy, provided that at least one of R$^1$ and R$^2$ is not H. In certain embodiments, one or both of R$^1$ or R$^2$ is methoxy; for example, sometimes R$^1$ is methoxy, sometimes R is methoxy, and sometimes both R$^1$ and R are methoxy. In certain embodiments, one or both of R$^1$ or R$^2$ is fluoro; for example, sometimes R$^1$ is fluoro, sometimes R$^2$ is fluoro, and sometimes both R$^1$ and R$^2$ are fluoro. In certain embodiments, one or both of R$^1$ or R$^2$ is fluoro; for example, sometimes R$^1$ is fluoro, sometimes R is fluoro, and sometimes both R$^1$ and R are fluoro. In certain embodiments, R$^2$ is H. In certain embodiments, R$^1$ is hydroxyl. In certain embodiments, R$^1$ is methyl. In certain embodiments, R$^1$ is ethyl. In some embodiments, one or both of R$^1$ or R$^2$ is hydroxyl; for example, sometimes R$^1$ is hydroxyl. In certain embodiments, Z is substituted with one or more electron withdrawing groups.

In certain embodiments, Z is a substituted or unsubstituted aryl or heteroaryl ring; R$^a$ is H; and R$^1$ and R$^2$ are, independently, H, halogen, such as fluoro or chloro, hydroxyl, methyl, ethyl, methoxy, or ethoxy, provided that at least one of R$^1$ and R$^2$ is not H. In certain embodiments, one or both of R$^1$ or R$^2$ is methoxy; for example, sometimes R$^1$ is methoxy, sometimes R is methoxy, and sometimes both R$^1$ and R$^2$ are methoxy. In certain embodiments, R is H. In certain embodiments, R$^1$ is hydroxyl. In certain embodiments, R$^1$ is methyl. In certain embodiments, R$^1$ is ethyl. In some embodiments, one or both of R$^1$ or R$^2$ is hydroxyl, for example, sometimes R$^1$ is hydroxyl. In certain embodiments, Z is substituted with one or more electron withdrawing groups.

In certain embodiments, compounds that may be useful in the present invention may be represented by general formula (I):

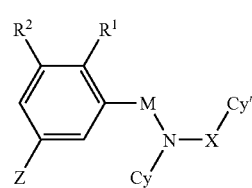

Formula II wherein, as valence and stability permit,

X is selected from —C(=O)—, —C(=S)—, —S(O)$_2$—, —S(O)—, and a methylene group optionally substituted with 1-2 lower alkyl groups;

Z is absent or represents a substituted or unsubstituted aryl, carbocyclyl, or heteroaryl ring, or a lower alkyl, nitro, cyano, azido, or halogen substituent;

M represents a direct bond or a substituted or unsubstituted methylene group;

Cy represents a substituted or unsubstituted aryl, heterocyclyl, heteroaryl, or cycloalkyl, including polycyclic groups, wherein Cy includes or is substituted with a primary, secondary, or tertiary amine other than N(X)(M);

Cy' represents a 3-halo-benzo[b]thien-2-yl or 3-methyl-benzo[b]thien-2-yl, wherein the benzo ring is optionally substituted with from 1-4 substituents selected from halogen, nitro, cyano, methyl, and ethyl;

$R^1$ and $R^2$ are, independently, H, halogen, hydroxyl, lower alkyl, or lower alkoxy, provided that at least one of $R^1$ and $R^2$ is not H;

In certain embodiments, M represents, independently for each occurrence, a substituted or unsubstituted methylene group, such as —$CH_2$—, —CHF—, —CHOH—, —CH(Me)-, C(=O)—, etc.

In certain embodiments, $R^1$ represents lower alkyl, e.g., Me, Et, or Pr. In other embodiments, $R^1$ represents hydroxyl or lower alkoxy, such as methoxy, or ethoxy, particularly methoxy. In some embodiments, $R^1$ or R represents halogen, for example, fluoro. In some embodiments, $R^2$ is H and $R^1$ is not H.

In certain embodiments, Cy represents a substituted or unsubstituted non-aromatic carbocyclic, such as cycloalkyl, or heterocyclic ring, such as heterocyclyl, i.e., including at least one $sp^3$ hybridized atom, and preferably a plurality of $sp^3$ hybridized atoms. In certain embodiments, Cy includes an amine within the atoms of the ring or on a substituent of the ring, e.g., Cy is pyridyl, imidazolyl, pyrrolyl, piperidyl, pyrrolidyl, piperazyl, etc., and/or bears an amino substituent. The amine within the atoms of the ring may be in a 1,2; 1,3; 1,5; or preferably 1,4 position relative to N. For example, Cy may be piperidine, wherein the amine in the piperidine ring is in a 1,4 position relative to N. In certain embodiments, Cy is a 5- to 7-membered ring. In certain embodiments, Cy is a 5- to 7-membered cycloalkyl ring, for example, a 6-membered ring, such as cyclohexyl. In certain embodiments Cy is a six-membered ring, such as cyclohexyl, attached directly to N and bears a primary, secondary or tertiary amino substituent represented by —$N(R^a)_2$, wherein $R^a$ represents, independently for each occurrence, H; substituted or unsubstituted aryl, heterocyclyl, carbocyclyl, heteroaryl, aralkyl, heteroaralkyl, heterocyclylalkyl, carbocyclylalkyl, alkynyl, alkenyl, or alkyl; or two $R^a$ taken together may form a 4- to 8-membered ring. The amino substituent of Cy may be at the 4 position of the ring relative to N(X)(M), and the N(X)(M) and amino substituents may be disposed trans on the ring. In certain embodiments, one or more $R^a$ in $N(R^a)_2$ is H and/or lower alkyl, i.e., $N(R^a)_2$ is $NH_2$, NH(lower alkyl), or N(lower alkyl)$_2$. In specific embodiments, $N(R^a)_2$ is $NH_2$ or NH(lower alkyl), preferably NH(lower alkyl) such as a methylamino group.

In certain embodiments, Cy' is a substituted or unsubstituted aryl or heteroaryl. In certain embodiments, Cy' is attached directly to X. In certain embodiments, Cy' is a substituted or unsubstituted bicyclic or heteroaryl ring. In certain embodiments, Cy' is both bicyclic and heteroaryl, such as benzothiophene, benzofuran, benzopyrrole, benzopyridine, etc. In particular embodiments, Cy' is a benzothiophene, such as a 3-halo-benzo[b]thien-2-yl, for example a 3-chloro-benzo[b]thien-2-yl or a 3-fluoro-benzo[b]thien-2-yl, or a 3-methyl-benzo[b]thien-2-yl. In embodiments of Cy' that comprise a benzo ring, the benzo ring may be substituted with from 1-4 substituents such as halogen, nitro, cyano, methyl (e.g., including halomethyl, such as $CHCl_2$ and $CF_3$), and ethyl (e.g., including haloethyl, such as $CH_2CCl_3$, $C_2F_5$, etc.), preferably with halogen and methyl (e.g., including halomethyl, such as $CHCl_2$ and $CF_3$). In certain such embodiments, Cy' represents a 3-chloro-benzo[b]thien-2-yl, 3-fluoro-benzo[b]thien-2-yl, or 3-methyl-benzo[b]thien-2-yl, wherein the benzo ring is substituted with fluoro at the 4-position (peri to the 3-substituent on the thienyl ring) and, optionally, at the 7-position ('peri' to the S of the thienyl ring). Alternatively, the benzo ring may be unsubstituted. In certain embodiments, the benzo ring is selected from:

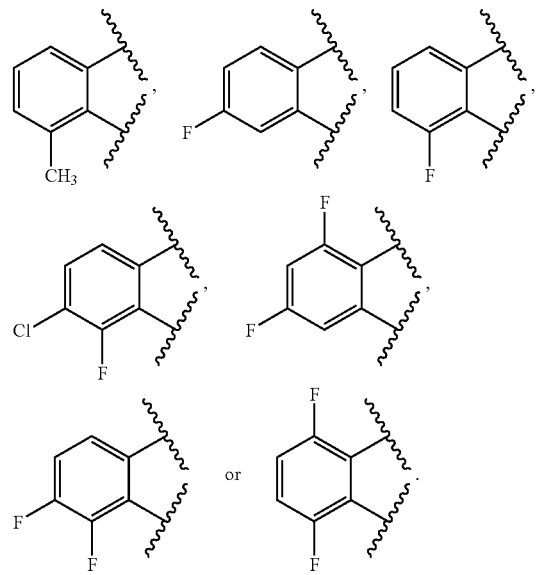

In yet further embodiments, Cy' is selected from:

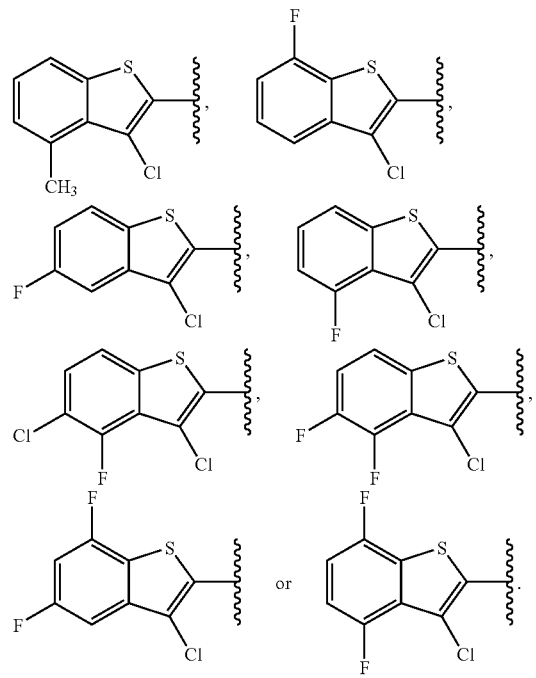

In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system.

In certain embodiments, Z represents an aryl or heteroaryl ring, e.g., unsubstituted or substituted with one or more groups including heteroatoms such as O, N, and S. In certain embodiments, Z represents a phenyl ring. In certain embodiments, Z represents a heteroaryl ring, e.g., a pyrrole, pyrazole, imidazole, pyridine, pyrimidine, pyrazine, pyridazine, triazine, tetrazine, furan, thiophene, thiazole, isothiazole, thiadiazole, oxazole, isoxazole, or oxadiazole ring. Z may be attached to the rest of the molecule at any position on its ring; for example, if Z is a pyridine ring, Z may be attached at the 2, 3, or 4 position relative to the nitrogen of the pyridine ring.

In certain embodiments, substituents on Z are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —$(CH_2)_p$alkyl, —$(CH_2)_p$alkenyl, —$(CH_2)_p$alkynyl, —$(CH_2)_p$aryl, —$(CH_2)_p$aralkyl, —$(CH_2)_p$OH, —$(CH_2)_p$O-lower alkyl, —$(CH_2)_p$O-lower alkenyl, —$O(CH_2)_nR$, —$(CH_2)_p$SH, —$(CH_2)_p$S-lower alkyl, —$(CH_2)_p$S-lower alkenyl, —$S(CH_2)_nR$, —$(CH_2)_pN(R)_2$, —$(CH_2)_p$NR-lower alkyl, —$(CH_2)_p$NR-lower alkenyl, —$NR(CH_2)_nR$, and protected forms of the above, wherein p and n, individually for each occurrence, represent integers from 0 to 10, preferably from 0 to 5.

In certain embodiments, Z is substituted with one or more groups selected from halogen, lower alkyl, —CN, azido, —$NR^xR^x$, —$NR^x$—$C(O)$—$R^x$, —$C(O)$—$NR^xR^x$, —$C(O)$—$R^x$, $NSO_2R^x$, —$SO_2R^x$, —$(C(R^x)_2)_n$—$OR^x$, —$(C(R^x)_2)_n$—$NR^xR^x$; wherein $R^x$ is, independently for each occurrence, H or lower alkyl; and n is an integer from 0-2.

In certain embodiments, Z is substituted with one or more electron withdrawing groups. For example, sometimes Z is substituted with one or more groups selected from halogen, —CN, azido, —$CO_{20}R^x$, —$C(O)$—$NR^xR^x$, and $C(O)$—$R^x$.

In certain embodiments, X is selected from —C(=O)—, —C(=S)—, and —$S(O_2)$—. In other embodiments, X represents a methylene group optionally substituted with 1-2 lower alkyl groups.

In certain embodiments, the N in N(M)(X)(Cy) is bonded to exactly three carbon atoms.

In certain embodiments, Z is a substituted or unsubstituted aryl or heteroaryl ring; $R^a$ is methyl; $R^1$ is halogen, such as fluoro or chloro, methoxy, or ethoxy; and $R^2$ is H. In some embodiments, $R^1$ is methoxy. In other embodiments, $R^1$ is fluoro. In some instances, $R^1$ is ethoxy. In some instances, Z is not a substituted or unsubstituted pyridine N-oxide ring or a pyridine ring substituted with one or more halogens. In certain embodiments, Z is substituted with one or more electron withdrawing groups.

In certain embodiments, Z is a substituted or unsubstituted aryl or heteroaryl ring; $R^a$ is H or methyl; $R^1$ is H; and $R^2$ is halogen, such as fluoro or chloro, hydroxyl, methyl, ethyl, methoxy, or ethoxy. In some embodiments, $R^2$ is methoxy. In certain embodiments, $R^a$ is methyl. In certain embodiments, Z is substituted with one or more electron withdrawing groups.

In certain embodiments, Z is a substituted or unsubstituted aryl or heteroaryl ring; $R^a$ is H or methyl; $R^1$ is hydroxyl, methyl, or ethyl; and $R^2$ is H, halogen, such as fluoro or chloro, hydroxyl, methyl, ethyl, methoxy, or ethoxy. In certain embodiments, $R^a$ is methyl. In certain embodiments, $R^2$ is H. In certain embodiments, $R^1$ is hydroxyl. In certain embodiments, $R^1$ is methyl. In certain embodiments, $R^1$ is ethyl. In some embodiments, one or both of $R^1$ or $R^2$ is hydroxyl; for example, sometimes $R^1$ is hydroxyl. In certain embodiments, Z is substituted with one or more electron withdrawing groups.

In certain embodiments, Z is a substituted or unsubstituted pyridine N-oxide ring; $R^a$ is H or methyl; and $R^1$ and $R^2$ are, independently, H, halogen, such as fluoro or chloro, hydroxyl, methyl, ethyl, methoxy, or ethoxy, provided that at least one of $R^1$ and $R^2$ is not H. In certain embodiments, one or both of $R^1$ or $R^2$ is methoxy; for example, sometimes $R^1$ is methoxy, sometimes $R^2$ is methoxy, and sometimes both $R^1$ and R are methoxy. In certain embodiments, one or both of $R^1$ or $R^2$ is fluoro; for example, sometimes $R^1$ is fluoro, sometimes $R^2$ is fluoro, and sometimes both $R^1$ and $R^2$ are fluoro. In certain embodiments, $R^2$ is H. In certain embodiments, R is hydroxyl. In certain embodiments, $R^1$ is methyl. In certain embodiments, $R^1$ is ethyl. In some embodiments, one or both of $R^1$ or $R^2$ is hydroxyl; for example, sometimes $R^1$ is hydroxyl. In certain embodiments, Z is substituted with one or more electron withdrawing groups.

In certain embodiments, Z is a pyridine ring substituted with one or more halogens, such as fluoro and/or chloro, and optionally further substituted; $R^a$ is H or methyl; and $R^1$ and $R^2$ are, independently, H, halogen, such as fluoro or chloro, hydroxyl, methyl, ethyl, methoxy, or ethoxy, provided that at least one of $R^1$ and $R^2$ is not H. In certain embodiments, one or both of $R^1$ or $R^2$ is methoxy; for example, sometimes $R^1$ is methoxy, sometimes $R^2$ is methoxy, and sometimes both $R^1$ and $R^2$ are methoxy. In certain embodiments, one or both of $R^1$ or $R^2$ is fluoro; for example, sometimes $R^1$ is fluoro, sometimes $R^2$ is fluoro, and sometimes both $R^1$ and $R^2$ are fluoro. In certain embodiments, one or both of $R^1$ or $R^2$ is fluoro; for example, sometimes $R^1$ is fluoro, sometimes R is fluoro, and sometimes both $R^1$ and R are fluoro. In certain embodiments, $R^2$ is H. In certain embodiments, $R^1$ is hydroxyl. In certain embodiments, $R^1$ is methyl. In certain embodiments, $R^1$ is ethyl. In some embodiments, one or both of $R^1$ or $R^2$ is hydroxyl; for example, sometimes $R^1$ is hydroxyl. In certain embodiments, Z is substituted with one or more electron withdrawing groups.

In certain embodiments, Z is a substituted or unsubstituted aryl or heteroaryl ring; $R^a$ is H; and $R^1$ and $R^2$ are, independently, H, halogen, such as fluoro or chloro, hydroxyl, methyl, ethyl, methoxy, or ethoxy, provided that at least one of $R^1$ and $R^2$ is not H. In certain embodiments, one or both of $R^1$ or $R^2$ is methoxy; for example, sometimes $R^1$ is methoxy, sometimes $R^2$ is methoxy, and sometimes both $R^1$ and $R^2$ are methoxy. In certain embodiments, $R^2$ is H. In certain embodiments, $R^1$ is hydroxyl. In certain embodiments, $R^1$ is methyl. In certain embodiments, $R^1$ is ethyl. In some embodiments, one or both of $R^1$ or $R^2$ is hydroxyl; for example, sometimes $R^1$ is hydroxyl. In certain embodiments, Z is substituted with one or more electron withdrawing groups.

In certain embodiments, compounds that may be useful in the present invention may be represented by general formula (O):

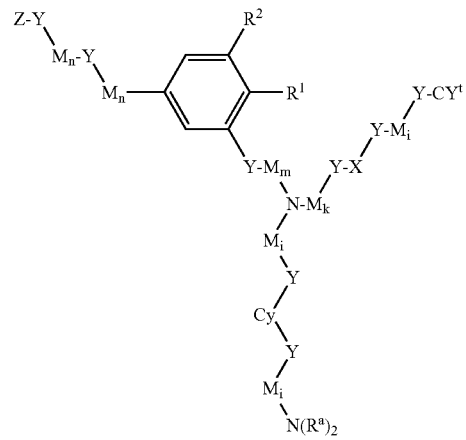

Formula III wherein, as valence and stability permit,

Z is absent or represents a substituted or unsubstituted aryl, carbocyclyl, or heteroaryl ring, or a lower alkyl, nitro, cyano, azido or halogen substituent;

Y, independently for each occurrence, is absent or represents —N(R)—, —O—, —S—, or —Se—, provided that if Z is not a ring, then Y attached to Z is absent;

X is selected from —C(=O)—, —C(=S)—, —S(O)$_2$—, —S(O)—, and a methylene group optionally substituted with 1-2 lower alkyl groups;

M represents, independently for each occurrence, a substituted or unsubstituted methylene group or two M taken together represent substituted or unsubstituted ethene or ethyne;

$R^1$ and $R^2$ are, independently, H, halogen, hydroxyl, lower alkyl, or lower alkoxy, provided that at least one of $R^1$ and $R^2$ is not H;

R and $R^a$ represent, independently for each occurrence, H or substituted or unsubstituted, alkynyl, alkenyl, or alkyl, or two $R^a$ taken together may form a 4- to 8-membered ring;

Cy and Cy' independently represent substituted or unsubstituted aryl, heterocyclyl, heteroaryl, or cycloalkyl, including polycyclic groups;

i represents, independently for each occurrence, an integer from 0 to 5;

k represents an integer from 0 to 3;

m represents an integer from 0 to 3; and n represents, independently for each occurrence, an integer from 0 to 5.

In certain embodiments, M represents, independently for each occurrence, a substituted or unsubstituted methylene group, such as —CH$_2$—, —CHF—, —CHOH—, —CH(Me)-, C(=O)—, etc.

In certain embodiments, $R^1$ represents lower alkyl, e.g., Me, Et, or Pr. In other embodiments, $R^1$ represents hydroxyl or lower alkoxy, such as methoxy, or ethoxy, particularly methoxy. In some embodiments, $R^1$ or $R^2$ represents halogen, for example, fluoro. In some embodiments, $R^2$ is H and $R^1$ is not H.

In certain embodiments, Cy represents a substituted or unsubstituted non-aromatic carbocyclic, such as cycloalkyl, or heterocyclic ring, such as heterocyclyl, i.e., including at least one sp$^3$ hybridized atom, and preferably a plurality of sp$^3$ hybridized atoms. In certain embodiments, Cy is a 5- to 7-membered ring. In certain embodiments, Cy is a 5- to 7-membered cycloalkyl ring, for example, a 6-membered ring, such as cyclohexyl. In certain embodiments, Cy is attached directly to N. In certain embodiments, Cy is a six-membered ring, such as cyclohexyl, attached directly to N. In certain embodiments, N($R^a$)$_2$ is attached directly to Cy. In certain embodiments, the chain containing N($R^a$)$_2$ is at the 4 position of the ring relative to other substituents, such as N(M$_m$)(M$_k$). In certain embodiments, substituents of Cy, for example N($R^a$)$_2$ and N(M$_m$)(M$_k$), are disposed trans on the ring. In certain embodiments, one or more $R^a$ in N($R^a$)$_2$ is H and/or lower alkyl, i.e., N($R^a$)$_2$ is NH$_2$, NH(lower alkyl), or N(lower alkyl)$_2$. In specific embodiments, N($R^a$)$_2$ is NH$_2$, while in other embodiments, it is NH(lower alkyl) such as a methylamino group.

In certain embodiments, Cy' is a substituted or unsubstituted aryl or heteroaryl. In certain embodiments, Cy' is attached directly to X. In certain embodiments, Cy' is a substituted or unsubstituted bicyclic or heteroaryl ring. In certain embodiments, Cy' is both bicyclic and heteroaryl, such as benzothiophene, benzofuran, benzopyrrole, benzopyridine, etc. In particular embodiments, Cy' is a benzothiophene, such as a 3-halo-benzo[b]thien-2-yl, for example a 3-chloro-benzo[b]thien-2-yl or a 3-fluoro-benzo[b]thien-2-yl, or a 3-methyl-benzo[b]thien-2-yl. In embodiments of Cy' that comprise a benzo ring, the benzo ring may be substituted with from 1-4 substituents such as halogen, nitro, cyano, methyl (e.g., including halomethyl, such as CHCl$_2$ and CF$_3$), and ethyl (e.g., including haloethyl, such as CH$_2$CCl$_3$, C$_2$F$_5$, etc.), preferably with halogen and methyl (e.g., including halomethyl, such as CHCl$_2$ and CF$_3$). In certain such embodiments, Cy' represents a 3-chloro-benzo[b]thien-2-yl, 3-fluoro-benzo[b]thien-2-yl, or 3-methyl-benzo[b]thien-2-yl, wherein the benzo ring is substituted with fluoro at the 4-position (peri to the 3-substituent on the thienyl ring) and, optionally, at the 7-position ('peri' to the S of the thienyl ring). Alternatively, the benzo ring may be unsubstituted. In certain embodiments, the benzo ring is selected from:

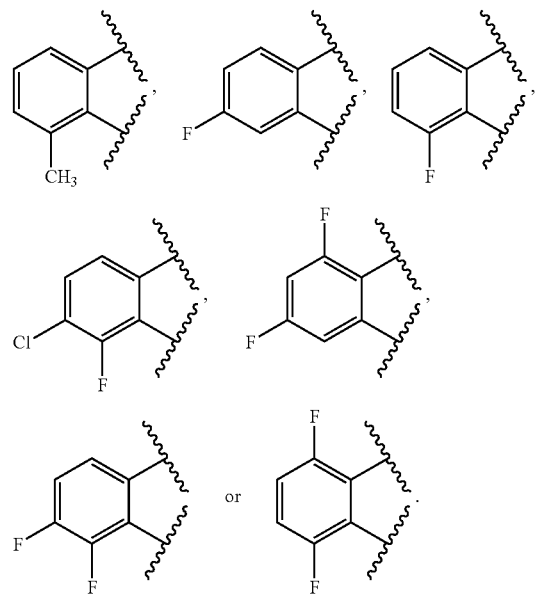

In yet further embodiments, Cy' is selected from:

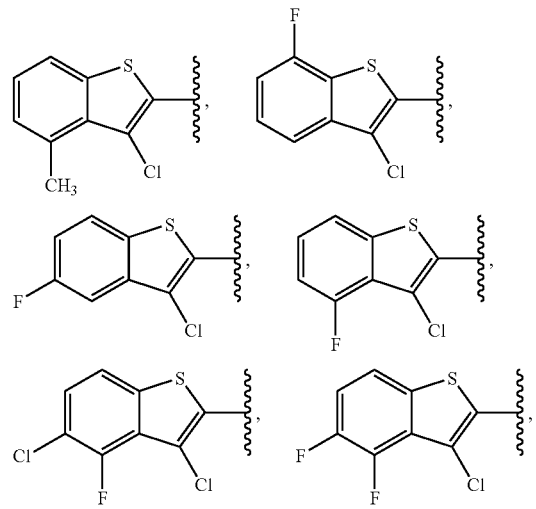

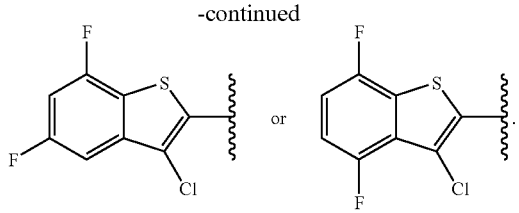

In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system.

In certain embodiments, Z represents an aryl or heteroaryl ring, e.g., unsubstituted or substituted with one or more groups including heteroatoms such as O, N, and S. In certain embodiments, Z represents a phenyl ring. In certain embodiments, Z represents a heteroaryl ring, e.g., a pyrrole, pyrazole, imidazole, pyridine, pyrimidine, pyrazine, pyridazine, triazine, tetrazine, furan, thiophene, thiazole, isothiazole, thiadiazole, oxazole, isoxazole, or oxadiazole ring. Z may be attached to the rest of the molecule at any position on its ring; for example, if Z is a pyridine ring, Z may be attached at the 2, 3, or 4 position relative to the nitrogen of the pyridine ring. In certain embodiments, $R^1$ and the chain containing Z are attached to the phenyl ring in a para (i.e., 1,4) relationship.

In certain embodiments, substituents on Z are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, $-(CH_2)_p$alkyl, $-(CH_2)_p$alkenyl, $-(CH_2)_p$alkynyl, $-(CH_2)_p$aryl, $-(CH_2)_p$aralkyl, $-(CH_2)_p$OH, $-(CH_2)_p$O-lower alkyl, $-(CH_2)_p$O-lower alkenyl, $-O(CH_2)_nR$, $-(CH_2)_p$SH, $-(CH_2)_p$S-lower alkyl, $-(CH_2)_p$S-lower alkenyl, $-S(CH_2)_nR$, $-(CH_2)_pN(R)_2$, $-(CH_2)_p$NR-lower alkyl, $-(CH_2)_p$NR-lower alkenyl, $-NR(CH_2)_nR$, and protected forms of the above, wherein p and n, individually for each occurrence, represent integers from 0 to 10, preferably from 0 to 5.

In certain embodiments, Z is substituted with one or more groups selected from halogen, lower alkyl, $-CN$, azido, $-NR^xR^x$, $-NR^x-C(O)-R^x$, $-C(O)-NR^xR^x$, $-C(O)-R^x$, $NSO_2R^x$, $-SO_2R^x$, $-(C(R^x)_2)_n-OR^x$, $-(C(R^x)_2)_n-NR^xR^x$; wherein $R^x$ is, independently for each occurrence, H or lower alkyl; and n is an integer from 0-2.

In certain embodiments, Z is substituted with one or more electron withdrawing groups. For example, sometimes Z is substituted with one or more groups selected from halogen, $-CN$, azido, $-CO_{20}R^x$, $-C(O)-NR^xR^x$, and $-C(O)-R^x$.

In certain embodiments, X is selected from $-C(=O)-$, $-C(=S)-$, and $-S(O_2)-$. In other embodiments, X represents a methylene group optionally substituted with 1-2 lower alkyl groups.

In certain embodiments, Y is absent from all positions, e.g., it is a direct bond if between two groups. In embodiments wherein Y is present in a position, i preferably represents an integer from 1-2 in an adjacent $M_i$ if i=0 would result in two occurrences of Y being attached directly, or an occurrence of Y being attached directly to N. In certain embodiments, Y, independently for each occurrence, represents $-N(R)-$, $-O-$, or $-S-$.

In certain embodiments, i is 0, k is 0, and m is 1.

In certain embodiments, the N in $N(M_m)(M_i)(M_k)$ is bonded to exactly three carbon atoms.

In certain embodiments, Z is a substituted or unsubstituted aryl or heteroaryl ring; $R^a$ is methyl; $R^1$ is halogen, such as fluoro or chloro, methoxy, or ethoxy; and $R^2$ is H. In some embodiments, $R^1$ is methoxy. In other embodiments, $R^1$ is fluoro. In some instances, $R^1$ is ethoxy. In some instances, Z is not a substituted or unsubstituted pyridine N-oxide ring or a pyridine ring substituted with one or more halogens. In certain embodiments, Z is substituted with one or more electron withdrawing groups.

In certain embodiments, Z is a substituted or unsubstituted aryl or heteroaryl ring; $R^a$ is H or methyl; $R^1$ is H; and $R^2$ is halogen, such as fluoro or chloro, hydroxyl, methyl, ethyl, methoxy, or ethoxy. In some embodiments, $R^2$ is methoxy. In certain embodiments, $R^a$ is methyl. In certain embodiments, Z is substituted with one or more electron withdrawing groups.

In certain embodiments, Z is a substituted or unsubstituted aryl or heteroaryl ring; $R^a$ is H or methyl; $R^1$ is hydroxyl, methyl, or ethyl; and $R^2$ is H, halogen, such as fluoro or chloro, hydroxyl, methyl, ethyl, methoxy, or ethoxy. In certain embodiments, $R^a$ is methyl. In certain embodiments, $R^2$ is H. In certain embodiments, $R^1$ is hydroxyl. In certain embodiments, $R^1$ is methyl. In certain embodiments, $R^1$ is ethyl. In some embodiments, one or both of $R^1$ or $R^2$ is hydroxyl; for example, sometimes $R^1$ is hydroxyl. In certain embodiments, Z is substituted with one or more electron withdrawing groups.

In certain embodiments, Z is a substituted or unsubstituted pyridine N-oxide ring; $R^a$ is H or methyl; and $R^1$ and $R^2$ are, independently, H, halogen, such as fluoro or chloro, hydroxyl, methyl, ethyl, methoxy, or ethoxy, provided that at least one of $R^1$ and $R^2$ is not H. In certain embodiments, one or both of $R^1$ or $R^2$ is methoxy; for example, sometimes $R^1$ is methoxy, sometimes $R^2$ is methoxy, and sometimes both $R^1$ and R are methoxy. In certain embodiments, one or both of $R^1$ or $R^2$ is fluoro; for example, sometimes $R^1$ is fluoro, sometimes $R^2$ is fluoro, and sometimes both $R^1$ and $R^2$ are fluoro. In certain embodiments, $R^2$ is H. In certain embodiments, $R^1$ is hydroxyl. In certain embodiments, $R^1$ is methyl. In certain embodiments, $R^1$ is ethyl. In some embodiments, one or both of $R^1$ or $R^2$ is hydroxyl; for example, sometimes $R^1$ is hydroxyl. In certain embodiments, Z is substituted with one or more electron withdrawing groups.

In certain embodiments, Z is a pyridine ring substituted with one or more halogens, such as fluoro and/or chloro, and optionally further substituted; $R^a$ is H or methyl; and $R^1$ and $R^2$ are, independently, H, halogen, such as fluoro or chloro, hydroxyl, methyl, ethyl, methoxy, or ethoxy, provided that at least one of $R^1$ and $R^2$ is not H. In certain embodiments, one or both of $R^1$ or $R^2$ is methoxy; for example, sometimes $R^1$ is methoxy, sometimes $R^2$ is methoxy, and sometimes both $R^1$ and R are methoxy. In certain embodiments, one or both of $R^1$ or R is fluoro; for example, sometimes $R^1$ is fluoro, sometimes $R^2$ is fluoro, and sometimes both $R^1$ and $R^2$ are fluoro. In certain embodiments, one or both of $R^1$ or $R^2$ is fluoro; for example, sometimes $R^1$ is fluoro, sometimes $R^2$ is fluoro, and sometimes both $R^1$ and $R^2$ are fluoro. In certain embodiments, $R^2$ is H. In certain embodiments, $R^1$ is hydroxyl. In certain embodiments, $R^1$ is methyl. In certain embodiments, $R^1$ is ethyl. In some embodiments, one or both of $R^1$ or $R^2$ is hydroxyl; for example, sometimes $R^1$ is hydroxyl. In certain embodiments, Z is substituted with one or more electron withdrawing groups.

In certain embodiments, Z is a substituted or unsubstituted aryl or heteroaryl ring; $R^a$ is H; and $R^1$ and $R^2$ are, independently, H, halogen, such as fluoro or chloro, hydroxyl, methyl, ethyl, methoxy, or ethoxy, provided that at least one of $R^1$ and $R^2$ is not H. In certain embodiments, one or both of $R^1$ or $R^2$ is methoxy; for example, sometimes $R^1$ is methoxy, sometimes $R^2$ is methoxy, and sometimes both $R^1$ and $R^2$ are methoxy. In certain embodiments, $R^2$ is H. In certain embodiments, $R^1$ is hydroxyl. In certain embodiments, $R^1$ is methyl. In certain embodiments, $R^1$ is ethyl. In some embodiments, one or both of $R^1$ or $R^2$ is hydroxyl; for example, sometimes $R^1$ is hydroxyl. In certain embodiments, Z is substituted with one or more electron withdrawing groups.

In certain embodiments, compounds that may be useful in the present invention include compounds represented by general formula (IV):

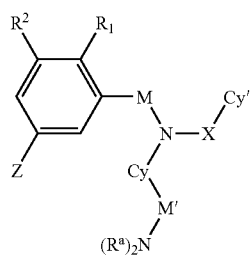

Formula IV wherein, as valence and stability permit,

X is selected from —C(═O)—, —C(═S)—, —S(O)$_2$—, —S(O)—, and a methylene group optionally substituted with 1-2 lower alkyl groups;

Z is absent or represents a substituted or unsubstituted aryl, carbocyclyl, or heteroaryl ring, or a lower alkyl, nitro, cyano, azido, or halogen substituent;

M and M' represent, independently for each occurrence, a direct bond or a substituted or unsubstituted methylene group;

Cy represents a substituted or unsubstituted aryl, heterocyclyl, heteroaryl, or cycloalkyl, including polycyclic groups;

Cy' represents a 3-halo-benzo[b]thien-2-yl or 3-methyl-benzo[b]thien-2-yl, wherein the benzo ring is optionally substituted with from 1-4 substituents selected from halogen, nitro, cyano, methyl, and ethyl;

$R^1$ and $R^2$ are, independently, H, halogen, hydroxyl, lower alkyl, or lower alkoxy, provided that at least one of $R^1$ and $R^2$ is not H;

$R^a$ represents, individually for each occurrence, H; substituted or unsubstituted alkynyl, alkenyl, or alkyl; or two $R^a$ taken together may form a 4- to 8-membered ring.

In certain embodiments, M represents, independently for each occurrence, a substituted or unsubstituted methylene group, such as —CH$_2$—, —CHF—, —CHOH—, —CH(Me)-, —C(═O)—, etc.

In certain embodiments, $R^1$ represents lower alkyl, e.g., Me, Et, or Pr. In other embodiments, $R^1$ represents hydroxyl or lower alkoxy, such as methoxy, or ethoxy, particularly methoxy. In some embodiments, $R^1$ or $R^2$ represents halogen, for example, fluoro. In some embodiments, R is H and $R^1$ is not H.

In certain embodiments, Cy represents a substituted or unsubstituted non-aromatic carbocyclic, such as cycloalkyl, or heterocyclic ring, such as heterocyclyl, i.e., including at least one sp$^3$ hybridized atom, and preferably a plurality of sp$^3$ hybridized atoms. In certain embodiments, Cy is a 5- to 7-membered ring. In certain embodiments, Cy is a 5- to 7-membered cycloalkyl ring, for example, a 6-membered ring, such as cyclohexyl. In certain embodiments, N($R^a$)$_2$ is attached directly to Cy. In certain embodiments, the chain containing N($R^a$)$_2$ is at the 4 position of the ring relative to other substituents, such as N(X)(M). In certain embodiments, substituents of Cy, for example N($R^a$)$_2$ and N(X)(M), are disposed trans on the ring. In certain embodiments, one or more $R^a$ in N($R^a$)$_2$ is H and/or lower alkyl, i.e., N($R^a$)$_2$ is NH$_2$, NH(lower alkyl), or N(lower alkyl)$_2$. In specific embodiments, N($R^a$)$_2$ is NH$_2$ or NH(lower alkyl), preferably NH(lower alkyl) such as a methylamino group.

In certain embodiments, Cy' is a substituted or unsubstituted aryl or heteroaryl. In certain embodiments, Cy' is attached directly to X. In certain embodiments, Cy' is a substituted or unsubstituted bicyclic or heteroaryl ring. In certain embodiments, Cy' is both bicyclic and heteroaryl, such as benzothiophene, benzofuran, benzopyrrole, benzopyridine, etc. In particular embodiments, Cy' is a benzothiophene, such as a 3-halo-benzo[b]thien-2-yl, for example a 3-chloro-benzo[b]thien-2-yl or a 3-fluoro-benzo[b]thien-2-yl, or a 3-methyl-benzo[b]thien-2-yl. In embodiments of Cy' that comprise a benzo ring, the benzo ring may be substituted with from 1-4 substituents such as halogen, nitro, cyano, methyl (e.g., including halomethyl, such as CHCl$_2$ and CF$_3$), and ethyl (e.g., including haloethyl, such as CH$_2$CCl$_3$, C$_2$F$_5$, etc.), preferably with halogen and methyl (e.g., including halomethyl, such as CHCl$_2$ and CF$_3$). In certain such embodiments, Cy' represents a 3-chloro-benzo[b]thien-2-yl, 3-fluoro-benzo[b]thien-2-yl, or 3-methyl-benzo[b]thien-2-yl, wherein the benzo ring is substituted with fluoro at the 4-position (peri to the 3-substituent on the thienyl ring) and, optionally, at the 7-position ('peri' to the S of the thienyl ring). Alternatively, the benzo ring may be unsubstituted. In certain embodiments, the benzo ring is selected from:

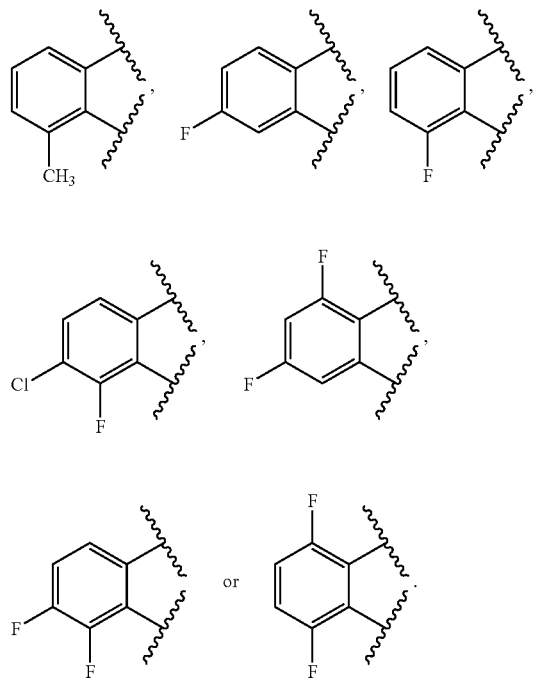

In yet further embodiments, Cy' is selected from:

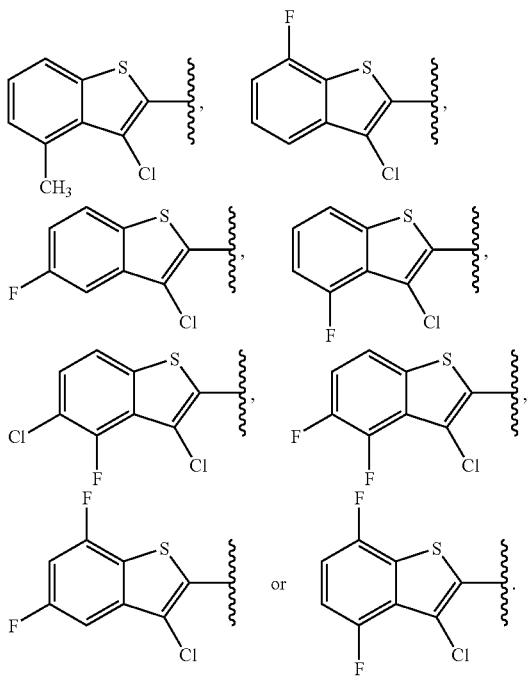

In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system.

In certain embodiments, Z represents an aryl or heteroaryl ring, e.g., unsubstituted or substituted with one or more groups including heteroatoms such as O, N, and S. In certain embodiments, Z represents a phenyl ring. In certain embodiments, Z represents a heteroaryl ring, e.g., a pyrrole, pyrazole, imidazole, pyridine, pyrimidine, pyrazine, pyridazine, triazine, tetrazine, furan, thiophene, thiazole, isothiazole, thiadiazole, oxazole, isoxazole, or oxadiazole ring. Z may be attached to the rest of the molecule at any position on its ring; for example, if Z is a pyridine ring, Z may be attached at the 2, 3, or 4 position relative to the nitrogen of the pyridine ring.

In certain embodiments, substituents on Z are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —$(CH_2)_p$alkyl, —$(CH_2)_p$alkenyl, —$(CH_2)_p$alkynyl, —$(CH_2)_p$aryl, —$(CH_2)_p$aralkyl, —$(CH_2)_p$OH, —$(CH_2)_p$O-lower alkyl, —$(CH_2)_p$O-lower alkenyl, —$O(CH_2)_nR$, —$(CH_2)_p$SH, —$(CH_2)_p$S-lower alkyl, —$(CH_2)_p$S-lower alkenyl, —$S(CH_2)_nR$, —$(CH_2)_pN(R)_2$, —$(CH_2)_p$NR-lower alkyl, —$(CH_2)_p$NR-lower alkenyl, —$NR(CH_2)_nR$, and protected forms of the above, wherein p and n, individually for each occurrence, represent integers from 0 to 10, preferably from 0 to 5.

In certain embodiments, Z is substituted with one or more groups selected from halogen, lower alkyl, —CN, azido, —$NR^xR^x$, —$NR^x$—C(O)—$R^x$, —C(O)—$NR^xR^x$, —C(O)—$R^x$, $NSO_2R^x$, —$SO_2R^x$, —$(C(R^x)_2)_n$—$OR^x$, —$(C(R^x)_2)_n$—$NR^xR^x$; wherein $R^x$ is, independently for each occurrence, H or lower alkyl; and n is an integer from 0-2.

In certain embodiments, Z is substituted with one or more electron withdrawing groups. For example, sometimes Z is substituted with one or more groups selected from halogen, —CN, azido, —$CO_2OR^x$, —C(O)—$NR^xR^x$, and —C(O)—$R^x$.

In certain embodiments, X is selected from —C(=O)—, —C(=S)—, and —S($O_2$)—. In other embodiments, X represents a methylene group optionally substituted with 1-2 lower alkyl groups.

In certain embodiments, the N in N(M)(X)(Cy) is bonded to exactly three carbon atoms.

In certain embodiments, Z is a substituted or unsubstituted aryl or heteroaryl ring; $R^a$ is methyl; $R^1$ is halogen, such as fluoro or chloro, methoxy, or ethoxy; and $R^2$ is H. In some embodiments, $R^1$ is methoxy. In other embodiments, R is fluoro. In some instances, $R^1$ is ethoxy. In some instances, Z is not a substituted or unsubstituted pyridine N-oxide ring or a pyridine ring substituted with one or more halogens. In certain embodiments, Z is substituted with one or more electron withdrawing groups.

In certain embodiments, Z is a substituted or unsubstituted aryl or heteroaryl ring; $R^a$ is H or methyl; $R^1$ is H; and $R^2$ is halogen, such as fluoro or chloro, hydroxyl, methyl, ethyl, methoxy, or ethoxy. In some embodiments, $R^2$ is methoxy. In certain embodiments, $R^a$ is methyl. In certain embodiments, Z is substituted with one or more electron withdrawing groups.

In certain embodiments, Z is a substituted or unsubstituted aryl or heteroaryl ring; $R^a$ is H or methyl; $R^1$ is hydroxyl, methyl, or ethyl; and $R^2$ is H, halogen, such as fluoro or chloro, hydroxyl, methyl, ethyl, methoxy, or ethoxy. In certain embodiments, $R^a$ is methyl. In certain embodiments, $R^2$ is H. In certain embodiments, $R^1$ is hydroxyl. In certain embodiments, $R^1$ is methyl. In certain embodiments, $R^1$ is ethyl. In some embodiments, one or both of $R^1$ or $R^2$ is hydroxyl; for example, sometimes $R^1$ is hydroxyl. In certain embodiments, Z is substituted with one or more electron withdrawing groups.

In certain embodiments, Z is a substituted or unsubstituted pyridine N-oxide ring; $R^a$ is H or methyl; and $R^1$ and $R^2$ are, independently, H, halogen, such as fluoro or chloro, hydroxyl, methyl, ethyl, methoxy, or ethoxy, provided that at least one of $R^1$ and $R^2$ is not H. In certain embodiments, one or both of $R^1$ or $R^2$ is methoxy; for example, sometimes $R^1$ is methoxy, sometimes $R^2$ is methoxy, and sometimes both $R^1$ and $R^2$ are methoxy. In certain embodiments, one or both of $R^1$ or $R^2$ is fluoro; for example, sometimes $R^1$ is fluoro, sometimes $R^2$ is fluoro, and sometimes both $R^1$ and $R^2$ are fluoro. In certain embodiments, $R^2$ is H. In certain embodiments, $R^1$ is hydroxyl. In certain embodiments, $R^1$ is methyl. In certain embodiments, $R^1$ is ethyl. In some embodiments, one or both of $R^1$ or $R^2$ is hydroxyl; for example, sometimes $R^1$ is hydroxyl. In certain embodiments, Z is substituted with one or more electron withdrawing groups.

In certain embodiments, Z is a pyridine ring substituted with one or more halogens, such as fluoro and/or chloro, and optionally further substituted; $R^a$ is H or methyl; and $R^1$ and $R^2$ are, independently, H, halogen, such as fluoro or chloro, hydroxyl, methyl, ethyl, methoxy, or ethoxy, provided that at least one of $R^1$ and $R^2$ is not H. In certain embodiments, one or both of $R^1$ or $R^2$ is methoxy; for example, sometimes $R^1$ is methoxy, sometimes $R^2$ is methoxy, and sometimes both $R^1$ and $R^2$ are methoxy. In certain embodiments, one or both of $R^1$ or $R^2$ is fluoro; for example, sometimes $R^1$ is fluoro, sometimes $R^2$ is fluoro, and sometimes both $R^1$ and $R^2$ are fluoro.

In certain embodiments, one or both of $R^1$ or $R^2$ is fluoro; for example, sometimes $R^1$ is fluoro, sometimes $R^2$ is fluoro, and sometimes both $R^1$ and R are fluoro. In certain embodiments, R is H. In certain embodiments, $R^1$ is hydroxyl. In certain embodiments, $R^1$ is methyl. In certain embodiments, $R^1$ is ethyl. In some embodiments, one or both of $R^1$ or $R^2$ is hydroxyl; for example, sometimes $R^1$ is hydroxyl. In certain embodiments, Z is substituted with one or more electron withdrawing groups.

In certain embodiments, Z is a substituted or unsubstituted aryl or heteroaryl ring; $R^a$ is H; and $R^1$ and $R^2$ are, independently, H, halogen, such as fluoro or chloro, hydroxyl, methyl, ethyl, methoxy, or ethoxy, provided that at least one of $R^1$ and $R^2$ is not H. In certain embodiments, one or both of $R^1$ or $R^2$ is methoxy; for example, sometimes $R^1$ is methoxy, sometimes $R^2$ is methoxy, and sometimes both $R^1$ and R are methoxy. In certain embodiments, $R^2$ is H. In certain embodiments, $R^1$ is hydroxyl. In certain embodiments, $R^1$ is methyl. In certain embodiments, $R^1$ is ethyl. In some embodiments, one or both of $R^1$ or $R^2$ is hydroxyl; for example, sometimes $R^1$ is hydroxyl. In certain embodiments, Z is substituted with one or more electron withdrawing groups.

In certain embodiments, suitable compounds of the present invention include those represented by Formula V:

Formula V

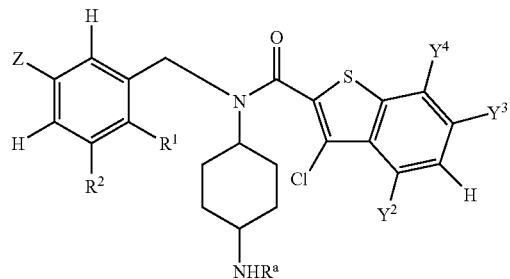

wherein, as valence and stability permit,
Z is a substituted or unsubstituted aryl or heteroaryl ring;
$R^a$ is H or methyl;
$R^1$ and $R^2$ are, independently, H, halogen, hydroxyl, lower alkyl, methoxy, or ethoxy, provided that at least one of $R^1$ and R is not H;
$Y^2$ and $Y^4$ are, independently, H or fluorine; and
$Y^3$ is H or fluorine.

In certain embodiments, suitable compounds of Formula V do not include one or more of the following compounds:

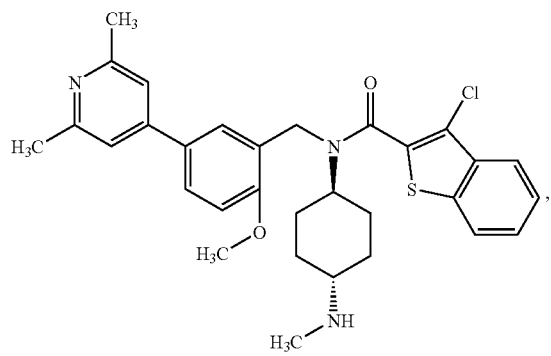

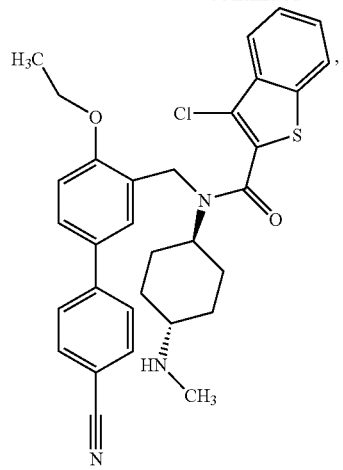

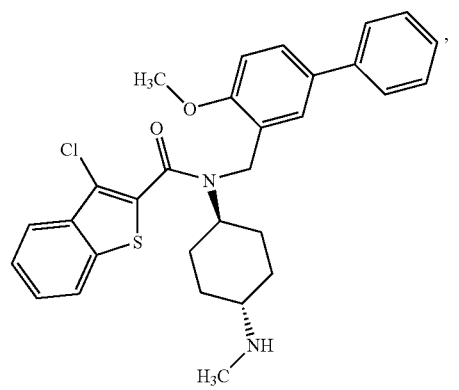

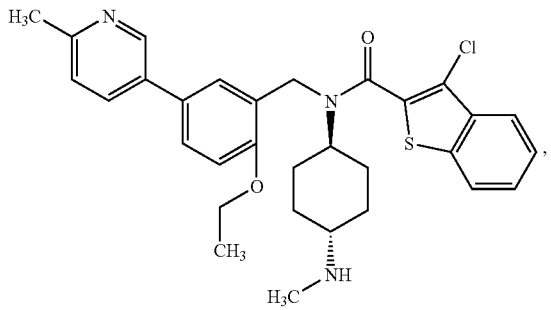

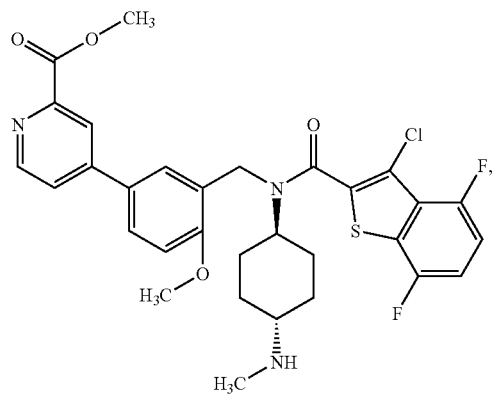

| 37 -continued | 38 -continued |
|---|---|
| 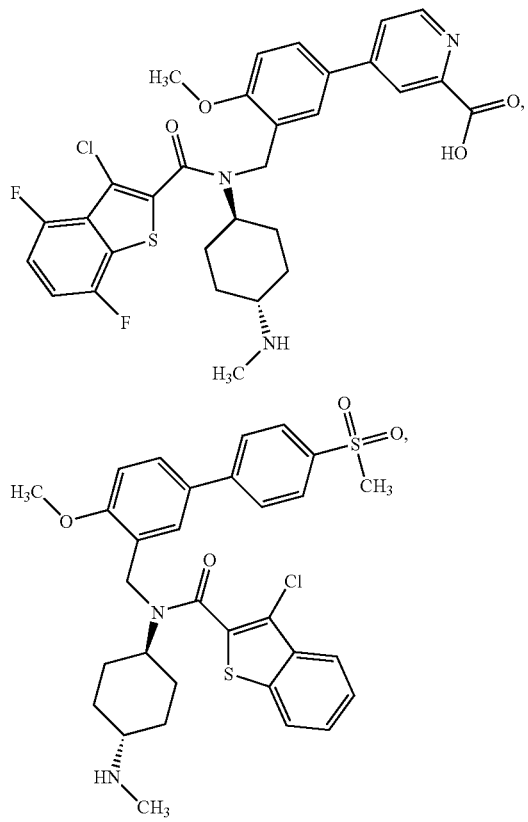 | 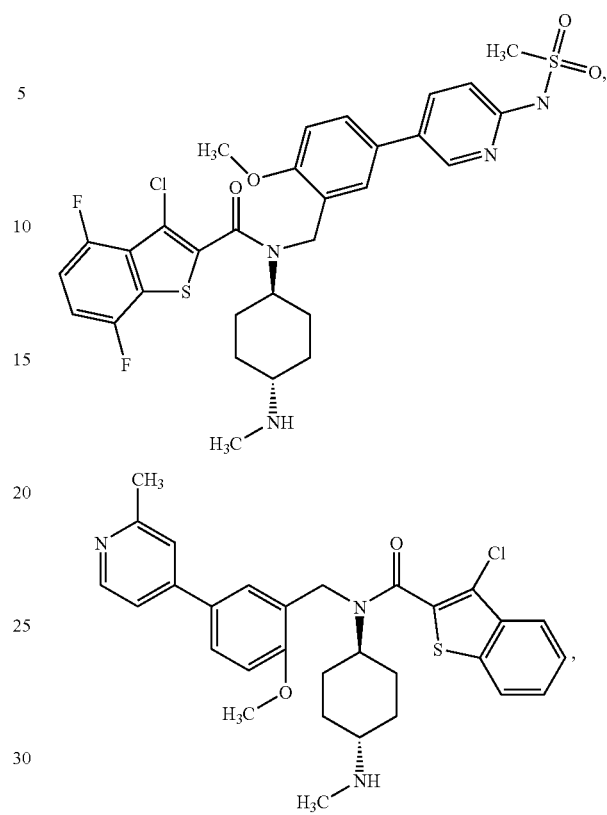 |
| 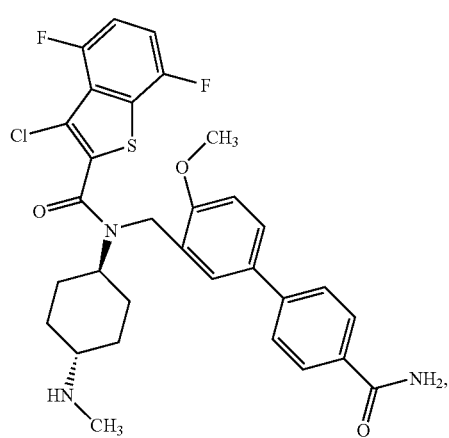 | 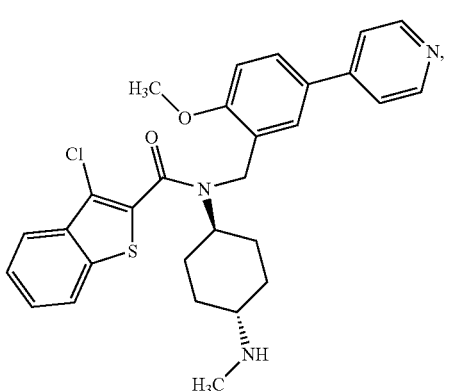 |
| 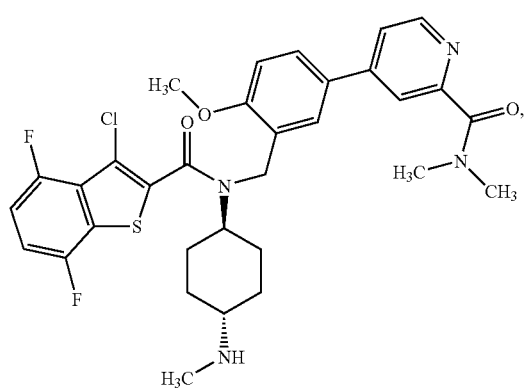 | 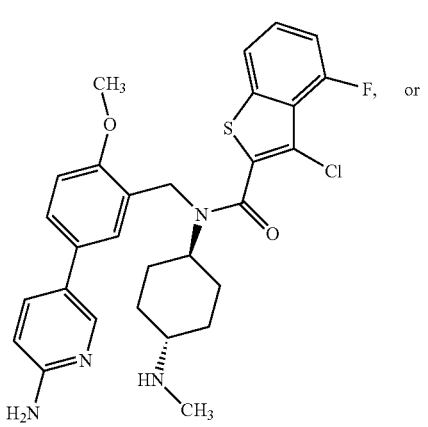 |

39
-continued
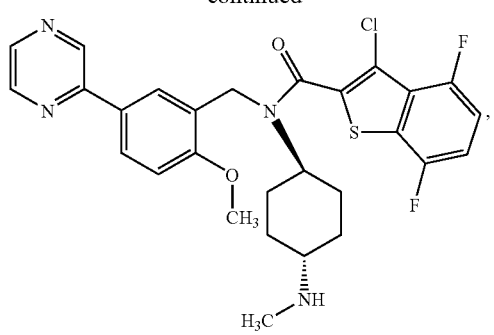
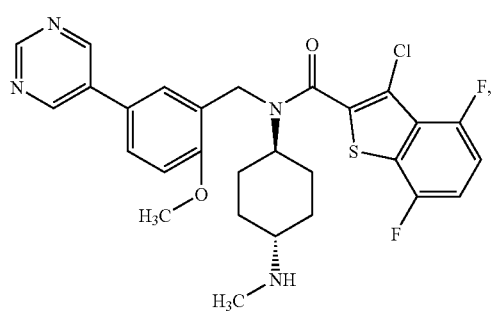
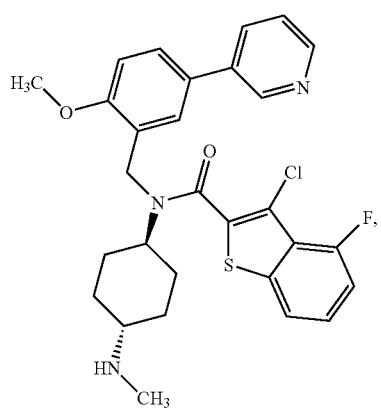
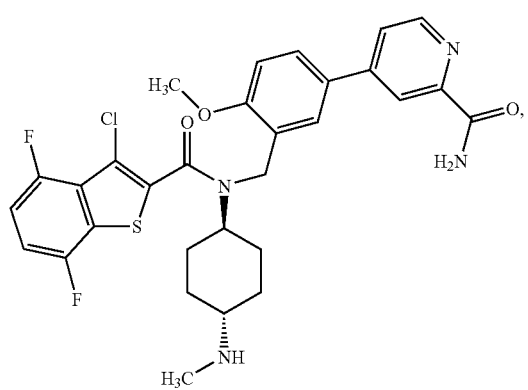
40
-continued
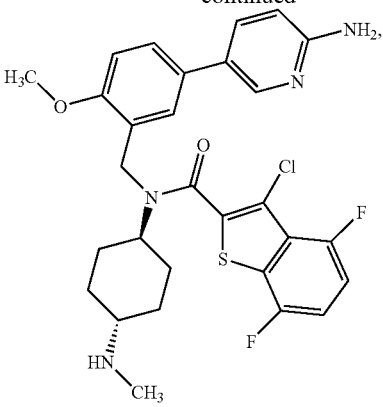
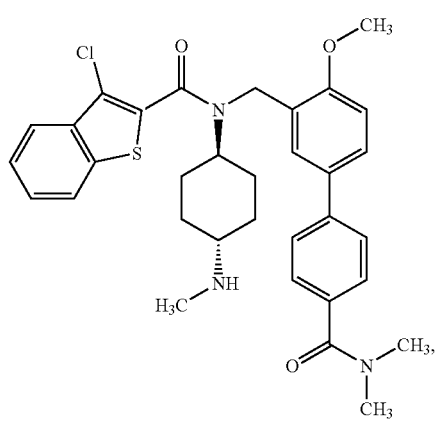
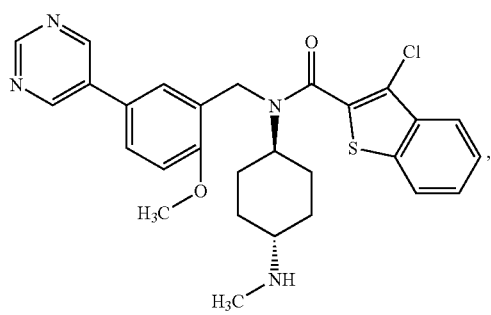
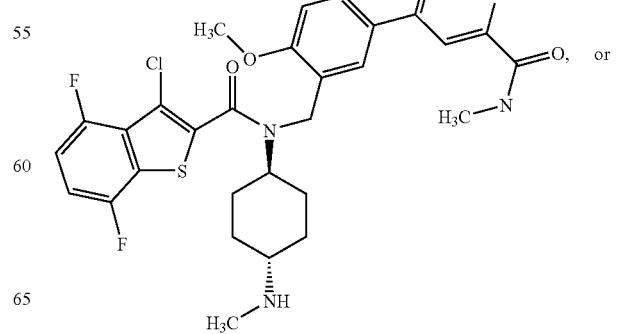
or

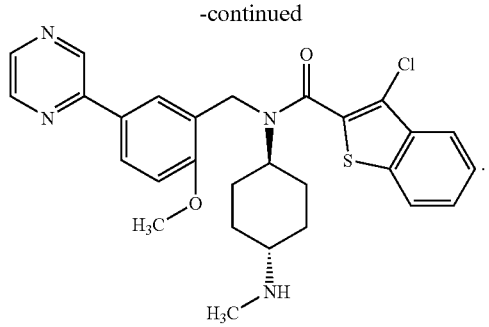
In other embodiments, suitable compounds of Formula V do include one or more of the above 22 compounds.
In certain embodiments, suitable compounds of Formula V do not include one or more of the following compounds:
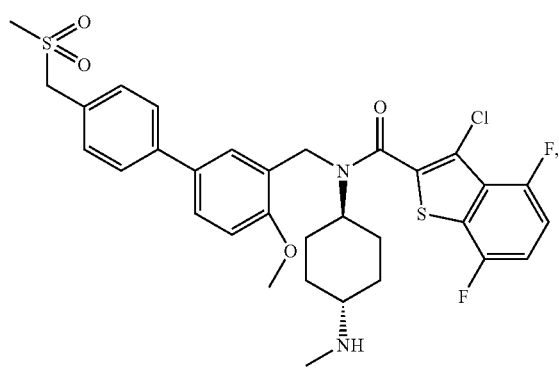
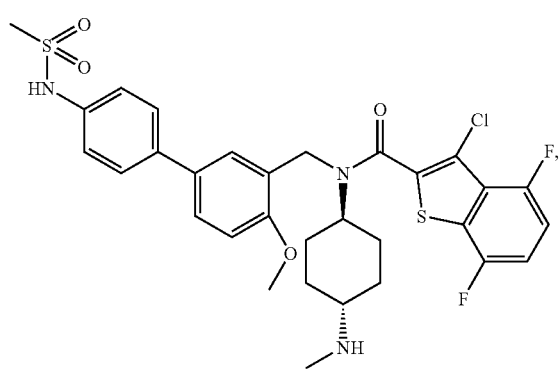
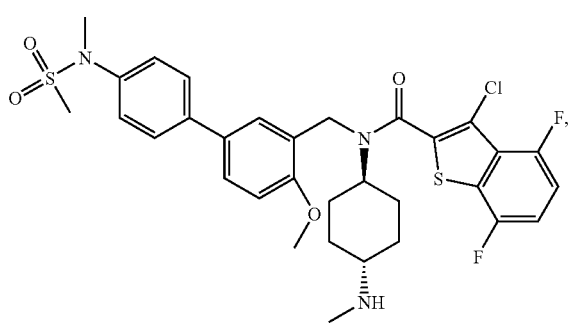
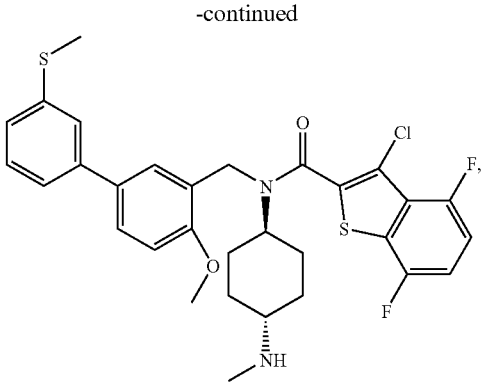
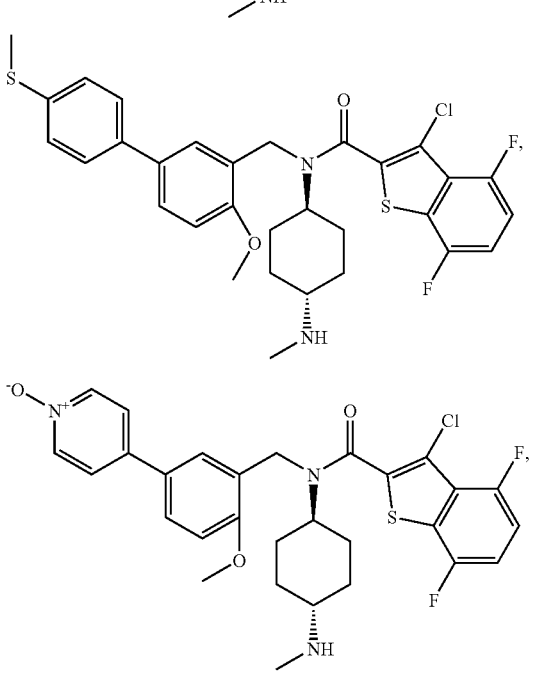
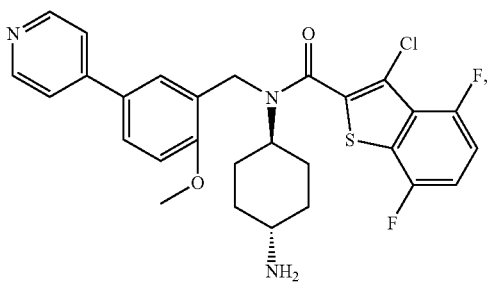
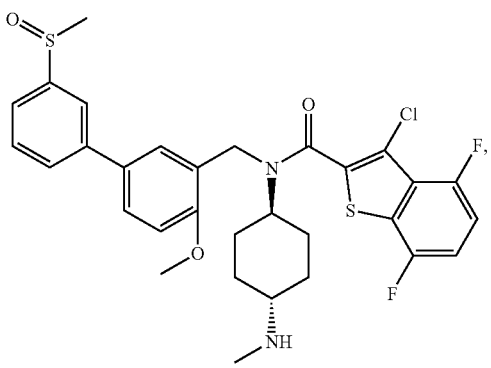

43
-continued
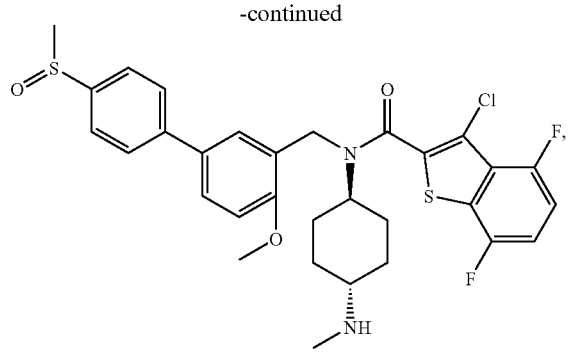
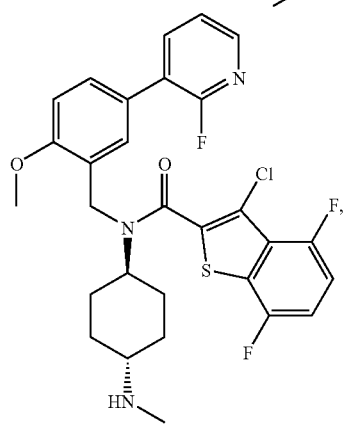

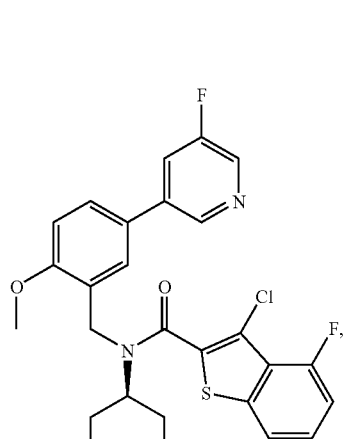
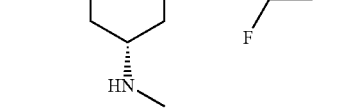
44
-continued
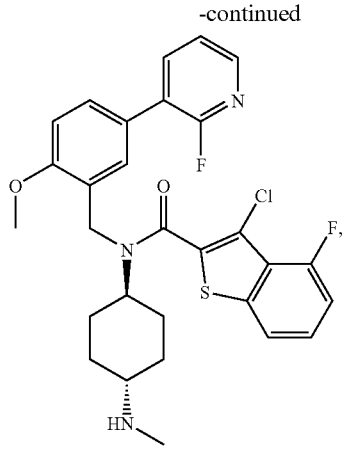
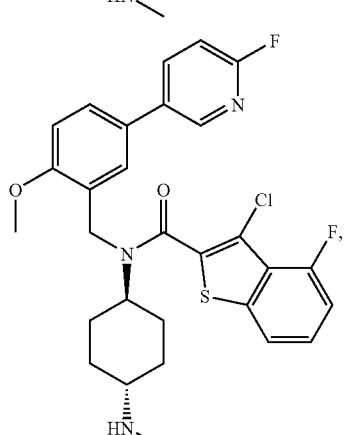
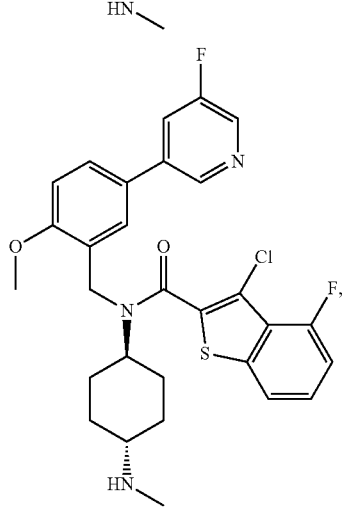
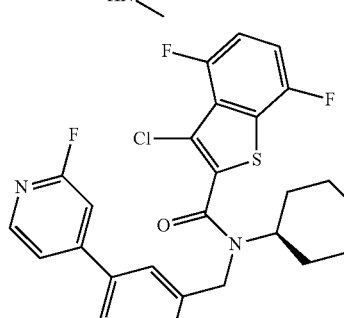

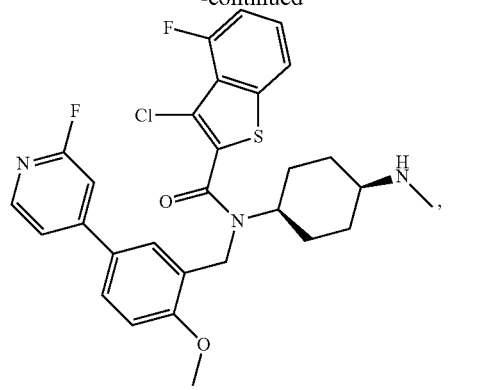
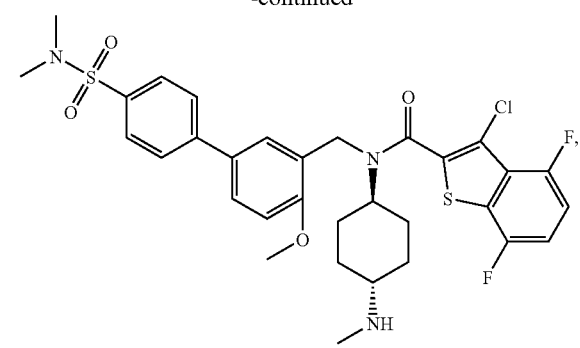
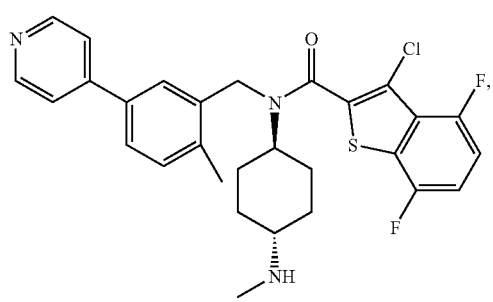
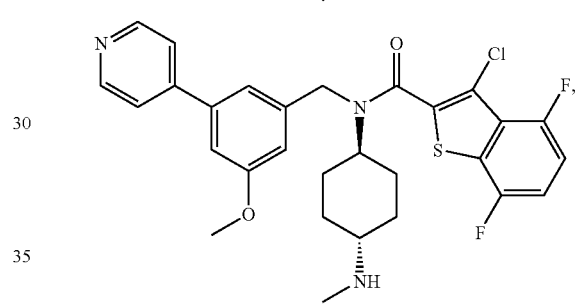
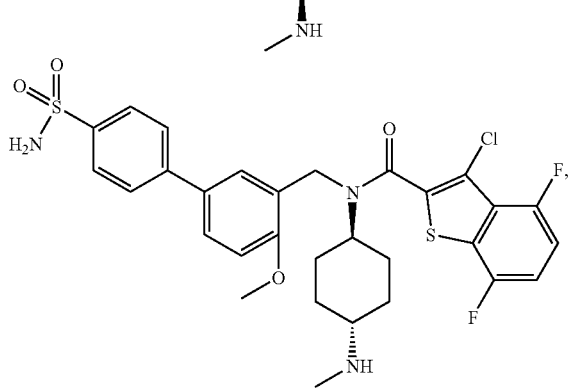
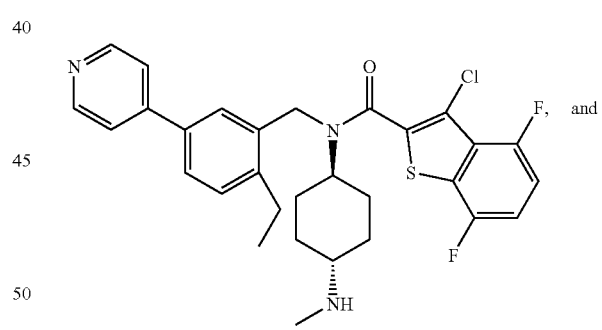
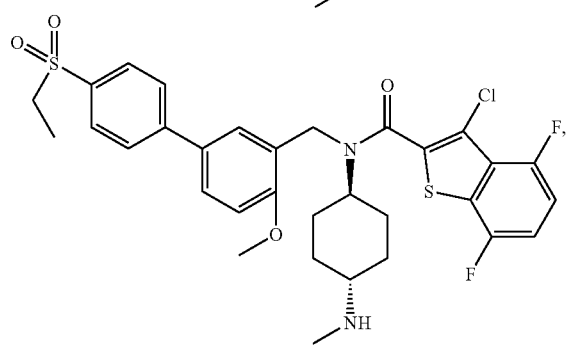
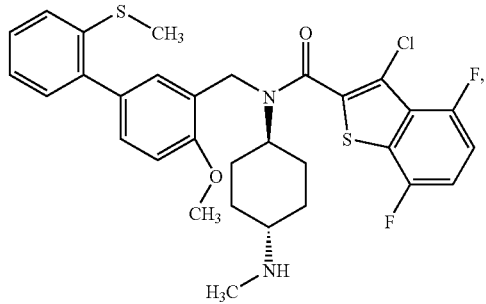

47
-continued
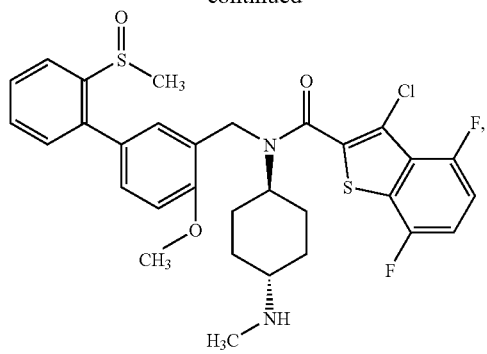
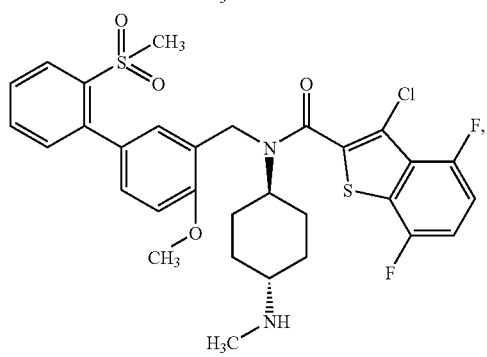
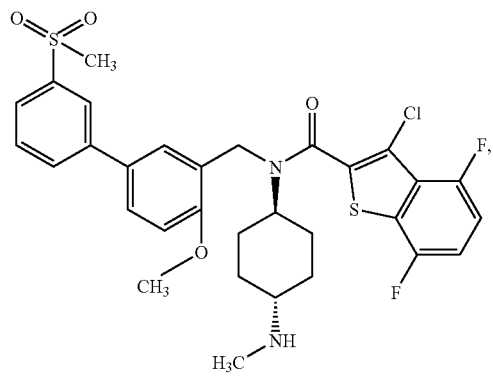
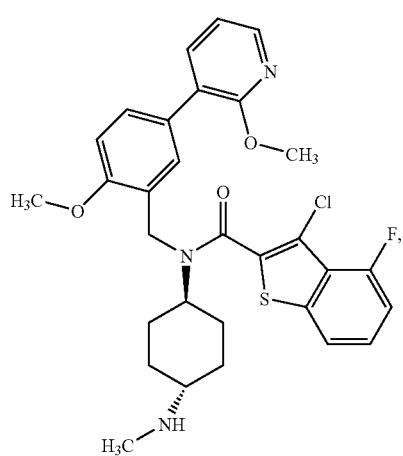
48
-continued
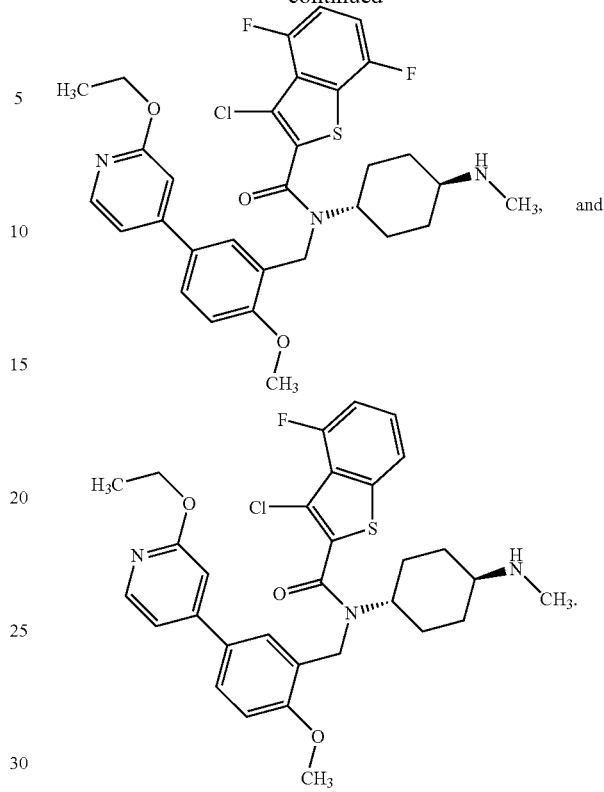
In other embodiments, suitable compounds of Formula V do include one or more of the above 32 compounds.
In certain embodiments, suitable compounds of Formula V do not include one or more of the following compounds:
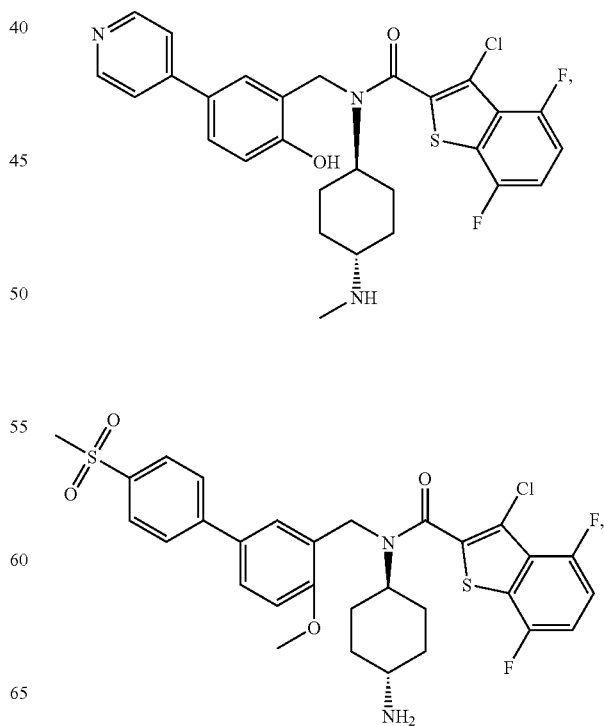

-continued

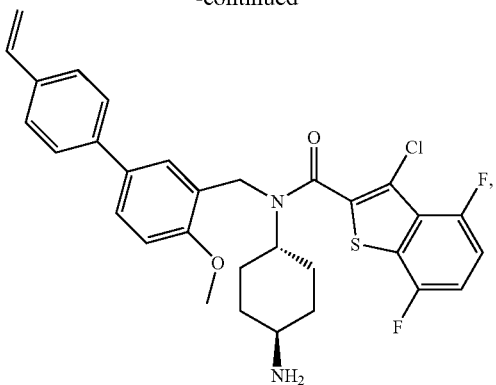

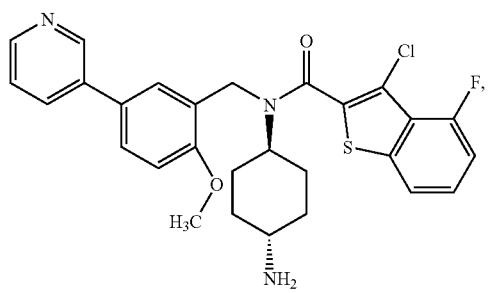

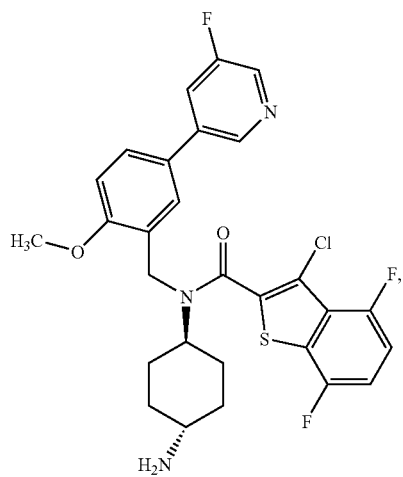

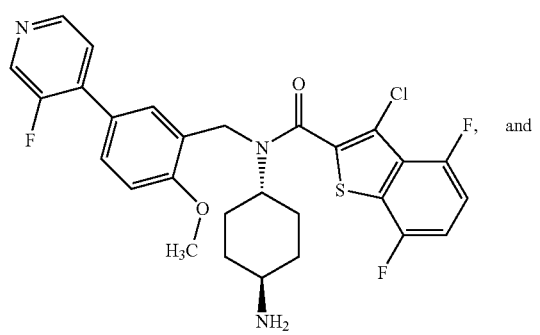

and

-continued

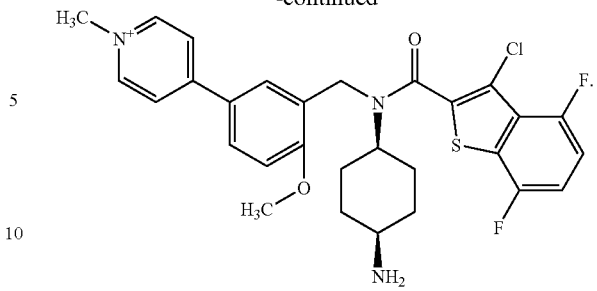

In other embodiments, suitable compounds of Formula V do include one or more of the above 7 compounds.

In certain embodiments, the two nitrogen atoms bonded to the cyclohexane ring depicted in Formula V are in a trans relationship. In other embodiments, these two nitrogen atoms are in a cis relationship. In some embodiments, the stereochemical relationship between these two nitrogens is undefined, e.g., there is a mixture of cis and trans isomers.

In certain embodiments, $R^a$ is methyl. In other embodiments, $R^a$ is H.

In some embodiments, at least one of $Y^2$ or $Y^4$ is F. For example, sometimes $Y^2$ is F and $Y^4$ is not. Other times $Y^4$ is F and $Y^2$ is not. In some instances, both $Y^2$ and $Y^4$ are F. In other embodiments, neither $Y^2$ or $Y^4$ is F.

In some embodiments, Z is a substituted or unsubstituted aryl ring, such as a phenyl ring.

In other embodiments, Z is a substituted or unsubstituted heteroaryl ring, such as a substituted or unsubstituted pyridine, pyrimidine, pyrazine, pyridazine, triazine, tetrazine, pyrrole, pyrazole, or imidazole ring or N-oxide thereof. In specific embodiments, Z is a substituted or unsubstituted pyridine, or pyrazine ring or N-oxide thereof, particularly a substituted or unsubstituted pyridine ring or N-oxide thereof.

In some examples, Z is a substituted or unsubstituted pyridine ring or N-oxide thereof where connection of the pyridine ring to the phenyl ring bearing $R^1$ and $R^2$ may occur at any location on the pyridine ring, for example, at a 2-, 3-, or 4-position relative to the nitrogen of the pyridine ring, i.e., at an ortho-, meta-, or para-position relative to the nitrogen of the pyridine ring. In certain embodiments, Z is a substituted or unsubstituted pyridine N-oxide.

In other embodiments, Z is a substituted or unsubstituted pyrimidine ring or N-oxide thereof where connection of the pyrimidine ring to the phenyl ring bearing $R^1$ and $R^2$ may occur at any location on the pyrimidine ring, for example, at a 2-, 3-, 4-, 5-, or 6-position relative to N1 of the pyrimidine ring.

In some embodiments, Z is unsubstituted. In other embodiments, Z is substituted with one or more groups selected from halogen, lower alkyl, lower alkenyl, —CN, azido, —$NR^xR^x$, —$CO_2OR^x$, —$C(O)$—$NR^xR^x$, —$C(O)$—$R^x$, —$NR^x$—C(O)—$R^x$, —$NR^xSO_2R^x$, —$SR^x$, —$S(O)R^x$, —$SO_2R^x$, —$SO_2NR^xR^x$, —$(C(R^x)_2)_n$—$OR^x$, —$(C(R^x)_2)_n$—$NR^xR^x$, and —$(C(R^x)_2)_n$—$SO_2R^x$; wherein $R^x$ are, independently for each occurrence, H or lower alkyl; and n is, independently for each occurrence, an integer from 0 to 2. For example, in some embodiments, Z is substituted with halogen, such as fluoro.

In certain embodiments, Z is substituted with one or more electron withdrawing groups. For example, sometimes Z is substituted with one or more groups selected from halogen, —CN, azido, —$CO_2OR^x$, —$C(O)$—$NR^xR^x$, and $C(O)$—$R^x$.

Combinations of the various values for Z are contemplated. In some instances, suitable compounds include those where Z is a pyridine ring or N-oxide thereof and Z is substituted by fluoro at any carbon position on the pyridine ring, such as a 2-, 3-, or 4-position relative to the nitrogen of the pyridine ring.

In certain embodiments, Z is a substituted or unsubstituted aryl or heteroaryl ring; $R^a$ is methyl; $R^1$ is halogen, such as fluoro or chloro, methoxy, or ethoxy; $R^2$ is H; $Y^2$ and $Y^4$ are, independently, H or fluoro; and $Y^3$ is H or fluoro. In some embodiments, $R^1$ is methoxy. In other embodiments, $R^1$ is fluoro. In some instances, $R^1$ is ethoxy. In some instances, Z is not a substituted or unsubstituted pyridine N-oxide ring or a pyridine ring substituted with one or more halogens. In certain embodiments, Z is substituted with one or more electron withdrawing groups.

In certain embodiments, Z is a substituted or unsubstituted aryl or heteroaryl ring; $R^a$ is H or methyl; $R^1$ is H; $R^2$ is halogen, such as fluoro or chloro, hydroxyl, methyl, ethyl, methoxy, or ethoxy; $Y^2$ and $Y^4$ are, independently, H or fluoro; and $Y^3$ is H or fluoro. In some embodiments, $R^2$ is methoxy. In certain embodiments, $R^a$ is methyl. In certain embodiments, Z is substituted with one or more electron withdrawing groups.

In certain embodiments, Z is a substituted or unsubstituted aryl or heteroaryl ring; $R^a$ is H or methyl; $R^1$ is hydroxyl, methyl, or ethyl; $R^2$ is H, halogen, such as fluoro or chloro, hydroxyl, methyl, ethyl, methoxy, or ethoxy; $Y^2$ and $Y^4$ are, independently, H or fluoro; and $Y^3$ is H or fluoro. In certain embodiments, $R^a$ is methyl. In certain embodiments, $R^2$ is H. In certain embodiments, $R^1$ is hydroxyl. In certain embodiments, $R^1$ is methyl. In certain embodiments, $R^1$ is ethyl. In some embodiments, one or both of $R^1$ or $R^2$ is hydroxyl; for example, sometimes $R^1$ is hydroxyl. In certain embodiments, Z is substituted with one or more electron withdrawing groups.

In certain embodiments, Z is a substituted or unsubstituted pyridine N-oxide ring; $R^a$ is H or methyl; $R^1$ and $R^2$ are, independently, H, halogen, such as fluoro or chloro, hydroxyl, methyl, ethyl, methoxy, or ethoxy, provided that at least one of $R^1$ and $R^2$ is not H; $Y^2$ and $Y^4$ are, independently, H or fluoro; and $Y^3$ is H or fluoro. In certain embodiments, one or both of $R^1$ or $R^2$ is methoxy; for example, sometimes $R^1$ is methoxy, sometimes $R^2$ is methoxy, and sometimes both $R^1$ and $R^2$ are methoxy. In certain embodiments, one or both of $R^1$ or $R^2$ is fluoro; for example, sometimes $R^1$ is fluoro, sometimes $R^2$ is fluoro, and sometimes both $R^1$ and $R^2$ are fluoro. In certain embodiments, $R^2$ is H. In certain embodiments, $R^1$ is hydroxyl. In certain embodiments, $R^1$ is methyl. In certain embodiments, $R^1$ is ethyl. In some embodiments, one or both of $R^1$ or $R^2$ is hydroxyl; for example, sometimes $R^1$ is hydroxyl. In certain embodiments, Z is substituted with one or more electron withdrawing groups.

In certain embodiments, Z is a pyridine ring substituted with one or more halogens, such as fluoro and/or chloro, and optionally further substituted; $R^a$ is H or methyl; $R^1$ and $R^2$ are, independently, H, halogen, such as fluoro or chloro, hydroxyl, methyl, ethyl, methoxy, or ethoxy, provided that at least one of $R^1$ and R is not H; $Y^2$ and $Y^4$ are, independently, H or fluoro; and $Y^3$ is H or fluoro. In certain embodiments, one or both of $R^1$ or R is methoxy; for example, sometimes R is methoxy, sometimes $R^2$ is methoxy, and sometimes both $R^1$ and $R^2$ are methoxy. In certain embodiments, one or both of $R^1$ or R is fluoro; for example, sometimes $R^1$ is fluoro, sometimes $R^2$ is fluoro, and sometimes both $R^1$ and $R^2$ are fluoro. In certain embodiments, one or both of $R^1$ or $R^2$ is fluoro; for example, sometimes $R^1$ is fluoro, sometimes $R^2$ is fluoro, and sometimes both $R^1$ and $R^2$ are fluoro. In certain embodiments, $R^2$ is H. In certain embodiments, $R^1$ is hydroxyl. In certain embodiments, $R^1$ is methyl. In certain embodiments, $R^1$ is ethyl. In some embodiments, one or both of $R^1$ or $R^2$ is hydroxyl; for example, sometimes $R^1$ is hydroxyl. In certain embodiments, Z is substituted with one or more electron withdrawing groups.

In certain embodiments, Z is a substituted or unsubstituted aryl or heteroaryl ring; $R^a$ is H; $R^1$ and $R^2$ are, independently, H, halogen, such as fluoro or chloro, hydroxyl, methyl, ethyl, methoxy, or ethoxy, provided that at least one of $R^1$ and $R^2$ is not H; $Y^2$ and $Y^4$ are, independently, H or fluoro; and $Y^3$ is H or fluoro. In certain embodiments, one or both of $R^1$ or $R^2$ is methoxy; for example, sometimes $R^1$ is methoxy, sometimes R is methoxy, and sometimes both $R^1$ and $R^2$ are methoxy. In certain embodiments, $R^2$ is H. In certain embodiments, $R^1$ is hydroxyl. In certain embodiments, $R^1$ is methyl. In certain embodiments, $R^1$ is ethyl. In some embodiments, one or both of $R^1$ or $R^2$ is hydroxyl; for example, sometimes $R^1$ is hydroxyl. In certain embodiments, Z is substituted with one or more electron withdrawing groups.

Moreover, all various combinations of the above definitions for variables M, X, Y, $Y^2$, $Y^3$, $Y^4$, Z, Cy, Cy', i, k, $R^1$, $R^2$, R, $R^a$, $R^x$, etc. recited herein are contemplated. Thus, although one or more combinations of the above variables may not be explicitly recited herein as a discrete combination, the present invention includes such combinations.

The following compounds, while not intended to be limiting, are examples of compounds which are within the scope of Formulae I-V and which may be useful in certain embodiments of the present invention:

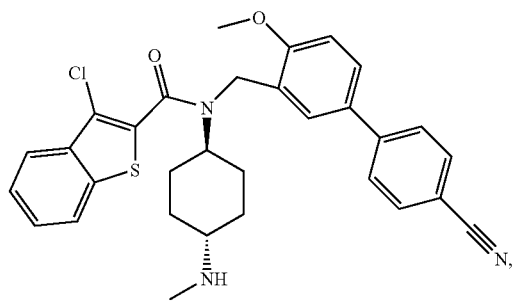

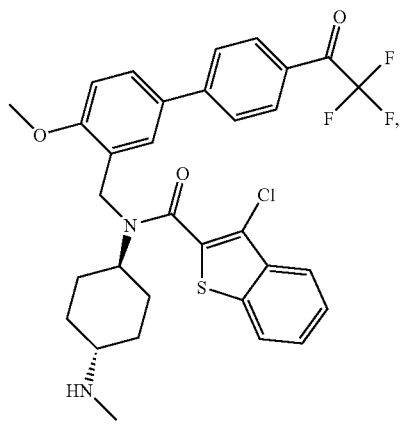

53
-continued
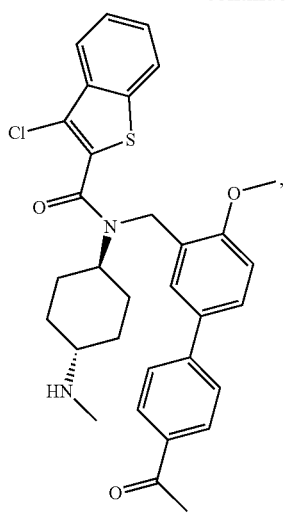
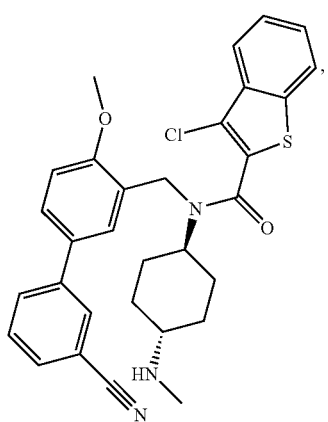
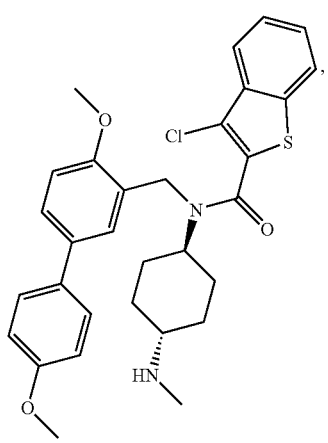
54
-continued
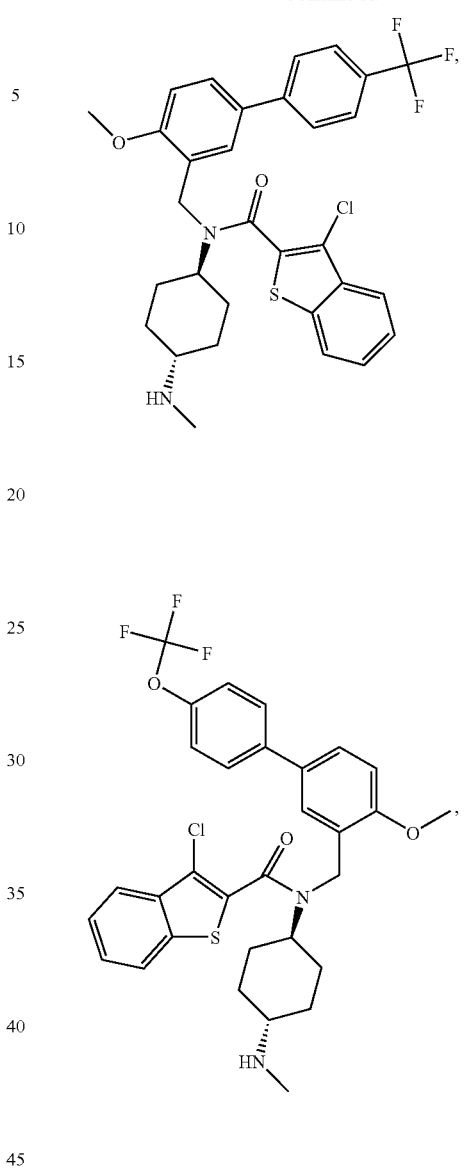

55
-continued
56
-continued
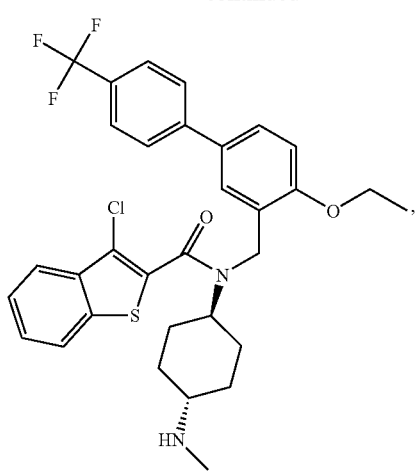
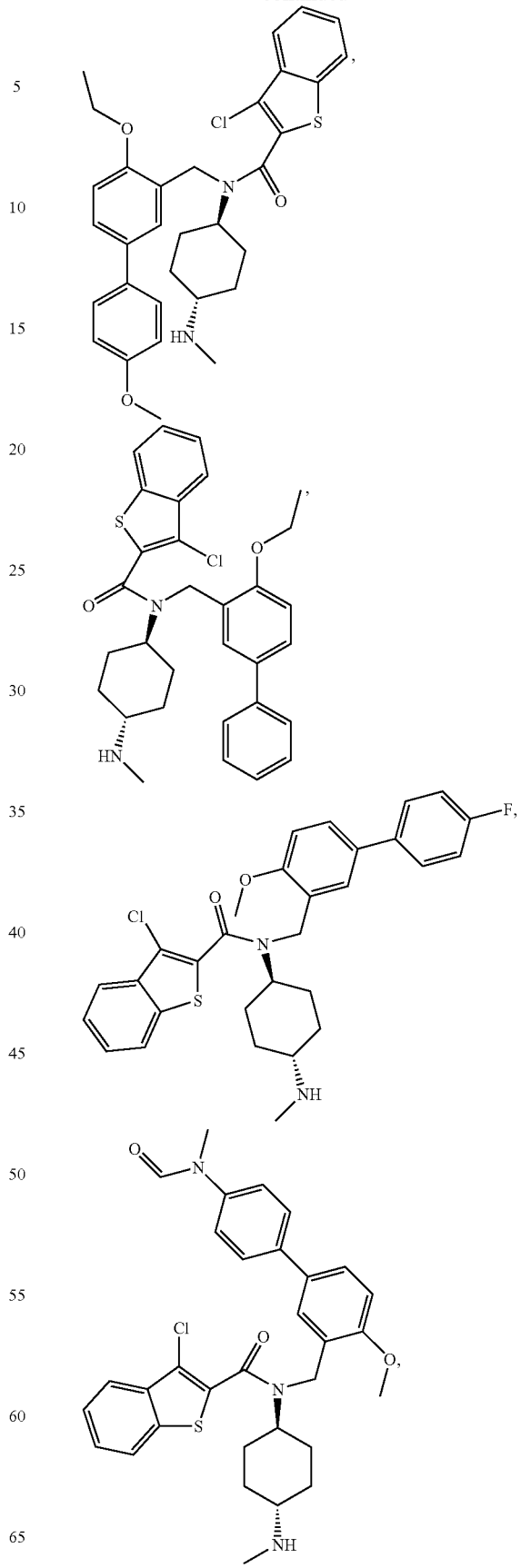

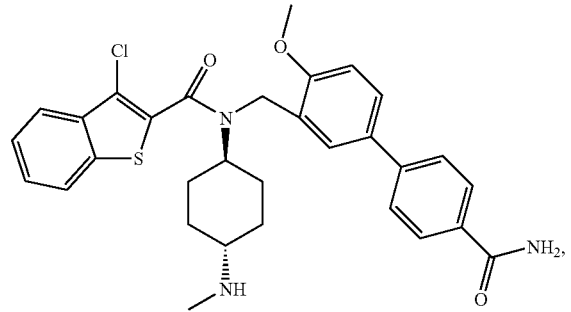
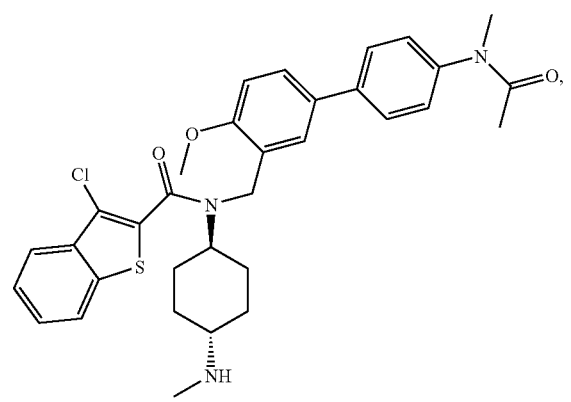
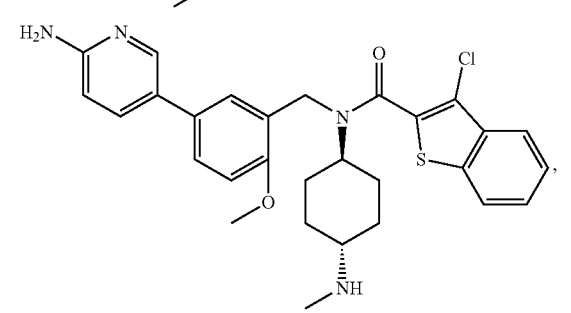
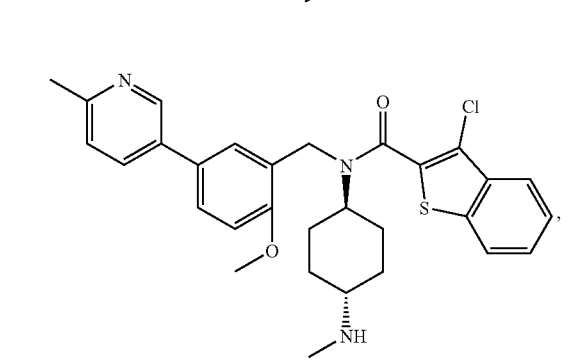
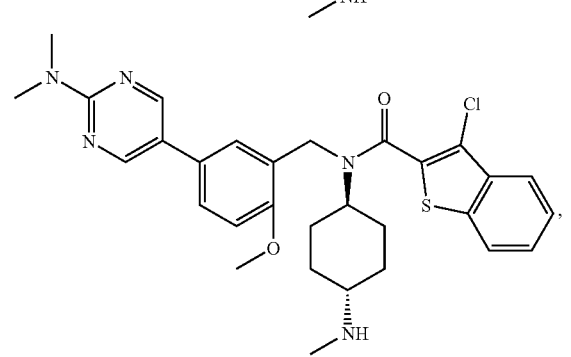
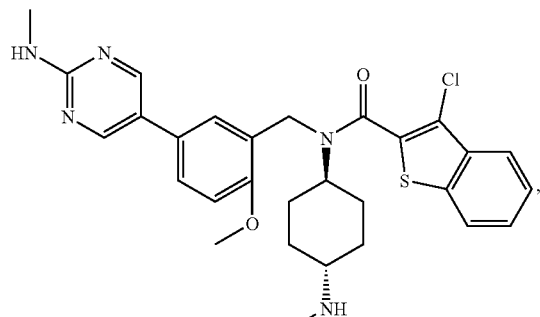
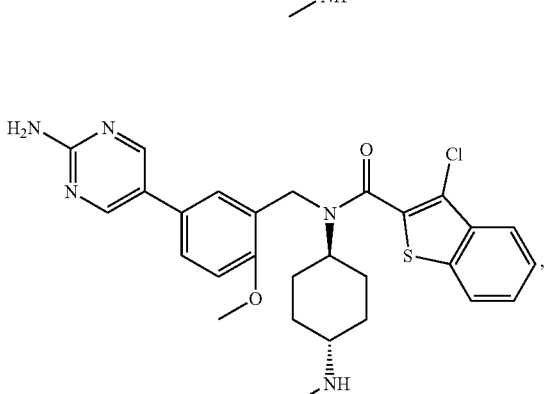
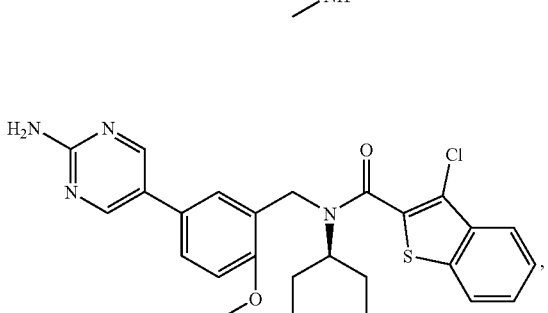
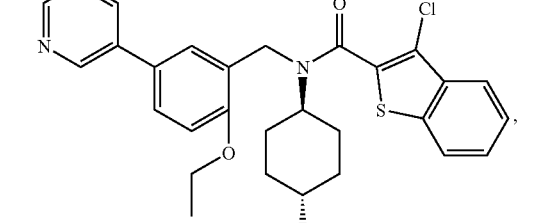
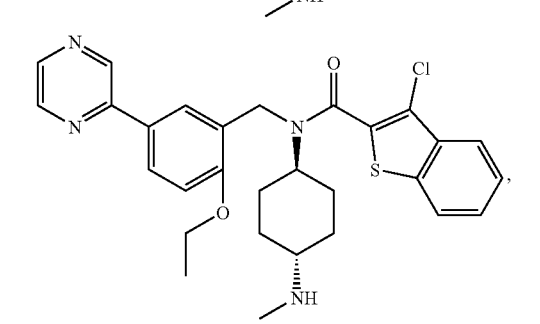

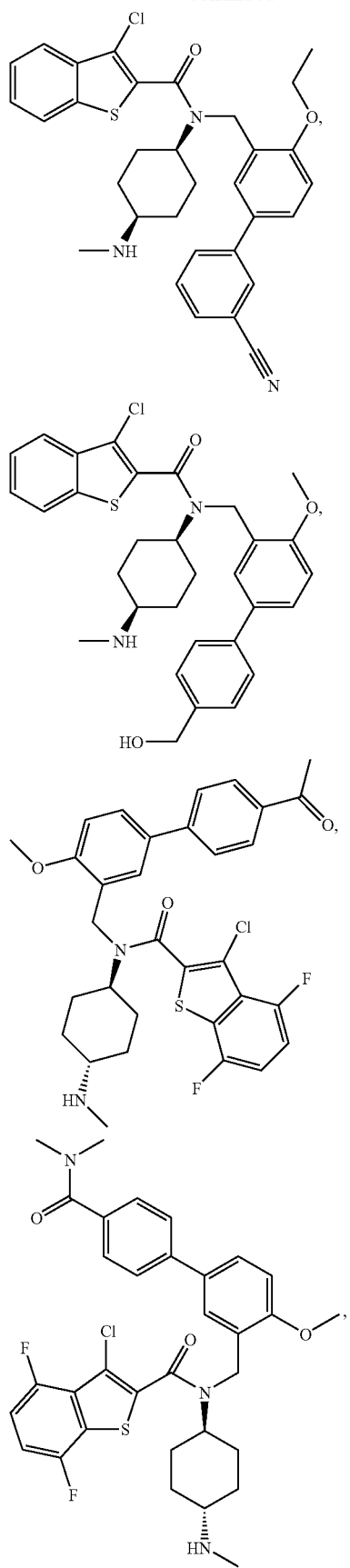
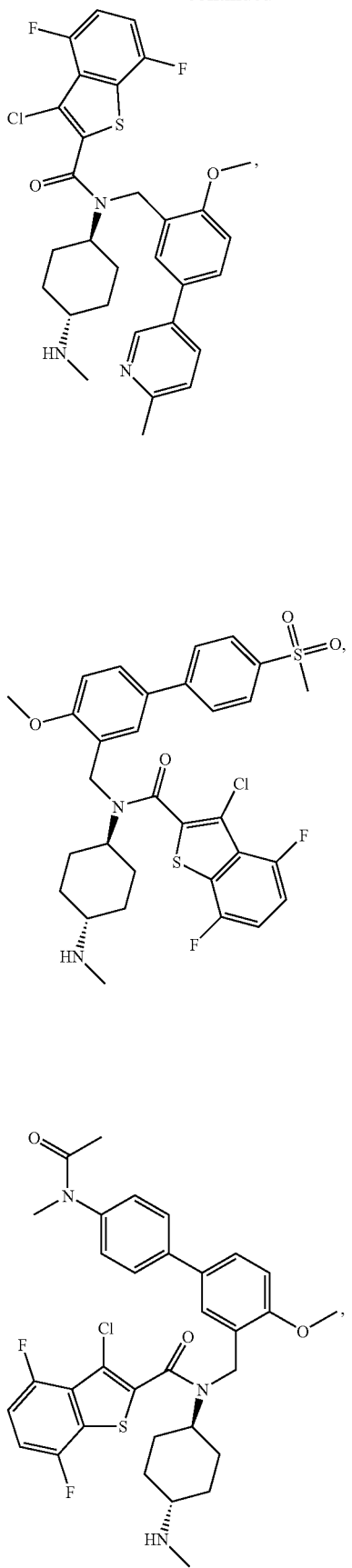

61
-continued
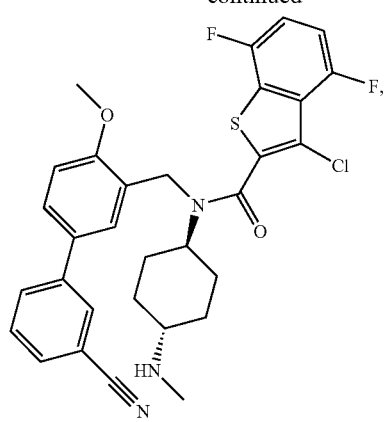
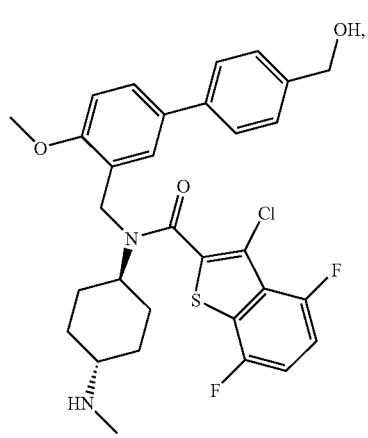
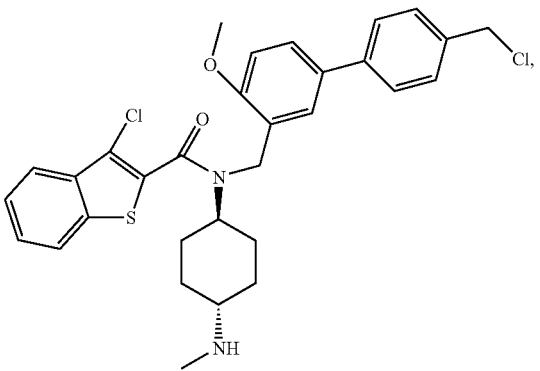
62
-continued
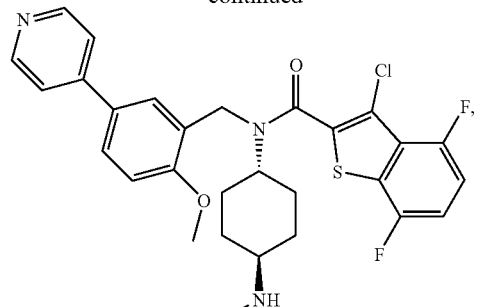
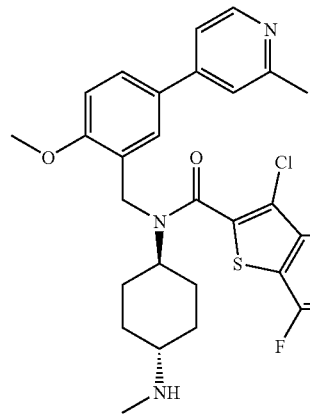
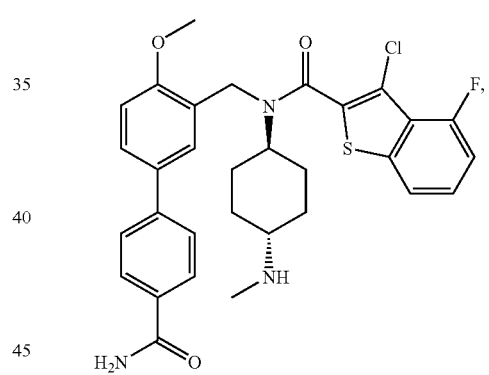
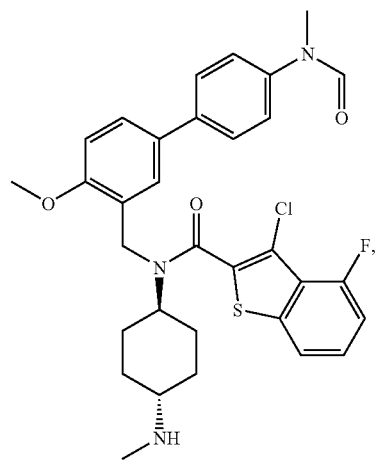

63
-continued
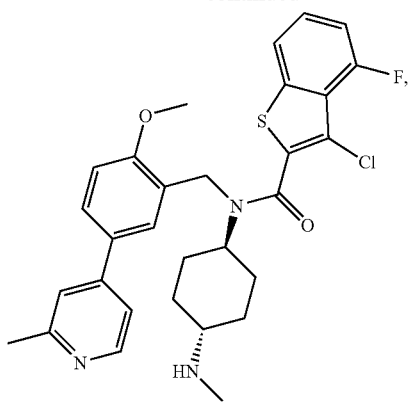
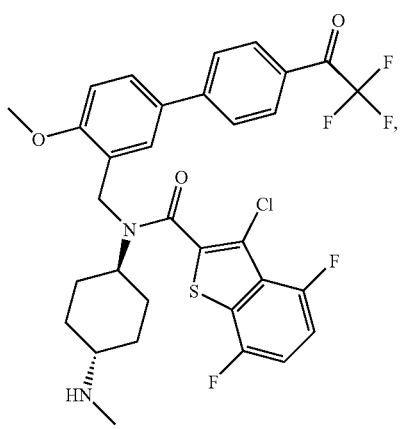
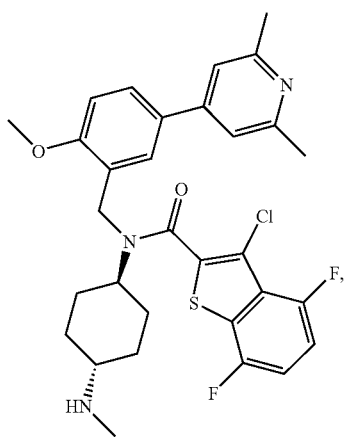
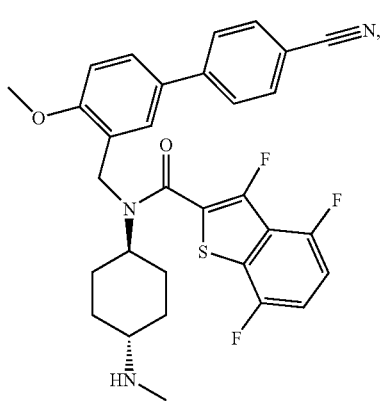
64
-continued
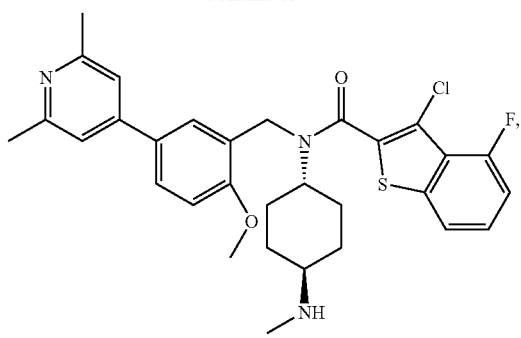
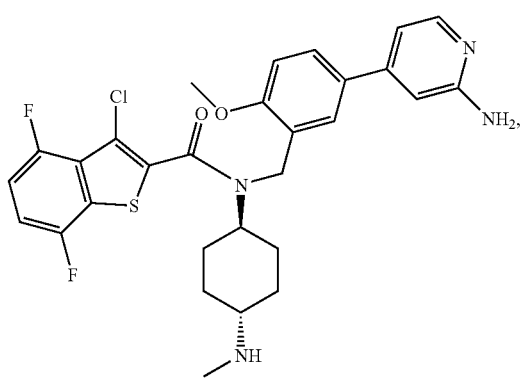
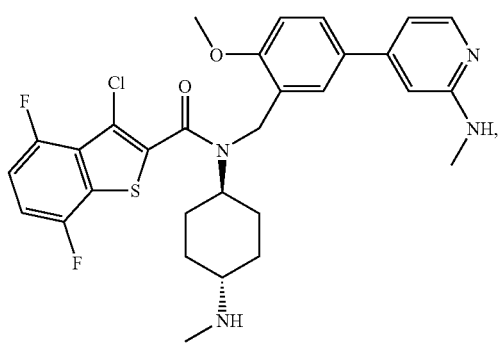
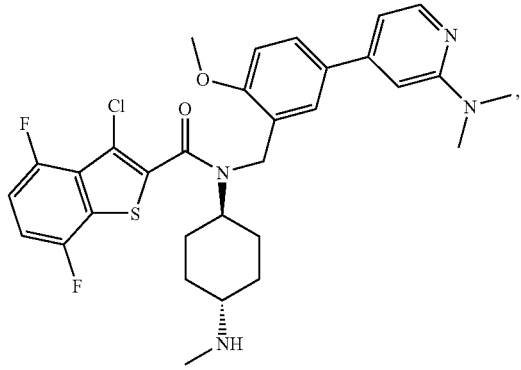

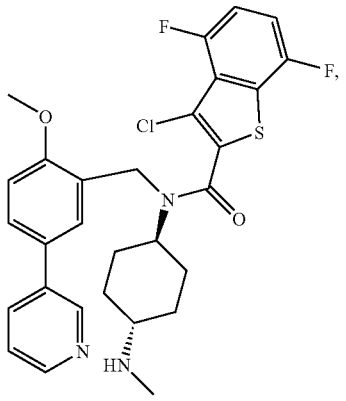
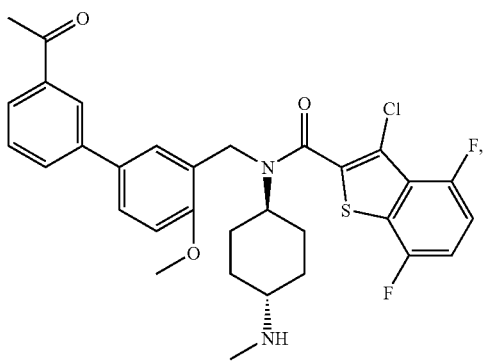
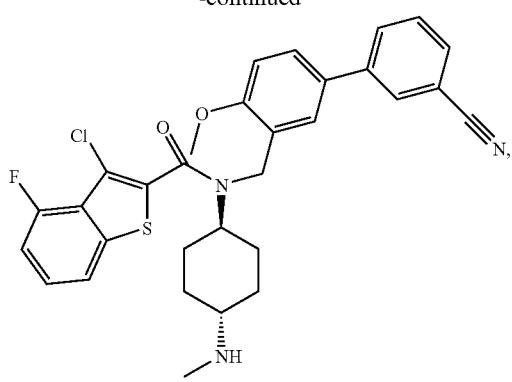
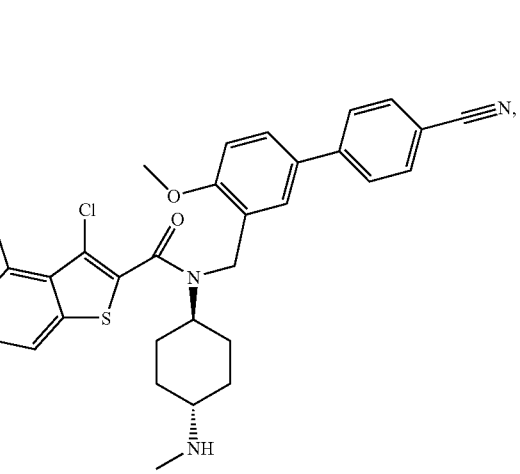
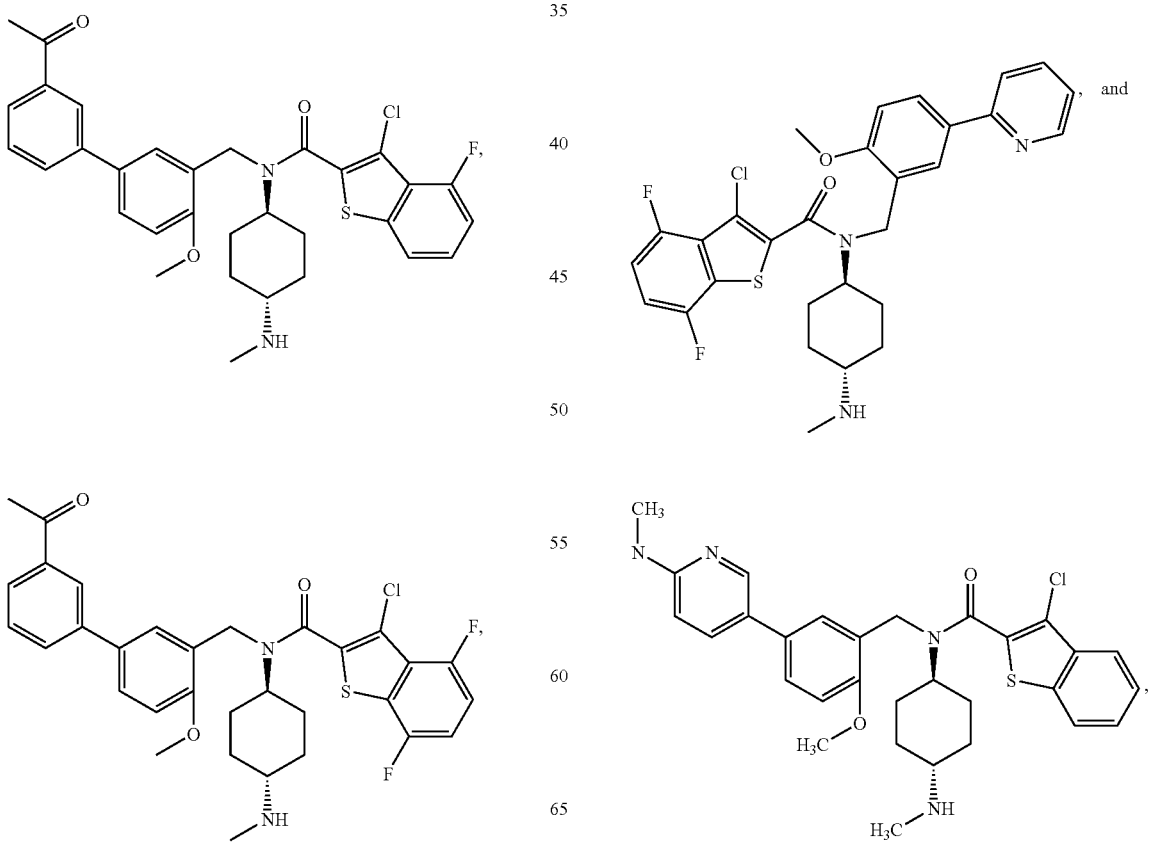
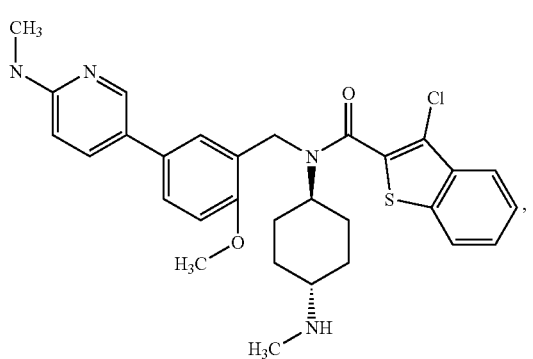

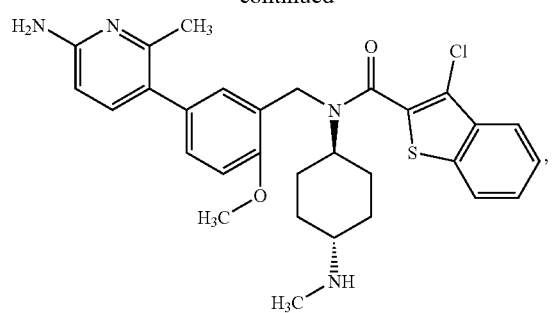
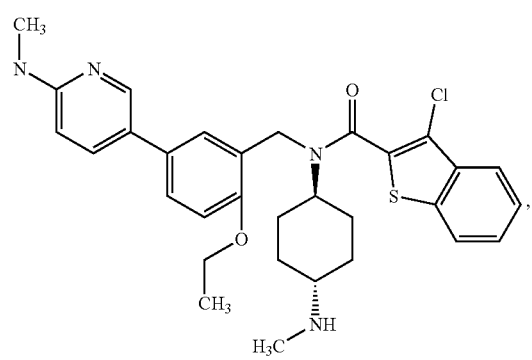
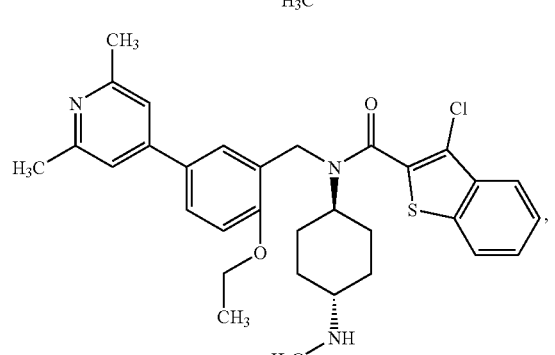
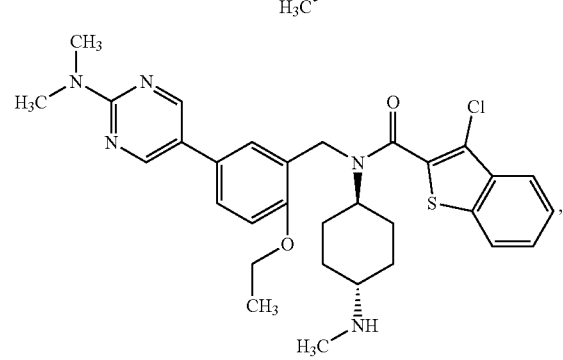
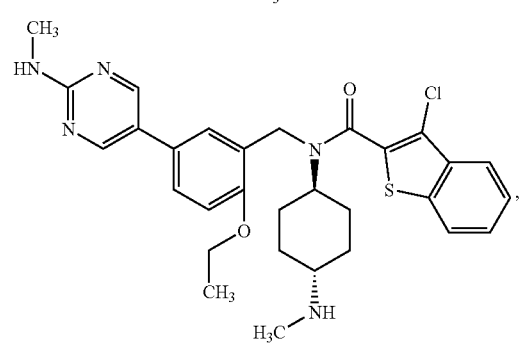
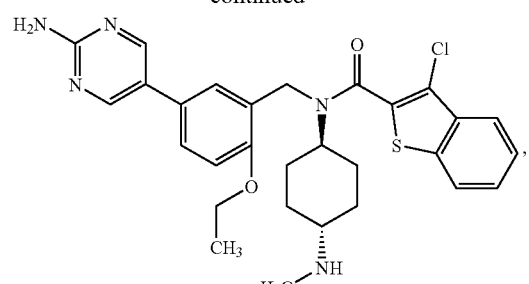
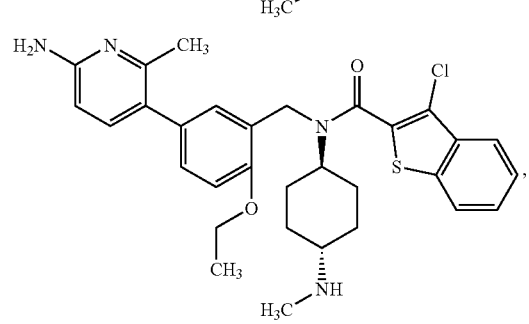
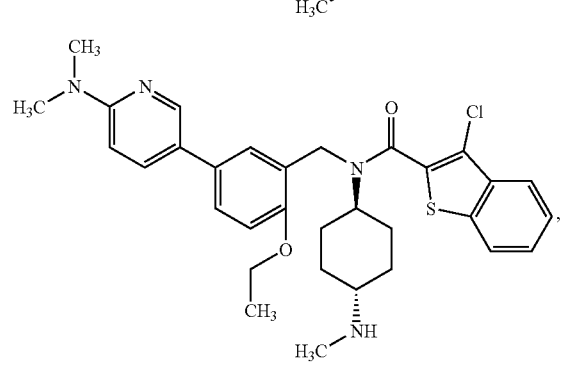
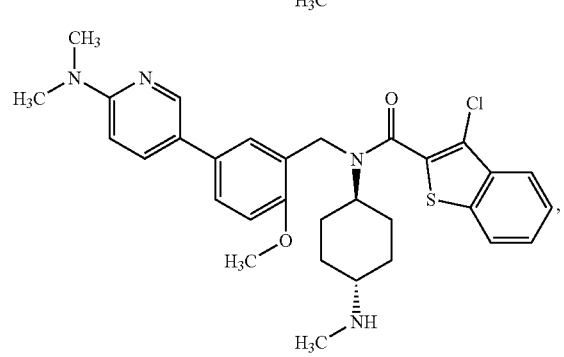
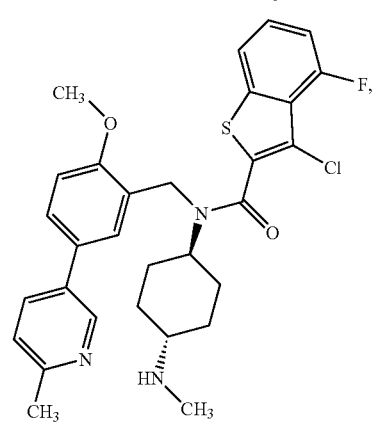

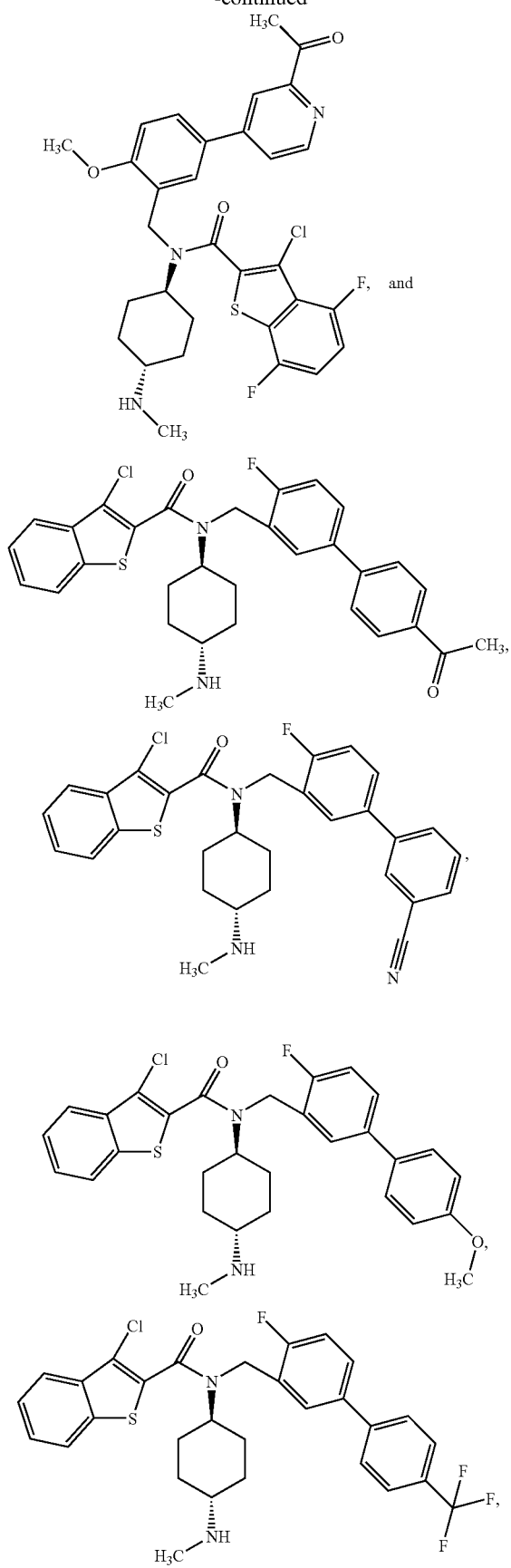
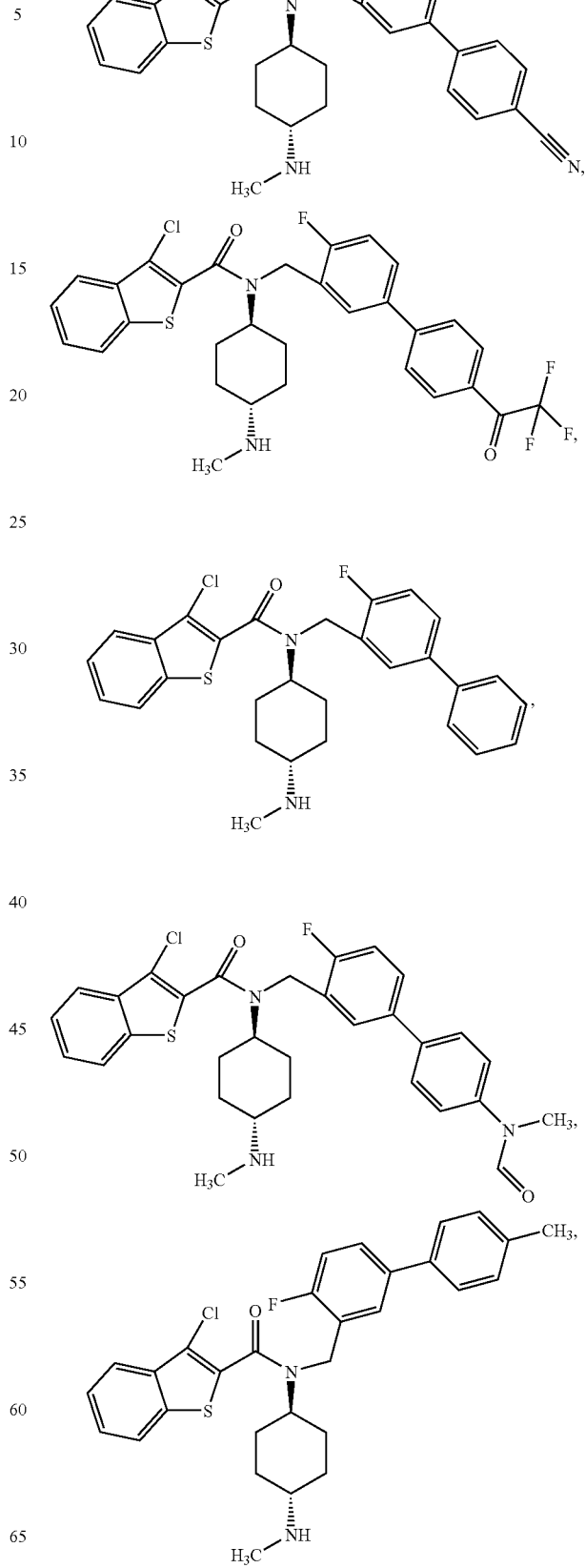

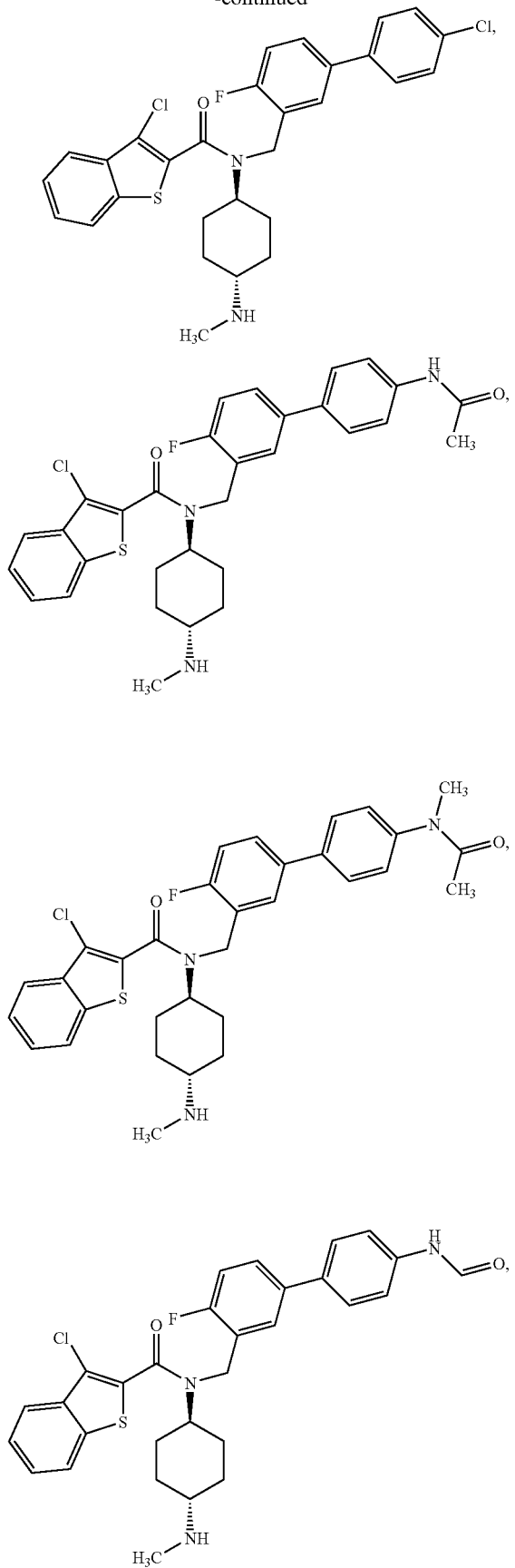
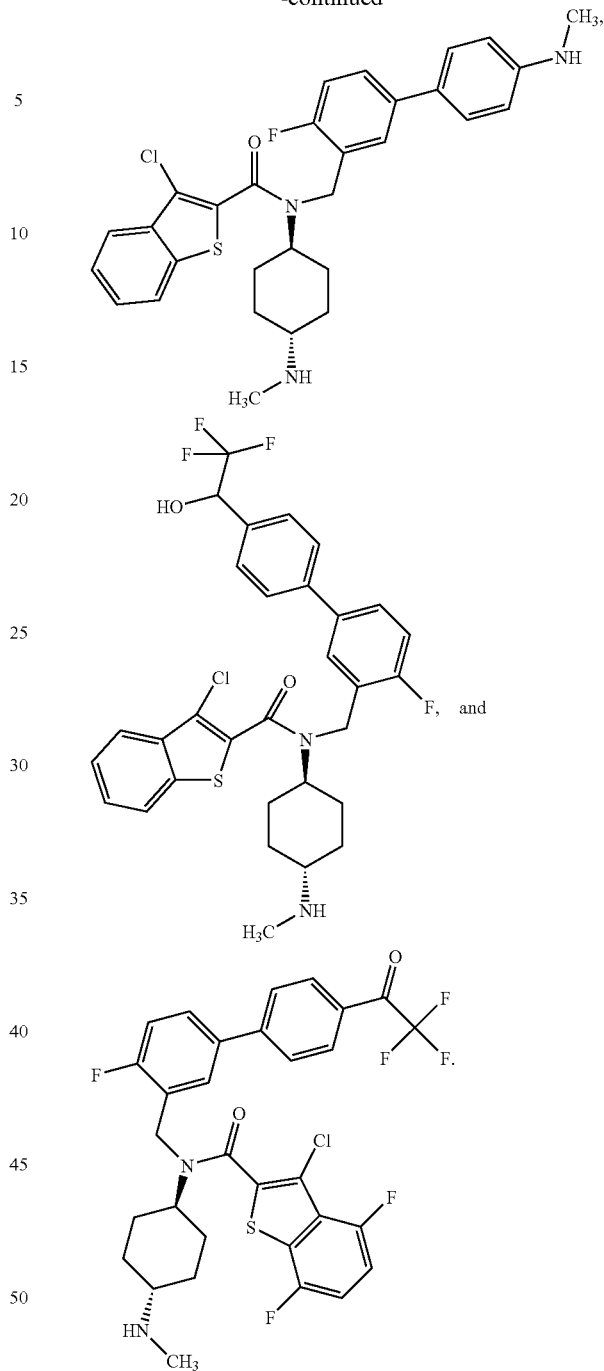

In certain embodiments, suitable compounds of Formulas I-V do not include one or more of the above compounds.

In certain embodiments, the compounds of the present invention may be chosen on the basis of their selectively for the hedgehog pathway. This selectivity may be for the hedgehog pathway versus other pathways, or for selectivity between particular hedgehog pathways, e.g., patched-1, patched-2, etc.

In certain preferred embodiments, the present compounds may modulate patched-smoothened mediated signal transduction with an $ED_{50}$ of about 1 mM or less, more preferably of about 1 μM or less, and even more preferably of about 1 nM or less. For hedgehog-dependent agonists, the present compounds may increase the activity of hedgehog about 10-fold, about 100-fold, or even about 1000-fold.

In particular embodiments, the present compound may be chosen for use because it is more selective for one patched isoform over the next, e.g., about 10-fold, and more preferably at least about 100- or even about 1000-fold more selective for one patched pathway (patched-1, patched-2) over another.

In certain embodiments, a compound which is an agonist of the hedgehog pathway is chosen to selectively agonize hedgehog activity over protein kinases other than PKA, such as PKC, e.g., the compound modulates the activity of the PKA/hedgehog pathway at least an order of magnitude more strongly than it modulates the activity of another protein kinase, preferably at least two orders of magnitude more strongly, even more preferably at least three orders of magnitude more strongly. Thus, for example, a preferred activator of the hedgehog pathway may activate hedgehog activity with a $K_i$ at least an order of magnitude lower than its $K_i$ for activation of PKC, preferably at least two orders of magnitude lower, even more preferably at least three orders of magnitude lower. In certain embodiments, the $K_i$ for PKA/hedgehog activation is less than about 10 nM, preferably less than about 1 nM, even more preferably less than about 0.1 nM.

For example, in certain embodiments, a compound of the invention may have an $A_{max}$ value of at least about 1, 5, 10, 20, 40, or 80, for example, at least about 10, 20, or 40. In some embodiments a compound of the present invention may have an $A_{max}$ value of at least about 20.

Synthesis of Present Compounds

Compounds of the present invention may be readily prepared by standard techniques of organic synthesis, e.g., according to examples set forth in the Exemplification below. For example, a present compound may be prepared by reacting a compound or pair of compounds designated A with a compound or pair of compounds designated B and a compound designated C, as set forth below:

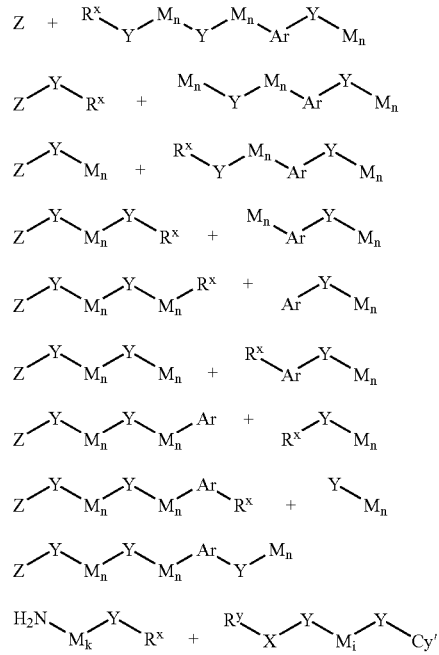

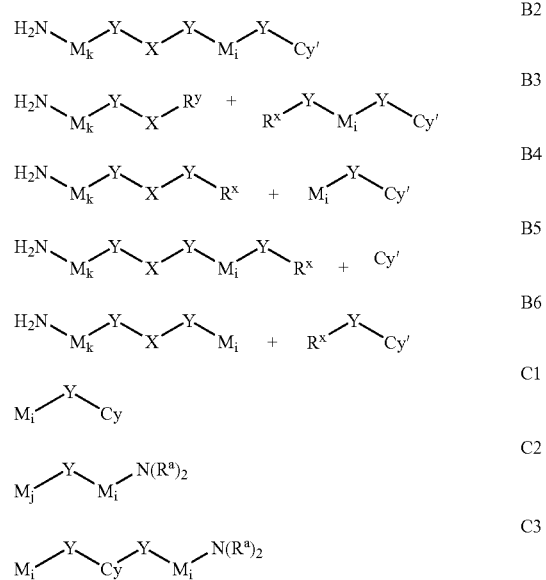

Similarly, a compound designated C above may be reacted with a compound or pair of compounds designated D and a compound or pair of compounds designated E:

-continued

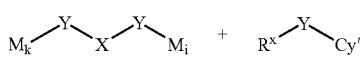
E6

Alternatively, a compound or pair of compounds designated A above and a compound or pair of compounds designated E above may be reacted with a compound designated F:

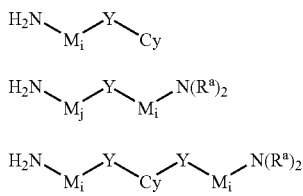
F1
F2
F3

Combinations of compounds as indicated above are preferably reacted with each other in series, e.g., two compounds are reacted together, the product is reacted with a third compound, etc., and the compounds may generally be coupled in series in any order, as will be understood by one of skill in the art. In certain embodiments, functional groups on one or more compounds may require protection during one or more reactions, as is well understood in the art, and any suitable protecting groups may be employed for this purpose. One of skill in the art may readily select suitable protecting groups for a particular functional group and a particular reaction. Elaboration steps may be performed at any time to modify functional groups or moieties on the product of a reaction, for example, to convert $N(R)_2=NH_2$ to $N(R)_2=NHR$, e.g., by nucleophilic substitution, reductive alkylation, or any other suitable method.

In the compounds designated A-F above and in other places herein, Ar is defined as:

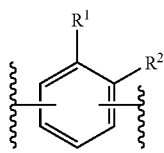

and the elements $M, X, Y, Z, Cy, Cy', i, k, R^1, R^2, R, R^a, R^x$ etc. are defined as above (as may be broadened by the description below), and $R^x$ independently for each occurrence represents H, a protecting group, or a labile reactive group, such as a trialkylsilyl (e.g., trimethylsilyl) group, and $R^y$ independently for each occurrence represents 1) a leaving group, such as a halogen (e.g., F, Cl, Br, or I), alkylthio, cyano, alkoxy, or any other group capable of being replaced by an amine nucleophile when attached to X, 2) an activatable group, such as OH, that may be activated by an activating agent, such as a carbodiimide (e.g., diisopropylcarbodiimide, dicyclohexylcarbodiimide, 1-(3-dimethylaminopropyl)-3-ethylcarbodiimide, etc.), phosphorous-based reagents (such as BOP-Cl, PyBROP, etc.), oxalyl chloride, phosgene, triphosgene, or any similar reagent, to result in a reactive intermediate having an increased susceptibility, relative to the compound wherein $R^y=OH$, towards coupling with an amine, or 3) X and $R^y$ taken together represent an electrophilic group capable of reacting with an amine, such as an isocyanate, isothiocyanate, or other similar reactive moiety.

The various subunits designated A-F may be combined using any of a plethora of reactions well known to those of skill in the art, depending on the particular moieties to be coupled. For example, an amine, such as one of the $NH_2$ groups indicated on the subunits A-F, may be coupled with an alkyl group by reductive alkylation (e.g., the terminal occurrence of M is an aldehyde), by nucleophilic displacement of a leaving group (such as a halogen, sulfonate, or other suitable substituent), by nucleophilic opening of an epoxide, or by any other suitable reaction known to those of skill in the art. Similarly, amines may be coupled with activated carboxylic acid derivatives or thiocarboxylic acid derivatives, e.g., prepared in situ from a carboxylic acid or thiocarboxylic acid and an activating agent or prepared as isolated compounds such as isocyanates, carboxylic acid chlorides, etc., to provide amides, ureas, thioureas, thioamides, etc., with chloroformate esters, sulfonyl chlorides, or other such compounds to provide urethanes, sulfonamides, etc., or with other electrophilic reagents that form a covalent bond with an amine.

Aryl and/or heteroaryl rings, such as Ar, may be readily coupled directly using Stille, Suzuki, Heck, or other related reactions, such as palladium-mediated cross-coupling reactions. Aryl and/or heteroaryl rings may be readily coupled through a heteroatom, e.g., using reactions such as the Ullman reaction, any of various palladium-mediated reactions developed by S. Buchwald and others, by nucleophilic aromatic substitution, or other such reactions. Similarly, amines, alcohols, thiols, and other such heteroatom-bearing compounds may be coupled to aryl and/or heteroaryl rings using palladium-mediated reactions developed by S. Buchwald and others, nucleophilic aromatic substitution, etc. Aryl and/or heteroaryl rings linked by substituted or unsubstituted hydrocarbon chains may be prepared by Stille, Suzuki, Heck, Friedel-Crafts, and other reactions as will be apparent to those of skill in the art.

A survey of a number of common synthetic reactions potentially useful for preparing compounds of the present invention are described in greater detail below and elsewhere herein. The variable groups included in the subunits designated A-F above may be varied to correspond with any of the Formulae I-V without departing from the general synthesis approaches outlined above.

Similarly, compounds of the present invention may be prepared by coupling a suitable moiety to a partially assembled structure. For example, a compound of Formula I may be prepared by any of the steps I-VI shown in the scheme below.

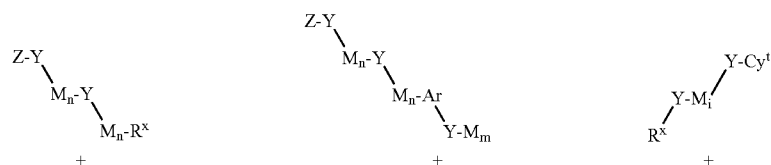

-continued
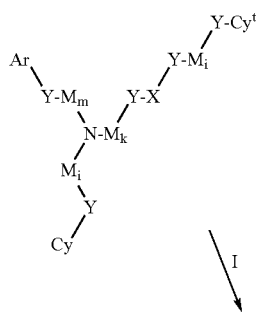
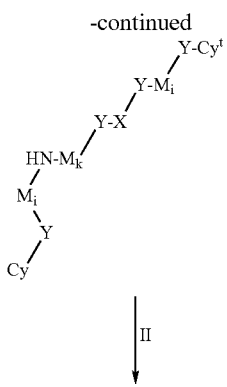
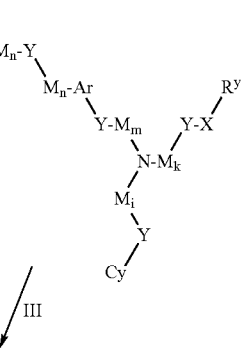
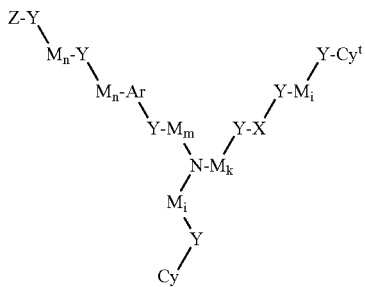
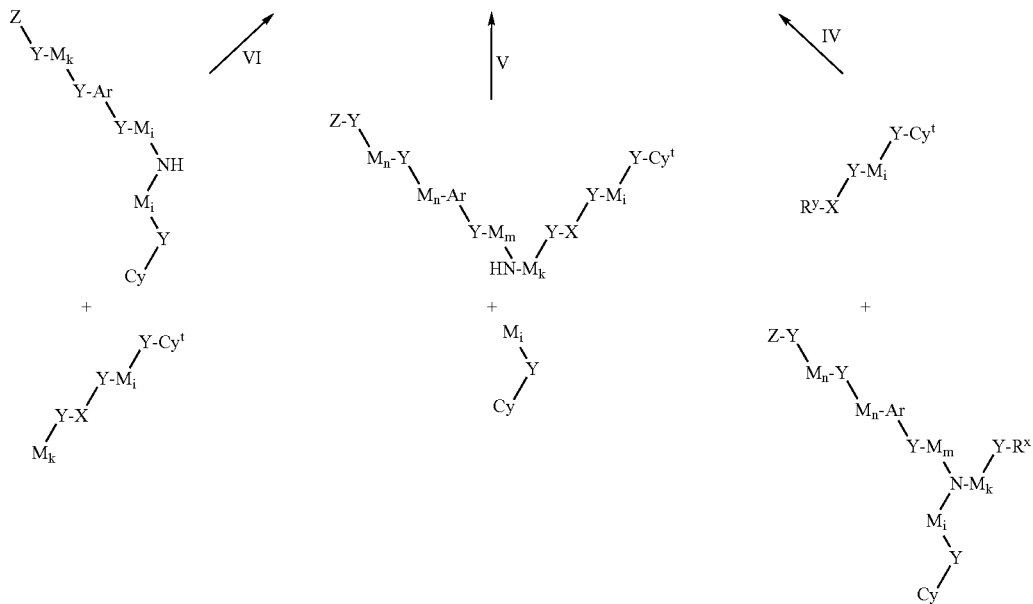
Similarly, a compound of Formula III may be prepared by any of the steps in the scheme below.
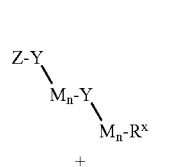
+
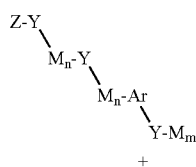
+
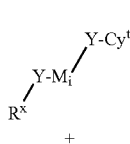
+

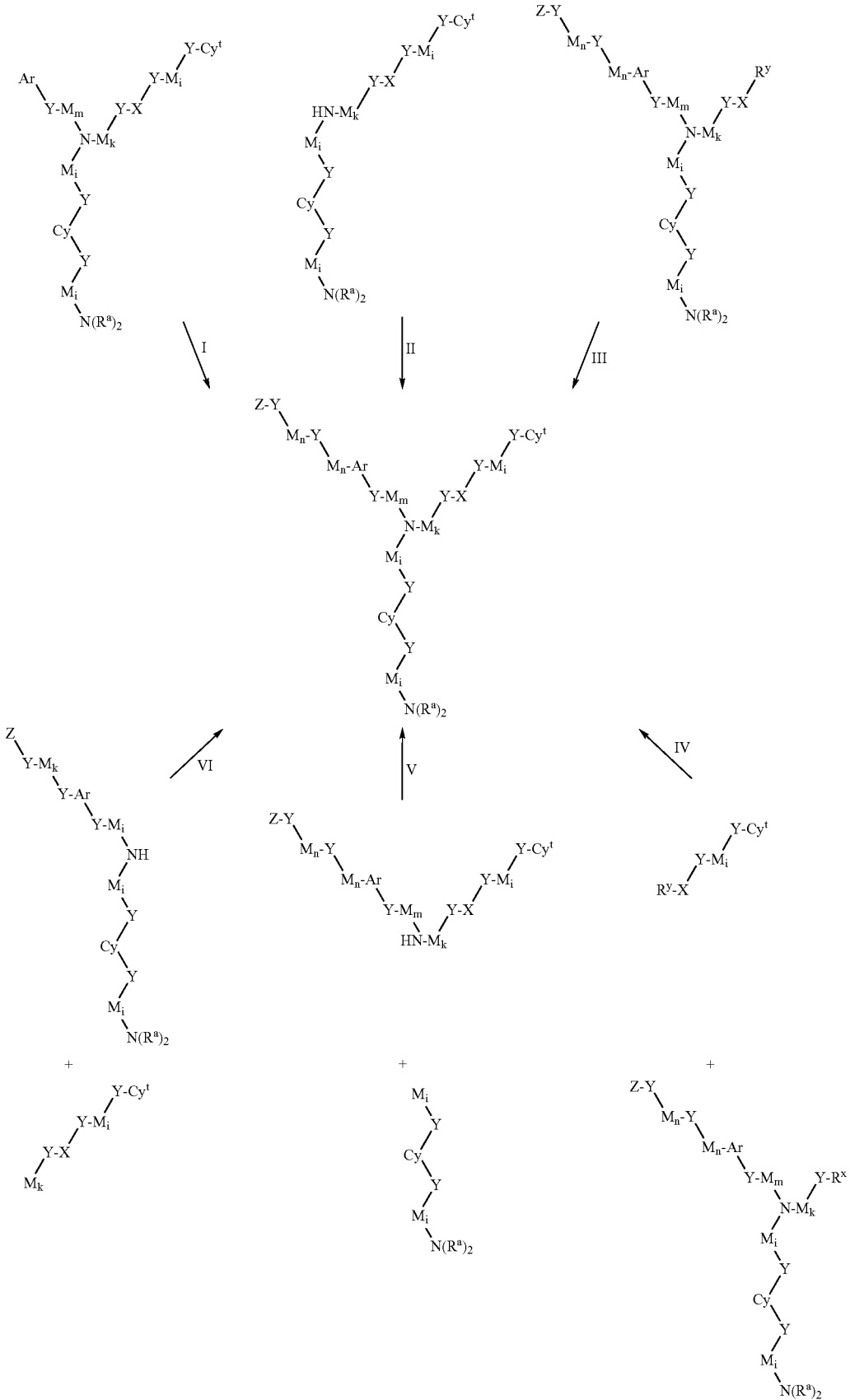

In the schemes above, M, Cy, Ar, X, Cy', Y, Z, R, $R^a$, i, k, $R^x$, and $R^y$ correspond to their use above, and may be more narrowly defined as set forth in the description of Formulae I-V.

Reactions suitable for performing Step I include palladium-mediated reactions developed by S. Buchwald and others, nucleophilic aromatic substitution, oxidative coupling, etc.

Reactions suitable for performing Step II include nucleophilic displacement of a leaving group on M, reductive alkylation, reaction of the amine with an electrophilic carboxylic/thiocarboxylic acid derivative (acid chloride, isocyanate, isothiocyanate, or a carboxylic acid activated by BOP-Cl, PyBroP, carbodiimide, or another activating reagent (such as are commonly used in the art of peptide coupling)), or other similar reactions, including those set forth in the accompanying description below, or, where M and Y are absent, a palladium-mediated coupling as developed by Buchwald and others.

Reactions suitable for performing Steps III or IV include reaction of Y—$R^x$ with an electrophilic carbonyl or sulfonyl derivative (X—$R^y$=acid chloride, isocyanate, isothiocyanate, chloroformate, sulfonyl chloride, or an acid activated by BOP-Cl, PyBroP, carbodiimide, or another activating reagent (such as are commonly used in the art of peptide coupling)), or other similar reactions, such as those set forth in the accompanying description below.

Reactions suitable for performing Step V include nucleophilic displacement of a leaving group, reductive alkylation, reaction of the amine with an electrophilic carboxylic/thiocarboxylic acid derivative (acid chloride, isocyanate, isothiocyanate, or a carboxylic acid activated by BOP-Cl, PyBroP, carbodiimide, or another activating reagent (such as are commonly used in the art of peptide coupling)), or other similar reactions, including those set forth in the accompanying description below.

Reactions suitable for performing Step VI include nucleophilic displacement of a leaving group, reductive alkylation, reaction of the amine with an electrophilic carboxylic/thiocarboxylic acid derivative (acid chloride, isothiocyanate, isocyanate, or a carboxylic acid activated by BOP-Cl, PyBroP, carbodiimide, or another activating reagent (such as are commonly used in the art of peptide coupling)), or other similar reactions, including those set forth in detail herein.

Reactions suitable for performing steps where Y is coupled with a present occurrence of M include nucleophilic displacement of a leaving group, reductive alkylation, reaction of the amine with an electrophilic carboxylic/thiocarboxylic acid derivative (acid chloride, isocyanate, isothiocyanate, or a carboxylic acid activated by BOP-Cl, PyBroP, carbodiimide, or another activating reagent (such as are commonly used in the art of peptide coupling)), or other similar reactions, including those set forth in the accompanying description below. In embodiments where occurrences of M is absent, suitable coupling reactions include palladium-mediated reactions developed by S. Buchwald and others, nucleophilic aromatic substitution, oxidative coupling, etc. In embodiments where M and Y are absent and Z represents an aryl or heteroaryl ring, suitable reactions include Stille, Suzuki, and other reactions suitable for forming biaryl systems.

Methods of the present invention further include reacting a compound of any of Formulae I-V wherein at least one $R^a$ of $N(R^a)_2$ represents H under conditions which convert that compound to a compound of the same formula wherein the corresponding occurrence of $R^a$ represents a lower alkyl group. For example, reductive alkylations with an aldehyde and a reducing agent, nucleophilic alkylations with an alkyl halide such as MeI, or other similar reactions may be employed. In certain embodiments, such reactions may proceed through a silylated (e.g., $R^a$=$SiMe_3$) intermediate.

One of skill in the art will readily appreciate that compounds of the present invention are amenable to synthesis according to a wide array of protocols well known in the art in addition to those described herein, all of which are intended to fall within the scope of the present invention.

IV. Exemplary Applications

Another aspect of the present invention relates to a method of modulating a differentiated state, survival, and/or proliferation of a cell, by contacting the cell with a hedgehog agonist, such as one or more present compounds or compositions, according to the present invention and as the circumstances may warrant.

Accordingly, in some embodiments, the present invention provides a method for modulating proliferation, differentiation, or survival of a cell, comprising contacting the cell with one or more of the present compounds or compositions.

For instance, it is contemplated by the present invention that, in light of the findings of an apparently broad involvement of hedgehog, patched, and smoothened in the formation of ordered spatial arrangements of differentiated tissues in vertebrates, the present invention may be used as part of a process for generating and/or maintaining an array of different vertebrate tissue both in vitro and in vivo. The hedgehog agonist, whether inductive or anti-inductive with respect proliferation or differentiation of a given tissue, may be, as appropriate, any of the compounds or preparations described herein.

For example, the present invention may be useful in cell culture techniques. In vitro neuronal culture systems have proved to be fundamental and indispensable tools for the study of neural development, as well as the identification of neurotrophic factors such as nerve growth factor (NGF), ciliary trophic factors (CNnT), and brain derived neurotrophic factor (BDNF). One use of the present invention may be in cultures of neuronal stem cells, such as in the use of such cultures for the generation of new neurons and glia. In such embodiments of the present invention, the cultured cells may be contacted with a present compound in order to alter the rate of proliferation of neuronal stem cells in the culture and/or alter the rate of differentiation, or to maintain the integrity of a culture of certain terminally differentiated neuronal cells. In an exemplary embodiment, the present invention may be used to culture, for example, sensory neurons or, alternatively, motor neurons. Such neuronal cultures may be used as convenient assay systems as well as sources of implantable cells for therapeutic treatments.

According to the present invention, large numbers of non-tumorigenic neural progenitor cells may be perpetuated in vitro and their rate of proliferation and/or differentiation may be affected by contact with the present compounds of the present invention. Generally, a method is provided comprising the steps of isolating neural progenitor cells from an animal, perpetuating these cells in vitro or in vivo, preferably in the presence of growth factors, and regulating the differentiation of these cells into particular neural phenotypes, e.g., neurons and glia, by contacting the cells with a present compound.

Thus, in some embodiments, the present invention provides for an in vitro method for growing or culturing cells, comprising contacting the cells with one or more of the present compounds or compositions. In some instances, the cells are progenitor cells, such as neural progenitor cells. In some instances, the cells are neuronal cells or neuronal progenitor cells.

In certain instances, the present invention provides for a method for inducing differentiation in a cell, for example a progenitor cell. The method may further comprise regulating the differentiation of these cells into particular phenotypes, for example, into neural phenotypes. Thus, one or more of the present compounds or compositions may be used to promote the differentiation of a cell (either a stem cell or a non-stem cell) to a particular differentiated cell type, such as a neuronal cell type including, but not limited to, a dopaminergic neuron, a motor neuron, a serotonergic neuron, an interneuron, a sensory neuron, and the like. In another embodiment, one or more of the present compounds or compositions promotes the differentiation of a cell to a mesodermal cell type including, but not limited to, osteocytes, chondrocytes, blood cells, cells of the immune system, skeletal muscle cells, cardiac muscle cells, smooth muscle cells, cells of the kidney, and the like. In yet another embodiment, one or more of the present compounds or compositions promotes the differentiation of a cell to an endodermal cell type including, but not limited to, pancreatic cell types (such as 1-islet cells), hepatocytes, cells of the lung, and cells of the gastrointestinal tract.

The present invention further provides a method for delivering cells to an anatomical site of a patient, comprising: culturing the cells, including contacting the cells with one or more of the present compounds or compositions; and implanting the cells at the anatomical site of the patient. In some instances, the cells are progenitor cells, such as neural progenitor cells. In some instances, the cells are neuronal cells or neuronal progenitor cells.

Progenitor cells are thought to be under a tonic inhibitory influence which maintains the progenitors in a suppressed state until their differentiation is required. However, recent techniques have been provided which permit these cells to proliferate, and unlike neurons which are terminally differentiated and therefore non-dividing, they may be produced in unlimited number and are highly suitable for implantation into heterologous and autologous hosts with neurodegenerative diseases.

By "progenitor" it is meant an oligopotent or multipotent stem cell which is able to divide without limit and, under specific conditions, may produce daughter cells which terminally differentiate such as into neurons and glia. These cells may be used for implantation into a heterologous or autologous host. By heterologous is meant a host other than the animal from which the progenitor cells were originally derived. By autologous is meant the identical host from which the cells were originally derived.

Cells may be obtained from embryonic, post-natal, juvenile or adult neural tissue from any animal. By any animal is meant any multicellular animal which contains nervous tissue. More particularly, is meant any fish, reptile, bird, amphibian or mammal and the like. The most preferable donors are mammals, especially mice and humans.

In the case of a heterologous donor animal, the animal may be euthanized, and the brain and specific area of interest removed using a sterile procedure. Brain areas of particular interest include any area from which progenitor cells may be obtained which will serve to restore function to a degenerated area of the host's brain. These regions include areas of the central nervous system (CNS) including the cerebral cortex, cerebellum, midbrain, brainstem, spinal cord and ventricular tissue, and areas of the peripheral nervous system (PNS) including the carotid body and the adrenal medulla. More particularly, these areas include regions in the basal ganglia, preferably the striatum which consists of the caudate and putamen, or various cell groups such as the globus pallidus, the subthalamic nucleus, the nucleus basalis which is found to be degenerated in Alzheimer's disease patients, or the substantia nigra pars compacta which is found to be degenerated in Parkinson's disease patients.

Human heterologous neural progenitor cells may be derived from fetal tissue obtained from elective abortion, or from a post-natal, juvenile or adult organ donor. Autologous neural tissue may be obtained by biopsy, or from patients undergoing neurosurgery in which neural tissue is removed, in particular during epilepsy surgery, and more particularly during temporal lobectomies and hippocampalectomies.

Cells may be obtained from donor tissue by dissociation of individual cells from the connecting extracellular matrix of the tissue. Dissociation may be obtained using any known procedure, including treatment with enzymes such as trypsin, collagenase and the like, or by using physical methods of dissociation such as with a blunt instrument or by mincing with a scalpel to a allow outgrowth of specific cell types from a tissue. Dissociation of fetal cells may be carried out in tissue culture medium, while a preferable medium for dissociation of juvenile and adult cells is artificial cerebral spinal fluid (aCSF). Regular aCSF contains 124 mM NaCl, 5 mM KCl, 1.3 mM $MgCl_2$, 2 mM $CaCl_2$, 26 mM $NaHCO_3$, and 10 mM D-glucose. Low $Ca^{2+}$ aCSF contains the same ingredients except for $MgCl_2$ at a concentration of 3.2 mM and $CaCl_2$ at a concentration of 0.1 mM.

Dissociated cells may be placed into any known culture medium capable of supporting cell growth, including MEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. A particularly preferable medium for cells is a mixture of DMEM and F-12.

Conditions for culturing may be close to physiological conditions. The pH of the culture media may be close to physiological pH, for example, between about pH 6-8, such as about pH 7-7.5, for example, about pH 7.4. Cells may be cultured at a temperature close to physiological temperature, for example, between about 30° C.-40° C., such as between about 32° C.-38° C., for example, between about 35° C.-37° C.

Cells may be grown in suspension or on a fixed substrate, but proliferation of the progenitors is preferably done in suspension to generate large numbers of cells by formation of "neurospheres" (see, for example, Reynolds et al. (1992) *Science* 255:1070-1709; and PCT Publications WO93/01275, WO94/09119, WO94/10292, and WO94/16718). In the case of propagating (or splitting) suspension cells, flasks are shaken well and the neurospheres allowed to settle on the bottom corner of the flask. The spheres are then transferred to a 50 ml centrifuge tube and centrifuged at low speed. The medium is aspirated, the cells resuspended in a small amount of medium with growth factor, and the cells mechanically dissociated and resuspended in separate aliquots of media.

Cell suspensions in culture medium are supplemented with any growth factor which allows for the proliferation of progenitor cells and seeded in any receptacle capable of sustaining cells, though as set out above, preferably in culture flasks or roller bottles. Cells typically proliferate within about 3-4 days in a 37° C. incubator, and proliferation may be reinitiated at any time after that by dissociation of the cells and resuspension in fresh medium containing growth factors.

In the absence of substrate, cells lift off the floor of the flask and continue to proliferate in suspension forming a hollow sphere of undifferentiated cells. After approximately 3-10 days in vitro, the proliferating clusters (neurospheres) are fed every 2-7 days, and more particularly every 24 days by gentle centrifugation and resuspension in medium containing growth factor.

After about 6-7 days in vitro, individual cells in the neurospheres may be separated by physical dissociation of the neurospheres with a blunt instrument, more particularly by triturating the neurospheres with a pipette. Single cells from the dissociated neurospheres are suspended in culture medium containing growth factors, and differentiation of the cells may be control in culture by plating (or resuspending) the cells in the presence of a present compound.

To further illustrate other uses of the present compounds, it is noted that intracerebral grafting has emerged as an additional approach to central nervous system therapies. For example, one approach to repairing damaged brain tissues involves the implantation of cells from fetal or neonatal animals into the adult brain (Dunnett et al. (1987) *J Exp Biol* 123:265-289; and Freund et al. (1985) *J Neurosci* 5:603-616). Fetal neurons from a variety of brain regions may be successfully incorporated into the adult brain, and such grafts may alleviate behavioral defects. For example, movement disorder induced by lesions of dopaminergic projections to the basal ganglia may be prevented by grafts of embryonic dopaminergic neurons. Complex cognitive functions that are impaired after lesions of the neocortex may also be partially restored by grafts of embryonic cortical cells. The present invention may be used to regulate the growth state in the culture, or where fetal tissue is used, especially neuronal stem cells, may be used to regulate the rate of differentiation of the stem cells.

Stem cells useful in the present invention are generally known. For example, several neural crest cells have been identified, some of which are multipotent and likely represent uncommitted neural crest cells, and others of which may generate only one type of cell, such as sensory neurons, and likely represent committed progenitor cells. The role of the present compounds employed in the present method to culture such stem cells may be to regulate differentiation of the uncommitted progenitor, or to regulate further restriction of the developmental fate of a committed progenitor cell towards becoming a terminally differentiated neuronal cell. For example, the present compounds may be used in vitro to regulate the differentiation of neural crest cells into glial cells, schwann cells, chromaffin cells, cholinergic sympathetic or parasympathetic neurons, as well as peptidergic and serotonergic neurons. The present compounds may be used alone, or may be used in combination with other neurotrophic factors which act to more particularly enhance a particular differentiation fate of the neuronal progenitor cell. In certain instances the present compounds and compositions may be used to enhance or improve the survival rate of a neuronal cell.

It has been shown that hedgehog agonists have the ability to bias the development of a progenitor or biased cells down a particular developmental pathway (see for example, U.S. Published Patent Application No. 2005-0019801, Wichterle et al. (2002) *Cell* 110: 385-397, and Novitch et al. (2003) *Neuron* 40(1):81-95, which are incorporated by reference herein in their entirety). Hence, in one embodiment, the present compounds may be used to bias the development of a progenitor or biased cell down a particular developmental pathway, i.e., to a particular differentiated cell type. In some embodiments, the particular differentiated cell type is a neuronal cell type. In yet another embodiment, the neuronal cell type is selected from motor neurons, dopaminergic neurons, cholinergic neurons, interneurons, sensory neurons, serotonergic neurons, peptidergic neurons, astrocytes, and oligodendrocytes.

In some aspects of the present invention, the present compounds may be used either locally or systemically to promote bone marrow-derived stem cell and/or progenitor cell release into the blood stream and/or homing to sites of tissue injury or wounds.

In addition to the implantation of cells cultured in the presence of the present compounds, yet another aspect of the present invention concerns the therapeutic application of a present compound to regulate the growth state of neurons and other neuronal cells in both the central nervous system and the peripheral nervous system. The ability of patched, hedgehog, and smoothened to regulate neuronal differentiation during development of the nervous system and also presumably in the adult state indicates that, in certain instances, the present compounds may be expected to facilitate control of adult neurons with regard to maintenance, functional performance, and aging of normal cells; repair and regeneration processes in chemically or mechanically lesioned cells; and treatment or prevention of degeneration in certain pathological conditions. In light of this understanding, the present invention specifically contemplates applications to the treatment or prevention protocol of (prevention and/or reduction of the severity of) neurological conditions deriving from: (i) acute, subacute, or chronic injury to the nervous system, including traumatic injury, chemical injury, vascular injury and deficits (such as the ischemia resulting from stroke), together with infectious/inflammatory and tumor-induced injury; (ii) aging of the nervous system including Alzheimer's disease; (iii) chronic neurodegenerative diseases of the nervous system, including Parkinson's disease, Huntington's chorea, amyotrophic lateral sclerosis and the like, as well as spinocerebellar degenerations; and (iv) chronic immunological diseases of the nervous system or affecting the nervous system, including multiple sclerosis (MS). Accordingly, the present disclosure provides a method for the treatment or prevention of MS comprising administering one or more of the present compounds or compositions. Some additional diseases or conditions treatable by the present compounds and compositions include stroke, peripheral neuropathy, and diabetic neuropathy.

Moreover, the present invention specifically contemplates applications to the treatment or prevention protocol (prevention and/or reduction of the severity of) of neurological conditions deriving from: (i) loss of dopaminergic cells, (ii) loss of GABAergic cells, and/or (iii) loss of neurons of the substantia nigra.

The present invention further contemplates applications to the treatment or prevention (prevention and/or reduction of the severity of) of neurological conditions deriving from exotoxic degeneration of neuronal cells, including cell death or loss of functional performance. In this regard, the present invention may be useful in the treatment or prevention of such neurologic disorders including Parkinson's disease, domoic acid poisoning; spinal cord trauma; hypoglycemia; mechanical trauma to the nervous system; senile dementia; Korsakoff's disease; schizophrenia; AIDS dementia, multi-infarct dementia; mood disorders; depression; chemical toxicity and neuronal damage associated with uncontrolled seizures, such as epileptic seizures; and chronic neurologic disorders such as Huntington's disease, neuronal injury associated with HIV and AIDS, neurodegeneration associated with Down's syndrome, neuropathic pain syndrome, olivopontocerebral atrophy, amyotrophic lateral sclerosis, mitochondrial abnormalities, Alzheimer's disease, hepatic encephalopathy, Tourette's syndrome, schizophrenia, and drug addiction.

For example, in the specific case of Parkinson's disease, intervention by increasing the activity of hedgehog by a present compound may improve the in vivo survival of fetal and adult dopaminergic neurons, and thus may provide a more effective treatment of this disease. Thus, in one embodiment, the present invention comprises administering to an animal afflicted with Parkinson's disease, or at risk of developing Parkinson's disease, an amount of a present compound effective for increasing the rate of survival of dopaminergic neurons in the animal. In one embodiment of the present invention, administration of one or more of the present compounds or compositions may be used in conjunction with surgical implantation of tissue in the treatment or prevention of Parkinson's disease.

As noted above, intracerebral neural grafting has emerged recently as an additional potential to CNS therapy. Transplantation of fetal brain cells, which contain precursors of the dopaminergic neurons, has been examined with success as a treatment for Parkinson's disease. In animal models and in patients with this disease, fetal brain cell transplantations have resulted in the reduction of motor abnormalities. Furthermore, it appears that the implanted fetal dopaminergic neurons form synapses with surrounding host neurons. However, in the art, the transplantation of fetal brain cells is limited due, for example, to the limited survival time of the implanted neuronal precursors and differentiated neurons arising therefrom. The present compounds and compositions may provide a means for extending the usefulness of such transplants by enhancing the survival of dopaminergic and/or GABAergic cells in the transplant.

In one aspect, a present therapeutic method may be characterized as including a step of administering to an animal an amount of one or more of the present compounds or compositions, optionally in combination with a neurotrophic factor, effective to enhance the survival of cholinergic, dopaminergic and/or GABAergic neuronal cells. The mode of administration and dosage regimens will vary depending on the severity of the degenerative disorder being treated, e.g., the dosage may be altered as between a prophylaxis and treatment.

One or more of the present compounds may be tested by any of number of well known animal disease models. For instance, regarding Parkinson's Disease, selected agents may be evaluated in animals treated with MPTP. The compound MPTP (1-methyl-4-phenyl-1,2,3,6-tetrahydropyridine) and its metabolite MPP+ have been used to induce experimental parkinsonism. MPP+ kills dopaminergic neurons in the substantia nigra, yielding a reasonable model of late parkinsonism. Turski et al., (1991) Nature 349:414.

It is known that hedgehog exerts trophic and survival-promoting actions on substantia nigra dopaminergic neurons. In vivo treatment or prevention with one or more of the present compounds or compositions is expected to stimulate the dopaminergic phenotype of substantia nigra neurons and restore functional deficits induced by axotomy or dopaminergic neurotoxins, and may be used in the treatment or prevention of Parkinson's disease, a neurodegenerative disease characterized by the loss of dopaminergic neurons. Thus, in one embodiment, the present invention comprises administering to an animal afflicted with Parkinson's disease, or at risk of developing Parkinson's disease, an amount of one or more of the present compounds or compositions effective for increasing the rate of survival of dopaminergic neurons in the animal. In preferred embodiments, the method may include administering to the animal an amount of one or more of the present compounds or compositions which would otherwise be effective at protecting the substantia nigra from MPTP-mediated toxicity when MPTP is administered at a dose of 0.5 mg/kg or more, such as a dose of 2 mg/kg, 5 mg/kg, 10 mg/kg, 20 mg/kg or 50 mg/kg or more, particularly at a dose of 100 mg/kg or more.

Hence in some embodiments, the present invention may be used to prevent or treat neurodegenerative conditions arising from the use of certain drugs, such as the compound MPTP (1-methyl-4-phenyl-1,2,3,6-tetrahydropyridine).

In another example, the present compounds may provide improved recovery from tissue damage, resulting from instances of ischemia and/or poor vascular flow, e.g., resulting from stroke. For example, in some instances, the present compounds may be administered immediately following an ischemic event, such as stroke. In other embodiments, the present compounds may be administered up to about 1, 5, 10, 30, or 60 minutes, or 2, 4, 8, 16, 24, or 48 hours, or 2, 4, or 8 days after an ischemic event, such as a stroke. Administration of the present compounds post-ischemia may promote regeneration of the affected tissue and/or the affected tissue's normal function. As such, the present compounds may provide improved neuroprotection for cells susceptible to damage from ischemic episodes.

Accordingly, the present invention may provide a method for treating tissues of a patient damaged by stroke, comprising administering one or more of the present compounds or compositions. In some instances, the compound or composition is administered after the stroke, for example, up to about 1, 5, 10, 30, or 60 minutes, or 2, 4, 8, 16, 24, or 48 hours, or 2, 4, or 8 days after the stroke.

The middle cerebral artery (MCA) is the cerebral blood vessel most susceptible to stroke in humans. In animals, coagulation, permanent ligation or permanent placement of an occluding thread in the artery produces a permanent focal stroke affecting the MCA territory. Transient ligation or occlusion results in transient focal stroke. Both transient and permanent focal strokes result in varying degrees of edema and infarction in the affected brain regions. In some instances, the present compounds may reduce the volumes of edema and infarction, which is a measure of their potential as anti-stroke treatment.

A direct approach to treating cerebral ischemia is to restore circulation. However, reperfusion following transient ischemia may induce additional mechanisms of tissue damage. This phenomenon is termed "reperfusion injury" and has been found to play a role in other organ systems as well, including the heart. Recently, it has been suggested that cerebral ischemic damage is mediated, to a large extent, via excitotoxic mechanisms. During ischemia, large elevations in extracellular glutamate occur, often reaching neurotoxic levels. Accordingly, the present compounds, compositions, and methods may be used as part of a treatment or prophylaxis for ischemic or epoxic damage, particularly to alleviate certain effects of reperfusion injury.

In certain embodiments, the present compounds may be used in a method for the treatment or prevention of conditions involving reduced or impeded blood flow to the tissues of a patient, for example, conditions such as cardiovascular disease (e.g., atherosclerosis, arterial stenosis, cardiac ischemia, coronary heart disease) and/or peripheral ischemia (e.g., peripheral artery disease). In certain such embodiments, the present compounds may be administered up to about 1, 5, 10, 30, or 60 minutes, or about 2, 4, 8, 16, 24, or 48 hours, or about 2, 4, or 8 days after such an ischemic event.

Accordingly, in some embodiments, the present invention provides a method for treating or preventing cardiovascular disease, comprising administering one or more of the present compounds or compositions. In some instances, the present compounds or compositions are released from a stent, for example, through controlled or sustained release as described in more detail herein. In certain embodiments, the present compounds or compositions may be released from the surface of a stent.

As noted herein, the present invention may be useful in cell culture techniques. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). Once a neuronal cell has become terminally differentiated it typically will not change to another terminally differentiated cell-type. However, neuronal cells may nevertheless readily lose their differentiated state. This is commonly observed when they are grown in culture from adult tissue, and when they form a blastema during regeneration. The present invention may provide a means for ensuring an adequately restrictive environment in order to maintain dopaminergic and GABAergic cells in differentiated states, and may be employed, for instance, in cell cultures designed to test the specific activities of other trophic factors.

In such embodiments of the present invention, a culture of differentiated cells including dopaminergic and/or GABAergic cells may be contacted with a present compound in order to maintain the integrity of a culture of terminally differentiated neuronal cells by preventing loss of differentiation. The present invention may be used in conjunction with agents which induce the differentiation of neuronal precursors, e.g., progenitor or stem cells, into dopaminergic or GABAergic neurons.

Many neurological disorders are associated with degeneration of discrete populations of neuronal elements and may be treatable with a therapeutic regimen which includes a hedgehog agonist. For example, Alzheimer's disease is associated with deficits in several neurotransmitter systems, both those that project to the neocortex and those that reside with the cortex. For instance, the nucleus basalis in patients with Alzheimer's disease have been observed to have a profound (75%) loss of neurons compared to age-matched controls. Although Alzheimer's disease is by far the most common form of dementia, several other disorders may produce dementia. Several of these are degenerative diseases characterized by the death of neurons in various parts of the central nervous system, especially the cerebral cortex. However, some forms of dementia are associated with degeneration of the thalamus or the white matter underlying the cerebral cortex. Here, the cognitive dysfunction results from the isolation of cortical areas by the degeneration of efferents and afferents. Huntington's disease involves the degeneration of intrastriatal and cortical cholinergic neurons and GABAergic neurons. Pick's disease is a severe neuronal degeneration in the neocortex of the frontal and anterior temporal lobes, sometimes accompanied by death of neurons in the striatum. Treatment of patients displaying such degenerative conditions may include the application of the present compounds in order to control, for example, differentiation and apoptotic events which give rise to loss of neurons (e.g., to enhance survival of existing neurons) as well as promote differentiation and repopulation by progenitor cells in the area affected.

As such, some aspects of the present invention concern the therapeutic application of the present compounds and/or compositions for cytoprotective or anti-apoptotic effects, which, for example, may occur in various disease processes such as ischemic stroke, ischemic heart disease, or ischemic peripheral vascular disease. In certain embodiments, one or more of the present compounds or compositions may be employed in methods for modulating apoptosis in a cell, for example, for inhibiting apoptosis, either in vitro or in vivo (e.g., in a patient). Such methods may be useful in promoting cell growth, proliferation, or survival in conditions characterized by excessive cell loss. Some conditions include degenerative diseases such as neurodegenerative diseases and degenerative conditions of cartilage and bone In another aspect of the present invention, the present compounds may be used to treat inflammatory or other lung diseases in which cytoprotective or reparative processes would be therapeutic. Possible treatment or prevention regimens include systemic or local (e.g., inhaled formulation) application of the present compounds or compositions.

Thus, the present invention may have a wide applicability for the treatment or prophylaxis of disorders afflicting lung tissue, as well as in in vitro cultures. In general, some of the present methods may be characterized as including a step of administering to a patient an amount of one or more of the present compounds or compositions effective to alter the growth state of a treated lung tissue. The mode of administration and dosage regimens will vary depending on the phenotype of and desired effect on the target lung tissue, for example, promotion of growth.

In one aspect, the present invention provides pharmaceutical preparations and methods for controlling the proliferation, for example, by promoting proliferation, of lung tissue utilizing, as an active ingredient, one or more of the present compounds or compositions. The present invention may also relate to methods of controlling proliferation, for example, by promoting proliferation, of mesenchymal and epithelial cells of the tissue by use of the present compounds or compositions.

The formulations of the present invention may be used as part of regimens in the treatment or prevention of disorders of, surgical repair of, or transplantation or implantation of lung tissues and whole organs. The methods and compositions disclosed herein also provide for the treatment or prevention of a variety of proliferative cancerous disorders effecting lung tissue. For instance, the present invention may be used to control wound healing processes, as for example may be desirable in connection with any surgery involving lung tissue.

In some embodiments, the present invention may be used to treat rheumatoid lung disease, which may be marked by pleural thickening, adhesions, and pleural effusions. Such lung (pulmonary) manifestations may occur in both adult and juvenile forms of rheumatoid arthritis.

In other embodiments, the present invention may be used to treat, e.g., to lessen the severity of, damage to lung tissue as a complication of respiratory diseases such as broncho-pneumonia, chronic bronchitis, cystic fibrosis and asthma, and bronchospasm, or other apical interstitial lung diseases, such as cystic fibrosis, ankylosing spondylitis, sarcoidosis, silicosis, eosinophlic granuloma, tuberculosis, and lung infections.

In certain embodiments, the present invention may be used to treat or prevent damage to lung tissue resulting from allergic rhinitis, asthma, emphysema, chronic bronchitis, pneumoconiosis, respiratory distress syndrome, idiopathic pulmonary fibrosis and primary pulmonary hypertension The present invention may be used in the treatment or prevention of occupational lung disease such as asbestos-related diseases, silicosis, occupational asthma, coal worker's pneumoconiosis, berylliosis, and industrial bronchitis.

In still other embodiments, the present invention may be used to treat certain health consequences of smoking which may result in degeneration of lung tissue.

Still another aspect of the present invention may provide a method of stimulating the growth and regulating the differentiation of epithelial tissue in tissue culture. In one embodiment, the present invention may be used to regulate the proliferation and/or differentiation of lung mesenchymal progenitor cells.

The maintenance of lung tissues and whole organs ex vivo is also highly desirable. Lung and heart-lung transplantation/implantation therapy is well established in the treatment of certain human diseases. The present invention may be used to maintain the tissue structure of lung tissue ex vivo, and in certain embodiments to accelerate the growth of certain lung tissue in vitro. The present method may also be used for improving the "take rate" of a lung transplants or implants in vivo.

Activating the hedgehog signaling pathway stimulates neurogenesis, differentiation and migration of neuronal stem cells. Therefore, according to the present invention, a present compound may be used in methods to treat various disorders and conditions that benefit from increased neuronal growth and differentiation, and from modulated synaptic activity.

One aspect of the present invention may provide methods for modulating activity of the CNS of a mammal by stimulating the neuronal stem cells via a hedgehog signaling pathway, thereby promoting differentiation and migration of the neuronal stem cells. The methods of the present invention may comprise administering a present compound to a subject experiencing certain deficits in CNS neuronal functions or to a subject that benefits from enhancement of certain CNS functions.

Accordingly, in some embodiments, the present invention provides a method for treating or preventing a condition of the CNS, comprising administering to a patient one or more of the present compounds or compositions. In certain instances, the condition is Parkinson's disease, Huntington's disease, or ischemia. In some applications, the one or more present compounds or compositions is administered orally. In other applications, the one or more present compounds or compositions is administered topically.

In some embodiments, the present compounds and compositions have neuroprotective activity and may be useful in applications and methods where neuroprotection is desired.

Central nervous system tissue is particularly vulnerable to damage caused by ischemic conditions. The present invention may have wide applicability to the treatment or prophylaxis of ischemic or hypoxic damage marked by neuronal cell death. The present invention may be used to treat or prevent injury or disease to brain tissue resulting from ischemia, e.g., as caused from insufficient oxygen. The types of ischemia for which the present invention may be used as part of a treatment include, but are not limited to those which may last for only transient periods of time to those which may last for lengthy durations, as in stroke. In this regard, the present invention may be useful for treatment and prevention of injury to the brain and spinal cord and edema due to head trauma, spinal trauma, stroke, hypotension, arrested breathing, cardiac arrest, Rey's syndrome, cerebral thrombosis, embolism, hemorrhages or tumors, encephalomyelitis, hydroencephalitis, and operative and postoperative brain injury.

In general, the method may be characterized as including a step of administering to an animal an amount of one or more of the present compounds or compositions effective to enhance the survival of neuronal cells under such ischemic or hypoxic conditions. The mode of administration and dosage regimens may vary depending on the severity of the ischemic or hypoxic attack, e.g., the dosage may be altered as between a transient ischemic attack (TIA), a partial nonprogressing stroke, and a complete stroke. In preferred embodiments, one or more of the present compounds or compositions may be administered systemically initially (i.e., while the blood brain barrier is disrupted), then locally for medium to long term care. In some cases, the ischemic or hypoxic attack may be associated with stroke. In some instances, the ischemic or hypoxic attack may be associated with a change in altitude, e.g., and increase in altitude.

When used to treat stroke, the clinician should not only define the level of stroke severity, but also the "pace" or "tempo" of the illness. This is because the pace of progression helps to dictate the urgency for evaluation and treatment. A patient who suffers a TIA in the morning has a higher risk for stroke in the afternoon than a patient who suffered a single TIA a month earlier. Where the risk of stroke remains high, one or more of the present compounds or compositions may be used prophylatically in order to minimize ischemic damage which may result from an eventual stroke. A patient who is worsening under supervision requires more urgent management than one who has been stable for a week or more.

The present invention may also find particular utility in treating or preventing the adverse neurological consequences of surgery. In one example, certain cranial surgery may result in degeneration of neuronal populations for which the present invention may be applied. In another example, coronary bypass surgery requires the use of heart-lung machines, which may introduce air bubbles into the circulatory system that may lodge in the brain. The presence of such air bubbles robs neuronal tissue of oxygen, resulting in anoxia and ischemia. Pre- or post-surgical administration of one or more of the present compounds or compositions may be employed to treat or prevent adverse affects resulting from such anoxia or ischemia, for example tissue damage. In some instances, one or more of the present compounds or compositions is administered to patients undergoing or having undergone cardiopulmonary bypass surgery or carotid endarterectomy surgery.

In some instances, one or more of the present compounds or compositions may be used in conjunction with growth and/or trophic factors, for example, to afford neuroprotective compositions. For instance, the trophic growth factor basic FGF has been demonstrated in the art to be useful in the functional recovery following experimental stroke. In experiments providing exogenous administration of bFGF after infarction, the early administration of bFGF was found to reduce infarct size. See, for example, Kawamata et al. (1997) Adv Neurol 73: 377-82. Likewise, progesterone has been shown to be neuroprotective after transient middle cerebral artery occlusion in male rats. Jiang et al. (1996) Brain Res 735:101-7. Other agents with which the present compounds and methods may be coadministered include nitro-1-arginine and transforming growth factor-b1 (TGF-beta 1), which has been shown to rescue cultured neurons from excitotoxic and hypoxic cell death and to reduce infarct size after focal cerebral ischemia in mice and rabbits. In other instances, the combinatorial therapy may include a trophic factor such as nerve growth factor, ciliary neurotrophic growth factor, schwanoma-derived growth factor, glial growth factor, striatal-derived neuronotrophic factor, platelet-derived growth factor, and scatter factor (HGF-SF). Antimitogenic agents may also be used with the present compounds and compositions, as for example, cytosine, arabinoside, 5-fluorouracil, hydroxyurea, and methotrexate.

Determination of a therapeutically effective amount and a prophylactically effective amount of a present compound or composition, e.g., to be adequately neuroprotective, may be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician, the severity of the condition being treated, the risk of further ischemic or hypoxic damage to the CNS, and the particular compound or composition being employed. In determining the therapeutically effective neuroprotective amount or dose, and the prophylactically effective amount or dose, a number of factors are considered by the attending clinician, including, but not limited to: the specific cause of the ischemic or hypoxic state and its likelihood of recurring or worsening; pharmacodynamic characteristics of the particular agent and its mode and route of administration; the desired time course of treatment; the species of mammal; its size, age, and general health; the response of the individual patient; the particular compound or composition administered; the bioavailability characteristics of the preparation administered; the dose regimen selected; the kind of concurrent treatment (i.e., the interaction of the hedgehog or patched therapeutic with other co-administered therapeutics); and other relevant circumstances.

Treatment or prevention may be initiated with smaller dosages which are less than the optimum dose of the compound or composition. Thereafter, the dosage should be increased by small increments until the optimum effect under the circumstances is reached. For convenience, the total daily dosage may be divided and administered in portions during the day if desired. A therapeutically effective antineoplastic amount and a prophylactically effective neuroprotective amount of a present compound or composition, for instance, is expected to vary from concentrations about 0.1 nanogram per kilogram of body weight per day (kg/day) to about 100 kg/day.

The present compounds and compositions, such as described herein, may be tested by measuring the volume of cerebral infarction in animals receiving systemic injections. For instance, selected agents may be evaluated in the focal stroke model involving permanent middle cerebral artery occlusion (MCAO) in the spontaneously hypertensive rat. This procedure results in a reliably large neocortical infarct volume that is measured by means of vital dye exclusion in serial slices through the brain 24 hours after MCAO. Tamura et al. (1981) J Cerebral Blood Flow and Metabolism 1:53-60.

The identification of those patients who are in need of prophylactic treatment for ischemic or hypoxic states is well within the ability and knowledge of one skilled in the art. Certain of the methods for identification of patients which are at risk of cerebral infarction which may be treated by the present invention are appreciated in the medical arts, such as family history of the development of a particular disease state and the presence of risk factors associated with the development of that disease state in the subject patient. A clinician skilled in the art may readily identify such candidate patients, by the use of, for example, clinical tests, physical examination and medical/family history.

In some instances, the present invention provides methods for treating behavioral and/or emotional disorders by modulating the activity of the CNS via the hedgehog signaling pathway.

The present invention contemplates the use of a present compound, for example in pharmaceutical compositions as described herein, for the treatment or prophylaxis of emotional disorders such as depression, panic disorder, obsessive compulsive disorders, anxiety, and social anxiety/phobic disorder. For any of these purposes, treatment may include partial or total alleviation of one or more symptoms of a condition, and prophylaxis may include delaying the onset of or reducing the severity of one or more symptoms of a condition.

A specific aspect of the present invention may be the treatment or prevention of depression. Anti-depressant small molecules have been shown to stimulate neurogenesis in hippocampus and that the neurogenesis contributes to the effect of the anti-depressants. A hedgehog agonist stimulates neurogenesis in the hippocampus and is expected to show a similar effect compared to known antidepressants.

Another aspect of the present invention may provide methods of enhancement of cognitive function and/or memory function of a subject. An aspect of the present invention may also provide enhancement of cognition, which is additionally contemplated to treat diseases that exhibit associated dementia, and to alleviate symptoms of these diseases and other disorders such as depression which exhibit degradation of memory and cognitive functions. Still another aspect of the present invention relates to the use of a present compound for prophylactically preventing the occurrence of learning and/or memory defects in a subject, and thus, altering the learning ability and/or memory capacity of the subject. In certain embodiments, the present invention may be used to treat patients who have been diagnosed as having or being at risk of developing disorders in which diminished declarative memory is a symptom, e.g., as opposed to procedural memory. As a result, the methods of the present invention may be useful for preventing memory impairment. Contemplated causes of memory impairment include toxicant exposure, brain injury, age-associated memory impairment, mild cognitive impairment, epilepsy, mental retardation in children, and dementia resulting from a disease, such as in certain cases of Parkinson's disease, AIDS, head trauma, Huntington's disease, Pick's disease, Creutzfeldt-Jakob disease, post cardiac surgery, Downs Syndrome, Anterior Communicating Artery Syndrome, and other symptoms of stroke. Yet another aspect of the present invention may provide methods of treatment or prevention of disorders which are accompanied by neuronal cell loss or lesion, by stimulating the neuronal stem cells to differentiate and migrate to the site of the damage. Such differentiation and migration may be promoted by activating the hedgehog signaling pathway by various agents. In addition, the present invention may be useful in enhancing memory in normal individuals. The present compounds and compositions may also be useful for decreasing the occurrence of learning and/or memory defects in an organism, and thus maintaining the learning ability and/or memory function of the organism.

The most common cause of dementia in the elderly is Alzheimer's disease (AD). AD is an etiologically unknown, non-infectious neurological disorder that shows progressive dementia. About 3 to 5% of people over 65 suffer from AD. While the definitive characteristic of AD is a postmortem observation of amyloid plaques and neurofibrillary tangles (malformations within nerve cells) in the brain of a patient, guidelines have been established to aid the diagnosis of AD in a living patient. The National Institute of Neurological and Communicative Disorders and Stroke-Alzheimer's Disease and Related Disorders Association (NINCDS-ADRDA) has devised a list of indicative symptoms to diagnose AD.

Hallmarks of Alzheimer's disease include progressive nature of dementia, characteristic positron emission tomography showing reduced 2FDG metabolism in parietal and temporal lobe association and posterior cingulate cortices. Reductions are usually bilateral, yet there often is an asymmetry in the severity or the extent of hypometabolism. Patients with advanced clinical symptoms often demonstrate reduced metabolism in the prefrontal association cortices as well. Metabolism is relatively spared in primary sensory and motor cortical regions, including the somatomotor, auditory and visual cortices. Subcortical structures, including the basal ganglia, thalamus, brainstem and cerebellum, are also preserved in typical AD. The overall distribution of metabolism in AD reflects in part the known regional losses of neurons and synapses but likely also includes effects of cortical disconnection resulting in reduced afferent input to the association areas. Additionally, increase in biomarkers such as total tau, and phosphorylated tau in the cerebrospinal fluid aids the diagnosis of Alzheimer's disease. Genetic factors that increase the risk of Alzheimer's, such as being homozygous for allele 4 of ApoE protein, support the diagnosis. For a recent review of biological markers of AD, see Frank, R. A. et al. (2003) *Neurobiol. Aging* 24:521-536, the disclosure of which is incorporated herein by reference in its entirety.

Alzheimer's Disease is also marked by widespread neurodegeneration in the brain including an enhanced loss of the cholinergic neurons that reside in the basal forebrain. This loss correlates to the severe cognitive deficits observed in Alzheimer's diseased patients. The induction of basal forebrain neurons during development has been shown to be dependent on exposure to the secreted inducing molecule sonic hedgehog (Shh) (Ericson et al., 1995). The loss of the basal forebrain cholinergic neurons contributes to the cognitive and spatial memory deficits in Alzheimer's diseased patients (Gilmor et al., 1999; Lehericy et al. 1993). According to the present invention, in vivo, treatment or prevention with one or more of the present compounds and/or compositions, optionally in combination with other neurotrophic factors, may be expected to restore and modulate cholinergic function in Alzheimer's patients.

The methods and compositions of the present invention may be used for the treatment or prevention of movement disorders. Hedgehog agonists may be used to treat patients displaying ataxia, corticobasal ganglionic degeneration (CBGD), dyskinesia, dystonia, tremors, hereditary spastic paraplegia, Huntington's disease, multiple sclerosis, multiple system atrophy, myoclonus, Parkinson's disease, progressive supranuclear palsy, restless legs syndrome, Rett syndrome, spasticity, Sydenham's chorea, other choreas, athetosis, ballism, stereotypy, tardive dyskinesia/dystonia, tics, Tourette's syndrome, olivopontocerebellar atrophy (OPCA), diffuse Lewy body disease, hemibalismus, hemi-facial spasm, restless leg syndrome, Wilson's disease, stiff man syndrome, akinetic mutism, psychomotor retardation, painful legs moving toes syndrome, a gait disorder, a drug-induced movement disorder, or other movement disorder.

The methods and compositions of the present invention may be used to treat or otherwise reduce the severity of behavioral disorders such as attention deficit disorder (ADD), attention deficit hyperactivity disorder (ADHD), and cognitive disorders such as dementias (including age related dementia, HIV-associated dementia, AIDS dementia complex (ADC), HIV encephalopathy and senile dementia). Characteristics of ADHD have been demonstrated to arise in early childhood for most individuals. This disorder is marked by chronic behaviors lasting at least six months with an onset often before seven years of age.

The methods, compounds, and compositions of the present invention may be used as part of therapy for treating patients displaying autistic disorders.

The methods, compounds, and compositions of the present invention may be used as part of therapy for patients displaying dyssomnias, parasomnias, sleep disorders associated with medical or psychiatric conditions, or other sleep disorders. In certain preferred embodiments, the dyssomnias are selected from intrinsic sleep disorders, extrinsic sleep disorders, and circadian rhythm sleep disorders. Examples of intrinsic sleep disorders may include psychophysiological insomnia, sleep state misperception, idiopathic insomnia, narcolepsy, recurrent hypersomnia, idiopathic hypersomnia, posttraumatic hypersomnia, obstructive sleep apnea syndrome, central sleep apnea syndrome, central alveolar hypoventilation, periodic limb movement disorder, restless leg syndrome (RLS), etc. Examples of extrinsic sleep disorders may include inadequate sleep hygiene, environmental sleep disorder, altitude insomnia, adjustment sleep disorder, insufficient sleep syndrome, limit-setting sleep disorder, sleep-onset association disorder, food allergy insomnia, nocturnal eating/drinking syndrome, hypnotic-dependent sleep disorder, stimulant-dependent sleep disorder, alcohol-dependent sleep disorder, toxin-induced sleep disorder, etc. Examples of circadian rhythm sleep disorders may include time-zone change (jet lag) syndrome, shift-work sleep disorder, irregular sleep/wake pattern, delayed sleep-phase syndrome, advanced sleep-phase syndrome, non-24-hour sleep/wake disorder, etc.

In certain embodiments, the present invention contemplates the treatment or prevention of amnesia. Complaints of memory problems are common. Poor concentration, poor arousal and poor attention all may disrupt the memory process to a degree. The subjective complaint of memory problems therefore must be distinguished from true amnesias. This is usually done at the bedside in a more gross evaluation and through specific neuropsychological tests. Defects in visual and verbal memory may be separated through such tests. In amnesias there is by definition a preservation of other mental capacities such as logic. The neurobiologic theory of memory would predict that amnesias would have relatively few pathobiologic variations. Clinically the problem of amnesias often appears as a result of a sudden illness in an otherwise healthy person. Amnesias are described as specific defects in declarative memory. Faithful encoding of memory requires a registration, rehearsal, and retention of information. The first two elements appear to involve the hippocampus and medial temporal lobe structures. The retention or storage appears to involve the heteromodal association areas. Amnesia may be experienced as a loss of stored memory or an inability to form new memories. The loss of stored memories is known as retrograde amnesia. The inability to form new memories is known as anterograde amnesia.

Exemplary forms of amnesias which may be treated by the present invention include amnesias of short duration, alcoholic blackouts, Wernicke-Korsakoff's (early), partial complex seizures, transient global amnesia, those which are related to medication, such as triazolam (Halcion), and basilar artery migraines. The present invention may also be used to treat amnesias of longer duration, such as post concussive or as the result of Herpes simplex encephalitis.

The methods and compositions of the present invention may be used to treat or otherwise reduce the severity of any other CNS related condition. Such conditions may include, for example, learning disabilities, memory-loss conditions, eating disorders, or drug addiction (e.g., nicotine addiction). In certain embodiments, the CNS-related condition is not a neurodegenerative disease and/or a movement disorder.

The present invention may also be used to treat normal individuals for whom improved declarative memory is desired.

Certain embodiments of the present invention relate to a method for treating any of the disorders described above, more specifically depression and ADHD (adult or child), comprising co-administering (e.g., simultaneously or at different times) to the subject an amount of a present compound sufficient to treat the attention component of ADHD, and optionally an amount of a dopamine reuptake inhibitor sufficient to treat the movement disorder component. Activating the hedgehog pathway is expected to positively modulate appropriate neurogenesis and augment synaptic transmission, alleviating symptoms of ADHD that stems from deficient neuronal signaling. In certain embodiments, the present compound and the dopamine reuptake inhibitor are administered simultaneously. In certain embodiments, the present compound and the dopamine reuptake inhibitor are administered as part of a single composition. In certain embodiments, the composition is for oral administration or for transdermal administration.

Furthermore, one aspect of the present invention may relate to the methods and compositions using a combination of a present compound and a dopamine re-uptake inhibitor. A variety of dopamine transporter inhibitors (also called dopamine uptake inhibitors; herein referred to as active compounds) of diverse structure are known. See, e.g., S. Berger, U.S. Pat. No. 5,217,987; J. Boja et al. (1995) *Molec. Pharmacol.* 47: 779-786; C. Xu et al. (1995) *Biochem. Pharmacol.* 49: 339-50; B. Madras et al. (1994) *Eur. J. Pharmacol.* 267: 167-73; F. Carroll et al. (1994) *J. Med. Chem.* 37: 2865-73; A. Eshleman et al. (1994) *Molec. Pharmacol.* 45: 312-16; R. Heikkila and L. Manzino (1984) *Eur. J. Pharmacol.* 103: 241-8. Dopamine transporter inhibitors are, in general, ligands that bind in a stereospecific manner to the dopamine transporter protein. Examples of such compounds are:

(1) tricyclic antidepressants such as buprion, nomifensine, and amineptin;

(2) 1,4-disubstituted piperazines, or piperazine analogs, such as 1-[2-[bis(4-fluorophenyl)methoxy]ethyl]-4-(3-phenylpropyl)piperazine dihydrochloride (or GBR 12909), 1-[2-[bis(phenyl)methoxy]ethyl]-4-(3-phenylpropyl)piperazine dihydrochloride (for GBR12934), and GBR13069;

(3) tropane analogs, or (disubstituted phenyl) tropane-2 beta-carboxylic acid methyl esters, such as 3 [beta]-(4-fluorophenyl)tropane-2 [beta]-carboxylic acid methyl ester (or WIN 35,428) and 3 [beta]-(4-iodophenyl)tropane-2 [beta]-carboxylic acid isopropyl ester (RTI-121);

(4) substituted piperidines, or piperidine analogs, such as N-[1-(2-benzo[beta]-thiophenyl)cyclohexyl]piperidine, indatraline, and 4-[2-[bis(4-fluorophenyl)methoxy]ethyl]-1-(3-phenylpropyl)piperidine (or O-526);

(5) quinoxaline derivatives, or quinoxaline analogs, such as 7-trifluoromethyl-4-(4-methyl-1-piperazinyl)pyrrolo[1,2-[alpha]]-quinoxaline (or CGS 12066b); and (6) other compounds that are inhibitors of dopamine reuptake, such as mazindol, benztropine, bupropion, phencyclidine, methylphenidate, etc.

In addition to degenerative-induced dementias, a pharmaceutical preparation of one or more of the present compounds may be applied opportunely in the treatment or prevention of neurodegenerative disorders which have manifestations of tremors and involuntary movements. Parkinson's disease, for example, primarily affects subcortical structures and is characterized by degeneration of the nigrostriatal pathway, raphe nuclei, locus cereleus, and the motor nucleus of vagus. Ballism is typically associated with damage to the subthalmic nucleus, often due to acute vascular accident. Also included are neurogenic and myopathic diseases which ultimately affect the somatic division of the peripheral nervous system and are manifest as neuromuscular disorders. Examples include chronic atrophies such as amyotrophic lateral sclerosis, Guillain-Barre syndrome and chronic peripheral neuropathy, as well as other diseases which may be manifest as progressive bulbar palsies.

The present invention may be useful in the treatment or prevention of disorders of the cerebellum which result in hypotonia or ataxia, such as those lesions in the cerebellum which produce disorders in the limbs ipsilateral to the lesion. For instance, a preparation of a present compound may used to treat a restricted form of cerebellar cortical degeneration involving the anterior lobes (vermis and leg areas) such as is common in alcoholic patients.

In an illustrative embodiment, the present invention may be used to treat amyotrophic lateral sclerosis (ALS). ALS is a name given to a complex of disorders that comprise upper and lower motor neurons. Patients may present with progressive bulbar palsy, primary lateral sclerosis, or a combination of these conditions. The major pathological abnormality is characterized by a selective and progressive degeneration of the lower motor neurons in the spinal cord and the upper motor neurons in the cerebral cortex. The therapeutic application of a present compound may be used alone, or in conjunction with other neurotrophic factors such as CNTF, BDNF or NGF to prevent and/or reverse motor neuron degeneration in ALS patients. Recently it has been reported that in certain ALS patients and animal models a significant loss of midbrain dopaminergic neurons occurs in addition to the loss of spinal motor neurons. For instance, the literature describes degeneration of the substantia nigra in some patients with familial amyotrophic lateral sclerosis. Kostic et al. (1997) Ann Neurol 41:497-504. Accordingly, the present invention may provide a method for the treatment or prevention of ALS comprising administering one or more of the present compounds or compositions.

The compounds of the present invention may also be used in the treatment or prevention of autonomic disorders of the peripheral nervous system, which include disorders affecting the enervation of smooth muscle and endocrine tissue (such as glandular tissue). For instance, the present invention may be used to treat tachycardia or atrial cardiac arrhythmias which may arise from a degenerative condition of the nerves innervating the striated muscle of the heart.

For example, in some embodiments, the present invention provides methods of treatment or prevention, compounds, uses and pharmaceutical compositions that ameliorate, prevent or treat any one or more disease states of the cardiovascular tree (including the heart) and dependent organs (e.g.; retina, kidney, nerves, etc.). Diseases of the cardiovascular tree and diseases of dependent organs include, for example, but are not limited to any one or more of:

disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy;

atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries;

toxic, drug-induced, and metabolic (including hypertensive and/or diabetic disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; and, plaque rupture of atheromatous lesions of major blood vessels such as the aorta, the coronary arteries, the carotid arteries, the cerebrovascular arteries, the renal arteries, the iliac arteries, the fermoral arteries and the popliteal arteries.

Also included within the categories of diseases that may be ameliorated, prevented or treated according to methods, compounds, and compositions of the present invention are, for example, any one or more of the following non-exhaustive list: diabetic acute coronary syndrome (e.g.; myocardial infarction—MI), diabetic hypertensive cardiomyopathy, acute coronary syndrome associated with impaired glucose tolerance (IGT), acute coronary syndrome associated with impaired fasting glucose (IFG), hypertensive cardiomyopathy associated with IGT, hypertensive cardiomyopathy associated with IFG, ischemic cardiomyopathy associated with IGT, ischemic cardiomyopathy associated with IFG, ischemic cardiomyopathy associated with coronary heart disease (CHD), acute coronary syndrome not associated with any abnormality of the glucose metabolism, hypertensive cardiomyopathy not associated with any abnormality of the glucose metabolism, ischemic cardiomyopathy not associated with any abnormality of the glucose metabolism (irrespective of whether or not such ischemic cardiomyopathy is associated with coronary heart disease or not), and any one or more disease of the vascular tree including, by way of example, disease states of the aorta, carotid, cerebrovascular, coronary, renal, retinal, vasa nervorum, iliac, femoral, popliteal, arteriolar tree and capillary bed.

Other disorders that may be treatable by compounds, compositions, and methods described herein include, for example, pulmonary hypertension including persistent pulmonary hypertension in human babies and primary and secondary pulmonary hypertension in human adults, acute respiratory distress syndrome (ARDS), asthma, cystic fibrosis, respiratory failure, angina, myocardial infarction, heart failure, hypertension, heart attack and stroke.

Additional disorders that may be treatable by compounds, compositions, and methods described herein include, for example, stable and unstable angina pectoris, coronary heart disease, Prinzmetal angina (spasm), acute coronary syndrome, heart failure, myocardial infarction, stroke, thrombosis, peripheral artery occlusive disease (PAOD), endothelial dysfunction, atherosclerosis, restenosis, endothelial damage after PTCA, hypertension including essential hypertension, pulmonary hypertension, and secondary hypertension (renovascular hypertension, chronic glomerulonephritis), erectile dysfunction, ventricular arrhythmia, and the lowering of cardiovascular risk of postmenopausal women or after intake of contraceptives.

Yet further disorders that may be treatable by compounds, compositions, and methods described herein include, for example, atrial and ventricular arrhythmias, Prinzmetal's (variant) angina, stable angina, ischemia and reperfusion injury in cardiac, kidney, liver and the brain, exercise induced angina, congestive heart disease, myocardial infarction, and Coronary Heart Disease Risk Factor (CHDRF) syndrome.

Furthermore, a potential role for certain of the present compounds derives from the role of hedgehog proteins in development and maintenance of dendritic processes of axonal neurons. Potential roles for the present compounds consequently include guidance for axonal projections and the ability to promote differentiation and/or maintenance of the innervating cells to their axonal processes. Accordingly, compositions comprising the present compounds may be employed to support the survival and reprojection of several types of ganglionic neurons sympathetic and sensory neurons as well as motor neurons. In particular, such therapeutic compositions may be useful in treatments designed to rescue, for example, various neurons from lesion-induced death as well as guiding reprojection of these neurons after such damage. Such diseases include, but are not limited to, CNS trauma infarction, infection (such as viral infection with varicella-zoster), metabolic disease, nutritional deficiency, toxic agents (such as cisplatin treatment).

As appropriate, the present invention may also be used in generating nerve prostheses for the repair of central and peripheral nerve damage. In particular, where a crushed or severed axon is intubulated by use of a prosthetic device, the present compounds may be added to the prosthetic device to regulate the rate of growth and regeneration of the dendritic processes. Exemplary nerve guidance channels are described in U.S. Pat. Nos. 5,092,871 and 4,955,892.

The present invention may have wide applicability to the treatment or prophylaxis of disorders affecting the regulation of peripheral nerves, including peripheral ganglionic neurons, sympathetic, sensory neurons, and motor neurons. In general, the present method may be characterized as including a step of administering to an animal an amount of a present compound or composition effective to alter the proliferative and/or differentiation state of treated peripheral nerve cells. Such therapeutic compositions may be useful in treatments designed to rescue, for example, retinal ganglia, inner ear and acoustical nerves, and motor neurons, from lesion-induced death as well as guiding reprojection of these neurons after such damage. Such diseases and conditions include, but are not limited to, chemical or mechanical trauma, infection (such as viral infection with varicella-zoster), metabolic disease such as diabetes, nutritional deficiency, and toxic agents (such as cisplatin treatment). The goals of treatment in each case may be twofold: (1) to eliminate the cause of the disease and (2) to relieve its symptoms.

Peripheral neuropathy is a condition involving nerve-ending damage in the hands and feet. Peripheral neuropathy generally refers to a disorder that affects the peripheral nerves, most often manifested as one or a combination of motor, sensory, sensorimotor, or autonomic neural dysfunction. The wide variety of morphologies exhibited by peripheral neuropathies may each be uniquely attributed to an equally wide variety of causes. For instance, peripheral neuropathies may be genetically acquired, may result from a systemic disease, or may be induced by a toxic agent. Some toxic agents that cause neurotoxicities are therapeutic drugs, antineoplastic agents, contaminants in foods or medicinals, and environmental and industrial pollutants. The present compounds and compositions may also be used in the treatment or prevention of peripheral neuropathies, such as those described herein.

In particular, chemotherapeutic agents known to cause sensory and/or motor neuropathies include vincristine, an antineoplastic drug used to treat hematological malignancies and sarcomas. The neurotoxicity is dose-related, and exhibits as reduced intestinal motility and peripheral neuropathy, especially in the distal muscles of the hands and feet, postural hypotension, and atony of the urinary bladder. Similar problems have been documented with taxol and cisplatin (Mollman, J. E., 1990, New Eng Jour Med. 322:126-127), although cisplatin-related neurotoxicity may be alleviated with nerve growth factor (NGF) (Apfel, S. C. et al, 1992, Annals of Neurology 31:76-80). Although the neurotoxicity is sometimes reversible after removal of the neurotoxic agent, recovery may be a very slow process (Legha, S., 1986, Medical Toxicology 1:421-427; Olesen, et al., 1991, Drug Safety 6:302-314).

There are a number of inherited peripheral neuropathies, including: Refsum's disease, abetalipoproteinemia, Tangier disease, Krabbe's disease, metachromatic leukodystrophy, Fabry's disease, Dejerine-Sottas syndrome, and others. Of all the inherited neuropathies, the most common by far is Charcot-Marie-Tooth disease.

Charcot-Marie-Tooth (CMT) Disease (also known as peroneal muscular atrophy, or hereditary motor sensory neuropathy (HMSN)) is a common hereditary neurological disorder. It is characterized by weakness and atrophy, primarily of the peroneal muscles, due to segmental demyelination of peripheral nerves and associated degeneration of axons and anterior horn cells. Autosomal dominant inheritance is usual, and associated degenerative CNS disorders, such as Friedreich's ataxia, are common.

In one aspect, the present invention may be useful in the treatment or prevention and maintenance of hereditary neuropathies, such as CMT and others described herein. This group of neuropathies is now becoming increasingly recognized due to the dramatic advances in molecular genetics. The symptoms of the various hereditary neuropathies are wide-ranging. A common denominator is usually the early onset of mild numbness and tingling in the feet that slowly progresses to involve the legs and the hands and later the rest of the upper extremities. Most of the hereditary neuropathies do have a motor component consisting of distal weakness in the lower and upper extremities. A majority of patients with hereditary neuropathies have high arches in their feet or other bony deformities. The symptoms are very slowly progressive and the majority of the patients are still walking two decades after the onset of their symptoms.

The diagnosis of a hereditary neuropathy is usually suggested with the early onset of neuropathic symptoms, especially when a positive family history is also present. Prior to the recent genetic advances, the diagnosis was supported by typical findings of marked slowing of the nerve conduction studies on electromyography and a nerve biopsy. Typical findings on a nerve biopsy include the presence of so-called onion-bulbs, indicating a recurring demyelinating and remyelinating of the nerve fibers. With the most recent genetic advances, major hereditary neuropathies, such as CMT disease and hereditary neuropathy with liability to pressure palsies may be diagnosed with a simple blood test that identifies the different mutations responsible for these two entities.

Hereditary neuropathies are caused by genetic abnormalities which are transmitted from generation to generation. For several of these, the genetic defect is known, and tests are available for diagnosis and prenatal counseling.

As set forth above, the present invention may be used as part of a therapeutic regimen in the treatment or prevention of CMT disease. This is a general term given to the hereditary sensorimotor neuropathies. CMT type 1 (CMT 1) is associated with demyelination or breakdown of the myelin sheaths. Several different abnormalities have been identified. CMT Type 1A is most commonly caused by duplication of A gene encoding a myelin protein called PMP-22, and CMT type 1B is caused by a mutation in a myelin protein called the Po glycoprotein. CMTX is a hereditary sensorimotor neuropathy which primarily affects men. It is caused by a mutation in A gene encoding a protein called Connexin 32 on the X-chromosome.

In another embodiment, the present invention may be used in the treatment or prevention of familial amyloidotic neuropathy and other related hereditary neuropathies. Amyloidotic neuropathy usually presents with pain, sensory loss and autonomic dysfunction. It is caused by a mutation in a protein called Transthyretin, resulting in deposition of the protein as amyloid in the peripheral nerves.

The present invention may be used in the treatment or prevention of hereditary porphyria, which may have components of peripheral neuropathy. Still another hereditary neuropathy for which the present invention may be used for treatment or prevention is hereditary sensory neuropathy Type II (HSN II). The methods, compounds, and compositions of the present invention may also be used in the treatment or prevention and maintenance of acquired neuropathies.

For example, the present compounds may be used to prevent diabetic neuropathies. Diabetes is the most common known cause of neuropathy. It produces symptoms in approximately 10% of people with diabetes. In most cases, the neuropathy is predominantly sensory, with pain and sensory loss in the hands and feet. But some diabetics have mononeuritis or mononeuritis multiplex which causes weakness in one or more nerves, or lumbosacral plexopathy or amyotrophy which causes weakness in the legs.

The present invention may also be used in the treatment or prevention of immune-mediated neuropathies. The main function of the immune system is to protect the body against infectious organisms which enter from outside. In some cases, however the immune system turns against the body and causes autoimmune disease. The immune system consists of several types of white blood cells, including T-lymphocytes, which also regulate the immune response; and B-lymphocytes or plasma cells, which secrete specialized proteins called antibodies. Sometimes, for unknown reasons, the immune system mistakenly attacks parts of the body such as the peripheral nenes. This is "autoimmune" Peripheral Neuropathy. There are several different types, depending on the part of the peripheral nerve which is attacked and the type of the immune reaction.

Thus, the present compounds may be used either locally or systemically to modulate the proliferation, maturation/differentiation, migration, and function of immune and inflammatory cells such as T lymphocytes, B lymphocytes, natural Killer cells, monocytes, macrophages, dendritic cells and other antigen presenting cells, and granulocytes as well as non-white cell regulatory cells (e.g., epithelial cells) in immune tissues such as the thymus, spleen, lymph nodes, and bone marrow.

In another aspect of the present invention, the present compounds may be used either locally or systemically to promote the repair of the lymphatic vascular system which may be damaged by surgery or other conditions resulting in a compromised lymph flow, such as lymphedema.

For instance, a present compound may be used to treat Guillain-Barre syndrome (GBS), an acute neuropathy that comes on suddenly or rapidly. Guillain-Barre syndrome may progress to paralysis and respiratory failure within days or weeks after onset. The neuropathy is caused when the immune system destroys the myelin sheaths of the motor and sensory nerves. It is often preceded by infection, vaccination or trauma, and that is thought to be what triggers the autoimmune reaction. The disease is self-limiting, with spontaneous recovery within six to eight weeks. But the recovery is often incomplete.

Other neuropathies which begin acutely, and which may be treated by the present invention, include acute motor neuropathy, acute sensory neuropathy, and acute autonomic neuropathy, in which there is an immune attack against the motor, sensory or autonomic nerves, respectively. The Miller-Fisher syndrome is another variant in which there is paralysis of eye gaze, incoordination, and unsteady gait.

Still another acquired neuropathy which may be treated by the present invention is chronic inflammatory demyelinating polyneuropathy (CIDP). CIDP is thought to be a chronic and more indolent form of the Guillain-Barre syndrome. The disease progresses either with repeated attacks, called relapses, or in a stepwise or steady fashion. As in GBS, there appears to be destruction of the myelin sheath by antibodies and T-lymphocytes. But since there is no specific test for CIDP, the diagnosis is based on the clinical and laboratory characteristics.

Chronic polyneuropathies with antibodies to peripheral nerves is still another peripheral neuropathy for which the present invention may be employed to treat or prevent. In some types of chronic neuropathies, antibodies to specific components of nerve have been identified. These include demyelinating neuropathy associated with antibodies to the myelin associated glycoprotein (MAG), motor neuropathy associated with antibodies to the gangliosides GM1 or GD1a, and sensory neuropathy associated with anti-sulfatide or GD1b ganglioside antibodies. The antibodies in these cases bind to oligosaccharide or sugar like molecules, which are linked to proteins (glycoproteins) or lipids (glycolipids or gangliosides) in the nerves. It is suspected that these antibodies may be responsible for the neuropathies.

The present invention may also be used as part of a therapeutic plan for treating neuropathies associated with vasculitis or inflammation of the blood vessels in peripheral nerves. Neuropathy may also be caused by vasculitis—an inflammation of the blood vessels in peripheral nerve. It produces small "strokes" along the course of the peripheral nerves, and may be restricted to the nerves or it may be generalized, include a skin rash, or involve other organs. Several rheumatological diseases like rheumatoid arthritis, lupus, periarteritis nodosa, or Sjogren's syndrome, are associated with generalized vasculitis, which may also involve the peripheral nerves. Vasculitis may cause polyneuritis, mononeuritis, or mononeuritis multiplex, depending on the distribution and severity of the lesions.

In still another embodiment, the present invention may be useful for treatment or prevention of brachial or lumbosacral plexitis. The brachial plexus, which lies under the armpit, contains the nerves to the arm and hand. Brachial plexitis is the result of inflammation of that nerve bundle, and produces weakness and pain in one or both arms. Umbosacral plexitis, which occurs in the pelvis, causes weakness and pain in the legs.

The present compounds may also be useful in the treatment or prevention of neuropathies associated with monoclonal gammopathies. In monoclonal gammopathy, single clones of B-cells or plasma cells in the bone marrow or lymphoid organs expand to form benign or malignant tumors and secrete antibodies. "Monoclonal" is because there are single clones of antibodies, and "gammopathy" stands for gamma-globulins, which is another name for antibodies. In some cases, the antibodies react with nerve components; in others, fragments of the antibodies form amyloid deposits.

Yet another aspect of the present invention relates to the treatment or prevention of neuropathies associated with tumors or neoplasms. Neuropathy may be due to direct infiltration of nerves by tumor cells or to indirect effect of the tumor. The latter is called paraneoplastic neuropathy. Several types have been described. For instance, the present invention may be used to manage sensory neuropathy associated with lung cancer. This neuropathy is associated with antibodies to a protein called Hu, which is present in the sensory neurons of the peripheral nerves. Likewise, the present invention may be used to treat neuropathies associated with multiple myeloma, myeloma, plasma cell myeloma, or Kahler's disease. Multiple myeloma is a bony tumor which is caused by antibody-secreting plasma cells in the bone marrow. The tumor is made up of a single clone of plasma cells, and the antibodies they produce are identical or monoclonal. Some people with multiple myeloma develop sensorimotor polyneuropathy with degeneration of axons in the peripheral nerves. In other embodiments, the present invention may be used to treat neuropathies associated with Waldenstrom's macroglobulemia, chronic lymphocytic leukemia, or B-cell lymphoma. These are tumors caused by antibody-secreting B-lymphocytes in the spleen, bone marrow or lymph nodes. These antibodies are monoclonal and frequently react with peripheral nerve components such as MAG, GM1, or sulfatide. In still other embodiments, the compounds of the present invention may be used as part of therapeutic protocol for the treatment of patients with cancers where neuropathy is a consequence of local irradiation or be caused by medications such as vincristine and cisplatin.

The present invention also contemplates the use of the present compounds for the treatment or prevention of neuropathies associated with amyloidosis. Amyloid is a substance deposited in the peripheral nerves and interferes with their operation: the disorder is amyloidosis. There are two main types: primary amyloidosis, in which the deposits contain fragments of monoclonal antibodies (see monoclonal gammopathy above); and hereditary amyloidosis in which the deposits contain a mutated protein called Transthyretin. Primary amyloidosis is usually associated with monoclonal gammopathies or myeloma.

Still another aspect of the present invention may provide the present invention as a means for treating neuropathies caused by infections. Peripheral neuropathies may be caused by infection of the peripheral nerves. Viruses that cause peripheral neuropathies include the AIDS virus, HIV-I, which causes slowly progressive sensory neuropathy, Cytomegalovirus which causes a rapidly progressive paralytic neuropathy, Herpes zoster which cause shingles, and poliovirus which causes a motor neuropathy. Hepatitis B or C infections are sometimes associated with vasculitic neuropathy.

Bacterial infections that cause neuropathy include leprosy, which causes a patchy sensory neuropathy, and diphtheria which may cause a rapidly progressive paralytic neuropathy. Other infectious diseases that cause neuropathy include Lyme disease, which is caused by a spirochete, and trypanosomiasis which is caused by a parasite. Both commonly present with a multifocal neuropathy Neuropathies caused by nutritional imbalance are also candidate disorders for treatment by the present invention. Deficiencies of vitamins B12, B1 (thiamine), B6 (pyridoxine), or E, for example, may produce polyneuropathies with degeneration of peripheral nerve axons. This may be due to poor diet, or inability to absorb the nutrients from the stomach or gut. Moreover, megadoses of vitamin B6 may also cause a peripheral neuropathy, and the present invention may be used as part of a detoxification program in such cases.

Yet another use of the present invention may be in the treatment or prevention of neuropathies arising in kidney diseases. Chronic renal failure may cause a predominantly sensory peripheral neuropathy with degeneration of peripheral nerve axons.

Another aspect of the present invention provides a method for treating hypothyroid neuropathies. Hypothyroidism is sometimes associated with a painful sensory polyneuropathy with axonal degeneration. Mononeuropathy or mononeuropathy multiplex may also occur due to compression of the peripheral nerves by swollen tissues.

The present invention may also be used in the treatment or prevention of neuropathies caused by alcohol and toxins. Certain toxins may cause peripheral neuropathy. Lead toxicity is associated with a motor neuropathy; arsenic or mercury cause a sensory neuropathy, and thallium may cause a sensory and autonomic neuropathy. Several organic solvents and insecticides may also cause polyneuropathy. Alcohol is directly toxic to nerves and alcohol abuse is a major cause of neuropathy. The present invention may be used, in certain embodiments, as part of a broader detoxification program.

In still another embodiment, the methods and compositions of the present invention may be used for the treatment or prevention of neuropathies caused by drugs. Several drugs are known to cause neuropathy. They include, among others, vincristine and cisplatin in cancer, nitrofurantoin, which is used in pyelonephritis, amiodarone in cardiac arrhythmias, disulfuram in alcoholism, ddC and ddI in AIDS, and dapsone which is used to treat leprosy. As above, the present invention may be used, in certain embodiments, as part of a broader detoxification program.

The present invention may also be used in the treatment or prevention of neuropathies caused by trauma or compression. Localized neuropathies may result from compression of nerves by external pressure or overlying tendons and other tissues. The best known of these are the carpal tunnel syndrome which results from compression at the wrist, and cervical or lumbar radiculopathies (sciatica) which result from compression of nerve roots as they exit the spine. Other common areas of nerve compression include the elbows, armpits, and the back of the knees.

The present invention may also be useful in variety of idiopathic neuropathies. The term "idiopathic" is used whenever the cause of the neuropathy may not be found. In these cases, the neuropathy is classified according to its manifestations, i.e., sensory, motor, or sensorimotor idiopathic polyneuropathy.

The present invention may have wide applicability to the treatment or prophylaxis of disorders afflicting muscle tissue. In general, the method may be characterized as including a step of administering to an animal an amount of a present compound effective to alter the proliferative state of a treated muscle tissue. The mode of administration and dosage regimens will vary depending on the muscle tissue(s) which is to be treated.

In one aspect, the present invention may be directed to a muscle-trophic factor, and its use in stimulating muscle growth or differentiation in mammals. Such stimulation of muscle growth may be useful for treating atrophy, or wasting, in particular, skeletal muscle atrophy and cardiac muscle atrophy. In addition, certain diseases wherein the muscle tissue is damaged, is abnormal or has atrophied, may be treatable using the present invention, such as, for example, normal aging, disuse atrophy, wasting or cachexia, and various secondary disorders associated with age and the loss of muscle mass, such as hypertension, glucose intolerance and diabetes, dyslipidemia and atherosclerotic cardiovascular disease. The treatment or prevention of muscular myopathies such as muscular dystrophies may also be embodied in the present invention.

With denervation or disuse, skeletal muscles undergo rapid atrophy which leads to a profound decrease in size, protein content and contractile strength. This atrophy is an important component of many neuromuscular diseases in humans. In a clinical setting, compositions comprising the present compounds may be used for inhibiting muscle degeneration, e.g., for decreasing the loss of muscle mass, such as part of treatment or prevention of such muscle wasting disorders.

In some embodiments, pharmaceutical compositions according to the present invention are administered to patients displaying a disorder, i.e., an abnormal physical condition, a disease or pathophysiological condition associated with abnormal and/or aberrant regulation of muscle tissue. Some disorders for which the compositions of the present invention may be administered are preferably those which directly or indirectly produce a wasting (i.e., loss) of muscle mass, that is, a muscle wasting disorder. These include muscular dystrophies, cardiac cachexia, emphysema, leprosy, malnutrition, osteomalacia, child acute leukemia, AIDS cachexia and cancer cachexia.

The muscular dystrophies are genetic diseases which are characterized by progressive weakness and degeneration of muscle fibers without evidence of neural degeneration. In Duchenne muscular dystrophy (DMD) patients display an average of a 67% reduction in muscle mass, and in myotonic dystrophy, fractional muscle protein synthesis has been shown to be decreased by an average of 28%, without any corresponding decrease in non-muscle protein synthesis (possibly due to impaired end-organ response to anabolic hormones or substrates). Accelerated protein degradation has been demonstrated in the muscles of DMD patients. The present invention may be used as part of a therapeutic strategy for preventing, and in some instance reversing, the muscle wasting conditions associated with such dystrophies.

Severe congestive heart failure (CHF) is characterized by a "cardiac cachexia," i.e., a muscle protein wasting of both the cardiac and skeletal muscles, with an average 19% body weight decrease. The cardiac cachexia is caused by an increased rate of myofibrillar protein breakdown. The present invention may be used as part of a treatment or prevention for cardiac cachexia.

Emphysema is a chronic obstructive pulmonary disease, defined by an enlargement of the air spaces distal to the terminal non-respiratory bronchioles, accompanied by destructive changes of the alveolar walls. Clinical manifestations of reduced pulmonary functioning include coughing, wheezing, recurrent respiratory infections, edema, and functional impairment and shortened lifespan. The efflux of tyrosine is increased by 47% in emphysematous patients. Also, whole body leucine flux remains normal, whole-body leucine oxidation is increased, and whole-body protein synthesis is decreased. The result is a decrease in muscle protein synthesis, accompanied by a decrease in whole body protein turnover and skeletal muscle mass. This decrease becomes increasingly evident with disease progression and long-term deterioration. The present compounds may be used to prevent and/or reverse, the muscle wasting conditions associated with such diseases.

In diabetes mellitus, there is a generalized wasting of small muscle of the hands, which is due to chronic partial denervation (neuropathy). This is most evident and worsens with long-term disease progression and severity. The present invention may be used as part of a therapeutic strategy for treatment or prevention of diabetes mellitus.

Leprosy is associated with a muscular wasting which occurs between the metacarpals of the thumb and index finger. Severe malnutrition is characterized by, inter alia, severe muscle wasting. The present invention may be used to treat muscle-wasting effects of leprosy.

Osteomalacia is a nutritional disorder caused by a deficiency of vitamin D and calcium. It is referred to as "rickets" in children, and "osteomalacia" in adults. It is marked by a softening of the bones (due to impaired mineralization, with excess accumulation of osteoid), pain, tenderness, muscle wasting and weakness, anorexia, and overall weight loss. It may result from malnutrition, repeated pregnancies and lactation (exhausting or depleting vitamin D and calcium stores), and vitamin D resistance. The present invention may be used as part of a therapeutic strategy for treatment or prevention of osteomalacia.

In childhood acute leukemia there is protein energy malnutrition which results in skeletal muscle wasting. Studies have shown that some children exhibit the muscle wasting even before diagnosis of the leukemia, with an average 27% decrease in muscle mass. There is also a simultaneous 33%-37% increase in adipose tissue, resulting in no net change in relative body weight and limb circumference. Such patients may be amenable to treatment with a present compound or composition.

Cancer cachexia is a complex syndrome which occurs with variable incidence in patients with solid tumors and hematological malignancies. Clinically, cancer cachexia is manifested as weight loss with massive depletion of both adipose tissue and lean muscle mass, and is one cause of death which results from cancer. Cancer cachexia patients have shorter survival times, and decreased response to chemotherapy. In addition to disorders which produce muscle wasting, other circumstances and conditions appear to be linked in some fashion with a decrease in muscle mass. Such afflictions include muscle wasting due to chronic back pain, advanced age, long-term hospitalization due to illness or injury, alcoholism and corticosteroid therapy. The present invention may be used as part of a therapeutic strategy for preventing, and in some instance reversing, the muscle wasting conditions associated with such cancers.

Studies have shown that in severe cases of chronic lower back pain, there is paraspinal muscle wasting. Decreasing paraspinal muscle wasting alleviates pain and improves function. A course of treatment or prevention for disorder may include administration of a therapeutic amount of a present compound.

It is also believed that general weakness in old age is due to muscle wasting. As the body ages, an increasing proportion of skeletal muscle is replaced by fibrous tissue. The result is a significant reduction in muscle power, but only a marginal reduction in fat-free mass. The present invention may be used as part of a treatment and preventive strategies for preventing/reversing muscle wasting in elderly patients.

Studies have also shown that in patients suffering injuries or chronic illnesses, and hospitalized for long periods of time, there is long-lasting unilateral muscle wasting, with an average 31% decrease in muscle mass. Studies have also shown that this may be corrected with intensive physiotherapy. However, it may be more effective for many patients to at least augment such therapies with treatment by the present invention In alcoholics there is wasting of the anterior tibial muscle. This proximal muscle damage is caused by neurogenic damage, namely, impaired glycolytic and phosphorylase enzyme activity. The damage becomes apparent and worsens the longer the duration of the alcohol abuse. Patients treated with corticosteroids experience loss of muscle mass. Such patients may also be amenable to treatment by the present invention.

The compounds of the present invention may be used to alleviate the muscle mass loss resulting from the foregoing conditions, as well as others. Additionally, the compounds of the present invention may be useful in veterinary and animal husbandry applications to counter weight loss in animals, or to promote growth. For instance, the present invention may also find use for increasing the efficiency of animal meat production. Specifically, animals may be fed or injected with a present compound in order to increase overall skeletal muscle mass, e.g., to increase the weight of such farm animals as cows, pigs, sheep, chickens and salmon.

The maintenance of tissues and organs ex vivo is also highly desirable. Tissue replacement therapy is well established in the treatment of human disease. There are many situations where one may wish to implant muscle cells, especially muscle stem cells, into a recipient host where the recipient's cells are missing, damaged or dysfunctional muscle cells in muscle wasting disease. For example, implantation of normal myoblasts may be useful to treat Duchenne muscular dystrophy and other muscle degeneration and wasting diseases. See, for example, Partridge (1991) *Muscle & Nerve* 14:197-212. In the case of myoblasts, they may be injected at various sites to treat muscle-wasting diseases.

The present invention may be used to regulate the growth of muscle cells and tissue in vitro, as well as to accelerate the grafting of implanted muscle tissue to an animal host. In this regard, the present invention also concerns myoblast cultures which have been expanded by treatment with a present compound. In an illustrative embodiment, such a method comprises obtaining a muscle sample, preferably one including myoblasts; optionally treating the cell sample enzymically to separate the cells; culturing, in the presence of a present compound.

Yet another aspect of the present invention may concern the observation in the art that patched, hedgehog, and/or smoothened are involved in morphogenic signals involved in other vertebrate organogenic pathways in addition to neuronal differentiation as described above, having apparent roles in other endodermal patterning, as well as both mesodermal and endodermal differentiation processes. Thus, it is contemplated by the present invention that compositions comprising the present compounds may also be utilized for both cell culture and therapeutic methods involving generation and maintenance of non-neuronal tissue.

Given that the present invention may provide compounds, compositions, and methods of identifying agents that promote differentiation of cells to mesodermal and endodermal cell types, as well as neuronal cell types, the present compounds and compositions may be used in methods of treating injuries or diseases of those tissues. Injuries and diseases of tissues derived from the mesoderm or endoderm include, but are not limited to, myocardial infarction, osteoarthritis, rheumatoid arthritis, diabetes, diabetes mellitus, cirrhosis, polycystic kidney disease, inflammatory bowel disease, pancreatic diseases, pancreatitis (both acute and chronic), pancreatic insufficiency, liver diseases (both acute and chronic), hepatitis, obstructions of the liver or ducts of the liver (e.g., gall stones), fatty liver, genetic liver disorders (such as Hemochromatosis, biliary atresia, galactosemia, and Wilson's disease), Crohn's disease, cancer of any mesodermal or endodermal tissue (e.g., pancreatic cancer, Wilms tumor, soft cell carcinoma, bone cancer, breast cancer, prostate cancer, ovarian cancer, uterine cancer, liver cancer, colon cancer, etc), and injuries to any mesodermal or endodermal tissue including breaks, tears, bruises, lacerations, burns, toxicity, bacterial infection, and viral infection.

In one embodiment, the present invention makes use of the discovery that patched, hedgehog, and smoothened are apparently involved in controlling the development of stem cells responsible for formation of the digestive tract, liver, lungs, and other organs which derive from the primitive gut. Shh serves as an inductive signal from the endoderm to the mesoderm, which is critical to gut morphogenesis. Therefore, for example, the present compounds may be employed for regulating the development and maintenance of an artificial liver which may have multiple metabolic functions of a normal liver. In an one embodiment, the present invention may be used to regulate the proliferation and differentiation of digestive tube stem cells to form hepatocyte cultures which may be used to populate extracellular matrices, or which may be encapsulated in biocompatible polymers, to form both implantable and extracorporeal artificial livers.

In another embodiment, therapeutic compositions of the present compounds may be utilized in conjunction with implantation of such artificial livers, as well as embryonic liver structures, to regulate uptake of intraperitoneal implantation, vascularization, and in vivo differentiation and maintenance of the engrafted liver tissue.

In yet another embodiment, the present invention may be employed therapeutically to regulate such organs after physical, chemical or pathological insult. For instance, therapeutic compositions comprising the present compounds may be utilized in liver repair subsequent to a partial hepatectomy.

The generation of the pancreas and small intestine from the embryonic gut depends on intercellular signalling between the endodermal and mesodermal cells of the gut. In particular, the differentiation of intestinal mesoderm into smooth muscle has been suggested to depend on signals from adjacent endodermal cells. One candidate mediator of endodermally derived signals in the embryonic hindgut is Sonic hedgehog. See, for example, Apelqvist et al. (1997) *Curr Biol* 7:801-4. The Shh gene is expressed throughout the embryonic gut endoderm with the exception of the pancreatic bud endoderm, which instead expresses high levels of the homeodomain protein Ipf1/Pdx1 (insulin promoter factor 1/pancreatic and duodenal homeobox 1), an essential regulator of early pancreatic development. Apelqvist et al., supra, have examined whether the differential expression of Shh in the embryonic gut tube controls the differentiation of the surrounding mesoderm into specialized mesoderm derivatives of the small intestine and pancreas. To test this, they used the promoter of the Ipf1/Pdx1 gene to selectively express Shh in the developing pancreatic epithelium. In Ipf1/Pdx1-Shh transgenic mice, the pancreatic mesoderm developed into smooth muscle and interstitial cells of Cajal, characteristic of the intestine, rather than into pancreatic mesenchyme and spleen. Also, pancreatic explants exposed to Shh underwent a similar program of intestinal differentiation. These results provide evidence that the differential expression of endodermally derived Shh controls the fate of adjacent mesoderm at different regions of the gut tube.

In the context of the present invention, it is contemplated therefore that the present compounds may be used to control or regulate the proliferation and/or differentiation of pancreatic tissue both in vivo and in vitro.

There are a wide variety of pathological cell proliferative and differentiative conditions for which the compounds of the present invention may provide therapeutic benefits, with the general strategy being, for example, the correction of aberrant insulin expression, or modulation of differentiation. More generally, however, the present invention may relate to a method of inducing and/or maintaining a differentiated state, enhancing survival and/or affecting proliferation of pancreatic cells, by contacting the cells with the present compounds. For instance, it is contemplated by the present invention that, in light of the apparent involvement of patched, hedgehog, and smoothened in the formation of ordered spatial arrangements of pancreatic tissues, the present invention may be used as part of a technique to generate and/or maintain such tissue both in vitro and in vivo. For instance, modulation of the function of hedgehog may be employed in both cell culture and therapeutic methods involving generation and maintenance β-cells and possibly also for non-pancreatic tissue, such as in controlling the development and maintenance of tissue from the digestive tract, spleen, lungs, and other organs which derive from the primitive gut.

In one embodiment, the present invention may be used in the treatment or prevention of hyperplastic and neoplastic disorders effecting pancreatic tissue, particularly those characterized by aberrant proliferation of pancreatic cells. For instance, pancreatic cancers are marked by abnormal proliferation of pancreatic cells which may result in alterations of insulin secretory capacity of the pancreas. For instance, certain pancreatic hyperplasias, such as pancreatic carcinomas, may result in hypoinsulinemia due to dysfunction of β-cells or decreased islet cell mass. To the extent that aberrant patched, hedgehog, and smoothened signaling may be indicated in disease progression, the present compounds may be used to enhance regeneration of the tissue after anti-tumor therapy.

Moreover, manipulation of hedgehog signaling properties at different points may be useful as part of a strategy for reshaping/repairing pancreatic tissue both in vivo and in vitro. In one embodiment, the present invention makes use of the apparent involvement of patched, hedgehog, and smoothened in regulating the development of pancreatic tissue. In general, the present invention may be employed therapeutically to regulate the pancreas after physical, chemical or pathological insult. In yet another embodiment, the present invention may be applied to cell culture techniques, and in particular, may be employed to enhance the initial generation of prosthetic pancreatic tissue devices. Manipulation of proliferation and differentiation of pancreatic tissue, for example, by altering hedgehog activity, may provide a means for more carefully controlling the characteristics of a cultured tissue. In one embodiment, the present invention may be used to augment production of prosthetic devices which require β-islet cells, such as may be used in the encapsulation devices described in, for example, the Aebischer et al. U.S. Pat. No. 4,892,538, the Aebischer et al. U.S. Pat. No. 5,106,627, the Lim U.S. Pat. No. 4,391,909, and the Sefton U.S. Pat. No. 4,353,888. Early progenitor cells to the pancreatic islets are multipotential, and apparently coactivate all the islet-specific genes from the time they first appear. As development proceeds, expression of islet-specific hormones, such as insulin, becomes restricted to the pattern of expression characteristic of mature islet cells. The phenotype of mature islet cells, however, is not stable in culture, as reappearance of embryonic traits in mature β-cells may be observed. By utilizing the present compounds, the differentiation path or proliferative index of the cells may be regulated.

Furthermore, manipulation of the differentiative state of pancreatic tissue may be utilized in conjunction with implantation of artificial pancreas so as to promote implantation, vascularization, and in vivo differentiation and maintenance of the engrafted tissue. For instance, manipulation of hedgehog function to affect tissue differentiation may be utilized as a means of maintaining graft viability.

Bellusci et al. (1997) *Development* 124:53 report that Sonic hedgehog regulates lung mesenchymal cell proliferation in vivo. Accordingly, the present invention may be used to regulate regeneration of lung tissue, e.g., in the treatment or prevention of emphysema.

In still another embodiment of the present invention, compositions comprising the present compounds may be used in the in vitro generation of skeletal tissue, such as from skeletogenic stem cells, as well as the in vivo treatment or prevention of skeletal tissue deficiencies. The present invention particularly contemplates the use of the present compounds to regulate the rate of chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g., whether as a result of surgical intervention, removal of tumor, ulceration, implant, fracture, or other traumatic or degenerative conditions.

For instance, the present compounds and compositions may be used as part of a regimen for restoring cartilage function to a connective tissue. For example, the use of one or more of the present compounds or compositions for promoting cartilage production in vitro is contemplated. Such methods may be useful in, for example, the production of three-dimensional cartilage grafts to repair defects or lesions in cartilage tissue. Such methods may also be useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a Taxation of a joint by a torn ligament, misalignment of joints, bone fracture, or by hereditary disease. The present invention may also be useful for remodeling cartilage matrix, such as in plastic or reconstructive surgery, as well as periodontal surgery. The present invention may also be applied to improving a previous reparative procedure, for example, following surgical repair of a meniscus, ligament, or cartilage. Furthermore, it may prevent the onset or exacerbation of degenerative disease if applied early enough after trauma.

In one embodiment, the present invention comprises treating the afflicted connective tissue with a therapeutically sufficient amount of a present compound, for example, a compound selective for Indian hedgehog signal transduction, to regulate a cartilage repair response in the connective tissue by managing the rate of differentiation and/or proliferation of chondrocytes embedded in the tissue. Such connective tissues as articular cartilage, interarticular cartilage (menisci), costal cartilage (connecting the true ribs and the sternum), ligaments, and tendons may be particularly amenable to treatment in reconstructive and/or regenerative therapies using the present invention. As used herein, regenerative therapies may include treatment of degenerative states which have progressed to the point of which impairment of the tissue is obviously manifest, as well as preventive treatments of tissue where degeneration is in its earliest stages or imminent.

In an illustrative embodiment, the present invention may be used as part of a therapeutic intervention in the treatment of cartilage of a diarthroidal joint, such as a knee, an ankle, an elbow, a hip, a wrist, a knuckle of either a finger or toe, or a tempomandibular joint. The treatment may be directed to the meniscus of the joint, to the articular cartilage of the joint, or both. To further illustrate, the present invention may be used to treat a degenerative disorder of a knee, such as which might be the result of traumatic injury (e.g., a sports injury or excessive wear) or osteoarthritis. The present compounds may be administered as an injection into the joint with, for instance, an arthroscopic needle. In some instances, the injected agent may be in the form of a hydrogel or other slow release vehicle described above in order to permit a more extended and regular contact of the agent with the treated tissue.

In one aspect of the present invention, the present compounds may be used in a controlled-release system (e.g., gel or mesh) that is applied to damaged tissue, for example, damaged blood vessels or heart tissue in acute MI or chronic MI or any other heart disease where cytoprotection against further damage and/or the induction of repair mechanisms are therapeutic goals. Additional uses may include application of the present compounds to surgical bypass vascular graft attachment sites that involve either the vasculature of the heart or peripheral vascular tissue. Such controlled release systems may be used when the present compounds are combined with medical devices, for example, with stents and catheters. In certain embodiments, one or more of the present compounds or compositions is released from a medical device, such as a stent or catheter, in a controlled or sustained release fashion, for example, over a given time period such as a period of at least about 4, 8, 12, 24, 48, or 72 hours, over a period of at least about 1, 2, 3, 4, or 5 days, over a period of at least about 1, 2, or 3 weeks, or over a period of at least about 1, 2, 3, 4, 5, or 6 months.

The present invention further contemplates the use of the present compounds in the field of cartilage implantation and prosthetic device therapies. In certain applications of implanted and prosthetic devises problems may arise, for instance, because the characteristics of cartilage and fibrocartilage vary between different tissues: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By regulating the rate of chondrogenesis, the present invention may be used to particularly address this problem, by helping to adaptively control the implanted cells in the new environment and effectively resemble hypertrophic chondrocytes of an earlier developmental stage of the tissue.

In similar fashion, the present invention may be applied to enhancing both the generation of prosthetic cartilage devices and to their implantation. The need for improved treatment has motivated research aimed at creating new cartilage that is based on collagen-glycosaminoglycan templates (Stone et al. (1990) *Clin Orthop Relat Red* 252:129), isolated chondrocytes (Grande et al. (1989) *J Orthop Res* 7:208; and Takigawa et al. (1987) *Bone Miner* 2:449), and chondrocytes attached to natural or synthetic polymers (Walitani et al. (1989) *J Bone Jt Surg* 71B:74; Vacanti et al. (1991) *Plast Reconstr Surg* 88:753; von Schroeder et al. (1991) *J Biomed Mater Res* 25:329; Freed et al. (1993) *J Biomed Mater Res* 27:11; and the Vacanti et al. U.S. Pat. No. 5,041,138). For example, chondrocytes may be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells may be cultured in vitro until adequate cell volume and density has developed for the cells to be implanted. One advantage of the matrices is that they may be cast or molded into a desired shape on an individual basis, so that the final product closely resembles the patient's own ear or nose (by way of example), or flexible matrices may be used which allow for manipulation at the time of implantation, as in a joint.

In one embodiment of the present invention, the implants may be contacted with a present compound during certain stages of the culturing process in order to manage the rate of differentiation of chondrocytes and the formation of hypertrophic chondrocytes in the culture.

In another embodiment, the implanted device may be treated with a present compound in order to actively remodel the implanted matrix and to make it more suitable for its intended function. As set forth above with respect to tissue implants, the artificial implants suffer from the same deficiency of not being derived in a setting which is comparable to the actual mechanical environment in which the matrix is implanted. The ability to regulate the chondrocytes in the matrix by the present invention may allow the implant to acquire characteristics similar to the tissue for which it is intended to replace.

In yet another embodiment, the present invention may be used to enhance attachment of prosthetic devices. To illustrate, the present invention may be used in the implantation of a periodontal prosthesis, wherein the treatment of the surrounding connective tissue stimulates formation of periodontal ligament about the prosthesis.

In still further embodiments, the present invention may be employed as part of a regimen for the generation of bone (osteogenesis) at a site in the animal where such skeletal tissue is deficient. Indian hedgehog is particularly associated with the hypertrophic chondrocytes that are ultimately replaced by osteoblasts. For instance, administration of a compound or composition of the present invention may be employed as part of a method for regulating the rate of bone loss in a subject. For example, preparations comprising the present compounds may be employed, for example, to control endochondral ossification in the formation of a "model" for ossification. Therapeutic compositions including the present compounds may be supplemented, if required, with other osteoinductive factors, such as bone growth factors (e.g. TGF-b factors, such as the bone morphogenetic factors BMP-2 and BMP-4, as well as activin), and may also include, or be administered in combination with, an inhibitor of bone resorption such as estrogen, bisphosphonate, sodium fluoride, calcitonin, or tamoxifen, or related compounds.

In yet another embodiment of the present invention, a present compound may be used to regulate spermatogenesis. The hedgehog proteins, particularly Dessert hedgehog (Dhh), have been shown to be involved in the differentiation and/or proliferation and maintenance of testicular germ cells. Dhh expression is initiated in Sertoli cell precursors shortly after the activation of Sry (testicular determining gene) and persists in the testis into the adult. Males are viable but infertile, owing to a complete absence of mature sperm. Examination of the developing testis in different genetic backgrounds suggests that Dhh regulates both early and late stages of spermatogenesis. Bitgood et al. (1996) *Curr Biol* 6:298. In a particular embodiment, a present compound may be used as a fertility agent. In similar fashion, the compounds of the present invention may be useful for modulating normal ovarian function.

The present invention may also have wide applicability to the treatment or prophylaxis of disorders afflicting epithelial tissue, as well as in cosmetic uses. In general, a present method may be characterized as including a step of administering to an animal an amount of a present compound effective to alter the growth state of a treated epithelial tissue. The mode of administration and dosage regimens will vary depending on the epithelial tissue(s) which is to be treated. For example, topical formulations will be preferred where the treated tissue is epidermal tissue, such as dermal or mucosal tissues.

A method which "promotes the healing of a wound" results in the wound healing more quickly as a result of the treatment than a similar wound heals in the absence of the treatment. "Promotion of wound healing" may also mean that the method regulates the proliferation and/or growth of, inter alia, keratinocytes, or that the wound heals with less scarring, less wound contraction, less collagen deposition and more superficial surface area. In certain instances, "promotion of wound healing" may also mean that certain methods of wound healing have improved success rates, (e.g., the take rates of skin grafts,) when used together with one or more of the present compounds or compositions.

As described in further detail herein, the present invention may provide a method for promoting wound healing, comprising administering to a patient one or more of the present compounds or compositions. In certain instances, the patient is a human. In other instances, the patient is a non-human, for example, an ape, monkey, chimpanzee, dog, cat, or other domestic pet or livestock, such as horse, cow, pig, etc. In some applications, the one or more of the present compounds or compositions is administered orally. In other applications, the one or more present compounds or compositions is administered topically.

Complications are a constant risk with wounds that have not fully healed and remain open. Although most wounds heal quickly without treatment, some types of wounds resist healing. Wounds which cover large surface areas also remain open for extended periods of time. In one embodiment of the present invention, the present invention may be used to accelerate the healing of wounds involving epithelial tissues, such as resulting from surgery, burns, inflammation or irritation. Certain of the compounds of the present invention may also be applied prophylactically, such as in the form of a cosmetic preparation, to enhance tissue regeneration processes, e.g., of the skin, hair and/or fingernails.

Despite significant progress in reconstructive surgical techniques, scarring can be an important obstacle in regaining normal function and appearance of healed skin. This is particularly true when pathologic scarring such as keloids or hypertrophic scars of the hands or face causes functional disability or physical deformity. In the severest circumstances, such scarring may precipitate psychosocial distress and a life of economic deprivation. Wound repair includes the stages of hemostasis, inflammation, proliferation, and remodeling. The proliferative stage involves multiplication of fibroblasts and endothelial and epithelial cells. Through the use of the present invention, the rate of proliferation of epithelial cells in and proximal to the wound may be controlled in order to accelerate closure of the wound and/or minimize the formation of scar tissue.

In one aspect of the present invention, the present compounds may be used either locally or systemically to promote the proliferation, differentiation, and/or migration of cardiomyocytes or endothelial cells or their progenitors to and within sites of injury to repair cardiovascular or peripheral vascular tissue.

Full and partial thickness burns are an example of a wound type which often covers large surface areas and therefore requires prolonged periods of time to heal. As a result, life-threatening complications such as infection and loss of bodily fluids often arise. In addition, healing in burns is often disorderly, resulting in scarring and disfigurement. In some cases wound contraction due to excessive collagen deposition results in reduced mobility of muscles in the vicinity of the wound. The compositions and methods of the present invention may be used to accelerate the rate of healing of burns and to promote healing processes that result in more desirable cosmetic outcomes and less wound contraction and scarring.

Severe burns which cover large areas are often treated by skin autografts taken from undamaged areas of the patient's body. The present invention may also be used in conjunction with skin grafts to improve "take" rates of the graft by accelerating growth of both the grafted skin and the patient's skin that is proximal to the graft.

Dermal ulcers are yet another example of wounds that may be amenable to treatment by the present invention, e.g., to cause healing of the ulcer and/or to prevent the ulcer from becoming a chronic wound. For example, one in seven individuals with diabetes develop dermal ulcers on their extremities, which are susceptible to infection. Individuals with infected diabetic ulcers often require hospitalization, intensive services, expensive antibiotics, and, in some cases, amputation. Dermal ulcers, such as those resulting from venous disease (venous stasis ulcers), excessive pressure (decubitus ulcers) and arterial ulcers also resist healing. The prior art treatments are generally limited to keeping the wound protected, free of infection and, in some cases, to restore blood flow by vascular surgery. According to the present invention, the afflicted area of skin may be treated by a therapy which includes a present compound which promotes epithelization of the wound, e.g., accelerates the rate of the healing of the skin ulcers.

The present treatment may also be effective as part of a therapeutic or prophylactic regimen for treating oral and paraoral ulcers, e.g., resulting from radiation and/or chemotherapy. Such ulcers commonly develop within days after chemotherapy or radiation therapy. These ulcers usually begin as small, painful irregularly shaped lesions usually covered by a delicate gray necrotic membrane and surrounded by inflammatory tissue. In many instances, lack of treatment results in proliferation of tissue around the periphery of the lesion on an inflammatory basis. For instance, the epithelium bordering the ulcer usually demonstrates proliferative activity, resulting in loss of continuity of surface epithelium. These lesions, because of their size and loss of epithelial integrity, lend the body to potential secondary infection. Routine ingestion of food and water becomes a very painful event and, if the ulcers proliferate throughout the alimentary canal, diarrhea usually is evident with all its complicating factors. According to the present invention, a treatment for such ulcers which includes application of a present compound may reduce the abnormal proliferation and differentiation of the affected epithelium, helping to reduce the severity of subsequent inflammatory events.

The compounds of the present invention may be used as part of regimens in the treatment or prevention of disorders of, or surgical or cosmetic repair of, the penis or clitoris, including systemic or controlled-release local administration.

In another embodiment, the present invention may be useful for treating or preventing gastrointestinal diseases. Briefly, a wide variety of diseases are associated with disruption of the gastrointestinal epithelium or villi, including chemotherapy- and radiation-therapy-induced enteritis (i.e., gut toxicity) and mucositis, peptic ulcer disease, gastroenteritis and colitis, villus atrophic disorders, and the like. For example, chemotherapeutic agents and radiation therapy used in bone marrow implantation and cancer therapy affect rapidly proliferating cells in both the hematopoietic tissues and small intestine, leading to severe and often dose-limiting toxicities. Damage to the small intestine mucosal barrier results in serious complications of bleeding and sepsis. The present invention may be used to promote proliferation of gastrointestinal epithelium and thereby increase the tolerated doses for radiation and chemotherapy agents. Effective treatment or prevention of gastrointestinal diseases may be determined by several criteria, including an enteritis score, other tests well known in the art.

Levine et al. (1997) *J Neurosci* 17:6277 show that hedgehog proteins may regulate mitogenesis and photoreceptor differentiation in the vertebrate retina, and Ihh is a candidate factor from the pigmented epithelium to promote retinal progenitor proliferation and photoreceptor differentiation. Likewise, Jensen et al. (1997) *Development* 124:363 demonstrated that treatment of cultures of perinatal mouse retinal cells with the amino-terminal fragment of Sonic hedgehog protein results in an increase in the proportion of cells that incorporate bromodeoxuridine, in total cell numbers, and in rod photoreceptors, amacrine cells and Muller glial cells, suggesting that Sonic hedgehog promotes the proliferation of retinal precursor cells. Thus, the present invention may be used in the treatment or prevention of degenerative diseases of retinal cells and regulate photoreceptor differentiation.

With age, the epidermis thins and the skin appendages atrophy. Hair becomes sparse and sebaceous secretions decrease, with consequent susceptibility to dryness, chapping, and fissuring. The dermis diminishes with loss of elastic and collagen fibers. Moreover, keratinocyte proliferation (which is indicative of skin thickness and skin proliferative capacity) decreases with age. An increase in keratinocyte proliferation is believed to counteract skin aging, i.e., wrinkles, thickness, elasticity and repair. According to the present invention, a present compound may be used either therapeutically or cosmetically to counteract, at least for a time, the effects of aging on skin. Accordingly, the present compounds may be useful in inhibiting aging effects on skin.

Hence, in some instances, the present invention provides a method for inhibiting aging effects on skin, comprising administering to a patient one or more of the present compounds or compositions. In some applications, the one or more present compounds or compositions is administered orally. In other applications, the one or more present compounds or compositions is administered topically.

In some instances, the present invention provides a method for regulating skin or hair growth, comprising administering to a patient one or more of the present compounds or compositions. In certain instances, the patient is a human, who, for example, may display a hair loss or growth disorder, for example, male or female pattern baldness. In other instances, the patient is a non-human, for example, a dog or cat. In some applications, the one or more present compounds or compositions is administered orally. In other applications, the one or more present compounds or compositions is administered topically.

Yet another aspect of the present invention relates to the use of the present compounds to promote hair growth. Hair is basically composed of keratin, a tough and insoluble protein; its chief strength lies in its disulphide bond of cysteine. Each individual hair comprises a cylindrical shaft and a root, and is contained in a follicle, a flask-like depression in the skin. The bottom of the follicle contains a finger-like projection termed the papilla, which consists of connective tissue from which hair grows, and through which blood vessels supply the cells with nourishment. The shaft is the part that extends outwards from the skin surface, whilst the root has been described as the buried part of the hair. The base of the root expands into the hair bulb, which rests upon the papilla. Cells from which the hair is produced grow in the bulb of the follicle; they are extruded in the form of fibers as the cells proliferate in the follicle. Hair "growth" refers to the formation and elongation of the hair fiber by the dividing cells.

As is well known in the art, the common hair cycle is divided into three stages: anagen, catagen, and telogen. During the active phase (anagen), the epidermal stem cells of the dermal papilla divide rapidly. Daughter cells move upward and differentiate to form the concentric layers of the hair itself. The transitional stage, catagen, is marked by the cessation of mitosis of the stem cells in the follicle. The resting stage is known as telogen, where the hair is retained within the scalp for several weeks before an emerging new hair developing below it dislodges the telogen-phase shaft from its follicle. From this model it has become clear that the larger the pool of dividing stem cells that differentiate into hair cells, the more hair growth occurs. Accordingly, methods for increasing or reducing hair growth may be carried out by potentiating or inhibiting, respectively, the proliferation of these stem cells.

It is well established that the hedgehog pathway impacts the development of hair follicles and that Shh is required for development of follicles beyond the hair germ stage of hair follicle development (Chiang et al. 1999, Dev Biol. 205(1): 1-9 and St. Jacques et al. 1998, Curr Biol. 8(19):1058-68). It has been further shown that post-natally, Shh is expressed in the anagen hair bulb close to the skin surface (Gat et al., 1998, Cell 95(5):605-14; Gambardella et al. 2000, Mech Dev. 96(2):215-8; and Oro et al. 2003, Dev Biol. 255(2):238-48). Moreover, Shh, patched, and Gli-1 expression is upregulated during the anagen stage and down regulated during the telogen stage of the hair cycle. (Sato et al., 1999, J Clin Invest. 104(7):855-64 and Oro et al. 2003, Dev Biol. 255(2):238-48). Infecting mice with a retroviral vector expressing Shh has been shown to induce anagen in telogenic skin (Sato et al., 1999, J Clin Invest. 104(7):855-64). Generally, Shh and pathway genes are expressed during follicle formation and upregulated during post-natal anagen stage. Thus, Shh is important in the growth and maturation of hair follicles and in inducing anagen in the adult hair follicle. For example, disrupting Shh activity, either in knockout mice lacking Shh expression or through immunoneutralization of endogenous Shh, prevents the normal appearance of hair. Furthermore, exogenously administered Shh, either through local application of Shh protein or through gene therapy using a dermally applied Shh-expressing vector, promotes hair growth.

In certain embodiments, the present compounds promote, induce, or prolong the anagen stage. For example, administration of the present compounds to follicle cells in the telogen stage may induce the anagen stage in such cells. Hence, the present compounds may also be considered to inhibit, cease, or truncate the telogen stage in follicle cells, for example, in favor of the anagen stage. As such, the present compounds have the ability to regulate the hair cell cycle.

Consequently, the present invention provides a method for inducing anagen in a telogenic hair follicle, comprising administering one or more of the present compounds or compositions. In certain embodiments, the above method is an ex vivo method. In other embodiments, the one or more present compounds or compositions is administered to a patient. In certain instances, the patient is a human, who, for example, may display a hair loss or growth disorder, for example, male or female pattern baldness. In other instances, the patient is a non-human, for example, a dog or cat. In some applications, the one or more present compounds or compositions is administered orally. In other applications, the one or more present compounds or compositions is administered topically.

Since the deregulation of the hair cycle is often an underlying cause of a number of hair growth disorders, hedgehog agonists, such as one or more of the present compounds, may be used to treat such disorders. For example, in some instances, the present compounds possess the ability to regulate hair growth, for example by promoting hair growth and/or by inhibiting or stopping hair loss. Thus, in certain embodiments, the present invention may be employed as a way of promoting the growth of human hair, e.g., to correct baldness, alopecia, or other diseases characterized by hair loss. In addition to other modes of administration described herein, present compounds may be administered topically for the treatment or prevention of hair loss or growth disorders.

As such, in some instances, the present invention provides a method for treating or preventing alopecia in a patient, comprising administering one or more of the present compounds or compositions. In certain instances, the patient is a human, who, for example, may display a hair loss or growth disorder, for example, male or female pattern baldness. In other instances, the patient is a non-human, for example, a dog or cat. In some applications, one or more present compounds or compositions is administered orally. In other applications, one or more present compounds or compositions is administered topically. In some cases, the alopecia is alopecia greata. In certain instances, the alopecia is alopecia totalis.

As further described herein, the ability of hedgehog to promote angiogenesis has been documented (Pola et al. 2001, Nat. Med. 7(6):706-11; Pola et al. 2003, Circulation 108(4): 479-85; Kusano et al., 2005, Nat. Med. 11(11):1197-204; and Lavine et al. 2006, Genes Dev. 20(12):1651-66). Since induction of anagen is associated with the induction of angiogenesis, the ability of the present compounds to promote angiogenesis may result in the promotion of anagen induction in hair follicles.

In some instances, the present invention provides a method for promoting the formation, expansion, and/or proliferation of hair follicles, comprising administering one or more of the present compounds or compositions. In certain embodiments, the above method is an ex vivo method. In other embodiments, the one or more present compounds or compositions is administered to a patient. In certain instances, the patient is a human, who, for example, may display a hair loss or growth disorder, for example, male or female pattern baldness. In other instances, the patient is a non-human, for example, a dog. In some applications, the one or more present compounds or compositions is administered orally. In other applications, the one or more present compounds or compositions is administered topically.

In certain instances, the present invention provides a method for the ex vivo culture, formation, growth, differentiation, and expansion of hair follicles for implantation to a patient with male pattern baldness, female pattern hair loss, or other conditions that result in hair loss.

As such, the present invention may provide a method for increasing hair coverage at an anatomical site of a patient comprising growing hair by ex vivo culture, formation, growth, differentiation, and/or expansion of hair follicles, comprising culturing cells in the presence of one or more of the present compounds or compositions or contacting cells with one or more of the present compounds or compositions; and implanting of the grown hair and/or follicle(s) to the anatomical site of the patient, for example, to a balding region, such as the scalp. In certain instances, the patient is a human, who, for example, may display a hair loss or growth disorder, for example, male or female pattern baldness. In other instances, the patient is a non-human, for example, a dog, cat, or other domestic or livestock animal. In some applications, the one or more present compounds or compositions is administered orally. In other applications, the one or more present compounds or compositions is administered topically.

In some instances, the present compounds may be used to increase the trichogenic potential or trichogenicity of cells, such as hair follicle cells. It has been shown that addition of hedgehog agonists to skin cell cultures results in an increase in trichogenic potential of these cells (Stenn et al., 2004, unpublished). The cells treated with hedgehog agonists afforded a several-fold increase in the number of follicles formed in vivo. The increased trichogenic potential achieved through administration of the present compounds further supports the compounds' ability to effect improved culture, growth, differentiation, and/or expansion of hair follicles.

Accordingly, in some instances, the present invention provides a method for increasing the trichogenicity of hair follicle cells, comprising contacting the cells with one or more of the present compounds or compositions. In certain embodiments, the above method is an ex vivo method. In other embodiments, the one or more present compounds or compositions is administered to a patient. In certain instances, the patient is a human, who, for example, may display a hair loss or growth disorder, for example, male or female pattern baldness. In other instances, the patient is a non-human, for example, a dog or cat. In some applications, the one or more present compounds or compositions is administered orally. In other applications, the one or more present compounds or compositions is administered topically.

In one embodiment, the present invention provides a means for altering the dynamics of the hair growth cycle to induce proliferation of hair follicle cells, particularly stem cells of the hair follicle. The present compounds, compositions, and methods may be used to increase hair follicle size and the rate of hair growth in warm-blooded animals, such as humans, e.g., by promoting proliferation of hair follicle stem cells. In one embodiment, the method comprises administering to the skin in the area in which hair growth is desired an amount of one or more of the present compounds or compositions sufficient to increase hair follicle size and/or the rate of hair growth in the animal. Typically, the one or more of the present compounds or compositions may be administered topically, e.g., as a cream, and will be applied on a daily basis until hair growth is observed and for a time thereafter sufficient to maintain the desired amount of hair growth. This method may have applications in the promotion of new hair growth or stimulation of the rate of hair growth, e.g., following chemotherapeutic treatment or for treating various forms of alopecia, e.g., male pattern baldness. For instance, one of several biochemical cellular and molecular disturbances that occur during the anagen phase or catagen phase of subjects with androgenic alopecia may be corrected or improved by treatment using one or more of the present compounds or compositions, e.g., in the functioning or formation of the stem cells, their migration process or during the mitosis phase of keratin production within the follicular papilla and matrix.

Also included in ailments which may be treated by the present invention are disorders generally associated with non-humans, such as mange. In one embodiment, one or more of the present compounds or compositions may be used in a veterinary method for the treatment or prevention of hair loss in a non-human animal, for example, an animal suffering from mange or another hair loss disorder.

The present invention may also be used in treatment of a wound to eye tissue. Generally, damage to corneal tissue, whether by disease, surgery or injury, may affect epithelial and/or endothelial cells, depending on the nature of the wound. Corneal epithelial cells are the non-keratinized epithelial cells lining the external surface of the cornea and provide a protective barrier against the external environment. Corneal wound healing has been of concern to both clinicians and researchers. Ophthalmologists are frequently confronted with corneal dystrophies and problematic injuries that result in persistent and recurrent epithelial erosion, often leading to permanent endothelial loss. The present compounds may be used in these instances to promote epithelialization of the affected corneal tissue.

To further illustrate, specific disorders typically associated with epithelial cell damage in the eye, and for which the present invention may provide beneficial treatment, include persistent corneal epithelial defects, recurrent erosions, neurotrophic corneal ulcers, keratoconjunctivitis sicca, microbial corneal ulcers, viral cornea ulcers, and the like. Surgical procedures typically causing injury to the epithelial cell layers include laser procedures performed on the ocular surface, any refractive surgical procedures such as radial keratotomy and astigmatic keratotomy, conjunctival flaps, conjunctival implants, epikeratoplasty, and corneal scraping. Moreover, superficial wounds such as scrapes, surface erosion, inflammation, etc. may cause lose of epithelial cells. According to the present invention, the corneal epithelium may be contacted with an amount of a present compound effective to cause proliferation of the corneal epithelial cells to appropriately heal the wound.

The maintenance of tissues and organs ex vivo is also highly desirable. Tissue replacement therapy is well established in the treatment of human disease. For example, more than 40,000 corneal transplants were performed in the United States in 1996. Human epidermal cells may be grown in vitro and used to populate burn sites and chronic skin ulcers and other dermal wounds. The present compounds, compositions, and methods may be used to accelerate in vitro the growth of epithelial tissue, such as corneal tissues and those associated with the eye and vision. The present compounds, compositions, and methods may also be used to accelerate the grafting of cultured epithelial tissue, such as corneal tissues and those associated with the eye and vision, to an animal host.

In another aspect, the present invention may be used to induce differentiation and/or promote proliferation of epithelially derived tissue. The present invention may be used for improving the "take rate" of a skin graft. Grafts of epidermal tissue may, if the take rate of the graft is to long, blister and shear, decreasing the likelihood that the autograft will "take", i.e. adhere to the wound and form a basement membrane with the underlying granulation tissue. Take rates may be increased by the present invention by inducing proliferation of the keratinocytes. The method of increasing take rates comprises contacting the skin autograft with an effective wound healing amount of a present compound described in the method of promoting wound healing and in the method of promoting the growth and proliferation of keratinocytes, as described above.

Skin equivalents have many uses not only as a replacement for human or animal skin for skin grafting, but also as test skin for determining the effects of pharmaceutical substances and cosmetics on skin. A major difficulty in pharmacological, chemical and cosmetic testing is the difficulties in determining the efficacy and safety of the products on skin. One advantage of the skin equivalents of the present invention may be their use as an indicator of the effects produced by such substances through in vitro testing on test skin.

Thus, in one embodiment, the present invention may be used as part of a protocol for skin grafting of, e.g., denuded areas, granulating wounds and burns. The use of the present compounds may enhance such grafting techniques as split thickness autografts and epidermal autografts (cultured autogenic keratinocytes) and epidermal allografts (cultured allogenic keratinocytes). In the instance of the allograft, the use of the present invention to enhance the formation of skin equivalents in culture may help to provide/maintain a ready supply of such grafts (e.g., in tissue banks) so that the patients might be covered in a single procedure with a material which allows permanent healing to occur.

In this regard, the present invention may also concern composite living skin equivalents comprising an epidermal layer of cultured keratinocyte cells which have been expanded by treatment with a present compound. The present invention may be used as part of a process for the preparation of composite living skin equivalents. In an illustrative embodiment, such a method comprises obtaining a skin sample, treating the skin sample enzymically to separate the epidermis from the dermis, treating the epidermis enzymically to release the keratinocyte cells, culturing, in the presence of a present compound, the epidermal keratinocytes until confluence, in parallel, or separately, treating the dermis enzymatically to release the fibroblast cells, culturing the fibroblasts cells until sub-confluence, inoculating a porous, cross-linked collagen sponge membrane with the cultured fibroblast cells, incubating the inoculated collagen sponge on its surface to allow the growth of the fibroblast cells throughout the collagen sponge, and then inoculating it with cultured keratinocyte cells, and further incubating the composite skin equivalent complex in the presence of a present compound to promote the growth of the cells.

In another aspect of the present invention, the present compounds may be used to effect the ex vivo culture, formation, growth, differentiation, and expansion of epithelial cells to create grafts of skin and skin organs; corneal, lens and other ocular tissue; mucosal membranes; and periodontal epithelium for implantation into or onto a patient.

In other embodiments, skin sheets containing both epithelial and mesenchymal layers may be isolated in culture and expanded with culture media supplemented with a present compound. Any skin sample amenable to cell culture techniques may be used in accordance with the present invention. The skin samples may be autogenic or allogenic.

In another aspect, the present invention may be used in conjunction with various periodontal procedures in which control of epithelial cell proliferation in and around periodontal tissue is desired. In one embodiment, the present compounds may be used to enhance reepithelialization around natural and prosthetic teeth, e.g., to promote formation of gum tissue.

Hedgehog gene products are able to regulate maturation of T lymphocytes. Certain aspects of the present invention may be directed to the present compounds and their uses as immunomodulatory agents against both acquired and hereditary immunological disorders.

For instance, such compositions may be used to increase the population of T-helper cells to optimum levels in the host, e.g., to stimulate the immune system of the animal. Such uses of the present compositions may be used in the treatment or prevention of bacterial or viral infections. Alternatively, these substances also enable the host to adjust to diseases arising from disarrangement of self-recognition processes in which there is excessive attack by host T-cells against endogenous tissues. In such instances, the present compositions may be used to reduce T-cell population so that the signs and symptoms of self-directed inflammatory (autoimmune) diseases such rheumatoid arthritis and multiple sclerosis are ameliorated.

As described herein, hedgehog proteins inhibit maturation of T lymphocytes. Based upon its inhibitory effect, the administration of the present compounds may be useful as a treatment for several types of immunological disorders involving unwanted activation of cellular immunity, e.g., graft rejection, autoimmune disorders, and the like.

In general, a method of the present invention may comprise administering to animal, or to cultured lymphocytes in vitro, an amount of a present compound which produces a non-toxic response by the cell of inhibition of maturation. The present invention may be carried out on cells which may be either dispersed in culture or a part of an intact tissue or organ. Moreover, the method may be performed on cells which are provided in culture (in vitro), or on cells in a whole animal (in vivo). The present invention may also relate to methods of controlling the functional performance of T cells by use of the present pharmaceutical preparations.

Without wishing to be bound by any particular theory, the inhibitory effect of hedgehog on T cell maturation may be due at least in part to the ability of hedgehog proteins to antagonize (directly or indirectly) patched-mediated regulation of gene expression and other physiological effects mediated by that protein. The patched gene product, a cell surface protein, is understood to signal through a pathway which causes transcriptional repression of members of the Wnt and Dpp/BMP families of morphogens, proteins which impart positional information. In other tissue, the introduction of hedgehog relieves (derepresses) this inhibition conferred by patched, allowing expression of particular gene programs.

Epilepsy is a recurrent paroxysmal disorder of cerebral function characterized by sudden brief attacks of altered consciousness, motor activity, sensory phenomena or inappropriate behavior caused by abnormal excessive discharge of cerebral neurons. Convulsive seizures, the most common form of attacks, begin with loss of consciousness and motor control, and tonic or clonic jerking of all extremities but any recurrent seizure pattern may be termed epilepsy.

The term primary or idiopathic epilepsy denotes those cases where no cause for the seizures may be identified. Secondary or symptomatic epilepsy designates the disorder when it is associated with such factors as trauma, neoplasm, infection, developmental abnormalities, cerebrovascular disease, or various metabolic conditions. Epileptic seizures are classified as partial seizures (focal, local seizures) or generalized seizures (convulsive or nonconvulsive). Classes of partial seizures include simple partial seizures, complex partial seizures and partial seizures secondarily generalized. Classes of generalized seizures include absence seizures, atypical absence seizures, myoclonic seizures, clonic seizures, tonic seizures, tonic-clonic seizures (grand mal) and atonic seizures.

Therapeutics having anticonvulsant properties are used in the treatment of seizures. Most therapeutics used to abolish or attenuate seizures act at least through effects that reduce the spread of excitation from seizure foci and prevent detonation and disruption of function of normal aggregates of neurons. Anticonvulsants which have been utilized include phenyloin, phenobarbital, primidone, carbamazepine, ethosuximide, clonazepam and valproate. For further details of seizures and their therapy (see Rall & Schleifer (1985) and The Merck Manual (1992)).

Due to the involvement of exotoxic-dependent neurodegeneration which may result from seizure, one or more of the present compounds or compositions may be useful as part of a regimen in the treatment or prevention of epilepsy, and also in conjunction with a treatment including an anticonvulsant agent.

Glaucoma is a complex set of diseases, which results in damage to axons in the optic nerve and death of the retinal ganglion cells, concluding in the permanent loss of vision. There are several mechanism that ultimately causes the axonal damage. For instance, an increase in intraocular pressure (IOP) overcomes the perfusion pressure of the optic nerve and results in an ischemic event which leads to axonal.

In addition to the primary insult and ensuing cell damage, there appears to be a secondary degenerative process in glaucoma. Clinically, patients often continue to lose visual field and optic nerve head substance even in the presence of what might be considered normal IOP. In addition, there are forms of glaucoma which manifest in the presence of normal IOP. It is thought that chemical mediators may be linked to intensification of cell degeneration and death in a secondary fashion. Much work has been done in the last five years which implicates the role of excitotoxins, such as glutamate, in the secondary damage to retinal neurons. Accordingly, the present compounds, compositions, and methods may be used as part of a treatment and/or prophylaxis for glaucoma.

The mechanism by which aminoglycosides produce permanent hearing loss is mediated, in part, through an excitotoxic process. Accordingly, the present compounds, compositions, and methods may be used as part of a treatment and/or prophylaxis for hearing loss, such as hearing loss induced by ototoxic chemicals, such as chemotherapeutics.

Angiogenesis, the process of sprouting new blood vessels from existing vasculature and arteriogenesis, the remodeling of small vessels into larger conduit vessels are both physiologically important aspects of vascular growth in adult tissues (Klagsbrun and D'Amore, 1991, Annu Rev Physiol. 53:217-39; Folkman and Shing, 1992, J Biol. Chem. 267(16): 10931-4; Beck and D'Amore, 1997, FASEB J. 11(5):365-73; Yancopoulos et al., 1998, Cell. 93(5):661-4; Buschmann and Schaper, 2000, News Physiol Sci. 14:121-125). These processes of vascular growth are required for beneficial processes such as tissue repair, wound healing, recovery from tissue ischemia and menstrual cycling. They are also required for the development of pathological conditions such as the growth of neoplasias, diabetic retinopathy, rheumatoid arthritis, and certain inflammatory pathologies (Chemington et al., 2000, Adv Cancer Res. 79:1-38).

The ability to stimulate vascular growth has potential utility for treatment of ischemia-induced pathologies such as myocardial infarction, coronary artery disease, peripheral vascular disease, and stroke. The sprouting of new vessels and/or the expansion of small vessels in ischemic tissues prevents ischemic tissue death and induces tissue repair. Certain growth factors such as those in the vascular endothelial growth factor (VEGF) and fibroblast growth factor (FGF) families are able to stimulate vascular growth by acting on endothelial cells to induce angiogenesis. Other factors have also been shown to have angiogenic and arteriogenic activities such as MCPI (Buschman and Schaper, 2000) and angiopoietins. In preclinical models of myocardial infarction, both FGFs and VEGFs have been able to improve myocardial revascularization and function (Yanagisawa-Miwa et al, 1992, Science. 257(5075):1401-3; Battler et al., 1993, J Am Coll Cardiol. 22(7):2001-6; Harada et al., 1994, J Clin Invest. 93(6):2490-6; Banai et al., 1994, Circulation. 89(5):2183-9; Unger et al., 1994, Am J. Physiol. 266(4 Pt 2):H1588-95; Mesri et al., 1995 Circ Res, 76(2):161-7; Pearlman et al., 1995 Nat. Med. 1(10):1085-9.; Landau et al, 1995 J Am Heart J. 129(5):924-31.; Lazarous et al., 1996 Circulation. 94(5): 1074-82.; Engler, 1996 Circulation. 94(7):1496-8.; Magovern et al., 1997 Hum Gene Ther. 8(2):215-27; Shou et al., 1997 J Am Coll Cardiol. 29(5):1102-6). Also in models of peripheral vascular disease, VEGF and other angiogenic factors are able to induce angiogenesis and improve vascular perfusion of the ischemic limb (Majesky, 1996 Circulation. 94(12):30624.; Takeshita et al, 1996 Biochem Biophys Res Commun. 227(2):628-35, Takeshita et al, 1996 Lab Invest. 75(4):487-501 and 1994 Circulation. 90(5 Pt 2):11228-34; Rivard et al., 1998 Mol. Med. 4(7):429-40; Rivard et al., 1999 Am J Pathol. 154(2):355-63, Isner et al, 1996 Lancet. 348 (9024):370-4, Isner et al, 1996 Hum Gene Ther. 7(8):959-88).

A number of these factors are also implicated in vascular growth in pathological conditions such as tumor expansion, diabetic retinopathy and rheumatoid arthritis. The inhibition of vascular growth in these contexts has also shown beneficial effects in preclinical animal models (Klohs and Hamby, 1999 Curr Opin Biotechnol. 10(6):544-9; Zhu and Witte, 1999 Invest New Drugs. 17(3):195-212; Chemington et al., 2000 Adv Cancer Res. 79:1-38). For example, inhibition of angiogenesis by blocking vascular endothelial growth factor or its receptor has resulted in inhibition of tumor growth and in retinopathy (Fong et al., 1999 Cold Spring Harb Symp Quant Biol. 64:329-34.; Wood et al., 2000 Prostate Cancer Prostatic Dis. 3(S1):S43; Ozaki et al., 2000 Am J Pathol. 156(2):697-707). Also, the development of pathological pannus tissue in rheumatoid arthritis involves angiogenesis and may be blocked by inhibitors of angiogenesis (Peacock et al., 1995 Cell Immunol. 160(2):178-84.; Storgard et al., 1999 J Clin Invest. 103(1):47-54).

Thus, the induction of angiogenesis and vascular growth is beneficial for tissue repair and would healing whereas inhibition of angiogenic growth factors may prevent angiogenesis driven pathologies. It would be useful to develop novel therapeutics that modulate angiogenesis.

Accordingly, in certain embodiments, the present invention contemplates a method for modulating cells of the blood and blood vessels, for example, promoting the growth of new blood vessels, i.e., angiogenesis, arteriogenesis or vascular growth in the tissues of a patient. A compound of the present invention may be considered to promote angiogenesis if it modulates angiogenesis in such a way as to enhance, elicit, accelerate or increase angiogenesis, regardless of the mode of action of the compound.

In certain embodiments, the methods of this invention employ the present compounds to promote angiogenesis, such as, to repair damage of tissue damaged during an ischemic event, for example, stroke or myocardial tissue as a result of myocardial infarction. Such methods may also include the repair of the cardiac vascular system after ischemia including the growth of collateral vasculature. Methods utilizing the present compounds may be employed to stimulate the growth of transplanted or implanted tissue and collateral vasculature where coronary bypass surgery is performed. Methods may also treat damaged vascular tissue as a result of coronary artery disease and peripheral or central nervous system vascular disease or ischemia.

Methods of the present invention may also promote wound healing through promotion of angiogenesis, particularly to re-vascularize damaged tissues or stimulate collateral blood flow during ischemia and where new capillary angiogenesis is desired. Other methods of the present invention may be employed to treat full-thickness wounds such as dermal ulcers, including pressure sores, venous ulcers, and diabetic ulcers. In addition, methods employing the present compounds may be employed to treat full-thickness burns and injuries where a skin graft or flap is used to repair such burns and injuries. The present compounds may also be employed for use in plastic surgery, for example, for the repair of lacerations, burns, or other trauma. In urology, methods of the present invention may assist in recovery of erectile function. In the field of female reproductive health, methods of the present invention may assist in the modulation of menstruation, ovulation, endometrial lining formation and maintenance, and placentation.

Since angiogenesis is important in keeping wounds clean and non-infected, the present methods, compounds, and compositions may be employed in association with surgery and following the repair of cuts. They may also be employed for the treatment of abdominal wounds where there is a high risk of infection. Methods using the present compounds described herein may be employed for the promotion of endothelialization in vascular graft surgery. In the case of vascular grafts using either transplanted or synthetic material, the present compounds may be applied to the surface of the graft or at the junction to promote the growth of vascular smooth muscle and adventitial cells in conjunction with endothelial cells.

Methods of the present invention may also be employed to coat artificial prostheses or natural organs which are to be implanted in the body to minimize rejection of the implanted material and to stimulate vascularization of the implanted materials and may also be employed for vascular tissue repair, for example, that occurring during arteriosclerosis and required following balloon angioplasty where vascular tissues are damaged. Specifically, methods of the present invention may be employed to promote recovery from arterial wall injury and thereby inhibit restenosis. Additional angiogenic uses for the present compounds are described in U.S. Published Patent Application 2005-0054568, which is incorporated by reference herein in its entirety.

In certain aspects of the present invention, one or more of the present compounds may be administered in combination with one or more other therapeutic agents having the same or differing mode of action, to attain an additive or synergistic effect on angiogenesis.

In certain embodiments, one or more of the present compounds and/or compositions stimulates hematopoiesis and/or vascular growth. Accordingly, the present compounds may be used to treat patients with blood disorders, such as blood development disorders.

In some embodiments, methods are provided for stimulating hematopoiesis in a subject to treat abnormalities associated with deficiencies in hematopoietic cell lineages. Examples of targets for such treatments include in vivo or in vitro exposure of undifferentiated mesodermally derived cells to a compound of the present invention. Examples of target cells include bone marrow stem cells, progenitor cells, and cord blood cells. These cells may be isolated from a subject and stored in a cell bank for subsequent use, or the cells may be freshly isolated and maintained in vitro in a culture medium. Exposure of such cells to one or more of the present compounds or compositions results in enhanced proliferation and/or differentiation of the cells, the stimulated cells being implanted in the same or different subject from which the cells were derived, by means of transplantation technology. Alternatively, undifferentiated mesodermally derived cells may be accessed in the embryo or adult in vivo by any of a number of routes including: oral, intradermal subcutaneous, transmucosal, intramuscular or intravenous routes.

In certain instances, one or more of the present compounds may be used to treat subjects (embryo or adult) suffering from blood abnormalities. These may arise from genetic lesions, side effects of therapeutic treatments such as radiation and chemotherapy for cancer or from disease caused by infectious agents such as human immune deficiency virus and may be treated using a method and compounds that stimulate hematopoiesis. The consequences of such abnormalities if untreated are various forms of anemia (associated with abnormally low levels of erythrocytes). Examples of anemias include: aplastic anemia (idiopathic, constitutional forms, or secondary forms); myelodysplastic anemia; anemia in patients with metastatic or necrotizing carcinoma; Hodgkin's disease; malignant lymphoma; anemia of chronic liver disease; anemia of chronic renal disease (renal failure); anemia of endocrine disorders; red cell aplasia; idiopathic or associated with other disorders, anemia due to chronic inflammatory disease; and thrombocytopenia of many etiologies. In addition, stimulation of hematopoiesis is beneficial in the treatment of leukopenias (for example, leukemia and AIDS).

According to certain embodiments, a method is further provided for treating abnormal blood vessel formation (hypervascularization) resulting from genetic diseases, chronic degenerative disease, aging, trauma, or infectious agents. Examples include diabetic chronic ulcers, burns, frostbite, ischemic events following stroke and transplantation. The present compounds and compositions may be used in the adult for induction of revascularization or formation of collateral vessels in ischemic myocardium or ischemic limbs, and in coronary artery bypasses and in promoting wound healing in general. For example, one or more of the present compounds may be used in treatment or prevention of duodenal ulcers by enhancing microvessel density and promoting more rapid healing. In addition, the present invention may be used to correct disorders of development in the embryo (as defined in above) caused by abnormalities in vascular growth.

According to some embodiments, one or more of the present compounds and/or compositions may be used in immunoregulatory disorders and diseases in non-human animals and humans, for the prevention or prophylaxis, control, diagnosis or treatment thereof.

The present compounds, compositions, and methods have wide applicability to the treatment or prophylaxis of disorders affecting the regulation of lymphocytes, particularly maturation and/or activation of T lymphocytes. In general, the method may be characterized as including a step of administering to an animal an amount of one or more of the present compounds and/or compositions effective to alter the proliferative and/or differentiation state of treated lymphocytes. Accordingly, the present compounds and/or compositions may be useful in treatments designed to modulate, e.g., increase or decrease, an immunological response. Such diseases and conditions include, but are not limited to, infection (such as bacterial or viral infection), metabolic disease such as diabetes, nutritional deficiency, toxic agents, graft rejection or other hyperacute response, or autoimmune disorders. The goals of treatment in each case may be twofold: (1) to eliminate the cause of the disease or unwanted immunological response, and/or (2) to relieve its symptoms.

In view of their immunosuppressant activity, the present compounds and compositions may be suitable for preventing and treating diseases and conditions which require a temporary or permanent reduction or suppression of an immune response. In particular, their use extends to suppressing the activation of the proliferation of lymphocytes or cytotoxic T-cells and/or immunocytes, e.g. for preventing or treating autoimmune diseases such as diseases of the rheumatic type, multiple sclerosis, or for preventing the rejection of transplanted or implanted tissues or organs such as kidneys, heart, lungs, bone marrow, spleen, skin or cornea, in undesirable reactions during or after transfusions, allergic diseases, particularly those which affect the gastrointestinal tract and which may take the form of an inflammation, or inflammatory, proliferative and hyperproliferative diseases and cutaneous manifestations of immunological disorders such as urticaria, vasculitis and scleroderma.

Thus, it may be useful to use immunosuppressive forms of the present compounds and compositions clinically for the disorders, diseases and conditions described herein, i.e., when it is desirable to achieve immunosuppression in an animal, such as a non-human animal or human.

Depending on the nature and cause of the disease or disorder to be treated or the condition which is to be influenced in an animal, it may be desirable to administer one or more of the compounds and/or compositions systemically, locally or topically to the tissue or organ in question. Systemic action is desirable, for example, when various organs or organ systems are in need of treatment, as is the case for example in systemic autoimmune diseases or allergies or in transplants of large, foreign organs or tissues. By contrast, a local effect would be considered if only local manifestations of an immunological occurrence had to be treated, e.g., in small transplants of skin or cornea.

Depending on the duration and intensity of the immunosuppressant activity required, the present compounds and compositions may be given one or more times a day, as well as intermittently, over a period of several days, weeks or months and in various dosages.

In still other embodiments, the present compounds and compositions may be used to treat disorders involving hypoimmunity, e.g., immunosuppressed or immunocompromised patients.

Thus, the present invention may contemplate the treatment of immunocompromised subjects to increase one or more indicia of cell mediated immunity (CMI), humoral immunity, or innate resistance to infection, by administering one or more of the present compounds and/or compositions. In certain embodiments, such immunity-promoting activities may be identified, e.g., by i) increased E-rosette forming cells (E-RFC) in thymocyte cultures after incubation with the present compounds and compositions; ii) increased E-RFC in cultures of thymocytes from aged animals after incubation with the present compounds and compositions; and, iii) increased expression of OKT 4<+> in cultures of human peripheral blood T-lymphocytes from patients with secondary immunodeficiency syndromes following treatment with the present compounds and compositions. Increased expression of CD2 and CD4 accessory molecules on T-lymphocytes is compatible with a heighten the state of innate or induced immunity to infection, e.g., by upregulating T-helper and cytotoxic T-lymphocytes to respond to lower levels of antigen.

Immunodeficiency states may fall into three general etiologic categories. First, there is immunosuppression that occurs as a consequence of disease processes. Second, there are immunodeficiencies that arise because of therapy for other diseases, so-called iatrogenic immunodeficiencies. Third, immunodeficiencies may result from direct attack of T-lymphocytes by the human immunodeficiency virus (HIV) that causes the acquired immunodeficiency syndrome (AIDS).

Common disease processes that lead to immunodeficiency may include malnutrition, neoplasias, aging, and infections. Malnourished people, patients with advanced widespread cancers and people with debilitating illnesses become sick and die more often because impaired cell-mediated and humoral immune responses increase susceptibility to infections by a variety of organisms. A state of generalized deficiency in immune responses is called anergy. Various types of infections, especially viral infections, lead to immunosuppression. A drug, such as one or more of the present compounds and/or compositions, e.g., capable of making the T-helper lymphocyte components of the immune system more robust, may be useful for increasing the resistance of the patient to infections. For example, one or more of the present compounds and/or compositions, may be:

administered to patients, especially older patients, before or just after admissions to hospitals in order to reduce the risks of nosocomial (hospital-induced) infections, a common and severe clinical problem;

administered to burn victims, because such individuals are especially prone to infections;

administered to patients in anticipation of epidemic infections, for example, in conjunction with influenza vaccinations or hepatitis vaccinations, to invigorate the immune response to pathogens;

administered to patients with asymptomatic viral infections, in order to enhance immune surveillance of pathogenic organisms and reduce the likelihood of recurrence of disease, for example, for individuals who are carriers of herpes viruses, varicella viruses, hepatitis viruses and HIV.

Iatrogenic immunosuppression is most often due to drug therapies which either kill or functionally inactivate lymphocytes. Various chemotherapeutic drugs are administered to cancer patients, and these drugs are usually cytotoxic to both mature and developing lymphocytes as well as to granulocyte and monocyte precursors. Thus, cancer chemotherapy is almost always accompanied by a period of immunosuppression and increased risk of infections. Radiation treatment of cancer carries the same risks. Medications (granulocyte-colony stimulating factor) exist for increasing neutrophils in blood to combat infections that occur after cancer chemotherapy, but no medications are currently used for restoring lymphocytic functions. Major surgery, for example repair of aneurysms or by-pass operations, also decrease immune function in humans. The reasons for the decline in blood lymphocytes that occur because of major surgery are not clear, but an agent that elevates lymphocyte functions in such patients have therapeutic value in decreasing the likelihood of infections.

Another form of acquired immunosuppression that should be mentioned results from the absence of a spleen, caused by surgical removal of the organ after trauma or for the treatment of certain hematologic diseases or as a result of infarction in sickle cell disease. Patients without spleens are more susceptible to infections by some organisms, particularly encapsulated bacteria such as *Streptococcus pneumoniae*. The spleen is apparently required for the induction of protective humoral immune responses to such organisms. The present compounds and compositions may help individuals without a spleen or without a thymus in resistance against infection by micro-organisms.

It is also contemplated that the present compounds or compositions may be delivered locally to the thymus, preferably in a slow-release format, to maintain the active level of hedgehog or hedgehog equivalent in thymus at desired concentration, so as to enhance or inhibit T cell development. There are numerous devices or implants suitable for sustained drug release in human body or bodies of other mammals; see, for example, U.S. Pat. No. 6,685,452 and U.S. Pat. Application publication 2003-0153901, which are incorporated by reference herein.

The present compounds, compositions, and methods may have wide applicability to the treatment or prophylaxis of disorders afflicting adipocyte tissue. In general, the methods may be characterized as including a step of administering to an animal an amount of a present compound or composition effective to alter the proliferative state of a treated adipocyte tissue. The mode of administration and dosage regimens may vary depending on the adipocyte tissue(s) which is to be treated.

In one aspect, the present invention may be used to inhibit adipocyte differentiation in mammals. Such aspects of the present invention may thus be directed to a method for inhibiting the differentiation of adipocyte precursor cells in a mammal (e.g., inhibiting differentiation of preadipocytes into adipocytes), and may comprise administering to the mammal an effective amount of one or more of the present compounds and/or compositions. In such embodiments, the present compounds and compositions of the present invention may be use to treat (reduce the severity of or ameliorate) body weight disorders which may include, for example, inhibition of adipose cell differentiation and an inhibition of the ability of adipocytes to synthesize fat, e.g., treatment or prevention of obesity or of disorders related to abnormal proliferation of adipocytes.

In certain embodiments, the present invention may be used to inhibit the differentiation of preadipocytes to adipocytes, therefore limiting the possibility of cellulite appearing.

In other embodiments, the present invention may be used in livestock to repartition nutrients between subcutaneous fat and other carcass components, including muscle, skin, bone and certain organs, e.g., by administration in the form of a veterinarian composition or as part of a livestock feed.

Physical injuries may result in cellular damage that ultimately limits the function of a particular cell or tissue. For example, physical injuries to cells in the CNS may limit the function of cells in the brain, spinal cord, or eye. Examples of physical injuries include, but are not limited to, crushing or severing of neuronal tissue, such as may occur following a fall, car accident, sports injury, gun shot or stabbing wound, etc. Further examples of physical injuries include those caused by extremes in temperature such as burning, freezing, or exposure to rapid and large temperature shifts.

Physical injuries to mesodermal cell types include injuries to skeletal muscle, cardiac muscle, tendon, ligament, cartilage, bone, and the like. Examples of physical injuries include, but are not limited to, crushing, severing, breaking, bruising, and tearing of muscle tissue, bone or cartilage such as may occur following a fall, car accident, sports injury, gun shot or stabbing wound, etc. Further examples of physical injuries include breaking, tearing, or bruising of muscle tissue, bone, cartilage, ligament, or tendon as may occur following a sports injury or due to aging. Further examples of physical injuries include those caused by extremes in temperature such as burning, freezing, or exposure to rapid and large temperature shifts.

Physical injuries to endodermal cell types include injuries to hepatocytes and pancreatic cell types. Examples of physical injuries include, but are not limited to, crushing, severing, and bruising, such as may occur following a fall, car accident, gun shot or stabbing wound, etc. Further examples of physical injuries include those caused by extremes in temperature such as burning, freezing, or exposure to rapid and large temperature shifts.

Further examples of an injury to any of the aforementioned cell types include those caused by infection such as by a bacterial or viral infection. Examples of bacterial or viral infections include, but are not limited to, meningitis, staph, HIV, hepatitis A, hepatitis B, hepatitis C, syphilis, human pappiloma virus, strep, etc. However, one of skill in the art will recognize that many different types of bacteria or viruses may infect cells and cause injury.

Additionally, injury to a particular cell type may occur as a consequence or side effect of other treatments being used to relieve some condition in an individual. For example, cancer treatments (chemotherapy, radiation therapy, surgery) may cause significant damage to both cancerous and healthy cells. Surgery; implantation of intraluminal devices; the placement of implants, pacemakers, shunts; and the like may all result in cellular damage.

Consequently, the present invention may contemplate methods for treating such physical and cellular injuries comprising administering one or more of the present compounds or compositions to a patient.

The present compounds, compositions, and methods may be administered as part of a therapeutic regimen along with other treatments appropriate for the particular injury or disease being treated. For example, in the case of Parkinson's disease, a present compound or composition may be administered in combination with L-dopa or other Parkinson's disease medications, or in combination with a cell based neuronal transplantation therapy for Parkinson's disease. In the case of an injury to the brain or spinal cord, a present compound may be administered in combination with physical therapy, hydrotherapy, massage therapy, and the like. In the case of peripheral neuropathy, as for example diabetic neuropathy, a present compounds may be administered in combination with insulin. In the case of myocardial infarction, the present compound may be administered along with angioplasty, surgery, blood pressure medication, and/or as part of an exercise and diet regimen.

In another aspect of the present invention, the present compounds may be used in combination with drug-eluting stents, for example, to prevent restenosis by promoting re-endothelialization of the blood vessels being treated for stenosis. One or more of the present compounds may be used either as a single agent or combination of agents on a stent or combined with other compounds and/or agents; for example, one or more of the present compounds may be used in combination with paclitaxel or sirilomus. The use of one or more of the present compounds with stents may reduce the risk or occurrence of thrombosis that may be associated with traditional drug-coated stents, for example, with stents coated only with anti-proliferative drugs (see Walter et al. *Circulation,* 2004, 36-45 and references cited therein).

In another aspect of the present invention, the present compounds may be used in combination with drug-eluting stents to provide local delivery of one or more present compounds to downstream heart muscle or blood vessels or for peripheral ischemic disease.

The delivery profiles of the present compounds from stents may be determined by delivery systems that are commonly used with traditional drug eluting stents. For example, the present compounds may be used with stents that deliver drugs slowly over a period of time or with stents that delivery one or more large doses of a drug at one or more given times. Additionally, the present compounds may be delivered either locally or parenterally from stents. Such stents may employ drug releasing polymers or other delivery vehicles to achieve the desired drug release profiles.

In addition to stents, the present compounds may be used in conjunction with other drug-releasing medical devices, for example, balloon catheters and injection catheters.

In another aspect, the present invention provides pharmaceutical preparations comprising the present compounds. The present compounds may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium may be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the present compound, its use in the pharmaceutical preparation of the present invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations".

Pharmaceutical formulations of the present invention may also include veterinary compositions, e.g., pharmaceutical preparations of the present compounds suitable for veterinary uses, e.g., for the treatment of livestock, such as goats, horses, sheep, etc., or domestic animals, e.g., dogs, cats, rabbits, etc., or other animals, such as apes, monkeys, and chimpanzees.

Rechargeable or biodegradable devices may also provide methods of introduction. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, may be used to form an implant for the sustained release of a present compound at a particular target site.

The preparations of the present invention may be given orally, parenterally, topically, or rectally. They are of course given by forms suitable for each administration route. For example, they are administered in tablets or capsule form, by injection, inhalation, eye lotion, ointment, suppository, controlled release patch, etc., administration by injection, infusion or inhalation; topical by lotion or ointment; and rectal by suppositories. Oral and topical administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular present compound employed, the age, sex, weight, condition, general health and prior medical history of the patient being treated, and like factors well known in the medical arts.

A physician or veterinarian having ordinary skill in the art may readily determine and prescribe the effective amount of the pharmaceutical composition required. For example, the physician or veterinarian may start doses of the compounds of the present invention employed in the pharmaceutical composition at levels lower than that required in order to achieve the desired therapeutic effect and gradually increase the dosage until the desired effect is achieved.

In general, a suitable daily dose of a compound of the present invention may be that amount of the compound which is the lowest dose effective to produce a therapeutic effect. Such an effective dose may generally depend upon the factors described above. Generally, intravenous, intracerebroventricular, and subcutaneous doses of the compounds of this invention for a patient may range from about 0.0001 to about 100 mg per kilogram of body weight per day, preferably from about 0.001 to about 10 mg per kilogram, even more preferably from about 0.01 to about 1 mg per kilogram.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy, and cure.

The patient receiving this treatment is any animal in need, including primates, in particular humans, and other mammals. For example, non-human animal subjects to which the present invention may be applicable include both domestic animals and livestock, raised either as pets or for commercial purposes. Such animals include apes, monkeys, chimpanzees, equines (such as horses), cattle, swine, sheep and goats; and poultry and pets in general, such as dogs, cats, rabbits, etc.

The compound of the present invention may be administered as such or in admixtures with pharmaceutically acceptable and/or sterile carriers and may also be administered in conjunction with other antimicrobial agents such as penicillins, cephalosporins, aminoglycosides, and glycopeptides. Conjunctive therapy thus includes sequential, simultaneous and separate administration of the active compound in a way that the therapeutic effects of the first administered one are not entirely dissipated when the subsequent is administered.

V. Pharmaceutical Compositions

While it is possible for a compound of the present invention to be administered alone, the present compounds may also be administered as a pharmaceutical formulation (composition). The present compounds may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments, the present compounds may be simply dissolved or suspended in sterile water. In certain embodiments, the pharmaceutical preparation is non-pyrogenic, i.e., does not elevate the body temperature of a patient.

The phrase "therapeutically effective amount" as used herein means that amount of a compound, material, or composition comprising a compound of the present invention which is effective for producing some desired therapeutic effect in at least a sub-population of cells in an animal and thereby blocking the biological consequences of that pathway in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, useful for preparing a medically or therapeutically useful composition of the present compounds. Each carrier must be "acceptable" in the sense of being compatible with the other ingredients of the formulation and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present compounds may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts may be prepared in situ during the final isolation and purification of the compounds of the present invention, or by separately reacting a purified compound of the present invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the present compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tararic, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts may likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants may also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which may be combined with a carrier material to produce a single dosage form will vary depending upon the host being treated, the particular mode of administration. The amount of active ingredient which may be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the present invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the present invention for oral administration (capsules, tablets, pills, dragees, powders, granules and the like), the active ingredient may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which may be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which may be used include polymeric substances and waxes. The active ingredient may also be in microencapsulated form, if appropriate, with one or more of the above-described excipients.

Liquid dosage forms for oral administration of the compounds of the present invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions may also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the present invention for rectal or vaginal administration may be presented as a suppository, which may be prepared by mixing one or more of the present compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active present compound.

Formulations of the present invention which may be useful for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a compound of this invention, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms may be made by dissolving or dispersing the present compounds in the proper medium. Absorption enhancers may also be used to increase the flux of the present compounds across the skin. The rate of such flux may be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the present invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms may be made by forming microencapsulated matrices of the present compounds in biodegradable polymers such as polylactide-polyglycolide. Depending on the ratio of drug to polymer, and the nature of the particular polymer employed, the rate of drug release may be controlled. Examples of other biodegradable polymers include poly (orthoesters) and poly(anhydrides). Depot injectable formulations may also be prepared by entrapping the drug in liposomes or microemulsions which are compatible with body tissue.

When the compounds of the present invention may be administered as pharmaceuticals, to humans and animals, they may be given per se or as a pharmaceutical composition containing, for example, about 0.1 to 99.5% (more preferably, about 0.5 to 90%) of active ingredient in combination with a pharmaceutically acceptable carrier.

The addition of one or more of the present compounds of the present invention to animal feed may be accomplished by preparing an appropriate feed premix containing the active compound in an effective amount and incorporating the premix into the complete ration.

Alternatively, an intermediate concentrate or feed supplement containing the active ingredient may be blended into the feed. The way in which such feed premixes and complete rations may be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

VI. Synthetic Schemes and Identification of Active Agonists

The present compounds, and congeners thereof, may be prepared readily by employing the cross-coupling technologies of Suzuki, Stille, Heck and the like. These coupling reactions are carried out under relatively mild conditions and tolerate a wide range of "spectator" functionality.

a. Combinatorial Libraries

The compounds of the present invention, particularly libraries of variants having various representative classes of substituents, are amenable to combinatorial chemistry and other parallel synthesis schemes (see, for example, PCT WO 94/08051). The result is that large libraries of related compounds, e.g., a variegated library of compounds represented above, may be screened rapidly in high throughput assays in order to identify potential hedgehog agonist lead compounds, as well as to refine the specificity, toxicity, and/or cytotoxickinetic profile of a lead compound. For instance, patched, hedgehog, or smoothened bioactivity assays may be used to screen a library of the present compounds for those having antagonist activity toward patched or agonist activity towards hedgehog or smoothened.

Simply for illustration, a combinatorial library for the purposes of the present invention may be a mixture of chemically related compounds which may be screened together for a desired property. The preparation of many related compounds in a single reaction greatly reduces and simplifies the number of screening processes which need to be carried out. Screening for the appropriate physical properties may be done by conventional methods.

Diversity in the library may be created at a variety of different levels. For instance, the substrate aryl groups used in the combinatorial reactions may be diverse in terms of the core aryl moiety, e.g., a variegation in terms of the ring structure, and/or may be varied with respect to the other substituents.

A variety of techniques are available in the art for generating combinatorial libraries of small organic molecules such as the present compounds. See, for example, Blondelle et al. (1995) Trends Anal. Chem. 14:83; the Affymax U.S. Pat. Nos. 5,359,115 and 5,362,899: the Ellman U.S. Pat. No. 5,288, 514: the Still et al. PCT publication WO 94/08051; the ArQule U.S. Pat. Nos. 5,736,412 and 5,712,171; Chen et al. (1994) JACS 116:2661: Kerr et al. (1993) JACS 115:252; PCT publications WO92/10092, WO93/09668 and WO91/07087; and the Lerner et al. PCT publication WO93/20242). Accordingly, a variety of libraries on the order of about 100 to 1,000,000 or more diversomers of the present compounds may be synthesized and screened for particular activity or property.

In one embodiment, a library of candidate compounds diversomers may be synthesized utilizing a scheme adapted to the techniques described in the Still et al. PCT publication WO 94/08051, e.g., being linked to a polymer bead by a hydrolyzable or photolyzable group, optionally located at one of the positions of the candidate agonists or a substituent of a synthetic intermediate. According to the Still et al. technique, the library is synthesized on a set of beads, each bead including a set of tags identifying the particular diversomer on that bead. The bead library may then be "plated" with hedgehog-responsive cells. The diversomers may be released from the bead, e.g., by hydrolysis.

The structures of the compounds useful in the present invention lend themselves readily to efficient synthesis. The nature of the structures of the present compounds, as generally set forth above, allows the rapid combinatorial assembly of such compounds. For example, as in the scheme set forth below, an activated aryl group, such as an aryl triflate or bromide, attached to a bead or other solid support may be linked to another aryl group by performing a Stille or Suzuki coupling with an aryl stannane or an aryl boronic acid. If the second aryl group is functionalized with an aldehyde, an amine substituent may be added through a reductive amination. Alternatively, the second aryl group may be functionalized with a leaving group, such as a triflate, tosylate, or halide, capable of being displaced by an amine. Or, the second aryl group may be functionalized with an amine group capable of undergoing reductive amination with an amine, e.g., $CyKNH_2$. Other possible coupling techniques include transition metal-mediated amine arylation reactions. The resultant secondary amine may then be further functionalized by an acylation, alkylation, or arylation to generate a tertiary amine or amide which may then be cleaved from the resin or support. These reactions generally are quite mild and have been successfully applied in combinatorial solid-phase synthesis schemes. Furthermore, the wide range of substrates and coupling partners suitable and available for these reactions permits the rapid assembly of large, diverse libraries of compounds for testing in assays as set forth herein. For certain schemes, and for certain substitutions on the various substituents of the present compounds, one of skill in the art will recognize the need for masking certain functional groups with a suitable protecting group. Such techniques are well known in the art and are easily applied to combinatorial synthesis schemes.

screening programs which test libraries of compounds and natural extracts, high throughput assays are desirable in order to maximize the number of compounds surveyed in a given period of time. Thus, libraries of synthetic and natural products may be sampled for other compounds which are the present compounds.

In addition to cell-free assays, test compounds may also be tested in cell-based assays. In one embodiment, cell which are responsive to the addition of hedgehog protein may be contacted with a test agent of interest, with the assay scoring for, e.g., promotion of proliferation of the cell in the presence of the test agent.

A number of gene products have been implicated in patched-mediated signal transduction, including patched, transcription factors of the cubitus interruptus (ci) family, the serine/threonine kinase fused (fu) and the gene products of costal-2, smoothened and suppressor of fused.

The induction of cells by hedgehog proteins sets in motion a cascade involving the activation and inhibition of downstream effectors, the ultimate consequence of which is, in some instances, a detectable change in the transcription or translation of A gene. Potential transcriptional targets of hedgehog-mediated signaling are the patched gene (Hidalgo and Ingham, 1990 *Development* 110, 291-301; Marigo et al., 1996 Nature. 384(6605):176-9) and the vertebrate homologs of the *drosophila* cubitus interruptus gene, the Gli genes (Hui et al. (1994) *Dev Biol* 162:402-413). Patched gene expression has been shown to be induced in cells of the limb bud and the neural plate that are responsive to Shh. (Marigo et al. (1996) *PNAS* 93:9346-51; Marigo et al. (1996) *Development* 122: 1225-1233). The Gli genes encode putative transcription factors having zinc finger DNA binding domains (Orenic et al. (1990) *Genes & Dev* 4:1053-1067; Kinzler et al. (1990) *Mol Cell Biol* 10:634-642). Transcription of the Gli gene has been reported to be upregulated in response to hedgehog in limb buds, while transcription of the Gli3 gene is downregulated in response to hedgehog induction (Marigo et al. (1996) *Development* 122:1225-1233). By selecting transcriptional regulatory sequences from such target genes, e.g., from patched or

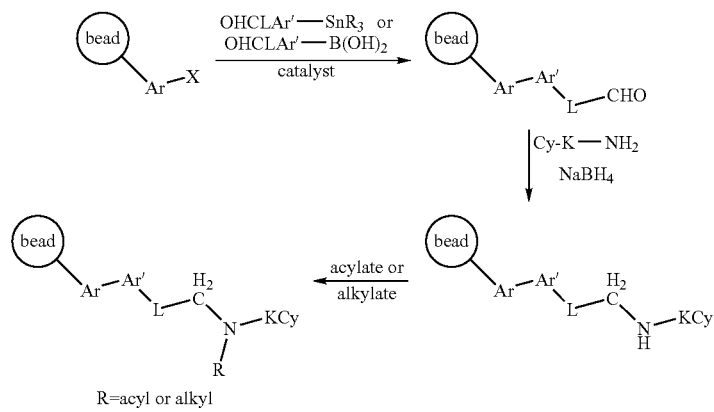

Many variations on the above and related pathways permit the synthesis of widely diverse libraries of compounds which may be tested as agonists of hedgehog function.

b. Screening Assays

There are a variety of assays available for determining the ability of a compound to antagonize patched function or agonize smoothened or hedgehog function, many of which may be disposed in high-throughput formats. In many drug- Gli genes, that are responsible for the up- or down-regulation of these genes in response to hedgehog signalling, and operatively linking such promoters to a reporter gene, one may derive a transcription based assay which is sensitive to the ability of a specific test compound to modify hedgehog-mediated signalling pathways. Expression of the reporter gene, thus, provides a valuable screening tool for the development of compounds that act as agonists of hedgehog.

Reporter gene based assays of this invention measure the end stage of the above-described cascade of events, e.g., transcriptional modulation. Accordingly, in practicing one embodiment of the assay, a reporter gene construct is inserted into the reagent cell in order to generate a detection signal dependent on activation of the hedgehog pathway, or stimulation by Shh itself. The amount of transcription from the reporter gene may be measured using any method known to those of skill in the art to be suitable. For example, mRNA expression from the reporter gene may be detected using RNAse protection or RNA-based PCR, or the protein product of the reporter gene may be identified by a characteristic stain or an intrinsic biological activity. The amount of expression from the reporter gene is then compared to the amount of expression in either the same cell in the absence of the test compound or it may be compared with the amount of transcription in a substantially identical cell that lacks the target receptor protein. Any statistically or otherwise significant increase in the amount of transcription indicates that the test compound has in some manner antagonized the normal patched signal (or agonized the hedgehog or smoothened signal), e.g., the test compound is a potential hedgehog agonist.

EXEMPLIFICATION

The present invention now being generally described, it will be more readily understood by reference to the following examples which are included merely for purposes of illustration of certain aspects and embodiments of the present invention, and are not intended to limit the present invention.

In the experimental section below, the term 'hedgehog protein' is used to designate octyl-Shh-N, a lipophilic form of a bacterially derived fragment of human sonic hedgehog protein (amino acids 24-198, Shh-N). Specifically, Shh-N has been covalently linked in vitro via its amino terminal cysteine to an octyl maleimide group. This modified form, like others described recently (Pepinsky et al., *J. Biol. Chem.* 1998, 273, 14037-45) exhibits higher specific potency than the corresponding unmodified fragment in several cell-based assays of hedgehog signalling.

Compound Synthesis

Compounds of the present invention are synthesized according to the following general methods.

Abbreviations
  AcOH glacial acetic acid
  BOC tert-butoxycarbonyl
  br. broad
  n-BuLi n-butyllithium
  conc. concentrated
  d doublet
  DCM dichloromethane
  DIPEA N,N-diisopropylethylamine
  DMF N,N-dimethylformamide
  DMSO dimethyl sulfoxide
  equiv. equivalent
  EtOAc ethyl acetate
  EtOH ethanol
  h hours
  HPLC high performance liquid chromatography
  LC liquid chromatography
  MeOH methanol
  min minutes
  MS mass spectroscopy
  NMR nuclear magnetic resonance
  obsc. obscured
  PhMe toluene
  ppm parts per million
  RT ambient (room) temperature
  s singlet
  TBME tert-butyl methyl ether
  TFA trifluoroacetic acid
  THF tetrahydrofuran
  vol volume (1 vol=1 mL:1 g)
General Methods
  Method A—Suzuki Coupling (Thermal Conditions)

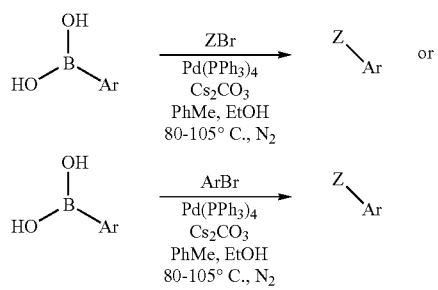

A stirred suspension of the boronic acid (1 equiv.), aryl halide/triflate (1-1.2 equiv.), cesium carbonate (2-2.2 equiv.) And tetrakis(triphenyl-phosphine)palladium(0) (0.05-0.1 equiv.) in toluene (40 vol) and EtOH (10 vol) at RT is degassed with nitrogen for 15 minutes. The mixture is then warmed to 80-105° C. (external temperature). The reaction is monitored by LC/MS and, if incomplete after 3-4 h, more tetrakis(triphenyl-phosphine)palladium(0) (0.05-0.1 equiv.) is added and the reaction heated further (1-2 h). On completion, the reaction mixture is allowed to cool to RT then filtered through celite, washing the solid residues with DCM (100 vol). The filtrate is then reduced in vacuo and the residue purified by chromatography (EtOAc in heptane plus 0.5% triethylamine) to afford the desired biaryl, Z—Ar.

Method B—Suzuki Coupling (Microwave Conditions)

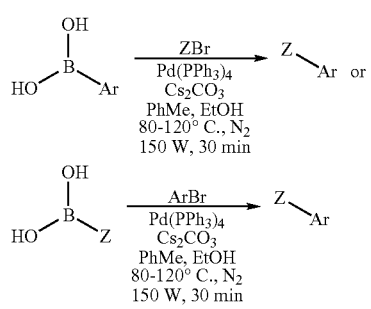

A suspension of the boronic acid (1 equiv.), aryl halide/triflate (1-1.2 equiv.), cesium carbonate (2-2.2 equiv.) And tetrakis(triphenylphosphine)palladium(0) (0.05-0.1 equiv.) in toluene (8 vol) and EtOH (2 vol) at RT is degassed with nitrogen for 15 minutes. The mixture is then irradiated (150 W, Discover® System microwave reactor by CEM Corporation, Matthews, N.C., USA) at 80° C. for 30 min. On cooling, the reaction is analysed by LC/MS and, if incomplete, irradiated again (150 W) at 120° C. for 30 min. If the reaction is still incomplete at this juncture, more tetrakis(triphenylphosphine) palladium(0) (0.05-0.1 equiv.) is added and the reaction irradiated again (150 W) at 120° C. for 30 min. On completion, the reaction mixture is cooled to RT then filtered through celite, washing the solid residues with DCM (100 vol). The filtrate is then reduced in vacuo and the residue purified by chromatography (EtOAc in heptane plus 0.5% triethylamine) to afford the desired biaryl, Z—Ar.

Method C—Reductive Amination

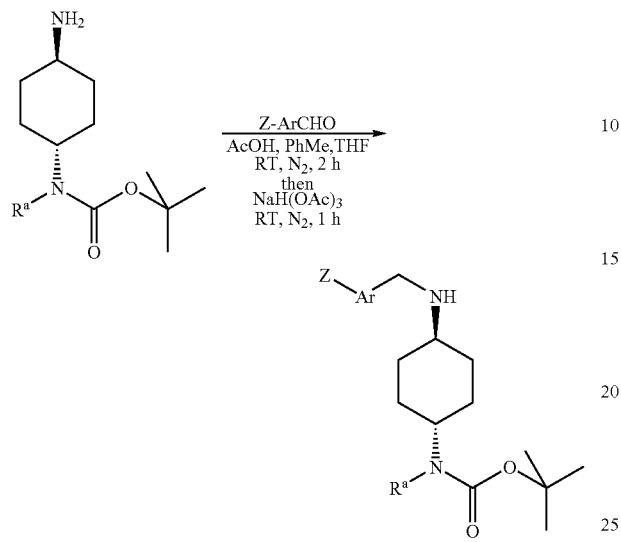

A stirred suspension of amine (1-1.2 equiv.) And aldehyde (1 equiv.) in a 1:1 mixture of THF (15 vol) and toluene (15 vol) is treated with AcOH (1.2 equiv.) at RT. After stirring a minimum of 2 h, the reaction mixture is treated with sodium triacetoxyborohydride (1.4 equiv.) And stirred a minimum of 1 h. Reaction progress is monitored by LC/MS. On completion, the reaction mixture is quenched with aqueous NaHCO$_3$ (30 vol) and extracted into EtOAc (3×30 vol). The combined organic phases are then dried over Na$_2$SO$_4$ and the solvents removed in vacuo to afford the desired crude amine.

Method D—Amide Formation

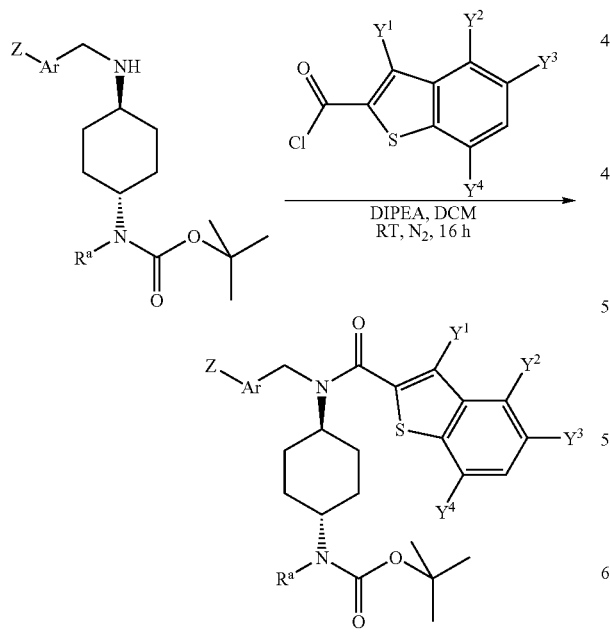

A stirred solution of the amine (1 equiv.) And DIPEA (2.2 equiv.) in DCM (30 vol) is treated with the benzo[b]thiophene acid chloride (1.2-1.5 equiv.) in one portion at 0° C. The solution is then allowed to warm to RT and the reaction progress monitored by LC/MS (typical duration 16 h). On completion the DCM is removed in vacuo and the residue purified by chromatography (EtOAc in heptane plus 0.5% triethylamine) to afford the desired amide.

Method E—BOC Deprotection (HCl in 1,4-dioxane)

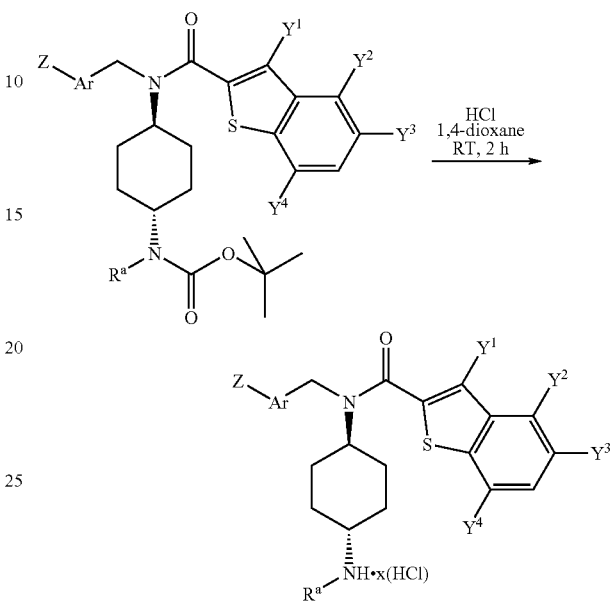

The tert-butyl carbamate is dissolved in a 4 M solution of HCl in 1,4-dioxane (40 vol) and stirred at RT. LC/MS is used to monitor the reaction (typical duration 2 h). On completion, the solvents are removed in vacuo to afford the amine as the HCl salt.

Method F—BOC Deprotection (HCl in EtOH)

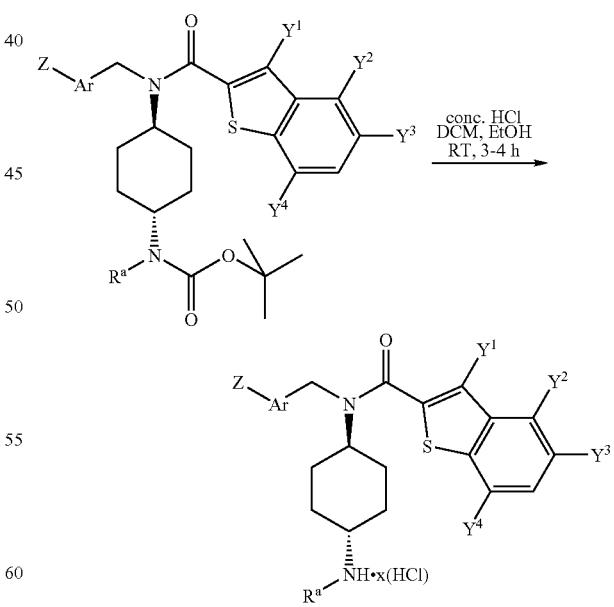

A solution of the tert-butyl carbamate in DCM (15 vol) at RT is diluted with EtOH (50 vol) then conc. HCl (15 vol) is added in one portion. LC/MS is then used to monitor the reaction (typical duration 3-4 h). On completion, the solvents are removed in vacuo to afford the amine as the HCl salt.

Method G—BOC Deprotection (TFA in DCM)

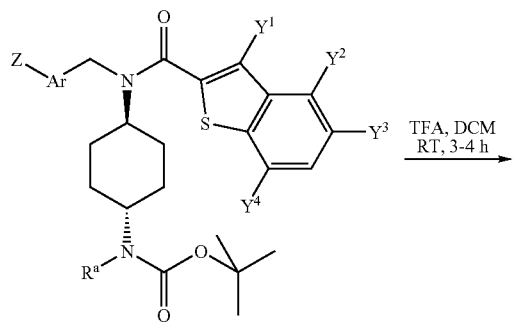

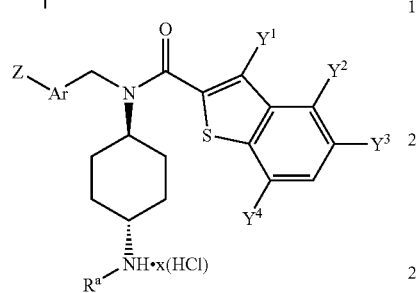

A stirred solution of the tert-butyl carbamate in DCM (120 vol) is treated with TFA (30 vol) at RT. LC/MS is then used to monitor the reaction (typical duration 2-3 h). On completion, the solvents are removed in vacuo to afford the amine as the TFA salt.

Method H—HCl Salt Formation

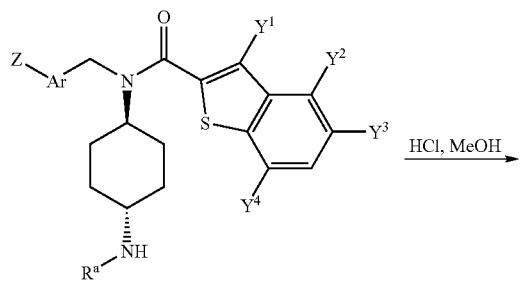

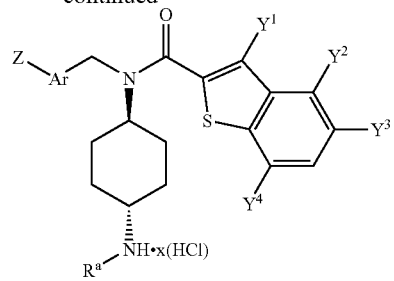

A stirred solution of the amine in MeOH (100 vol) is treated with conc. HCl (25 vol) at RT. The solvents are then removed in vacuo to afford the amine as the HCl salt.

Method J—TFA Salt Formation

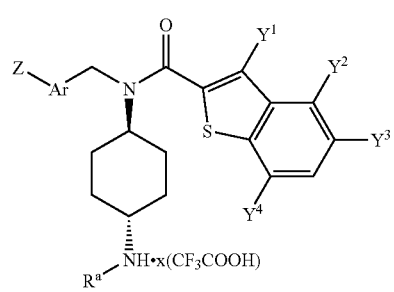

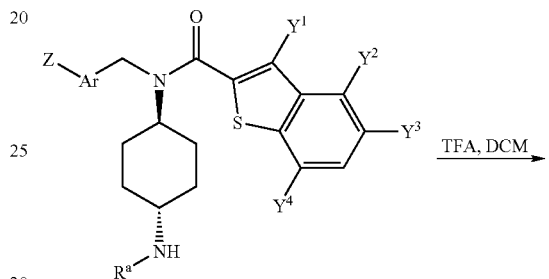

A stirred solution of the amine in DCM (100 vol) is treated with TFA (25 vol) at RT. The solvents are then removed in vacuo to afford the amine as the TFA salt.

Method L1—Synthetic Procedures Used for a Biaryl Library

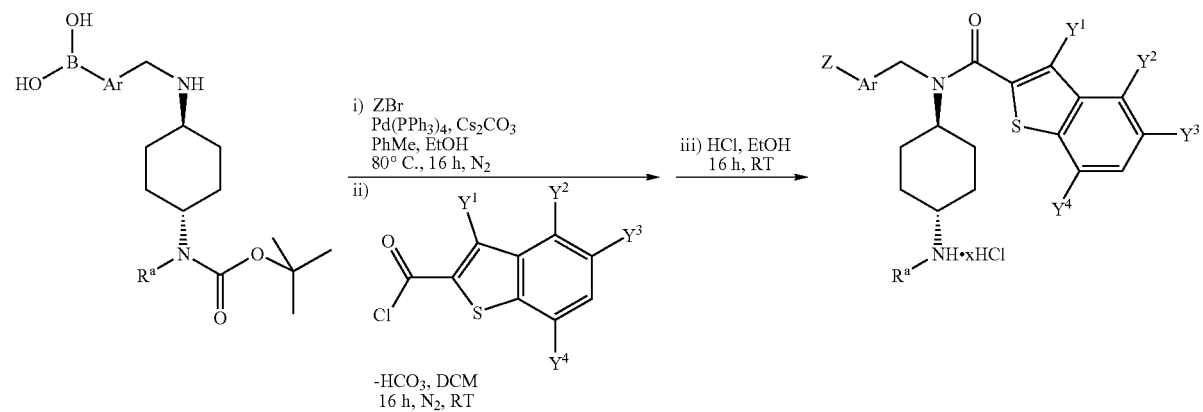

The boronic acid (1.2 equiv.), aryl halide (1.0 equiv.), cesium carbonate (2.2 equiv.) And tetrakis(triphenylphosphine)palladium(0) (0.01 equiv.) Are combined and suspended in a mixture of toluene (4 mL) and EtOH (1 mL). The reaction mixtures are warmed to 80° C. (external temperature), degassed with nitrogen for 5 minutes then agitated for 16 h at 80° C. The reactions are allowed to cool to RT then the solvents removed in vacuo. The crude residues are purified by chromatography using firstly 20% EtOAc in heptane to remove triphenylphosphine oxide, then 20% MeOH in EtOAc to isolate the desired amines. On removal of the solvents in vacuo, the amines are dissolved in DCM (4 mL) and treated with bicarbonate resin (2 equiv.) followed by 3-chlorobenzo[b]thiophene-2-carbonyl chloride (1.2 equiv.) At RT. After stirring 16 h, the reaction mixtures are filtered then directly purified by chromatography using firstly 20% EtOAc in heptane to remove reaction by-products, then 50% EtOAc in heptane to isolate the desired amides. On removal of the solvents in vacuo, the amides are dissolved in EtOH (0.66 mL) and treated with conc. HCl (0.33 mL) (or TFA in DCM to give the TFA salt) at RT. After stirring 16 h, the solvents are removed in vacuo, the residues taken up in acetonitrile and analysed by LC/MS. If the purity of the final compound is >50% no further purification is attempted. Thus the acetonitrile is simply removed in vacuo to yield the title compound. If the purity of the final compound is <50%, the title compound is obtained after preparative HPLC.

Method L2—Synthetic Procedures Used for a Biaryl Library

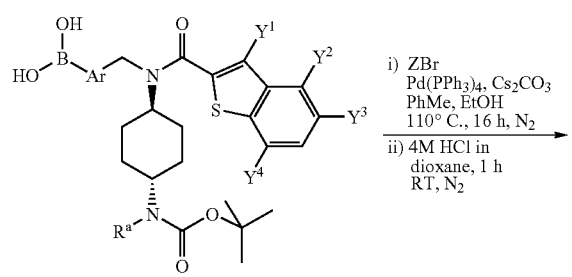

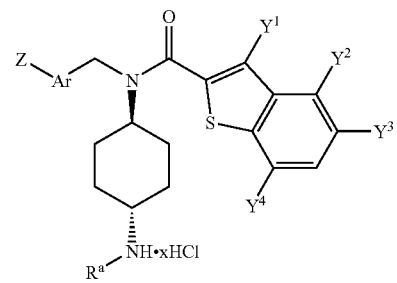

Cesium carbonate (2.2 equiv.) And tetrakis(triphenylphosphine)palladium(0) (0.01 equiv.) Are combined and degassed with nitrogen for 5 minutes. A solution of the boronic acid (1.2 equiv.) And aryl halide (1.0 equiv.) in toluene (3 mL) and EtOH (1 mL) is then added, the reaction mixtures degassed with nitrogen for a further 5 minutes, then warmed for 16 h at 110° C. (external temperature). The reactions are allowed to cool to RT then the solvents removed in vacuo. The crude residues are purified by chromatography (EtOAc in heptane) to give the intermediate Suzuki products. These are treated with a 4 M solution of HCl in 1,4-dioxane (0.5 mL) for 1 h at RT, after which the solvents are removed in vacuo. The reaction residues are then dissolved in MeOH and analysed by LC/MS. If the purity of the final compound is >50% no further purification is attempted. Thus the MeOH is simply removed in vacuo to yield the title compound. If contamination by triphenylphosphine oxide is extensive, the MeOH is removed in vacuo and the residue taken up in water (1 mL). This aqueous solution is washed with TBME (3×1 mL) then reduced in vacuo to afford the title compound.

Compounds of the present invention are also synthesized by the methods detailed in the following scheme:

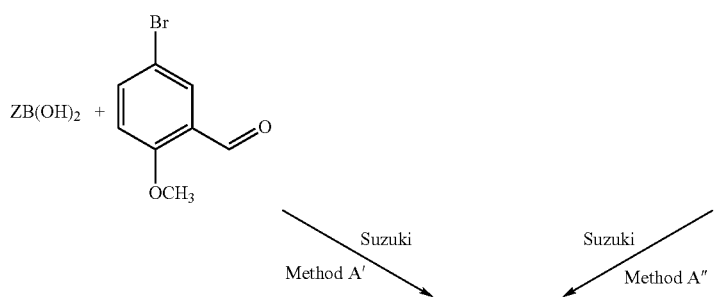

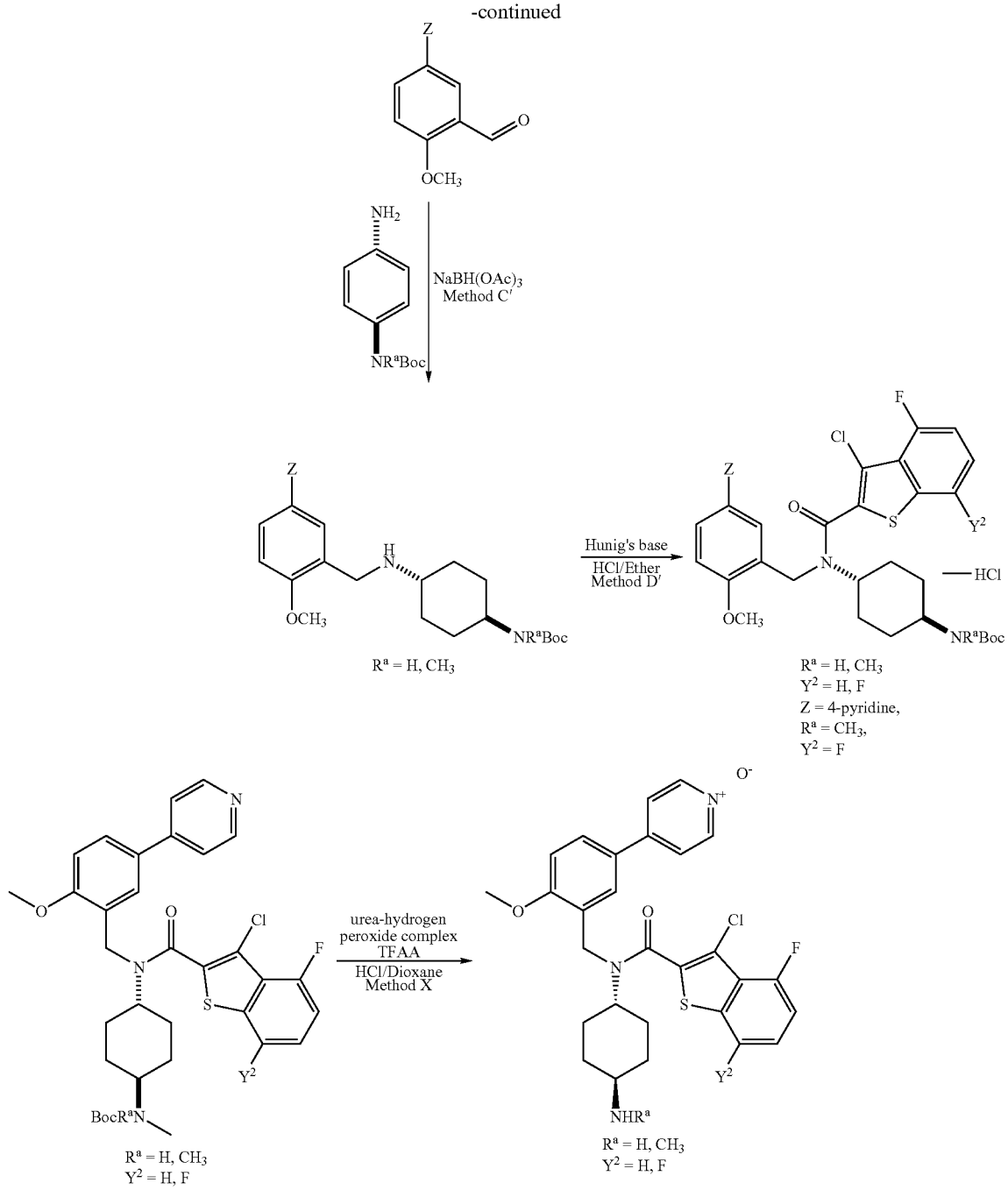

Method A':

A suspension of the 5-bromo-2-methoxybenzaldehyde (1.0 equiv.), aryl boronic acid (1.0 equiv.), and cesium carbonate (2.2 equiv.) in ethanol (0.4 mL) and toluene (1.6 mL) is degassed with Argon for 30 minutes. Then tetrakis(triphenylphosphine)palladium(0) (0.05 equiv.) is added. The reaction mixture is filtered through a pad of celite and the solids are washed with dichloromethane. The dark filtrate is reduced in vacuo and the crude residue is purified by column chromatography (20-40% ethyl acetate in heptanes) to give the desired biaryl aldehyde as a solid. Product is analyzed by HPLC, MS and Hnmr.

Method A":

A suspension of the 3-formyl-4-methoxyphenylboronic acid (1.0 equiv.), aryl bromide (1.0 equiv.), and cesium carbonate (2.2 equiv.) in ethanol (0.4 mL) and toluene (1.6 mL) is degassed with Argon for 30 minutes. Then tetrakis(triphenylphosphine) palladium(0) (0.05 equiv.) is used. The reaction mixture is then filtered through a pad of celite and the solids obtained washed with dichloromethane. The dark filtrate is then reduced in vacuo and the crude residue obtained purified by column chromatography (20-40% ethyl acetate in heptanes) to give the desired biaryl aldehyde as a solid. Product is analyzed by HPLC, MS and Hnmr.

Method C':

To a stirred solution of the amine (1.2 equiv.) in anhydrous methanol (5 mL) with 4 Å molecular sieves (4-5) is added biaryl aldehyde (1.0 equiv.) in one portion. Additional methanol is added to dissolve all the reactants. The solution is then stirred for 2 hours at ambient temperature, and then cooled to 0° C. Sodium triacetoxyborohydride (2.5 equiv.) is added in several portions over the course of 45 minutes. The reaction mixture is then left to stir at ambient temperature for 16 hours. The suspension is then filtered over a celite bed and methanol is removed in vacuo. The crude residue is purified by column chromatography (gradient elution—10% methanol in dichloromethane with 0.5% ammonium hydroxide) to give the desired secondary amine as a solid. Product is analyzed by HPLC, MS and Hnmr.

Method D':

To a stirred solution of the biaryl secondary amine (1.0 equiv.) in dichloromethane (5.5 mL) at 0° C. is added di-isopropylethylamine (2.2 equiv.) followed by the acid chloride (1.5 equiv.) in one portion. The reaction mixture is then stirred for 16 hours, over which a noticeable darkening occurred. The dichloromethane is then removed in vacuo and the crude, brown residue obtained purified by column chromatography (gradient elution—10% methanol in dichloromethane with 0.5% ammonium hydroxide) to give the desired amide as a solid. The isolated solid is then taken in dioxane and treated with 4N HCl/dioxane (2.00 equiv.) to give the hydrochloride salt of the desired amide product. Product is analyzed by HPLC, MS and Hnmr.

Method X:

Trifluoroacetic anhydride (1.0 mmol) is added dropwise to a stirred suspension of ura-hydrogen peroxide complex (1.1 mmol) in methylene chloride at 0° C. The mixture is stirred for 5 minutes and then a solution of the Boc-protected biaryl is added dropwise. The reaction is warmed to room temperature and stirring continued for 3 hours. Upon reaction is complete as indicated by HPLC, methylene chloride is added and the reaction mixture is washed with aqueous sodium bicarbonate and brine. The dichloromethane is then removed in vacuo and the crude, brown residue obtained purified by column chromatography (gradient elution—10% methanol in dichloromethane with 0.5% ammonium hydroxide) to give the desired amide as a solid. The isolated solid is then taken in dioxane and treated with 4N HCl/dioxane (2.00 equiv.) to give the hydrochloride salt of the desired amide product. Product is analyzed by HPLC, MS and Hnmr.

COMMON INTERMEDIATES

Synthesis of
trans-4-(BOC-methylamino)cyclohexylamine (3)

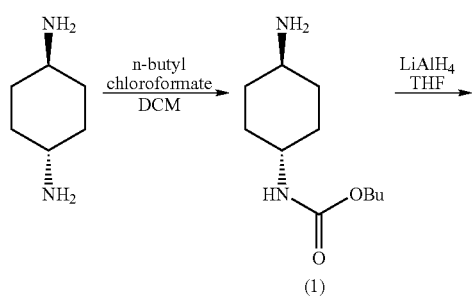

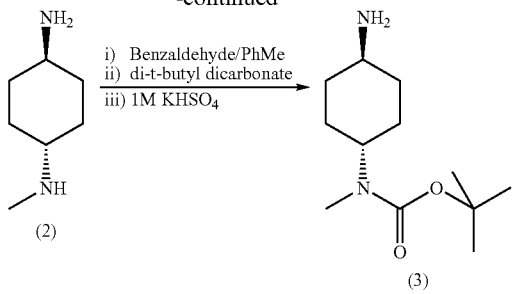

n-Butyl trans-4-(aminocyclohexyl)-carbamate (1)

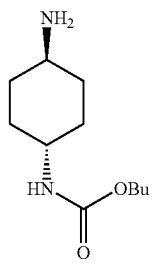

A solution of n-butylchloroformate (102 mL, 0.79 mol) in DCM (1.8 L) is added to a solution of 1,4-trans-diaminocyclohexane (180 g, 1.58 mol) in DCM (1.8 L) while maintaining the temperature between 0-5° C. (ice/salt bath). The resulting suspension is stirred 60-70 minutes then allowed to warm to 5-10° C. A solution of Na$_2$CO$_3$ (92.0 g, 0.87 mol) in water (720 mL) is added and the reaction stirred a further 5 minutes whilst warming to RT. The mixture is then transferred to a separating funnel and allowed to stand for approximately 5 minutes. The phases are separated and the aqueous phase washed with DCM (720 mL). The DCM phases are combined, dried over Na$_2$SO$_4$ (360 g), filtered and concentrated in vacuo to give a crude mixture of diamine, bis- and mono-carbamate. The crude material (164 g) is suspended in water (410 m/L) and stirred vigorously for 10-15 minutes at RT. The solid bis-carbamate is then removed by filtration, the filter cake washed with water (164 mL) and the aqueous filtrate extracted with TBME (3×3.28 L). The TBME phases are combined, washed with water (246 mL), dried over Na$_2$SO$_4$ (492 g), filtered and concentrated in vacuo to afford the title product.

Yield: 87.5 g (52%).

trans-4-(Methylamino)cyclohexylamine (2)

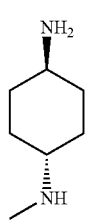

A solution of n-butyl carbamate 1 (102 g, 0.48 mol) in THF (1 L) is added over 30 minutes to a suspension of LiAlH₄ (90.4 g, 2.38 mol) in THF (2 L) at 0° C. Once the addition is complete, the reaction is heated to reflux 2 h then left to cool to RT over 16 h. The reaction is then cooled to 0-5° C. and quenched by careful addition of water (90 mL), 15% NaOH (90 mL) then more water (270 mL) over a period of 70 minutes. The resultant suspension is stirred at RT 1 h then filtered, washing the filter cake with TBME (2×2 L) and DCM (2×2 L). The solvents are removed in vacuo and residual water/n-butanol removed by azeotroping with toluene (2 L) to afford the title compound.

Yield: 55.4 g (91%).

trans-4-(BOC-methylamino)cyclohexylanine (3)

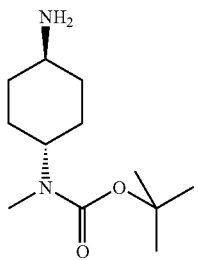

A solution of amine 2 (55.4 g, 0.43 mol) and benzaldehyde (46 mL, 0.45 mol) in toluene (554 mL) is heated at reflux using a Dean-Stark apparatus for 6 h, during which time the calculated volume of water (7.5 mL) is removed. The solution is then cooled to RT, at which point di-tert-butyl dicarbonate (103.7 g, 0.43 mol) is added portionwise over 15 minutes. The reaction is stirred 3 h and monitored by ¹H-NMR. On reaching completion, the toluene is removed in vacuo and the residue suspended in 1 M KHSO₄ (1.47 L). After stirring 4 h at RT, the reaction mixture is extracted with TBME (600 mL then 3×300 mL). The aqueous phase is then basified to pH 13 with 6 M NaOH (75 mL) and extracted with DCM (2×735 mL). The combined DCM phases are washed with brine (2×500 mL), dried (Na₂SO₄), filtered and reduced in vacuo to afford the title compound.

Yield: 67.8 g (69%).

3-{[4-(BOC-methyl-amino)-cyclohexylamino]-methyl}-4-methoxy-benzene boronic acid (4)

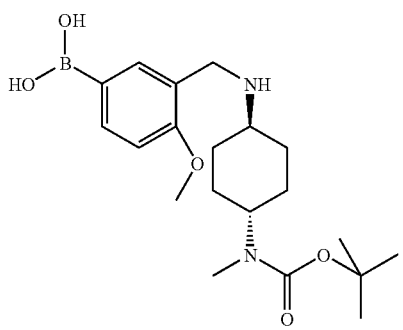

A stirred suspension of amine 3 (7.84 g, 34.3 mmol) and 3-formyl-4-methoxyphenyl boronic acid (6.18 g, 34.3 mmol) in THF (43 mL) and toluene (43 mL) is treated with AcOH (2.40 mL, 41.2 mmol) at RT. After stirring 1 h, further aliquots of THF and toluene are added (24 mL) to improve the solubility of the reagents. The addition of MeOH (30 mL) produces a homogeneous solution. After stirring 3 h, the resultant thick yellow suspension is treated with sodium triacetoxyborohydride (10.2 g, 48 mmol) and stirred a further hour. Analysis by LC/MS at this juncture confirmed the reaction is complete. The solvents are removed in vacuo and the viscous residue diluted with aqueous NaHCO₃ (150 mL) and extracted into EtOAc (3×150 mL). The combined organic phases are dried (MgSO₄) and the solvent removed in vacuo to afford the title compound.

Yield: 10.31 g (77%) @ 73% purity by LC trace. This material contained approximately 20% residual 3-formyl-4-methoxyphenyl boronic acid.

LC/MS t, 1.12 min.
MS (ES+) m/z 393 (M+H).

3-{[[4-(BOC-methyl-amino)-cyclohexyl]-(3-chlorobenzo[b]thiophene-2-carbonyl)-amino]-methyl}-4-methoxy-benzene boronic acid (5)

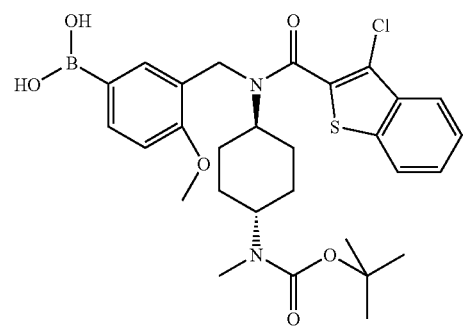

A solution of boronic acid 4 (1.95 g, 4.99 mmol) in DCM (20 mL) is treated with DIPEA (1.04 mL, 5.98 mmol), followed by 3-chlorobenzo[b]thiophene-2-carbonyl chloride (1.38 g, 5.98 mmol) in one portion. The resulting solution is stirred 16 h at RT. LC/MS at this juncture showed the reaction had reached completion. The reaction mixture is washed with water (3×10 mL) and brine (1×10 mL). The organic layer is dried over MgSO₄ and the solvent removed in vacuo to afford the title compound.

Yield: 2.50 g (86%).
LC/MS t, 1.76 min.
MS (ES+) m/z 589, 587 (M+H), 533, 531 (M-C(CH₃)₃+H).

3-Chloro-4-fluorobenzo[b]thiophene-2-carbonyl chloride (6)

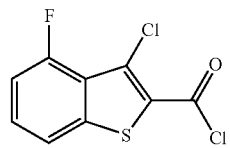

A stirred suspension of 2-fluorocinnamic acid (5.0 g, 30 mmol) in thionyl chloride (7.70 mL, 0.105 mol) is treated carefully with pyridine (0.82 mL, 7.5 mmol) at RT then heated 2 h at 140° C. (external temperature). The refluxing reaction mixture is then treated with heptane (5 mL), heated a further 5 minutes and the resultant supernatant decanted off and cooled to 0° C. The forthcoming precipitate is isolated by filtration, washed with heptane (2×2.5 mL) and dried to afford the title compound.

Yield: 2.69 g (36%).

3-{[[4-(BOC-methyl-amino)-cyclohexyl]-(3-chloro-4,fluoro-benzo[b]thiophene-2-carbonyl)-amino]-methyl}-4-methoxy-benzene boronic acid (7)

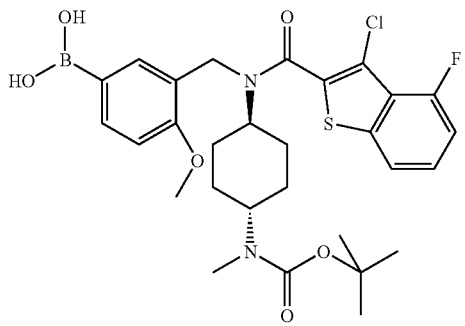

A solution of boronic acid 4 (300 mg, 0.77 mmol) in DCM (7.5 mL) is treated with triethylamine (160 μL, 1.45 mmol), followed by acid chloride 6 (223 mg, 1.50 mmol) in one portion. The resulting solution is stirred 16 h at RT. LC/MS at this juncture showed the reaction had reached completion. The reaction mixture is washed with water (3×10 mL) and brine (1×10 mL). The organic layer is dried over MgSO₄ and the solvent removed in vacuo. Purification by column chromatography (gradient elution—70% EtOAc in heptane increasing to 100% EtOAc, then 50% MeOH in EtOAc) gives the title compound.

Yield: 385 mg (83%).

LC/MS $t_r$ 1.71 min.

MS (ES+) m/z 551, 549 (M-C(CH₃)₃+H).

3-Chloro-4,7-difluorobenzo[b]thiophene-2-carbonyl chloride (8)

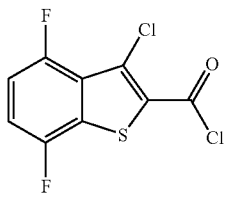

A stirred suspension of 2,5-difluorocinnamic acid (26 g, 0.14 mol) in thionyl chloride (36 mL, 0.49 mol) is treated carefully with pyridine (2.85 mL, 35 mmol) at RT then heated 16 h at 140° C. (external temperature). The hot reaction mixture is then decanted into refluxing heptane (260 mL) and heated at reflux 10 minutes before cooling to 0° C. The resultant precipitate is isolated by filtration, washed with heptane (2×25 mL) and dried to afford the title compound.

Yield: 17.4 g (46%).

3-{[[4-(BOC-methyl-amino)-cyclohexyl]-(3-chloro-4,7-difluoro-benzo[b]thiophene-2-carbonyl)-amino]-methyl}-4-methoxy-benzene boronic acid (9)

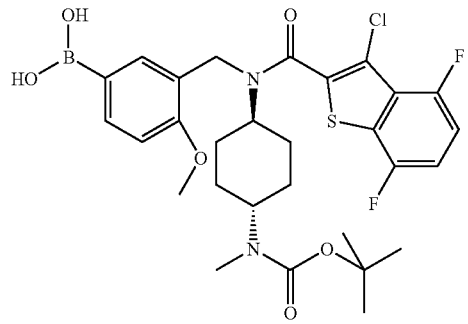

A solution of boronic acid 4 (7.60 g, 19.4 mmol) in DCM (300 mL) at 0° C. is treated with DIPEA (7.40 mL, 42.7 mmol), followed by acid chloride 8 (6.21 g, 23.3 mmol) in one portion. After warming to RT, the solution is stirred 3 h. Analysis by LC/MS at this juncture confirmed the reaction is complete. Thus the solvent is removed in vacuo and the residue purified by chromatography (gradient elution—60% EtOAc in heptane with 0.5% triethylamine increasing to neat EtOAc with 0.5% triethylamine, then 10-20% MeOH in EtOAc with 0.5% triethylamine) to afford the title compound.

Yield: 5.70 g (47%).

LC/MS $t_r$ 1.69 min.

MS (ES+) m/z 625, 623 (M+H).

4-Ethoxy-3-formyl-benzene boronic acid (10)

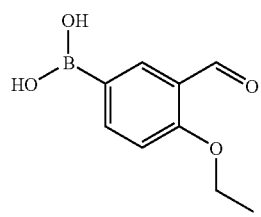

To a solution of 5-bromo-2-ethoxybenzaldehyde (1.0 g, 4.37 mmol) in EtOH (10 mL) is added triethylorthoformate (1.09 mL, 6.55 mmol) and ammonium chloride (12 mg, 0.22 mmol). The resulting solution is stirred 1 h at 45° C. to afford the protected aldehyde. TLC (1:1 EtOAc:heptane) at this juncture confirmed consumption of the starting material. The solvent is removed in vacuo to give the protected aldehyde as a yellow oil (1.5 g). This is dissolved in diethyl ether (10 mL) and cooled to −78° C. under N₂. n-BuLi (3.0 mL, 4.80 mmol, 1.6 M in hexanes) is added dropwise via syringe over 10 minutes and the reaction mixture stirred 30 minutes at −78° C. Triethylborate (2.95 mL, 10.9 mmol) is added as a solution in diethyl ether (5 mL) dropwise via syringe over 10 minutes, then stirring at −78° C. is continued for 4 h. 6 M HCl (1.3 mL) is added, the reaction warmed to RT, stirred 16 h then heated to reflux 1.5 h. The reaction is then cooled (0° C.) And basified with 4 M NaOH to pH 14. The layers are separated and the organic layer washed with 2 M NaOH (2×20 mL); the aqueous phases are then combined and washed with TBME (2×40 mL). The aqueous layer is cooled to 0° C. and Acidified with 2 M HCl to pH 1. The resultant precipitate is isolated by filtration to give the title compound.

Yield: 306 mg (36%).
LC/MS $t_r$ 1.05 min.
MS (ES+) m/z 195 (M+H).

3-{[4-(BOC-methyl-amino)-cyclohexylamino]-methyl}-4-ethoxy-benzene boronic acid (11)

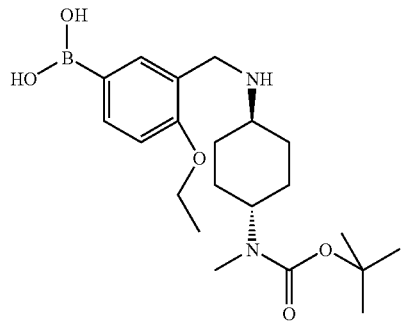

A stirred suspension of amine 3 (1.18 g, 5.16 mmol) and aldehyde 10 (835 mg, 4.30 mmol) in THF (12 mL) and toluene (12 mL) is treated with AcOH (310 µL, 5.16 mmol) at RT. After stirring 2 h the reaction mixture is treated with sodium triacetoxyborohydride (1.28 g, 5.16 mmol) and stirred a further 16 h. Analysis by LC/MS at this juncture confirmed the reaction is complete. The reaction is quenched with aqueous $NaHCO_3$ (50 mL) and extracted into EtOAc (2×50 mL). The combined organic phases are dried over $Na_2SO_4$ and the solvents removed in vacuo to give the title compound.

Yield: 1.69 g (96%).
LC/MS $t_r$ 1.26 min.
MS (ES+) m/z 407 (M+H).

3-{[[4-(BOC-methyl-amino)-cyclohexyl]-(3-chlorobenzo[b]thiophene-2-carbonyl)-amino]-methyl}-4-ethoxy-benzene boronic acid (12)

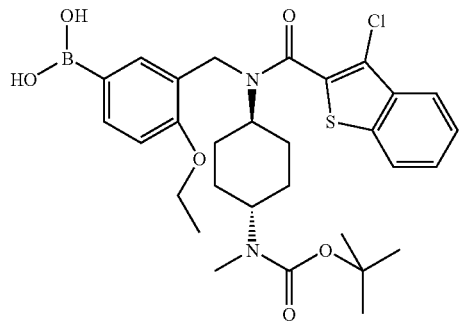

A solution of boronic acid 11 (700 mg, 1.72 mmol) in DCM (15 mL) at 0° C. is treated with triethylamine (0.48 mL, 3.45 mmol), followed by 3-chlorobenzo-[b]thiophene-2-carbonyl chloride (439 mg, 1.90 mmol) in one portion. After warming to RT, the solution is stirred 16 h. Analysis by LC/MS at this juncture confirmed the reaction is complete. Thus the reaction is diluted with aqueous $NaHCO_3$ (20 mL) and extracted into EtOAc (3×25 mL). The combined EtOAc phases are dried ($Na_2SO_4$) and reduced in vacuo to afford the title compound.

Yield: 978 mg (94%).
LC/MS $t_r$ 1.86 min.
MS (ES+) m/z 547, 545 (M-C($CH_3$)$_3$+H).

Exemplary Compounds

Synthesis of Compound 301

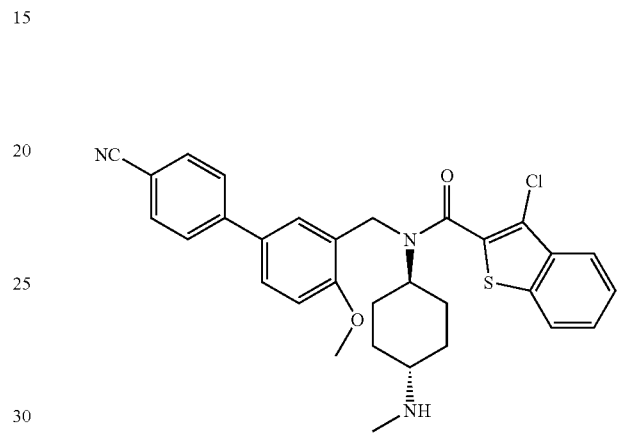

tert-Butyl {4-[(4'-cyano-4-methoxy-biphenyl-3-ylmethyl)-amino]-cyclohexyl}-methyl-carbamate (13)

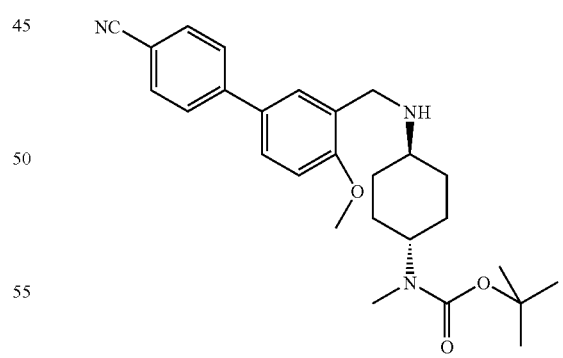

Boronic acid 4 (300 mg, 0.76 mmol) is coupled to 4-bromobenzonitrile (167 mg, 0.92 mmol) using Method B to give the title compound.

Yield: 367 mg (quant.). Contains ca. 36% triphenylphosphine oxide.

LC/MS $t_r$ 1.42 min.
MS (ES+) m/z 450 (M+H), 394 (M-C($CH_3$)$_3$+H).

tert-Butyl {4-[(3-chloro-benzo[b]thiophene-2-carbonyl)-(4'-cyano-4-methoxy-biphenyl-3-ylmethyl)-amino]-cyclohexyl}-methyl-carbamate (14)

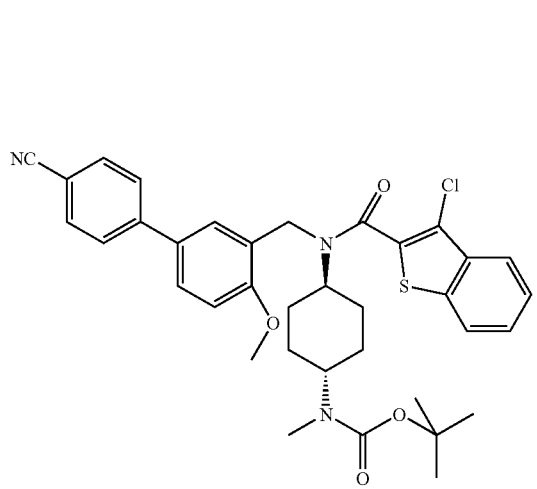

Biaryl amine 13 (367 mg, 0.82 mmol) is treated with 3-chlorobenzo-[b]thiophene-2-carbonyl chloride (226 mg, 0.98 mmol) using Method D to give the title compound.
Yield: 110 mg (21%).
LC/MS $t_r$ 1.97 min.
MS (ES+) m/z 590, 588 (M-C(CH$_3$)$_3$+H).

3-Chloro-benzo[b]thiophene-2-carboxylic acid (4'-cyano-4-methoxy-biphenyl-3-ylmethyl)-(4-methylamino-cyclohexyl)-amide hydrochloride (15)

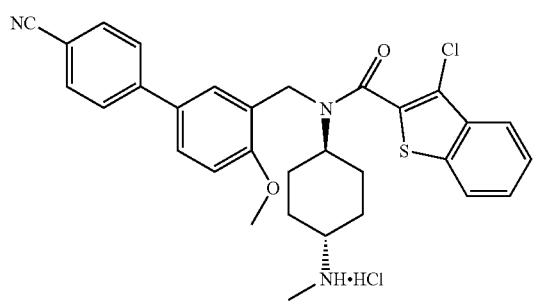

tert-Butyl carbamate 14 (110 mg, 0.17 mmol) is deprotected using Method F to give the title compound.
Yield: 100 mg (quant.).
LC/MS $t_r$ 1.47 min.
MS (ES+) m/z 546, 544 (M+H), 515, 513 (M-31+H).

Synthesis of Compound 302

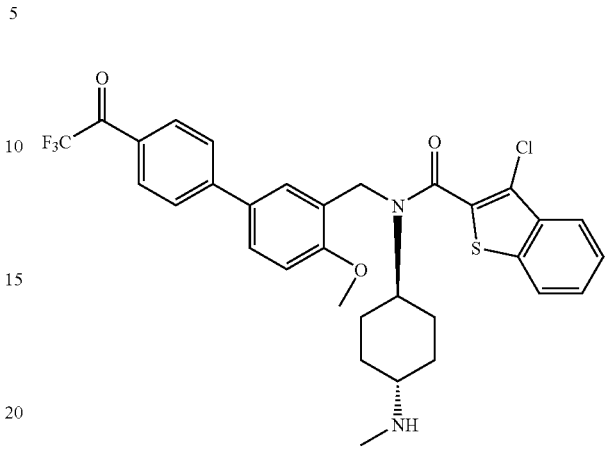

tert-Butyl (4-{[4-methoxy-4'-(2,2,2-trifluoro-acetyl)-biphenyl-3-ylmethyl]-amino}-cyclohexyl)-methyl-carbamate (16)

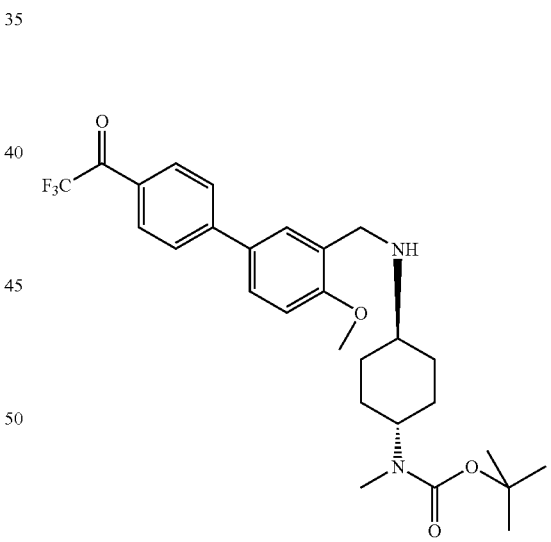

Boronic acid 4 (620 mg, 1.60 mmol) is coupled to 4'-bromo-2,2,2-trifluoroacetophenone (400 mg, 1.60 mmol) using Method B to give the title compound.
Yield: 467 mg (57%).
LC/MS $t_r$ 1.34 min.
MS (ES+) m/z 521 (M+H) 465 (M-C(CH$_3$)$_3$+H).

tert-Butyl (4-{(3-chloro-benzo[b]thiophene-2-carbonyl)-[4-methoxy-4'-(2,2,2-trifluoro-acetyl)-biphenyl-3-ylmethyl]-amino}-cyclohexyl)-methyl-carbamate (17)

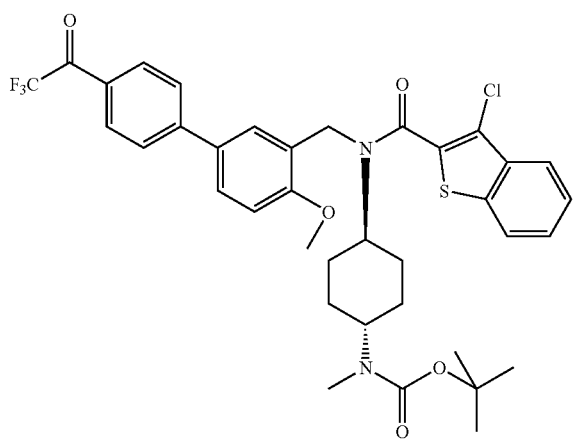

Biaryl amine 16 (467 mg, 0.90 mmol) is treated with 3-chlorobenzo-[b]thiophene-2-carbonyl chloride (290 mg, 1.26 mmol) using Method D to give the title compound.

Yield: 539 mg (88%).

LC/MS $t_r$ 1.94 min.

MS (ES+) m/z 735, 733 (M+H$_2$O+H) 679, 677 (M-C(CH$_3$)$_3$+H$_2$O+H).

3-Chloro-benzo[b]thiophene-2-carboxylic acid [4-methoxy-4'-(2,2,2-trifluoro-acetyl)-biphenyl-3-ylmethyl]-(4-methylamino-cyclohexyl)-amide trifluoroacetate (18)

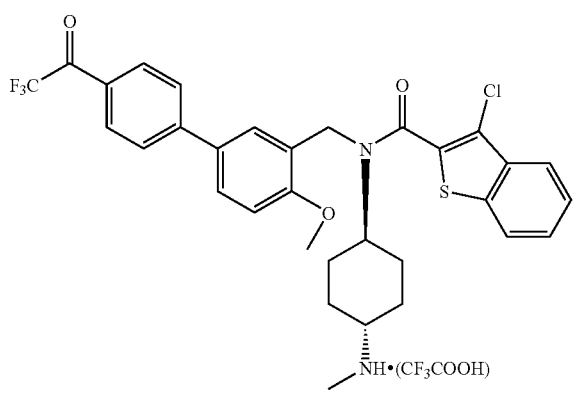

tert-Butyl carbamate 17 (539 mg, 0.75 mmol) is deprotected using Method E. Preparative HPLC then gives the title compound as the TFA salt.

Yield: 410 mg (88%).

LC/MS $t_r$ 1.63 min.

MS (ES+) m/z 635, 633 (M+H$_2$O+H), 604, 602 (M-31+H$_2$O+H).

Synthesis of Compound 303

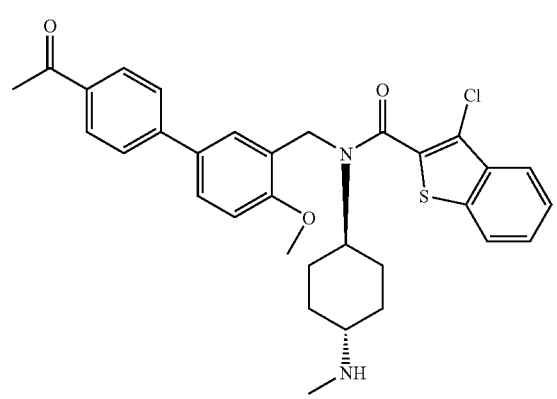

tert-Butyl {4-[(4'-acetyl-4-methoxy-biphenyl-3-ylmethyl)-amino]-cyclohexyl}-methyl-carbamate (19)

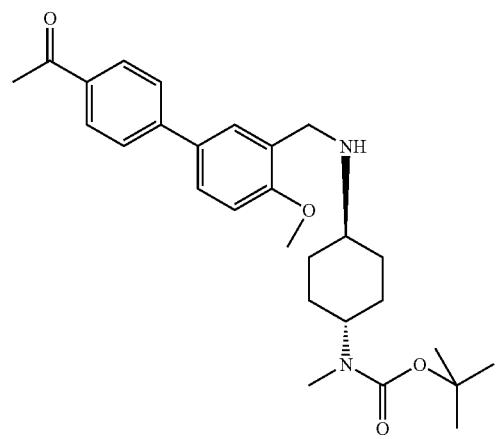

Boronic acid 4 (329 mg, 0.83 mmol) is coupled to 4'-bromoacetophenone (200 mg, 1.00 mmol) using Method B to give the title compound.

Yield: 400 mg (quant.). Contains ca. 15% triphenylphosphine oxide.

LC/MS $t_r$ 1.42 min.

MS (ES+) m/z 467 (M+H), 411 (M-C(CH$_3$)$_3$+H).

tert-Butyl {4-[(4'-acetyl-4-methoxy-biphenyl-3-ylm-ethyl)-(3-chloro-benzo[b]thiophene-2-carbonyl)-amino]-cyclohexyl}-methyl-carbamate (20)

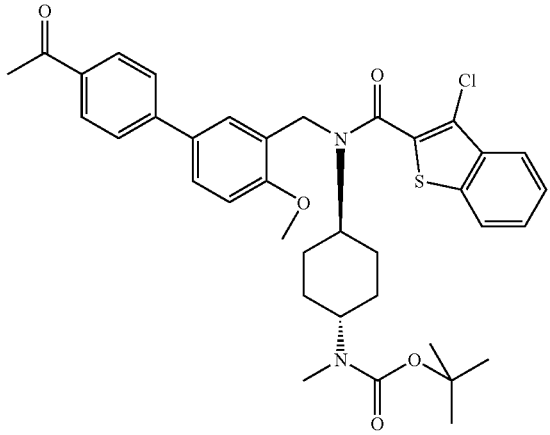

Biaryl amine 19 (400 mg, 0.86 mmol) is treated with 3-chloro-benzo[b]thiophene-2-carbonyl chloride (237 mg, 1.03 mmol) using Method D to give the title compound.
Yield: 134 mg (24%).
LC/MS $t_r$ 2.06 min.
MS (ES+) m/z 607, 605 (M-C(CH$_3$)$_3$+H).

3-Chloro-benzo[b]thiophene-2-carboxylic acid (4'-acetyl-4-methoxy-biphenyl-3-ylmethyl)-(4-methy-lamino-cyclohexyl)-amide hydrochloride (21)

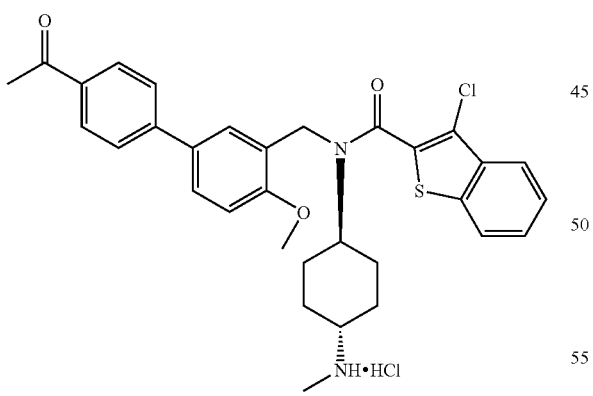

tert-Butyl carbamate 20 (134 mg, 0.20 mmol) is deprotected using Method E to give the title compound.
Yield: 94 mg (83%).
LC/MS $t_r$ 1.48 min.
MS (ES+) m/z 563, 561 (M+H), 532, 530 (M-31+H).

Synthesis of Compound 304

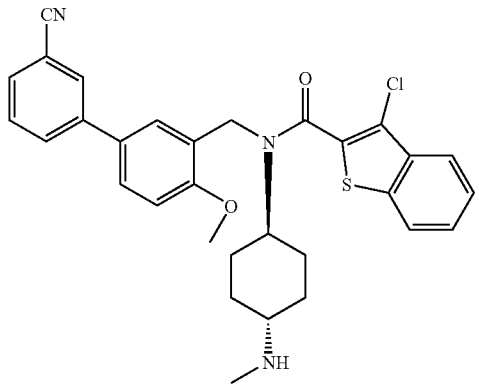

tert-Butyl {4-[(3'-cyano-4-methoxy-biphenyl-3-ylm-ethyl)-amino]-cyclohexyl}-methyl-carbamate (22)

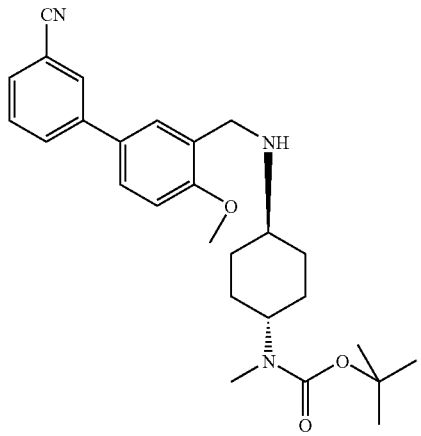

Boronic acid 4 (359 mg, 0.92 mmol) is coupled to 3-bromobenzonitrile (200 mg, 1.10 mmol) using Method B to give the title compound.
Yield: 386 mg (93%).
LC/MS $t_r$ 1.46 min.
MS (ES+) m/z 450 (M+H), 394 (M-C(CH$_3$)$_3$+H).

tert-Butyl {4-[(3-chloro-benzo[b]thiophene-2-carbonyl)-(3'-cyano-4-methoxy-biphenyl-3-ylmethyl)-amino]-cyclohexyl}-methyl-carbamate (23)

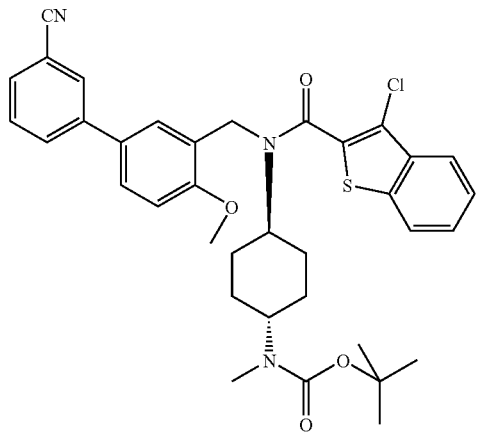

Biaryl amine 22 (386 mg, 0.86 mmol) is treated with 3-chloro-benzo[b]thiophene-2-carbonyl chloride (238 mg, 1.03 mmol) using Method D to give the title compound.
Yield: 60 mg (11%).
LC/MS $t_r$ 1.94 min.
MS (ES+) m/z 590, 588 (M-C(CH$_3$)$_3$+H).

3-Chloro-benzo[b]thiophene-2-carboxylic acid (3'-cyano-4-methoxy-biphenyl-3-ylmethyl)-(4-methylamino-cyclohexyl)-amide hydrochloride (24)

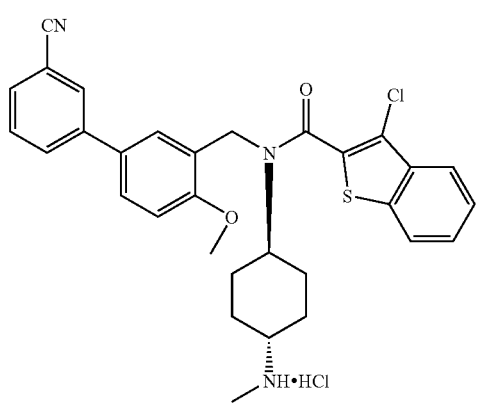

tert-Butyl carbamate 23 (60 mg, 0.11 mmol) is deprotected using Method E to give the title compound.
Yield: 51 mg (quant.).
LC/MS $t_r$ 1.51 min.
MS (ES+) m/z 546, 544 (M+H), 515, 513 (M-31+H).

Synthesis of Compound 305

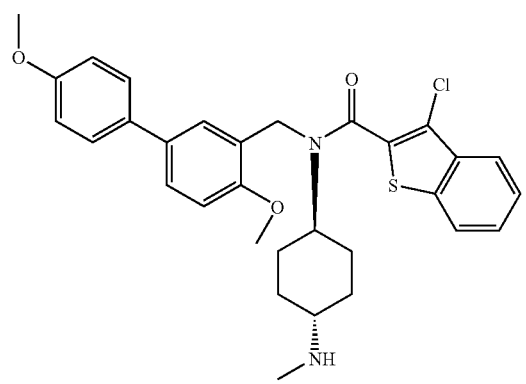

tert-Butyl {4-[(4,4'-dimethoxy-biphenyl-3-ylmethyl)-amino]-cyclohexyl}-methyl-carbamate (25)

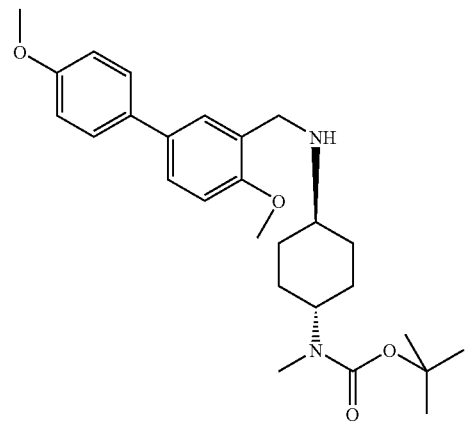

Boronic acid 4 (329 mg, 1.00 mmol) is coupled to 4-bromoanisole (125 μL, 1.00 mmol) using Method B to give the title compound.
Yield: 212 mg (47%).
LC/MS $t_r$ 1.59 min.
MS (ES+) m/z 455 (M+H).

tert-Butyl {4-[(3-chloro-benzo[b]thiophene-2-carbonyl)-(4,4'-dimethoxy-biphenyl-3-ylmethyl)-amino]-cyclohexyl}-methyl-carbamate (26)

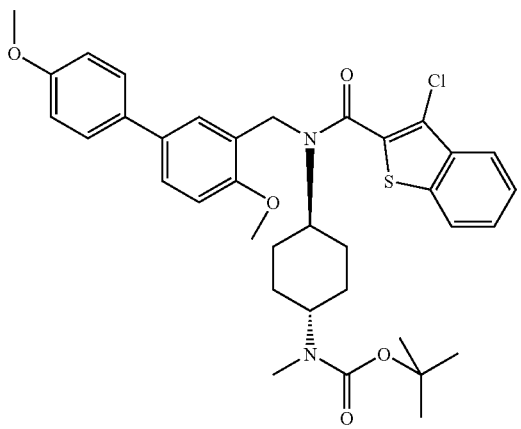

Biaryl amine 25 (212 mg, 0.46 mmol) is treated with 3-chloro-benzo[b]thiophene-2-carbonyl chloride (108 mg, 0.46 mmol) using Method D to give the title compound.

Yield: 213 mg (76%).
LC/MS $t_r$ 2.18 min.
MS (ES+) m/z 595, 593 (M-C(CH$_3$)$_3$+H).

3-Chloro-benzo[b]thiophene-2-carboxylic acid (4,4'-dimethoxy-biphenyl-3-ylmethyl)-(4-methylamino-cyclohexyl)-amide hydrochloride (27)

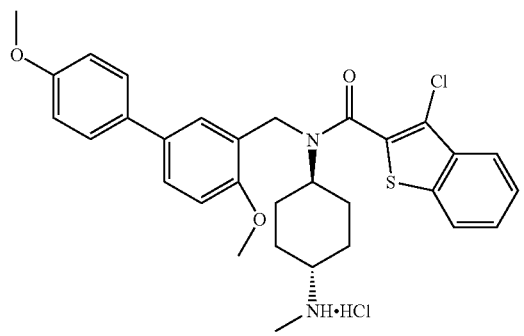

tert-Butyl carbamate 26 (159 mg, 0.23 mmol) is deprotected using Method E to give the title compound.

Yield: 130 mg (quant.).
LC/MS $t_r$ 1.57 min.
MS (ES+) m/z 551, 549 (M+H).

Synthesis of Compound 306

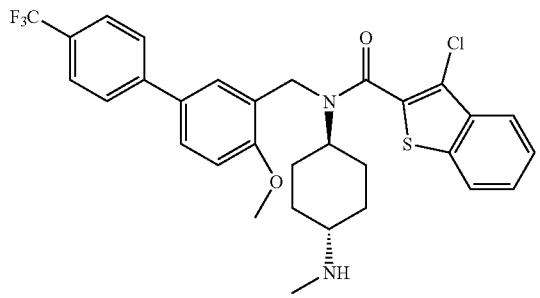

tert-Butyl {4-[(4-methoxy-4'-trifluoromethyl-biphenyl-3-ylmethyl)-amino]-cyclohexyl}-methyl-carbamate (28)

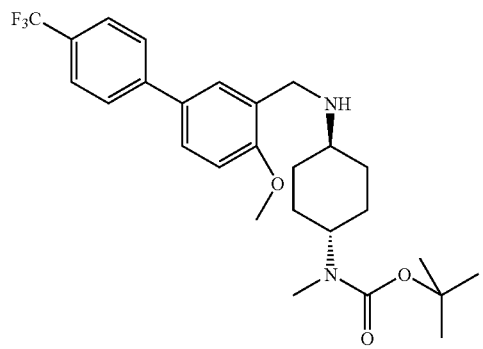

Boronic acid 4 (349 mg, 0.90 mmol) is coupled to 1-bromo-4-trifluoro-methylbenzene (200 mg, 0.90 mmol) using Method B to give the title compound. Yield: 465 mg (quant.). Contains ca. 22% triphenylphosphine oxide.

LC/MS $t_r$ 1.61 min.
MS (ES+) m/z 493 (M+H), 437 (M-C(CH$_3$)$_3$+H).

tert-Butyl 4-[(3-chloro-benzo[b]thiophene-2-carbonyl)-(4-methoxy-4'-trifluoromethyl-biphenyl-3-ylmethyl)-amino]-cyclohexyl}-methyl-carbamate (29)

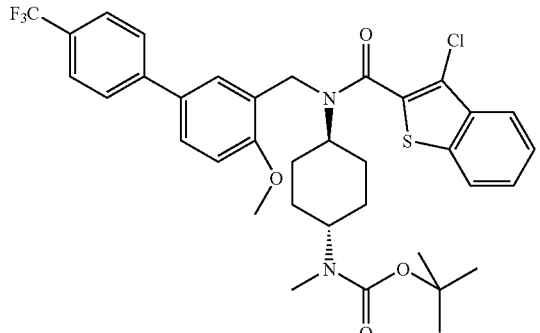

Biaryl amine 28 (465 mg, 0.94 mmol) is treated with 3-chloro-benzo[b]thiophene-2-carbonyl chloride (306 mg, 1.32 mmol) using Method D to give the title compound.

Yield: 266 mg (41%).
LC/MS $t_r$ 2.23 min.
MS (ES+) m/z 689, 687 (M+H), 633, 631 (M-C(CH$_3$)$_3$+H).

3-Chloro-benzo[b]thiophene-2-carboxylic acid (4-methoxy-4'-trifluoromethyl-biphenyl-3-ylmethyl)-(4-methylamino-cyclohexyl)-amide trifluoroacetate (30)

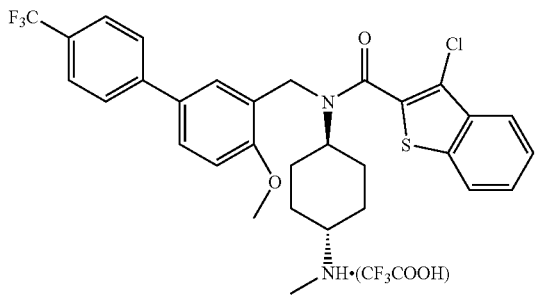

tert-Butyl carbamate 29 (366 mg, 0.53 mmol) is deprotected using Method E. Preparative HPLC then gives the title compound as the TFA salt.
Yield: 95 mg (26%).
LC/MS $t_r$ 1.86 min.
MS (ES+) m/z 589, 587 (M+H), 558, 556 (M-31+H).

Synthesis of Compound 307

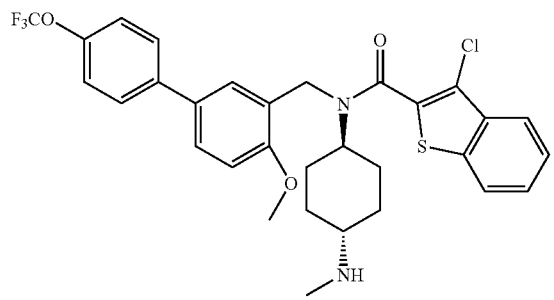

tert-Butyl {4-[(4-methoxy-4'-trifluoromethoxy-biphenyl-3-ylmethyl)-amino]-cyclohexyl}-methyl-carbamate (31)

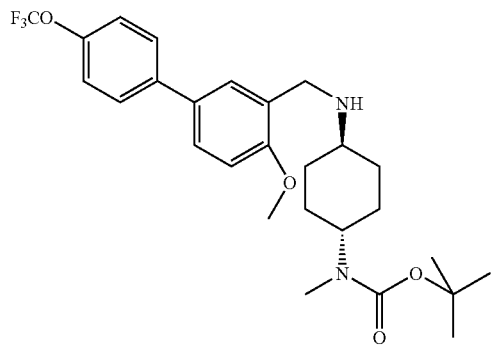

Boronic acid 4 (271 mg, 0.69 mmol) is coupled to 1-bromo-4-(trifluoromethoxy)benzene (200 mg, 0.83 mmol) using Method B to give the title compound.
Yield: 220 mg (62%).

tert-Butyl {4-[(3-chloro-benzo[b]thiophene-2-carbonyl)-(4-methoxy-4'-trifluoromethoxy-biphenyl-3-ylmethyl)-amino]-cyclohexyl}-methyl-carbamate (32)

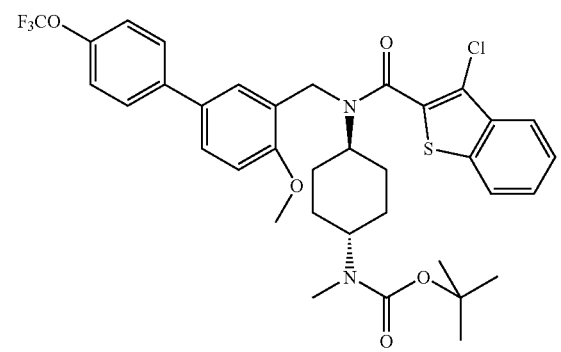

Biaryl amine 31 (220 mg, 0.43 mmol) is treated with 3-chloro-benzo[b]thiophene-2-carbonyl chloride (120 mg, 0.52 mmol) using Method D to give the title compound.
Yield: 150 mg (53%).

3-Chloro-benzo[b]thiophene-2-carboxylic acid (4-methoxy-4'-trifluoromethoxy-biphenyl-3-ylmethyl)-(4-methylamino-cyclohexyl)-amide hydrochloride (33)

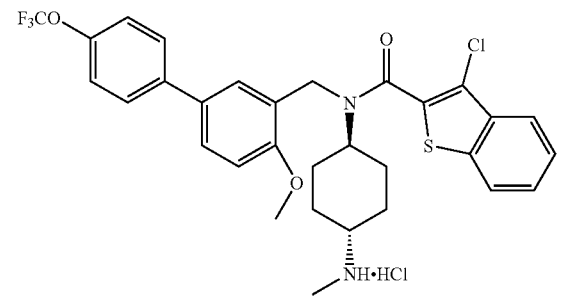

tert-Butyl carbamate 32 (150 mg, 0.21 mmol) is deprotected using Method F to give the title compound.
Yield: 110 mg (86%).
LC/MS $t_r$ 1.90 min.
MS (ES+) m/z 605, 603 (M+H).

Synthesis of Compound 308

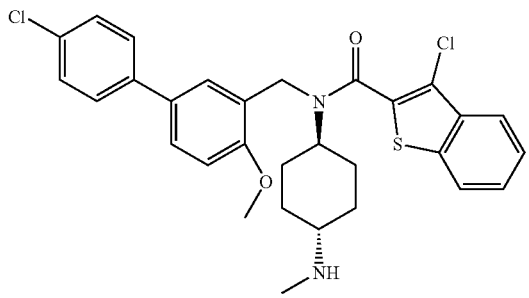

tert-Butyl {4-[(4'-chloro-4-methoxy-biphenyl-3-ylmethyl)-amino]-cyclohexyl}-methyl-carbamate (34)

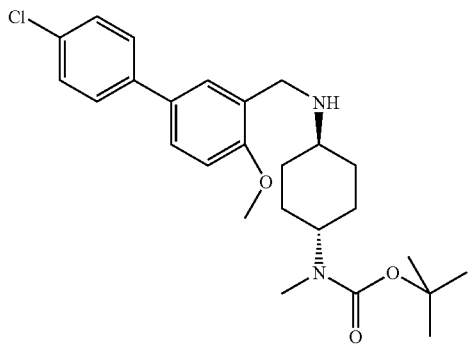

Boronic acid 4 (342 mg, 0.87 mmol) is coupled to 1-bromo-4-chlorobenzene (200 mg, 1.05 mmol) using Method B to give the title compound.

Yield: 348 mg (87%).

tert-Butyl {4-[(3-chloro-benzo[b]thiophene-2-carbonyl)-(4'-chloro-4-methoxy-biphenyl-3-ylmethyl)-amino]-cyclohexyl}-methyl-carbamate (35)

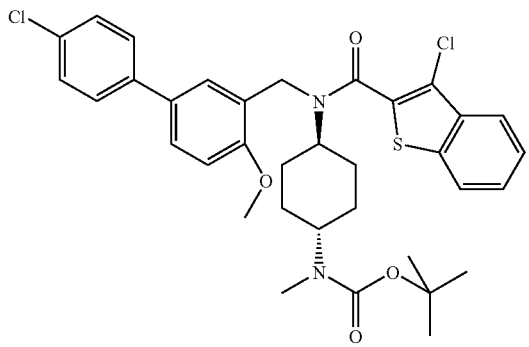

Biaryl amine 34 (348 mg, 0.76 mmol) is treated with 3-chloro-benzo[b]thiophene-2-carbonyl chloride (210 mg, 0.91 mmol) using Method D to give the title compound.

Yield: 162 mg (33%).

3-Chloro-benzo[b]thiophene-2-carboxylic acid (4'-chloro-4-methoxy-biphenyl-3-ylmethyl)-(4-methylamino-cyclohexyl)-amide hydrochloride (36)

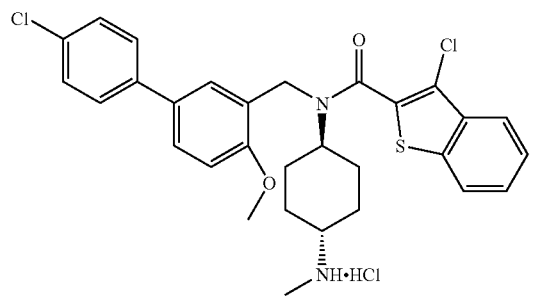

tert-Butyl carbamate 35 (162 mg, 0.25 mmol) is deprotected using Method F to give the title compound.

Yield: 100 mg (73%).

LC/MS $t_r$ 1.66 min.

MS (ES+) m/z 555, 553 (M+H), 524, 522 (1-31+H).

Synthesis of Compound 309

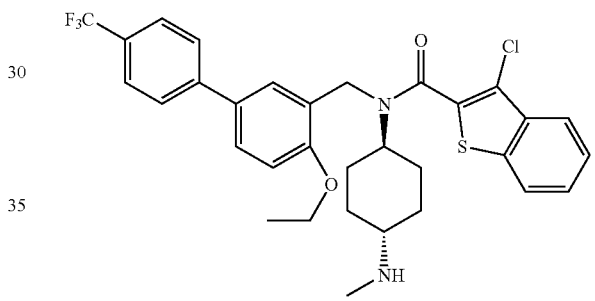

3-Chloro-benzo[b]thiophene-2-carboxylic acid (4-ethoxy-4'-trifluoromethyl-biphenyl-3-ylmethyl)-(4-methylamino-cyclohexyl)-amide hydrochloride (37)

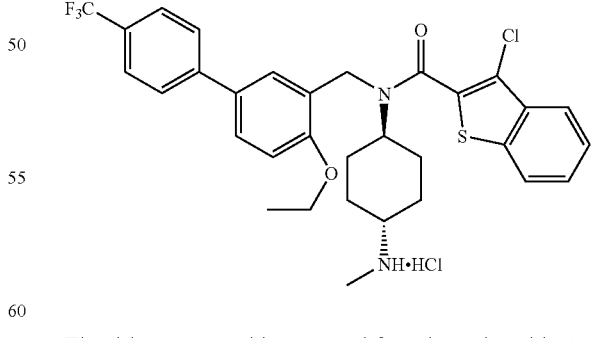

The title compound is prepared from boronic acid 11 (20 mg, 49 mmol) and 1-bromo-4-trifluoromethylbenzene (9.2 mg, 41 µmol) in accordance with Method L1.

Yield: 8.4 mg (32%).

LC/MS $t_r$ 1.61 min.

MS (ES+) m/z 644, 642 (M+CH₃CN+H), 603, 601 (M+H).

Synthesis of Compound 310

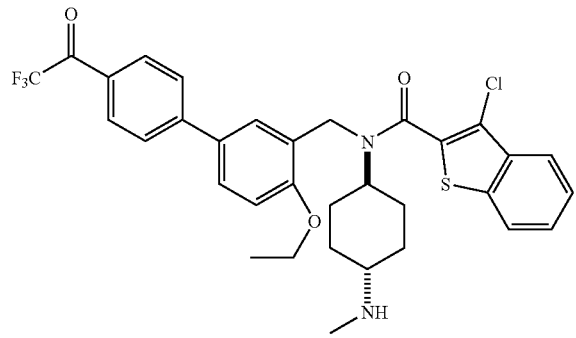

3-Chloro-benzo[b]thiophene-2-carboxylic acid [4-ethoxy-4'-(2,2,2-trifluoro-acetyl)-biphenyl-3-ylmethyl]-(4-methylamino-cyclohexyl)-amide hydrochloride (246)

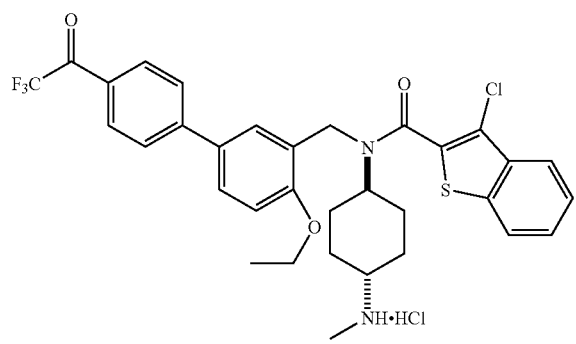

The title compound is prepared from boronic acid 11 (20 mg, 49 µmol) and 4'-bromo-2,2,2-trifluoroacetophenone (10.4 mg, 41 µmol) in accordance with Method L1.

Yield: 17.3 mg (63%).
LC/MS $t_r$ 1.49 min.
MS (ES+) m/z 649, 647 (M+H$_2$O+H), 618, 616 (M-31+ H$_2$O+H).

Synthesis of Compound R2

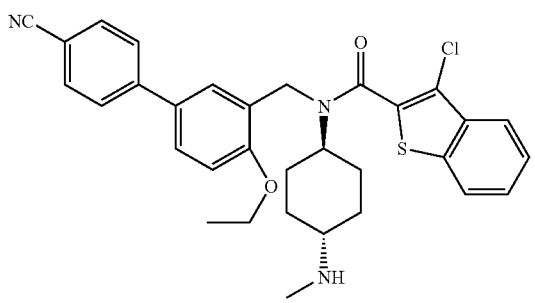

4'-Ethoxy-3'-formyl-biphenyl-4-carbonitrile (38)

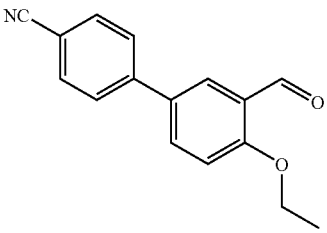

4-cyanophenylboronic acid (500 mg, 3.40 mmol) is coupled to 5-bromo-2-ethoxybenzaldehyde (780 mg, 3.40 mmol) using Method A to give the title compound.

Yield: 625 mg (73%).
LC/MS $t_r$ 1.58 min.
MS (ES+) m/z 252 (M+H).

tert-Butyl {4-[(4'-cyano-4-ethoxy-biphenyl-3-ylmethyl)-amino]-cyclohexyl}-methyl-carbamate (39)

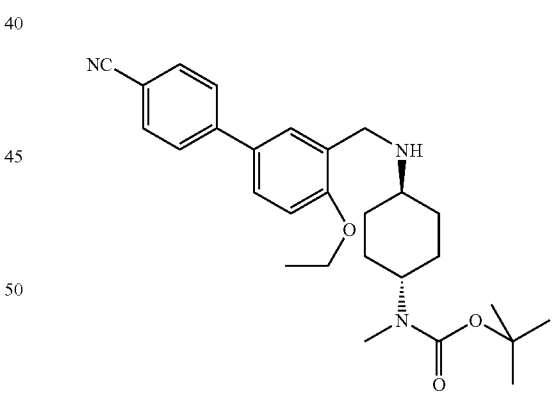

Amine 3 (300 mg, 1.19 mmol) is treated with aldehyde 38 (272 mg, 1.19 mmol) in accordance with Method C to give the crude title compound.

Yield: 613 mg.
LC/MS $t_r$ 1.39 min.
MS (ES+) m/z 464 (M+H).

tert-Butyl {4-[(3-chloro-benzo[b]thiophene-2-carbonyl)-(4'-cyano-4-ethoxy-biphenyl-3-ylmethyl)-amino]-cyclohexyl}-methyl-carbamate (40)

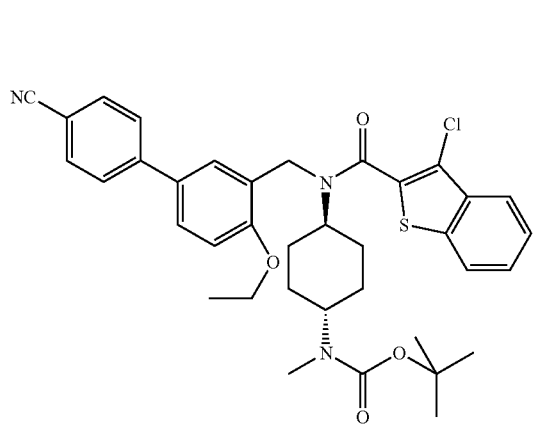

Crude biaryl amine 39 (613 mg, 1.32 mmol) is treated with 3-chloro-benzo[b]thiophene-2-carbonyl chloride (366 mg, 1.58 mmol) using Method D to give the title compound.
Yield: 550 mg (70% over two steps).
LC/MS $t_r$ 2.03 min.
MS (ES+) m/z 660, 658 (M+H), 604, 602 (M-C(CH$_3$)$_3$+H).

3-Chloro-benzo[b]thiophene-2-carboxylic acid (4'-cyano-4-ethoxy-biphenyl-3-ylmethyl)-(4-methylamino-cyclohexyl)-amide hydrochloride (41)

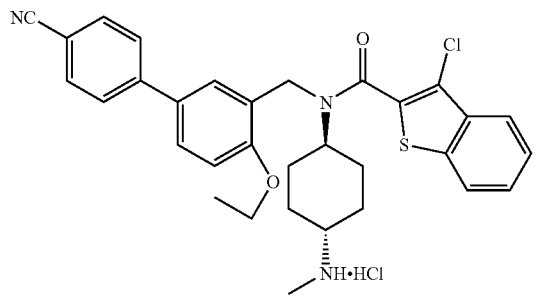

tert-Butyl carbamate 40 (550 mg, 0.25 mmol) is deprotected using Method F. Purification by column chromatography (5% MeOH in DCM with 0.5% triethylamine) then acidification of the free base using Method H gives the title compound.
Yield: 226 mg (27%).
LC/MS $t_r$ 1.53 min.
MS (ES+) m/z 560, 558 (M+H).

Synthesis of Compound 311

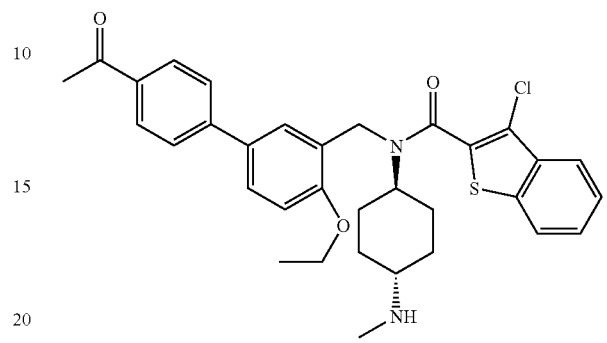

tert-Butyl {4-[(4'-acetyl-4-ethoxy-biphenyl-3-ylmethyl)-(3-chloro-benzo[b]thiophene-2-carbonyl)-amino]-cyclohexyl}-methyl-carbamate (42)

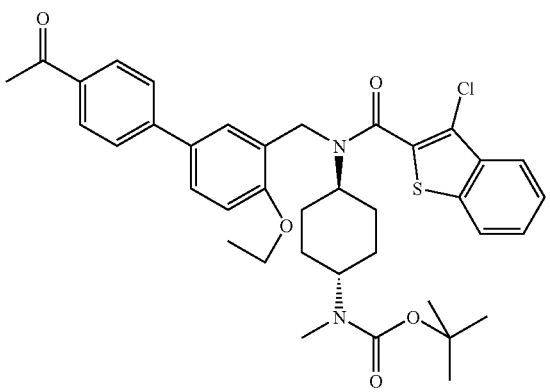

Boronic acid 12 (200 mg, 0.33 mmol) is coupled to 4'-bromoacetophenone (79 mg, 0.39 mmol) using Method B to give the title compound.
Yield: 64 mg (24%).
LC/MS $t_r$ 2.02 min.
MS (ES+) m/z 677, 675 (M+H), 621, 619 (M-C(CH$_3$)$_3$+H).

3-Chloro-benzo[b]thiophene-2-carboxylic acid (4'-acetyl-4-ethoxy-biphenyl-3-ylmethyl)-(4-methylamino-cyclohexyl)-amide hydrochloride (43)

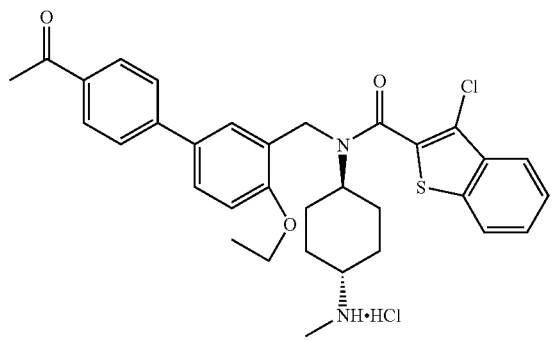

tert-Butyl carbamate 42 (64 mg, 0.51 mmol) is deprotected using Method E to give the title compound.

Yield: 50 mg (92%).
LC/MS $t_r$ 1.69 min.
MS (ES+) m/z 577, 575 (M+H), 546, 544 (M-31+H).
Synthesis of Compound 312

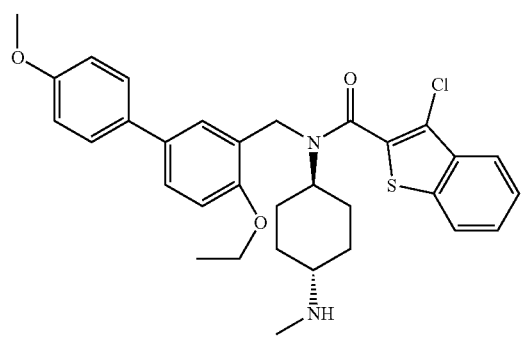

3-Chloro-benzo[b]thiophene-2-carboxylic acid (4-ethoxy-4'-methoxy-biphenyl-3-ylmethyl)-(4-methylamino-cyclohexyl)-amide hydrochloride (44)

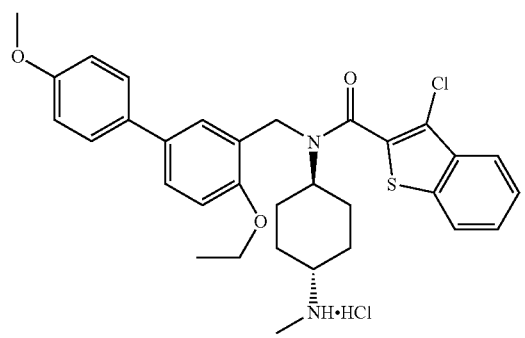

The title compound is prepared from boronic acid 11 (20 mg, 49 μmol) and 4-bromoanisole (7.7 mg, 41 μmol) in accordance with Method L1.

Yield: 36.6 mg (148%).
LC/MS $t_r$ 1.48 min.
MS (ES+) m/z 606, 604 (M+CH$_3$CN+H), 565, 563 (M+H).
Synthesis of Compound 313

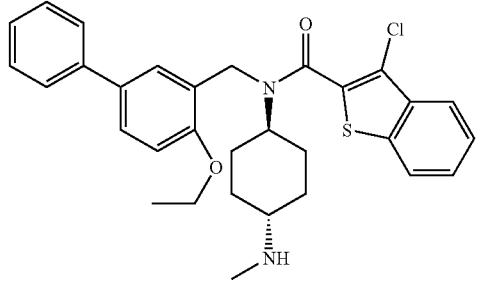

3-Chloro-benzo[b]thiophene-2-carboxylic acid (4-ethoxy-biphenyl-3-ylmethyl)-(4-methylamino-cyclohexyl)-amide hydrochloride (45)

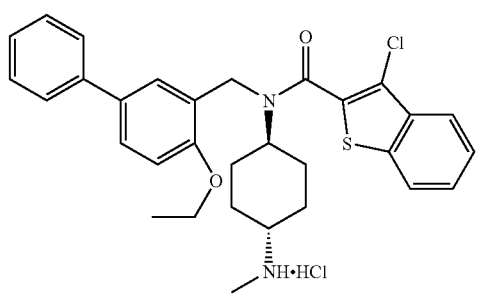

The title compound is prepared from boronic acid 11 (20 mg, 49 μmol) and bromobenzene (6.4 mg, 41 μmol) in accordance with Method L1.

Yield: 7.7 mg (33%).
LC/MS $t_r$ 1.50 min.
MS (ES+) m/z 576, 574 (M+CH$_3$CN+H), 535, 533 (M+H).
Synthesis of Compound R3

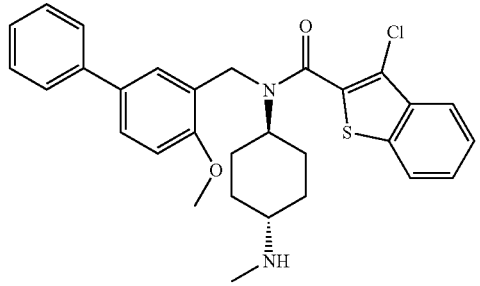

tert-Butyl {4-[(4-methoxy-biphenyl-3-ylmethyl)-amino]-cyclohexyl}-methyl-carbamate (46)

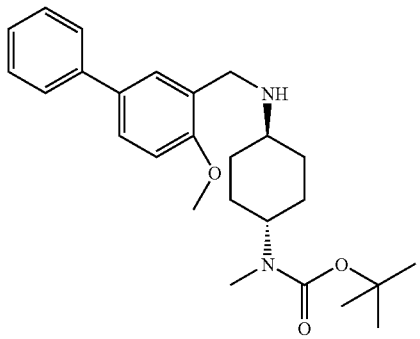

Boronic acid 4 (1.0 g, 2.55 mmol) is coupled to bromobenzene (0.32 mL, 3.0 mmol) using Method A to give the title compound.
Yield: 437 mg (40%).
LC/MS $t_r$ 1.51 min.
MS (ES+) m/z 425 (M+H).

tert-Butyl {4-[(3-chloro-benzo[b]thiophene-2-carbonyl)-(4-methoxy-biphenyl-3-ylmethyl)-amino]-cyclohexyl}-methyl-carbamate (47)

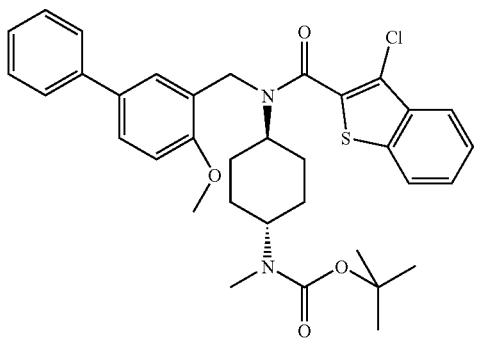

Biaryl amine 46 (423 mg, 1.00 mmol) is treated with 3-chloro-benzo[b]thiophene-2-carbonyl chloride (507 mg, 2.20 mmol) using Method D to give the title compound.
Yield: 320 mg (52%).
LC/MS $t_r$ 2.06 min.
MS (ES+) m/z 621, 619 (M+H), 565, 563 (M-C(CH$_3$)$_3$+H).

3-Chloro-benzo[b]thiophene-2-carboxylic acid (4-methoxy-biphenyl-3-ylmethyl)-(4-methylamino-cyclohexyl)-amide hydrochloride (48)

tert-Butyl carbamate 47 (320 mg, 0.52 mmol) is deprotected using Method F to give the title compound.
Yield: 184 mg (64%).
LC/MS $t_r$ 1.42 min.
MS (ES+) m/z 521, 519 (M+H).

Synthesis of Compound 314

3-Chloro-benzo[b]thiophene-2-carboxylic acid (4'-fluoro-4-methoxy-biphenyl-3-ylmethyl)-(4-methylamino-cyclohexyl)-amide hydrochloride (49)

The title compound is prepared from boronic acid 4 (20 mg, 51 µmol) and 1-bromo-4-fluorobenzene (7.4 mg, 42 µmol) in accordance with Method L1.
Yield: 5.8 mg (24%).
LC/MS $t_r$ 1.53 min.
MS (ES+) m/z 539, 537 (M+H), 508, 506 (M-31+H).

Synthesis of Compound 315

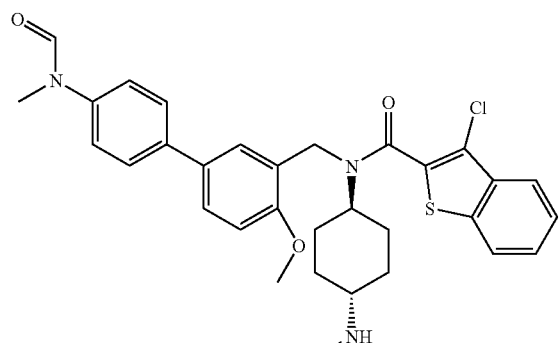

N-(4-Bromophenyl)-formamide (50)

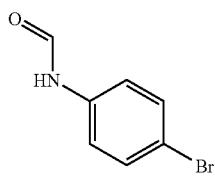

A stirred solution of formic acid (2.5 mL, 88% in water) is cooled to 0° C., treated with acetic anhydride (0.82 mL, 9.0 mmol) then warmed to RT over 30 minutes. The solution is then cooled to 0° C. and 4-bromoaniline (500 mg, 3.0 mmol) added dropwise over 5 minutes. After stirring a further 16 h at RT, the reaction mixture is diluted with water (20 mL) and extracted into DCM (3×20 mL). The combined DCM phases are washed with 1 M HCl (20 mL) and aqueous $NaHCO_3$ (20 mL), dried over $Na_2SO_4$ and reduced in vacuo. Purification by column chromatography (20% EtOAc in heptane) affords the title compound.

Yield: 468 mg (78%).

N-(4-Bromophenyl)-N-methyl-formamide (51)

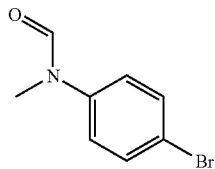

A solution of N-(4-bromophenyl)-formamide 50 (250 mg, 1.25 mmol) in DMF (3 mL) is added dropwise to a suspension of sodium hydride (65 mg, 1.63 mmol, 60% dispersion in mineral oil) in DMF (3 mL) at 0° C. After stirring 1 h, iodomethane (113 µl, 1.63 mmol) is added, the reaction mixture warmed to RT and stirred 16 h. The reaction is then quenched with water (10 mL) and extracted into EtOAc (3×10 mL). The combined organic phases are dried over $Na_2SO_4$ and reduced in vacuo to give the title compound.

Yield: 223 mg (83%).
LC/MS $t_r$ 1.19 min.
MS (ES+) m/z 216, 214 (M+H).

tert-Butyl (4-{[4'-(formyl-methyl-amino)-4-methoxy-biphenyl-3-ylmethyl]-amino}-cyclohexyl)-methyl-carbamate (52)

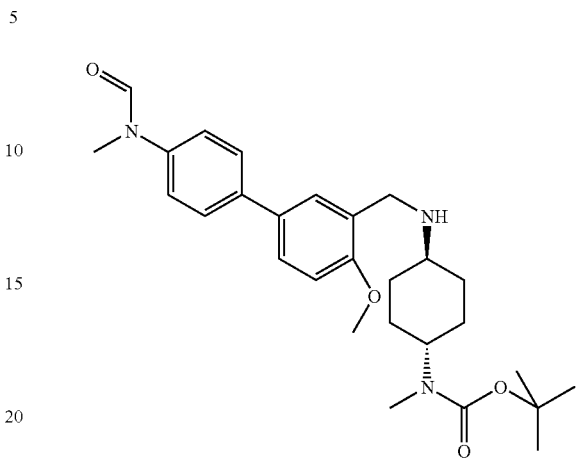

Boronic acid 4 (260 mg, 0.66 mmol) is coupled to aryl bromide 51 (170 mg, 0.79 mmol) using Method B to give the title compound.

Yield: 300 mg (94%).
LC/MS $t_r$ 1.30 min.
MS (ES+) m/z 426 (M-$C(CH_3)_3$+H).

tert-Butyl (4-{(3-chloro-benzo[b]thiophene-2-carbonyl)-[4'-(formyl-methyl-amino)-4-methoxy-biphenyl-3-ylmethyl]-amino}-cyclohexyl)-methyl-carbamate (53)

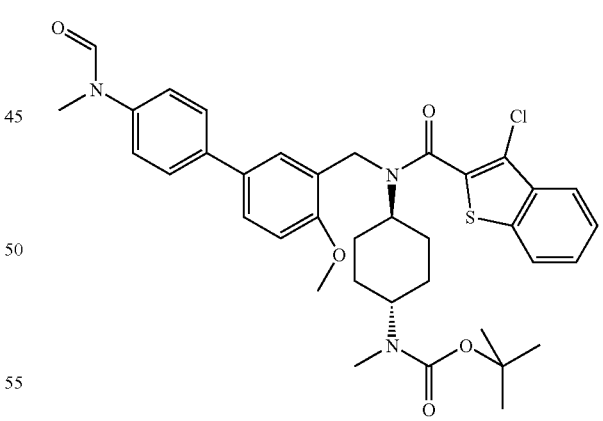

Biaryl amine 52 (325 mg, 0.64 mmol) is treated with 3-chloro-benzo[b]thiophene-2-carbonyl chloride (171 mg, 0.74 mmol) using Method D to give the title compound.

Yield: 160 mg (35%).
LC/MS $t_r$ 2.09 min.
MS (ES+) m/z 578, 576 (M-$CO_2C(CH_3)_3$+H).

3-Chloro-benzo[b]thiophene-2-carboxylic acid [4'-(formyl-methyl-amino)-4-methoxy-biphenyl-3-ylmethyl]-(4-methylamino-cyclohexyl)-amide trifluoroacetate (54)

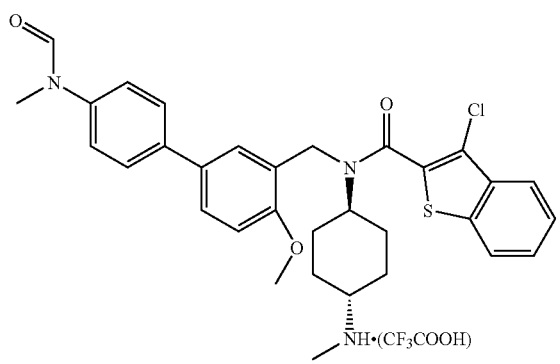

tert-Butyl carbamate 53 (190 mg, 0.28 mmol) is deprotected using Method G to give the title compound.
Yield: 170 mg (quant.).
LC/MS $t_r$ 1.58 min.
MS (ES+) m/z 578, 576 (M+H).

Synthesis of Compound 316

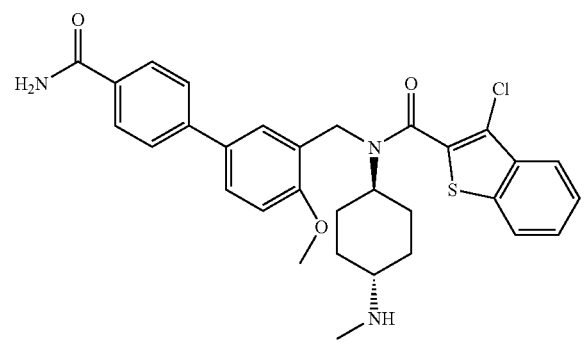

tert-Butyl {4-[(4'-carbamoyl-4-methoxy-biphenyl-3-ylmethyl)-amino]-cyclohexyl}-methyl-carbamate (55)

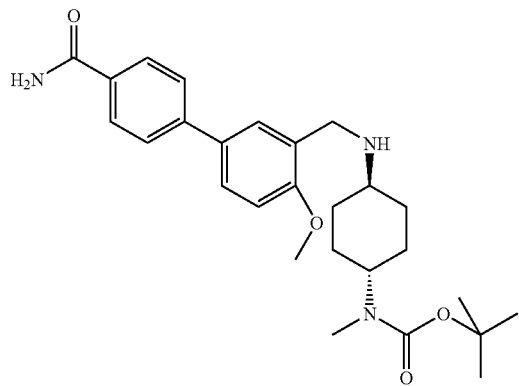

Boronic acid 4 (326 mg, 0.83 mmol) is coupled to 4-bromobenzamide (200 mg, 0.99 mmol) using Method B to give the title compound.
Yield: 267 mg (69%).
LC/MS $t_r$ 1.29 min.
MS (ES+) m/z 468 (M+H), 412 (M-C(CH$_3$)$_3$+H).

tert-Butyl {4-[(4'-carbamoyl-4-methoxy-biphenyl-3-ylmethyl)-(3-chloro-benzo[b]thiophene-2-carbonyl)-amino]-cyclohexyl}-methyl-carbamate (56)

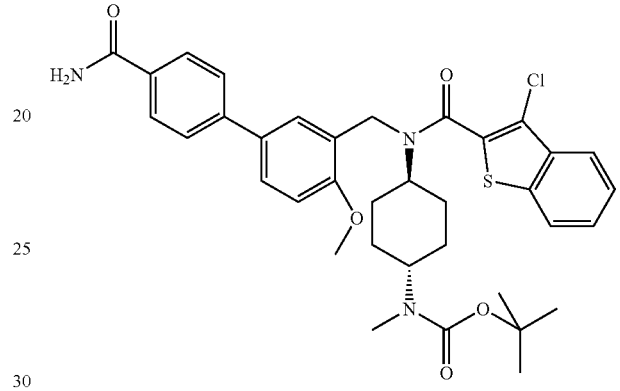

Biaryl amine 55 (267 mg, 0.57 mmol) is treated with 3-chloro-benzo[b]thiophene-2-carbonyl chloride (158 mg, 0.69 mmol) using Method D to give the title compound.
Yield: 266 mg (70%).
LC/MS $t_r$ 1.85 min.
MS (ES+) m/z 608, 606 (M-C(CH$_3$)$_3$+H).

3-Chloro-benzo[b]thiophene-2-carboxylic acid (4'-carbamoyl-4-methoxy-biphenyl-3-ylmethyl)-(4-methylamino-cyclohexyl)-amide hydrochloride (57)

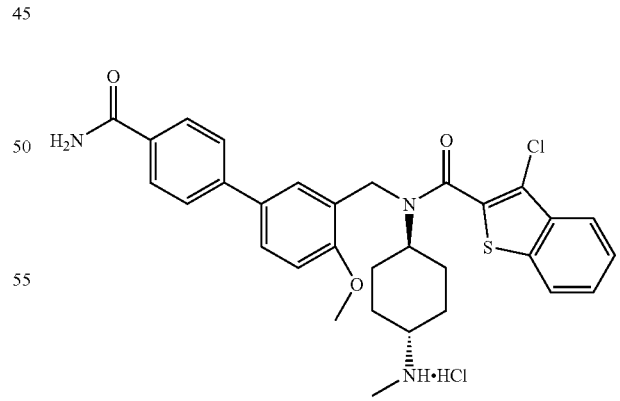

tert-Butyl carbamate 56 (266 mg, 0.39 mmol) is deprotected using Method E to give the title compound.
Yield: 220 mg (97%).
LC/MS $t_r$ 1.29 min.
MS (ES+) m/z 564, 562 (M+H), 533, 531 (M-31+H).

Synthesis of Compound 317 (R19)

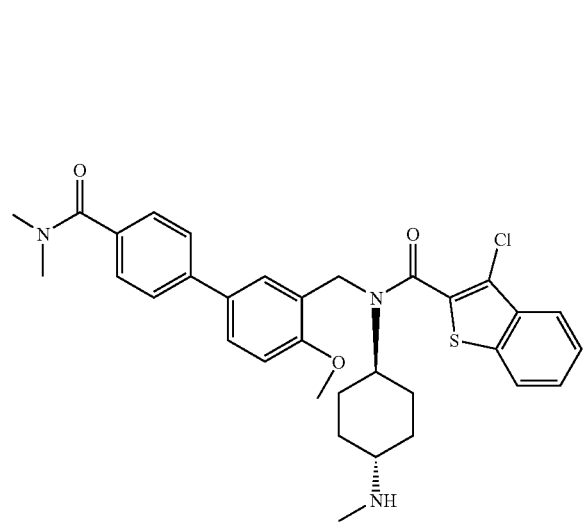

4-Bromo-N,N'-dimethylbenzamide (58)

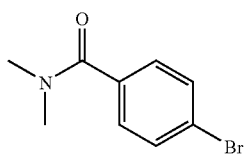

A suspension of hexane-washed sodium hydride (600 mg, 15 mmol, 60% dispersion in mineral oil) in DMF (12 mL) is treated portionwise with 4-bromobenzamide (1.0 g, 5.0 mmol) at 0° C. over 1-2 minutes. After warming to RT and stirring 1 h, iodomethane (7.50 mL, 15 mmol, 2.0 M solution in TBME) is added via syringe and the reaction stirred a further 16 h. The reaction mixture is then diluted with water (50 mL) and extracted into TBME (3×25 mL). The TBME phases are combined, washed with water (2×25 mL) and brine (25 mL), dried (MgSO$_4$) and reduced in vacuo to a clear oil. Column chromatography (gradient elution—50-70% EtOAc in heptane) affords the title compound.

Yield: 863 mg (76%).
LC/MS t$_r$ 1.12 min.
MS (ES+) m/z 230, 228 (M+H).

tert-Butyl {4-[(4'-dimethylcarbamoyl-4-methoxy-biphenyl-3-ylmethyl)-amino]-cyclohexyl}-methyl-carbamate (59)

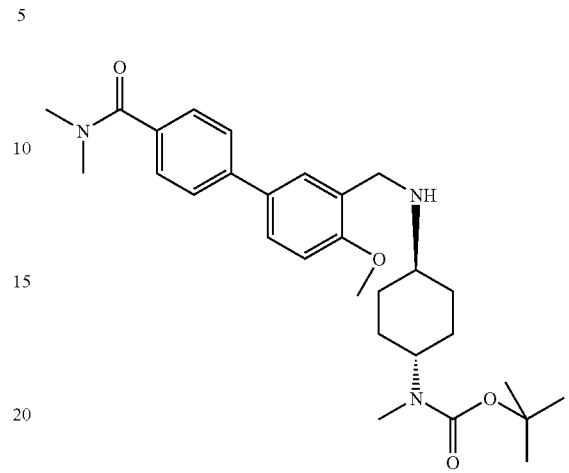

Boronic acid 4 (354 mg, 0.84 mmol) is coupled to aryl bromide 58 (230 mg, 1.01 mmol) using Method B to give the title compound.

Yield: 110 mg (29%).
LC/MS t$_r$ 1.36 min.
MS (ES+) m/z 496 (M+H).

tert-Butyl {4-[(3-chloro-benzo[b]thiophene-2-carbonyl)-(4'-dimethylcarbamoyl-4-methoxy-biphenyl-3-ylmethyl)-amino]-cyclohexyl}-methyl-carbamate (60)

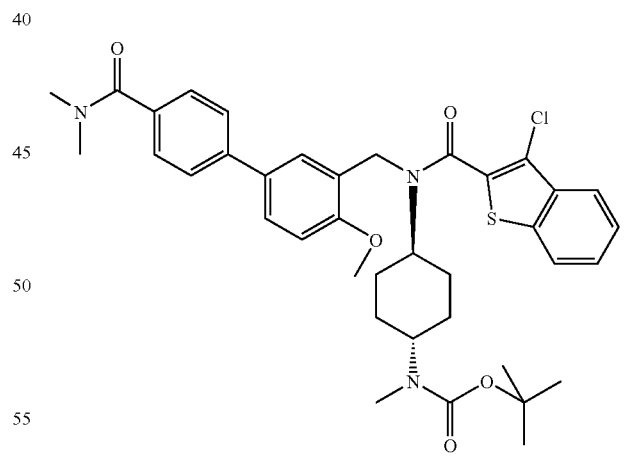

Biaryl amine 59 (110 mg, 0.22 mmol) is treated with 3-chloro-benzo[b]thiophene-2-carbonyl chloride (56 mg, 0.24 mmol) using Method D to give the title compound.

Yield: 100 mg (65%).
LC/MS t$_r$ 1.93 min.
MS (ES+) m/z 592, 590 (M-CO$_2$C(CH$_3$)$_3$+H).

3-Chloro-benzo[b]thiophene-2-carboxylic acid (4'-dimethylcarbamoyl-4-methoxy-biphenyl-3-ylmethyl)-(4-methylamino-cyclohexyl)-amide hydrochloride (61)

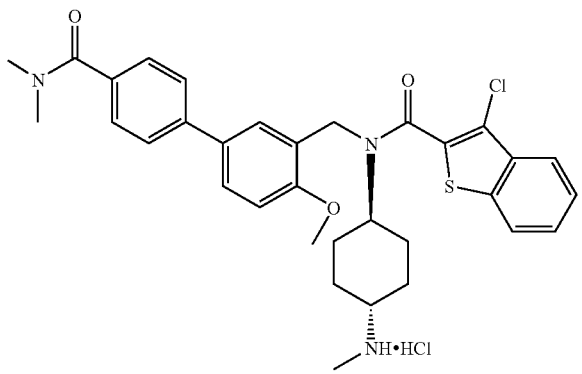

tert-Butyl carbamate 60 (120 mg, 0.18 mmol) is deprotected using Method E to give the title compound.
Yield: 120 mg (quant.).
LC/MS $t_r$ 1.39 min.
MS (ES+) m/z 592, 590 (M+H).

Synthesis of Compound 318

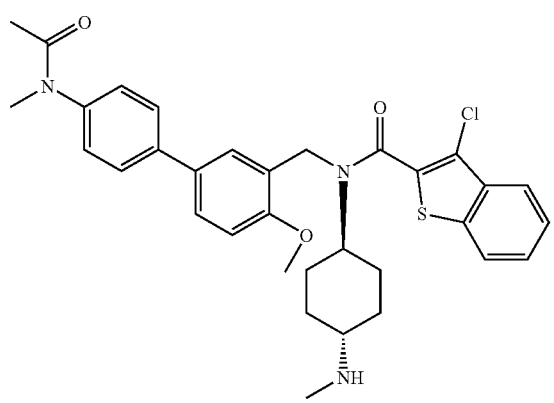

N-(4-Bromophenyl)-N-methyl-acetamide (62)

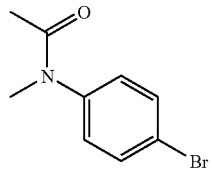

4-bromoacetanilide (1.0 g, 4.67 mmol) in DMF (5 mL) is added dropwise to a suspension of sodium hydride (224 mg, 5.61 mmol, 60% dispersion in mineral oil) in DMF (5 mL) at 0° C. After stirring 1 h at 0° C., iodomethane (349 µl, 5.61 mmol) is added and the reaction mixture warmed to RT and stirred 16 h. The reaction is quenched with water (15 mL) and extracted into EtOAc (3×15 mL); the combined organic phases are then dried over $Na_2SO_4$ and reduced in vacuo. Purification by column chromatography (40% EtOAc in heptane) gives the title compound.
Yield: 780 mg (74%).
LC/MS $t_r$ 1.17 min.
MS (ES+) m/z 230, 228 (M+H).

tert-Butyl {4-[[4'-(acetyl-methyl-amino)-4-methoxy-biphenyl-3-ylmethyl]-(3-chloro-benzo[b]thiophene-2-carbonyl)-amino]-cyclohexyl}-methyl-carbamate (63)

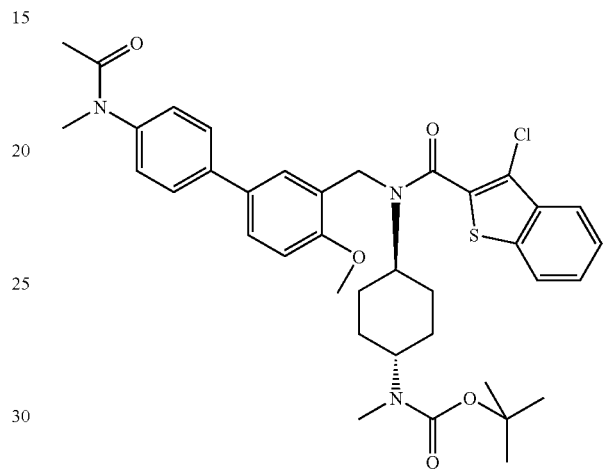

Boronic acid 5 (200 mg, 0.34 mmol) is coupled to aryl bromide 62 (93 mg, 0.41 mmol) using Method B to give the title compound.
Yield: 170 mg (72%).
LC/MS $t_r$ 1.96 min.
MS (ES+) nm/z 636, 634 (M-C(CH$_3$)$_3$+H), 592, 590 (M-CO$_2$C(CH$_3$)$_3$+H).

3-Chloro-benzo[b]thiophene-2-carboxylic acid [4'-(acetyl-methyl-amino)-4-methoxy-biphenyl-3-ylmethyl]-(4-methylamino-cyclohexyl)-amide hydrochloride (64)

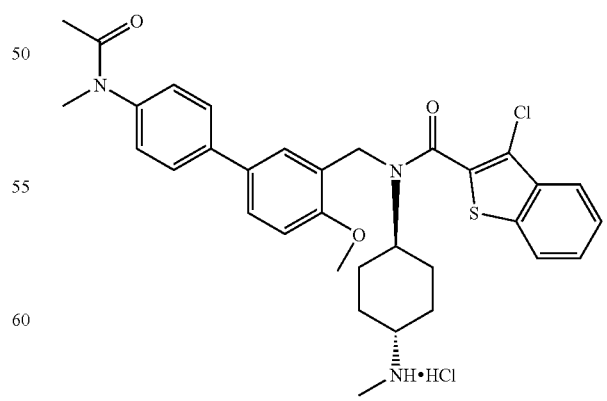

tert-Butyl carbamate 63 (170 mg, 0.25 mmol) is deprotected using Method E. On removal of the solvent in vacuo, the residue is dissolved in MeOH (100 µL) and water (3 mL)

and this aqueous phase washed with TBME (3×3 mL). The water is then removed in vacuo to afford the title compound.

Yield: 120 mg (83%).

LC/MS $t_r$ 1.39 min.

MS (ES+) m/z 592, 590 (M+H), 561, 559 (M-31+H).

Synthesis of Compound 319

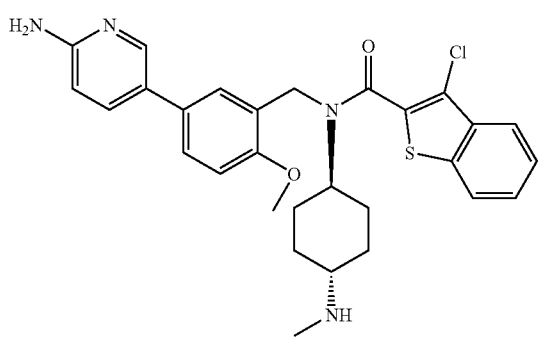

tert-Butyl {4-[[5-(6-amino-pyridin-3-yl)-2-methoxy-benzyl]-(3-chloro-benzo[b]thiophene-2-carbonyl)-amino]-cyclohexyl}-methyl-carbamate (65)

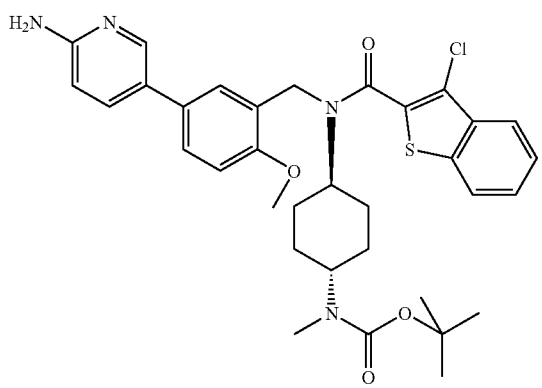

Boronic acid 5 (175 mg, 0.29 mmol) is coupled to 2-amino-5-bromopyridine (62 mg, 0.36 mmol) using Method B to give the title compound.

Yield: 66 mg (35%).

LC/MS $t_r$ 1.67 min.

MS (ES+) m/z 637, 635 (M+H), 581, 579 (M-C(CH$_3$)$_3$+H).

3-Chloro-benzo[b]thiophene-2-carboxylic acid [5-(6-amino-pyridin-3-yl)-2-methoxy-benzyl]-(4-methylamino-cyclohexyl)-amide dihydrochloride (66)

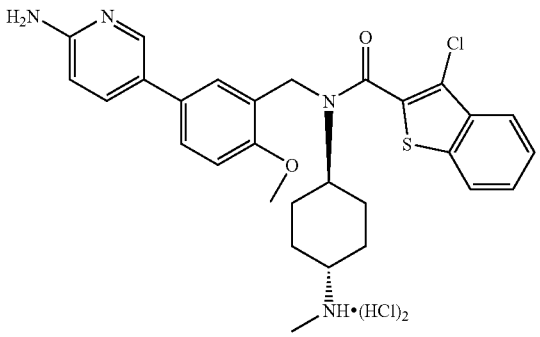

tert-Butyl carbamate 65 (66 mg, 0.10 mmol) is deprotected using Method E to give the title compound.

Yield: 62 mg (98%).

LC/MS $t_r$ 1.17 min.

MS (ES+) m/z 537, 535 (M+H).

Synthesis of Compound 320

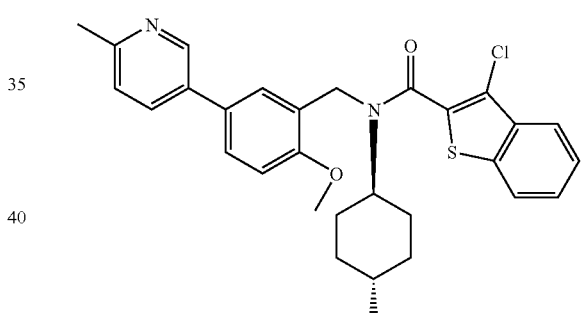

6-Methylpyridin-3-yl trifluoromethanesulfonate (67)

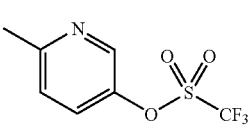

A solution of 5-hydroxy-2-methylpyridine (1.0 g, 9.17 mmol) and trifluoro-methanesulfonic anhydride (1.85 mL, 11.0 mmol) in DCM (20 mL) is treated with triethylamine (1.53 mL, 11.0 mmol) dropwise via syringe at 0° C. After 4 h stirring at RT, the reaction mixture is reduced in vacuo to afford the crude title compound.

Yield: 2.10 g (95%).

191 tert-Butyl {4-[2-methoxy-5-(6-methyl-pyridin-3-yl)-benzylamino]-cyclohexyl}-methyl-carbamate (68)

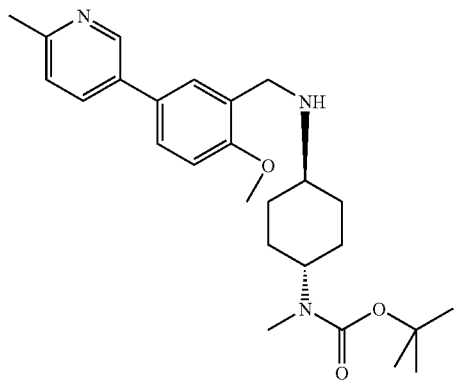

Boronic acid 4 (1.6 g, 4.08 mmol) is coupled to pyridyl triflate 67 (982 mg, 4.08 mmol) using Method A to give the title compound.
Yield: 813 mg (45%) but the compound is contaminated by the following, co-eluting dimer:
LC/MS $t_r$ 1.09 min.
MS (ES+) m/z 440 (M+H), 384 (M-C(CH$_3$)$_3$+H).

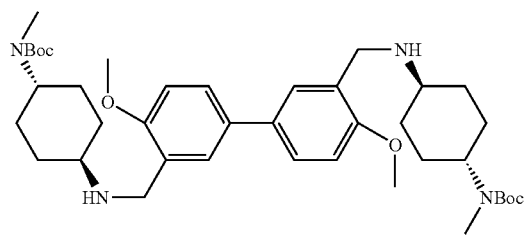

tert-Butyl (4-{(3-chloro-benzo[b]thiophene-2-carbonyl)-[2-methoxy-5-(6-methyl-pyridin-3-yl)-benzyl]-amino}-cyclohexyl)-methyl-carbamate (69)

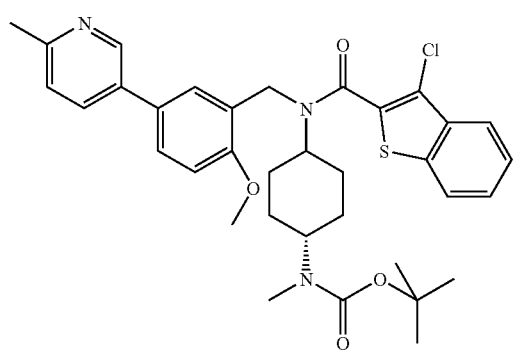

Biaryl amine 68 (175 mg, 0.40 mmol) is treated with 3-chlorobenzo-[b]thiophene-2-carbonyl chloride (110 mg, 0.48 mmol) using Method D to give the title compound.
Yield: 81 mg (32%).
LC/MS $t_r$ 1.61 min.
MS (ES+) m/z 636, 634 (M+H).

192

3-Chloro-benzo[b]thiophene-2-carboxylic acid [2-methoxy-5-(6-methyl-pyridin-3-yl)-benzyl]-(4-methylamino-cyclohexyl)-amide dihydrochloride (70)

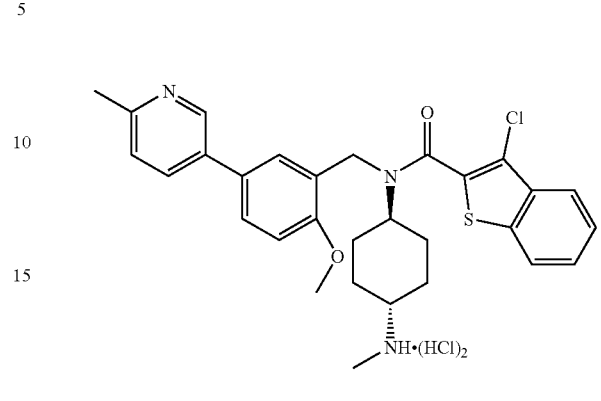

tert-Butyl carbamate 69 (81 mg, 0.13 mmol) is deprotected using Method F to give the title compound.
Yield: 74 mg (95%).
LC/MS $t_r$ 1.56 min.
MS (ES+) m/z 650, 648 (M+CF$_3$COOH+H), 536, 534 (M+H).

Synthesis of Compound 321

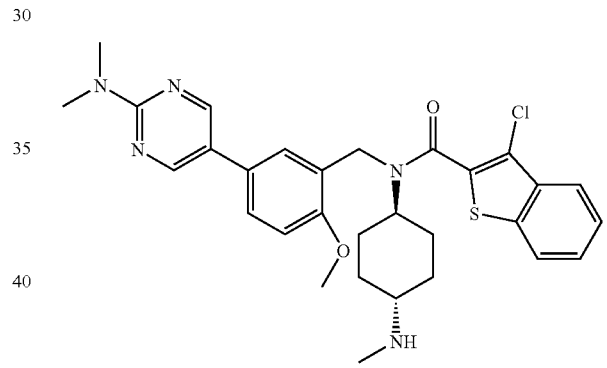

3-Chloro-benzo[b]thiophene-2-carboxylic acid [5-(2-dimethylamino-pyrimidin-5-yl)-2-methoxy-benzyl]-(4-methylamino-cyclohexyl)-amide dihydrochloride (71)

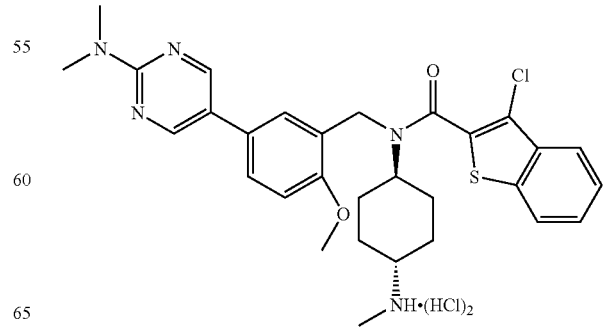

The title compound is prepared from boronic acid 5 (25 mg, 43 µmol) and 5-bromo-2-(dimethylamino)pyrimidine (7.2 mg, 36 µmol) in accordance with Method L2.
Yield: 12.0 mg (52%).
LC/MS $t_r$ 1.25 min.
MS (ES+) m/z 566, 564 (M+H).
Synthesis of Compound 322

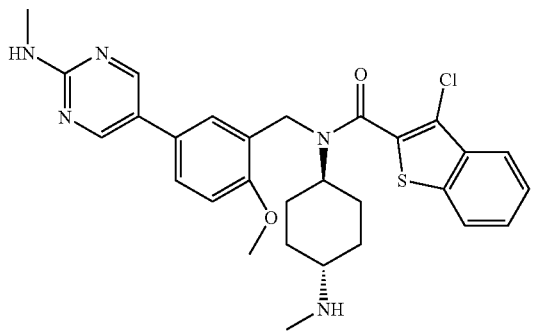

3-Chloro-benzo[b]thiophene-2-carboxylic acid [2-methoxy-5-(2-methylamino-pyrimidin-5-yl)-benzyl]-(4-methylamino-cyclohexyl)-amide dihydrochloride (72)

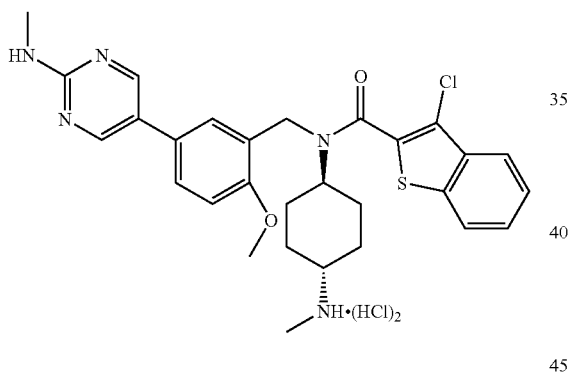

The title compound is prepared from boronic acid 5 (25 mg, 43 µmol) and 5-bromo-2-(methylamino)pyrimidine (6.7 mg, 36 µmol) in accordance with Method L2.
Yield: 5.0 mg (22%).
LC/MS $t_r$ 1.17 min.
MS (ES+) m/z 552, 550 (M+H).
Synthesis of Compound 323

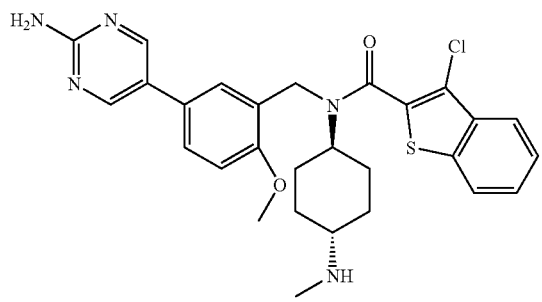

3-Chloro-benzo[b]thiophene-2-carboxylic acid [5-(2-amino-pyrimidin-5-yl)-2-methoxy-benzyl]-(4-methylamino-cyclohexyl)-amide dihydrochloride (73)

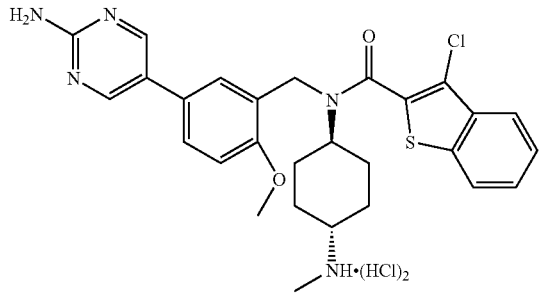

The title compound is prepared from boronic acid 5 (25 mg, 43 µmol) and 2-amino-5-bromopyrimidine (6.2 mg, 36 mmol) in accordance with Method L2.
Yield: 5.7 mg (26%).
LC/MS $t_r$ 1.13 min.
MS (ES+) m/z 538, 536 (M+H).
Synthesis of Compound 324 (R20)

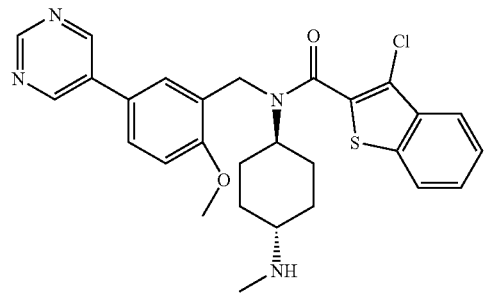

3-Chloro-benzo[b]thiophene-2-carboxylic acid (2-methoxy-5-pyrimidin-5-yl-benzyl)-(4-methylamino-cyclohexyl)-amide dihydrochloride (74)

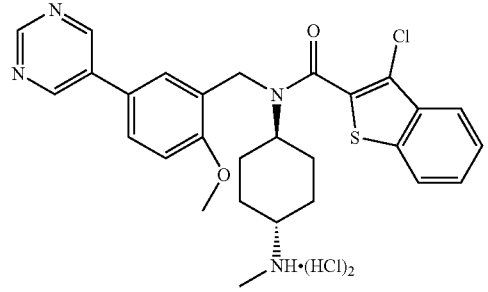

The title compound is prepared from boronic acid 5 (25 mg, 43 µmol) and 5-bromopyrimidine (5.6 mg, 36 µmol) in accordance with Method L2.
Yield: 4.1 mg (18%).
LC/MS $t_r$ 1.24 min.
MS (ES+) nm/z 523, 521 (M+H), 492, 490 (M-31+H).

Synthesis of Compound R4

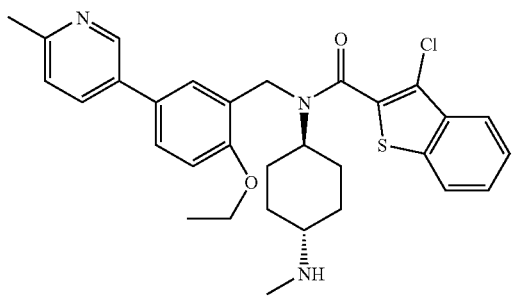

tert-Butyl {4-[2-ethoxy-5-(6-methyl-pyridin-3-yl)-benzylamino]-cyclohexyl}-methyl-carbamate (75)

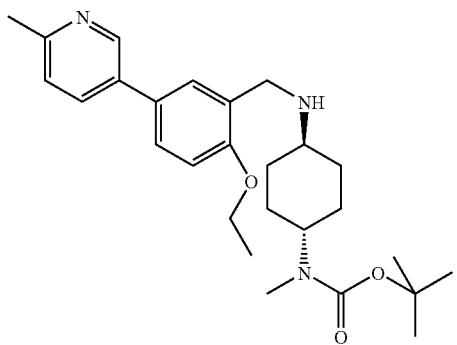

Boronic acid 11 (812 mg, 2.0 mmol) is coupled to 5-bromo-2-methylpyridine (344 mg, 2.0 mmol) using Method A to give the title compound.
Yield: 373 mg (41%).
LC/MS $t_r$ 1.12 min.
MS (ES+) m/z 907 (2M+H), 454 (M+H).

tert-Butyl (4-{(3-chloro-benzo[b]thiophene-2-carbonyl)-[2-ethoxy-5-(6-methyl-pyridin-3-yl)-benzyl]-amino}-cyclohexyl)-methyl-carbamate (76)

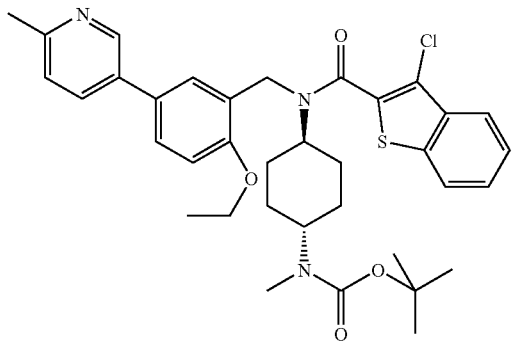

Biaryl amine 75 (373 mg, 0.82 mmol) is treated with 3-chlorobenzo-[b]thiophene-2-carbonyl chloride (227 mg, 1.80 mmol) using Method D to give the title compound.
Yield: 224 mg (42%).
LC/MS $t_r$ 1.59 min.
MS (ES+) m/z 650, 648 (M+H).

3-Chloro-benzo[b]thiophene-2-carboxylic acid [2-ethoxy-5-(6-methyl-pyridin-3-yl)-benzyl]-(4-methylamino-cyclohexyl)-amide dihydrochloride (77)

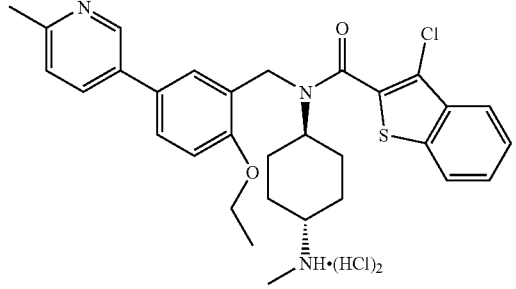

tert-Butyl carbamate 76 (200 mg, 0.31 mmol) is deprotected using Method F to give the title compound.
Yield: 192 mg (quant.).
LC/MS $t_r$ 1.73 min.
MS (ES+) m/z 550, 548 (M+H).

Synthesis of Compound 325

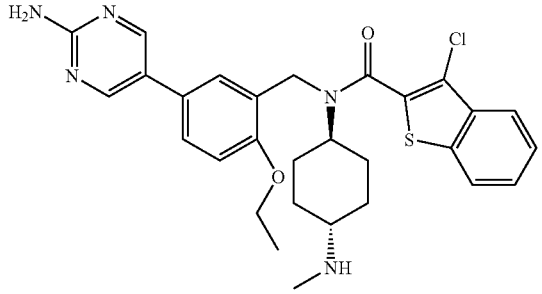

3-Chloro-benzo[b]thiophene-2-carboxylic acid [5-(2-amino-pyrimidin-5-yl)-2-ethoxy-benzyl]-(4-methylamino-cyclohexyl)-amide dihydrochloride (78)

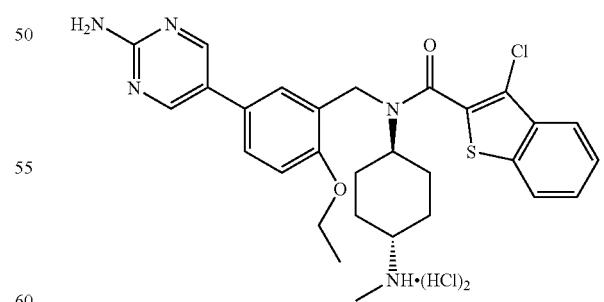

The title compound is prepared from boronic acid 12 (25 mg, 42 µmol) and 2-amino-5-bromopyrimidine (6.0 mg, 35 µmol) in accordance with Method L2.
Yield: 8.1 mg (37%).
LC/MS $t_r$ 1.18 min.
MS (ES+) m/z 552, 550 (M+H).

Synthesis of Compound 326

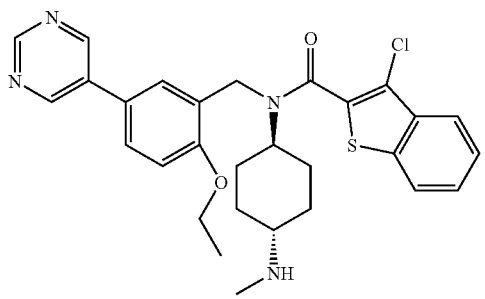

3-Chloro-benzo[b]thiophene-2-carboxylic acid (2-ethoxy-5-pyrimidin-5-yl-benzyl)-(4-methylamino-cyclohexyl)-amide dihydrochloride (79)

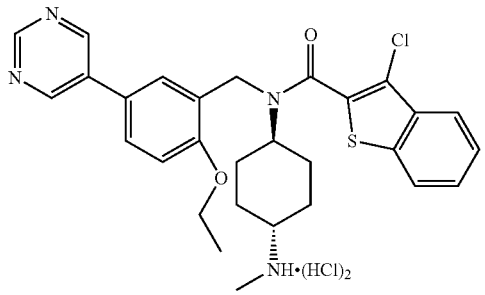

The title compound is prepared from boronic acid 12 (25 mg, 42 µmol) and 5-bromopyrimidine (5.5 mg, 35 µmol) in accordance with Method L2.
Yield: 6.3 mg (30%).
LC/MS $t_r$ 1.26 min.
MS (ES+) m/z 537, 535 (M+H).
Synthesis of Compound 327

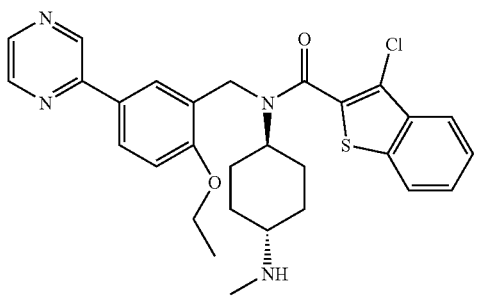

3-Chloro-benzo[b]thiophene-2-carboxylic acid (2-ethoxy-5-pyrazin-2-yl-benzyl)-(4-methylamino-cyclohexyl)-amide dihydrochloride (80)

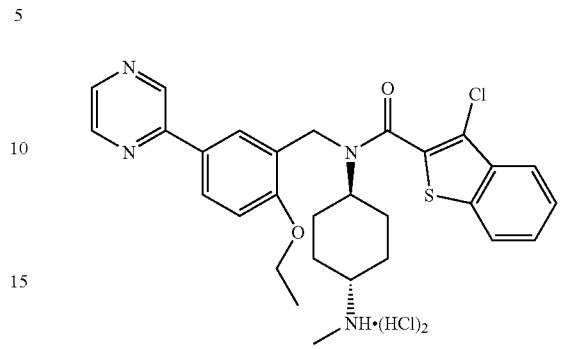

The title compound is prepared from boronic acid 12 (25 mg, 42 µmol) and 2-chloropyrazine (4.0 mg, 35 µmol) in accordance with Method L2.
Yield: 13.6 mg (64%).
LC/MS $t_r$ 1.76 min.
MS (ES+) m/z 537, 535 (M+H).
Synthesis of Compound 328

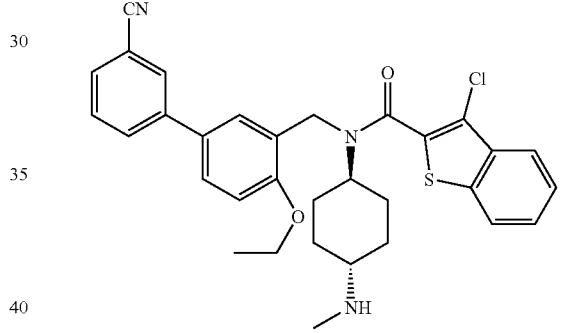

tert-Butyl {4-[(3'-cyano-4-ethoxy-biphenyl-3-ylmethyl)-amino]-cyclohexyl}-methyl-carbamate (81)

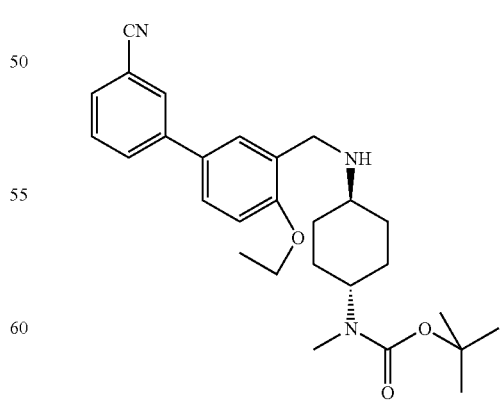

Boronic acid 11 (374 mg, 0.92 mmol) is coupled to 3-bromobenzonitrile (200 mg, 1.10 mmol) using Method B to give the title compound.

Yield: 390 mg (91%).

LC/MS $t_r$ 1.56 min.

MS (ES+) m/z 464 (M+H), 408 (M-C(CH$_3$)$_3$+H).

tert-Butyl {4-[(3-chloro-benzo[b]thiophene-2-carbonyl)-(3'-cyano-4-ethoxy-biphenyl-3-ylmethyl)-amino]-cyclohexyl}-methyl-carbamate (82)

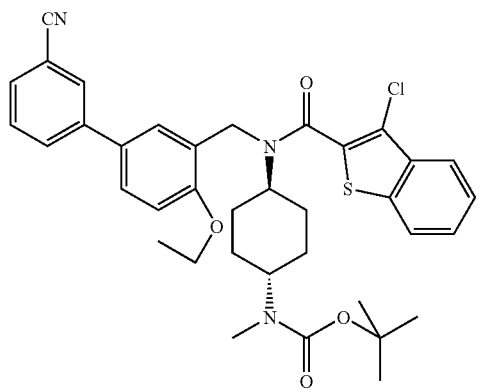

Biaryl amine 81 (390 mg, 0.84 mmol) is treated with 3-chlorobenzo-[b]thiophene-2-carbonyl chloride (233 mg, 1.01 mmol) using Method D to give the title compound.

Yield: 329 mg (59%).

LC/MS $t_r$ 2.16 min.

MS (ES+) m/z 604, 602 (M-C(CH$_3$)$_3$+H).

3-Chloro-benzo[b]thiophene-2-carboxylic acid (3'-cyano-4-ethoxy-biphenyl-3-ylmethyl)-(4-methylamino-cyclohexyl)-amide hydrochloride (83)

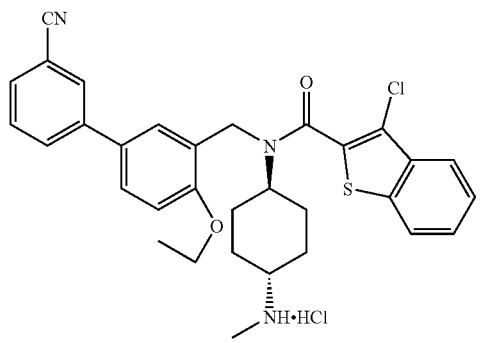

tert-Butyl carbamate 82 (329 mg, 0.50 mmol) is deprotected using Method E. The solvents are then removed in vacuo and the residue purified by column chromatography (gradient elution—100% EtOAc increasing to 50% MeOH in EtOAc with 5% triethylamine). Treatment of the isolated free base in accordance with Method H gives the title compound.

Yield: 100 mg (36%).

LC/MS $t_r$ 1.60 min.

MS (ES+) m/z 560, 558 (M+H), 529, 527 (M-31+H).

Synthesis of Compound 329

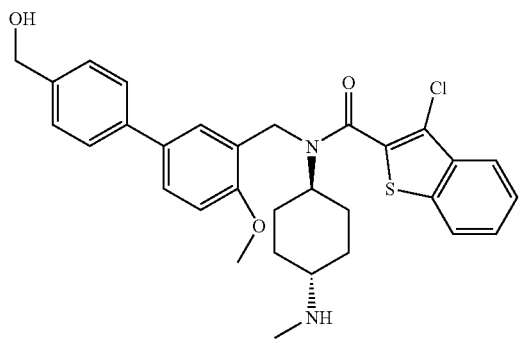

tert-Butyl {4-[(3-chloro-benzo[b]thiophene-2-carbonyl)-(4'-hydroxymethyl-4-methoxy-biphenyl-3-ylmethyl)-amino]-cyclohexyl}-methyl-carbamate (84)

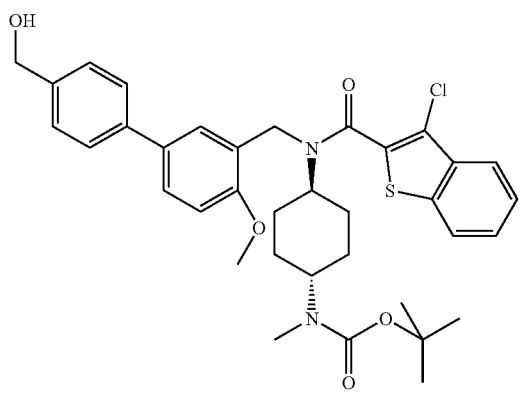

Boronic acid 5 (210 mg, 0.36 mmol) is coupled to (4-bromophenyl)-methanol (80 mg, 0.43 mmol) using Method B to give the title compound.

Yield: 150 mg (64%).

LC/MS $t_r$ 1.99 min.

MS (ES+) m/z 595, 593 (M-C(CH$_3$)$_3$+H).

3-Chloro-benzo[b]thiophene-2-carboxylic acid (4'-hydroxymethyl-4-methoxy-biphenyl-3-ylmethyl)-(4-methylamino-cyclohexyl)-amide hydrochloride (85)

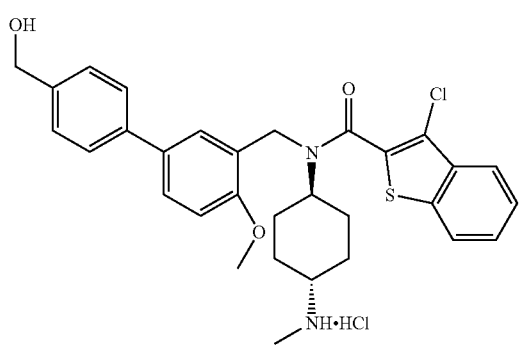

tert-Butyl carbamate 84 (70 mg, 0.11 mmol) is deprotected using Method E to give the title compound.

Yield: 64 mg (quant.).
LC/MS $t_r$ 1.50 min.
MS (ES+) 551, 549 (M+H), 520, 518 (M-31+H).

Synthesis of Compound 330 (R22)

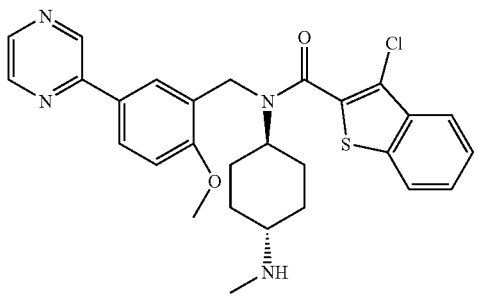

3-Chloro-benzo[b]thiophene-2-carboxylic acid (2-methoxy-5-pyrazin-2-yl-benzyl)-(4-methylamino-cyclohexyl)-amide bis(trifluoroacetate) (86)

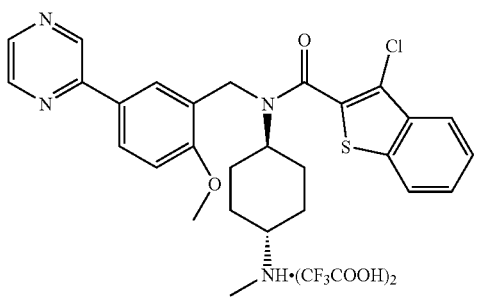

Boronic acid 5 (25 mg, 43 μmol) and 2-chloropyrazine (4.1 mg, 36 μmol) are coupled in accordance with Method L1. The title compound is obtained after preparative HPLC.

Yield: 3.2 mg (10%).
LC/MS $t_r$ 1.34 min.
MS (ES+) m/z 523, 521 (M+H), 492, 490 (M-31+H).

Synthesis of Compound 331 (R11)

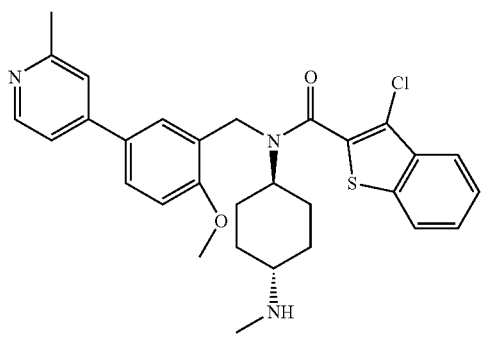

2-Methoxy-5-(2-methyl-pyridin-4-yl)-benzaldehyde (87)

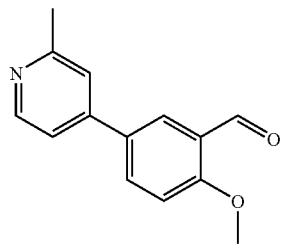

A stirred suspension of 3-formyl-4-methoxybenzeneboronic acid (700 mg, 3.89 mmol), 4-chloro-2-picoline (494 mg, 3.89 mmol), potassium carbonate (1.45 g, 10.5 mmol) and tetrakis(triphenylphosphine)palladium(0) (225 mg, 0.19 mmol) in 1,2-dimethoxyethane (14 mL) and water (5 mL) is degassed at RT with N₂ for 15 minutes then warmed for 16 h at 85° C. The reaction mixture is then cooled to RT and 2 M HCl (15 mL) added. The aqueous layer is washed with TBME (15 mL) then basified to pH 10 with aqueous K₂CO₃ and extracted into EtOAc (3×50 mL); The combined organic phases are dried over Na₂SO₄ and the solvents removed in vacuo to give the title compound.

Yield: 820 mg (93%).
LC/MS $t_r$ 0.91 min.
MS (ES+) m/z 228 (M+H).

tert-Butyl {4-[2-methoxy-5-(2-methyl-pyridin-4-yl)-benzylamino]-cyclohexyl}-methyl-carbamate (88)

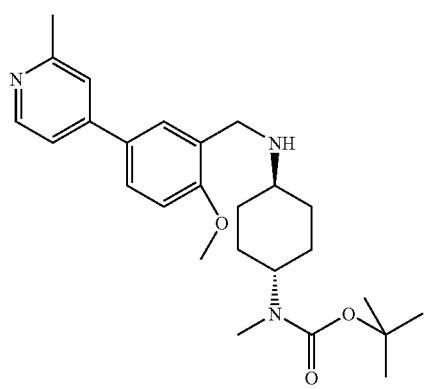

Amine 3 (823 mg, 3.61 mmol) is treated with aldehyde 87 (820 mg, 3.61 mmol) in accordance with Method C. The reaction mixture is then diluted with TBME (10 mL) and 0.5 M HCl (10 mL) and the layers separated. The aqueous phase is basified to pH 10 with aqueous K₂CO₃ and extracted into EtOAc (3×50 mL). The combined organic phases are dried over Na₂SO₄ and the solvents removed in vacuo to give the title compound.

Yield: 720 mg (45%).
LC/MS $t_r$ 1.08 min.
MS (ES+) m/z 440 (M+H), 384 (M-C(CH₃)₃+H).

3-Chloro-benzo[b]thiophene-2-carboxylic acid [2-methoxy-5-(2-methyl-pyridin-4-yl)-benzyl]-(4-methylamino-cyclohexyl)-amide dihydrochloride (89)

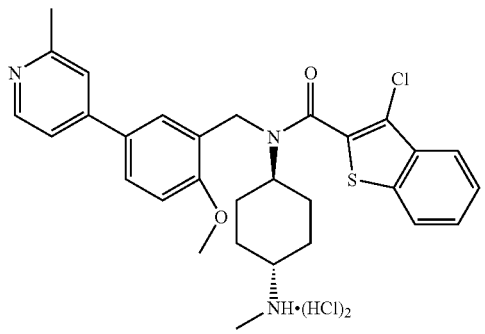

Biaryl amine 88 (250 mg, 0.57 mmol) is treated with 3-chlorobenzo-[b]thiophene-2-carbonyl chloride (157 mg, 0.68 mmol) using Method D. The resultant amide (175 mg, 0.28 mmol) isolated after chromatography is then directly deprotected using Method F to afford the title compound.

Yield: 138 mg (40% over two steps).
LC/MS $t_r$ 1.08 min.
MS (ES+) m/z 536, 534 (M+H).

Synthesis of Compound R1

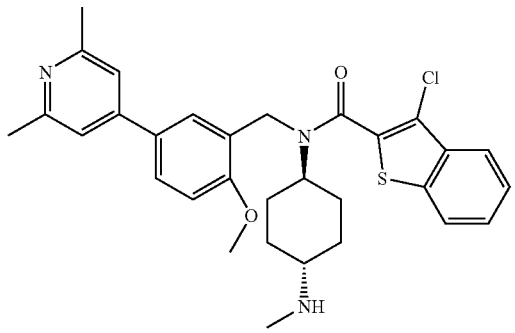

2,6-Dimethyl-pyridin-4-ol (90)

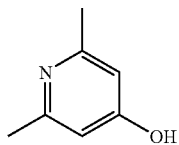

Five separate batches of dehydroacetic acid (1.5 g, 8.92 mmol) are each suspended in conc. ammonia (4 mL) and irradiated at 120° C. for 20 minutes (150 W, Discover® System microwave reactor by CEM Corporation, Matthews, N.C., USA) in the microwave. Once cooled, the solutions are combined and evaporated to dryness to afford the title compound.

Yield: 5.91 g (108%) @ 73% purity by LC/MS. The remaining mass balance is unreacted dehydroacetic acid.
LC/MS $t_r$ 0.67 min.
MS (ES+) m/z 168 (M+CH$_3$CN+H).

2,6-Dimethyl-pyridin-4-yl trifluoromethanesulfonate (91)

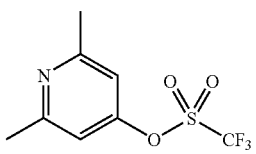

A suspension of pyridone 90 (5.0 g, 40.6 mmol) in DCM (100 mL) at 0° C. is treated with triethylamine (8.50 mL, 60.9 mmol) followed by trifluoromethane-sulfnic anhydride (10.2 mL, 60.9 mmol), added dropwise via syringe over 5 minutes. After warming to RT and stirring 2 h, the reaction mixture is washed with aqueous NaHCO$_3$ (3×100 mL) and reduced in vacuo to afford the title compound.

Yield: 9.25 g (quant.).
LC/MS $t_r$ 0.96 min.
MS (ES+) m/z 256 (M+H).

tert-Butyl {4-[5-(2,6-dimethyl-pyridin-4-yl)-2-methoxy-benzylamino]-cyclohexyl}-methyl-carbamate (92)

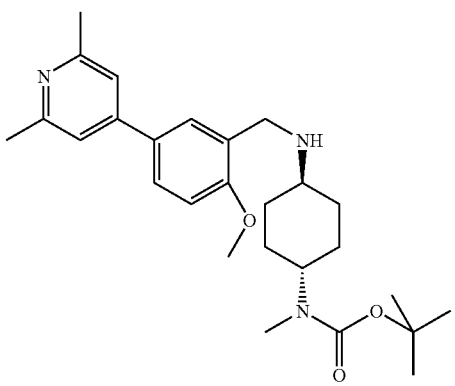

Boronic acid 4 (400 mg, 1.02 mmol) is coupled to pyridyl triflate 91 (260 mg, 1.02 mmol) using Method B to give the title compound.

Yield: 268 mg (58%).
LC/MS $t_r$ 1.07 min.
MS (ES+) m/z 454 (M+H).

tert-Butyl (4-{(3-chloro-benzo[b]thiophene-2-carbo-nyl)-[5-(2,6-dimethyl-pyridin-4-yl)-2-methoxy-benzyl]-amino}-cyclohexyl)-methyl-carbamate (93)

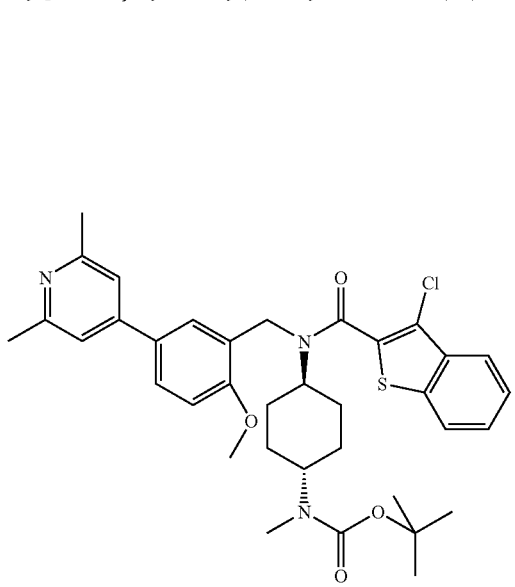

Biaryl amine 92 (100 mg, 0.22 mmol) is treated with 3-chlorobenzo-[b]thiophene-2-carbonyl chloride (61 mg, 0.26 mmol) using Method D to give the title compound.
Yield: 91 mg (64%).
LC/MS t$_r$ 1.63 min.
MS (ES+) m/z 650, 648 (M+H), 594, 592 (M-C(CH$_3$)$_3$+H).

3-Chloro-benzo[b]thiophene-2-carboxylic acid [5-(2,6-dimethyl-pyridin-4-yl)-2-methoxy-benzyl]-(4-methylamino-cyclohexyl)-amide dihydrochloride (94)

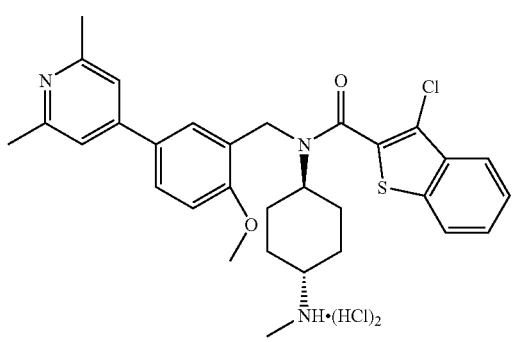

tert-Butyl carbamate 93 (91 mg, 0.14 mmol) is deprotected using Method F to give the title compound.
Yield: 73 mg (96%).
LC/MS t$_r$ 1.71 min.
MS (ES+) m/z 550, 548 (M+H).

Synthesis of Compound 332

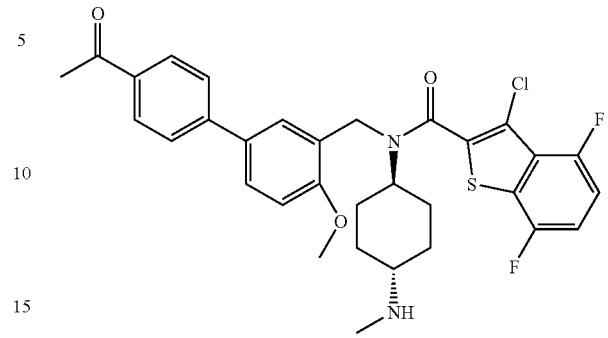

tert-Butyl {4-[(4'-acetyl-4-methoxy-biphenyl-3-ylmethyl)-(3-chloro-4,7-difluoro-benzo[b]thiophene-2-carbonyl)-amino]-cyclohexyl}-methyl-carbamate (95)

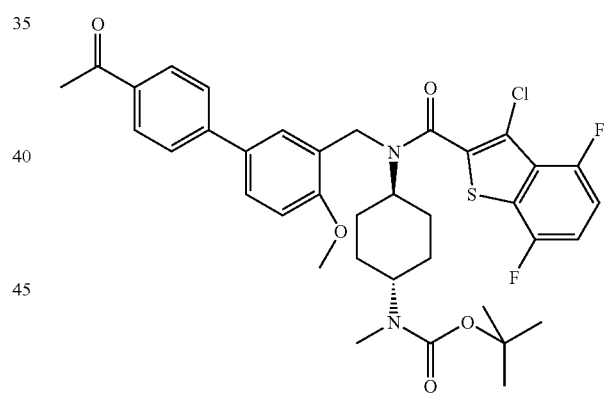

Boronic acid 9 (700 mg, 1.12 mmol) is coupled to 4'-bromoacetophenone (268 mg, 1.34 mmol) using Method A to give the title compound.
Yield: 396 mg (51%).
LC/MS t$_r$ 1.96 min.
MS (ES+) m/z 699, 697 (M+H), 643, 641 (M-C(CH$_3$)$_3$+H).

207

3-Chloro-4,7-difluoro-benzo[b]thiophene-2-carboxylic acid (4'-acetyl-4-methoxy-biphenyl-3-ylmethyl)-(4-methylamino-cyclohexyl)-amide hydrochloride (96)

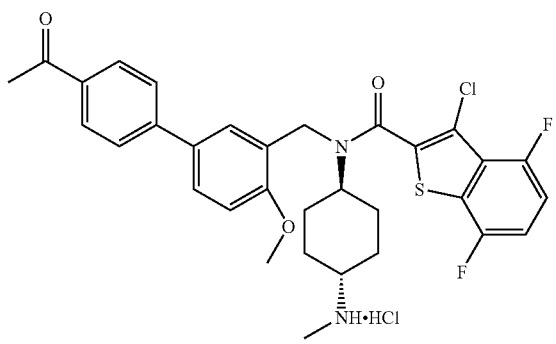

tert-Butyl carbamate 95 (396 mg, 0.57 mmol) is deprotected using Method F to give the title compound.

Yield: 354 mg (98%).

LC/MS $t_r$ 1.49 min.

MS (ES+) m/z 599, 597 (M+H).

$^1$H NMR $\delta_H$ ppm (400 MHz, D$_6$-DMSO, 95° C.): 8.59 (2H, br. s), 7.85 (2H, d), 7.54 (2H, d), 7.48 (1H, dd), 7.43 (1H, s), 7.25-7.13 (2H, m), 6.95 (1H, d), 4.54 (2H, s), 3.75 (1H, br. s), 3.71 (3H, s), 2.79-2.70 (1H, obsc. m), 2.44 (3H, s), 2.31 (3H, s), 2.00-1.91 (2H, m), 1.78-1.61 (4H, m), 1.32-1.19 (2H, m).

Synthesis of Compound 333

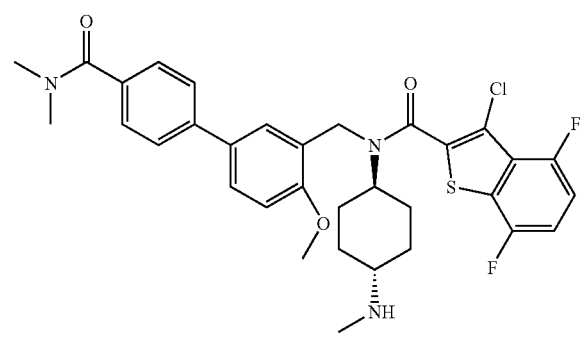

208 tert-Butyl {4-[(3-chloro-4,7-difluoro-benzo[b]thiophene-2-carbonyl)-(4'-dimethylcarbamoyl-4-methoxy-biphenyl-3-ylmethyl)-amino]-cyclohexyl}-methyl-carbamate (97)

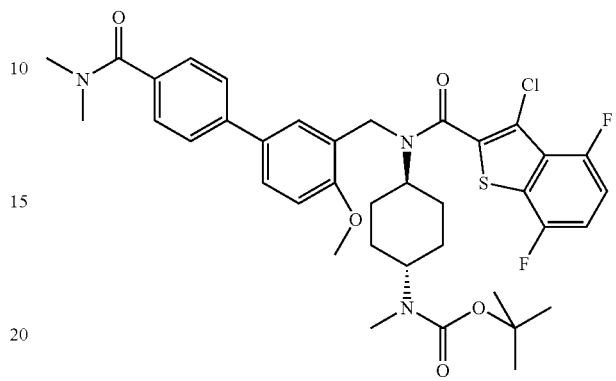

Boronic acid 9 (700 mg, 1.12 mmol) is coupled to aryl bromide 58 (306 mg, 1.34 mmol) using Method A to give the title compound.

Yield: 250 mg (32%) containing triphenylphosphine oxide (ca. 27%) plus 317 mg (40%) cruder material.

LC/MS $t_r$ 1.84 min.

MS (ES+) m/z 728, 726 (M+H), 672, 670 (M-C(CH$_3$)$_3$+H).

3-Chloro-4,7-difluoro-benzo[b]thiophene-2-carboxylic acid (4'-dimethylcarbamoyl-4-methoxy-biphenyl-3-ylmethyl)-(4-methylamino-cyclohexyl)-amide hydrochloride (98)

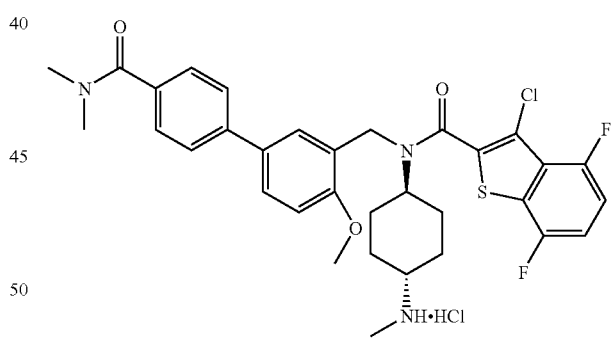

tert-Butyl carbamate 97 (250 mg, 0.34 mmol) is deprotected using Method F. The isolated salt is then dissolved in the minimum amount of DCM and added dropwise to cold (0° C.) TBME (25 mL). The resultant white precipitate is isolated by filtration and dried to afford the title compound.

Yield: 169 mg (75%).

LC/MS $t_r$ 1.38 min.

MS (ES+) m/z 628, 626 (M+H).

$^1$H NMR $\delta_H$ ppm (400 MHz, D$_6$-DMSO, 95° C.): 8.46 (2H, br. s), 7.41 (2H, d), 7.38 (1H, obsc. dd), 7.35 (1H, s), 7.27 (2H, d), 7.21-7.08 (2H, m), 6.88 (1H, d), 4.49 (2H, s), 3.70 (1H, br. s), 3.66 (3H, s), 2.80 (6H, s), 2.74-2.64 (1H, obsc. m), 2.27 (3H, s), 1.95-1.85 (2H, m), 1.74-1.56 (4H, m), 1.27-1.13 (2H, m).

Synthesis of Compound 334

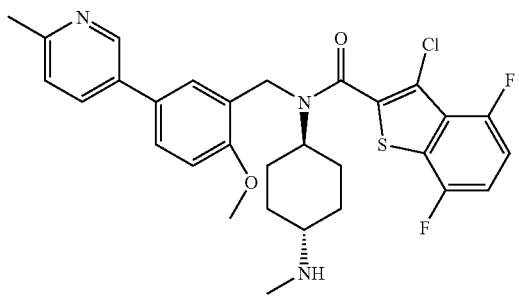

tert-Butyl (4-{(3-chloro-4,7-difluoro-benzo[b]
thiophene-2-carbonyl)-[2-methoxy-5-(6-methyl-
pyridin-3-yl)-benzyl]-amino}-cyclohexyl)-methyl-
carbamate (99)

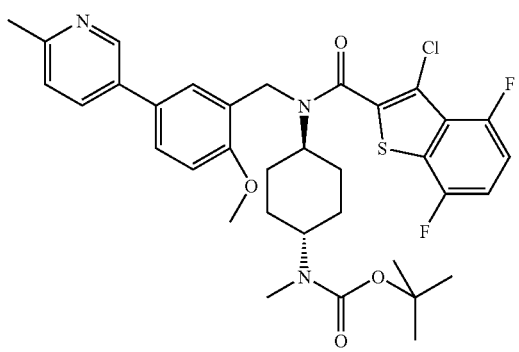

Biaryl amine 68 (813 mg, 1.85 mmol) is treated with acid chloride 8 (542 mg, 2.03 mmol) using Method D to give the title compound.
Yield: 133 mg (11%).
LC/MS $t_r$ 1.67 min.
MS (ES+) m/z 672, 670 (M+H), 616, 614 (M-C(CH$_3$)$_3$+H).

3-Chloro-4,7-difluoro-benzo[b]thiophene-2-carboxy-
lic acid [2-methoxy-5-(6-methyl-pyridin-3-yl)-ben-
zyl]-(4-methylamino-cyclohexyl)-amide bis(trifluo-
roacetate) (100)

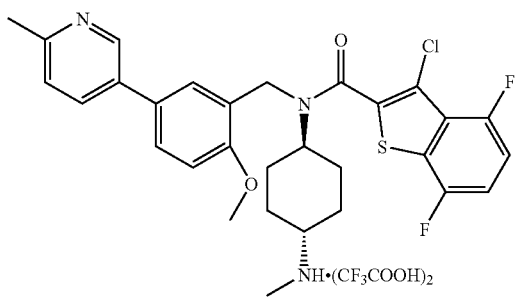

tert-Butyl carbamate 99 (133 mg, 0.20 mmol) is deprotected using Method G to afford the title compound.

Yield: 158 mg (quant.).
LC/MS $t_r$ 1.72 min.
MS (ES+) m/z 572, 570 (M+H).

Synthesis of Compound R7

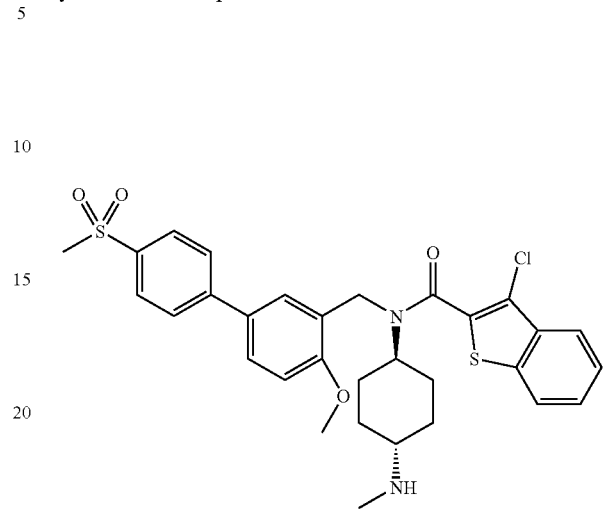

tert-Butyl {4-[(3-chloro-benzo[b]thiophene-2-carbo-
nyl)-(4'-methanesulfonyl-4-methoxy-biphenyl-3-
ylmethyl)-amino]-cyclohexyl}-methyl-carbamate
(101)

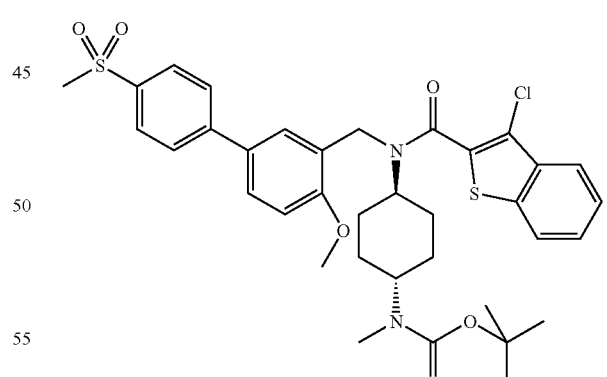

Boronic acid 5 (330 mg, 0.84 mmol) is coupled to 4'-bromophenyl methyl sulfone (237 mg, 1.01 mmol) using Method A to give the title compound.
Yield: 176 mg (30%).

3-Chloro-benzo[b]thiophene-2-carboxylic acid (4'-methanesulfonyl-4-methoxy-biphenyl-3-ylmethyl)-(4-methylamino-cyclohexyl)-amide hydrochloride (102)

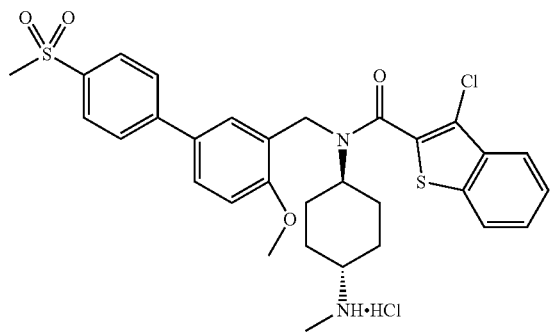

tert-Butyl carbamate 101 (173 mg, 0.25 mmol) is deprotected using Method F to afford the title compound.
Yield: 170 mg (quant.).
LC/MS $t_r$ 1.41 min.
MS (ES+) m/z 599, 597 (M+H), 568, 566 (M-31+H).

Synthesis of Compound 335

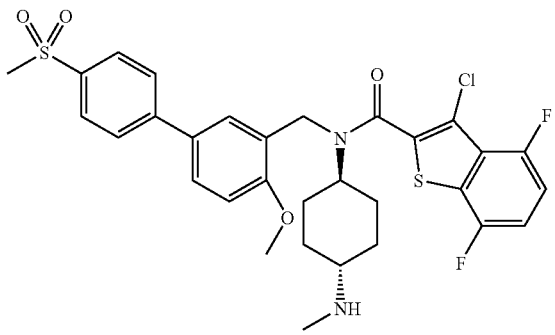

tert-Butyl {4-[(4'-methanesulfonyl-4-methoxy-biphenyl-3-ylmethyl)-amino]-cyclohexyl}-methyl-carbamate (103)

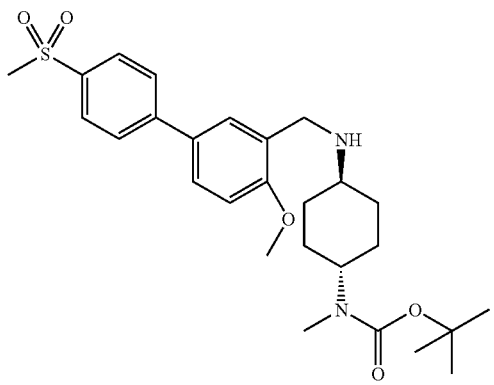

Boronic acid 4 (3.0 g, 7.64 mmol) is coupled to 4'-bromophenyl methyl sulfone (1.80 g, 7.64 mmol) using Method A to give the title compound.
Yield: 1.84 g (48%).
LC/MS $t_r$ 1.28 min.
MS (ES+) m/z 503 (M+H).

tert-Butyl {4-[(3-Chloro-4,7-difluoro-benzo[b]thiophene-2-carbonyl)-(4'-methanesulfonyl-4-methoxy-biphenyl-3-ylmethyl)-amino]-cyclohexyl}-methyl-carbamate (104)

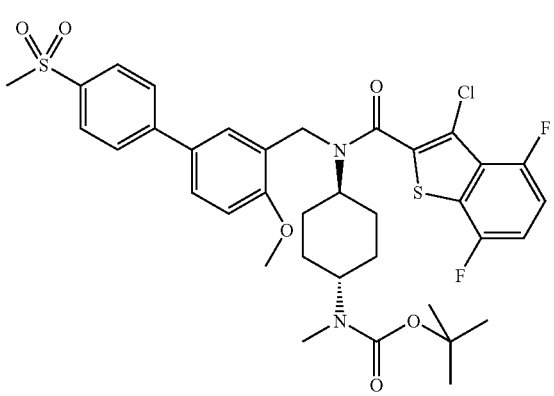

Biaryl amine 103 (1.84 g, 3.66 mmol) is treated with acid chloride 8 (1.17 g, 4.38 mmol) using Method D to give the title compound.
Yield: 2.10 g (78%).
LC/MS $t_r$ 1.84 min.
MS (ES+) m/z 735, 733 (M+H), 679, 677 (M-C(CH$_3$)$_3$+H).

3-Chloro-4,7-difluoro-benzo[b]thiophene-2-carboxylic acid (4'-methanesulfonyl-4-methoxy-biphenyl-3-ylmethyl)-(4-methylamino-cyclohexyl)-amide hydrochloride (105)

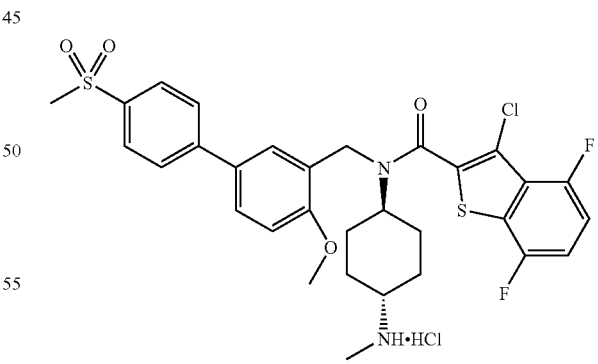

tert-Butyl carbamate 104 (2.10 g, 2.86 mmol) is deprotected using Method F then purified by column chromatography (gradient elution—1-5% MeOH in DCM with 0.5% triethylamine). The free base is then converted to the title compound using Method H.
Yield: 1.64 g (85%).
LC/MS $t_r$ 1.94 min.
MS (ES+) m/z 635, 633 (M+H).

¹H NMR δ_H ppm (400 MHz, D₆-DMSO, 95° C.): 9.13 (2H, br. s), 7.98 (2H, d), 7.82 (2H, d), 7.65 (1H, dd), 7.60 (1H, s), 7.41-7.26 (2H, m), 7.12 (1H, d), 4.71 (2H, s), 3.92 (1H, br. s), 3.88 (3H, s), 3.22 (3H, s), 2.95-2.83 (1H, m), 2.46 (3H, s), 2.20-2.08 (2H, m), 1.94-1.76 (4H, m), 1.54-1.39 (2H, m).

Synthesis of Compound 336 tert-Butyl {4-[[4'-(acetyl-methyl-amino)-4-methoxy-biphenyl-3-ylmethyl]-(3-chloro-4,7-difluoro-benzo[b]thiophene-2-carbonyl)-amino]-cyclohexyl}-methyl-carbamate (107)

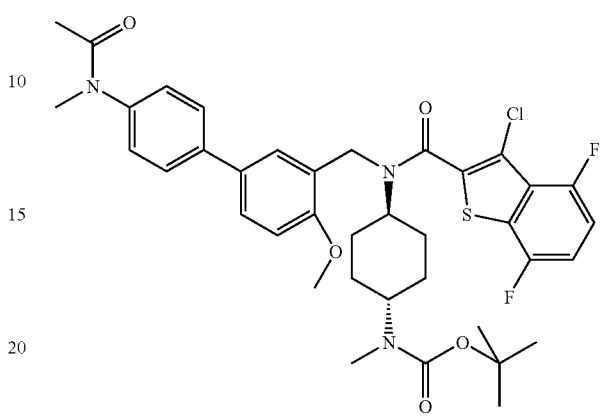

Biaryl amine 106 (420 mg, 0.84 mmol) is treated with acid chloride 8 (249 mg, 0.93 mmol) using Method D to give the title compound.

Yield: 280 mg (46%).

LC/MS t_r 1.85 min.

MS (ES+) m/z 672, 670 (M-C(CH₃)₃+H), 628, 626 (M-CO₂C(CH₃)₃+H).

3-Chloro-4,7-difluoro-benzo[b]thiophene-2-carboxylic acid [4'-(acetyl-methyl-amino)-4-methoxy-biphenyl-3-ylmethyl]-(4-methylamino-cyclohexyl)-amide hydrochloride (108)

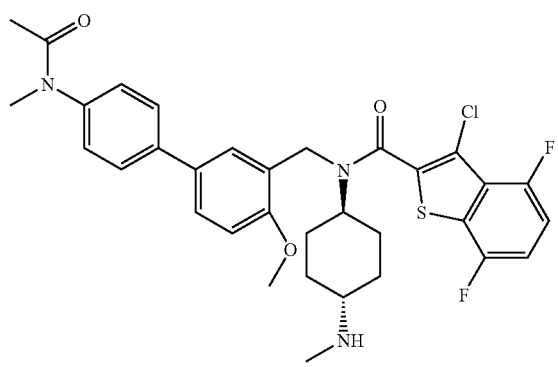

tert-Butyl (4-{[4'-(acetyl-methyl-amino)-4-methoxy-biphenyl-3-ylmethyl]-amino}-cyclohexyl)-methyl-carbamate (106)

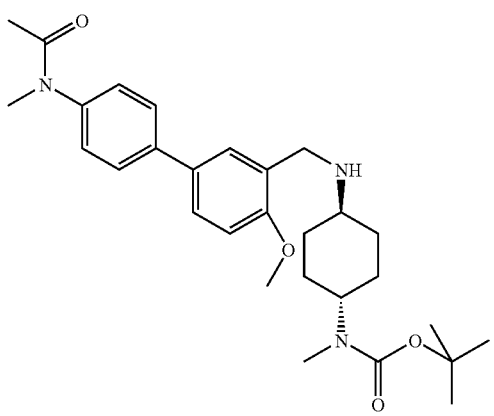

Boronic acid 4 (650 mg, 1.04 mmol) is coupled to aryl bromide 62 (238 mg, 1.04 mmol) using Method A to give the title compound.

Yield: 420 mg (51%).

LC/MS t_r 1.27 min.

MS (ES+) m/z 496 (M+H).

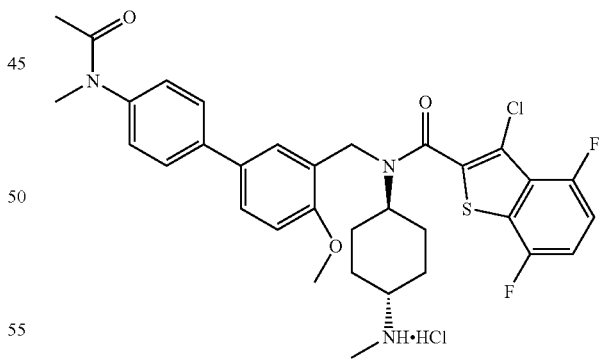

tert-Butyl carbamate 107 (280 mg, 0.38 mmol) is deprotected using Method F to give the title compound.

Yield: 185 mg (77%).

LC/MS t_r 1.33 min.

MS (ES+) m/z 628, 626 (M+H).

Synthesis of Compound 337

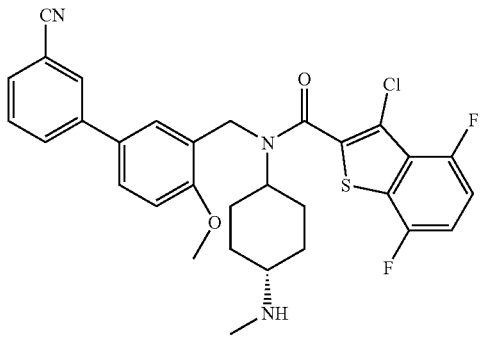

tert-Butyl {4-[(3-chloro-4,7-difluoro-benzo[b]thiophene-2-carbonyl)-(3'-cyano-4-methoxy-biphenyl-3-ylmethyl)-amino]-cyclohexyl}-methyl-carbamate (109)

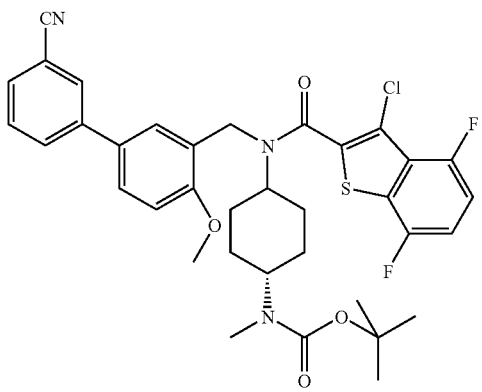

Biaryl amine 22 (475 mg, 1.06 mmol) is treated with acid chloride 8 (338 mg, 1.27 mmol) using Method D to give the title compound.
Yield: 395 mg (55%).
LC/MS $t_r$ 1.97 min.
MS (ES+) m/z 626, 624 (M-C(CH$_3$)$_3$+H).

3-Chloro-4,7-difluoro-benzo[b]thiophene-2-carboxylic acid (3'-cyano-4-methoxy-biphenyl-3-ylmethyl)-(4-methylamino-cyclohexyl)-amide hydrochloride (110)

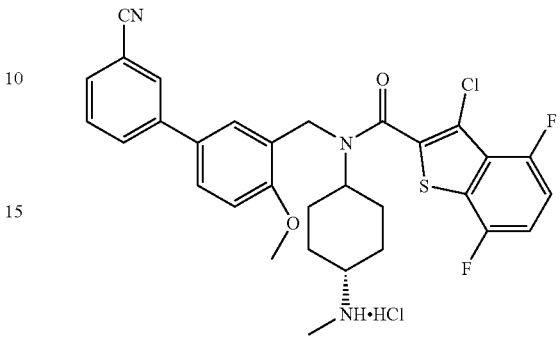

tert-Butyl carbamate 109 (395 mg, 0.58 mmol) is deprotected using Method F. On removal of the solvents in vacuo, the residue is dissolved in water (15 mL) and washed with TBME (3×10 mL). Reduction of the aqueous phase in vacuo affords the title product.
Yield: 340 mg (95%).
LC/MS $t_r$ 1.46 min.
MS (ES+) m/z 582, 580 (M+H).

Synthesis of Compound R8

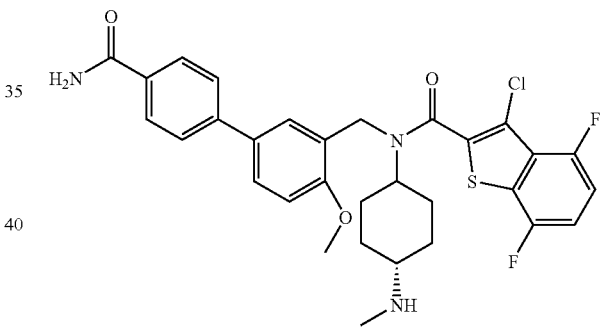

tert-Butyl {4-[(4'-carbamoyl-4-methoxy-biphenyl-3-ylmethyl)-(3-chloro-4,7-difluoro-benzo[b]thiophene-2-carbonyl)-amino]-cyclohexyl}-methyl-carbamate (111)

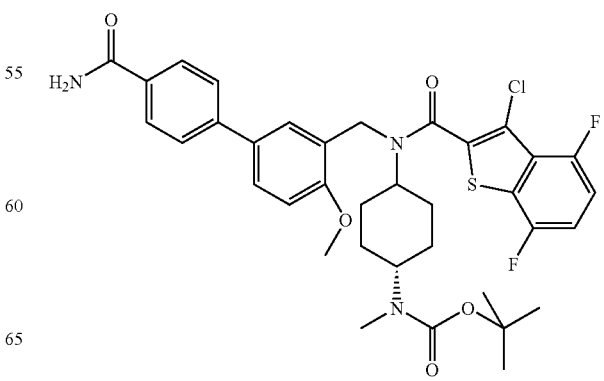

Biaryl amine 55 (80 mg, 0.17 mmol) is treated with acid chloride 8 (55 mg, 0.21 mmol) using Method D to give the title compound.
Yield: 50 mg (46%).
LC/MS $t_r$ 1.88 min.
MS (ES+) m/z 644, 642 (M-C(CH$_3$)$_3$+H).

3-Chloro-4,7-difluoro-benzo[b]thiophene-2-carboxylic acid (4'-carbamoyl-4-methoxy-biphenyl-3-ylmethyl)-(4-methylamino-cyclohexyl)-amide hydrochloride (112)

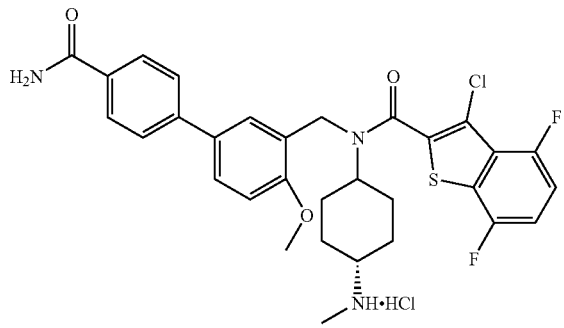

tert-Butyl carbamate 111 (50 mg, 72 µmol) is deprotected using Method F to afford the title compound.
Yield: 40 mg (88%).
LC/MS $t_r$ 1.26 min.
MS (ES+) m/z 600, 598 (M+H), 569, 567 (M-31+H).
Synthesis of Compound 338

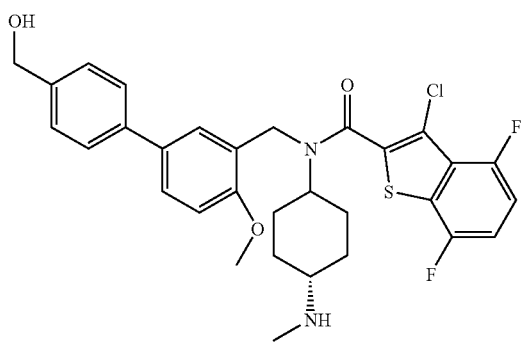

tert-Butyl {4-[(3-chloro-4,7-difluoro-benzo[b]thiophene-2-carbonyl)-(4'-formyl-4-methoxy-biphenyl-3-ylmethyl)-amino]-cyclohexyl}-methyl-carbamate (113)

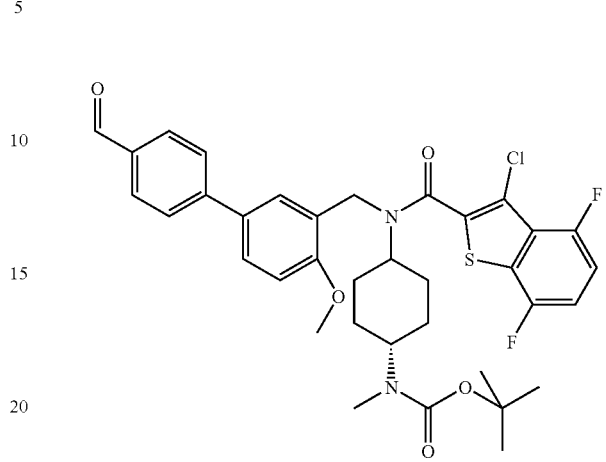

Boronic acid 9 (600 mg, 0.96 mmol) is coupled to 4-bromobenzaldehyde (213 mg, 1.15 mmol) using Method A to give the title compound.
Yield: 338 mg (52%).
LC/MS $t_r$ 1.95 min.
MS (ES+) m/z 685, 683 (M+H), 629, 627 (M-C(CH$_3$)$_3$+H).

3-Chloro-4,7-difluoro-benzo[b]thiophene-2-carboxylic acid (4'-formyl-4-methoxy-biphenyl-3-ylmethyl)-(4-methylamino-cyclohexyl)-amide (114)

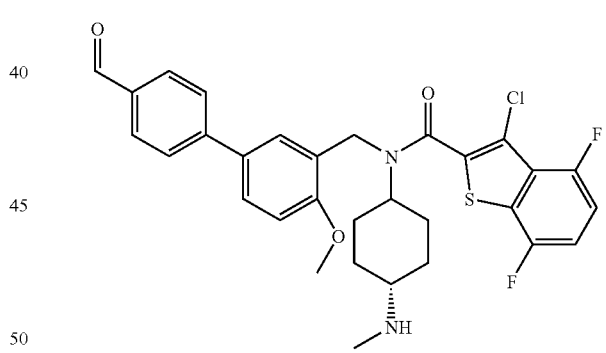

tert-Butyl carbamate 113 (338 mg, 0.49 mmol) is deprotected using Method F. However, the insolubility of the starting material made it difficult to achieve full removal of the BOC-group. After stirring 4 h at RT, further portions of conc. HCl (3 mL), EtOH (18 mL) and DCM (4 mL) are added and the reaction stirred 1 h. 1,4-Dioxane (20 mL) is then added and the reaction stirred another hour. The reaction mixture is then reduced in vacuo and aqueous NaHCO$_3$ (50 mL) added. The aqueous phase is extracted with DCM (3×50 mL) and the combined DCM phases dried (Na$_2$SO$_4$) and reduced in vacuo to give the title compound.
Yield: 315 mg (110%), containing ca. 38% unreacted starting material.
LC/MS $t_r$ 1.44 min.
MS (ES+) m/z 585, 583 (M+H).

3-Chloro-4,7-difluoro-benzo[b]thiophene-2-carboxylic acid (4'-hydroxymethyl-4-methoxy-biphenyl-3-ylmethyl)-(4-methylamino-cyclohexyl)-amide trifluoroacetate (115)

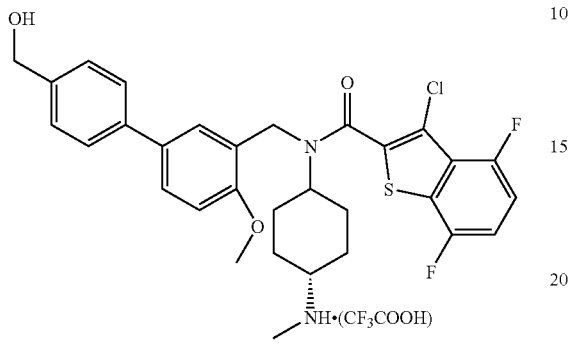

A stirred solution of crude aldehyde 114 (315 mg, ca. 0.49 mmol) in MeOH (10 mL) is treated with sodium borohydride (23 mg, 0.59 mmol) in one portion at 0° C. The reaction mixture is then warmed to RT and stirred 1 h. On reduction in vacuo, the white residue is suspended in water (50 mL) and extracted into DCM (3×25 mL). The combined DCM phases are then dried (Na$_2$SO$_4$) and reduced in vacuo. Purification is then attempted by column chromatography (gradient elution—5-10% MeOH in DCM with 0.5% triethylamine).

The purest fractions from this column are combined, converted to the TFA salt using Method J then dissolved in the minimum amount of DCM and added dropwise to cold (0° C.) TBME (25 mL). The resultant precipitate is isolated by filtration and dried to afford the title compound (46 mg, 16%).

The cruder fractions from the column are combined and further purified by preparative HPLC to give more of the title compound (43 mg, 15%).

LC/MS t$_r$ 1.43 min.

MS (ES+) m/z 587, 585 (M+H).

$^1$H NMR δ$_H$ ppm (400 MHz, D$_6$-DMSO, 95° C.): 8.60 (2H, br. s), 7.70-7.61 (4H, m), 7.54-7.40 (2H, m), 7.53 (2H, d), 7.19 (1H, d), 5.41 (1H, s), 4.82 (2H, s), 4.70 (2H, s), 4.08-3.93 (1H, obsc. m), 3.98 (3H, s), 3.06-2.95 (1H, obsc. m), 2.63 (3H, obsc. s), 2.27-2.18 (2H, m), 2.06-1.89 (4H, m), 1.59-1.46 (2H, m).

Synthesis of Compound 339 (R$^{12}$)

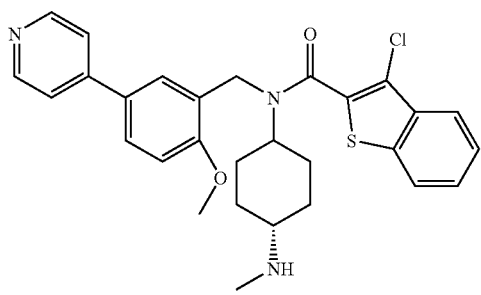

tert-Butyl {4-[(3-Chloro-benzo[b]thiophene-2-carbonyl)-(2-methoxy-5-pyridin-4-yl-benzyl)-amino]-cyclohexyl}-methyl-carbamate (116)

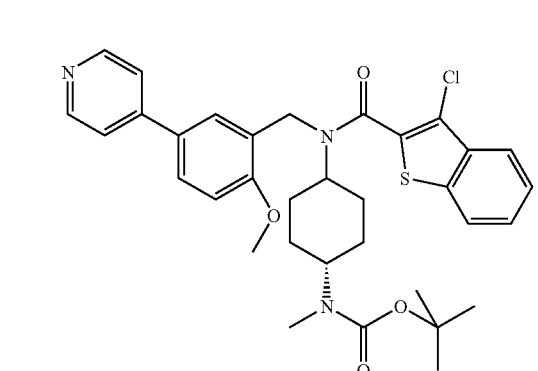

Boronic acid 5 (350 mg, 0.59 mmol) is coupled to 4-bromopyridine hydrochloride (115 mg, 0.59 mmol) using Method B to give the title compound.

Yield: 75 mg (20%).

LC/MS t$_r$ 1.61 min.

MS (ES+) m/z 622, 620 (M+H), 566, 564 (M-C(CH$_3$)$_3$+H).

3-Chloro-benzo[b]thiophene-2-carboxylic acid (2-methoxy-5-pyridin-4-yl-benzyl)-(4-methylamino-cyclohexyl)-amide dihydrochloride (117)

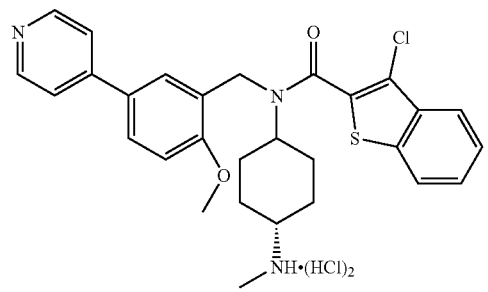

tert-Butyl carbamate 116 (75 mg, 0.12 mmol) is deprotected using Method E. On removal of the solvent in vacuo, the residue obtained is dissolved in water (5 mL) and washed with TBME (3×5 mL). Reduction of the aqueous phase in vacuo affords the title product.

Yield: 55 mg (87%).

LC/MS t$_r$ 1.07 min.

MS (ES+) m/z 522, 520 (M+H).

221

Synthesis of Compound 340

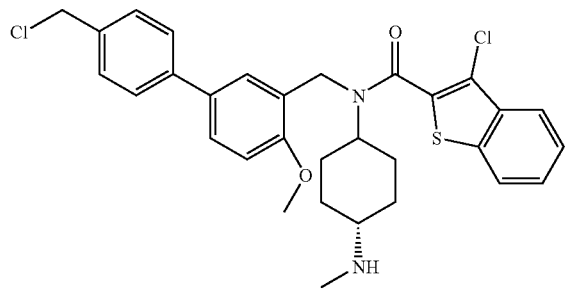

3-Chloro-benzo[b]thiophene-2-carboxylic acid (4'-chloromethyl-4-methoxy-biphenyl-3-ylmethyl)-(4-methylamino-cyclohexyl)-amide hydrochloride (118)

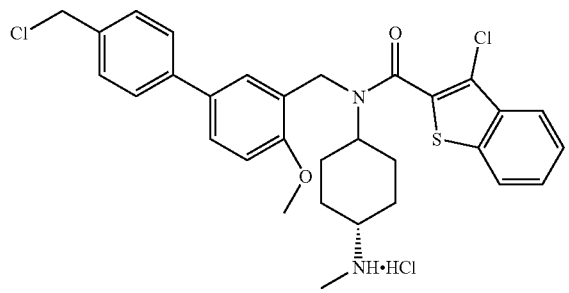

tert-Butyl carbamate 84 (10 mg, 15 μmol) is treated with HCl using Method F to afford the title compound.
Yield: 5 mg (55%).
LC/MS $t_r$ 1.50 min.
MS (ES+) m/z 571, 569, 567 (M+H).

Synthesis of Compound 341

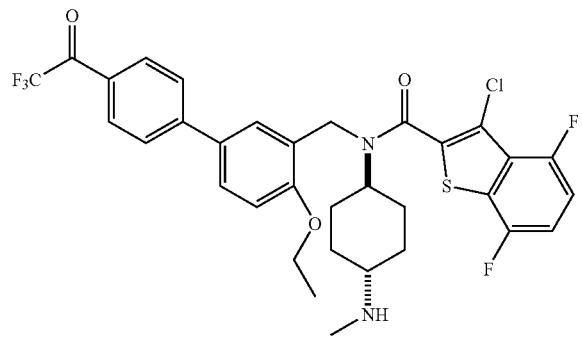

222 tert-Butyl (4-{[4-ethoxy-4'-(2,2,2-trifluoro-1,1-dihydroxy-ethyl)-biphenyl-3-ylmethyl]-amino}-cyclohexyl)-methyl-carbamate (119)

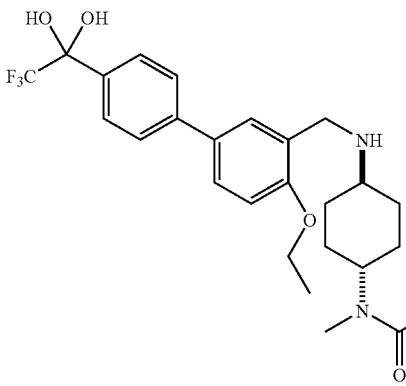

Boronic acid 11 (609 mg, 1.50 mmol) is coupled to 1-(4-bromophenyl)-2,2,2-trifluoroethanone (379 mg, 1.50 mmol) using Method B in two equal batches to give the title compound.
Yield: 487 mg (59%).

tert-Butyl (4-{(3-chloro-4,7-difluoro-benzo[b]thiophene-2-carbonyl)-[4-ethoxy-4'-(2,2,2-trifluoroacetyl)-biphenyl-3-ylmethyl]-amino}-cyclohexyl)-methyl-carbamate (120)

Biaryl amine 119 (487 mg, 0.88 mmol) is treated with acid chloride 8 (235 mg, 0.88 mmol) using Method D to give the title compound.
Yield: 248 mg (36%).
LC/MS $t_r$ 2.15 min. The hydrate appears at 1.92 min.
MS (ES+) m/z 785, 783 (M+H$_2$O+H), 767, 765 (M+H), 729, 727 (M-C(CH$_3$)$_3$+H$_2$O+H), 711, 709 (M-C(CH$_3$)$_3$+H).

3-Chloro-4,7-difluoro-benzo[b]thiophene-2-carboxylic acid [4-ethoxy-4'-(2,2,2-trifluoro-acetyl)-biphenyl-3-ylmethyl]-(4-methylamino-cyclohexyl)-amide trifluoroacetate (121)

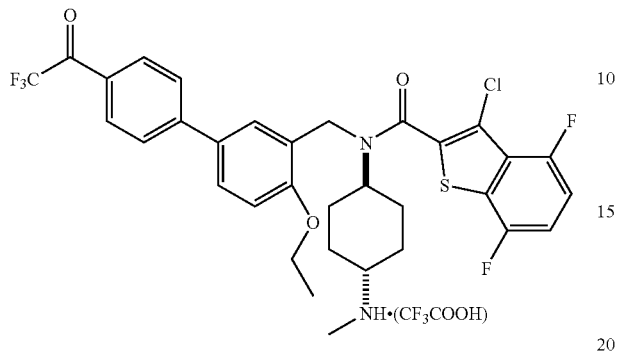

tert-Butyl carbamate 120 (248 mg, 0.32 mmol) is deprotected using Method F then purified by column chromatography (20% MeOH in EtOAc with 0.25% conc. ammonia) followed by preparative HPLC to afford the title compound.
Yield: 113 mg (45%).
LC/MS $t_r$ 1.74 min. The hydrate appears at 1.46 min.
MS (ES+) m/z 685, 683 (M+H$_2$O+H), 667, 665 (M+H), 654, 652 (M-31+H$_2$O+H), 636, 634 (M-31+H).
Synthesis of Compound 342

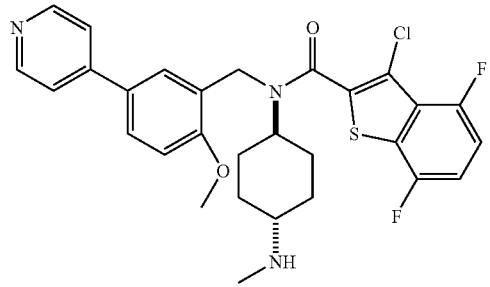

tert-Butyl {4-[(3-chloro-4,7-difluoro-benzo[b]thiophene-2-carbonyl)-(2-methoxy-5-pyridin-4-yl-benzyl)-amino]-cyclohexyl}-methyl-carbamate (122)

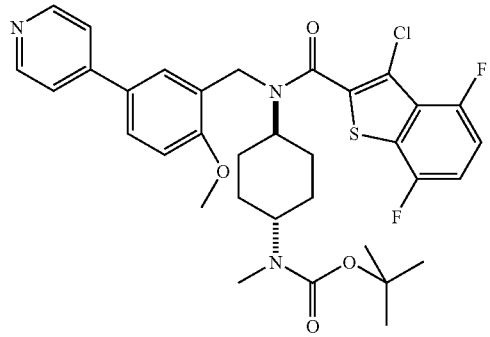

Boronic acid 9 (5.70 g, 9.14 mmol) is coupled to 4-bromopyridine hydrochloride (2.13 g, 11.0 mmol) using Method A to give the title compound.

Yield: 5.71 g (95%). Contains triphenylphosphine oxide (ca. 29%).
LC/MS $t_r$ 1.59 min.
MS (ES+) m/z 658, 656 (M+H).

3-Chloro-4,7-difluoro-benzo[b]thiophene-2-carboxylic acid (2-methoxy-5-pyridin-4-yl-benzyl)-(4-methylamino-cyclohexyl)-amide dihydrochloride (123)

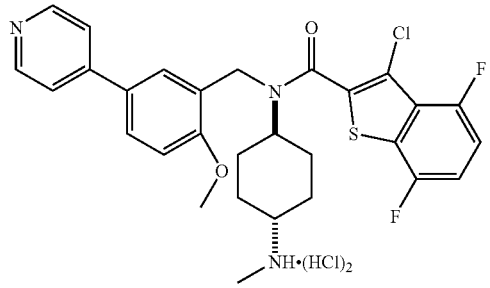

tert-Butyl carbamate 122 (5.71 g, 8.70 mmol) is deprotected using Method F. On removal of the solvents in vacuo, the reaction mixture is dissolved in DCM (250 mL) and extracted into 2 M HCl (4×50 mL). The combined HCl phases are washed with DCM (2×50 mL) then taken to pH 9 by careful addition of solid NaHCO$_3$. The resultant aqueous suspension is then extracted into DCM (3×100 mL), the combined DCM phases dried (Na$_2$SO$_4$) and reduced in vacuo. This residue is purified by chromatography (gradient elution—5-10% MeOH in DCM with 0.5% triethylamine) then converted to the title compound by Method H.
Yield: 4.0 g (78%).
LC/MS $t_r$ 1.08 min.
MS (ES+) m/z 558, 556 (M+H), 279, 278 [(M+H)/2].
$^1$H NMR $\delta_H$ ppm (400 MHz, D$_6$-DMSO, 95° C.): 8.92 (2H, br. s), 8.61 (2H, d), 7.85 (2H, d), 7.72 (1H, d), 7.60 (1H, s), 7.26-7.12 (2H, m), 7.04 (1H, d), 4.55 (2H, s), 3.82-3.68 (1H, obsc. m), 3.75 (3H, s), 2.74 (1H, br. s), 2.29 (3H, s), 2.02-1.92 (2H, m), 1.80-1.58 (4H, m), 1.36-1.16 (2H, m).
Synthesis of Compound 343 (R15)

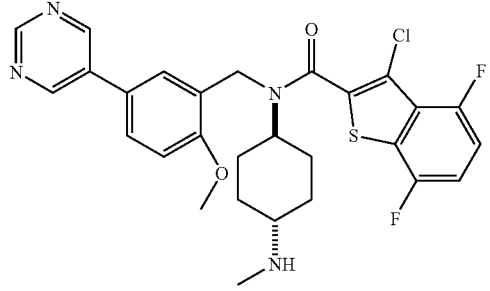

225 tert-Butyl {4-[(3-chloro-4,7-difluoro-benzo[b]thiophene-2-carbonyl)-(2-methoxy-5-pyrimidin-5-yl-benzyl)-amino]-cyclohexyl}-methyl-carbamate (124)

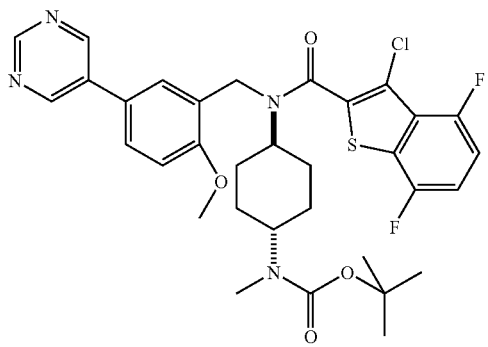

Boronic acid 9 (275 mg, 0.44 mmol) is coupled to 5-bromopyrimidine (79 mg, 0.48 mmol) using Method B to give the title compound.

Yield: 178 mg (61%).
LC/MS $t_r$ 1.73 min.
MS (ES+) m/z 559, 557 (M-O$_2$C(CH$_3$)$_3$+H).

3-Chloro-4,7-difluoro-benzo[b]thiophene-2-carboxylic acid (2-methoxy-5-pyrimidin-5-yl-benzyl)-(4-methylamino-cyclohexyl)-amide dihydrochloride (125)

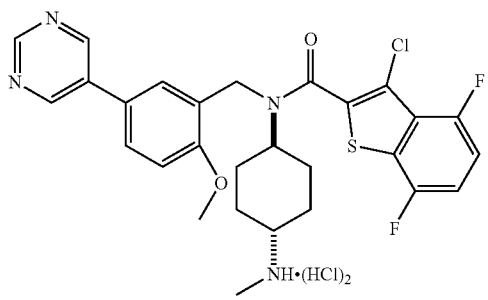

tert-Butyl carbamate 124 (178 mg, 0.27 mmol) is deprotected using Method E to give the title compound.

Yield: 146 mg (86%).
LC/MS $t_r$ 1.23 min.
MS (ES+) m/z 559, 557 (M+H).

226

Synthesis of Compound 344 (R14)

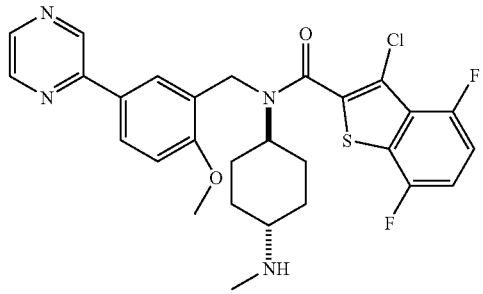

tert-Butyl {4-[(3-chloro-4,7-difluoro-benzo[b]thiophene-2-carbonyl)-(2-methoxy-5-pyrazin-2-yl-benzyl)-amino]-cyclohexyl}-methyl-carbamate (126)

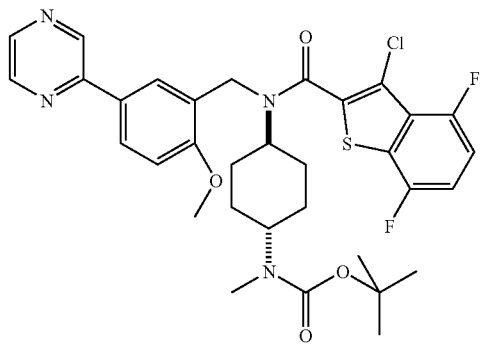

Boronic acid 9 (201 mg, 0.32 mmol) is coupled to 2-chloropyrazine (50 µL, 0.35 mmol) using Method B to give the title compound.

Yield: 129 mg (61%).
LC/MS $t_r$ 1.86 min.
MS (ES+) m/z 659, 657 (M+H), 603, 601 (M-C(CH$_3$)$_3$+H).

3-Chloro-4,7-difluoro-benzo[b]thiophene-2-carboxylic acid (2-methoxy-5-pyrazin-2-yl-benzyl)-(4-methylamino-cyclohexyl)-amide dihydrochloride (127)

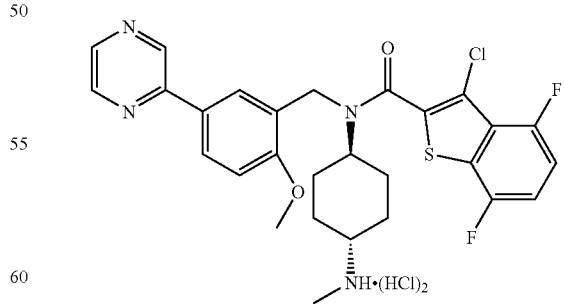

tert-Butyl carbamate 126 (129 mg, 0.19 mmol) is deprotected using Method F. Purification by column chromatography (20% MeOH in EtOAc with 2% triethylamine) followed by formation of the HCl salt by Method H gives the title compound.

Yield: 50 mg (42%).
LC/MS $t_r$ 1.30 min.
MS (ES+) m/z 559, 557 (M+H).

Synthesis of Compound 345

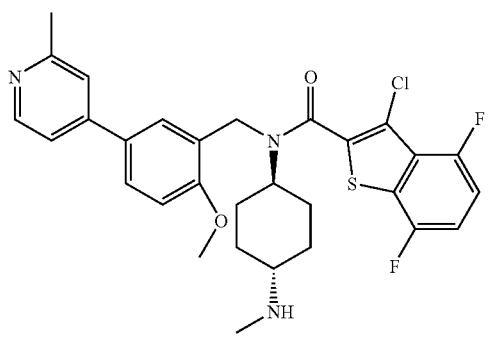

tert-Butyl (4-{(3-chloro-4,7-difluoro-benzo[b]thiophene-2-carbonyl)-[2-methoxy-5-(2-methyl-pyridin-4-yl)-benzyl]-amino}-cyclohexyl)-methyl-carbamate (128)

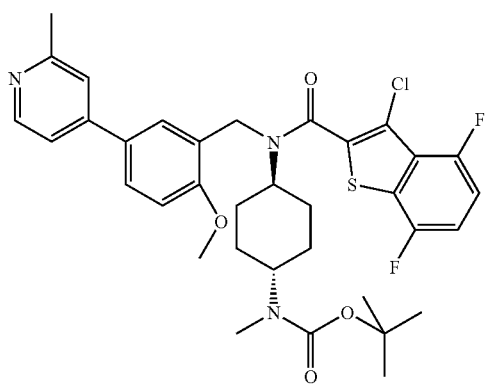

Crude biaryl amine 88 (1.96 g, 4.45 mmol) is treated with acid chloride 8 (1.43 g, 5.35 mmol) using Method D to give the title compound.
Yield: 784 mg (26%).
LC/MS $t_r$ 1.62 min.
MS (ES+) m/z 672, 670 (M+H).

3-Chloro-4,7-difluoro-benzo[b]thiophene-2-carboxylic acid [2-methoxy-5-(2-methyl-pyridin-4-yl)-benzyl]-(4-methylamino-cyclohexyl)-amide dihydrochloride (129)

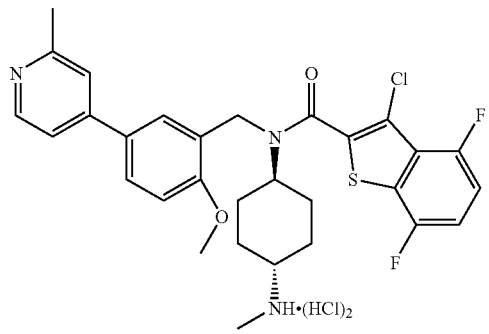

tert-Butyl carbamate 128 (784 mg, 1.17 mmol) is deprotected using Method F. On removal of the solvents in vacuo, the residue is dissolved in water (50 mL) and washed with EtOAc (3×25 mL). The aqueous phase is then reduced in vacuo to afford the title compound.
Yield: 694 mg (92%).
LC/MS $t_r$ 1.14 min.
MS (ES+) m/z 572, 570 (M+H).

Synthesis of Compound 346

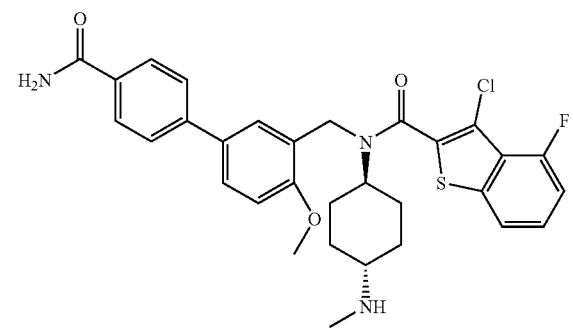

tert-Butyl {4-[(4'-carbamoyl-4-methoxy-biphenyl-3-ylmethyl)-(3-chloro-4-fluoro-benzo[b]thiophene-2-carbonyl)-amino]-cyclohexyl}-methyl-carbamate (130)

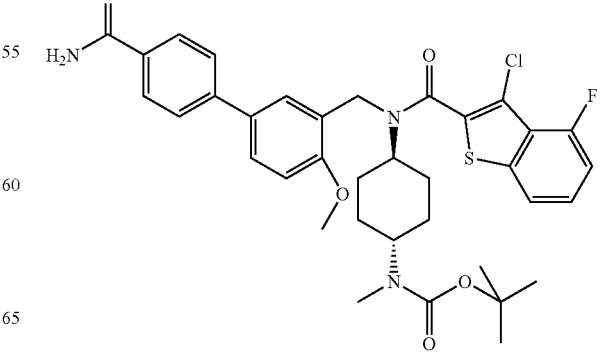

Biaryl amine 55 (216 mg, 0.46 mmol) is treated with acid chloride 6 (137 mg, 0.55 mmol) using Method D to give the title compound.

Yield: 105 mg (34%).
LC/MS $t_r$ 1.72 min.
MS (ES+) m/z 626, 624 (M-C(CH$_3$)$_3$+H), 582, 580 (M-CO$_2$C(CH$_3$)$_3$+H).

3-Chloro-4-fluoro-benzo[b]thiophene-2-carboxylic acid (4'-carbamoyl-4-methoxy-biphenyl-3-ylmethyl)-(4-methylamino-cyclohexyl)-amide hydrochloride (131)

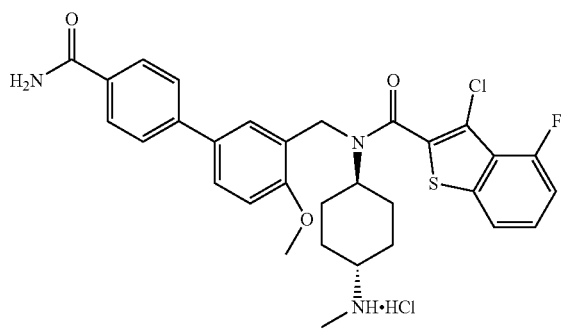

tert-Butyl carbamate 130 (105 mg, 0.15 mmol) is deprotected using Method F to give the title compound.

Yield: 49 mg (55%).
LC/MS $t_r$ 1.21 min.
MS (ES+) m/z 582, 580 (M+H), 551, 549 (M-31+H).
Synthesis of Compound 347

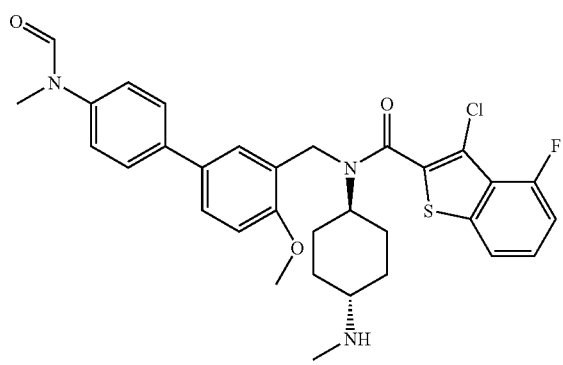

tert-Butyl (4-{(3-chloro-4-fluoro-benzo[b]thiophene-2-carbonyl)-[4'-(formyl-methyl-amino)-4-methoxy-biphenyl-3-ylmethyl]-amino}-cyclohexyl)-methyl-carbamate (132)

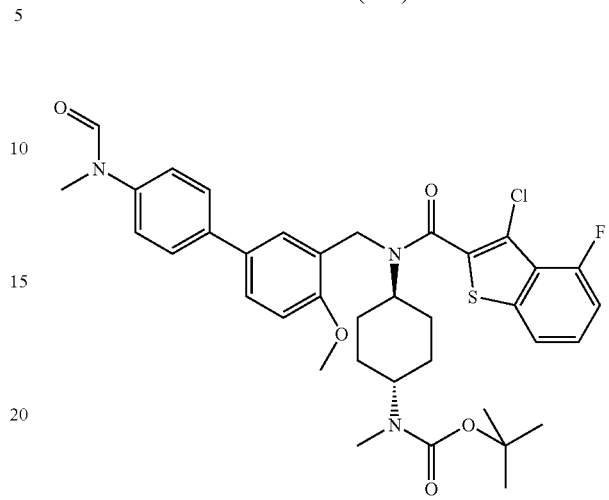

Biaryl amine 52 (200 mg, 0.42 mmol) is treated with acid chloride 6 (120 mg, 0.49 mmol) using Method D to afford the title compound.

Yield: 190 mg (66%).
LC/MS $t_r$ 1.88 min.
MS (ES+) m/z 640, 638 (M-C(CH$_3$)$_3$+H).

3-Chloro-4-fluoro-benzo[b]thiophene-2-carboxylic acid [4'-(formyl-methyl-amino)-4-methoxy-biphenyl-3-ylmethyl]-(4-methylamino-cyclohexyl)-amide trifluoroacetate (133)

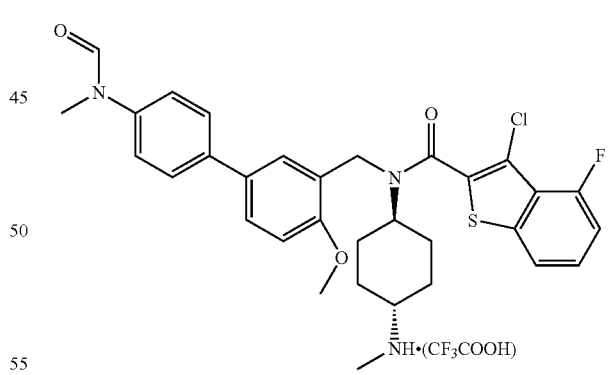

tert-Butyl carbamate 132 (190 mg, 0.27 mmol) is deprotected using Method G. The reaction mixture is then diluted with water (10 mL) and the DCM removed in vacuo to give a precipitate in the water layer. Acetonitrile (5 mL) is added to dissolve the solid and the resulting solution is lyophilised to give the title compound.

Yield: 180 mg (quant.).
LC/MS $t_r$ 1.36 min.
MS (ES+) m/z 596, 594 (M+H).

231

Synthesis of Compound 348

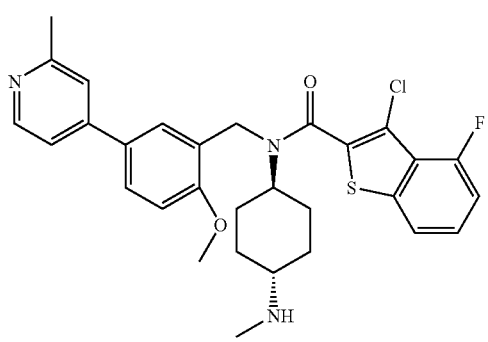

tert-Butyl (4-{(3-chloro-4-fluoro-benzo[b]thiophene-2-carbonyl)-[2-methoxy-5-(2-methyl-pyridin-4-yl)-benzyl]-amino}-cyclohexyl)-methyl-carbamate (134)

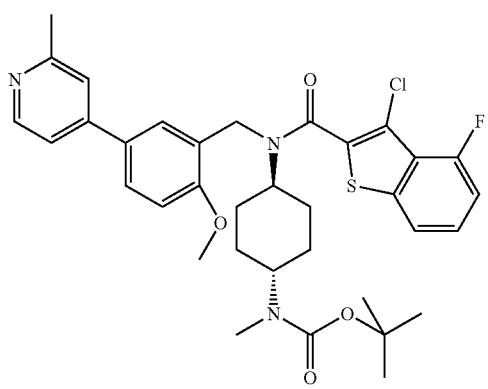

Biaryl amine 88 (160 mg, 0.36 mmol) is treated with acid chloride 6 (99 mg, 0.40 mmol) using Method D to give the title compound.
Yield: 140 mg (61%).
LC/MS $t_r$ 1.59 min.
MS (ES+) m/z 654, 652 (M+H).

232

3-Chloro-4-fluoro-benzo[b]thiophene-2-carboxylic acid [2-methoxy-5-(2-methyl-pyridin-4-yl)-benzyl]-(4-methylamino-cyclohexyl)-amide bis(trifluoroacetate) (135)

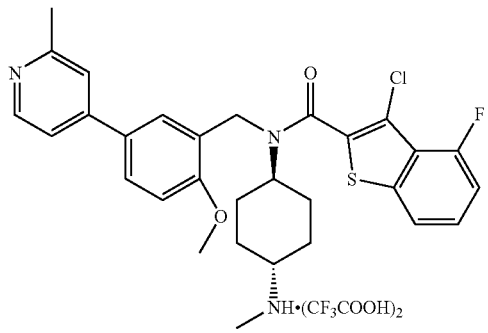

tert-Butyl carbamate 134 (140 mg, 0.22 mmol) is deprotected using Method G to give the title compound.
Yield: 167 mg (quant.).
LC/MS $t_r$ 1.12 min.
MS (ES+) m/z 554, 552 (M+H).

Synthesis of Compound 349

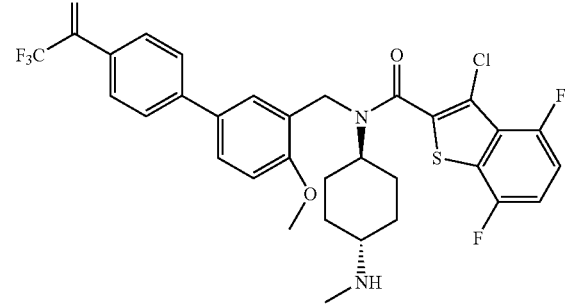

tert-Butyl (4-{(3-chloro-4,7-difluoro-benzo[b]thiophene-2-carbonyl)-[4-methoxy-4'-(2,2,2-trifluoro-acetyl)-biphenyl-3-ylmethyl]-amino}-cyclohexyl)-methyl-carbamate (136)

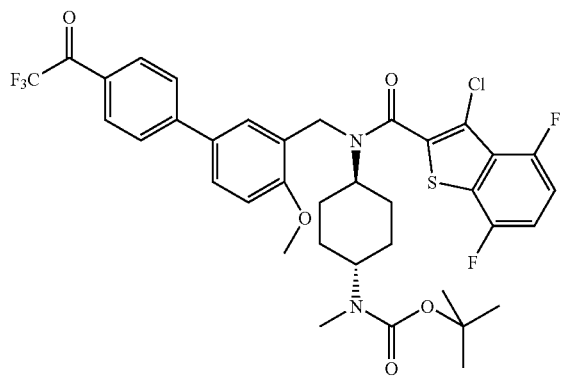

Boronic acid 9 (250 mg, 0.40 mmol) is coupled to 4'-bromo-2,2,2-trifluoroacetophenone (120 mg, 0.48 mmol) using Method B to give the title compound.

Yield: 230 mg (76%).
LC/MS $t_r$ 1.88 min.
MS (ES+) m/z 771, 769 (M+H$_2$O+H), 697, 695 (M-C(CH$_3$)$_3$+H).

3-Chloro-4,7-difluoro-benzo[b]thiophene-2-carboxylic acid [4-methoxy-4'-(2,2,2-trifluoro-acetyl)-biphenyl-3-ylmethyl]-(4-methylamino-cyclohexyl)-amide trifluoroacetate (137)

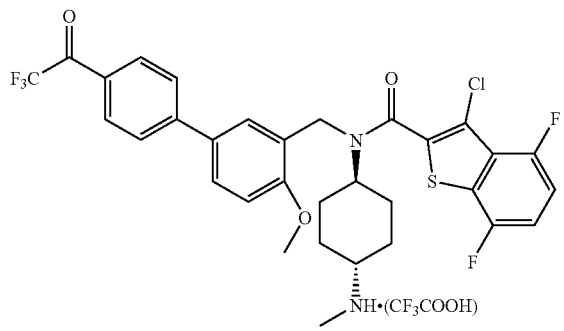

tert-Butyl carbamate 136 (170 mg, 0.23 mmol) is deprotected using Method E. Purification by preparative HPLC then gives the title compound as the TFA salt.

Yield: 92 mg (62%).
LC/MS $t_r$ 1.39 min.
MS (ES+) m/z 671, 669 (M+H$_2$O+H), 653, 651 (M+H).

Synthesis of Compound 350

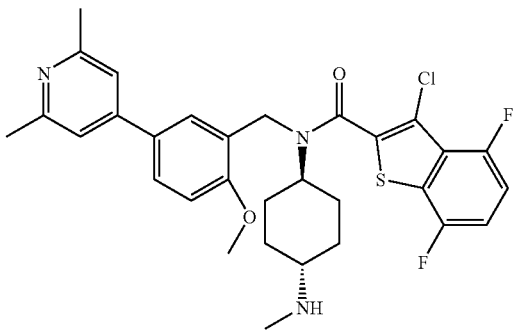

tert-Butyl (4-{(3-chloro-4,7-difluoro-benzo[b]thiophene-2-carbonyl)-[5-(2,6-dimethyl-pyridin-4-yl)-2-methoxy-benzyl]-amino}-cyclohexyl)-methyl-carbamate (138)

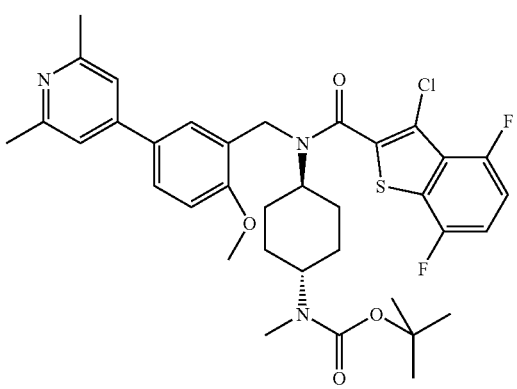

Biaryl amine 92 (268 mg, 0.59 mmol) is treated with acid chloride 8 (205 mg, 0.77 mmol) using Method D to afford the title compound.

Yield: 101 mg (25%).
LC/MS $t_r$ 1.68 min.
MS (ES+) m/z 686, 684 (M+H).

3-Chloro-4,7-difluoro-benzo[b]thiophene-2-carboxylic acid [5-(2,6-dimethyl-pyridin-4-yl)-2-methoxy-benzyl]-(4-methylamino-cyclohexyl)-amide dihydrochloride (139)

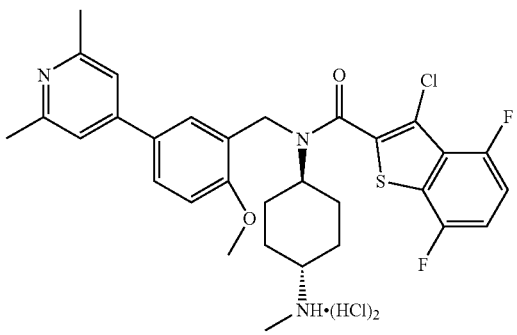

tert-Butyl carbamate 138 (101 mg, 0.15 mmol) is deprotected using Method F to give the title compound.

Yield: 63 mg (73%).

LC/MS $t_r$ 1.12 min.

MS (ES+) m/z 586, 584 (M+H).

Synthesis of Compound 351

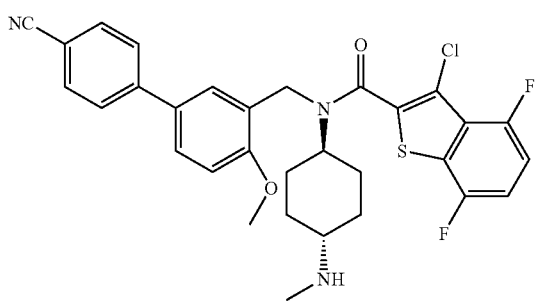

tert-Butyl {4-[(3-chloro-4,7-difluoro-benzo[b]thiophene-2-carbonyl)-(4'-cyano-4-methoxy-biphenyl-3-ylmethyl)-amino]-cyclohexyl}-methyl-carbamate (140)

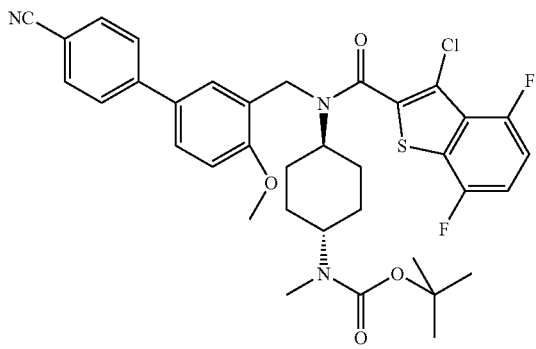

Biaryl amine 13 (300 mg, 0.70 mmol) is treated with acid chloride 8 (214 mg, 0.80 mmol) using Method D to afford the title compound.

Yield: 355 mg (75%).

LC/MS $t_r$ 1.94 min.

MS (ES+) nm/z 626, 624 (M-C(CH$_3$)$_3$+H).

3-Chloro-4,7-difluoro-benzo[b]thiophene-2-carboxylic acid (4'-cyano-4-methoxy-biphenyl-3-ylmethyl)-(4-methylamino-cyclohexyl)-amide hydrochloride (141)

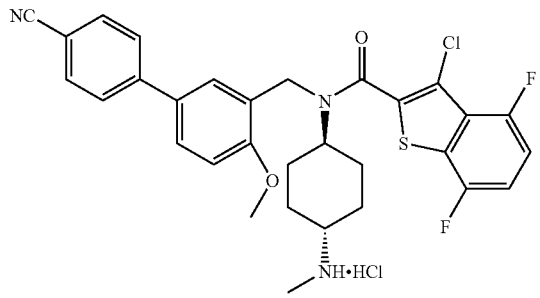

tert-Butyl carbamate 140 (350 mg, 0.50 mmol) is deprotected using Method F to give the title compound.

Yield: 308 mg (quant.).

LC/MS (10 min) $t_r$ 5.79 min.

MS (ES+) m/z 623, 621 (M+CH$_3$CN+H), 582, 580 (M+H).

Synthesis of Compound 352 (R18)

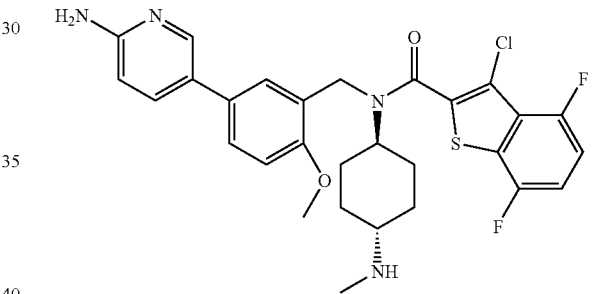

tert-Butyl {4-[5-(6-amino-pyridin-3-yl)-2-methoxy-benzylamino]-cyclohexyl}-methyl-carbamate (142)

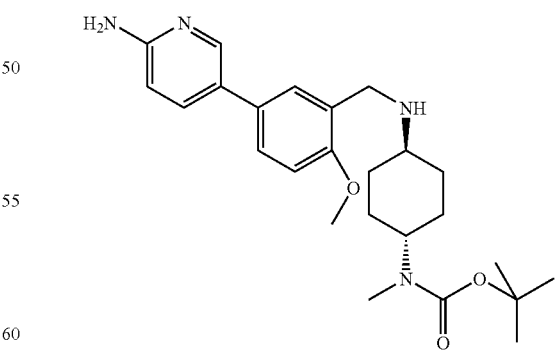

Boronic acid 4 (900 mg, 2.29 mmol) is coupled to 2-amino-5-bromopyridine (475 mg, 2.74 mmol) using Method A. On completion, the cooled reaction mixture is diluted with 1 M HCl (10 mL) and extracted with TBME (3×10 mL). The aqueous phase is then basified to pH 9 by careful addition of solid NaHCO₃ and extracted into EtOAc (50 mL) and DCM (3×50 mL). The combined organic phases are dried over Na₂SO₄ and reduced in vacuo to yield the crude title product.
Yield: 470 mg (47%).

tert-Butyl {4-[[5-(6-amino-pyridin-3-yl)-2-methoxy-benzyl]-(3-chloro-4,7-difluoro-benzo[b]thiophene-2-carbonyl)-amino]-cyclohexyl}-methyl-carbamate (143)

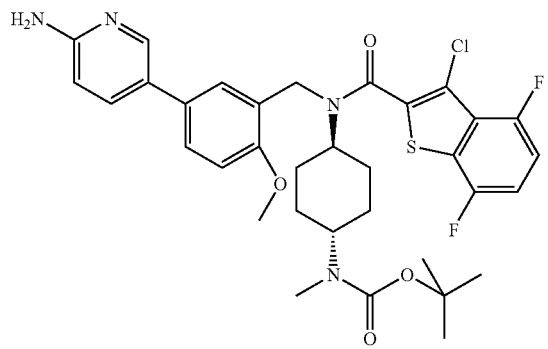

Crude biaryl amine 142 (300 mg, 0.68 mmol) is treated with acid chloride 8 (182 mg, 0.68 mmol) using Method D to give the title compound.
Yield: 120 mg (26%).

3-Chloro-4,7-difluoro-benzo[b]thiophene-2-carboxylic acid [5-(6-amino-pyridin-3-yl)-2-methoxy-benzyl]-(4-methylamino-cyclohexyl)-amide dihydrochloride (144)

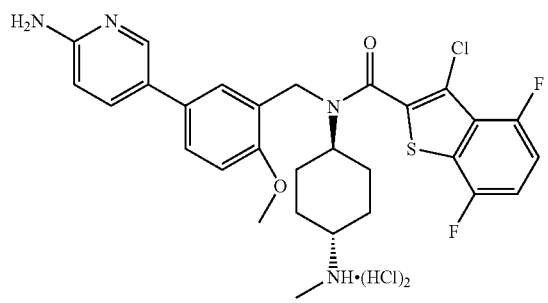

tert-Butyl carbamate 143 (120 mg, 0.18 mmol) is deprotected using Method F. On removal of the solvents in vacuo, the residue is dissolved in water (15 mL) and washed with TBME (3×10 mL). Reduction of the aqueous phase in vacuo affords the title product.
Yield: 72 mg (62%).
LC/MS t, 1.16 min.
MS (ES+) m/z 573, 571 (M+H).

Synthesis of Compound 353

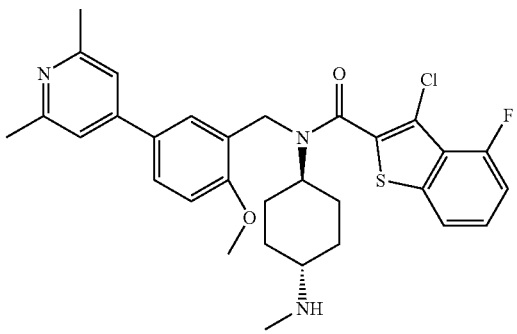

tert-Butyl (4-{(3-chloro-4-fluoro-benzo[b]thiophene-2-carbonyl)-[5-(2,6-dimethyl-pyridin-4-yl)-2-methoxy-benzyl]-amino}-cyclohexyl)-methyl-carbamate (145)

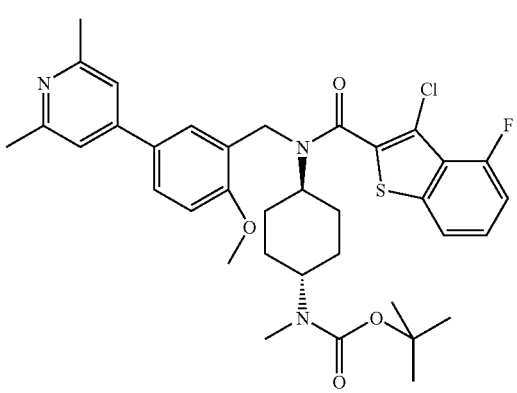

Biaryl amine 92 (62 mg, 0.14 mmol) is treated with acid chloride 6 (51 mg, 0.21 mmol) using Method D to afford the title compound.
Yield: 30 mg (33%).
LC/MS t, 1.58 min.
MS (ES+) m/z 668, 666 (M+H).

3-Chloro-4-fluoro-benzo[b]thiophene-2-carboxylic acid [5-(2,6-dimethyl-pyridin-4-yl)-2-methoxy-benzyl]-(4-methylamino-cyclohexyl)-amide dihydrochloride (146)

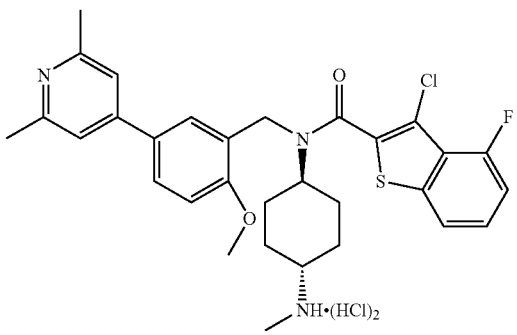

tert-Butyl carbamate 145 (10 mg, 0.02 mmol) is deprotected using Method F to give the title compound.
Yield: 10 mg (quant.).
LC/MS t$_r$ 1.08 min.
MS (ES+) m/z 558, 556 (M+H).

Synthesis of Compound R5

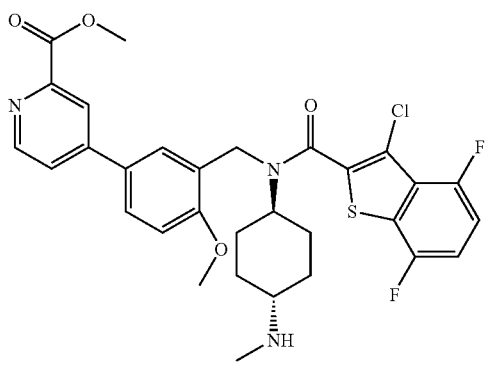

Methyl 4-bromopyridine-2-carboxylate (147)

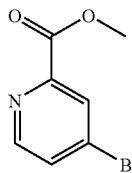

A solution of 4-bromopyridine hydrochloride (595 mg, 3.06 mmol) in DCM (20 mL) is washed with aqueous NaHCO$_3$ (2×20 mL), dried (MgSO$_4$) and filtered. The filtrate is made up to 45 mL by the addition of more DCM, then water (3 mL) is added, followed by iron(II) sulphate heptahydrate (8.51 g, 30.6 mmol) and conc. H$_2$SO$_4$ (0.95 mL, 9.18 mmol). In a separate flask, methyl pyruvate (4.15 mL, 46 mmol) is treated with hydrogen peroxide (3.5 mL, 30.6 mmol, 30% solution in water) at −10° C., then this solution is added to the DCM/water mixture at −10° C. with vigorous stirring. After 15 minutes, the reaction is diluted with iced water (100 mL) and extracted into DCM (4×20 mL). The combined DCM phases are dried (MgSO$_4$) and removed in vacuo. The title compound is obtained after sequential column chromatography (gradient elution—10-40% EtOAc in heptane with 0.5% triethylamine, then repeating with 0-20% EtOAc in heptane with 0.5% triethylamine).
Yield: 211 mg (32%).
LC/MS t$_r$ 0.98 min.
MS (ES+) m/z 218, 216 (M+H).

Methyl 4-(3-{[[4-(tert-butoxycarbonyl-methyl-amino)-cyclohexyl]-(3-chloro-4,7-difluoro-benzo[b]thiophene-2-carbonyl)-amino]-methyl}-4-methoxy-phenyl)-pyridine-2-carboxylate (148)

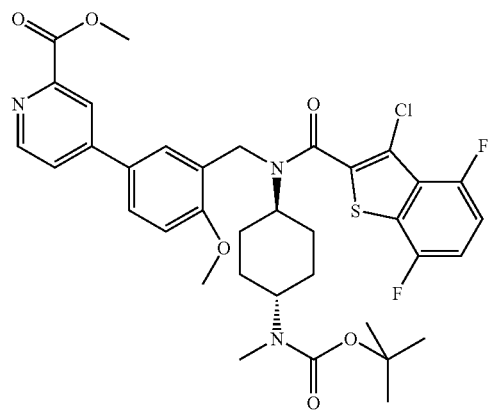

Boronic acid 9 (748 mg, 1.20 mmol) is coupled to pyridyl bromide 147 (258 mg, 1.20 mmol) using Method A. However, the reaction temperature is lowered to 87° C. to avoid hydrolysis of the methyl ester. In addition, EtOH is replaced by MeOH and is used in a 1:30 ratio to toluene.
Yield: 247 mg (29%), containing ca. 37% triphenylphosphine oxide.
LC/MS t$_r$ 1.77 min.
MS (ES+) nm/z 716, 714 (M+H).

Methyl 4-(3-{[(3-chloro-4,7-difluoro-benzo[b]thiophene-2-carbonyl)-(4-methylamino-cyclohexyl)-amino]-methyl}-4-methoxy-phenyl)-pyridine-2-carboxylate (149)

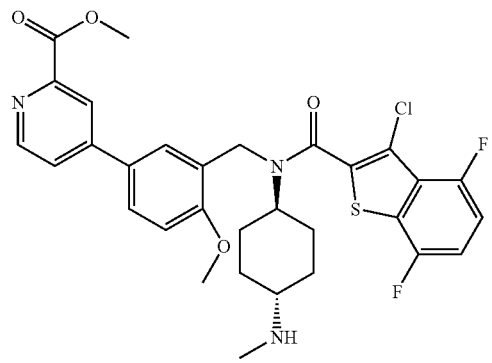

Acetyl chloride (5 mL) is added to anhydrous MeOH (10 mL) at 0° C. tert-Butyl carbamate 148 (247 mg, 0.35 mmol) is then treated with this solution and stirred 2 h. On removal of the solvents in vacuo, the reaction mixture is dissolved in DCM (25 mL) and extracted into 2 M HCl (4×10 mL). The combined HCl phases are washed with DCM (2×20 mL) then taken to pH 9 by careful addition of solid NaHCO$_3$. The resultant aqueous suspension is then extracted into DCM (3×20 mL), the combined DCM phases dried (Na$_2$SO$_4$) and reduced in vacuo to afford the title compound.

Yield: 110 mg (51%).
LC/MS $t_r$ 1.29 min.
MS (ES+) m/z 616, 614 (M+H).

Synthesis of Compound 354 (R17)

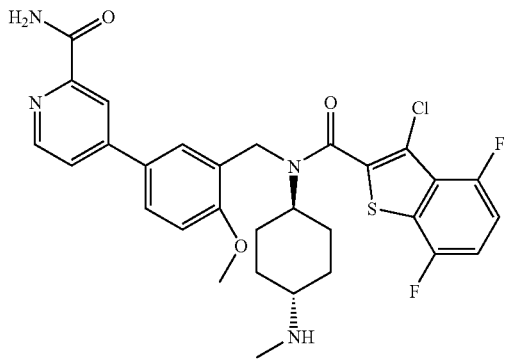

tert-Butyl {4-[[5-(2-carbamoyl-pyridin-4-yl)-2-methoxy-benzyl]-(3-chloro-4,7-difluoro-benzo[b]thiophene-2-carbonyl)-amino]-cyclohexyl}-methyl-carbamate (150)

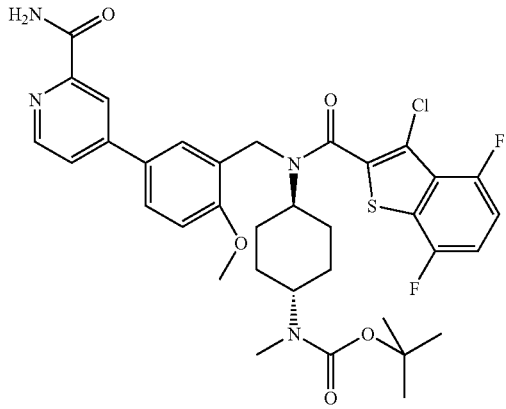

A solution of methyl ester 148 (50 mg, 0.07 mmol) in 1,4-dioxane (2 mL) is treated with conc. ammonia (1 mL) and the reaction stirred at RT 6 h. LC/MS at this juncture showed some residual starting material so more conc. ammonia (1 mL) is added and the reaction mixture heated 2 h at 40° C. LC/MS at this juncture showed the reaction is complete. The solvents are removed in vacuo to give the title compound.

Yield: 45 mg (93%).
LC/MS $t_r$ 1.74 min.
MS (ES+) m/z 701, 699 (M+H), 645, 643 (M-C(CH$_3$)$_3$+H).

4-(3-{[(3-Chloro-4,7-difluoro-benzo[b]thiophene-2-carbonyl)-(4-methylamino-cyclohexyl)-amino]-methyl}-4-methoxy-phenyl)-pyridine-2-carboxylic acid amide dihydrochloride (151)

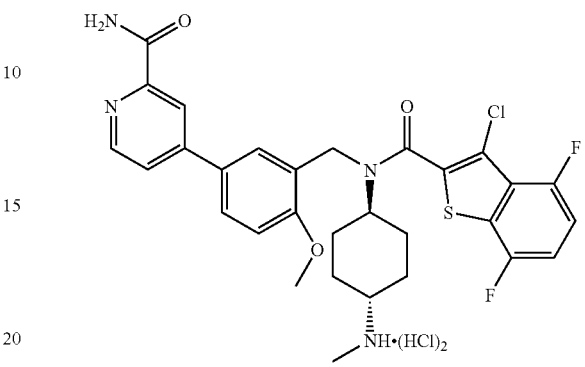

tert-Butyl carbamate 150 (45 mg, 0.06 mmol) is deprotected using Method F. Purification by column chromatography followed by formation of the HCl salt by Method H gives the title compound.

Yield: 27 mg (70%).
LC/MS $t_r$ 1.23 min.
MS (ES+) m/z 601, 599 (M+H).

Synthesis of Compound 355

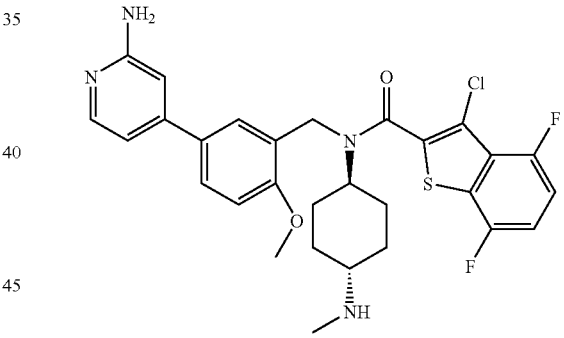

4-Amino-2-methylpyridine (152)

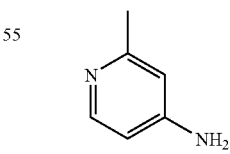

A stirred solution of 4-nitro-2-methylpyridine-N-oxide (20 g, 0.13 mol) in AcOH (300 mL) is treated with iron powder (40 g, 0.72 mol) in one portion at RT. This grey suspension is then gently heated to 100° C. and stirred 2 h. The reaction mixture is then filtered through celite, and the solids collected washed with acetonitrile (1 L). The dark brown filtrate is then reduced in vacuo, diluted with 6 M NaOH (500 mL) and extracted into TBME (4×200 mL). The TBME phases are combined, dried (MgSO$_4$) and reduced in vacuo to afford the title compound.

Yield: 10.1 g (72%).

LC/MS t$_r$ 0.52 min.

MS (ES+) m/z 216 (2M+H).

4-Bromo-2-methylpyridine (153)

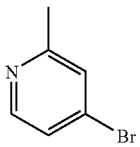

A stirred solution of amino-pyridine 152 (10.1 g, 93.4 mmol) in 48% aqueous HBr (165 mL) at −10° C. is treated with a pre-cooled (0° C.) solution of sodium nitrite (7.04 g, 0.102 mol) in water (165 mL) dropwise over 0.5 h. The solution is then warmed to RT and stirred 16 h. It is then diluted with 4 M NaOH (400 mL) and extracted into TBME (4×150 mL). The TBME phases are combined, dried (MgSO$_4$) and reduced in vacuo to afford the title compound.

Yield: 14.8 g (92%).

LC/MS t$_r$ 0.57 min.

MS (ES+) m/z 174, 172 (M+H).

4-Bromopyridine-2-carboxylic acid (154)

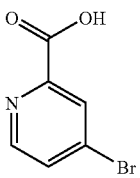

A stirred solution of pyridyl bromide 153 (5.03 g, 29.0 mmol) in water (130 mL) is treated at RT with KMnO$_4$ (4.72 g, 29.5 mmol) in one portion then heated to reflux 1.5 h. At this juncture more KMnO$_4$ is added (4.72 g, 29.5 mmol) and the solution heated at reflux a further 2 h. Another portion of KMnO$_4$ is then added (9.43 g, 59 mmol), the reaction heated at reflux a further 3 h then filtered whilst still hot, washing the isolated solids with boiling water (200 mL). The aqueous filtrate is then concentrated in vacuo to approximately 40 mL, acidified to pH 4 by careful addition of 1 M HCl and the resultant white precipitate isolated by filtration. The filtrate is then reduced in vacuo to approximately 10 mL and the forthcoming precipitate also isolated by filtration. Combining these two isolated precipitates gives the title compound.

Yield: 1.28 g (22%).

LC/MS t$_r$ 0.67 min.

MS (ES+) m/z 204, 202 (M+H).

tert-Butyl (4-bromo-pyridin-2-yl)-carbamate (155)

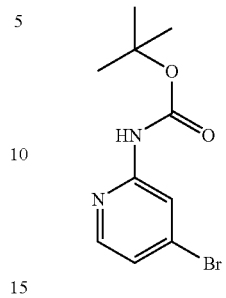

This compound is prepared from 4-bromopyridine-2-carboxylic acid (154, 600 mg, 2.97 mmol) in accordance with the procedure of Deady, Korytsky and Rowe (Deady, L. W.; Korytsky, O. L.; Rowe, J. E. *Aust. J. Chem.*, 1982, 35, 2025-2034).

Yield: 750 mg (93%).

tert-Butyl [4-(3-{[[4-(BOC-methyl-amino)-cyclohexyl]-(3-chloro-4,7-difluoro-benzo[b]thiophene-2-carbonyl)-amino]-methyl}-4-methoxy-phenyl)-pyridin-2-yl]-carbamate (156)

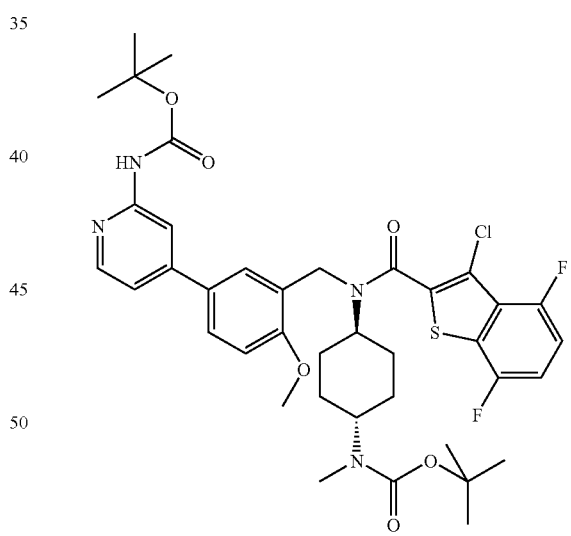

Boronic acid 9 (686 mg, 1.10 mmol) is coupled to pyridyl bromide 155 (300 mg, 1.10 mmol) using Method A to give the title compound.

Yield: 50 mg (6%).

LC/MS t$_r$ 1.80 min.

MS (ES+) m/z 773, 771 (M+H), 717, 715 (M-C(CH$_3$)$_3$+H).

245

3-Chloro-4,7-difluoro-benzo[b]thiophene-2-carboxylic acid [5-(2-amino-pyridin-4-yl)-2-methoxy-benzyl]-(4-methylamino-cyclohexyl)-amide dihydrochloride (157)

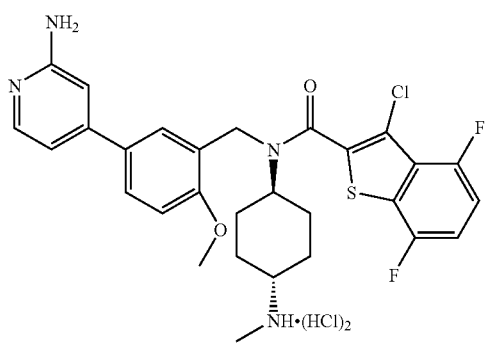

tert-Butyl carbamate 156 (50 mg, 0.06 mmol) is deprotected using Method F. Purification by column chromatography (10% MeOH in EtOAc with 2% triethylamine) followed by formation of the HCl salt using Method H gives the title compound.

Yield: 11 mg (30%).

LC/MS $t_r$ 1.12 min.

MS (ES+) m/z 573, 571 (M+H).

Synthesis of Compound 356 (R21)

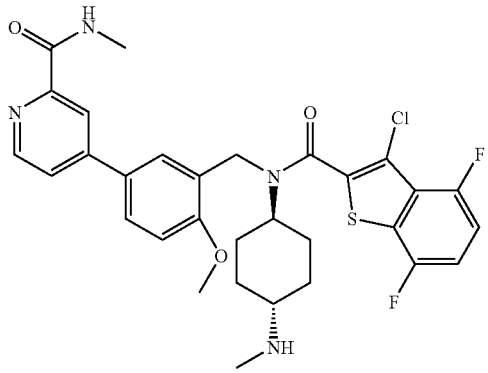

246 tert-Butyl (4-{(3-chloro-4,7-difluoro-benzo[b]thiophene-2-carbonyl)-[2-methoxy-5-(2-methylcarbamoyl-pyridin-4-yl)-benzyl]-amino}-cyclohexyl)-methyl-carbamate (158)

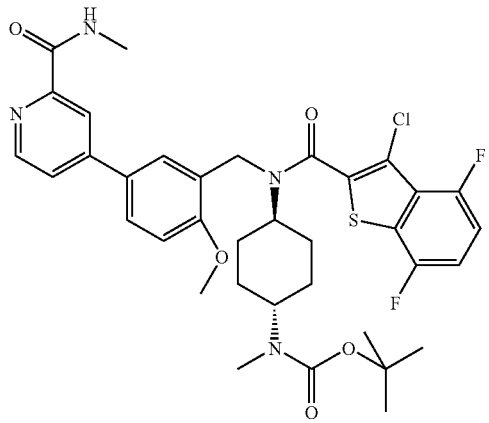

A stirred solution of methyl ester 148 (30 mg, 0.05 mmol) in MeOH (2 mL) is treated with methylamine (1 mL, 40% solution in water) at RT. After 1 h, the reaction mixture is reduced in vacuo and the residue purified by column chromatography (75% EtOAc in heptane) to give the title compound.

Yield: 25 mg (83%).

LC/MS $t_r$ 1.82 min.

MS (ES+) m/z 715, 713 (M+H), 659, 657 (M-C(CH$_3$)$_3$+H), 615, 613 (M-CO$_2$C(CH$_3$)$_3$+H).

4-(3-{[(3-Chloro-4,7-difluoro-benzo[b]thiophene-2-carbonyl)-(4-methylamino-cyclohexyl)-amino]-methyl}-4-methoxy-phenyl)-pyridine-2-carboxylic acid methylamide dihydrochloride (159)

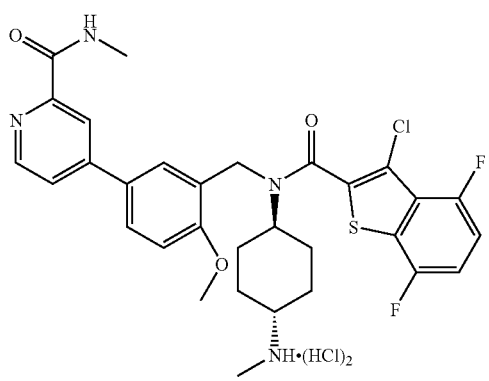

tert-Butyl carbamate 158 (25 mg, 0.04 mmol) is deprotected using Method F to give the title compound.

Yield: 16 mg (75%).

LC/MS $t_r$ 1.28 min.

MS (ES+) m/z 615, 613 (M+H).

Synthesis of Compound 357

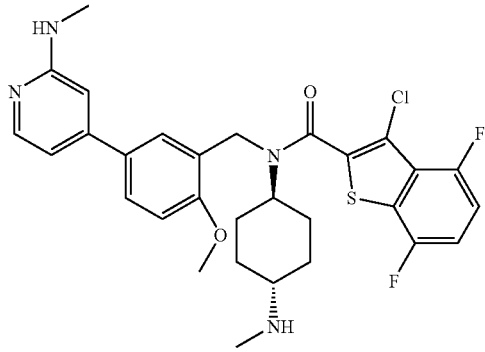

tert-Butyl (4-bromo-pyridin-2-yl)-methyl-carbamate (160)

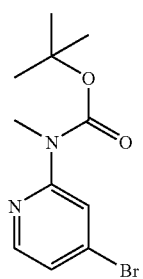

To a solution of tert-butyl carbamate 155 (300 mg, 1.10 mmol) in THF (5 mL) at 0° C. is added sodium hydride (53 mg, 1.32 mmol, 60% dispersion in mineral oil) in one portion. After stirring 15 minutes, iodomethane is added (82 μL, 1.32 mmol) and the reaction mixture warmed to RT and stirred 16 h. The reaction is then quenched with 5% citric acid (10 mL) and extracted into EtOAc (2×10 mL). The combined organic phases are dried over $Na_2SO_4$ and purified by column chromatography (70% EtOAc in heptane) to give the title compound.

Yield: 240 mg (76%).

LC/MS $t_r$ 1.62 min.

MS (ES+) m/z 289, 287 (M+H), 233, 231 (M-C(CH$_3$)$_3$+H).

tert-Butyl [4-(3-{[[4-(BOC-methyl-amino)-cyclohexyl]-(3-chloro-4,7-difluoro-benzo[b]thiophene-2-carbonyl)-amino]-methyl}-4-methoxy-phenyl)-pyridin-2-yl]-methyl-carbamate (161)

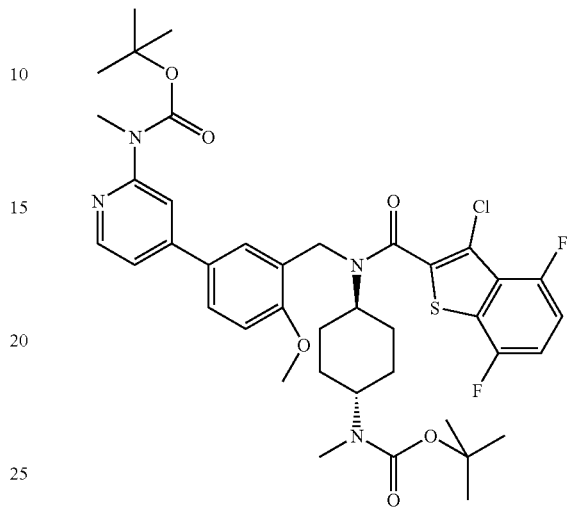

Boronic acid 9 (520 mg, 0.83 mmol) is coupled to pyridyl bromide 160 (240 mg, 0.83 mmol) using Method A to give the title compound.

Yield: 230 mg (35%).

LC/MS $t_r$ 1.89 min.

MS (ES+) m/z 787, 785 (M+H), 731, 729 (M-C(CH$_3$)$_3$+H).

3-Chloro-4,7-difluoro-benzo[b]thiophene-2-carboxylic acid [2-methoxy-5-(2-methylamino-pyridin-4-yl)-benzyl]-(4-methylamino-cyclohexyl)-amide bis(trifluoroacetate) (162)

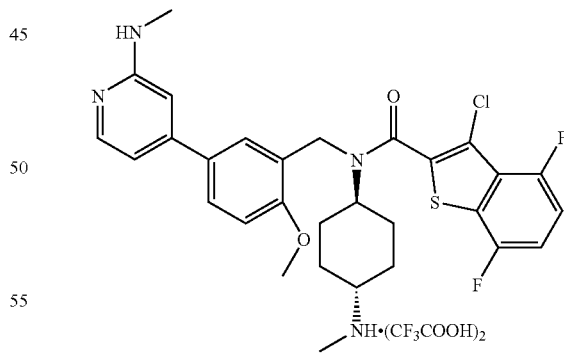

tert-Butyl carbamate 161 (130 mg, 0.17 mmol) is deprotected using Method F. Purification by column chromatography (10% MeOH in EtOAc with 2% triethylamine) followed by preparative HPLC gives the title compound as the TFA salt.

Yield: 45 mg (33%).

LC/MS $t_r$ 1.15 min.

MS (ES+) m/z 587, 585 (M+H).

Synthesis of Compound R9

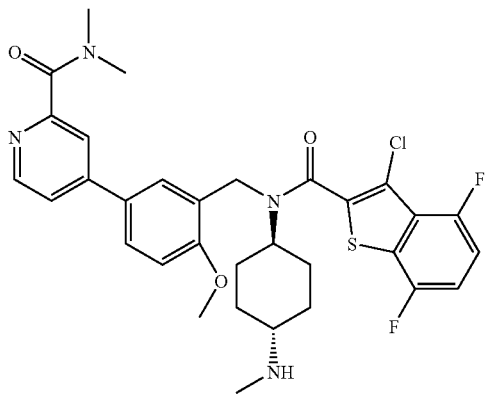

tert-Butyl (4-{(3-chloro-4,7-difluoro-benzo[b]thiophene-2-carbonyl)-[5-(2-dimethylcarbamoyl-pyridin-4-yl)-2-methoxy-benzyl]-amino}-cyclohexyl)-methyl-carbamate (163)

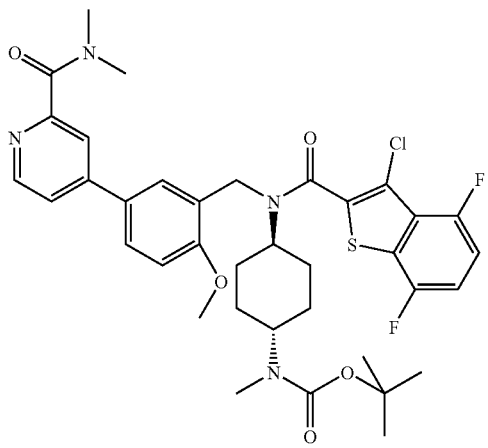

A stirred solution of amide 158 (125 mg, 0.175 mmol) in THF (5 mL) is treated with sodium hydride (11 mg, 0.26 mmol, 60% dispersion in mineral oil) at 0° C. After warming to RT and stirring 0.5 h, iodomethane (0.13 mL, 0.26 mmol, 2 M solution in TBME) is added via syringe and the reaction stirred 1 h. Analysis by LC/MS at this juncture revealed the reaction is only 75% complete. Hence more sodium hydride (11 mg, 0.26 mmol, 60% dispersion in mineral oil) is added, followed after 0.5 h by iodomethane (0.13 mL, 0.26 mmol, 2 M solution in TBME). After a further hour at RT, the reaction is diluted with water (10 mL) and extracted into EtOAc (3×20 mL). The combined EtOAc phases are dried ($Na_2SO_4$) and the solvent removed in vacuo. The title compound is obtained after chromatography (gradient elution—50-80% EtOAc in heptane with 0.5% triethylamine).

Yield: 105 mg (83%).
LC/MS $t_r$ 1.67 min.
MS (ES+) m/z 729, 727 (M+H).

4-(3-{[(3-Chloro-4,7-difluoro-benzo[b]thiophene-2-carbonyl)-(4-methylamino-cyclohexyl)-amino]-methyl}-4-methoxy-phenyl)-pyridine-2-carboxylic acid dimethylamide dihydrochloride (164)

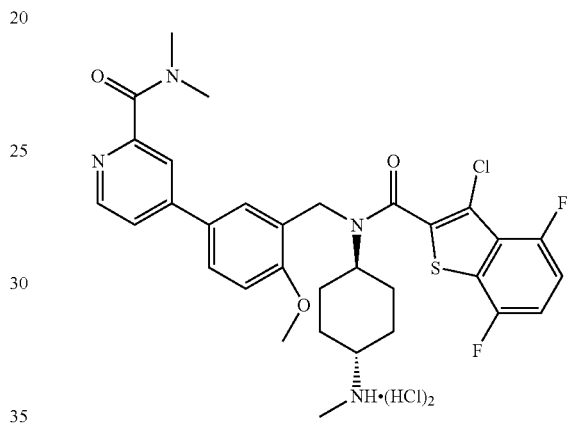

tert-Butyl carbamate 163 (105 mg, 0.14 mmol) is deprotected using Method F. On removal of the solvents in vacuo, the reaction mixture is dissolved in DCM (20 mL) and extracted into 2 M HCl (4×10 mL). The combined HCl phases are washed with DCM (2×20 mL) then taken to pH 9 by careful addition of solid $NaHCO_3$. The resultant aqueous suspension is then extracted into DCM (3×20 mL), the combined DCM phases dried ($Na_2SO_4$) and reduced in vacuo. The title compound is then obtained by Method H.

Yield: 67 mg (72%).
LC/MS $t_r$ 1.20 min.
MS (ES+) m/z 629, 627 (M+H), 315, 314 [(M+H)/2].

Synthesis of Compound R6

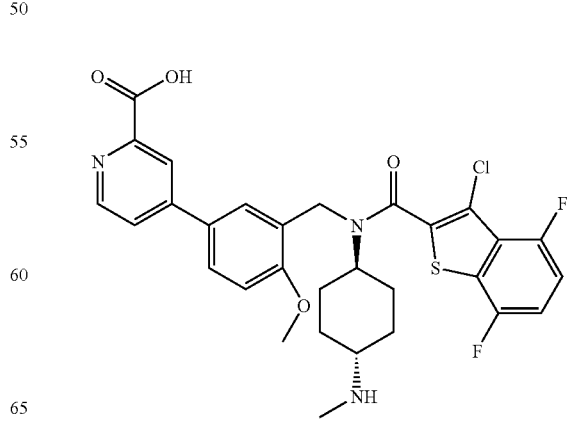

4-(3-{[(3-Chloro-4,7-difluoro-benzo[b]thiophene-2-carbonyl)-(4-methylamino-cyclohexyl)-amino]-methyl}-4-methoxy-phenyl)-pyridine-2-carboxylic acid bis(trifluoroacetate) (165)

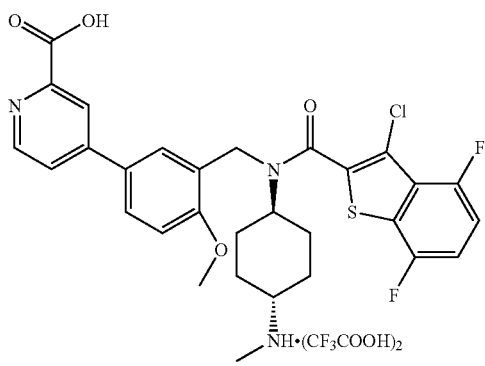

Methyl ester 149 (69 mg, 0.09 mmol) is dissolved in MeOH (2 mL) and treated with 6 M sodium hydroxide (500 µL). The reaction mixture is stirred 2 h during which time a precipitate formed. The precipitate is filtered off, suspended in DCM (2 mL) and TFA (300 µL) added dropwise. The solvents are then removed in vacuo to give a yellow oil. Purification by preparative HPLC gives the product as the TFA salt.

Yield: 49 mg (83%).
LC/MS $t_r$ 1.71 min.
MS (ES+)/Z 602, 600 (M+H).

Synthesis of Compound 358

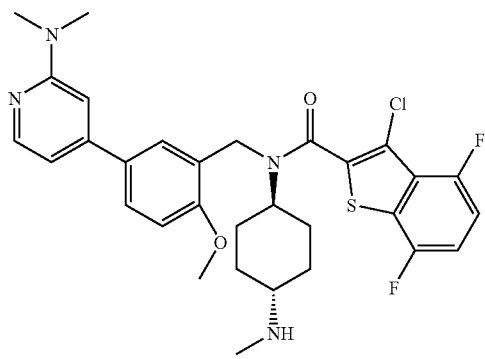

2-Amino-4-bromopyridine (166)

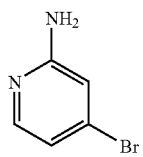

tert-Butyl carbamate 155 (200 mg, 0.73 mol) is suspended in water (1 mL) and treated with HBr (1 mL, 48 wt. % in water). After stirring 16 h, the reaction mixture is poured onto aqueous NaHCO$_3$ (25 mL) and extracted into EtOAc (3×25 mL). The combined EtOAc phases are dried (MgSO$_4$) and reduced in vacuo. The title compound is obtained after chromatography of this residue (neat EtOAc).

Yield: 73 mg (58%).
LC/MS $t_r$ 0.69 min.
MS (ES+) m/z 175, 173 (M+H).

4-Bromo-2-(dimethylamino)pyridine (167)

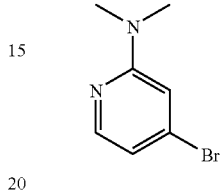

A stirred solution of amino-pyridine 166 (73 mg, 0.42 mmol) in THF (5 mL) is treated with sodium hydride (50 mg, 1.26 mmol, 60% dispersion in mineral oil) at 0° C. After warming to RT and stirring 10 minutes, iodomethane (58 µL, 0.93 mmol) is added via syringe and the reaction stirred 16 h. The reaction is then diluted with water (10 mL) and extracted into EtOAc (3×20 mL). The combined EtOAc phases are dried (Na$_2$SO$_4$) and the solvent removed in vacuo to afford the title compound.

Yield: 92 mg (quant.).

3-Chloro-4,7-difluoro-benzo[b]thiophene-2-carboxylic acid [5-(2-dimethylamino-pyridin-4-yl)-2-methoxy-benzyl]-(4-methylamino-cyclohexyl)-amide dihydrochloride (168)

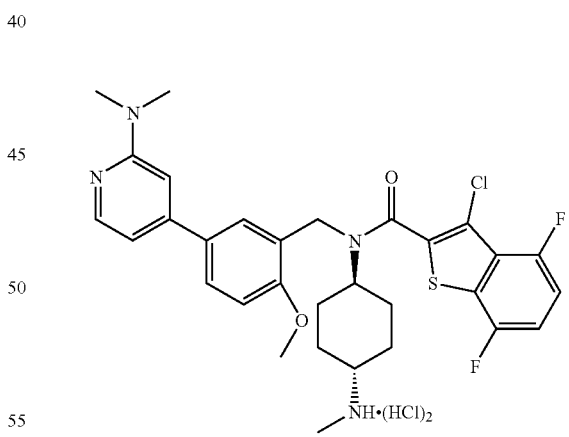

Boronic acid 9 (200 mg, 0.32 mmol) is coupled to pyridyl bromide 167 (71 mg, 0.35 mmol) using Method A. The tert-butyl carbamate (180 mg, 0.26 mmol) isolated after chromatography is then directly deprotected using Method F to afford the title compound.

Yield: 183 mg (85% over two steps).
LC/MS $t_r$ 1.16 min.
MS (ES+) m/z 601, 599 (M+H).

Synthesis of Compound 359

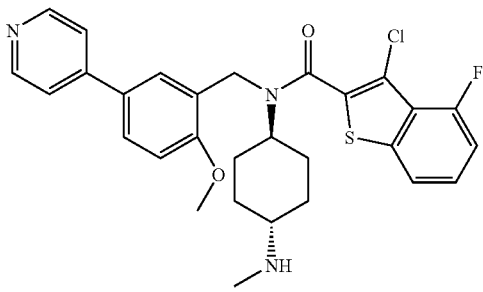

tert-Butyl {4-[(3-chloro-4-fluoro-benzo[b]thiophene-2-carbonyl)-(2-methoxy-5-pyridin-4-yl-benzyl)-amino]-cyclohexyl}-methyl-carbamate (169)

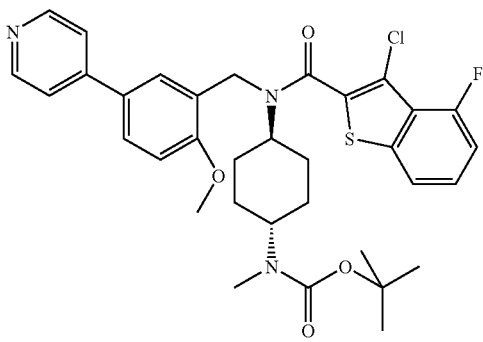

Boronic acid 7 (150 mg, 0.25 mmol) is coupled to 4-bromopyridine hydrochloride (61 mg, 0.31 mmol) using Method B to give the title compound.
Yield: 45 mg (28%). Contains ca. 47% triphenylphosphine oxide.
LC/MS $t_r$ 1.53 min.
MS (ES+) m/z 640, 638 (M+H).

3-Chloro-4-fluoro-benzo[b]thiophene-2-carboxylic acid (2-methoxy-5-pyridin-4-yl-benzyl)-(4-methylamino-cyclohexyl)-amide dihydrochloride (170)

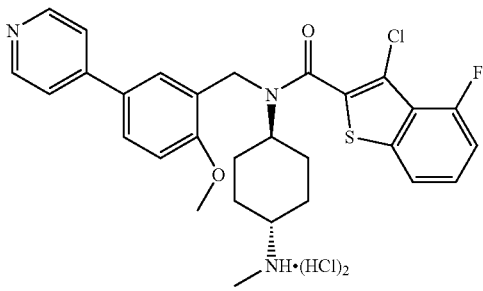

tert-Butyl carbamate 169 (45 mg, 71 μmol) is deprotected using Method F. On removal of the solvents in vacuo, the residue is dissolved in water (3 mL) and washed with TBME (3×1 mL). Reduction of the aqueous phase in vacuo affords the title product.

Yield: 34 mg (78%).
LC/MS $t_r$ 1.08 min.
MS (ES+) m/z 540, 538 (M+H).

Synthesis of Compound 360 (R16)

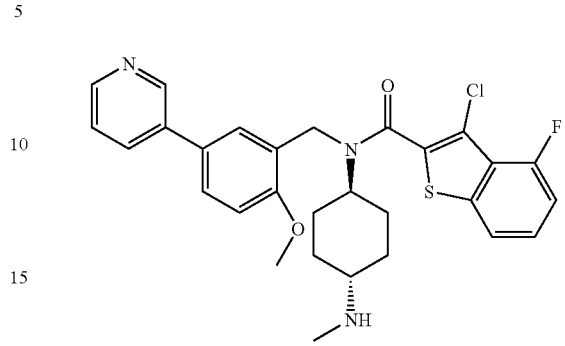

tert-Butyl {4-[(3-chloro-4-fluoro-benzo[b]thiophene-2-carbonyl)-(2-methoxy-5-pyridin-3-yl-benzyl)-amino]-cyclohexyl}-methyl-carbamate (171)

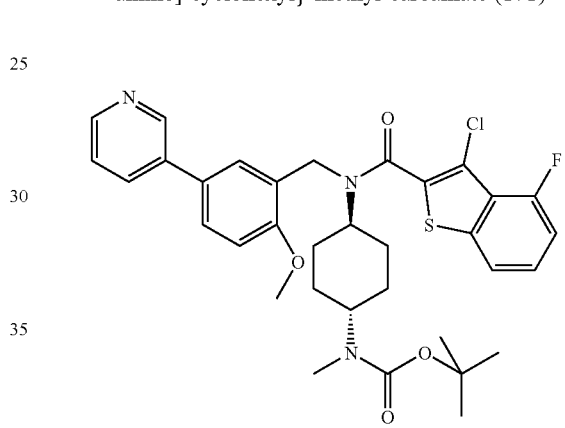

Boronic acid 7 (50 mg, 83 μmol) is coupled to 3-bromopyridine (16 mg, 0.10 mmol) using Method B to give the title compound.
Yield: 34 mg (64%).
LC/MS $t_r$ 1.62 min.
MS (ES+) m/z 640, 638 (M+H).

3-Chloro-4-fluoro-benzo[b]thiophene-2-carboxylic acid (2-methoxy-5-pyridin-3-yl-benzyl)-(4-methylamino-cyclohexyl)-amide dihydrochloride (172)

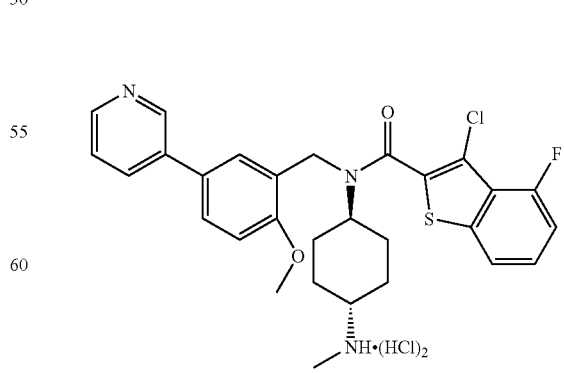

tert-Butyl carbamate 171 (34 mg, 53 μmol) is deprotected using Method F. On removal of the solvents in vacuo, the residue is dissolved in water (3 mL) and washed with TBME (3×1 mL). Reduction of the aqueous phase in vacuo affords the title product.

Yield: 24 mg (74%).
LC/MS $t_r$ 1.05 min.
MS (ES+) m/z 540, 538 (M+H).

Synthesis of Compound 361

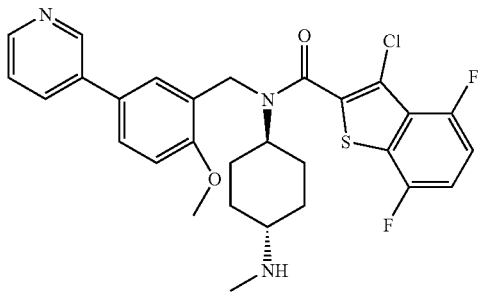

tert-Butyl [4-(2-methoxy-5-pyridin-3-yl-benzylamino)-cyclohexyl]-methyl-carbamate (173)

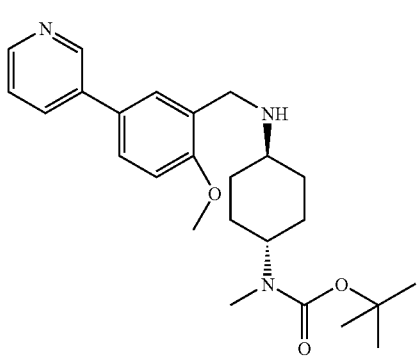

Boronic acid 4 (500 mg, 1.27 mmol) is coupled to 3-bromopyridine (202 mg, 1.27 mmol) using Method A to afford the title compound.

Yield: 320 mg (59%).
LC/MS $t_r$ 1.04 min.
MS (ES+) m/z 851 (2M+H), 426 (M+H).

tert-Butyl {4-[(3-chloro-4,7-difluoro-benzo[b]thiophene-2-carbonyl)-(2-methoxy-5-pyridin-3-yl-benzyl)-amino]-cyclohexyl}-methyl-carbamate (174)

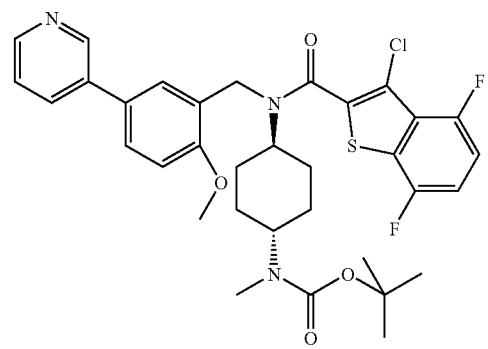

Biaryl amine 173 (320 mg, 0.75 mmol) is treated with acid chloride 8 (221 mg, 0.83 mmol) using Method D to give the title compound.

Yield: 170 mg (35%).
LC/MS $t_r$ 1.60 min.
MS (ES+) m/z 658, 656 (M+H).

3-Chloro-4,7-difluoro-benzo[b]thiophene-2-carboxylic acid (2-methoxy-5-pyridin-3-yl-benzyl)-(4-methylamino-cyclohexyl)-amide dihydrochloride (175)

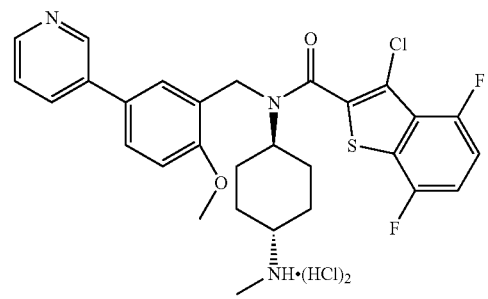

tert-Butyl carbamate 174 (170 mg, 0.26 mmol) is deprotected using Method F to afford the title compound.

Yield: 107 mg (66%).
LC/MS $t_r$ 1.08 min.
MS (ES+) m/z 558, 556 (M+H).

Synthesis of Compound 362 (R13)

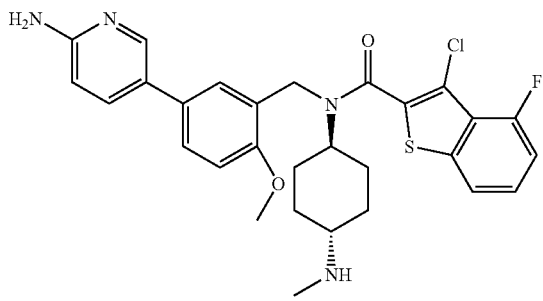

tert-Butyl {4-[[5-(6-amino-pyridin-3-yl)-2-methoxy-benzyl]-(3-chloro-4-fluoro-benzo[b]thiophene-2-carbonyl)-amino]-cyclohexyl}-methyl-carbamate (176)

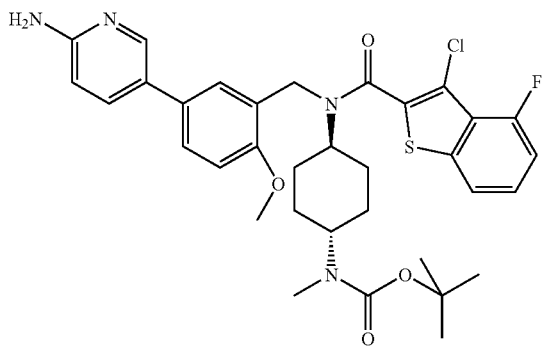

Boronic acid 7 (50 mg, 0.08 mmol) is coupled to 2-amino-5-bromopyridine (17 mg, 0.10 mmol) using Method A to give the title compound.
Yield: 29 mg (55%).
LC/MS t$_r$ 1.64 min.
MS (ES+) m/z 655, 653 (M+H).

3-Chloro-4-fluoro-benzo[b]thiophene-2-carboxylic acid [5-(6-amino-pyridin-3-yl)-2-methoxy-benzyl]-(4-methylamino-cyclohexyl)-amide dihydrochloride (177)

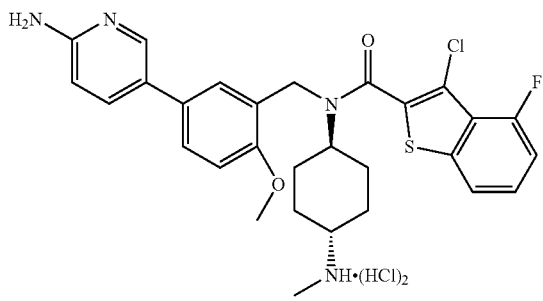

tert-Butyl carbamate 176 (29 mg, 0.04 mmol) is deprotected using Method F to give the title compound.

Yield: 20 mg (72%).
LC/MS t$_r$ 1.12 min.
MS (ES+) m/z 555, 553 (M+H).

Synthesis of Compound 363

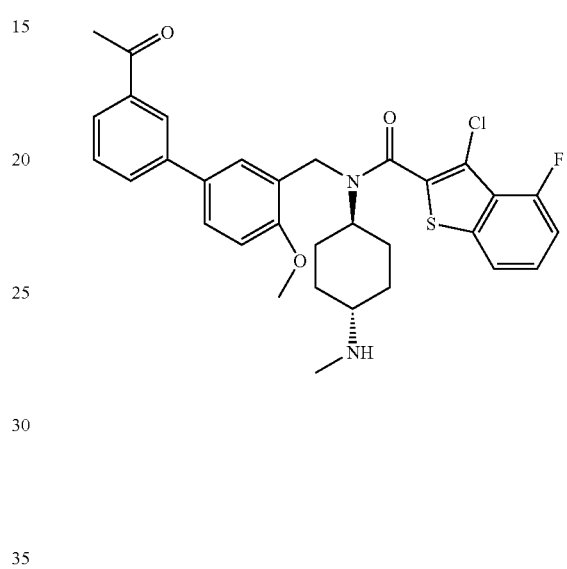

tert-Butyl {4-[(3'-acetyl-4-methoxy-biphenyl-3-ylm-ethyl)-amino]-cyclohexyl}-methyl-carbamate (178)

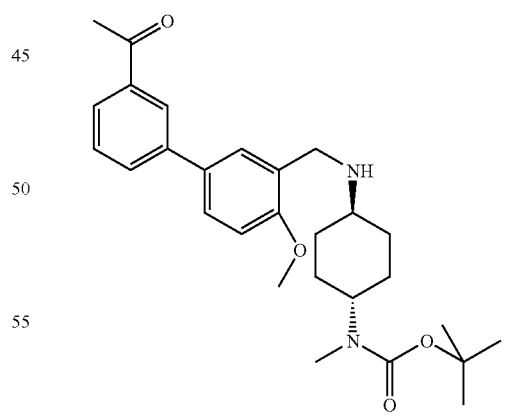

Boronic acid 4 (140 mg, 0.36 mmol) is coupled to 3'-bromoacetophenone (85 mg, 0.43 mmol) using Method B to give the title compound.
Yield: 160 mg (96%).
LC/MS t$_r$ 1.39 min.
MS (ES+) m/z 467 (M+H).

tert-Butyl {4-[(3'-acetyl-4-methoxy-biphenyl-3-ylmethyl)-(3-chloro-4-fluoro-benzo[b]thiophene-2-carbonyl)-amino]-cyclohexyl}-methyl-carbamate (179)

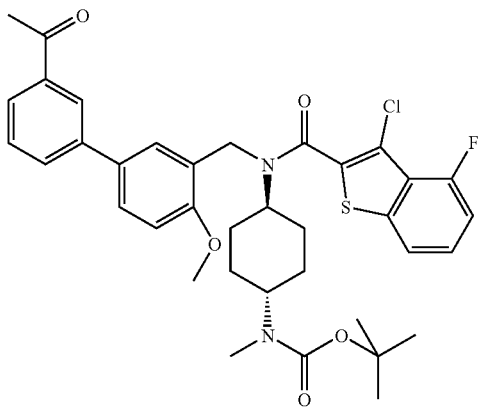

Biaryl amine 178 (80 mg, 0.15 mmol) is treated with acid chloride 6 (53 mg, 0.21 mmol) using Method D to give the title compound.
Yield: 62 mg (92%).
LC/MS $t_r$ 1.92 min.
MS (ES+) m/z 625, 623 (M-C(CH$_3$)$_3$+H).

3-Chloro-4-fluoro-benzo[b]thiophene-2-carboxylic acid (3'-acetyl-4-methoxy-biphenyl-3-ylmethyl)-(4-methylamino-cyclohexyl)-amide hydrochloride (180)

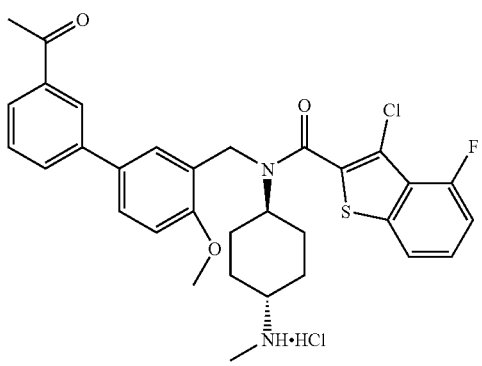

tert-Butyl carbamate 179 (32 mg, 0.05 mmol) is deprotected using Method F to give the title compound.
Yield: 28 mg (quant.).
LC/MS $t_r$ 1.46 min.
MS (ES+) m/z 581, 579 (M+H).

Synthesis of Compound 364

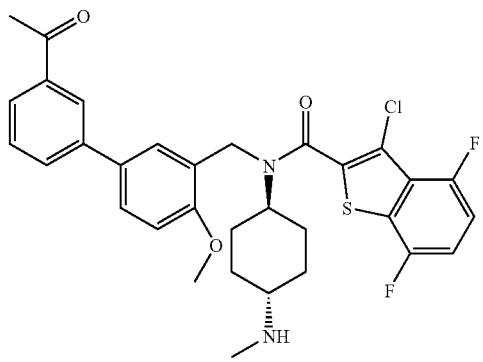

tert-Butyl {4-[(3'-acetyl-4-methoxy-biphenyl-3-ylmethyl)-(3-chloro-4,7-difluoro-benzo[b]thiophene-2-carbonyl)-amino]-cyclohexyl}-methyl-carbamate (181)

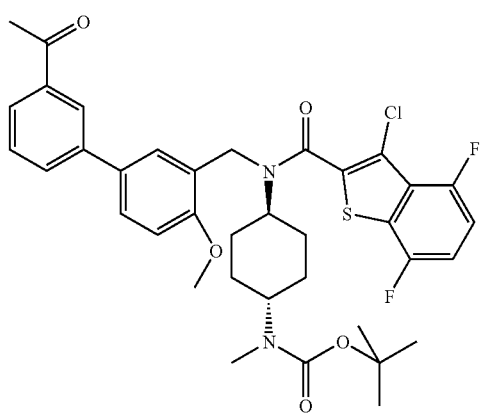

Biaryl amine 178 (80 mg, 0.15 mmol) is treated with acid chloride 8 (57 mg, 0.21 mmol) using Method D to give the title compound.
Yield: 70 mg (57%).
LC/MS $t_r$ 1.95 min.
MS (ES+) m/z 643, 641 (M-C(CH$_3$)$_3$+H).

261

3-Chloro-4,7-difluoro-benzo[b]thiophene-2-carboxylic acid (3'-acetyl-4-methoxy-biphenyl-3-ylmethyl)-(4-methylamino-cyclohexyl)-amide hydrochloride (182)

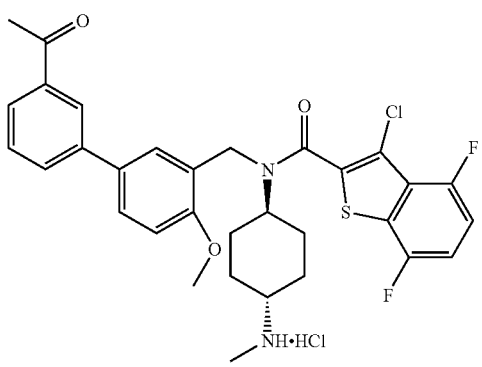

tert-Butyl carbamate 181 (70 mg, 0.10 mmol) is deprotected using Method F to give the title compound.
Yield: 69 mg (quant.).
LC/MS $t_r$ 1.45 min.
MS (ES+) m/z 599, 597 (M+H).
Synthesis of Compound 365

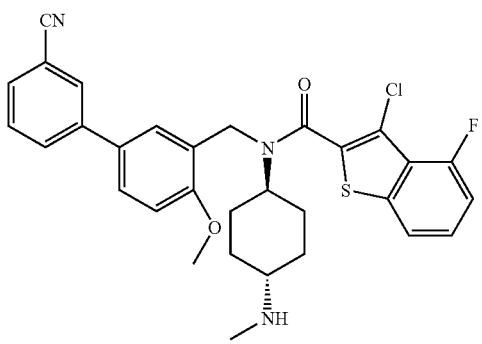

tert-Butyl {4-[(3-chloro-4-fluoro-benzo[b]thiophene-2-carbonyl)-(3'-cyano-4-methoxy-biphenyl-3-ylmethyl)-amino]-cyclohexyl}-methyl-carbamate (183)

Biaryl amine 22 (57 mg, 0.13 mmol) is treated with acid chloride 6 (38 mg, 0.15 mmol) using Method D to give the title compound.
Yield: 50 mg (17%).
LC/MS $t_r$ 1.92 min.
MS (ES+) m/z 608, 606 (M-C(CH$_3$)$_3$+H).

3-Chloro-4-fluoro-benzo[b]thiophene-2-carboxylic acid (3'-cyano-4-methoxy-biphenyl-3-ylmethyl)-(4-methylamino-cyclohexyl)-amide hydrochloride (184)

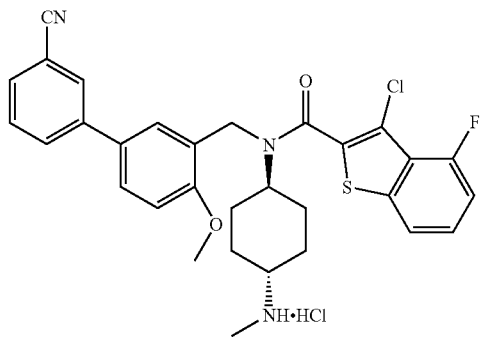

tert-Butyl carbamate 183 (50 mg, 0.08 mmol) is deprotected using Method F. Purification by preparative HPLC followed by formation of the HCl salt using Method H gives the title compound.
Yield: 31 mg (74%).
LC/MS $t_r$ 1.44 min.
MS (ES+) m/z 564, 562 (M+H).
Synthesis of Compound 366

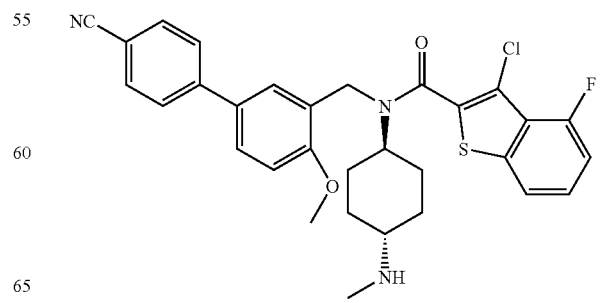

tert-Butyl {4-[(3-chloro-4-fluoro-benzo[b]thiophene-2-carbonyl)-(4'-cyano-4-methoxy-biphenyl-3-ylmethyl)-amino]-cyclohexyl}-methyl-carbamate (185)

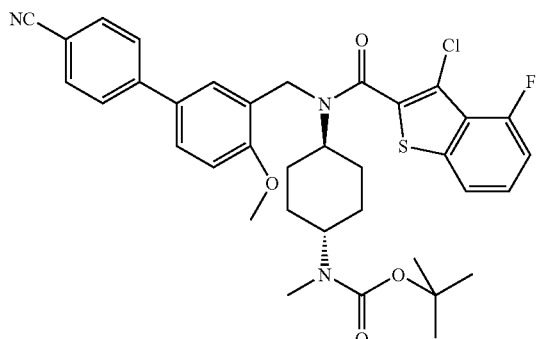

Biaryl amine 13 (87 mg, 0.19 mmol) is treated with acid chloride 6 (58 mg, 0.23 mmol) using Method D to give the title compound.

Yield: 63 mg (49%).
LC/MS $t_r$ 1.90 min.
MS (ES+) m/z 608, 606 (M-C(CH$_3$)$_3$+H).

3-Chloro-4-fluoro-benzo[b]thiophene-2-carboxylic acid (4'-cyano-4-methoxy-biphenyl-3-ylmethyl)-(4-methylamino-cyclohexyl)-amide hydrochloride (186)

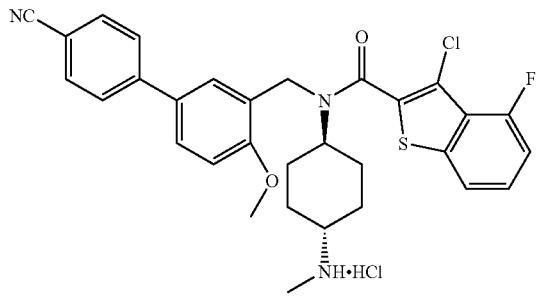

tert-Butyl carbamate 185 (60 mg, 0.09 mmol) is deprotected using Method F to give the title compound.

Yield: 53 mg (quant.).
LC/MS $t_r$ 1.09 min.
MS (ES+) m/z 564, 562 (M+H).

Synthesis of Compound 367

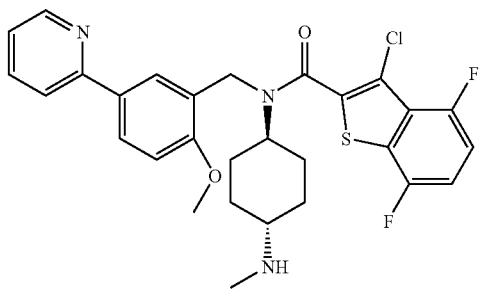

tert-Butyl {4-[(3-chloro-4,7-difluoro-benzo[b]thiophene-2-carbonyl)-(2-methoxy-5-pyridin-2-yl-benzyl)-amino]-cyclohexyl}-methyl-carbamate (187)

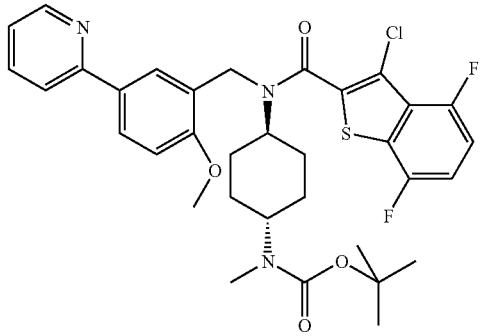

Boronic acid 9 (500 mg, 0.80 mmol) is coupled to 2-bromopyridine (77 μL, 0.80 mmol) using Method B to give the title compound.

Yield: 236 mg (45%).
LC/MS $t_r$ 1.59 min.
MS (ES+) m/z 658, 656 (M+H).

3-Chloro-4,7-difluoro-benzo[b]thiophene-2-carboxylic acid (2-methoxy-5-pyridin-2-yl-benzyl)-(4-methylamino-cyclohexyl)-amide dihydrochloride (188)

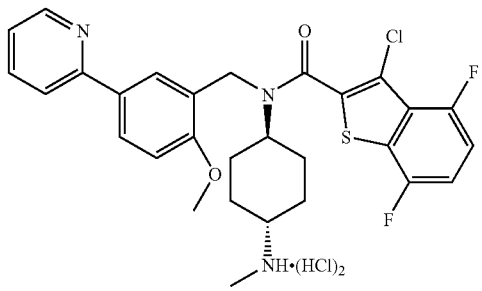

tert-Butyl carbamate 187 (236 mg, 0.36 mmol) is deprotected using Method F to afford the title compound.

Yield: 210 mg (98%).
LC/MS $t_r$ 1.09 min.
MS (ES+) m/z 558, 556 (M+H).

Synthesis of Compound R10 tert-Butyl (4-{(3-chloro-4,7-difluoro-benzo[b]thiophene-2-carbonyl)-[5-(6-methanesulfonylamino-pyridin-3-yl)-2-methoxy-benzyl]-amino}-cyclohexyl)-methyl-carbamate (190)

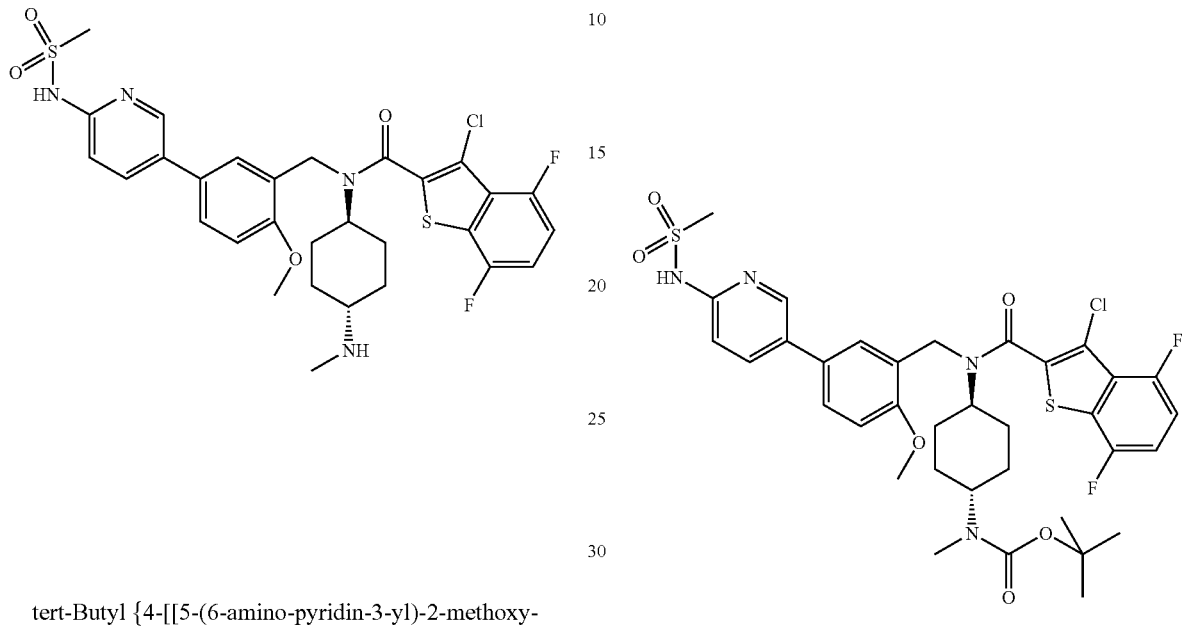

tert-Butyl {4-[[5-(6-amino-pyridin-3-yl)-2-methoxy-benzyl]-(3-chloro-4,7-difluoro-benzo[b]thiophene-2-carbonyl)-amino]-cyclohexyl}-methyl-carbamate (189)

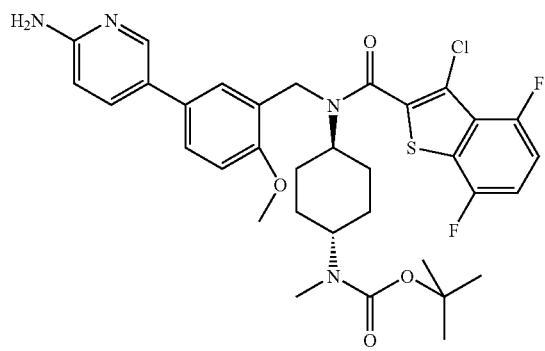

Boronic acid 9 (1.10 g, 1.76 mmol) is coupled to 2-amino-5-bromopyridine (365 mg, 2.11 mmol) using Method A to give the title compound.
Yield: 483 mg (41%).
LC/MS $t_r$ 1.59 min.
MS (ES+) m/z 673, 671 (M+H).

A stirred solution of amino-pyridine 189 (483 mg, 0.72 mmol) and triethylamine (1.20 mL, 8.64 mmol) in DCM (50 mL) is treated with methanesulfonyl chloride (0.62 mL, 8.0 mmol) at 0° C. The reaction is then warmed to RT and stirred 16 h. The solvents are removed in vacuo, the residue treated with aqueous $NaHCO_3$ (50 mL) and the resultant suspension extracted into EtOAc (3×50 mL). The EtOAc phases are combined, dried ($MgSO_4$) and reduced in vacuo to give the crude bis-sulfonamide. The residue is then dissolved in MeOH (17 mL) and THF (33 mL) and treated with conc. ammonia solution (17 mL) at RT. After stirring 1.5 h, analysis by LC/MS indicated that only 37% of the bis-sulfonamide had been converted to the title compound. Hence more conc. ammonia solution (17 mL) is added and the reaction stirred a further 2 h. The solvents are then removed in vacuo and the residue purified by chromatography (gradient elution—60% EtOAc in heptane with 0.5% triethylamine increasing to neat EtOAc with 0.5% triethylamine, then 0-10% MeOH in EtOAc with 0.5% triethylamine) to afford the title compound.
Yield: 384 mg (71%).
LC/MS $t_r$ 1.75 min.
MS (ES+) m/z 751, 749 (M+H).

267

3-Chloro-4,7-difluoro-benzo[b]thiophene-2-carboxylic acid [5-(6-methanesulfonylamino-pyridin-3-yl)-2-methoxy-benzyl]-(4-methylamino-cyclohexyl)-amide dihydrochloride (191)

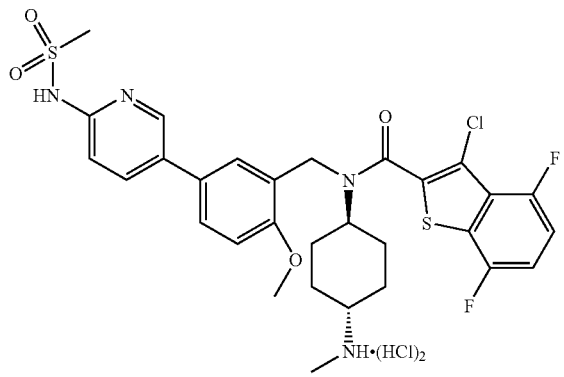

tert-Butyl carbamate 190 (384 mg, 0.51 mmol) is deprotected using Method F. On removal of the solvents in vacuo, the reaction mixture is dissolved in DCM (50 mL) and extracted into 2 M HCl (4×10 mL). The combined HCl phases are washed with DCM (2×25 mL) then taken to pH 9 by careful addition of solid NaHCO$_3$. The resultant aqueous suspension is then extracted into DCM (3×50 mL), these combined DCM phases dried (Na$_2$SO$_4$) and reduced in vacuo to afford the title compound. The DCM phases remaining are also combined, dried (MgSO$_4$) and the solvent removed in vacuo. Treating this residue according to Method H gives more of the title compound at greater purity.

Yield: 246 mg (66%).
LC/MS t$_r$ 1.26 min.
MS (ES+) m/z 651, 649 (M+H).

Synthesis of Compound 368

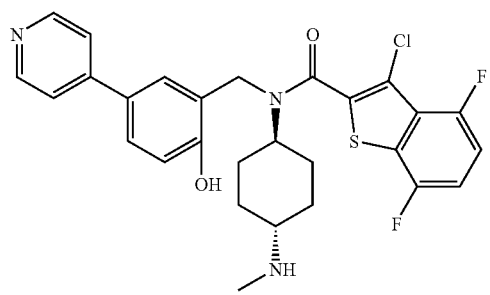

2-Methoxy-5-pyridin-4-yl-benzaldehyde (192)

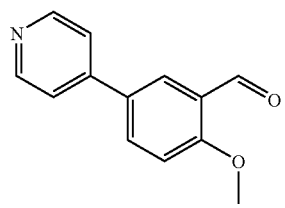

268

3-formyl-4-methoxybenzeneboronic acid (393 mg, 2.19 mmol) is coupled to 4-bromopyridine hydrochloride (400 mg, 2.19 mmol) using Method A to give the title compound.

Yield: 240 mg (52%).
LC/MS t$_r$ 0.85 min.
MS (ES+) m/z 214 (M+H).

2-Hydroxy-5-pyridin-4-yl-benzaldehyde (193)

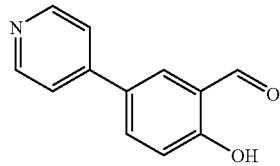

A solution of aldehyde 192 (700 mg, 3.29 mmol) in DCM (8 mL) at −78° C. is treated with boron tribromide (0.93 mL, 9.85 mmol) dropwise over 5 minutes. After 1 h at −78° C., the reaction is warmed to RT and stirred 2 h. The reaction mixture is then cooled (0° C.), quenched with water (5 mL), basified with aqueous NaHCO$_3$ (10 mL) and extracted into DCM (3×20 mL). The combined organic phases are dried over Na$_2$SO$_4$ and the solvent removed in vacuo to give the title compound.

Yield: 330 mg (50%).
LC/MS t$_r$ 0.78 min.
MS (ES+) m/z 200 (M+H).

tert-Butyl [4-(2-hydroxy-5-pyridin-4-yl-benzylamino)-cyclohexyl]-methyl-carbamate (194)

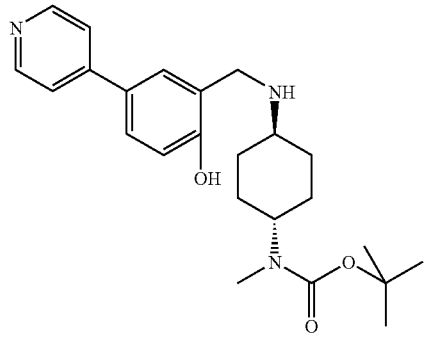

Amine 3 (453 mg, 1.98 mmol) is treated with aldehyde 193 (330 mg, 1.65 mmol) in accordance with Method C. Purification by column chromatography (60% EtOAc in heptane) gives the title compound.

Yield: 240 mg (35%).
LC/MS t$_r$ 1.00 min.
MS (ES+) m/z 412 (M+H), 356 (M-C(CH$_3$)$_3$+H).

tert-Butyl {4-[(3-chloro-4,7-difluoro-benzo[b]thiophene-2-carbonyl)-(1-hydroxy-5-pyridin-4-yl-benzyl)-amino]-cyclohexyl}-methyl-carbamate (195)

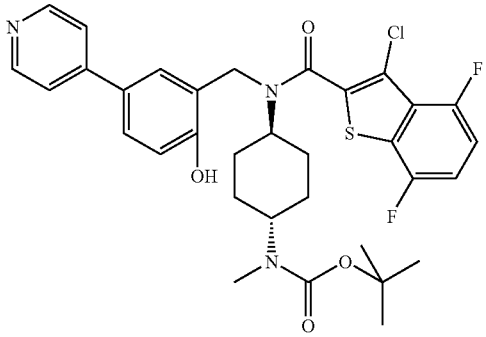

Biaryl amine 194 (240 mg, 0.58 mmol) is treated with acid chloride 8 (389 mg, 1.46 mmol) using Method D, resulting in the functionalisation of both amine and phenol. The resulting amide-ester (310 mg, 0.35 mmol) is dissolved in EtOH (3 mL), treated with 4 M NaOH (1 mL) and stirred 0.5 h at RT. The reaction mixture is then diluted with water (10 mL) and extracted into EtOAc (3×15 mL). The combined organic phases are dried over $Na_2SO_4$ then reduced in vacuo. Purification by column chromatography gives the title compound.
Yield: 210 mg (56%).
LC/MS $t_r$ 1.48 min.
MS (ES+) m/z 644, 642 (M+H), 588, 586 (M-C(CH$_3$)$_3$+H).

3-Chloro-4,7-difluoro-benzo[b]thiophene-2-carboxylic acid (2-hydroxy-5-pyridin-4-yl-benzyl)-(4-methylamino-cyclohexyl)-amide dihydrochloride (196)

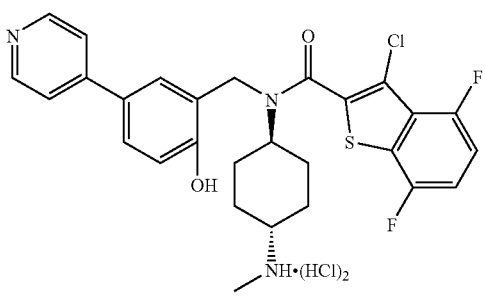

tert-Butyl carbamate 195 (210 mg, 0.33 mmol) is deprotected using Method F to give the title compound.
Yield: 171 mg (96%).
LC/MS $t_r$ 1.04 min.
MS (ES+) m/z 544, 542 (M+H).

Synthesis of Compound 369

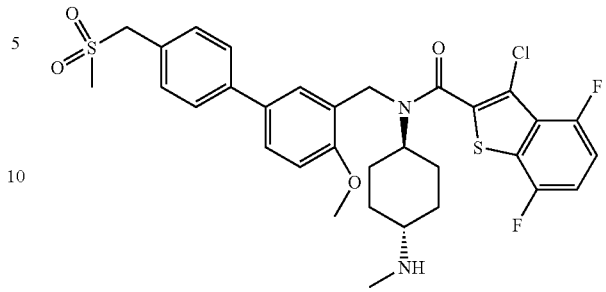

1-Bromo-4-methanesulfonylmethylbenzene (197)

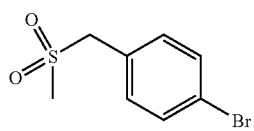

A stirred suspension of 4-bromobenzyl bromide (1.0 g, 4.0 mmol) and sodium methanesulfinate (2.04 g, 20 mmol) in DMF (10 mL) is heated 1 h at 60° C. The reaction mixture is then cooled to RT, diluted with water (200 mL) and extracted into EtOAc (3×25 mL). The combined EtOAc phases are washed with water (2×50 mL) and brine (25 mL) then dried (MgSO$_4$) and reduced in vacuo to afford the title compound.
Yield: 850 mg (85%).
LC/MS $t_r$ 1.10 min
MS (ES+) mass ion not detected.

tert-Butyl {4-[(4'-methanesulfonylmethyl-4-methoxy-biphenyl-3-ylmethyl)-amino]-cyclohexyl}-methyl-carbamate (198)

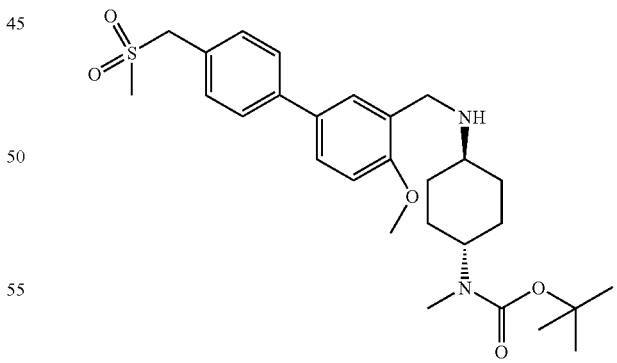

Boronic acid 4 (200 mg, 0.51 mmol) is coupled to aryl bromide 197 (127 mg, 0.51 mmol) using Method A. On filtration of the cooled reaction mixture through celite and removal of the solvents in vacuo, the crude residue obtained is used in the next synthetic step without further purification.
Yield: 362 mg.
LC/MS $t_r$ 1.31 min.
MS (ES+) m/z 517 (M+H).

tert-Butyl {4-[(3-chloro-4,7-difluoro-benzo[b]thiophene-2-carbonyl)-(4'-methanesulfonylmethyl-4-methoxy-biphenyl-3-ylmethyl)-amino]-cyclohexyl}-methyl-carbamate (199)

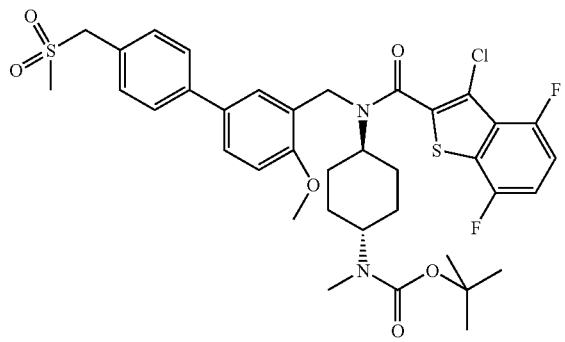

Crude biaryl amine 198 (362 mg) is treated with acid chloride 8 (224 mg, 0.84 mmol) using Method D to give the title compound.

Yield: 224 mg (59% over two steps).

LC/MS $t_r$ 1.88 min.

MS (ES+) m/z 749, 747 (M+H), 693, 691 (M-C(CH$_3$)$_3$+H).

3-Chloro-4,7-difluoro-benzo[b]thiophene-2-carboxylic acid (4'-methanesulfonylmethyl-4-methoxy-biphenyl-3-ylmethyl)-(4-methylamino-cyclohexyl)-amide hydrochloride (200)

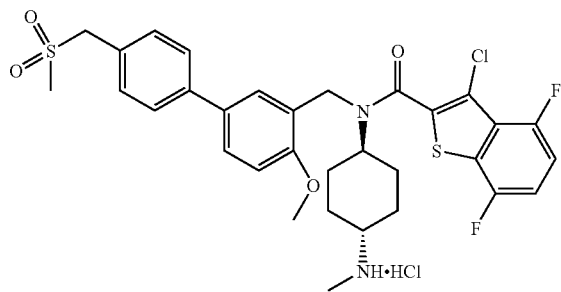

tert-Butyl carbamate 199 (224 mg, 0.30 mmol) is deprotected using Method F. On removal of the solvents in vacuo, the residue is suspended in aqueous NaHCO$_3$ (20 mL) and extracted into DCM (3×20 mL). The combined DCM phases are washed with water (2×20 μL) and brine (20 mL) then dried (Na$_2$SO$_4$) and reduced in vacuo. The free base thus obtained is converted to the HCl salt by Method H. The isolated salt is then dissolved in the minimum amount of DCM and added dropwise to cold (0° C.) TBME (25 mL). The resultant pale yellow precipitate is isolated by filtration, washed with TBME (10 mL) and diethyl ether (10 mL) and dried to afford the title compound.

Yield: 174 mg (90%).

LC/MS $t_r$ 1.34 min.

MS (ES+) m/z 649, 647 (M+H).

Synthesis of Compound 370

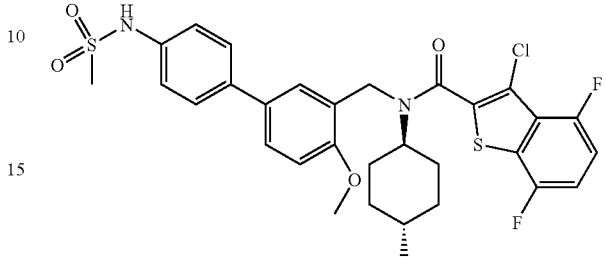

N-(4-Bromophenyl)-methanesulfonamide (201)

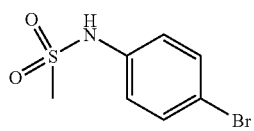

A stirred solution of 4-bromoaniline (1.0 g, 5.81 mmol) and triethylamine (2.43 mL, 17.4 mmol) in DCM (10 mL) at 0° C. is treated with methanesulfonyl chloride (0.47 mL, 6.10 mmol) over 5 minutes via syringe. The reaction is then warmed to RT and stirred 1 h. Analysis by LC/MS at this juncture indicated the reaction mixture contained unreacted starting material, the desired mono-sulfonamide and undesired bis-sulfonamide in a 1:1:1 ratio. Thus more triethylamine (5.0 mL, 35.9 mmol) and methanesulfonyl chloride (1.0 mL, 12.9 mmol) is added and the reaction stirred at RT a further 2 h. On confirmation by LC/MS that all the starting aniline had been converted to the mono- or bis-sulfonamide, the reaction is diluted with water (15 mL) and extracted into EtOAc (3×25 mL). The combined EtOAc phases are then dried (Na$_2$SO$_4$) and reduced in vacuo. The residue thus obtained is dissolved in THF (50 mL) and MeOH (50 mL) then treated with conc. ammonia solution (75 mL) at RT and stirred 16 h. The reaction mixture is then concentrated in vacuo, diluted with water (50 mL) and extracted into EtOAc (3×25 mL). The combined EtOAc phases are dried (MgSO$_4$) and reduced in vacuo to afford the title compound.

Yield: 1.57 g (quant.).

LC/MS $t_r$ 1.16 min

MS (ES+) m/z 252, 250 (M+H)

273 tert-Butyl {4-[(4'-methanesulfonylamino-4-methoxy-biphenyl-3-ylmethyl)-amino]-cyclohexyl}-methyl-carbamate (202)

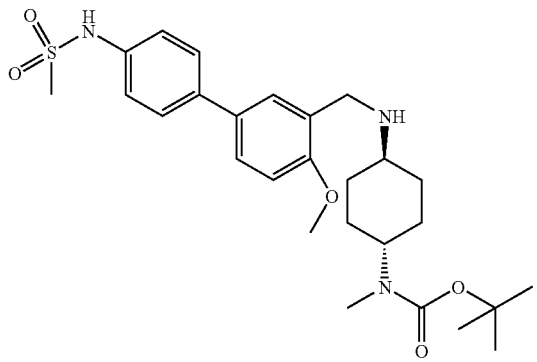

Boronic acid 4 (200 mg, 0.51 mmol) is coupled to aryl bromide 201 (134 mg, 0.54 mmol) using Method A to give the title compound.

Yield: 42 mg (15%).
LC/MS $t_r$ 1.34 min.
MS (ES+) m/z 518 (M+H).

tert-Butyl {4-[(3-chloro-4,7-difluoro-benzo[b]thiophene-2-carbonyl)-(4'-methanesulfonylamino-4-methoxy-biphenyl-3-ylmethyl)-amino]-cyclohexyl}-methyl-carbamate (203)

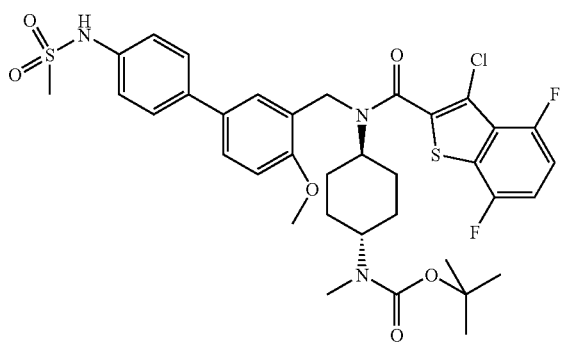

Biaryl amine 202 (42 mg, 81 mmol) is treated with acid chloride 8 (24 mg, 89 μmol) using Method D to give the title compound.

Yield: 45 mg (74%).
LC/MS $t_r$ 1.85 min.
MS (ES+) m/z 750, 748 (M+H), 694, 692 (M-C(CH$_3$)$_3$+H).

274

3-Chloro-4,7-difluoro-benzo[b]thiophene-2-carboxylic acid (4'-methanesulfonylamino-4-methoxy-biphenyl-3-ylmethyl)-(4-methylamino-cyclohexyl)-amide hydrochloride (204)

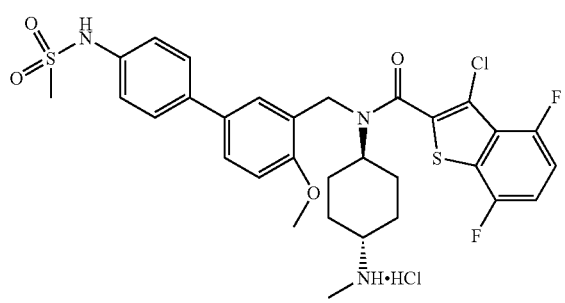

tert-Butyl carbamate 203 (18 mg, 24 μmol) is deprotected using Method F. On removal of the solvents in vacuo, the residue is suspended in aqueous NaHCO$_3$ (10 mL) and extracted into DCM (3×10 mL). The combined DCM phases are washed with water (2×10 mL) and brine (10 mL) then dried (Na$_2$SO$_4$) and reduced in vacuo. The free base thus obtained is then converted to the title compound using Method H.

Yield: 18 mg (quant.).
LC/MS $t_r$ 1.36 min.
MS (ES+) m/z 672, 670 (M+Na), 650, 648 (M+H).

Synthesis of Compound 371

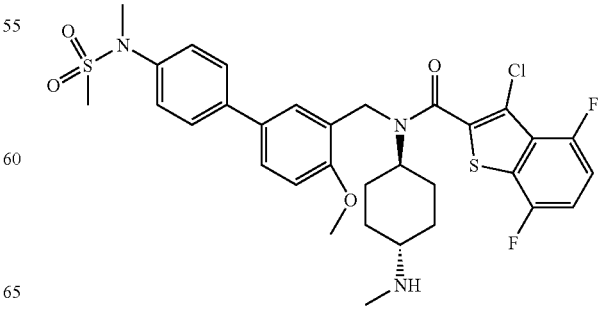

tert-Butyl (4-{(3-chloro-4,7-difluoro-benzo[b]thiophene-2-carbonyl)-[4'-(methanesulfonyl-methyl-amino)-4-methoxy-biphenyl-3-ylmethyl]-amino}-cyclohexyl)-methyl-carbamate (205)

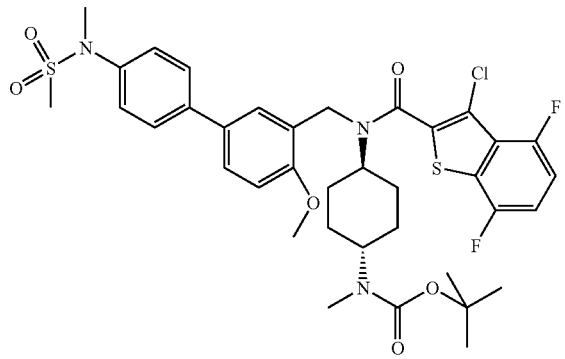

A stirred solution of sulfonamide 203 (23 mg, 31 µmol) in THF (2 mL) is treated with sodium hydride (2 mg, 46 µmol, 60% dispersion in mineral oil) at 0° C. After warming to RT and stirring 0.5 h, iodomethane (10 µL, 0.15 mmol) is added via syringe and the reaction stirred 2 h. Analysis by LC/MS at this juncture revealed the reaction is only 40% complete. Hence more sodium hydride (6 mg, 0.15 mmol, 60% dispersion in mineral oil) is added, followed after 0.5 h by iodomethane (30 µL, 0.46 mmol). After a further 16 h at RT, the reaction is diluted with water (10 mL) and extracted into EtOAc (3×15 mL). The combined EtOAc phases are dried ($Na_2SO_4$) and reduced in vacuo to afford the title compound.
Yield: 23 mg (quant.).
LC/MS $t_r$ 1.92 min.
MS (ES+) m/z 708, 706 (M-C(CH$_3$)$_3$+H).

3-Chloro-4,7-difluoro-benzo[b]thiophene-2-carboxylic acid [4'-(methanesulfonyl-methyl-amino)-4-methoxy-biphenyl-3-ylmethyl]-(4-methylamino-cyclohexyl)-amide hydrochloride (206)

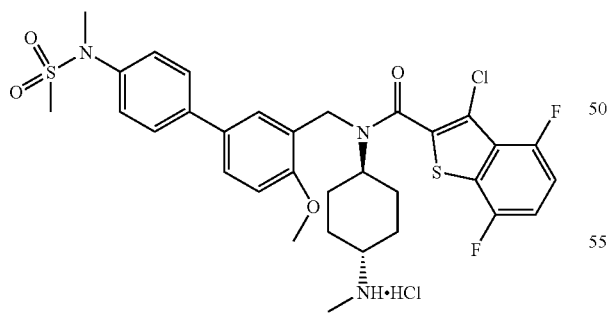

tert-Butyl carbamate 205 (23 mg, 31 mmol) is deprotected using Method F. The isolated salt is then dissolved in the minimum amount of DCM and added dropwise to cold (0° C.) hexane (10 mL). The resultant cream precipitate is isolated by filtration and dried to afford the title compound.
Yield: 19 mg (89%).
LC/MS $t_r$ 1.50 min.
MS (ES+) m/z 664, 662 (M+H).

Synthesis of Compound 372

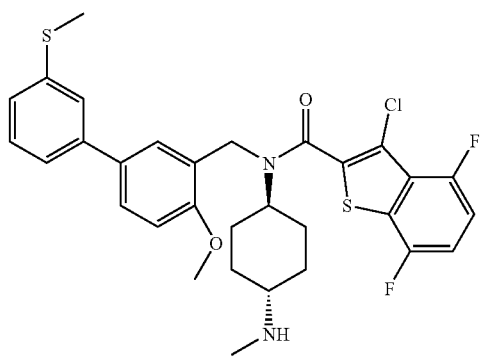

tert-Butyl {4-[(3-chloro-4,7-difluoro-benzo[b]thiophene-2-carbonyl)-(4-methoxy-3'-methylsulfanyl-biphenyl-3-ylmethyl)-amino]-cyclohexyl}-methyl-carbamate (207)

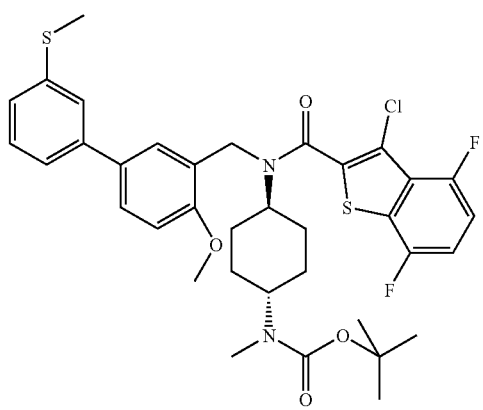

Boronic acid 4 (300 mg, 0.77 mmol) is coupled to 3-bromothioanisole (156 mg, 0.77 mmol) using Method A. On filtration of the cooled reaction mixture through celite and removal of the solvents in vacuo, the crude biaryl amine is treated with acid chloride 8 (246 mg, 0.92 mmol) using Method D to give the title compound.
Yield: 229 mg (42%).
LC/MS $t_r$ 2.06 min.
MS (ES+) m/z 647, 645 (M-C(CH$_3$)$_3$+H).

277

3-Chloro-4,7-difluoro-benzo[b]thiophene-2-carboxylic acid (4-methoxy-3'-methylsulfanyl-biphenyl-3-ylmethyl)-(4-methylamino-cyclohexyl)-amide hydrochloride (208)

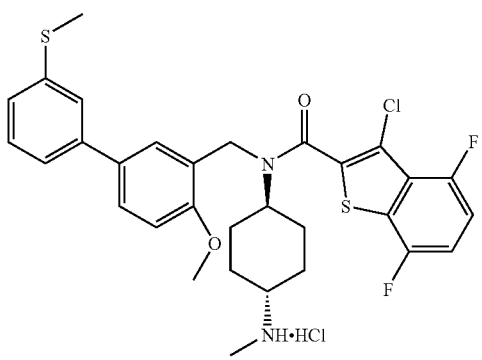

tert-Butyl carbamate 207 (25 mg, 0.04 mmol) is deprotected using Method F to give the title compound.

Yield: 23 mg (quant.).

LC/MS $t_r$ 2.20 min.

MS (ES+) m/z 603, 601 (M+H).

Synthesis of Compound 373

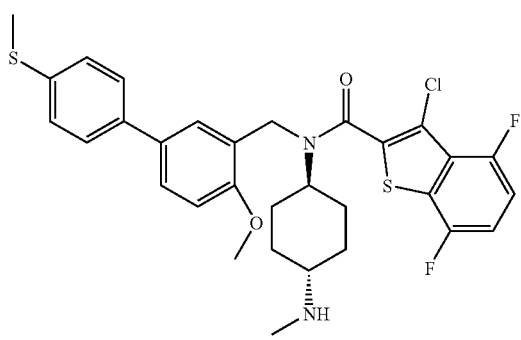

278 tert-Butyl {4-[(3-chloro-4,7-difluoro-benzo[b]thiophene-2-carbonyl)-(4-methoxy-4'-methylsulfanyl-biphenyl-3-ylmethyl)-amino]-cyclohexyl}-methyl-carbamate (209)

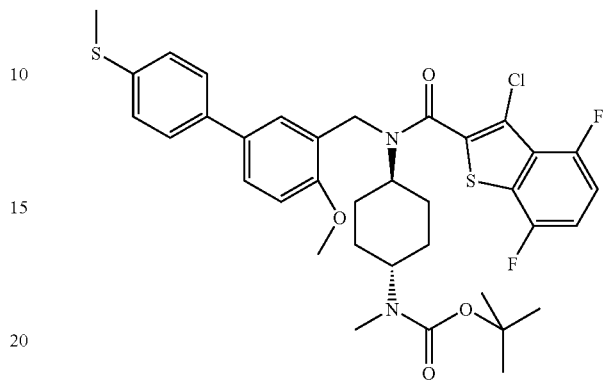

Boronic acid 4 (200 mg, 0.51 mmol) is coupled to 4-bromothioanisole (104 mg, 0.51 mmol) using Method A. On filtration of the cooled reaction mixture through celite and removal of the solvents in vacuo, the crude biaryl amine is treated with acid chloride 8 (163 mg, 0.61 mmol) using Method D to give the title compound.

Yield: 232 mg (65%).

LC/MS $t_r$ 2.06 min.

MS (ES+) m/z 647, 645 (M-C(CH$_3$)$_3$+H).

3-Chloro-4,7-difluoro-benzo[b]thiophene-2-carboxylic acid (4-methoxy-4'-methylsulfanyl-biphenyl-3-ylmethyl)-(4-methylamino-cyclohexyl)-amide hydrochloride (210)

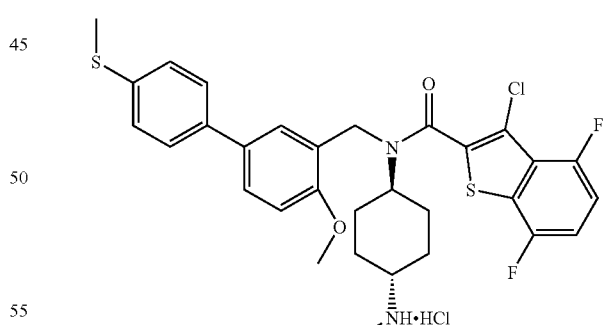

tert-Butyl carbamate 209 (25 mg, 0.04 mmol) is deprotected using Method F to give the title compound.

Yield: 23 mg (quant.).

LC/MS $t_r$ 2.21 min.

MS (ES+) m/z 603, 601 (M+H).

Synthesis of Compound 374

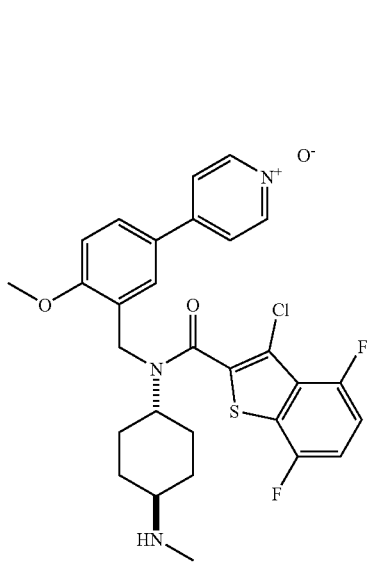

4-(3-((3-chloro-4,7-difluoro-N-((1s,4s)-4-(methylamino)cyclohexyl)benzo[b]thiophene-2-carboxamido)methyl)-4-methoxyphenyl)pyridine 1-oxide Following the synthetic protocol described in Method X; 4-(3-((3-chloro-4,7-difluoro-N-((1s,4s)-4-(methylamino)cyclohexyl)benzo[b]thiophene-2-carboxamido)methyl)-4-methoxyphenyl)pyridine 1-oxide is prepared starting from tert-butyl (1s,4s)-4-(3-chloro-4,7-difluoro-N-(2-methoxy-5-(pyridin-4-yl)benzyl)benzo[b]thiophene-2-carboxamido)cyclohexyl(methyl)carbamate. The desired product is isolated in 65%.

$^1$H NMR (300 MHz, DMSO-$d_6$, 60° C.) δ ppm 1.18-1.48 (m, 2H) 1.59-1.95 (m, 4H) 1.97-2.14 (m, 2H) 2.41-2.48 (m, 3H) 2.77-3.02 (m, 1H) 3.73-3.95 (m, 4H) 4.65 (s, 2H) 7.05-7.20 (m, 1H) 7.31-7.49 (m, 2H) 7.60 (d, J=2.38 Hz, 1H) 7.65-7.76 (m, 3H) 8.34 (d, J=6.95 Hz, 2H) 8.58-8.77 (m, 2H)

ESI MS m/z 572 $[C_{29}H_{28}ClF_2N_3O_3S+H]^+$.

Synthesis of Compound 375

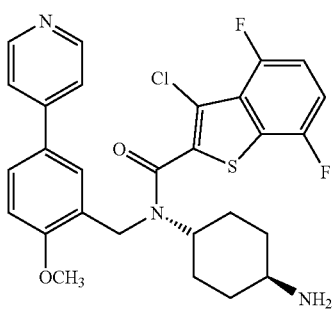

tert-Butyl (1r,4r)-4-(2-methoxy-5-(pyridin-4-yl)benzylamino)cyclohexylcarbamate

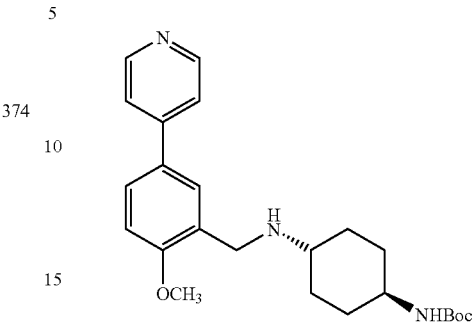

Following the synthetic protocol described in Method C'; tert-butyl (1r,4r)-4-(2-methoxy-5-(pyridin-4-yl)benzylamino)cyclohexylcarbamate is prepared starting from 2-methoxy-5-(pyridin-4-yl)benzaldehyde and tert-butyl (1r,4r)-4-aminocyclohexylcarbamate. The desired product is isolated in 58%.

ESI MS m/z 412 $[C_{24}H_{33}N_3O_3+H]^+$.

N-((1r,4r)-4-aminocyclohexyl)-3-chloro-4,7-difluoro-N-(2-methoxy-5-(pyridin-4-yl)benzyl)benzo[b]thiophene-2-carboxamide hydrochloride

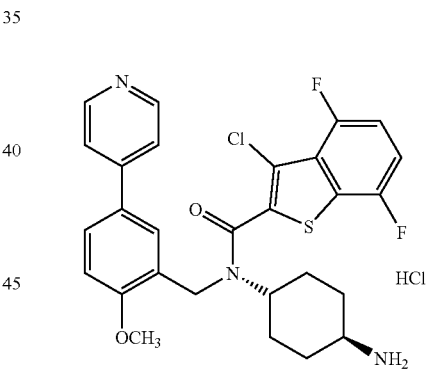

Following the synthetic protocol described in Method D'; N-((1r,4r)-4-aminocyclohexyl)-3-chloro-4,7-difluoro-N-(2-methoxy-5-(pyridin-4-yl)benzyl)benzo[b]thiophene-2-carboxamide hydrochloride is prepared starting from tert-butyl (1r,4r)-4-(2-methoxy-5-(pyridin-4-yl)benzylamino)cyclohexylcarbamate and 3-Chloro-4,7-difluoro-benzo[b]thiophene-2-carbonyl chloride. The desired product is isolated in 49% as the HCl salt.

$^1$H NMR (400 MHz, DMSO-$d_6$, 60° C.) δ ppm 1.14-1.57 (m, 2H) 1.61-2.20 (m, 6H) 2.65-3.08 (m, 2H) 4.68 (s, 2H) 7.00-7.59 (m, 5H) 7.68-7.85 (m, 1H) 7.86-8.24 (m, 6H) 8.59-8.96 (m, 3H)

ESI MS m/z 556 $[C_{29}H_{28}ClF_2N_3O_2S+H]^+$.
ESI MS m/z 542 $[C_{28}H_{26}ClF_2N_3O_2S+H]^+$.

Synthesis of Compound 376

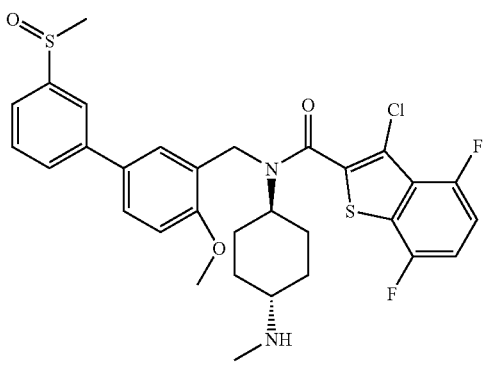

tert-Butyl {4-[(3-chloro-4,7-difluoro-benzo[b]thiophene-2-carbonyl)-(3'-methanesulfinyl-4-methoxy-biphenyl-3-ylmethyl)-amino]-cyclohexyl}-methyl-carbamate (211) and tert-Butyl {4-[(3-chloro-4,7-difluoro-benzo[b]thiophene-2-carbonyl)-(3'-methanesulfonyl-4-methoxy-biphenyl-3-ylmethyl)-amino]-cyclohexyl}-methyl-carbamate (212)

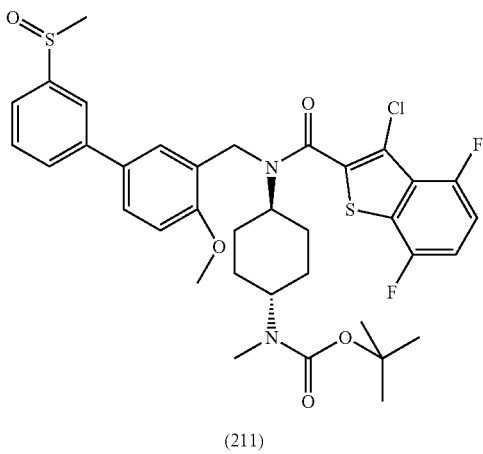

(211)

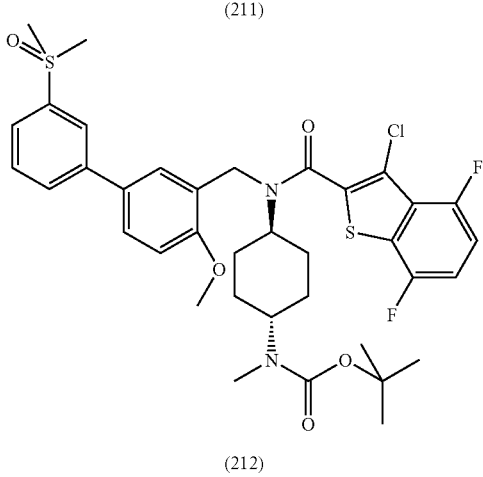

(212)

A stirred suspension of methyl sulfide 207 (75 mg, 0.11 mmol) and NaHCO$_3$ (6 mg, 0.55 mmol) in DCM (3 mL) at 0° C. is treated with a solution of m-chloroperbenzoic acid (34 mg, 0.20 mmol) in DCM (1 mL) dropwise over 2 minutes. After stirring 2 h at RT, the reaction is diluted with aqueous Na$_2$SO$_3$ (10 mL) and extracted into DCM (3×10 mL). The combined DCM phases are then dried (Na$_2$SO$_4$) and reduced in vacuo. The residue is purified by column chromatography (gradient elution—10-90% EtOAc in heptane with 0.5% triethylamine) to give both the desired sulfoxide 211 and the analogous sulfone 212.

Yield (sulfoxide 211): 17 mg (22%).

LC/MS $t_r$ 1.82 min.

MS (ES+) m/z 719, 717 (M+H).

Yield (sulfone 212): 24 mg (30%).

LC/MS $t_r$ 1.88 min.

MS (ES+) m/z 735, 733 (M+H), 679, 677 (M-C(CH$_3$)$_3$+H).

3-Chloro-4,7-difluoro-benzo[b]thiophene-2-carboxylic acid (3'-methanesulfinyl-4-methoxy-biphenyl-3-ylmethyl)-(4-methylamino-cyclohexyl)-amide trifluoroacetate (213)

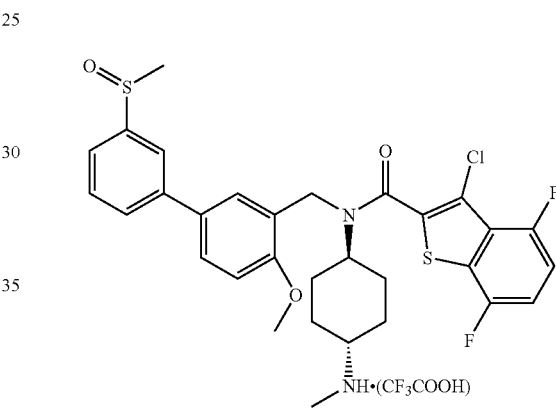

tert-Butyl carbamate 211 (17 mg, 24 μmol) is deprotected using Method G to afford the title compound.

Yield: 23 mg (quant.).

LC/MS $t_r$ 1.40 min.

MS (ES+) m/z 619, 617 (M+H).

Synthesis of Compound 377

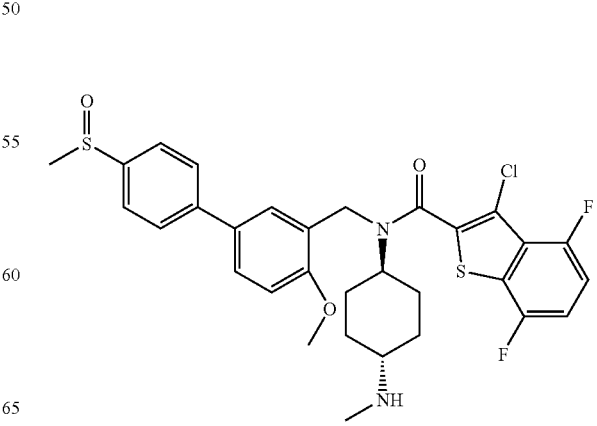

tert-Butyl {4-[(3-chloro-4,7-difluoro-benzo[b]thiophene-2-carbonyl)-(4'-methanesulfinyl-4-methoxy-biphenyl-3-ylmethyl)-amino]-cyclohexyl}-methyl-carbamate (214)

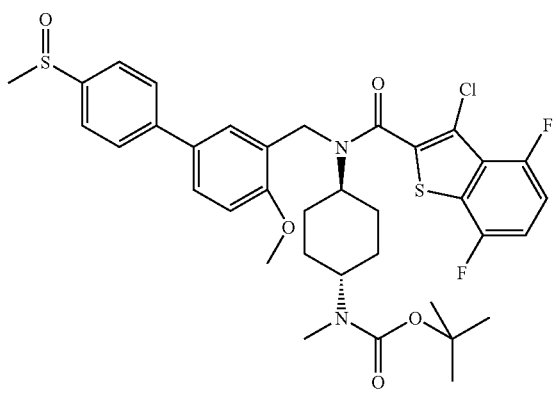

A stirred suspension of methyl sulfide 209 (75 mg, 0.11 mmol) and NaHCO₃ (46 mg, 0.55 mmol) in DCM (3 mL) at 0° C. is treated with a solution of m-chloroperbenzoic acid (20 mg, 0.12 mmol) in DCM (1 mL) dropwise over 2 minutes. After stirring 2 h at RT, the reaction is diluted with aqueous Na₂SO₃ (10 mL) and extracted into DCM (3×10 mL). The combined DCM phases are then dried (Na₂SO₄) and reduced in vacuo. The residue is purified by column chromatography (gradient elution—10-90% EtOAc in heptane with 0.5% triethylamine) to give the title compound.

Yield: 43 mg (54%).

LC/MS $t_r$ 1.80 min.

MS (ES+) m/z 719, 717 (M+H), 663, 661 (M-C(CH₃)₃+H).

3-Chloro-4,7-difluoro-benzo[b]thiophene-2-carboxylic acid (4'-methanesulfinyl-4-methoxy-biphenyl-3-ylmethyl)-(4-methylamino-cyclohexyl)-amide trifluoroacetate (215)

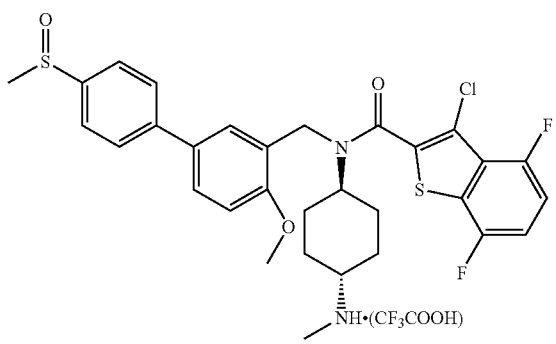

tert-Butyl carbamate 214 (43 mg, 60 μmol) is deprotected using Method G to afford the title compound.

Yield: 54 mg (quant.).

LC/MS $t_r$ 1.40 min.

MS (ES+) m/z 619, 617 (M+H).

Synthesis of Compound 378

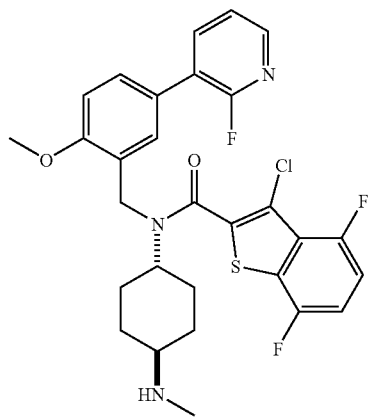

378

Synthesis of 5-(2-Fluoro-pyridin-3-yl)-2-methoxy-benzaldehyde

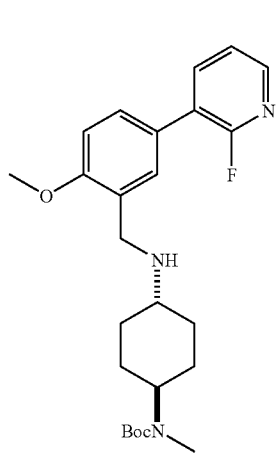

Following the synthetic protocol described in Method A'; 5-(2-Fluoro-pyridin-3-yl)-2-methoxy-benzaldehyde is prepared starting from 2-Fluoro-3-boronic acid pyridine and 5-Bromo-2-methoxy-benzaldehyde. The desired product is isolated in 72%.

ESI MS m/z 232 [C₁₃H₁₀FNO₂+H]⁺.

Synthesis of {4-[5-(2-Fluoro-pyridin-3-yl)-2-methoxy-benzylamino]-cyclohexyl}-methyl-carbamic acid tert-butyl ester Following the synthetic protocol described in Method C'; {4-[5-(2-Fluoro-pyridin-3-yl)-2-methoxy-benzylamino]-cyclohexyl}-methyl-carbamic acid tert-butyl ester is prepared starting from 5-(2-Fluoro-pyridin-3-yl)-2-methoxy-benzaldehyde and (4-Amino-cyclohexyl)-methyl-carbamic acid tert-butyl ester. The desired product is isolated in 70%.

ESI MS m/z 444 [C$_{25}$H$_{34}$FN$_3$O$_3$+H]$^+$.

$^1$H NMR (400 MHz, CHLOROFORM-d) δ ppm 1.42 (s, 4H) 1.46 (s, 9H) 1.68-1.76 (m, J=11.47 Hz, 2H) 1.93-2.01 (m, 1H) 2.01-2.13 (m, J=12.20 Hz, 2H) 2.42-2.56 (m, 1H) 2.70 (s, 3H) 3.40 (br. s., 1H) 3.80-3.98 (m, 5H) 6.94-6.99 (m, J=9.03 Hz, 1H) 7.23-7.28 (m, 1H) 7.47-7.53 (m, 2H) 7.87 (ddd, J=9.76, 7.56, 1.95 Hz, 1H) 8.15 (dt, J=3.17, 1.71 Hz, 1H Synthesis of 3-Chloro-4,7-difluoro-benzo[b]thiophene-2-carboxylic acid [5-(2-fluoro-pyridin-3-yl)-2-methoxy-benzyl]-(4-methylamino-cyclohexyl)-amide

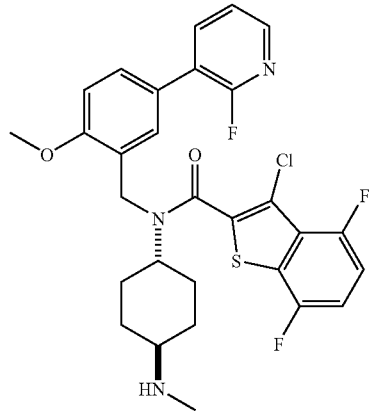

378

Following the synthetic protocol described in Method D'; 3-Chloro-4,7-difluoro-benzo[b]thiophene-2-carboxylic acid [5-(2-fluoro-pyridin-3-yl)-2-methoxy-benzyl]-(4-methylamino-cyclohexyl)-amide is prepared starting from {4-[5-(2-Fluoro-pyridin-3-yl)-2-methoxy-benzylamino]-cyclohexyl}-methyl-carbamic acid tert-butyl ester and 3-Chloro-4,7-difluoro-benzo[b]thiophene-2-carbonyl chloride. The desired product is isolated in 45%.

$^1$H NMR (400 MHz, DMSO-d$_6$, 60° C.) δ ppm 1.12-1.44 (m, 2H) 1.56-2.14 (m, 6H) 2.40-2.48 (m, 3H) 2.82-3.01 (m, 1H) 3.64-4.14 (m, 4H) 4.56-4.70 (m, 2H) 6.98-7.26 (m, 1H) 7.31-7.60 (m, 5H) 7.99-8.08 (m, 1H) 8.14-8.41 (m, 3H)

ESI MS m/z 574 [C$_{29}$H$_{27}$ClF$_3$N$_3$O$_2$S+H]$^+$.

Synthesis of Compound 379

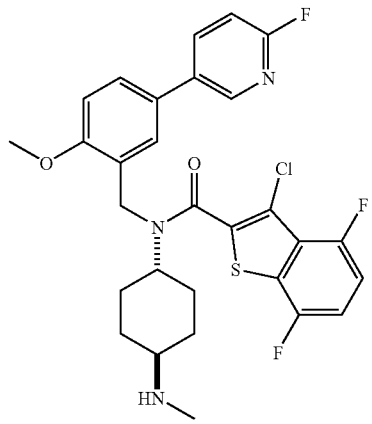

379

5-(6-Fluoro-pyridin-3-yl)-2-methoxy-benzaldehyde

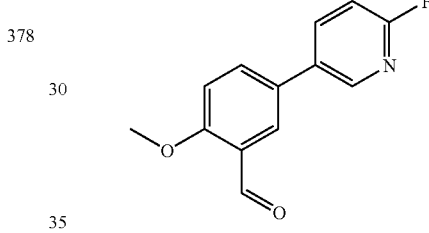

Following the synthetic protocol described in Method A'; 5-(6-Fluoro-pyridin-3-yl)-2-methoxy-benzaldehyde is prepared starting from 6-Fluoro-2-boronic acid pyridine and 5-Bromo-2-methoxy-benzaldehyde. The desired product is isolated in 88%.

ESI MS m/z 232 [C$_{13}$H$_{10}$FNO$_2$+H]$^+$.

{4-[5-(6-Fluoro-pyridin-3-yl)-2-methoxy-benzylamino]-cyclohexyl}-methyl-carbamic acid tert-butyl ester

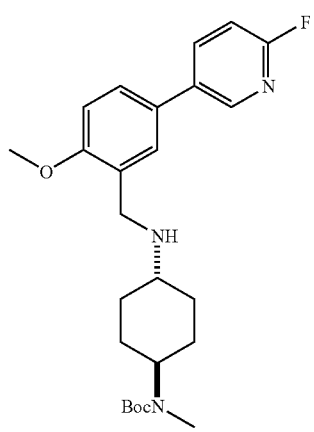

Following the synthetic protocol described in Method C'; {4-[5-(6-Fluoro-pyridin-3-yl)-2-methoxy-benzylamino]-cyclohexyl}-methyl-carbamic acid tert-butyl ester is prepared starting from 5-(6-Fluoro-pyridin-3-yl)-2-methoxy-benzaldehyde and (4-Amino-cyclohexyl)-methyl-carbamic acid tert-butyl ester. The desired product is isolated in 84%.

ESI MS m/z 444 $[C_{25}H_{34}FN_3O_3+H]^+$.

3-Chloro-4,7-difluoro-benzo[b]thiophene-2-carboxylic acid [5-(6-fluoro-pyridin-3-yl)-2-methoxy-benzyl]-(4-methylamino-cyclohexyl)-amide

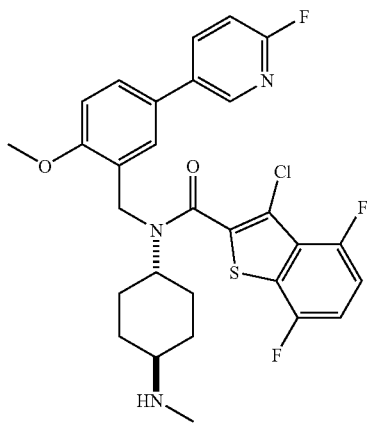

379

Following the synthetic protocol described in Method D'; 3-Chloro-4,7-difluoro-benzo[b]thiophene-2-carboxylic acid [5-(6-fluoro-pyridin-3-yl)-2-methoxy-benzyl]-(4-methylamino-cyclohexyl)-amide is prepared starting from {4-[5-(6-Fluoro-pyridin-3-yl)-2-methoxy-benzylamino]-cyclohexyl}-methyl-carbamic acid tert-butyl ester and 3-Chloro-4,7-difluoro-benzo[b]thiophene-2-carbonyl chloride. The desired product is isolated in 57%.

$^1$H NMR (400 MHz, DMSO-d$_6$, 60° C.) δ ppm 1.12-1.46 (m, 2H) 1.52-2.14 (m, 6H) 2.39-2.50 (m, 3H) 2.79-2.99 (m, 1H) 3.59-4.12 (m, 4H) 4.56-4.70 (m, 2H) 6.96-7.22 (m, 1H) 7.22-7.58 (m, 4H) 7.63 (dd, J=8.54, 2.20 Hz, 1H) 8.07-8.25 (m, 2H) 8.25-8.37 (m, 1H) 8.39-8.49 (m, 1H)

ESI MS m/z 574 $[C_{29}H_{27}ClF_3N_3O_2S+H]^+$.

Synthesis of Compound 380

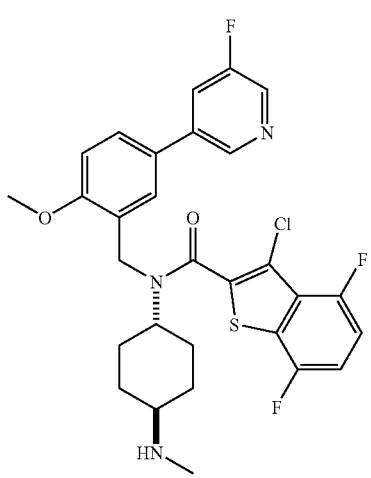

380

5-(5-Fluoro-pyridin-3-yl)-2-methoxy-benzaldehyde

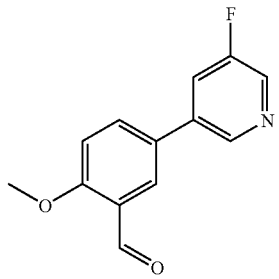

Following the synthetic protocol described in Method A'; 5-(5-Fluoro-pyridin-3-yl)-2-methoxy-benzaldehyde is prepared starting from 5-Fluoro-2-boronic acid pyridine and 5-Bromo-2-methoxy-benzaldehyde. The desired product is isolated in 44%.

ESI MS m/z 232 $[C_{13}H_{10}FNO_2+H]^+$.

{4-[5-(5-Fluoro-pyridin-3-yl)-2-methoxy-benzylamino]-cyclohexyl}-methyl-carbamic acid tert-butyl ester

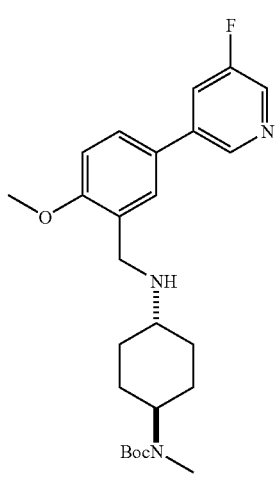

Following the synthetic protocol described in Method C'; {4-[5-(5-Fluoro-pyridin-3-yl)-2-methoxy-benzylamino]-cyclohexyl}-methyl-carbamic acid tert-butyl ester is prepared starting from 5-(5-Fluoro-pyridin-3-yl)-2-methoxy-benzaldehyde and (4-Amino-cyclohexyl)-methyl-carbamic acid tert-butyl ester. The desired product is isolated in 64%.

ESI MS m/z 444 $[C_{25}H_{34}FN_3O_3+H]^+$.

1H NMR (400 MHz, CHLOROFORM-d) δ ppm 1.37-1.54 (m, 12H) 1.67-1.81 (m, 2H) 1.99 (s, 2H) 2.07-2.20 (m, 2H) 2.52-2.63 (m, 1H) 2.70 (s, 3H) 3.92 (s, 3H) 3.96 (s, 2H) 5.32 (s, 1H) 6.98 (d, J=8.54 Hz, 1H) 7.50 (dd, J=2.44 Hz, 1H) 7.57 (t, J=2.32 Hz, 1H) 7.58-7.62 (m, 1H) 8.41 (d, J=2.68 Hz, 1H) 8.63 (t, J=1.71 Hz, 1H).

3-Chloro-4,7-difluoro-benzo[b]thiophene-2-carboxylic acid [5-(5-fluoro-pyridin-3-yl)-2-methoxy-benzyl]-(4-methylamino-cyclohexyl)-amide

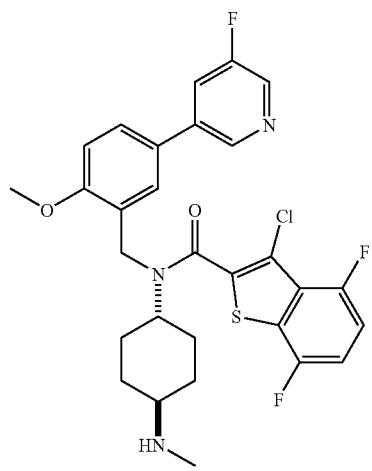

380

Following the synthetic protocol described in Method D'; 3-Chloro-4,7-difluoro-benzo[b]thiophene-2-carboxylic acid [5-(5-fluoro-pyridin-3-yl)-2-methoxy-benzyl]-(4-methylamino-cyclohexyl)-amide is prepared starting from {4-[5-(5-Fluoro-pyridin-3-yl)-2-methoxy-benzylamino]-cyclohexyl}-methyl-carbamic acid tert-butyl ester and 3-Chloro-4,7-difluoro-benzo[b]thiophene-2-carbonyl chloride. The desired product is isolated in 52%.

$^1$H NMR (300 MHz, DMSO-d$_6$, 60° C.) δ ppm 1.24-1.49 (m, 2H) 1.63-1.97 (m, 4H) 2.08 (d, J=10.98 Hz, 2H) 2.45 (t, J=4.85 Hz, 3H) 2.81-2.98 (m, 1H) 4.59-4.71 (m, 3H) 7.13 (d, J=7.87 Hz, 2H) 7.28-7.53 (m, 2H) 7.60 (d, J=2.20 Hz, 1H) 7.70 (dd, J=8.60, 2.38 Hz, 1H) 7.89 (dt, J=10.43, 2.20 Hz, 1H) 8.53 (d, J=2.38 Hz, 1H) 8.71 (s, 1H) 8.80 (s, 2H)

ESI MS m/z 574 $[C_{29}H_{27}ClF_3N_3O_2S+H]^+$.

Synthesis of Compound 381

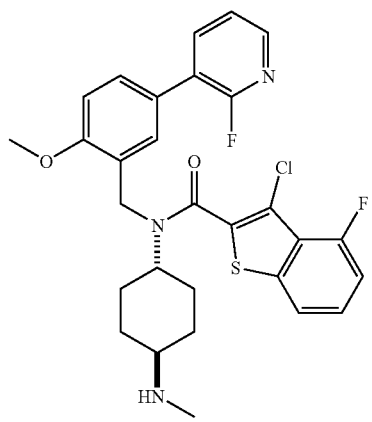

381

3-Chloro-4,7-difluoro-benzo[b]thiophene-2-carboxylic acid [5-(2-fluoro-pyridin-3-yl)-2-methoxy-benzyl]-(4-methylamino-cyclohexyl)-amide Following the synthetic protocol described in Method D'; 3-Chloro-4,7-difluoro-benzo[b]thiophene-2-carboxylic acid [5-(2-fluoro-pyridin-3-yl)-2-methoxy-benzyl]-(4-methylamino-cyclohexyl)-amide is prepared starting from {4-[5-(2-Fluoro-pyridin-3-yl)-2-methoxy-benzylamino]-cyclohexyl}-methyl-carbamic acid tert-butyl ester and 3-Chloro-4-fluoro-benzo[b]thiophene-2-carbonyl chloride. The desired product is isolated in 18%.

$^1$H NMR (400 MHz, DMSO-d$_6$, 60° C.) δ ppm 1.12-1.45 (m, 2H) 1.58-1.91 (m, 4H) 1.91-2.12 (m, 2H) 2.35-2.47 (m, 3H) 2.77-3.02 (m, 1H) 3.58-4.17 (m, 4H) 4.50-4.74 (m, 2H) 6.95-7.22 (m, 1H) 7.24-7.42 (m, 1H) 7.42-7.63 (m, 4H) 7.77-8.09 (m, 2H) 8.09-8.26 (m, 2H) 8.27-8.43 (m, 1H)

ESI MS m/z 556 $[C_{29}H_{28}ClF_2N_3O_2S+H]^+$.

Synthesis of Compound 382

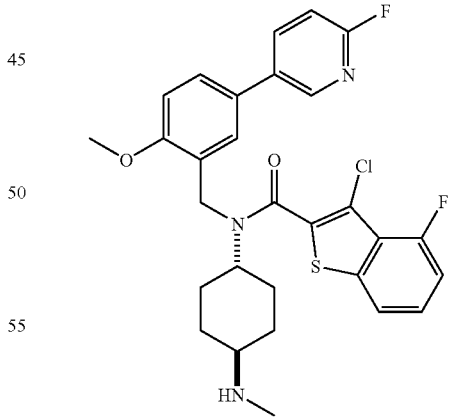

382

3-Chloro-4-fluoro-benzo[b]thiophene-2-carboxylic acid [5-(6-fluoro-pyridine-3-yl)-2-methoxy-benzyl]-(4-methylamino-cyclohexyl)-amide Following the synthetic protocol described in Method D'; 3-Chloro-4,7-difluoro-benzo[b]thiophene-2-carboxylic acid [5-(6-fluoro-pyridin-3-yl)-2-methoxy-benzyl]-(4-methylamino-cyclohexyl)-amide is prepared starting from {4-[5-(6-Fluoro-pyridin-3-yl)-2-methoxy-benzylamino]-cyclohexyl}-methyl-carbamic acid tert-butyl ester and 3-Chloro-4-fluoro-benzo[b]thiophene-2-carbonyl chloride. The desired product is isolated in 50%.

$^1$H NMR (400 MHz, DMSO-d$_6$, 60° C.) δ ppm 1.09-1.45 (m, 2H) 1.55-2.16 (m, 6H) 2.33-2.49 (m, 2H) 2.80-3.02 (m, 1H) 3.59-4.15 (m, 4H) 4.51-4.72 (m, 2H) 6.97-7.22 (m, 1H) 7.23-7.69 (m, 5H) 7.76-8.07 (m, 1H) 8.08-8.55 (m, 4H)

ESI MS m/z 556 [C$_{29}$H$_{28}$ClF$_2$N$_3$O$_2$S+H]$^+$.

Synthesis of Compound 383

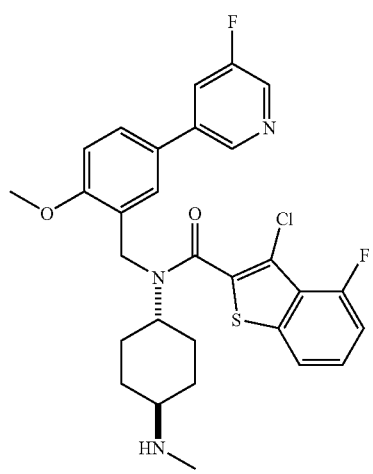

383

3-chloro-4-fluoro-N-(5-(5-fluoropyridin-3-yl)-2-methoxybenzyl)-N-((1s,4s)-4-(methylamino)cyclohexyl)benzo[b]thiophene-2-carboxamide Following the synthetic protocol described in Method D'; 3-Chloro-4,7-difluoro-benzo[b]thiophene-2-carboxylic acid [5-(5-fluoro-pyridin-3-yl)-2-methoxy-benzyl]-(4-methylamino-cyclohexyl)-amide is prepared starting from {4-[5-(5-Fluoro-pyridin-3-yl)-2-methoxy-benzylamino]-cyclohexyl}-methyl-carbamic acid tert-butyl ester and 3-Chloro-4,7-difluoro-benzo[b]thiophene-2-carbonyl chloride. The desired product is isolated in 46%.

$^1$H NMR (400 MHz, DMSO-d$_6$, 60° C.) δ ppm 1.22-1.46 (m, 2H) 1.63-1.96 (m, 4H) 1.99-2.14 (m, 2H) 2.40-2.48 (m, 3H) 2.81-2.97 (m, 1H) 3.76-3.98 (m, 4H) 4.62-4.71 (m, 2H) 7.06-7.21 (m, 1H) 7.23-7.38 (m, 1H) 7.45-7.57 (m, 1H) 7.57-7.62 (m, 1H) 7.64-7.73 (m, 1H) 7.82-7.95 (m, 2H) 8.50-8.54 (m, 1H) 8.58-8.77 (m, 3H)

ESI MS m/z 556 [C$_{29}$H$_{28}$ClF$_2$N$_3$O$_2$S+H]$^+$.

Synthesis of Compound 384

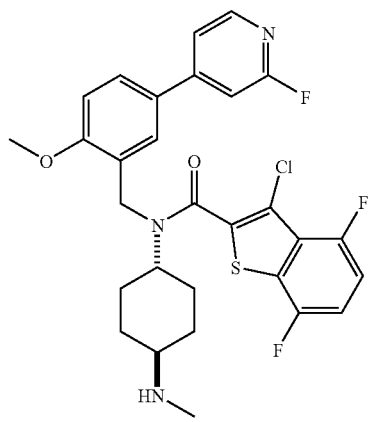

384

5-(3-Fluoro-pyridin-4-yl)-2-methoxy-benzaldehyde

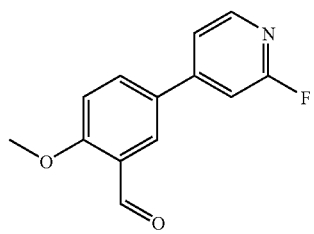

Following the synthetic protocol described in Method A'; 5-(3-Fluoro-pyridin-4-yl)-2-methoxy-benzaldehyde is prepared starting from 2-Fluoro-4-boronic acid pyridine and 5-Bromo-2-methoxy-benzaldehyde. The desired product is isolated in 82%.

ESI MS m/z 232 [C$_{13}$H$_{10}$FNO$_2$+H]$^+$.

{4-[5-(2-Fluoro-pyridin-4-yl)-2-methoxy-benzylamino]-cyclohexyl}-methyl-carbamic acid tert-butyl ester

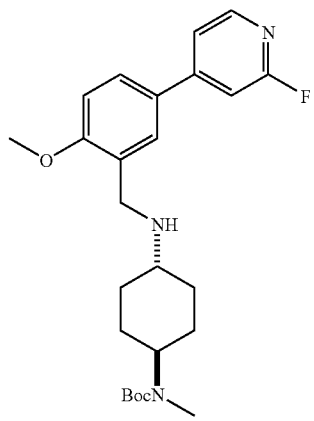

Following the synthetic protocol described in Method C'; {4-[5-(2-Fluoro-pyridin-4-yl)-2-methoxy-benzylamino]-cyclohexyl}-methyl-carbamic acid tert-butyl ester is prepared starting from 5-(3-Fluoro-pyridin-4-yl)-2-methoxy-benzaldehyde and (4-Amino-cyclohexyl)-methyl-carbamic acid tert-butyl ester. The desired product is isolated in 58%.

ESI MS m/z 444 $[C_{25}H_{34}FN_3O_3+H]^+$.

3-Chloro-4,7-difluoro-benzo[b]thiophene-2-carboxylic acid [5-(2-fluoro-pyridin-4-yl)-2-methoxy-benzyl]-(4-methylamino-cyclohexyl)-amide

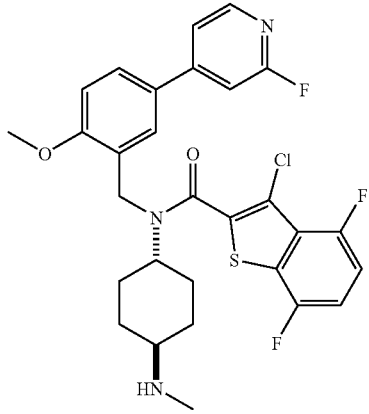

384

Following the synthetic protocol described in Method D'; 3-Chloro-4,7-difluoro-benzo[b]thiophene-2-carboxylic acid [5-(2-fluoro-pyridin-4-yl)-2-methoxy-benzyl]-(4-methylamino-cyclohexyl)-amide is prepared starting from {4-[5-(2-Fluoro-pyridin-4-yl)-2-methoxy-benzylamino]-cyclohexyl}-methyl-carbamic acid tert-butyl ester and 3-Chloro-4,7-difluoro-benzo[b]thiophene-2-carbonyl chloride. The desired product is isolated in 52%.

$^1$H NMR (400 MHz, DMSO-d$_6$, 60° C.) δ ppm 1.21-1.43 (m, 2H) 1.58-2.14 (m, 6H) 2.81-3.02 (m, 1H) 4.62-4.70 (m, 4H) 7.09-7.20 (m, 1H) 7.30-7.50 (m, 3H) 7.56 (dt, J=3.57, 1.65 Hz, 1H) 7.66 (d, J=2.20 Hz, 1H) 7.79 (dd, J=8.60, 2.38 Hz, 1H) 8.15-8.30 (m, J=5.31 Hz, 2H) 8.27 (d, J=5.31 Hz, 1H)

ESI MS m/z 574 $[C_{29}H_{27}ClF_3N_3O_2S+H]^+$.

Synthesis of Compound 385

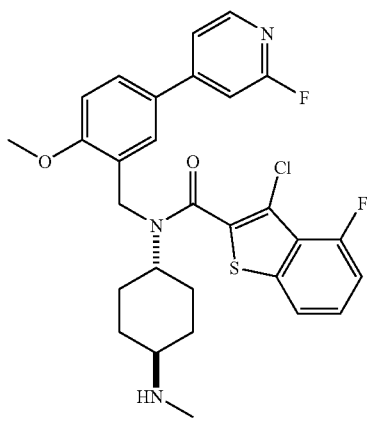

385

3-Chloro-4-fluoro-benzo[b]thiophene-2-carboxylic acid [5-(2-fluoro-pyridin-4-yl)-2-methoxy-benzyl]-(4-methylamino-cyclohexyl)-amide Following the synthetic protocol described in Method D'; 3-Chloro-4-fluoro-benzo[b]thiophene-2-carboxylic acid [5-(2-fluoro-pyridin-4-yl)-2-methoxy-benzyl]-(4-methylamino-cyclohexyl)-amide is prepared starting from {4-[5-(2-Fluoro-pyridin-4-yl)-2-methoxy-benzylamino]-cyclohexyl}-methyl-carbamic acid tert-butyl ester and 3-Chloro-4-fluoro-benzo[b]thiophene-2-carbonyl chloride. The desired product is isolated in 49%.

$^1$H NMR (400 MHz, DMSO-d$_6$, 60° C.) δ ppm 1.17-1.41 (m, 2H) 1.61-1.93 (m, 4H) 1.93-2.10 (m, 2H) 2.45-2.48 (m, 1H) 2.81-2.99 (m, 1H) 3.76-4.01 (m, 4H) 4.60-4.71 (m, 2H) 7.07-7.23 (m, 1H) 7.24-7.41 (m, 2H) 7.52 (br. s., 1H) 7.56 (dt, J=3.52, 1.74 Hz, 1H) 7.66 (d, J=2.20 Hz, 1H) 7.79 (dd, J=8.51, 2.29 Hz, 1H) 7.91 (br. s., 1H) 8.19 (m, 2H) 8.28 (d, J=5.49 Hz, 1H)

ESI MS m/z 556 $[C_{29}H_{28}ClF_2N_3O_2S+H]^+$.

Synthesis of Compound 386

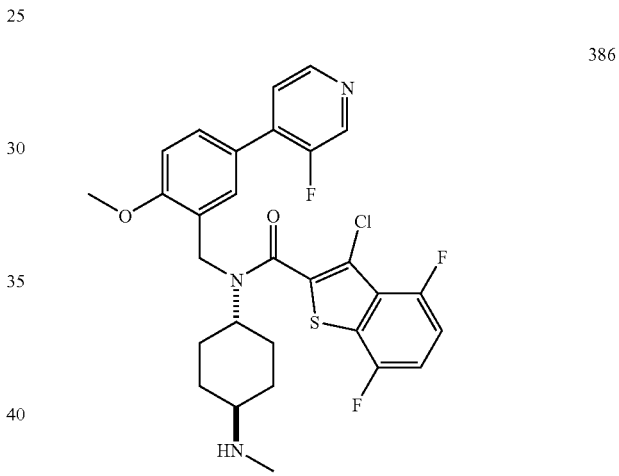

386

Synthesis of 5-(3-Fluoro-pyridin-4-yl)-2-methoxy-benzaldehyde

Following the synthetic protocol described in Method A'; 5-(3-Fluoro-pyridin-4-yl)-2-methoxy-benzaldehyde is prepared starting from 3-Fluoro-4-boronic acid pyridine and 5-Bromo-2-methoxy-benzaldehyde. The desired product is isolated in 49%.

ESI MS m/z 232 $[C_{13}H_{10}FNO_2+H]^+$.

{4-[5-(3-Fluoro-pyridin-4-yl)-2-methoxy-benzylamino]-cyclohexyl}-methyl-carbamic acid tert-butyl ester

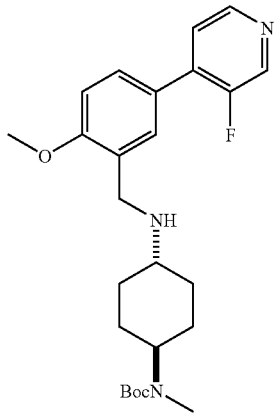

Following the synthetic protocol described in Method C'; {4-[5-(3-Fluoro-pyridin-4-yl)-2-methoxy-benzylamino]-cyclohexyl}-methyl-carbamic acid tert-butyl ester is prepared starting from 5-(3-Fluoro-pyridin-4-yl)-2-methoxy-benzaldehyde and (4-Amino-cyclohexyl)-methyl-carbamic acid tert-butyl ester. The desired product is isolated in 67%.

ESI MS m/z 444 $[C_{25}H_{34}FN_3O_3+H]^+$.

3-Chloro-4,7-difluoro-benzo[b]thiophene-2-carboxylic acid [5-(3-fluoro-pyridin-4-yl)-2-methoxy-benzyl]-(4-methylamino-cyclohexyl)-amide

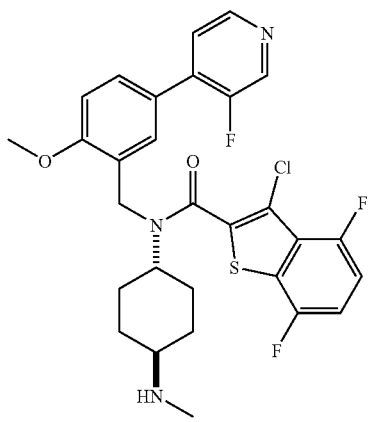

386

Following the synthetic protocol described in Method D'; 3-Chloro-4,7-difluoro-benzo[b]thiophene-2-carboxylic acid [5-(3-fluoro-pyridin-4-yl)-2-methoxy-benzyl]-(4-methylamino-cyclohexyl)-amide is prepared starting from {4-[5-(3-Fluoro-pyridin-4-yl)-2-methoxy-benzylamino]-cyclohexyl}-methyl-carbamic acid tert-butyl ester and 3-Chloro-4,7-difluoro-benzo[b]thiophene-2-carbonyl chloride. The desired product is isolated in 54%.

$^1$H NMR (400 MHz, DMSO-d$_6$, 60° C.) δ ppm 1.25-1.51 (m, 2H) 1.63-1.94 (m, 4H) 2.00-2.14 (m, 2H) 2.41-2.47 (m, 3H) 2.82-2.96 (m, 1H) 3.71-4.06 (m, 4H) 4.67 (s, 2H) 7.51-7.65 (m, 3H) 8.49 (d, J=4.94 Hz, 1H) 8.63 (d, J=2.93 Hz, 1H) 8.85 (m, 2H)

ESI MS m/z 574 $[C_{29}H_{27}ClF_3N_3O_2S+H]^+$.

Synthesis of Compound 387

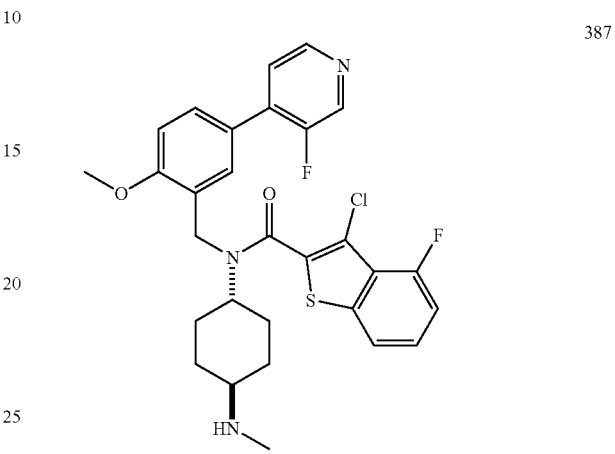

387

3-Chloro-4-fluoro-benzo[b]thiophene-2-carboxylic acid [5-(3-fluoro-pyridin-4-yl)-2-methoxy-benzyl]-(4-methylamino-cyclohexyl)-amide Following the synthetic protocol described in Method D'; 3-Chloro-4-fluoro-benzo[b]thiophene-2-carboxylic acid [5-(3-fluoro-pyridin-4-yl)-2-methoxy-benzyl]-(4-methylamino-cyclohexyl)-amide is prepared starting from {4-[5-(2-Fluoro-pyridin-4-yl)-2-methoxy-benzylamino]-cyclohexyl}-methyl-carbamic acid tert-butyl ester and 3-Chloro-4-fluoro-benzo[b]thiophene-2-carbonyl chloride. The desired product is isolated in 61%.

$^1$H NMR (400 MHz, DMSO-d$_6$, 60° C.) δ ppm 1.26-1.46 (m, 2H) 1.64-1.95 (m, 4H) 1.97-2.18 (m, 2H) 2.37-2.48 (m, 3H) 2.77-3.00 (m, 1H) 3.70-4.05 (m, 4H) 4.66 (s, 2H) 7.47-7.66 (m, 4H) 7.81-8.02 (m, 1H) 8.49 (d, J=4.94 Hz, 1H) 8.63 (d, J=2.75 Hz, 1H) 8.73-9.00 (m, 2H)

ESI MS m/z 556 $[C_{29}H_{28}ClF_2N_3O_2S+H]^+$.

Synthesis of Compound 388

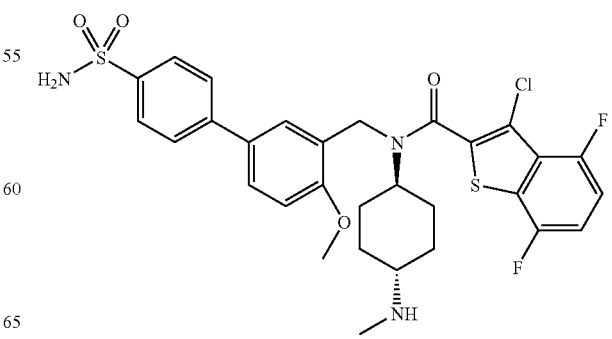

297 tert-Butyl {4-[(4-methoxy-4'-sulfamoyl-biphenyl-3-ylmethyl)-amino]-cyclohexyl}-methyl-carbamate (216)

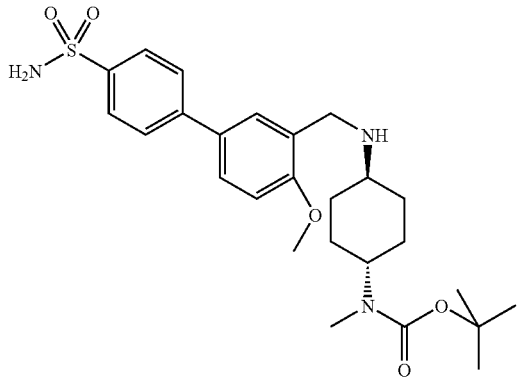

Boronic acid 4 (400 mg, 1.02 mmol) is coupled to 4-bromobenzene-sulfonamide (241 mg, 1.02 mmol) using Method A. On filtration of the cooled reaction mixture through celite and removal of the solvents in vacuo, the crude residue obtained is used in the next synthetic step without further purification.

Yield: 514 mg.

LC/MS $t_r$ 1.24 min.

MS (ES+) m/z 504 (M+H).

tert-Butyl {4-[(3-chloro-4,7-difluoro-benzo[b]thiophene-2-carbonyl)-(4-methoxy-4'-sulfamoyl-biphenyl-3-ylmethyl)-amino]-cyclohexyl}-methyl-carbamate (217)

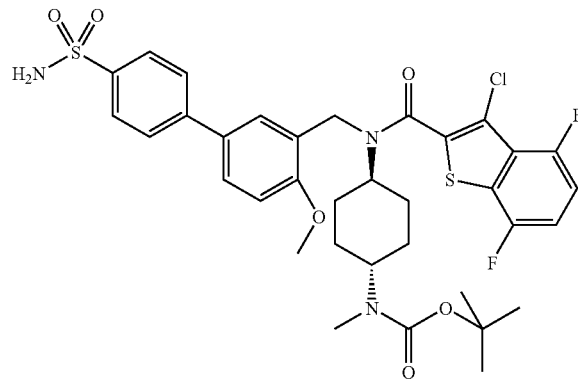

Crude biaryl amine 216 (514 mg) is treated with acid chloride 8 (327 mg, 1.22 mmol) using Method D to give the title compound.

Yield: 324 mg (43% over two steps) containing triphenylphosphine oxide (ca. 14%).

LC/MS $t_r$ 1.79 min.

MS (ES+) m/z 736, 734 (M+H), 680, 678 (M-C(CH$_3$)$_3$+H).

298

3-Chloro-4,7-difluoro-benzo[b]thiophene-2-carboxylic acid (4-methoxy-4'-sulfamoyl-biphenyl-3-ylmethyl)-(4-methylamino-cyclohexyl)-amide hydrochloride (218)

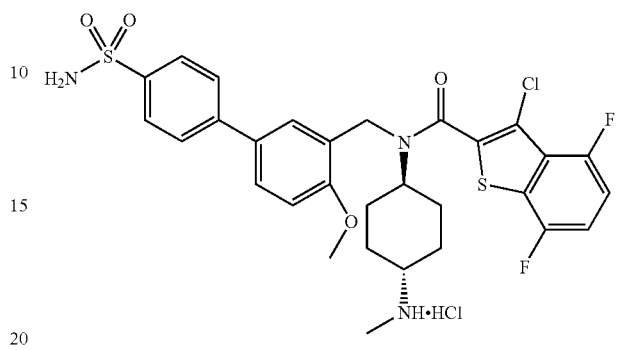

tert-Butyl carbamate 217 (100 mg, 0.14 mmol) is deprotected using Method F. The isolated salt is then dissolved in the minimum amount of DCM and added dropwise to cold (0° C.) TBME (25 mL). The resultant pale yellow precipitate is isolated by filtration, washed with TBME (10 mL) and diethyl ether (10 mL) and dried to afford the title compound.

Yield: 65 mg (69%).

LC/MS $t_r$ 1.33 min.

MS (ES+) m/z 636, 634 (M+H).

Synthesis of Compound 389

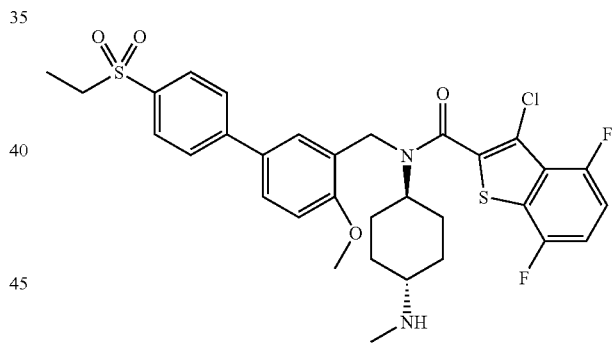

tert-Butyl [4-(5-bromo-2-methoxy-benzylamino)-cyclohexyl]-methyl-carbamate (219)

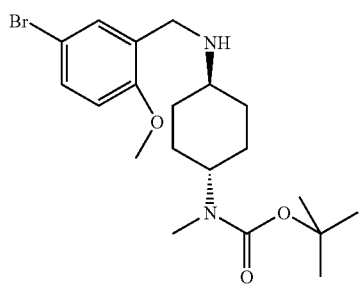

Amine 3 (1.0 g, 4.38 mmol) is treated with 5-bromo-2-methoxy-benzaldehyde (943 mg, 4.38 mmol) in accordance with Method C. Purification by column chromatography (2:1 EtOAc to heptane then 1:1 MeOH and DCM with 2% triethylamine) gives the title compound.

Yield: 1.27 g (68%).
LC/MS $t_r$ 1.30 min.
MS (ES+) m/z 429, 427 (M+H).

tert-Butyl {4-[(5-bromo-2-methoxy-benzyl)-(3-chloro-4,7-difluoro-benzo[b]thiophene-2-carbonyl)-amino]-cyclohexyl}-methyl-carbamate (220)

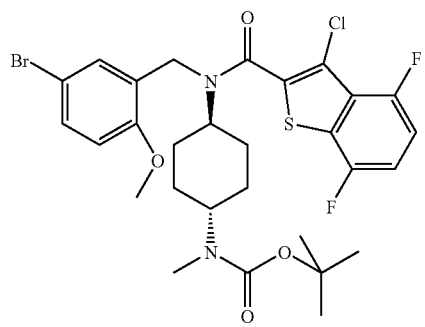

Biaryl amine 219 (0.50 g, 1.17 mmol) is treated with acid chloride 8 (344 mg, 1.29 mmol) using Method D to give the title compound.

Yield: 520 mg (67%).
LC/MS $t_r$ 2.01 min.
MS (ES+) m/z 605, 603, 601 (M-C(CH$_3$)$_3$+H).

tert-Butyl {4-[(3-chloro-4,7-difluoro-benzo[b]thiophene-2-carbonyl)-(4'-ethanesulfonyl-4-methoxy-biphenyl-3-ylmethyl)-amino]-cyclohexyl}-methyl-carbamate (221)

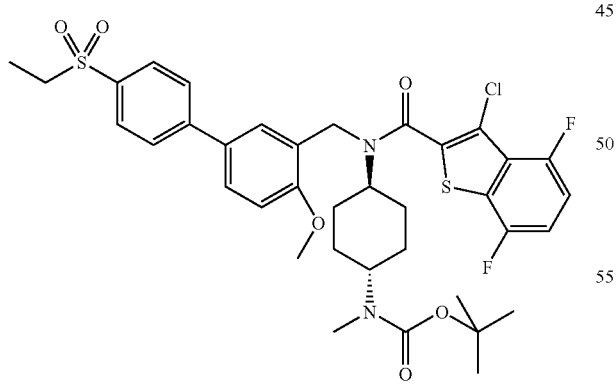

Aryl bromide 220 (200 mg, 0.30 mmol) is coupled to 4-(ethanesulfonyl)-benzene boronic acid (65 mg, 0.30 mmol) using Method A to afford the title compound.

Yield: 94 mg (42%).
LC/MS $t_r$ 1.92 min.
MS (ES+) m/z 693, 691 (M-C(CH$_3$)$_3$+H).

3-Chloro-4,7-difluoro-benzo[b]thiophene-2-carboxylic acid (4'-ethanesulfonyl-4-methoxy-biphenyl-3-ylmethyl)-(4-methylamino-cyclohexyl)-amide hydrochloride (222)

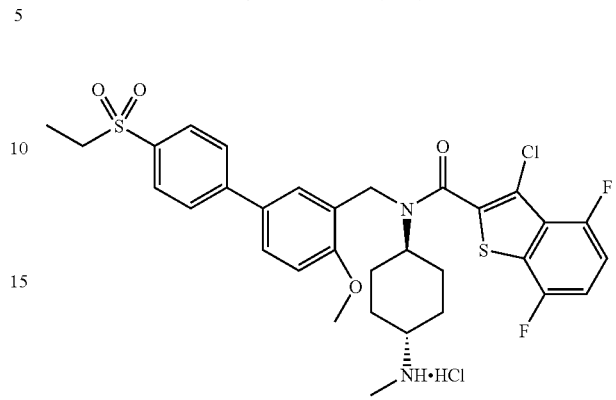

tert-Butyl carbamate 221 (94 mg, 0.13 mmol) is deprotected using Method F to afford the title compound.

Yield: 88 mg (quant.).
LC/MS $t_r$ 1.39 min.
MS (ES+) m/z 649, 647 (M+H).

Synthesis of Compound 390

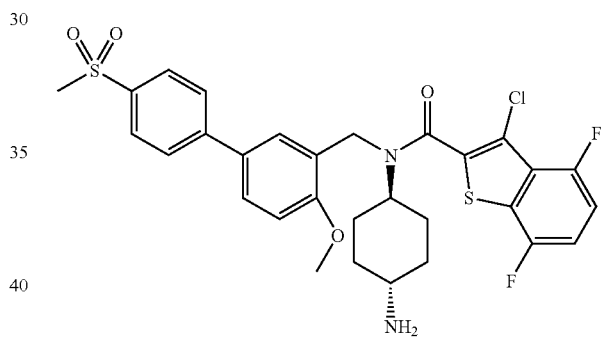

tert-Butyl (4-amino-cyclohexyl)-carbamate (223)

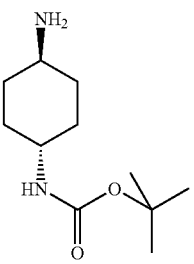

A solution of trans-1,4-diaminocyclohexane (1 kg, 8.76 mol) in THF (14 L) at 0° C. is treated with a solution of di-tert-butyl dicarbonate (238 g, 1.09 mol) in THF (500 mL) over 30 minutes. The reaction mixture is then warmed to RT, stirred 16 h and filtered. The isolated solids are washed with THF (3×2 L) and then the filtrate is reduced in vacuo. The residue thus obtained is suspended in water (8 L) and filtered

3-[(4-BOC-cyclohexylamino)-methyl]-4-methoxy-benzene boronic acid (224)

once more. The filtrate is extracted with DCM (3×2 L) and the combined organic phases dried over Na$_2$SO$_4$ and reduced in vacuo. The residue is taken up in TBME (2.4 L), washed with water (3×300 mL) then concentrated to ~400 mL. Heptane (1 L) is added to induce precipitation of the desired amine; the resulting suspension is stirred 1 h at 0° C., filtered and washed with heptane (2×100 mL) to afford the title compound.

Yield: 100.5 g (43%).

3-[(4-BOC-cyclohexylamino)-methyl]-4-methoxy-benzene boronic acid (224)

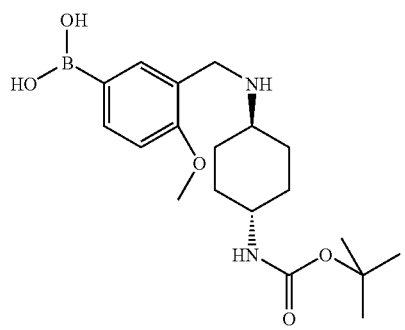

Amine 223 (598 mg, 2.79 mmol) is treated with 3-formyl-4-methoxyphenylboronic acid (500 mg, 2.79 mmol) in accordance with Method C to give the crude title compound.

Yield: 968 mg (quant.).

LC/MS t$_r$ 1.10 min.

MS (ES+) m/z 379 (M+H), 323 (M-C(CH$_3$)$_3$+H).

tert-Butyl {4-[(4'-methanesulfonyl-4-methoxy-biphenyl-3-ylmethyl)-amino]-cyclohexyl}-carbamate (225)

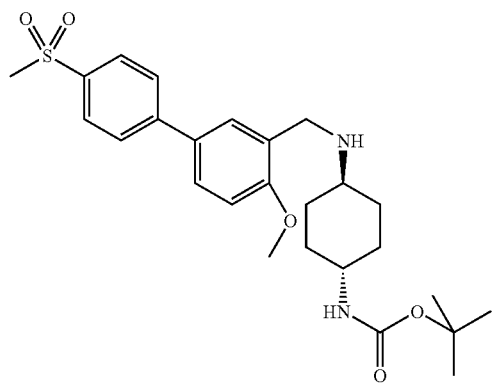

Boronic acid 224 (500 mg, 1.32 mmol) is coupled to 4-bromophenyl methyl sulfone (311 mg, 1.32 mmol) using Method A to give the title compound.

Yield: 502 mg (77%).

LC/MS t$_r$ 1.28 min.

MS (ES+) m/z 489 (M+H).

tert-Butyl {4-[(3-chloro-4,7-difluoro-benzo[b]thiophene-2-carbonyl)-(4'-methanesulfonyl-4-methoxy-biphenyl-3-ylmethyl)-amino]-cyclohexyl}-carbamate (226)

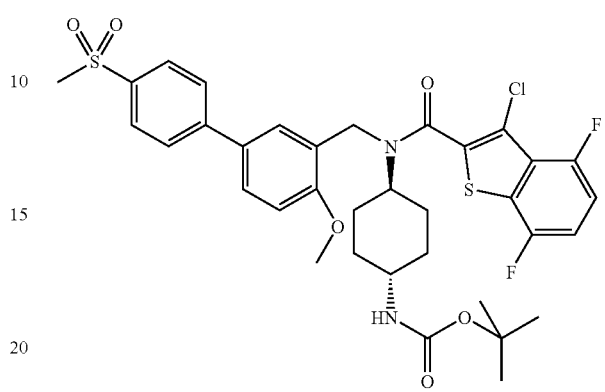

Biaryl amine 225 (502 mg, 1.02 mmol) is treated with acid chloride 8 (301 mg, 1.13 mmol) using Method D to give the title compound.

Yield: 452 mg (62%).

LC/MS t$_r$ 1.79 min.

MS (ES+) m/z 721, 719 (M+H), 665, 663 (M-C(CH$_3$)$_3$+H).

3-Chloro-4,7-difluoro-benzo[b]thiophene-2-carboxylic acid (4-amino-cyclohexyl)-(4'-methanesulfonyl-4-methoxy-biphenyl-3-ylmethyl)-amide hydrochloride (227)

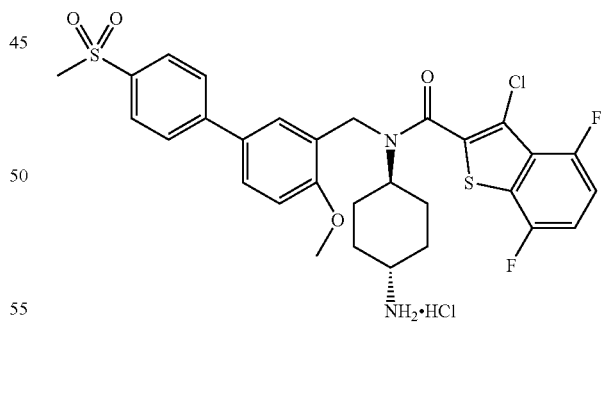

tert-Butyl carbamate 226 (452 mg, 0.62 mmol) is deprotected using Method F to give the title compound.

Yield: 332 mg (85%).

LC/MS t$_r$ 1.35 min.

MS (ES+) m/z 621, 619 (M+H).

Synthesis of Compound 391

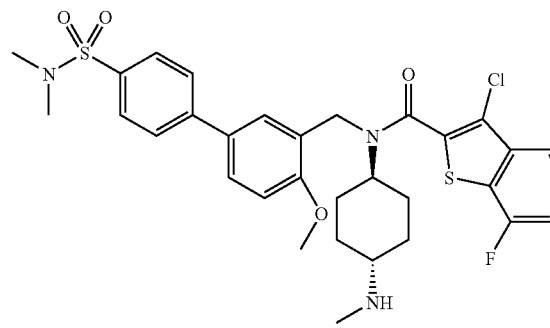

tert-Butyl {4-[(3-chloro-4,7-difluoro-benzo[b]thiophene-2-carbonyl)-(4'-dimethylsulfamoyl-4-methoxy-biphenyl-3-ylmethyl)-amino]-cyclohexyl}-methyl-carbamate (228)

A stirred suspension of hexane-washed sodium hydride (27 mg, 0.68 mmol, 60% dispersion in mineral oil) in THF (10 mL) at 0° C. is treated with sulfonamide 217 (100 mg, 0.14 mmol) in one portion. After stirring 0.5 h, the reaction mixture is treated with iodomethane (90 μL, 1.40 mmol) via syringe and stirred 16 h at RT. The reaction is then diluted with water (10 mL) and extracted into EtOAc (3×20 mL). The combined EtOAc phases are dried ($Na_2SO_4$) and reduced in vacuo to afford the title compound.

Yield: 107 mg (quant.).
LC/MS $t_r$ 1.92 min.
MS (ES+) m/z 708, 706 (M-C($CH_3$)$_3$+H).

3-Chloro-4,7-difluoro-benzo[b]thiophene-2-carboxylic acid (4'-dimethylsulfamoyl-4-methoxy-biphenyl-3-ylmethyl)-(4-methylamino-cyclohexyl)-amide trifluoroacetate (229)

tert-Butyl carbamate 228 (107 mg, 0.14 mmol) is deprotected using Method G. The isolated salt is then dissolved in the minimum amount of DCM and added dropwise to cold (0° C.) TBME (10 mL), but the product failed to precipitate out cleanly. Thus the TBME is removed in vacuo and the residue purified by column chromatography (gradient elution—30-100% EtOAc in heptane with 0.5% triethylamine) followed by preparative HPLC to afford the title compound.

Yield: 23 mg (21%).
LC/MS $t_r$ 1.46 min.
MS (ES+) m/z 664, 662 (M+H).

Synthesis of Compound 392

5-Bromo-2-methylbenzaldehyde (230)

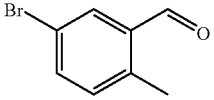

This compound is prepared from o-tolualdehyde (1.0 g, 8.32 mmol) in accordance with the procedure of Kelly et al. (Kelly, T. R.; Silva, R. A.; De Silva, H.; Jasmin, S.; Zhao, Y. *J. Am. Chem. Soc.*, 2000, 122, 6935-6949).

Yield: 19 mg (1.1%).

2-Methyl-5-pyridin-4-ylbenzaldehyde (231)

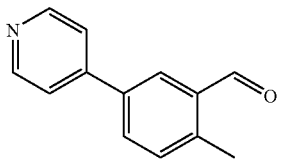

Pyridine-4-boronic acid (14 mg, 96 μmol) is coupled to aryl bromide 230 (19 mg, 96 μmol) using Method A to give the title compound.

Yield: 16 mg (84%).
LC/MS $t_r$ 0.89 min.
MS (ES+) m/z 198 (M+H).

tert-Butyl methyl-[4-(2-methyl-5-pyridin-4-yl-benzylamino)-cyclohexyl]-carbamate (232)

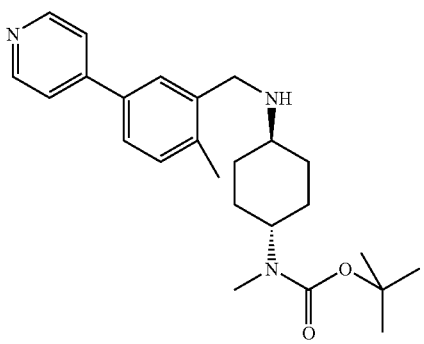

Amine 3 (19 mg, 81 μmol) is treated with aldehyde 231 (16 mg, 81 μmol) in accordance with Method C to give the crude title compound.

Yield: 36 mg.
LC/MS $t_r$ 0.73 min.
MS (ES+) m/z 310 (M-CO$_2$C(CH$_3$)$_3$+H).

tert-Butyl {4-[(3-chloro-4,7-difluoro-benzo[b]thiophene-2-carbonyl)-(2-methyl-5-pyridin-4-yl-benzyl)-amino]-cyclohexyl}-methyl-carbamate (233)

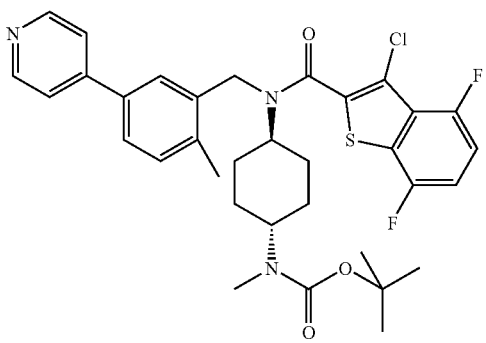

Crude biaryl amine 232 (36 mg) is treated with acid chloride 8 (29 mg, 0.11 mmol) using Method D to afford the title compound.

Yield: 27 mg (52% over two steps).
LC/MS $t_r$ 1.65 min.
MS (ES+) m/z 642, 640 (M+H).

3-Chloro-4,7-difluoro-benzo[b]thiophene-2-carboxylic acid (4-methylamino-cyclohexyl)-(2-methyl-5-pyridin-4-yl-benzyl)-amide bis(trifluoroacetate) (234)

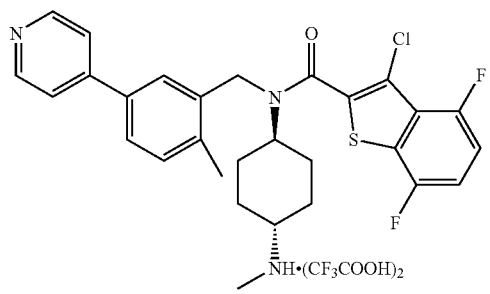

tert-Butyl carbamate 233 (27 mg, 42 μmol) is deprotected using Method G. The isolated salt is then dissolved in the minimum amount of DCM and added dropwise to cold (0° C.) TBME (5 mL). The resultant cream precipitate is isolated by filtration and dried to afford the title compound.

Yield: 13 mg (41%).
LC/MS $t_r$ 1.16 min.
MS (ES+) m/z 542, 540 (M+H).

Synthesis of Compound 393

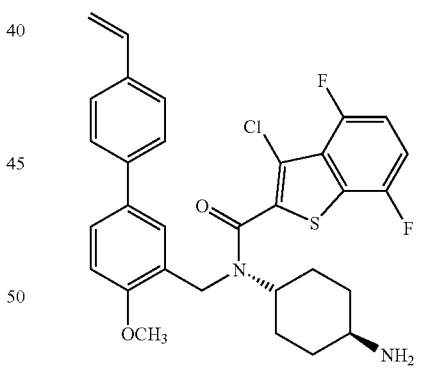

393

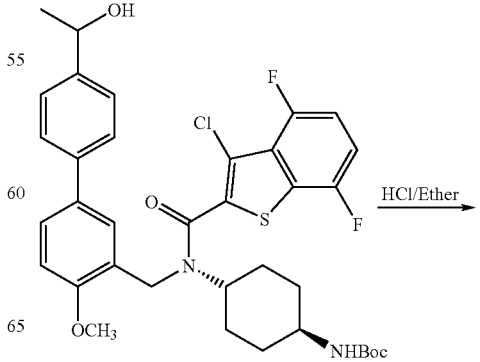

HCl/Ether

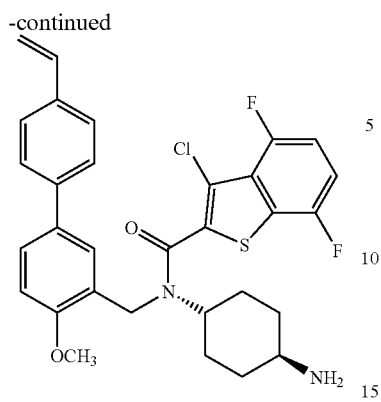

Treatment of tert-butyl (1r,4r)-4-(3-chloro-4,7-difluoro-N-((4'-(1-hydroxyethyl)-4-methoxybiphenyl-3-yl)methyl)benzo[b]thiophene-2-carboxamido)cyclohexylcarbamate (preparable by methods described herein) with ethereal hydrochloric leads to the quantitative formation of N-((1r,4r)-4-aminocyclohexyl)-3-chloro-4,7-difluoro-N-((4-methoxy-4'-vinylbiphenyl-3-yl)methyl)benzo[b]thiophene-2-carboxamide as the HCl salt.

$^1$H NMR (400 MHz, DMSO-d$_6$, 60° C.) δ ppm 0.51-0.69 (m, 1H) 0.63-0.85 (m, 2H) 1.05-1.47 (m, 6H) 1.69-1.87 (m, 2H) 2.16-2.43 (m, 3H) 2.91-3.26 (m, 3H) 3.78-3.89 (m, 1H) 3.97 (s, 2H) 6.20-6.31 (m, 1H) 6.31-6.46 (m, 1H) 6.58-6.94 (m, 4H) 7.10 (1H) 7.21 (d, J=8.24 Hz, 1H)

ESI MS m/z 567 [C$_{31}$H$_{29}$ClF$_2$N$_2$O$_2$S+H]$^+$.

Synthesis of Compound 394

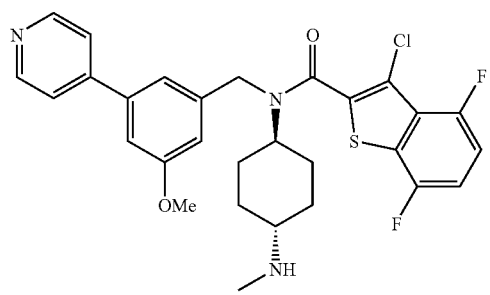

3-Hydroxy-5-methoxybenzaldehyde (240)

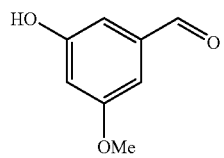

A stirred solution of 3,5-dihydroxybenzaldehyde (1.0 g, 7.24 mmol) in DMF (20 mL) is treated with sodium hydride (319 mg, 8.0 mmol, 60% dispersion in mineral oil) at 0° C. After warming to RT and stirring 0.5 h, the reaction is treated with iodomethane (0.50 mL, 8.0 mmol) via syringe and stirred 16 h. It is then diluted with 1 M HCl (100 mL) and extracted into EtOAc (50 mL). The EtOAc phase is washed with 1 M HCl (50 mL), water (2×50 mL) and brine (50 mL), dried over Na$_2$SO$_4$ then the EtOAc removed in vacuo. The title compound is obtained after chromatography (gradient elution—0-50% EtOAc in heptane).

Yield: 315 mg (29%).

3-Formyl-5-methoxyphenyl trifluoromethanesulfonate (241)

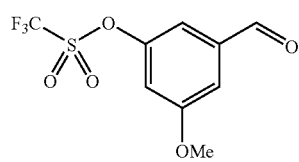

A stirred solution of phenol 240 (315 mg, 2.07 mmol) and pyridine (0.33 μL, 4.14 mmol) in DCM (8 mL) and THF (8 mL) at 0° C. is treated with trifluoromethanesulfonic anhydride (0.40 mL, 2.38 mmol) dropwise via syringe over 5 minutes. After warming to RT and stirring 16 h, the reaction is diluted with water (25 mL) and extracted into DCM (3×50 mL). The combined DCM phases are then dried over Na$_2$SO$_4$ and reduced in vacuo. The title compound is obtained after chromatography (gradient elution—0-40% EtOAc in heptane).

Yield: 387 mg (66%).

LC/MS t$_r$ 1.54 min.

MS (ES+) mass ion not detected.

3-Methoxy-5-pyridin-4-ylbenzaldehyde (242)

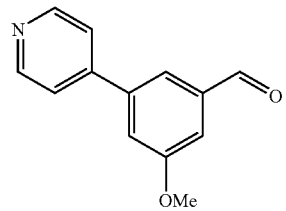

Pyridine-4-boronic acid (50 mg, 0.35 mmol) is coupled to aryl triflate 241 (66 mg, 0.23 mmol) using Method A to give the title compound.

Yield: 22 mg (45%).

LC/MS t$_r$ 0.91 min.

MS (ES+) m/z 214 (M+H).

309 tert-Butyl [4-(3-methoxy-5-pyridin-4-yl-benzylamino)-cyclohexyl]-methyl-carbamate (243)

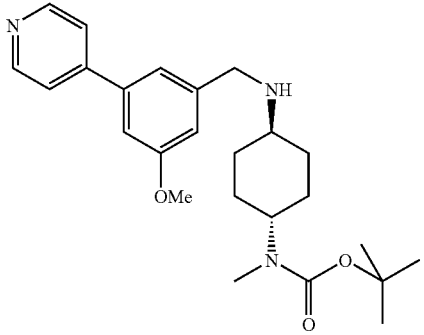

Amine 3 (17 mg, 75 μmol) is treated with aldehyde 242 (16 mg, 75 mmol) in accordance with Method C. The title compound is obtained after chromatography (gradient elution—40-100% EtOAc in heptane with 0.5% triethylamine).

Yield: 18 mg (56%).
LC/MS $t_r$ 1.08 min.
MS (ES+) m/z 426 (M+H).

tert-Butyl {4-[(3-chloro-4,7-difluoro-benzo[b]thiophene-2-carbonyl)-(3-methoxy-5-pyridin-4-yl-benzyl)-amino]-cyclohexyl}-methyl-carbamate (244)

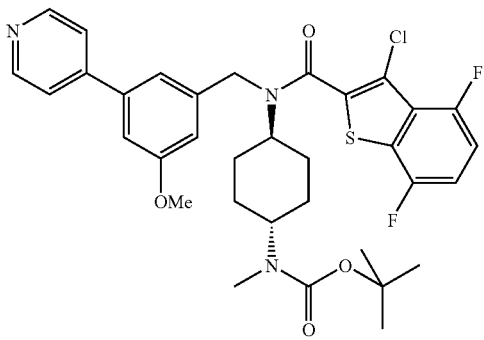

Biaryl amine 243 (18 mg, 42 μmol) is treated with acid chloride 8 (14 mg, 51 μmol) using Method D to afford the title compound.

Yield: 15 mg (54%).
LC/MS $t_r$ 1.60 min.
MS (ES+) m/z 658, 656 (M+H).

310

3-Chloro-4,7-difluoro-benzo[b]thiophene-2-carboxylic acid (3-methoxy-5-pyridin-4-yl-benzyl)-(4-methylamino-cyclohexyl)-amide bis(trifluoroacetate) (245)

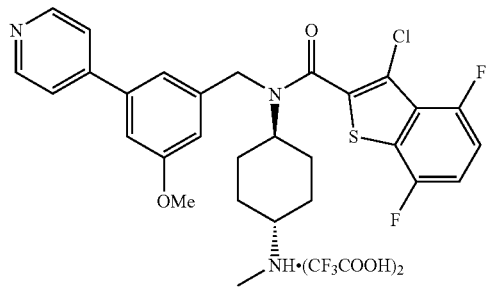

tert-Butyl carbamate 244 (15 mg, 23 μmol) is deprotected using Method G to afford the title compound.

Yield: 18 mg (quant.).
LC/MS $t_r$ 1.50 min.
MS (ES+) m/z 558, 556 (M+H).
$^1$H NMR $\delta_H$ ppm (400 MHz, D$_6$-DMSO, 95° C.): 8.58 (2H, d), 8.15 (2H, br. s), 7.57 (2H, d), 7.36-7.20 (2H, m), 7.17 (1H, br. s), 7.13 (1H, dd), 6.91 (1H, br. s), 4.66 (2H, s), 3.92-3.73 (1H, obsc. m), 3.75 (3H, s), 2.93-2.78 (1H, m), 2.42 (3H, obsc. s), 2.06-1.92 (2H, m), 1.87-1.63 (4H, m), 1.36-1.16 (2H, m).

Synthesis of Compound 395

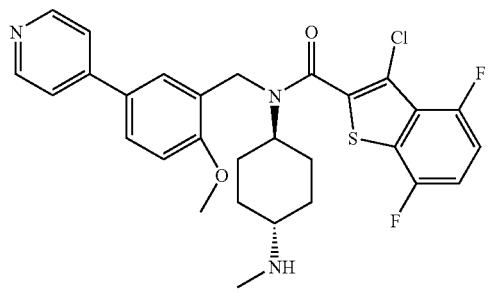

5-Bromo-2-ethyl-benzaldehyde (235)

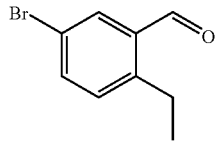

A stirred suspension of 2-ethylbenzaldehyde (0.98 mL, 7.45 mmol) and AlCl$_3$ (1.74 g, 13 mmol) in DCM (4.5 mL) at 0° C. is treated with a solution of Br$_2$ (0.38 mL, 7.45 mmol) in DCM (4.5 mL) dropwise over 6 h then stirred 16 h at RT. After this time, the reaction mixture is poured over ice-water (50 mL), the layers separated and the aqueous layer extracted with DCM (3×50 mL). The organic phases are combined and washed with 2M HCl (100 mL), aqueous NaHCO$_3$ (100 mL)

and brine (100 mL), dried over Na$_2$SO$_4$ then the solvents removed in vacuo. Purification by column chromatography (gradient elution—100% heptane increasing to 10% EtOAc in heptane) gives the title compound.

Yield: 925 mg (58%).
LC/MS t$_r$ 1.55 min.
MS (ES+) m/z mass ion not detected.

2-Ethyl-5-pyridin-4-yl-benzaldehyde (236)

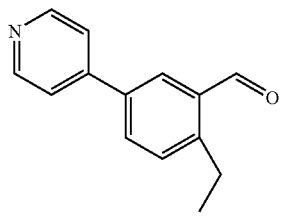

Pyridine-4-boronic acid (75 mg, 0.52 mmol) is coupled to aryl bromide 235 (111 mg, 0.52 mmol) using Method A to give the title compound.

Yield: 59 mg (54%).
LC/MS t$_r$ 1.01 min.
MS (ES+) m/z 212 (M+H).

tert-Butyl [4-(2-ethyl-5-pyridin-4-yl-benzylamino)-cyclohexyl]-methyl-carbamate (237)

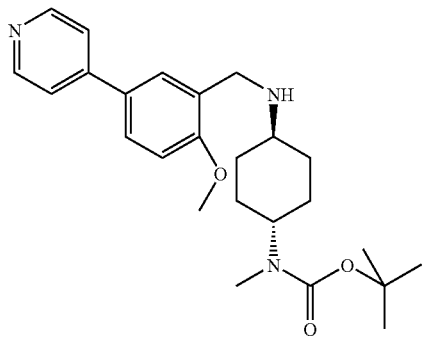

Amine 3 (54 mg, 0.23 mmol) is treated with aldehyde 236 (50 mg, 0.23 mmol) in accordance with Method C. Purification by column chromatography (50% EtOAc in heptane with 2% triethylamine) gives the title compound.

Yield: 45 mg (45%).
LC/MS t$_r$ 1.14 min.
MS (ES+) m/z 424 (M+H), 368 (M-C(CH$_3$)$_3$+H).

tert-Butyl {4-[(3-chloro-4,7-difluoro-benzo[b]thiophene-2-carbonyl)-(2-ethyl-5-pyridin-4-yl-benzyl)-amino]-cyclohexyl}-methyl-carbamate (238)

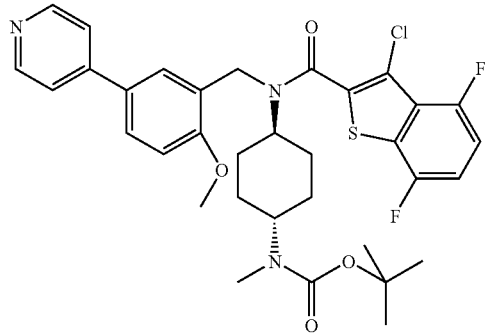

Biaryl amine 237 (45 mg, 0.10 mmol) is treated with acid chloride 8 (31 mg, 0.11 mmol) using Method D to afford the title compound.

Yield: 40 mg (58%).
LC/MS t$_r$ 1.72 min.
MS (ES+) m/z 656, 654 (M+H), 600, 598 (M-C(CH$_3$)$_3$+ H).

3-Chloro-4,7-difluoro-benzo[b]thiophene-2-carboxylic acid (2-ethyl-5-pyridin-4-yl-benzyl)-(4-methylamino-cyclohexyl)-amide dihydrochloride (239)

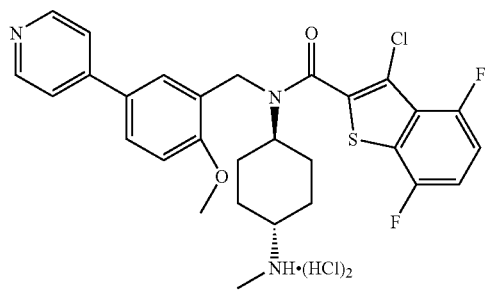

tert-Butyl carbamate 238 (40 mg, 0.06 mmol) is deprotected using Method F. The isolated salt is then dissolved in the minimum amount of DCM and added dropwise to cold (0° C.) TBME (5 mL). The resultant precipitate is isolated by filtration and dried to afford the title compound.

Yield: 6 mg (18%).
LC/MS t$_r$ 1.55 min.
MS (ES+) m/z 556, 554 (M+H).

Synthesis of Compound 396

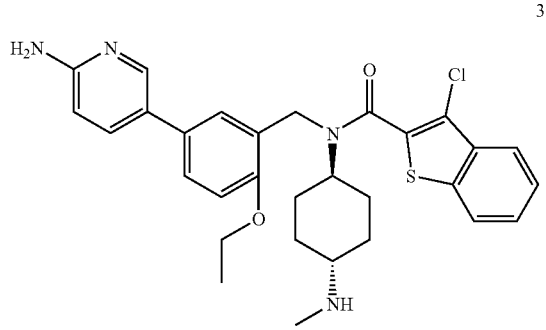

3-Chloro-benzo[b]thiophene-2-carboxylic acid [2-ethoxy-5-(6-amino-pyridin-3-yl)-benzyl]-(4-methylamino-cyclohexyl)-amide dihydrochloride (271)

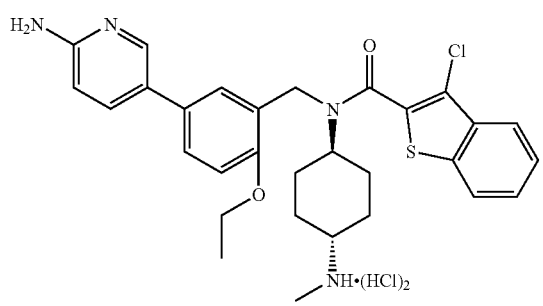

The title compound was prepared from boronic acid (12) (25 mg, 42 μmol) and 6-amino-3-bromo-2-methylpyridine (6.5 mg, 40 μmol) in accordance with Method L2.
Yield: 8.3 mg (37%)
LC/MS $t_r$ 1.16 min.
MS (ES+) m/z 551, 549 (M+H).

Synthesis of Compound 397

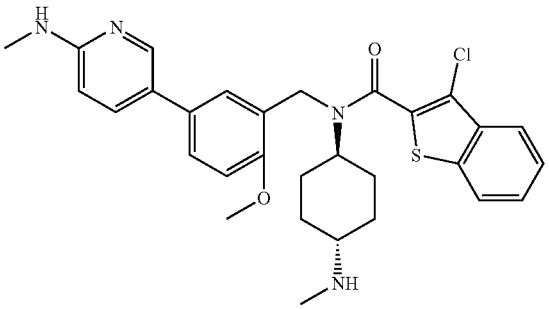

3-Chloro-benzo[b]thiophene-2-carboxylic acid [2-methoxy-5-(6-methylamino-pyridin-3-yl)-benzyl]-(4-methylamino-cyclohexyl)-amide dihydrochloride (268)

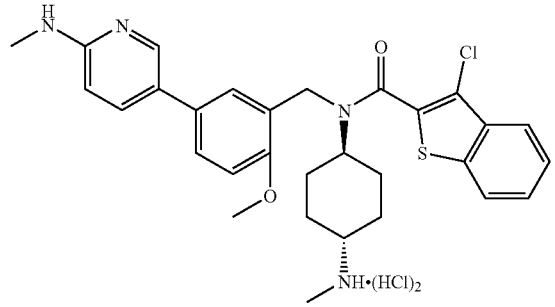

The title compound was prepared from boronic acid (5) (25 mg, 43 μmol) and 5-bromo-2-methylaminopyridine (6.6 mg, 41 μmol) in accordance with Method L2.
Yield: 5.0 mg (22%)
LC/MS $t_r$ 1.14 min.
MS (ES+) m/z 551, 549 (M+H).

Synthesis of Compound 398

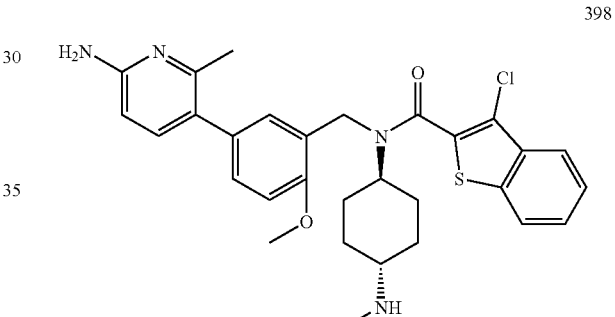

3-Chloro-benzo[b]thiophene-2-carboxylic acid [5-(6-amino-2-methyl-pyridin-3-yl)-2-methoxy-benzyl]-(4-methylamino-cyclohexyl)-amide dihydrochloride (269)

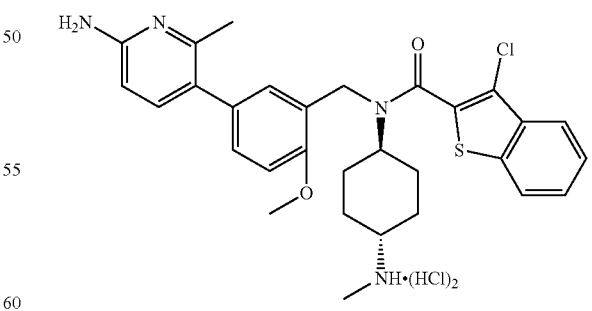

The title compound was prepared from boronic acid (5) (25 mg, 43 μmol) and 6-amino-3-bromo-2-methylpyridine (6.6 mg, 41 μmol) in accordance with Method L2.
Yield: 7.5 mg (33%)
LC/MS $t_r$ 1.54 min.
MS (ES+) m/z 551, 549 (M+H).

Synthesis of Compound 399

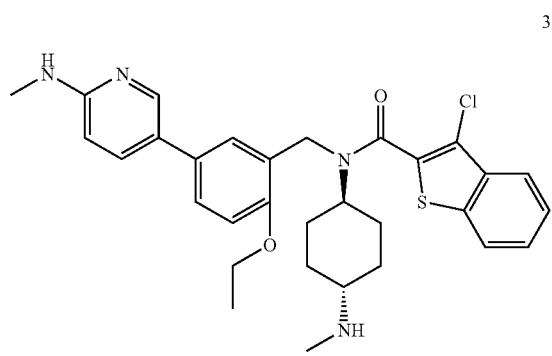

3-Chloro-benzo[b]thiophene-2-carboxylic acid [2-ethoxy-5-(6-methylamino-pyridin-3-yl)-benzyl]-(4-methylamino-cyclohexyl)-amide dihydrochloride (270)

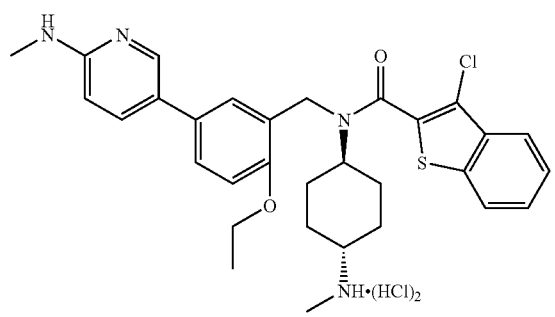

The title compound was prepared from boronic acid (12) (25 mg, 42 µmol) and 6-amino-3-bromo-2-methylpyridine (6.5 mg, 40 µmol) in accordance with Method L2.

Yield: 2.5 mg (11%)
LC/MS $t_r$ 1.16 min.
MS (ES+) m/z 565, 563 (M+H).

Synthesis of Compound 400

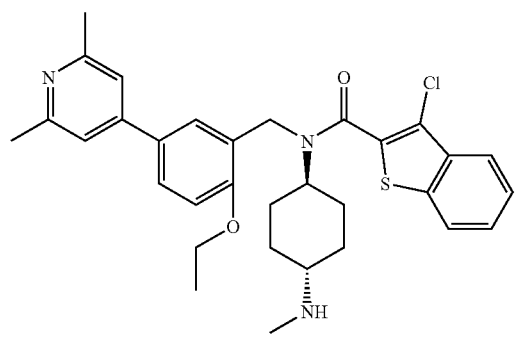

3-Chloro-benzo[b]thiophene-2-carboxylic acid [5-(2,6-dimethyl-pyridin-4-yl)-2-ethoxy-benzyl]-(4-methylamino-cyclohexyl)-amide dihydrochloride (272)

The title compound was prepared from boronic acid (12) (25 mg, 42 µmol) and 2,6-dimethylpyridin-4-yl trifluoromethanesulphonate (91) (8.8 mg, 40 µmol) in accordance with Method L2.

Yield: 6.6 mg (29%)
LC/MS $t_r$ 1.17 min.
MS (ES+) m/z 551, 549 (M+H).

Synthesis of Compound 401

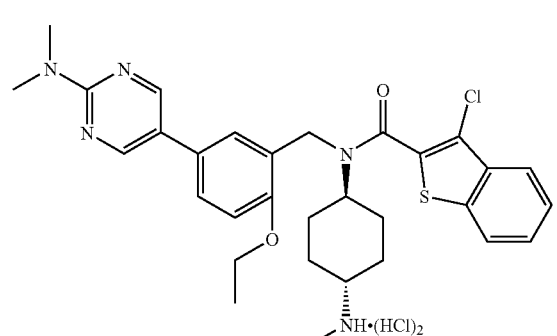

3-Chloro-benzo[b]thiophene-2-carboxylic acid [5-(2-dimethylamino-pyrimidin-5-yl)-2-ethoxy-benzyl]-(4-methylamino-cyclohexyl)-amide dihydrochloride (273)

The title compound was prepared from boronic acid (12) (25 mg, 42 µmol) and 5-bromo-2-dimethylaminopyrimidine (7.0 mg, 40 µmol) in accordance with Method L2.

Yield: 14.1 mg (59%)

LC/MS $t_r$ 1.26 min.

MS (ES+) m/z 580, 578 (M+H).

Synthesis of Compound 402

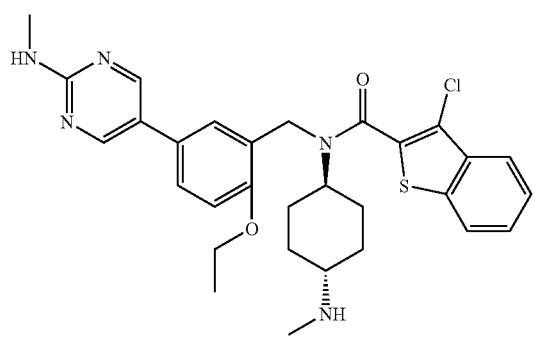

3-Chloro-benzo[b]thiophene-2-carboxylic acid [2-ethoxy-5-(2-methylamino-pyrimidin-5-yl)-benzyl]-(4-methylamino-cyclohexyl)-amide dihydrochloride (274)

The title compound was prepared from boronic acid (12) (25 mg, 42 µmol) and 5-bromo-2-methylaminopyrimidine (6.5 mg, 41 µmol) in accordance with Method L2.

Yield: 5.4 mg (23%)

LC/MS $t_r$ 1.22 min.

MS (ES+) m/z 566, 564 (M+H).

Synthesis of Compound 403

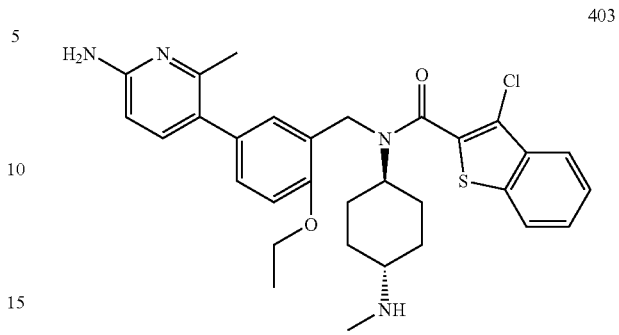

3-Chloro-benzo[b]thiophene-2-carboxylic acid [5-(6-amino-2-methyl-pyridin-3-yl)-2-ethoxy-benzyl]-(4-methylamino-cyclohexyl)-amide dihydrochloride (275)

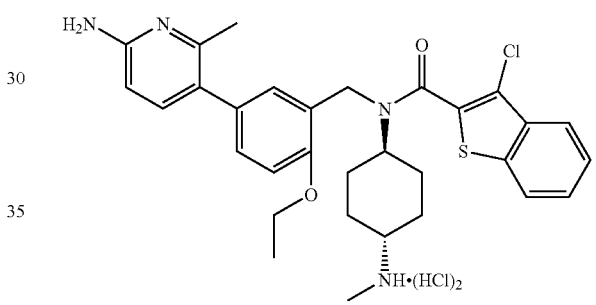

The title compound was prepared from boronic acid (12) (25 mg, 42 µmol) and 6-amino-3-bromo-2-methylpyridine (6.5 mg, 41 µmol) in accordance with Method L2.

Yield: 4.5 mg (19%)

LC/MS $t_r$ 1.17 min.

MS (ES+) m/z 565, 563 (M+H).

Synthesis of Compound 404

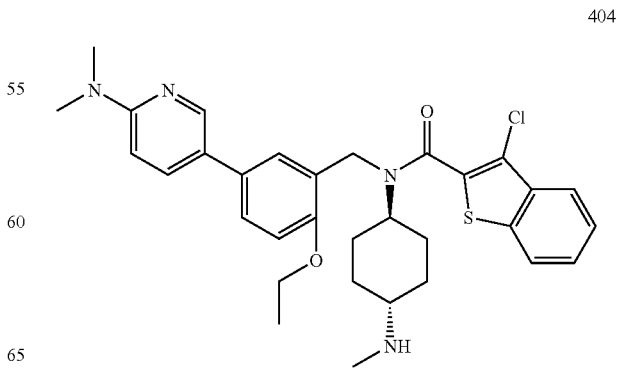

319

3-Chloro-benzo[b]thiophene-2-carboxylic acid [5-(6-dimethylamino-pyridin-3-yl)-2-ethoxy-benzyl]-(4-methylamino-cyclohexyl)-amide bis(trifluoroacetate) (277)

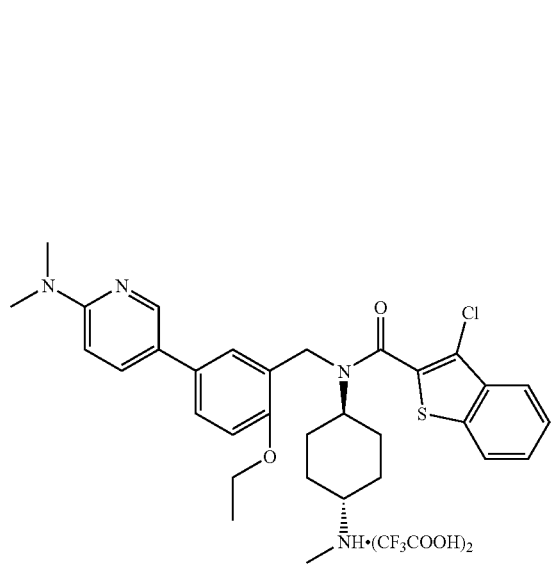

The title compound was prepared from boronic acid (12) (25 mg, 42 µmol) and 5-bromo-2-dimethylaminopyridine (7.0 mg, 41 µmol) in accordance with Method L2. The product was purified by preparative HPLC.

Yield: 4.2 mg (18%)

LC/MS $t_r$ 1.18 min.

MS (ES+) m/z 579, 577 (M+H).

Synthesis of Compound 405

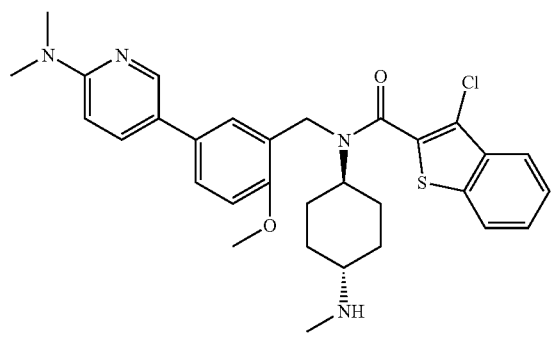

405

320

3-Chloro-benzo[b]thiophene-2-carboxylic acid [5-(6-dimethylamino-pyridin-3-yl)-2-methoxy-benzyl]-(4-methylamino-cyclohexyl)-amide bis(trifluoroacetate) (276)

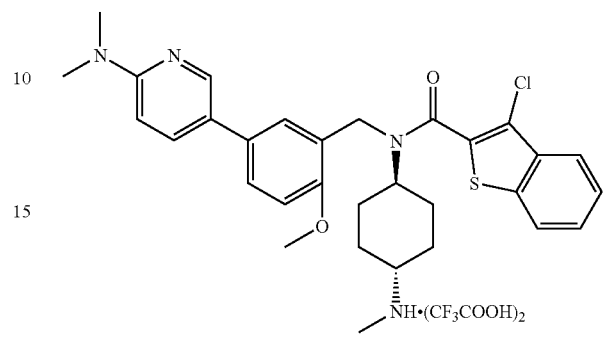

The title compound was prepared from boronic acid (12) (25 mg, 43 µmol) and 5-bromo-2-dimethylaminopyridine (7.1 mg, 41 µmol) in accordance with Method L2. The product was purified by preparative HPLC.

Yield: 3.1 mg (13%)

LC/MS $t_r$ 1.13 min.

MS (ES+) m/z 565, 563 (M+H).

Synthesis of Compound 406

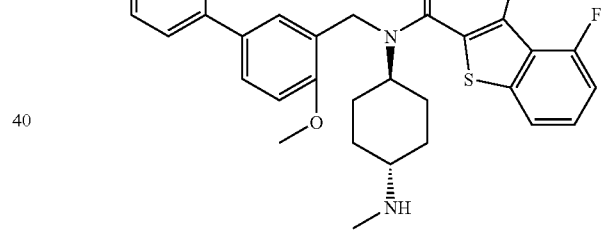

406

{4-[2-Methoxy-5-(6-methyl-pyridin-3-yl)-benzylamino]-cyclohexyl}-methyl-carbamic acid tert-butyl ester (281)

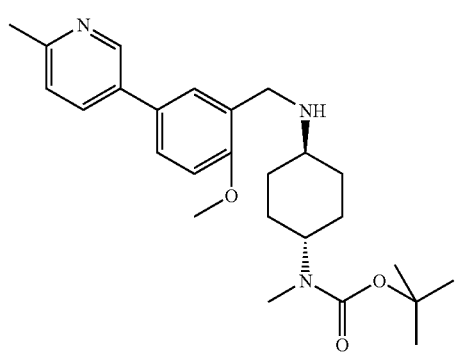

The title compound was prepared from boronic acid 4 (400 mg, 1.05 mmol) and 5-bromo-2-methylpyridine (181 mg, 1.05 mmol) in accordance with Method B.

Yield: 373 mg (81%).

(4-{(3-Chloro-4-fluoro-benzo[b]thiophene-2-carbonyl)-[2-methoxy-5-(6-methyl-pyridin-3-yl)-benzyl]-amino}-cyclohexyl)-methyl-carbamic acid tert-butyl ester (282)

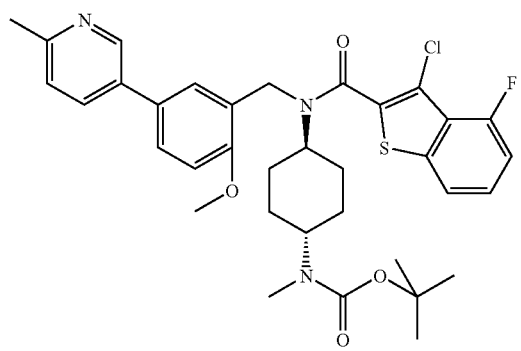

The title compound was prepared from amine (281) (200 mg, 0.45 mmol) and acid chloride 6 (170 mg, 6.8 mmol) following Method D.

Yield: 280 mg (94%).

LC/MS $t_r$ 1.62 min.

MS (ES+) m/z 654, 652 (M+H).

3-Chloro-4-fluoro-benzo[b]thiophene-2-carboxylic acid [2-methoxy-5-(6-methyl-pyridin-3-yl)-benzyl]-(4-methylamino-cyclohexyl)-amide dihydrochloride (283)

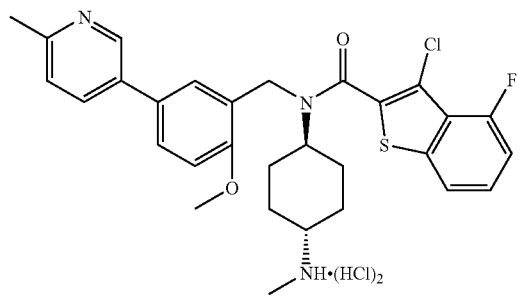

tert-Butyl carbamate (282) (280 mg, 0.43 mmol) was deprotected using Method F to give the title compound.

Yield: 86 mg (36%).

LC/MS $t_r$ 1.14 min.

MS (ES+) m/z 554, 552 (M+H), 277.5, 276.5 (M+2H/2).

$^1$H NMR $\delta_H$ ppm (400 MHz, D$_6$-DMSO, 95° C.): 8.75 (1H, s), 8.70 (2H, br.s), 8.15 (1H, d), 7.87 (1H, d), 7.70-7.45 (4H, m), 7.25 (1H, m), 7.15 (1H, d), 4.70 (2H, s), 3.90 (3H, s), 3.30-2.80 (2H, m), 2.65 (3H, s), 2.60-2.45 (3H, obsc. s), 2.10 (2H, m), 1.95-1.75 (4H, m), 1.50-1.30 (2H, m).

Synthesis of Compound 407

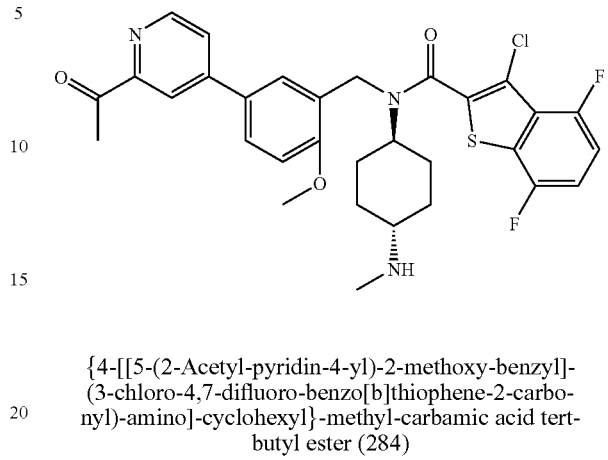

407

{4-[[5-(2-Acetyl-pyridin-4-yl)-2-methoxy-benzyl]-(3-chloro-4,7-difluoro-benzo[b]thiophene-2-carbonyl)-amino]-cyclohexyl}-methyl-carbamic acid tert-butyl ester (284)

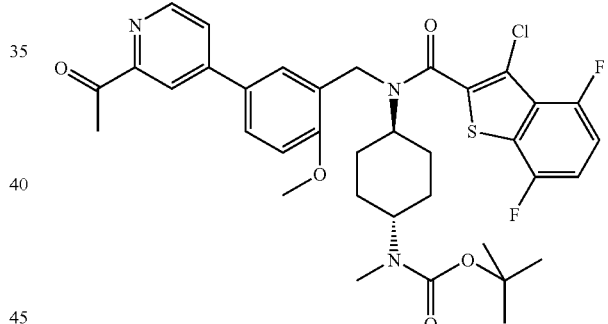

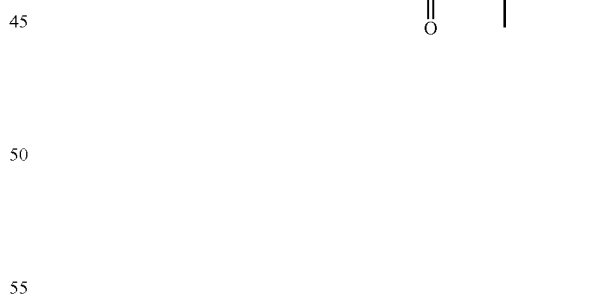

To a solution of dimethyl amide 163 (50 mg, 0.07 mmol) in dry THF (3 ml) at 0° C. was added a 3M solution of methyl magnesium bromide (0.18 ml, 0.55 mmol) in THF. After 1 h, the completed reaction was quenched with 1.2 M HCl, basified and extracted with EtOAc. The combined organic layers were dried (Na$_2$SO$_4$), filtered, reduced in vacuo and purified by chromatography with 70% EtOAc in heptane to give the title compound.

Yield: 21 mg (43%)

LC/MS $t_r$ 1.81 min.

MS (ES+) m/z 700, 698 (M+H), 644, 642 (M-C(CH$_3$)$_3$+H).

323

3-Chloro-4,7-difluoro-benzo[b]thiophene-2-carboxylic acid [5-(2-acetyl-pyridin-4-yl)-2-methoxy-benzyl]-(4-methylamino-cyclohexyl)-amide dihydrochloride (285)

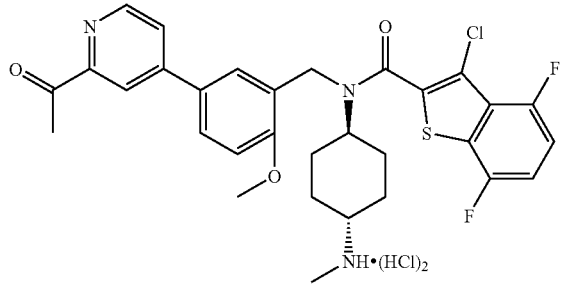

tert-Butyl carbamate (284) (42 mg, 0.06 mmol) was deprotected using Method F to give the title compound.

Yield: 19 mg (53%).

LC/MS $t_r$ 1.35 min.

MS (ES+) m/z 600, 598 (M+H), 320 (M-C$_9$H$_2$ClF$_2$OS—CH$_3$NH$_2$—CH$_3$).

$^1$H NMR $\delta_H$ ppm (400 MHz, D$_6$-DMSO, 95° C.): 8.60 (2H, br.s), 8.55 (1H, d), 8.15 (1H, s), 7.85 (1H, d), 7.75 (1H, d), 7.67 (1H, s), 7.45-7.25 (2H, m), 7.15 (1H, d), 4.70 (2H, s), 3.90 (4H, br. s), 3.00-2.90 (1H, m), 2.70 (3H, s), 2.60-2.45 (3H, obsc. s), 2.31 (3H, s), 2.10 (2H, m), 1.95-1.75 (4H, m), 1.50-1.30 (2H, m).

Synthesis of Compound 408

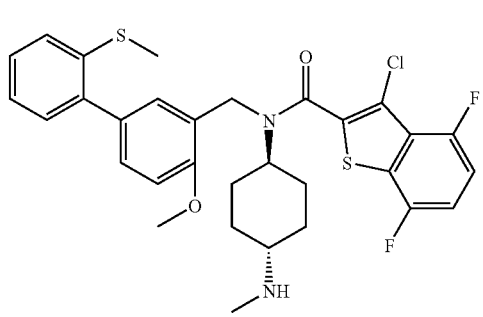

324

{4-[(3-Chloro-4,7-difluoro-benzo[b]thiophene-2-carbonyl)-(4-methoxy-2'-methylsulfanyl-biphenyl-3-ylmethyl)-amino]-cyclohexyl}-methyl-carbamic acid tert-butyl ester (286)

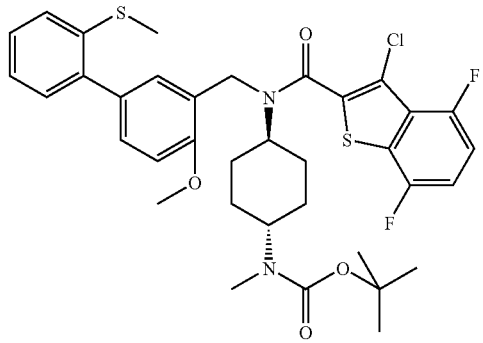

Boronic acid 4 (300 mg, 0.76 mmol) was coupled to 2-bromothioanisole (156 mg, 0.77 mmol) using Method A. The crude reaction mixture was reacted with acid chloride 8 (246 mg, 0.92 mmol) using Method D to give the title compound.

Yield: 238 mg (44%).

LC/MS $t_r$ 2.04 min.

MS (ES+) m/z 725, 723 (M+Na), 647, 645 (M-C(CH$_3$)$_3$+Na).

3-Chloro-4,7-difluoro-benzo[b]thiophene-2-carboxylic acid (4-methoxy-2'-methylsulfanyl-biphenyl-3-ylmethyl)-(4-methylamino-cyclohexyl)-amide hydrochloride (287)

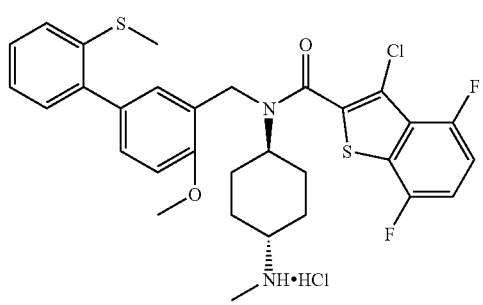

tert-Butyl carbamate (286) (25 mg, 36 mmol) was deprotected using Method F to give the title compound.

Yield: 21 mg (quant.).

LC/MS $t_r$ 2.17 min.

MS (ES+) m/z 603, 601 (M+H).

$^1$H NMR $\delta_H$ ppm (400 MHz, D$_6$-DMSO, 95° C.): 8.60 (2H, br.s), 7.5-7.2 (7H, m), 7.17 (1H, d), 7.06 (1H, d), 4.66 (2H, s), 3.85 (4H, br. s), 2.92 (1H, m), 2.60-2.45 (3H, obsc. s), 2.35 (3H, s), 2.10 (2H, m), 1.95-1.75 (4H, m), 1.50-1.30 (2H, m).

Synthesis of Compound 409

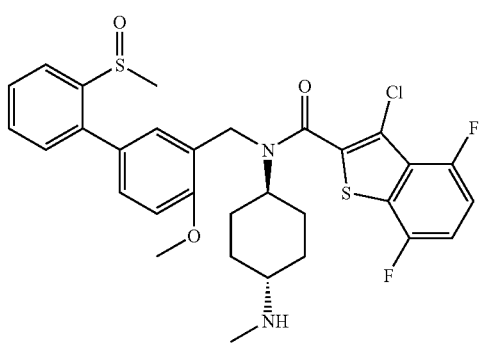

{4-[(3-Chloro-4,7-difluoro-benzo[b]thiophene-2-carbonyl)-(2'-methanesulfinyl-4-methoxy-biphenyl-3-ylmethyl)-amino]-cyclohexyl}-methyl-carbamic acid tert-butyl ester (288)

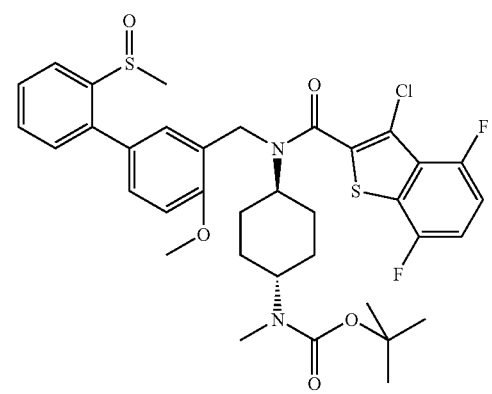

To a stirred suspension of thioanisole (286) (75 mg, 0.11 mmol) and NaHCO$_3$ (46 mg, 0.55 mmol) in DCM (2 ml) at 0° C. was added dropwise a solution of m-chloroperbenzoic acid (34 mg, 0.2 mmol) in DCM (1 ml) over 2 min. After 2 h, LCMS showed a mixture of sulphoxide and sulphone. The reaction was diluted with aqueous Na$_2$SO$_3$ and extracted with DCM. The combined organic layers were dried (Na$_2$SO$_4$), filtered and reduced in vacuo before purification by chromatography with EtOAc/heptane to give the title compound.

Yield: 20 mg (25%).
LC/MS t$_r$ 1.83 min.
MS (ES+) m/z 764, 762 (M+46), 719, 717 (M+H).

3-Chloro-4,7-difluoro-benzo[b]thiophene-2-carboxylic acid (2'-methanesulfinyl-4-methoxy-biphenyl-3-ylmethyl)-(4-methylamino-cyclohexyl)-amide trifluoroacetate (289)

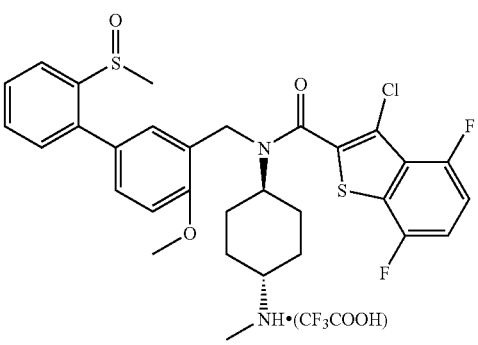

tert-Butyl carbamate (288) (20 mg, 28 μmol) was deprotected using Method G to give the title compound.

Yield: 22 mg (quant.).
LC/MS t$_r$ 1.40 min.
MS (ES+) m/z 619, 617 (M+H).
$^1$H NMR δ$_H$ ppm (400 MHz, D$_6$-DMSO, 95° C.): 8.30 (2H, br.s), 8.02 (1H, d), 7.69 (1H, t), 7.61 (1H, t), 7.5-7.25 (5H, m), 7.10 (1H, m), 4.67 (2H, s), 3.86 (3H, br. s), 3.8-3.4 (1H, obsc.), 2.93 (1H, m), 2.60-2.45 (3H, obsc. s), 2.41 (3H, s), 2.04 (2H, m), 1.95-1.75 (4H, m), 1.50-1.30 (2H, m).

Synthesis of compound 410

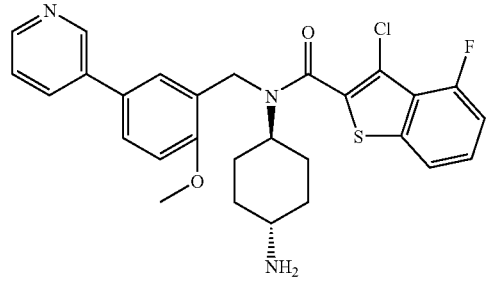

2-Methoxy-5-pyridin-3-yl-benzaldehyde (N1)

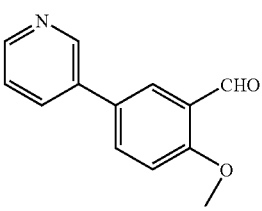

N1 is prepared according to a method similar to Method A. Commercially available 3-formyl-4-methoxyphenylboronic acid (1.66 g, 9.22 mmol) is dissolved in 56 mL toluene and 14 mL ethanol. 3-Bromopyridine (0.98 mL, 10.2 mmol) is added followed by cesium carbonate (3.0 g, 9.21 mmol). Nitrogen is bubbled through the mixture for 10 minutes, then palladium tetrakistriphenylphosphine (0.53 g, 0.46 mmol) is added and nitrogen bubbling is resumed for another ten minutes. The mixture is heated to reflux for 5 hours. The mixture is allowed to cool and is filtered through Celite. The Celite pad is washed with ethyl acetate and methylene chloride. The filtrate is pumped dry and the residue is chromatographed on silica gel using a gradient elution of methanol/methylene chloride. 2-Methoxy-5-pyridin-3-yl-benzaldehyde (N1) is obtained (0.635 g, 2.98 mmol; 32% yield).

[4-(2-Methoxy-5-pyridin-3-yl-benzylamino)-cyclohexyl]-carbamic acid tert-butyl ester (N2)

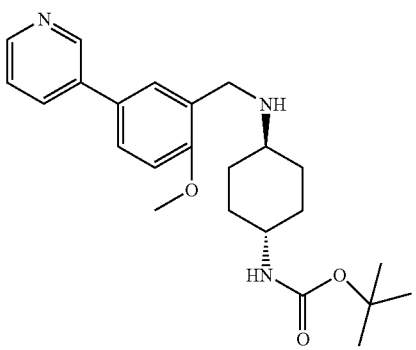

N2 is prepared according to a method similar to Method C'. 2-Methoxy-5-pyridin-3-yl-benzaldehyde (N1) (0.635 g, 2.98 mmol) is dissolved in 30 mL methanol. Commercially available (trans-4-amino-cyclohexyl)-carbamic acid tert-butyl ester (3) (0.638 g, 2.98 mmol) is added followed by acetic acid (0.41 mL, 7.15 mmol). The mixture is allowed to stir 5 minutes at room temperature, and then sodium triacetoxy borohydride is added. The mixture is allowed to stir 8 hours at room temperature. The mixture is pumped dry, and then partitioned between ethyl acetate and half-saturated aqueous sodium bicarbonate solution. The organic phase is dried (MgSO$_4$) and evaporated to afford [4-(2-methoxy-5-pyridin-3-yl-benzylamino)-cyclohexyl]-carbamic acid tert-butyl ester (N2) (1.035 g, 2.52 mmol; 85% yield) of suitable purity to be used in the next step.

{4-[(3-Chloro-4-fluoro-benzo[b]thiophene-2-carbonyl)-(2-methoxy-5-pyridin-3-yl-benzyl)-amino]-cyclohexyl}-carbamic acid tert-butyl ester (N3)

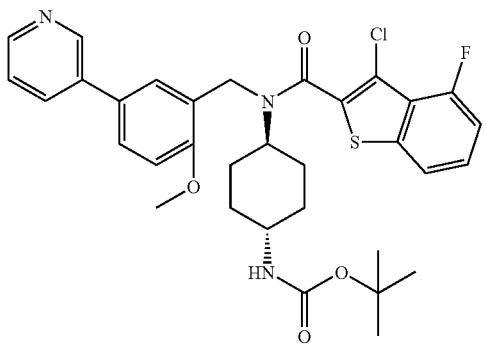

N3 is prepared according to a method similar to Method D. [4-(2-methoxy-5-pyridin-3-yl-benzylamino)-cyclohexyl]-carbamic acid tert-butyl ester (N2) (1.035 g, 2.52 mmol) is dissolved in 10 mL anhydrous methylene chloride. N,N-Diisopropylethylamine (0.526 mL, 3.02 mmol) is added followed by 3-chloro-4-fluoro-benzo[b]thiophene-2-carbonyl chloride (6) (0.690 g, 2.77 mmol). The mixture is allowed to stir overnight at room temperature and then is partitioned between ethyl acetate and water. The organic phase is dried (MgSO$_4$) and evaporated, and the residue is chromatographed on silica gel using a gradient elution of methanol/methylene chloride. {4-[(3-Chloro-4-fluoro-benzo[b]thiophene-2-carbonyl)-(2-methoxy-5-pyridin-3-yl-benzyl)-amino]-cyclohexyl}-carbamic acid tert-butyl ester (N3) is obtained (0.93 g, 1.48 mmol; 59% yield).

3-Chloro-4-fluoro-benzo[b]thiophene-2-carboxylic acid (4-amino-cyclohexyl)-(2-methoxy-5-pyridin-3-yl-benzyl)-amide (410)

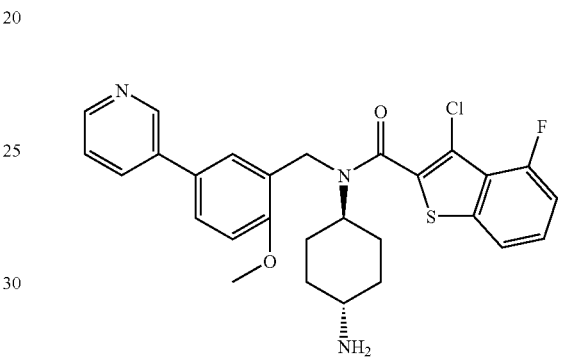

410 is prepared according to a method similar to Method G. {4-[(3-Chloro-4-fluoro-benzo-[b]thiophene-2-carbonyl)-(2-methoxy-5-pyridin-3-yl-benzyl)-amino]-cyclohexyl}-carbamic acid tert-butyl ester (N3) (0.93 g, 1.48 mmol) is dissolved in 10 mL methylene chloride. Trifluoroacetic acid is added (0.35 mL) and the mixture is stirred at room temperature for 20 minutes. The reaction mixture is evaporated and pumped dry. The residue is partitioned between 5% methanol/methylene chloride and half-saturated aqueous sodium bicarbonate. The aqueous layer is extracted with 5% methanol/methylene chloride, and the combined organic extracts are dried (MgSO$_4$), filtered and evaporated to yield an ivory solid (0.375 g, 0.717 mmol; 48% yield) that was pure by LCMS analysis.

MS (ES+) m/z 524.1 (M+H)$^+$.

Synthesis of Compound 411

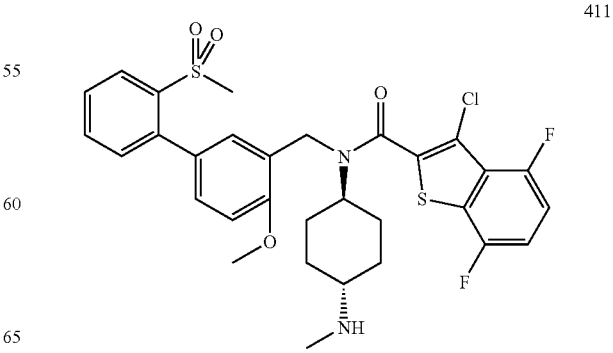

{4-[(3-Chloro-4,7-difluoro-benzo[b]thiophene-2-carbonyl)-(2'-methanesulfonyl-4-methoxy-biphenyl-3-ylmethyl)-amino]-cyclohexyl}-methyl-carbamic acid tert-butyl ester (290)

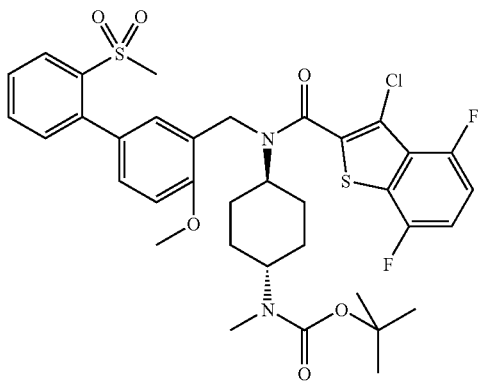

The title compound was isolated from the reaction which gave sulphoxide (288).

Yield: 14 mg (17%).

LC/MS $t_r$ 1.92 min.

MS (ES+) m/z 735, 733 (M+H).

3-Chloro-4,7-difluoro-benzo[b]thiophene-2-carboxylic acid (2'-methanesulfonyl-4-methoxy-biphenyl-3-ylmethyl)-(4-methylamino-cyclohexyl)-amide hydrochloride (291)

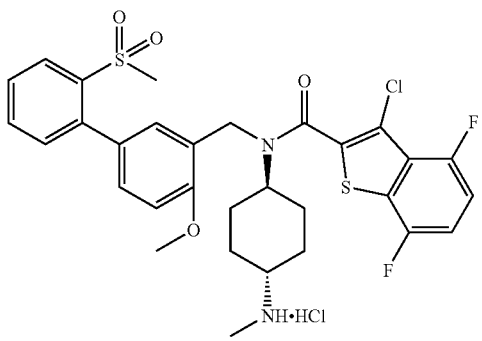

tert-Butyl carbamate (290) (14 mg, 19 μmol) was deprotected using Method F to give the title compound.

Yield: 13 mg (quant.).

LC/MS $t_r$ 1.99 min.

MS (ES+) m/z 635, 633 (M+H).

$^1$H NMR $\delta_H$ ppm (400 MHz, D$_6$-DMSO, 95° C.): 8.71 (2H, br.s), 8.15 (1H, d), 7.77 (1H, t), 7.70 (1H, t), 7.5-7.3 (5H, m), 7.09 (1H, m), 4.67 (2H, s), 4.1-3.6 (4H, br. s), 2.93 (1H, m), 2.85 (3H, s), 2.50 (3H, s), 2.08 (2H, m), 1.95-1.75 (4H, m), 1.50-1.30 (2H, m).

Synthesis of Compound 412

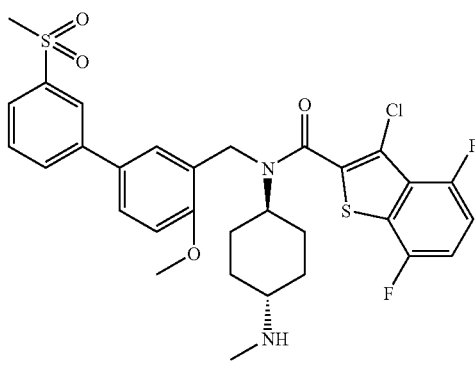

3-Chloro-4,7-difluoro-benzo[b]thiophene-2-carboxylic acid (3'-methanesulfonyl-4-methoxy-biphenyl-3-ylmethyl)-(4-methylamino-cyclohexyl)-amide hydrochloride (292)

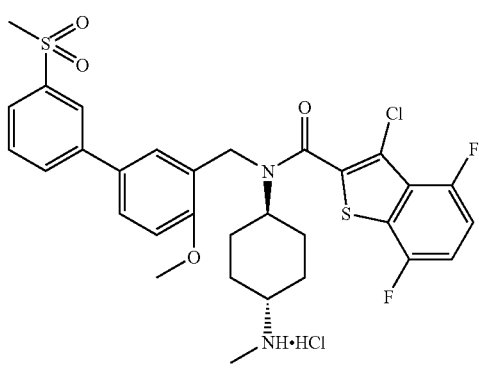

tert-Butyl carbamate (212) (24 mg, 33 μmol) was deprotected using Method F to give the title compound.

Yield: 22 mg (quant.).

LC/MS $t_r$ 2.05 min.

MS (ES+) m/z 635, 633 (M+H).

$^1$H NMR $\delta_H$ ppm (400 MHz, D$_6$-DMSO, 95° C.): 8.73 (2H, br.s), 8.12 (1H, s), 8.0-7.9 (2H, m), 7.76 (1H, t), 7.70 (1H, d), 7.61 (1H, s), 7.5-7.3 (2H, m), 7.18 (1H, m), 4.74 (2H, s), 3.93 (4H, br. s), 3.27 (3H, s), 2.93 (1H, br.s), 2.50 (3H, br.s), 2.2-2.0 (2H, m), 1.95-1.70 (4H, m), 1.50-1.30 (2H, m).

Synthesis of Compound 413

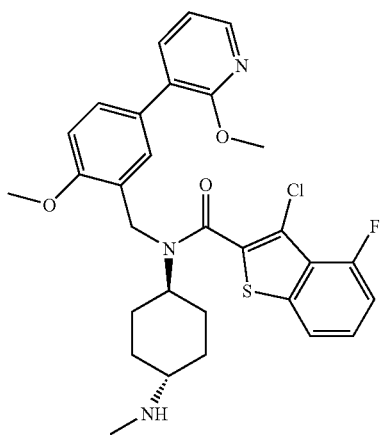

Compound 413 was prepared according to procedures described in Schemes P7, P8, P10, P11 and P12.

$^1$H NMR (300 MHz, DMSO-$d_6$) δ ppm 1.27 (br. s., 2H) 1.66-1.92 (m, 4H) 2.04 (d, J=11.0 Hz, 2H) 2.92 (t, J=12.3 Hz, 1H) 3.28 (none, 7H) 3.68-3.90 (m, 3H) 3.88 (s, 3H) 4.63 (s, 2H) 6.96-7.12 (m, 2H) 7.24-7.36 (m, 1H) 7.42 (dd, J=8.6, 2.2 Hz, 1H) 7.46-7.56 (m, 2H) 7.66 (dd, J=7.3, 1.8 Hz, 1H) 7.87 (br. s., 1H) 8.14 (dd, J=3.4 Hz, 1H).

MS (ES+) m/z 568 (M+H)

Synthesis of Compound 414

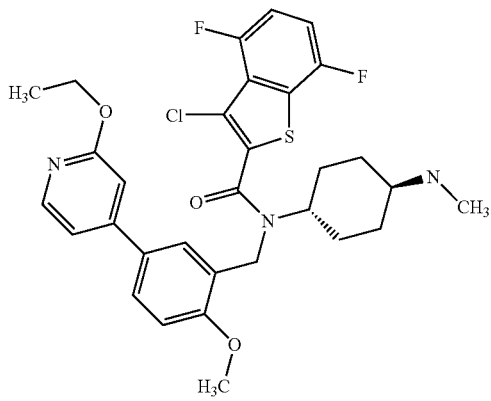

Compound 414 was prepared according to procedures described in Schemes P7, P8, P10, P11 and P12.

$^1$H NMR (300 MHz, DMSO-$d_6$) δ ppm 1.24-1.38 (m, 2H) 1.36 (t, J=7.0 Hz, 3H) 1.71-1.91 (m, 4H) 2.03 (d, J=10.1 Hz, 2H) 2.83-3.00 (m, 1H) 3.87 (s, 3H) 3.90-3.93 (m, 1H) 4.38 (q, J=7.1 Hz, 2H) 4.66 (s, 2H) 6.91-6.99 (m, 1H) 7.11 (d, J=8.2 Hz, 1H) 7.17 (dd, J=3.5 Hz, 1H) 7.31-7.48 (m, 2H) 7.60 (d, J=2.2 Hz, 1H) 7.70 (dd, J=8.5, 2.3 Hz, 1H) 8.13-8.25 (m, J=5.3 Hz, 2H) 8.18 (d, J=5.3 Hz, 1H)

MS (ES+) m/z 600 (M+H)

Synthesis of Compound 415

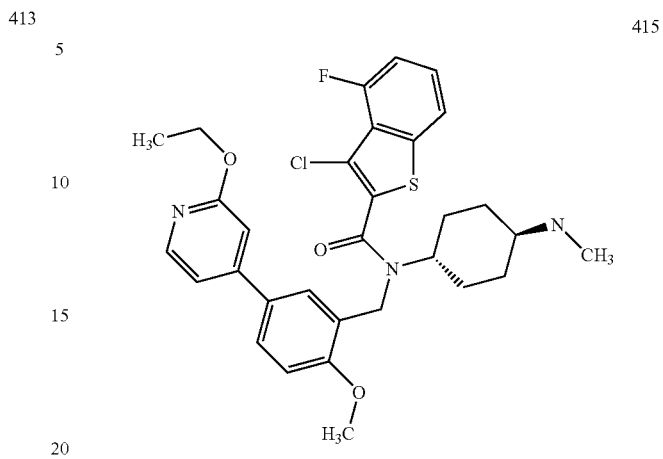

Compound 415 was prepared according to procedures described in Schemes P7, P8, P10, P11 and P12.

$^1$H NMR (300 MHz, DMSO-$d_6$) δ ppm 1.19-1.43 (m, J=8.3, 8.3, 8.3 Hz, 2H) 1.36 (t, J=7.0 Hz, 3H) 1.65-1.91 (m, 4H) 2.03 (d, J=10.6 Hz, 2H) 2.85-2.99 (m, 1H) 3.83-4.01 (m, 3H) 4.38 (q, J=7.0 Hz, 2H) 4.66 (s, 2H) 6.94-6.99 (m, 1H) 7.07-7.15 (m, 1H) 7.18 (dd, J=3.5 Hz, 1H) 7.26-7.38 (m, 1H) 7.53 (s, 1H) 7.62 (s, 1H) 7.69 (dd, J=8.4, 2.4 Hz, 1H) 7.86-7.94 (m, 1H) 8.12-8.26 (m, J=4.2, 4.2 Hz, 1H) 8.19 (d, J=5.3 Hz, 1H)

MS (ES+) m/z 582 (M+H)

Synthesis of Compound 416

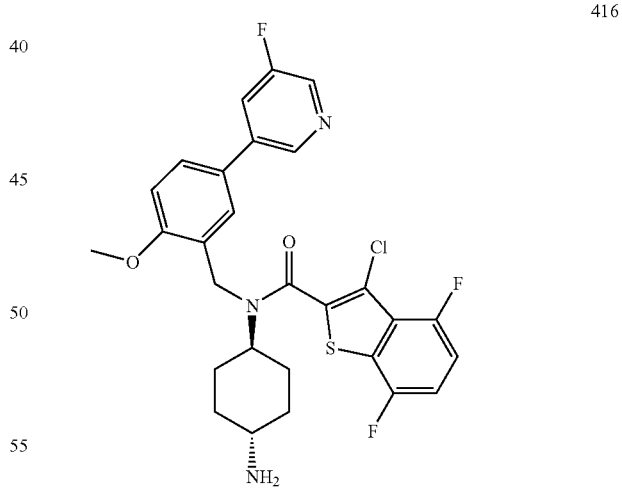

Compound 416 was prepared according to procedures described in Schemes P7, P8, P10, P11 and P12.

$^1$H NMR (300 MHz, DMSO-$d_6$) δ ppm 1.36 (s, 2H) 1.83 (s, 4H) 1.89-2.13 (m, J=10.1 Hz, 2H) 2.94 (s, 1H) 3.82-4.01 (m, 3H) 4.66 (s, 2H) 7.04 (s, 1H) 7.12 (d, J=8.4 Hz, 1H) 7.21 (s, 1H) 7.29-7.48 (m, 2H) 7.59 (d, J=2.0 Hz, 1H) 7.69 (dd, J=8.6, 2.4 Hz, 1H) 7.76-8.06 (m, 4H) 8.53 (s, 1H) 8.71 (s, 1H)

MS (ES+) m/z 560 (M+H)

Synthesis of Compound 417

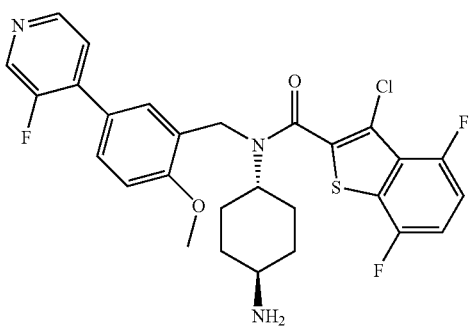

Compound 417 was prepared according to procedures described in Schemes P7, P8, P10, P11 and P12.

$^1$H NMR (300 MHz, DMSO-$d_6$) δ ppm 1.26-1.46 (m, 2H) 1.83 (s, 4H) 1.90-2.08 (m, 2H) 2.83-3.08 (m, 1H) 3.58 (s, 3H) 3.87 (s, 3H) 4.67 (s, 2H) 7.06-7.21 (m, 1H) 7.27-7.49 (m, 2H) 7.48-7.67 (m, 3H) 7.74-7.97 (m, 2H) 8.49 (d, J=5.1 Hz, 1H) 8.63 (d, J=2.9 Hz, 1H)

MS (ES+) m/z 560 (M+H)

Synthesis of Compound 418

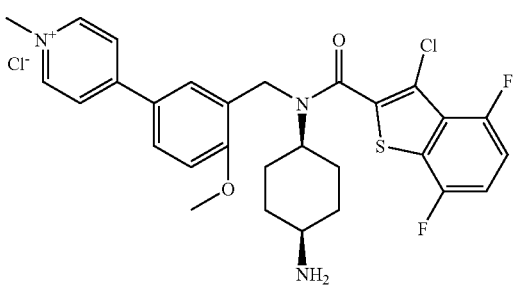

cis-4-tert-Butoxycarbonylamino-cyclohexanecarboxylic acid (293)

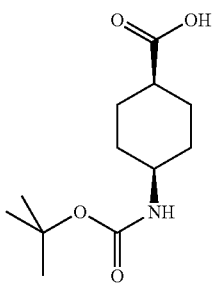

Cis-4-aminocyclohexane carboxylic acid (500 mg, 3.5 mmol) was dissolved in THF (10 mL). 2M sodium hydroxide solution (3.5 mL, 7.0 mmol) was added and the mixture cooled on ice before adding di-tert-butyl dicarbonate (840 mg, 3.9 mmol). The reaction was warmed to RT and left stirring overnight before washing with TBME. The aqueous was acidified with 1M KHSO$_4$ solution and extracted with EtOAc. The organic phase was dried (Na$_2$SO$_4$), filtered and reduced in vacuo to leave the title compound.

Yield: 401 mg (47%)

$^1$H NMR $δ_H$ ppm (250 MHz, D$_4$-MeOD): 3.49 (1H, m), 2.49 (1H, m), 2.07-1.91 (2H, m), 1.77-1.51 (6H, m), 1.46 (9H, s).

cis-(4-tert-Butoxycarbonylamino-cyclohexyl)-carbamic acid benzyl ester (294)

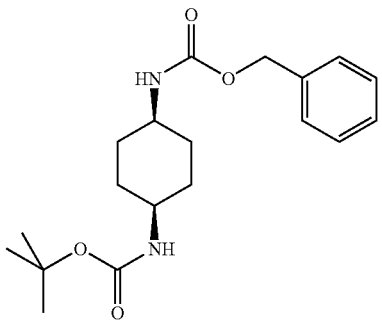

To BOC amino acid (293) (255 mg, 1.05 mmol) and triethylamine (0.58 mL, 4.2 mmol) in toluene (3 mL) at 45° C. was added dropwise diphenyl phosphoryl azide (0.23 ml, 1.15 mmol). Benzyl alcohol (0.16 mL, 1.58 mmol) was then added and the reaction heated at 55° C. for 4 h. The reaction was cooled to RT then washed with H$_2$O, 1M KHSO$_4$, and saturated sodium bicarbonate solution. The organic layer was dried (Na$_2$SO$_4$), filtered and reduced in vacuo to give the title compound.

Yield: 458 mg (125%) [contaminated with some benzyl alcohol].

LC/MS t$_r$ 1.56 min.

MS (ES+) m/z 371 (M+Na), 249 (M-CO$_2$C(CH$_3$)$_3$+H).

cis-(4-Amino-cyclohexyl)-carbamic acid tert-butyl ester (295)

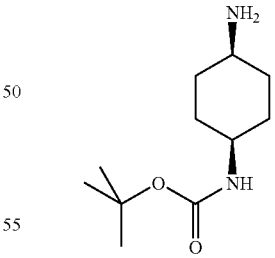

Cbz BOC diamine (294) (458 mg, 1.05 mmol) (containing residual benzyl alcohol) and 10% palladium on charcoal (92 mg, 20% by weight) in EtOH (9 mL) was stirred under a hydrogen atmosphere until the reaction was complete. The reaction was filtered through celite, washed with more EtOH and reduced in vacuo to give the title compound.

Yield: 131 mg (58%)

LC/MS t$_r$ 0.92 min.

MS (ES+) m/z 215 (M+H).

335

2-Methoxy-5-pyridin-4-yl-benzaldehyde (296)

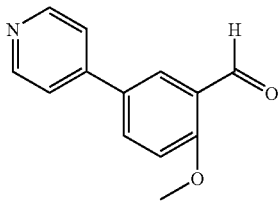

3-Formyl-4-methoxyphenyl boronic acid (393 mg, 2.19 mmol) and 4-bromopyridine hydrochloride (400 mg, 2.19 mmol) were coupled using Method A to give the title compound.

Yield: 240 mg (52%)-20% triphenyl phosphine oxide was present

LC/MS $t_r$ 0.85 min.

MS (ES+) m/z 214 (M+H).

[4-(2-Methoxy-5-pyridin-4-yl-benzylamino)-cyclohexyl]-carbamic acid tert-butyl ester (297)

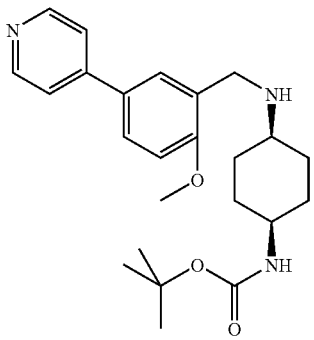

A stirred suspension of amine (295) (131 mg, 0.61 mmol) and aldehyde (296) (130 mg, 0.61 mmol) in THF (1 mL) and toluene (1 mL) was treated with AcOH (42 μL, 0.73 mmol) at RT. After stirring 1.5 h, the resultant suspension was treated with sodium triacetoxyborohydride (181 mg, 0.86 mmol) and stirred for 18 h. The reaction was diluted with aqueous NaHCO$_3$ and extracted into EtOAc. The organic phase was dried (Na$_2$SO$_4$), filtered, the solvent removed in vacuo and the residue chromatographed with 10% MeOH in EtOAc to afford the title compound.

Yield: 156 mg (62%)

LC/MS $t_r$ 1.02 min.

MS (ES+) m/z 412 (M+H).

336

{4-[(3-Chloro-4,7-difluoro-benzo[b]thiophene-2-carbonyl)-(2-methoxy-5-pyridin-4-yl-benzyl)-amino]-cyclohexyl}-carbamic acid tert-butyl ester (298)

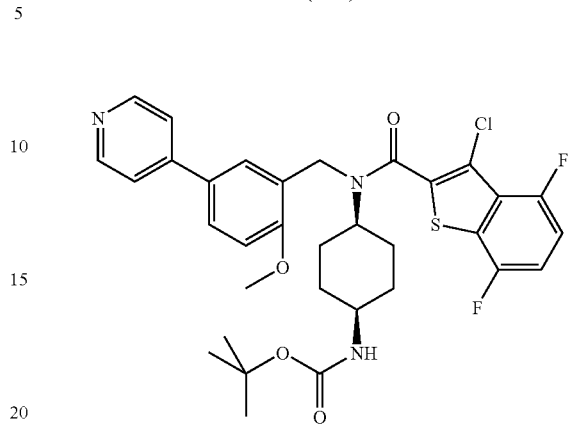

Amine (297) (156 mg, 0.38 mmol) was reacted with acid chloride 8 (110 mg, 0.42 mmol) using Method D to give the title compound.

Yield: 120 mg (49%)

LC/MS $t_r$ 1.60 min.

MS (ES+) m/z 644, 642 (M+H), 588, 586 (M-C(CH$_3$)$_3$+H).

4-(3-{[(4-tert-Butoxycarbonylamino-cyclohexyl)-(3-chloro-4,7-difluoro-benzo[b]thiophene-2-carbonyl)-amino]-methyl}-4-methoxy-phenyl)-1-methyl-pyridinium methosulphate (299)

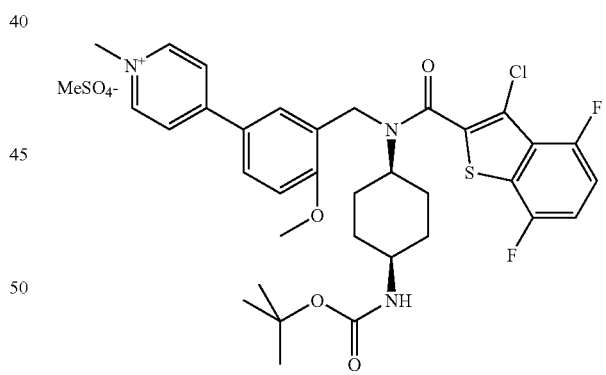

Pyridine (298) (40 mg, 62 μmol) was dissolved in THF (1 mL) and sodium hydride (60% suspension in oil) (6 mg, 0.14 mmol) added. After 10 min at RT, dimethyl sulphate (13 μL, 0.14 mmol) added. After 30 min, the reaction was quenched with H$_2$O and extracted with EtOAc. The organic phase was dried (Na$_2$SO$_4$), filtered, reduced in vacuo and then chromatographed with 10% MeOH in DCM containing 2% ammonia to give the title compound.

Yield: 17 mg (42%)

LC/MS $t_r$ 1.62 min.

MS (ES+) m/z 658, 656 (M+).

337

4-(3-{[(4-Amino-cyclohexyl)-(3-chloro-4,7-difluoro-benzo[b]thiophene-2-carbonyl)-amino]-methyl}-4-methoxy-phenyl)-1-methyl-pyridinium chloride hydrochloride (300)

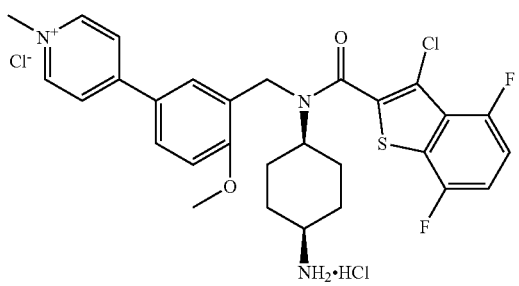

tert-Butyl carbamate (299) (17 mg, 26 μmol) was deprotected using Method F to give the title compound.

Yield: 17 mg (quant.).

LC/MS $t_r$ 1.47 min.

MS (ES+) m/z 558, 556 (M+), 461, 459 (M-C6H11N), 279.5, 278.5 (M+H/2).

$^1$H NMR $\delta_H$ ppm (400 MHz, D$_6$-DMSO, 95° C.): 8.70 (2H, d), 8.05 (2H, s), 8.0-7.65 (2H, br. s), 7.77 (1H, d), 7.61 (1H, s), 7.17 (2H, m), 7.05 (1H, d), 4.65 (2H, s), 4.14 (3H, s), 3.90 (1H, m), 3.72 (3H, s), 3.15 (1H, m), 2.00-1.75 (4H, m), 1.70-1.50 (4H, m).

Synthesis of Compound 419

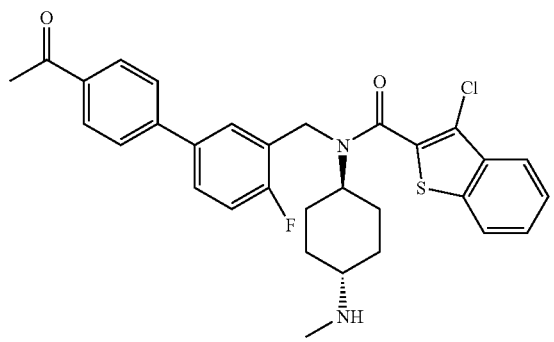

338

3-{[4-(BOC-methyl-amino)-cyclohexylamino]-methyl}-4-fluoro-benzene boronic acid (247)

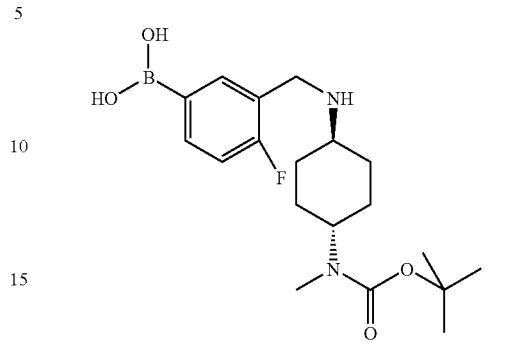

To a solution of 4-fluoro-3-formyl benzene boronic acid (0.88 g, 5.99 mmol) in THF (5 mL) and toluene (5 mL) was added amine (3) (1.4 g, 7.19 mmol) followed by AcOH (0.34 mL, 7.19 mmol), and the resulting solution was stirred at RT for 18 h. After this time sodium triacetoxyborohydride (1.57 g, 8.38 mmol) was added and the resulting solution was stirred at RT for a further 6 h. EtOAc (10 mL) was added to the reaction mixture followed by dropwise addition of sat. NaHCO$_3$ solution (10 mL). The organic layer was separated and the aqueous layer was extracted into EtOAc (2×10 mL). The combined organic layers were dried (MgSO$_4$), filtered and reduced in vacuo to give the title compound as a yellow solid.

Yield: 1.6 g (80%).

3-Chloro-benzo[b]thiophene-2-carboxylic acid (4'-acetyl-4-fluoro-biphenyl-3-ylmethyl)-(4-methylamino-cyclohexyl)-amide trifluoroacetate (248)

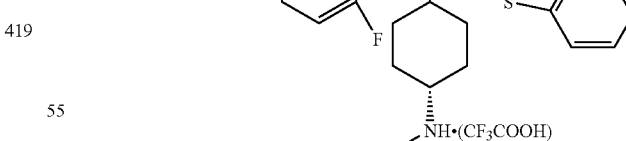

The title compound was prepared from boronic acid (247) (20 mg, 49 mmol) and 4-bromoacetophenone (8.5 mg, 41 μmol) in accordance with Method L1.

LC/MS $t_r$ 1.79 min.

MS (ES+) m/z 592, 590 (M+CH$_3$CN+H), 551, 549 (M+H).

Synthesis of Compound 420

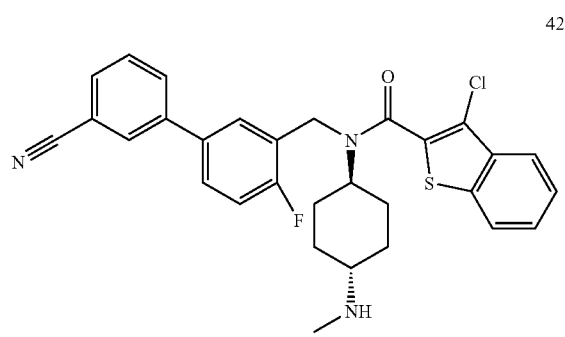

3-Chloro-benzo[b]thiophene-2-carboxylic acid (3'-cyano-4-fluoro-biphenyl-3-ylmethyl)-(4-methylamino-cyclohexyl)-amide trifluoroacetate (249)

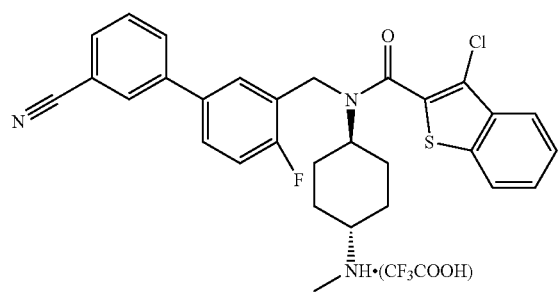

The title compound was prepared from boronic acid (247) (20 mg, 49 µmol) and 3-bromobenzonitrile (7.7 mg, 41 µmol) in accordance with Method L1.

LC/MS $t_r$ 1.81 min.
MS (ES+) m/z 534, 532 (M+H).

Synthesis of Compound 421

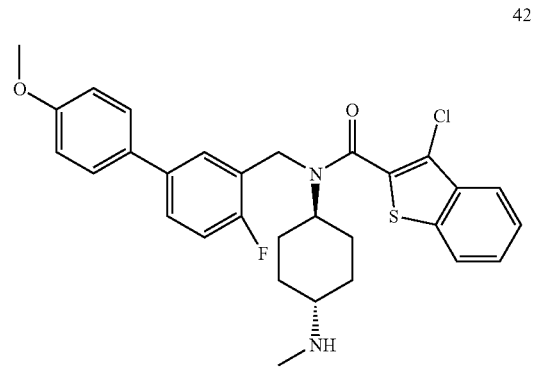

3-Chloro-benzo[b]thiophene-2-carboxylic acid (4-fluoro-4'-methoxy-biphenyl-3-ylmethyl)-(4-methylamino-cyclohexyl)-amide trifluoroacetate (250)

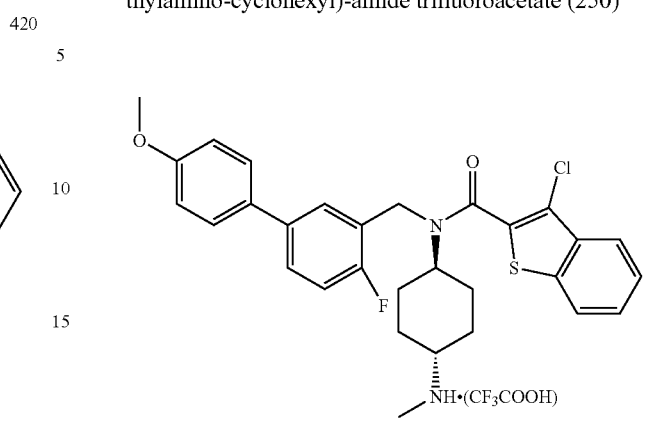

The title compound was prepared from boronic acid (247) (20 mg, 49 µmol) and 4-bromoanisole (7.9 mg, 41 µmol) in accordance with Method L1.

LC/MS $t_r$ 1.87 min.
MS (ES+) m/z 580, 578 (M+CH$_3$CN+H), 539, 537 (M+H).

Synthesis of Compound 422

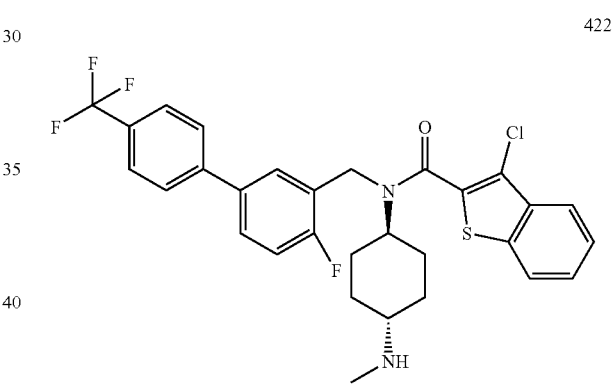

3-Chloro-benzo[b]thiophene-2-carboxylic acid (4-fluoro-4'-trifluoromethyl-biphenyl-3-ylmethyl)-(4-methylamino-cyclohexyl)-amide trifluoroacetate (251)

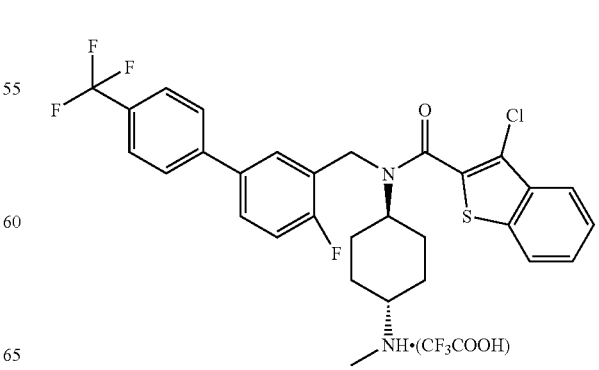

The title compound was prepared from boronic acid (247) (20 mg, 49 μmol) and 1-bromo-4-(trifluoromethyl)benzene (9.5 mg, 41 μmol) in accordance with Method L1.
LC/MS t$_r$ 2.01 min.
MS (ES+) m/z 618, 616 (M+CH$_3$CN+H), 577, 575 (M+H).

Synthesis of Compound 423

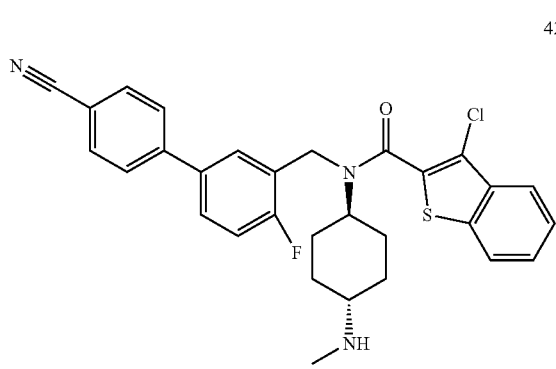

3-Chloro-benzo[b]thiophene-2-carboxylic acid (4'-cyano-4-fluoro-biphenyl-3-ylmethyl)-(4-methylamino-cyclohexyl)-amide trifluoroacetate (252)

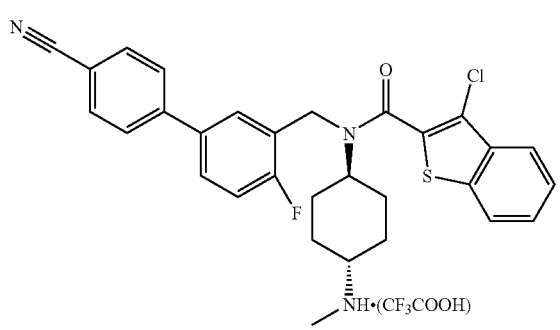

The title compound was prepared from boronic acid (247) (20 mg, 49 μmol) and 4-bromobenzonitrile (7.7 mg, 41 μmol) in accordance with Method L1.
LC/MS t$_r$ 1.83 min.
MS (ES+) m/z 575, 573 (n+CH$_3$CN+H), 534, 532 (M+H).

Synthesis of Compound 424

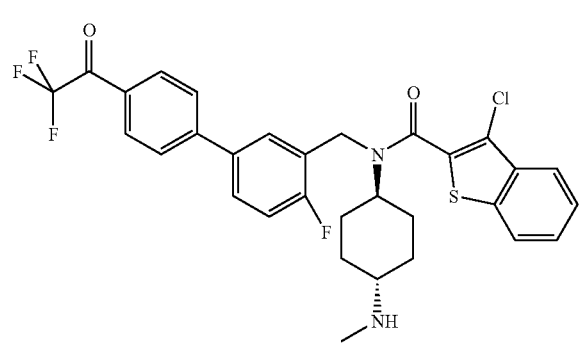

3-Chloro-benzo[b]thiophene-2-carboxylic acid [4-fluoro-4'-(2,2,2-trifluoro-acetyl)-biphenyl-3-ylmethyl]-(4-methylamino-cyclohexyl)-amide trifluoroacetate (253)

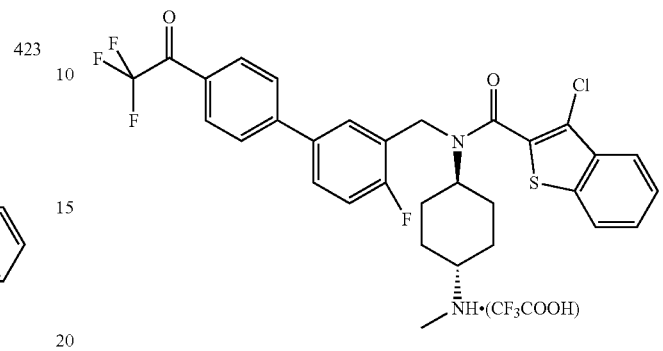

The title compound was prepared from boronic acid (247) (20 mg, 49 μmol) and 1-(4-bromophenyl)-2,2,2-trifluoroethanone (10.7 mg, 41 μmol) in accordance with Method L1.
LC/MS t$_r$ 1.84 min.
MS (ES+) m/z 646 (M+CH$_3$CN+H), 605 (M+H).

Synthesis of Compound 425

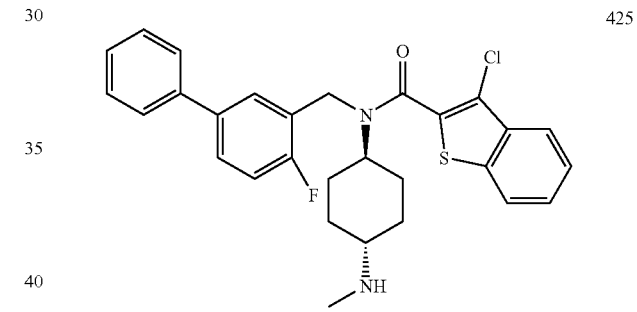

3-Chloro-benzo[b]thiophene-2-carboxylic acid (4-fluoro-biphenyl-3-ylmethyl)-(4-methylamino-cyclohexyl)-amide trifluoroacetate (254)

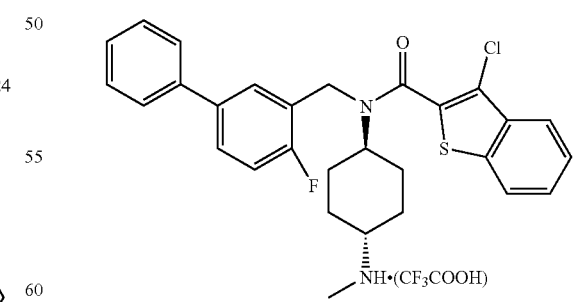

The title compound was prepared from boronic acid (247) (20 mg, 49 μmol) and 4-bromobenzene (6.7 mg, 41 μmol) in accordance with Method L1.
LC/MS t$_r$ 1.91 min.
MS (ES+) m/z 550, 548 (M+CH$_3$CN+H), 509, 507 (M+H).

Synthesis of Compound 426

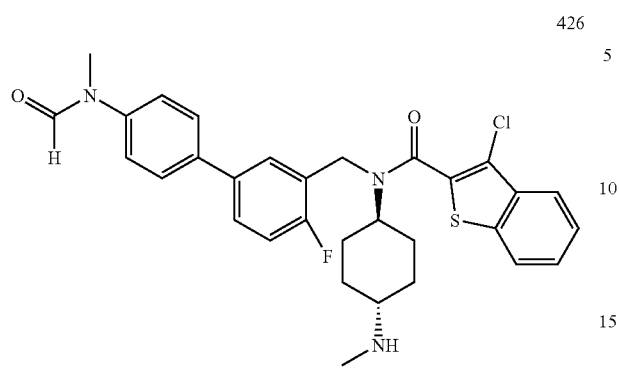

3-Chloro-benzo[b]thiophene-2-carboxylic acid [4-fluoro-4'-(formyl-methyl-amino)-biphenyl-3-ylmethyl]-(4-methylamino-cyclohexyl)-amide trifluoroacetate (255)

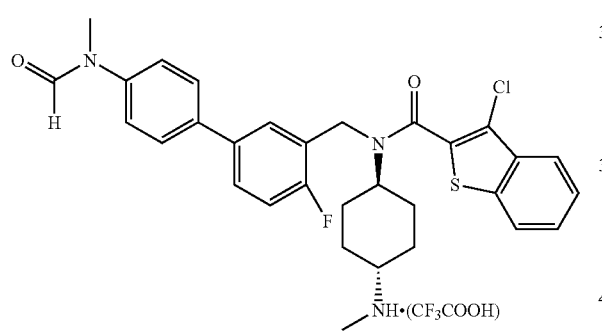

The title compound was prepared from boronic acid (247) (20 mg, 49 µmol) and N-(-4-bromophenyl)-N-methylformamide (51) (9.1 mg, 41 µmol) in accordance with Method L1.

LC/MS $t_r$ 1.73 min.

MS (ES+) m/z 566, 564 (M+H).

Synthesis of Compound 427

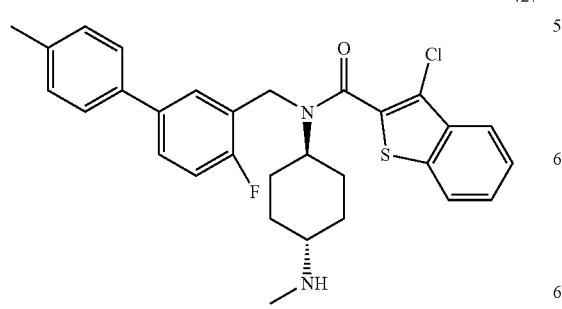

3-Chloro-benzo[b]thiophene-2-carboxylic acid (4-fluoro-4'-methyl-biphenyl-3-ylmethyl)-(4-methylamino-cyclohexyl)-amide trifluoroacetate (256)

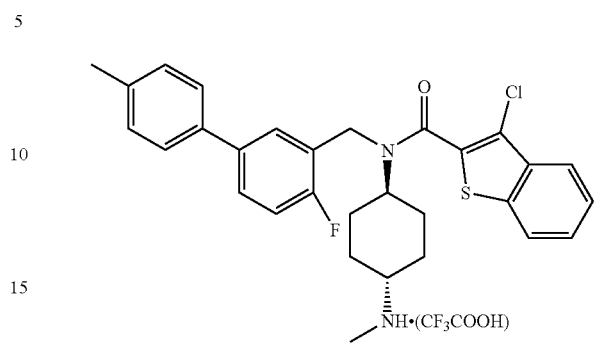

The title compound was prepared from boronic acid (247) (20 mg, 49 µmol) and 4-bromotoluene (7.3 mg, 41 µmol) in accordance with Method L1.

LC/MS $t_r$ 1.54 min.

MS (ES+) m/z 564, 562 (M+CH$_3$CN+H), 523, 521 (M+H).

Synthesis of Compound 428

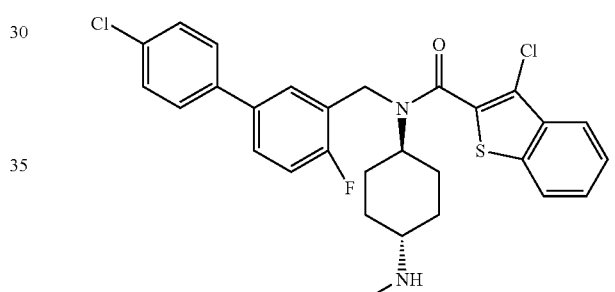

3-Chloro-benzo[b]thiophene-2-carboxylic acid (4'-chloro-4-fluoro-biphenyl-3-ylmethyl)-(4-methylamino-cyclohexyl)-amide trifluoroacetate (257)

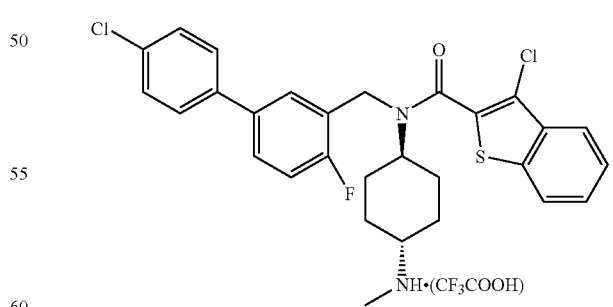

The title compound was prepared from boronic acid (247) (20 mg, 49 µmol) and 4-bromochlorobenzene (8.1 mg, 41 µmol) in accordance with Method L1.

LC/MS $t_r$ 1.57 min.

MS (ES+) m/z 584, 582 (M+CH$_3$CN+H), 543, 541 (M+H).

Synthesis of Compound 429

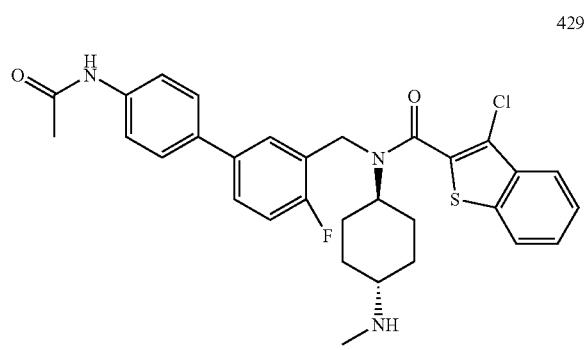

429

3-Chloro-benzo[b]thiophene-2-carboxylic acid (4'-acetylamino-4-fluoro-biphenyl-3-ylmethyl)-(4-methylamino-cyclohexyl)-amide trifluoroacetate (258)

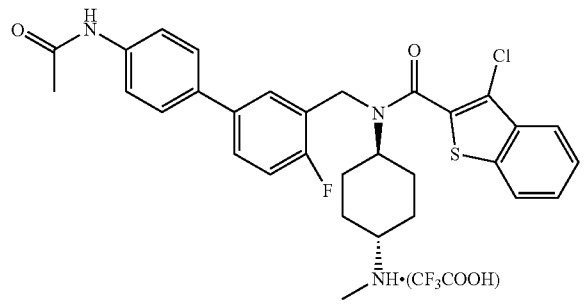

The title compound was prepared from boronic acid (247) (20 mg, 49 μmol) and 4-bromoacetanilide (9.1 mg, 41 μmol) in accordance with Method L1.

LC/MS $t_r$ 1.71 min.

MS (ES+) m/z 566, 564 (M+H).

Synthesis of Compound 430

430

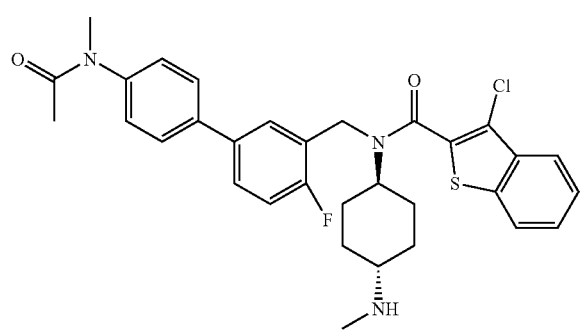

3-Chloro-benzo[b]thiophene-2-carboxylic acid [4'-(acetyl-methyl-amino)-4-fluoro-biphenyl-3-ylmethyl]-(4-methylamino-cyclohexyl)-amide trifluoroacetate (259)

The title compound was prepared from boronic acid (247) (20 mg, 49 μmol) and N-(4-bromophenyl)-N-methylacetamide (62) (9.7 mg, 41 μmol) in accordance with Method L1.

LC/MS $t_r$ 1.70 min.

MS (ES+) m/z 580, 578 (M+H).

Synthesis of Compound 431

431

3-Chloro-benzo[b]thiophene-2-carboxylic acid (4-fluoro-4'-formylamino-biphenyl-3-ylmethyl)-(4-methylamino-cyclohexyl)-amide trifluoroacetate (260)

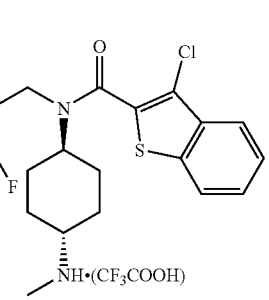

The title compound was prepared from boronic acid (247) (20 mg, 49 μmol) and N-(4-bromophenyl)formamide (50) (8.5 mg, 41 μmol) in accordance with Method L1

LC/MS $t_r$ 1.67 min.

MS (ES+) m/z 552, 550 (M+H).

Synthesis of Compound 432

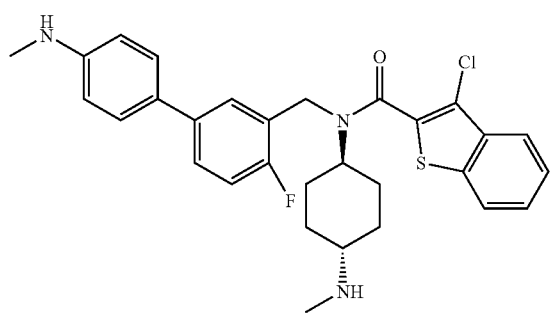

(4-{[4-Fluoro-4'-(formyl-methyl-amino)-biphenyl-3-ylmethyl]-amino}-cyclohexyl)-methyl-carbamic acid tert-butyl ester (261)

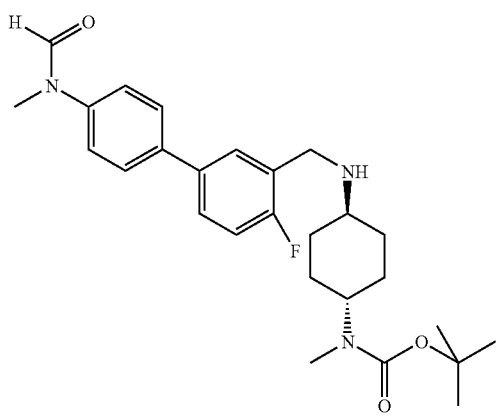

The title compound was prepared from boronic acid (247) (300 mg, 0.79 mmol) and aryl bromide (51) (200 mg, 0.95 mmol) in accordance with Method B.

Yield: 270 mg (73%)

LC/MS $t_r$ 1.08 min.

MS (ES+) m/z 512 (M+CH$_3$CN+H), 414 (M-C(CH$_3$)$_3$+H).

(4-{(3-Chloro-benzo[b]thiophene-2-carbonyl)-[4-fluoro-4'-(formyl-methyl-amino)-biphenyl-3-ylmethyl]-amino}-cyclohexyl)-methyl-carbamic acid tert-butyl ester (262)

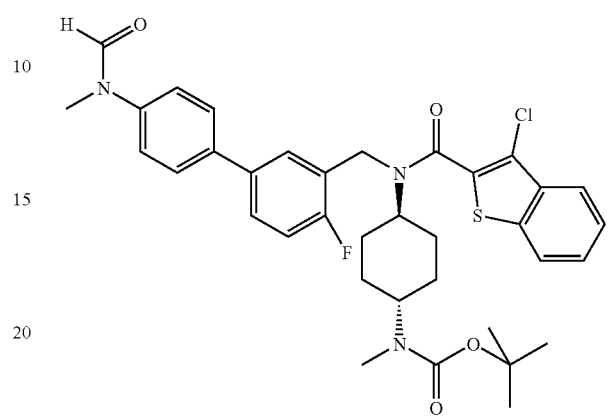

The title compound was prepared from amine (261) (270 mg, 0.58 mmol) and 3-chlorobenzo[b]thiophene-2-carbonyl chloride (150 mg, 0.63 mmol) following Method D.

Yield: 250 mg (66%).

LC/MS $t_r$ 1.95 min.

MS (ES+) m/z 688, 686 (M+Na), 610, 608 (M-C(CH$_3$)$_3$+H), 566, 564 (M-CO$_2$C(CH$_3$)$_3$+H).

3-Chloro-benzo[b]thiophene-2-carboxylic acid (4-fluoro-4'-methylamino-biphenyl-3-ylmethyl)-(4-methylamino-cyclohexyl)-amide dihydrochloride (263)

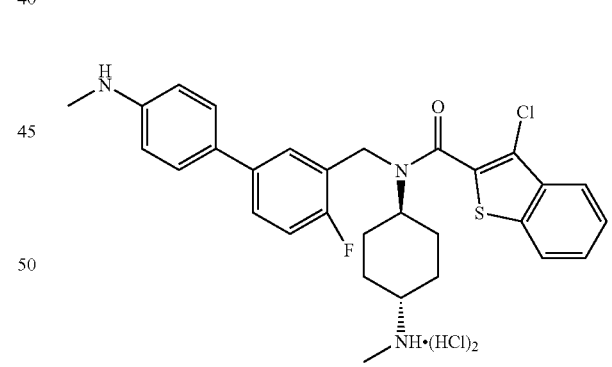

tert-Butyl carbamate (262) (220 mg, 0.33 mmol) was deprotected using Method F to give the title compound.

Yield: 200 mg (99%).

LC/MS $t_r$ 1.21 min

MS (ES+) m/z 538, 536 (M+H), 507, 505 (M-31+H).

$^1$H NMR $\delta_H$ ppm (400 MHz, D$_6$-DMSO, 95° C.): 8.55 (2H, br. s), 7.85 (1H, d), 7.65 (1H, d), 7.4-7.1 (6H), 6.95 (1H, t), 6.65 (2H, d), 4.50 (2H, s), 3.65 (1H, br. s), 2.7-2.6 (1H, m), 2.55 (3H, s), 2.15 (3H, s), 1.85 (2H, m), 1.7-1.5 (4H, m), 1.2-1.0 (2H, m).

Synthesis of Compound 433

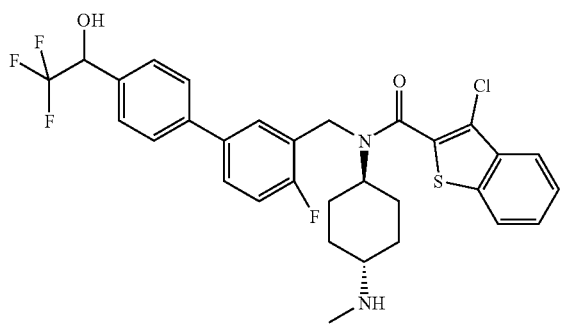

(4-{[4-Fluoro-4'-(2,2,2-trifluoro-acetyl)-biphenyl-3-ylmethyl]-amino}-cyclohexyl)-methyl-carbamic acid tert-butyl ester (264)

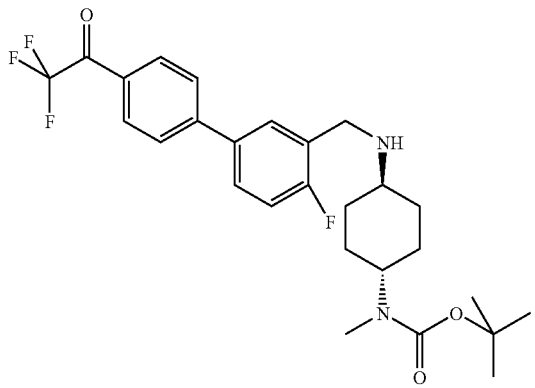

The title compound was prepared from boronic acid (247) (300 mg, 0.79 mmol) and 1-(4-bromophenyl)-2,2,2-trifluoroethanone (240 mg, 0.95 mmol) in accordance with Method B.

Yield: 200 mg (50%)
LC/MS $t_r$ 1.56 min.
MS (ES+) m/z 527 (M+H$_2$O+H).

(4-{(3-Chloro-benzo[b]thiophene-2-carbonyl)-[4-fluoro-4'-(2,2,2-trifluoro-acetyl)-biphenyl-3-ylmethyl]-amino}-cyclohexyl)-methyl-carbamic acid tert-butyl ester (265)

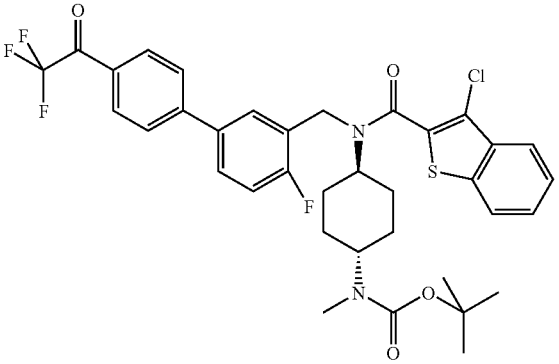

The title compound was prepared from amine (264) (220 mg, 0.43 mmol) and 3-chlorobenzo[b]thiophene-2-carbonyl chloride (110 mg, 0.48 mmol) following Method D.

Yield: 200 mg (66%).
LC/MS $t_r$ 2.13 min. The hydrate appears at 1.90 min.
MS (ES+) m/z 667, 665 (M+H$_2$O—C(CH$_3$)$_3$+H) and 649, 647 (M-C(CH$_3$)$_3$+H), 625, 623 (M-CO$_2$C(CH$_3$)$_3$+Na).

(4-{(3-Chloro-benzo[b]thiophene-2-carbonyl)-[4-fluoro-4'-(2,2,2-trifluoro-1-hydroxy-ethyl)-biphenyl-3-ylmethyl]-amino}-cyclohexyl)-methyl-carbamic acid tert-butyl ester (266)

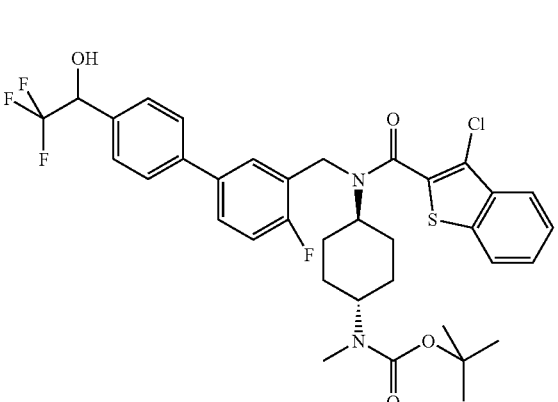

Trifluoroacetophenone (265) (90 mg, 0.13 mmol) was dissolved in EtOH (0.9 mL) with a little DCM. Sodium borohydride (8 mg, 0.21 mmol) was added portionwise and the reaction stirred at RT until complete. H$_2$O (5 mL) was added and the product extracted with EtOAc (2×5 mL). Drying (MgSO$_4$), filtration, reduction in vacuo and chromatography with EtOAc/heptanes gave the title compound.

Yield: 54 mg (60%).

351

3-Chloro-benzo[b]thiophene-2-carboxylic acid [4-fluoro-4'-(2,2,2-trifluoro-1-hydroxy-ethyl)-biphenyl-3-ylmethyl]-(4-methylamino-cyclohexyl)-amide hydrochloride (267)

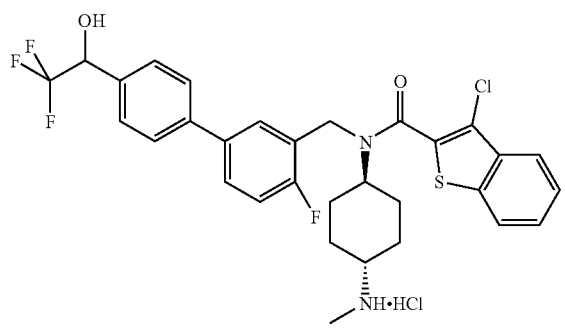

tert-Butyl carbamate (266) (54 mg, 77 μmol) was deprotected using Method E to give the title compound.

Yield: 51 mg (99%).

LC/MS $t_r$ 1.49 min.

MS (ES+) nm/z 607, 605 (M+H), 576, 574 (M-31+H).

$^1$H NMR $\delta_H$ ppm (400 MHz, D$_4$-MeOH): 8.0-7.2 (10H), 7.0-7.2 (1H), 4.95 (1H, q), 3.7-4.1 (1H), 2.80 (1H), 2.4-2.6 (4H), 2.2-1.2 (9H).

Synthesis of Compound 434

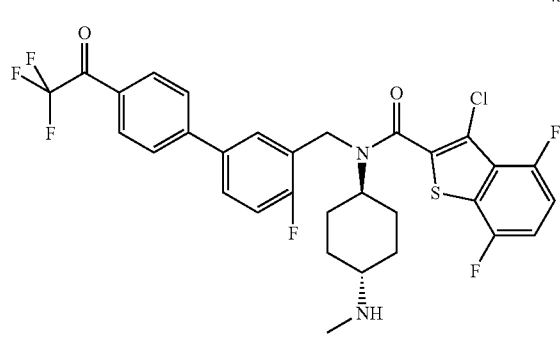

434

352

(4-{[4-Fluoro-4'-(2,2,2-trifluoro-acetyl)-biphenyl-3-ylmethyl]-amino}-cyclohexyl)-methyl-carbamic acid tert-butyl ester (278)

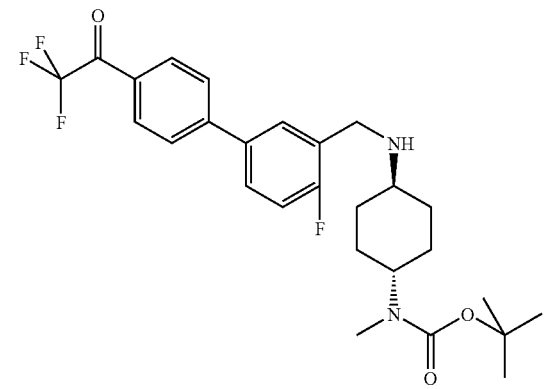

The title compound was prepared from boronic acid (247) (600 mg, 1.58 mmol) and 1-(4-bromophenyl)-2,2,2-trifluoroethanone (400 mg, 1.58 mmol) in accordance with Method A.

Yield: 510 mg (61%).

LC/MS $t_r$ 1.36 min.

MS (ES+) m/z 527 (M+H$_2$O+H), 471 (M-C(CH$_3$)$_3$+H$_2$O+H).

(4-{((3-Chloro-4,7-difluoro-benzo[b]thiophene-2-carbonyl)-[4-fluoro-4'-(2,2,2-trifluoro-acetyl)-biphenyl-3-ylmethyl]-amino}-cyclohexyl)-methyl-carbamic acid tert-butyl ester (279)

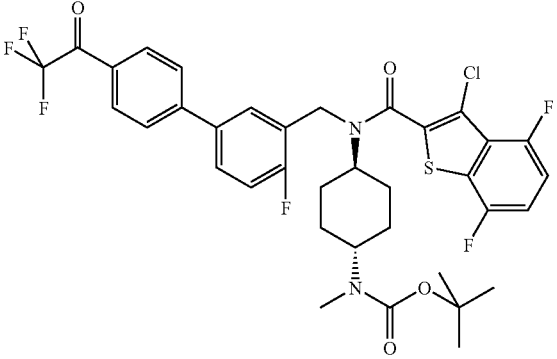

The title compound was prepared from amine (278) (502 mg, 0.95 mmol) and acid chloride 8 (267 mg, 1.0 mmol) following Method D.

3-Chloro-4,7-difluoro-benzo[b]thiophene-2-carboxylic acid [4-fluoro-4'-(2,2,2-trifluoro-acetyl)-biphenyl-3-ylmethyl]-(4-methylamino-cyclohexyl)-amide hydrochloride (280)

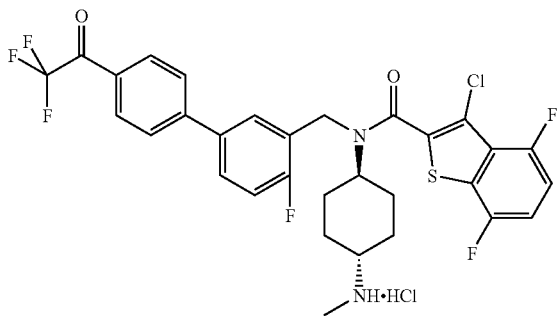

tert-Butyl carbamate (279) was deprotected using Method F to give the title compound. It was purified by preparative HPLC.

Yield: 57 mg (9%) over 2 steps.

LC/MS $t_r$ 1.63 min. The hydrate appears at 1.37 min.

MS (ES+) m/z 659, 657 (M+H$_2$O+H) and 641, 639 (M+H).

$^1$H NMR $\delta_H$ ppm (400 MHz, D$_6$-DMSO, 95° C.): 8.25 (2H, br.s), 7.95 (2H, d), 7.72 (2H, d), 7.55 (2H, br.s), 7.45 (2H, m), 7.25-7.15 (3H, m), 4.62 (2H, s), 3.73 (1H, br.s), 3.05-2.65 (1H, obsc. br.s), 2.45-2.25 (3H, obsc. s), 2.00-1.85 (2H, m), 1.83-1.55 (4H, m), 1.30-1.10 (2H, m).

Compound Screening

Human Hedgehog, Reporter Assays (HEPM-GliLuc (HGL) & Daoy-GliLuc (DGL))

Mouse (TM3: mouse Leydig cells; S12: mouse embryonic mesenchymal cells) and human (Daoy: human medulloblastoma cell; HepM: human embryonic palatal mesenchymal cell) cell lines are used to screen small molecules for their ability to modulate the activity of the sonic hedgehog pathway (Table 1, Table 2, and Table 3). Stable hedgehog pathway reporter cell lines are established by specific antibiotic selection following transfection of a reporter plasmid containing a luciferase gene located directly downstream from the gli promoter. Consequently, any observable changes in cellular luciferase activity may be attributed to changes in sonic hedgehog pathway activity in mouse and human cells, respectively, since gli is the major by-product of this pathway. To calculate activity, we generate an eleven point dose curve for each compound using 1:3 dilutions in 96 well assay plates. Each plate tested also contains low and high control to establish maximal pathway activation so to establish/compare a percentage activation of each tested compound (AMAX) on respective plates. Also we calculate EC$_{50}$ values, or a concentration where the pathway will be exactly 50% activated, for each tested compound to determine potency. In these cell lines, compounds that register >20% AMAX values are considered active.

Stable hedgehog pathway reporter cell lines are established following specific antibiotic selection following transfection of a reporter plasmid In short, typically cells are plated in MicroTiter-plates at 10,000-20,000 cells per well, in growth media (containing 10%-20% FBS). After 48-72 hrs (HGL and DGL respectively) the media in the assay plates is switched to low-serum containing media (0.5% FBS). At that time compounds are added (at 1-5 µM) to the assay plates, in the presence or absence of hedgehog protein (octyl-modified version; 1-5 ng/ml). After another 24 hrs of incubation, the media from the assay plates is discarded and replaced with luciferase assay-mix. Subsequently, plates are incubated at RT for ~15-30 mins and then read in a luminometer. [note: addition of the Hedgehog protein, although not critical, will sensitize the assay allowing the identification of weak actives].

TABLE 1

(2.5 µM > A ≧ 1 µM > B ≧ 250 nM > C ≧ 50 nm > D)

| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| (structure shown) | 301 | D | | C | D |

TABLE 1-continued
(2.5 μM > A ≧ 1 μM > B ≧ 250 nM > C ≧ 50 nm > D)
| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 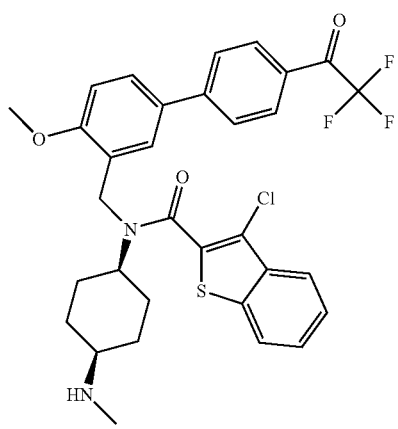 | 302 | D |  | D | D |
| 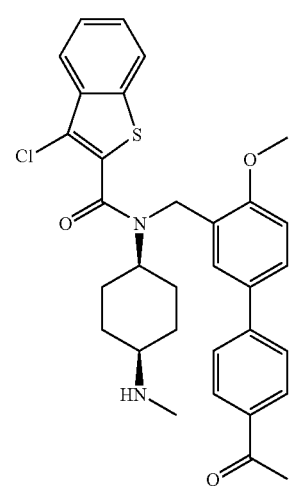 | 303 | D | D | D | D |
| 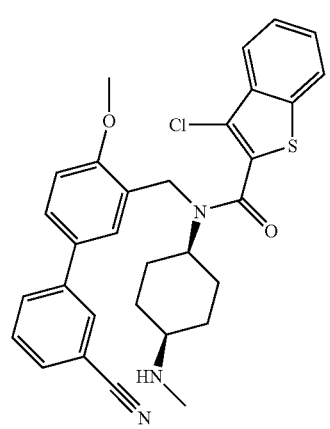 | 304 | D |  | D | D |

TABLE 1-continued (2.5 μM > A ≧ 1 μM > B ≧ 250 nM > C ≧ 50 nm > D)

| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 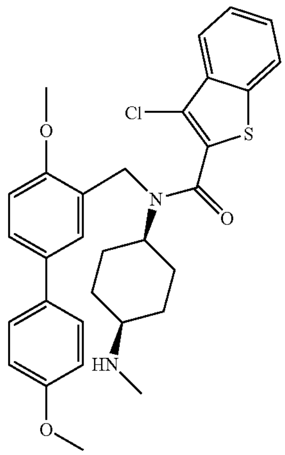 | 305 | D |  | B | D |
| 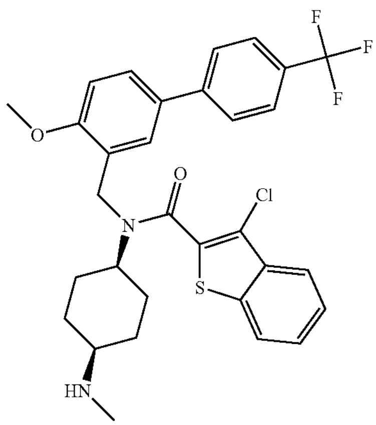 | 306 | C |  |  | D |
| 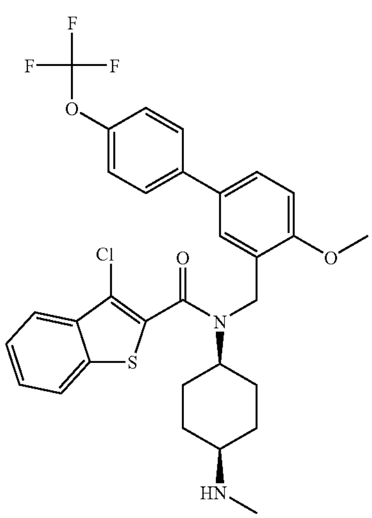 | 307 | D |  |  | D |

TABLE 1-continued
| | | (2.5 μM > A ≧ 1 μM > B ≧ 250 nM > C ≧ 50 nm > D) | | | |
|---|---|---|---|---|---|
| STRUCTURE | COMPOUND | TM3 Avg. EC$_{50}$ | S12 Avg. EC$_{50}$ | HEPM Avg. EC$_{50}$ | Daoy Avg. EC$_{50}$ |
| 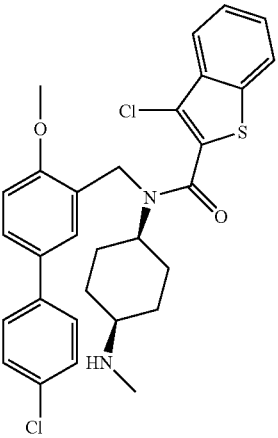 | 308 | D | | | D |
| 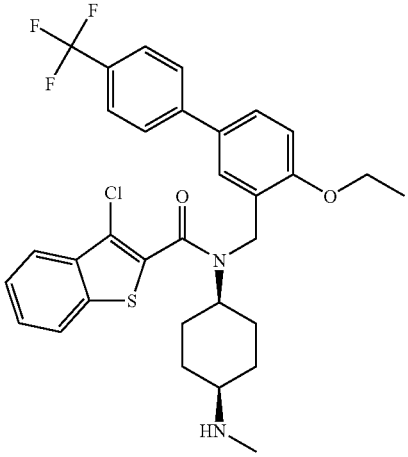 | 309 | C | | | D |
| 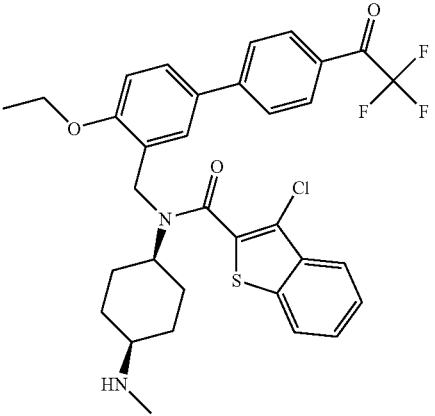 | 310 | D | | D | D |

TABLE 1-continued (2.5 µM > A ≧ 1 µM > B ≧ 250 nM > C ≧ 50 nm > D)

| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 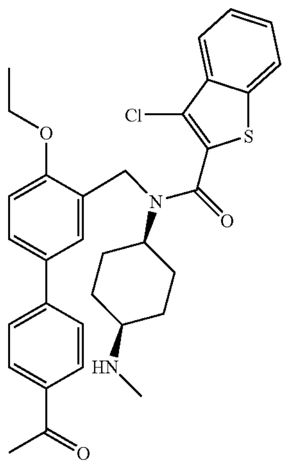 | 311 | D |  | C | D |
| 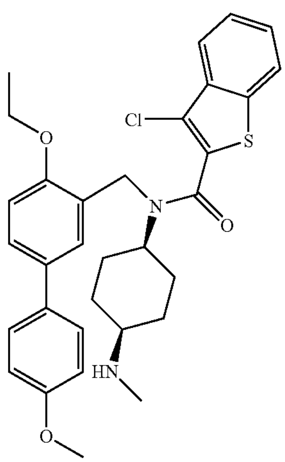 | 312 |  |  |  | C |
| 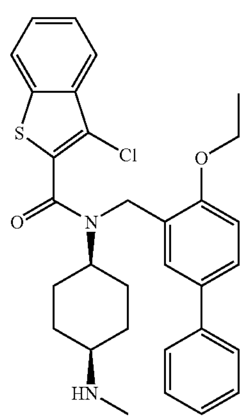 | 313 | C |  |  | D |

TABLE 1-continued
| | | (2.5 μM > A ≧ 1 μM > B ≧ 250 nM > C ≧ 50 nm > D) | | | |
|---|---|---|---|---|---|
| STRUCTURE | COMPOUND | TM3 Avg. EC$_{50}$ | S12 Avg. EC$_{50}$ | HEPM Avg. EC$_{50}$ | Daoy Avg. EC$_{50}$ |
| 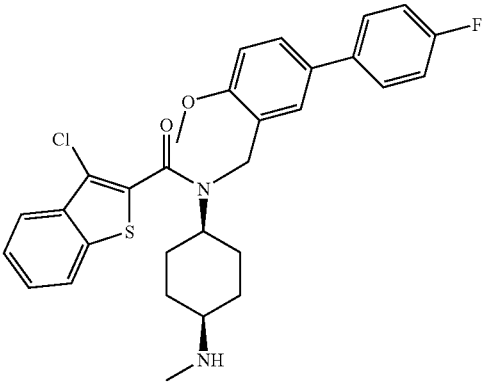 | 314 | D | | | D |
| 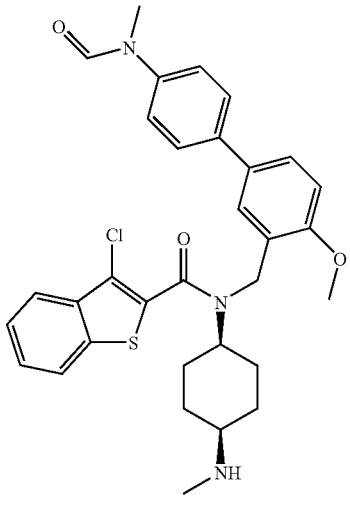 | 315 | D | | B | C |
| 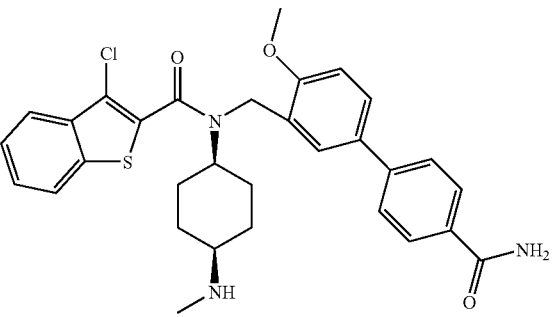 | 316 | D | D | D | |

TABLE 1-continued
(2.5 μM > A ≧ 1 μM > B ≧ 250 nM > C ≧ 50 nm > D)
| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 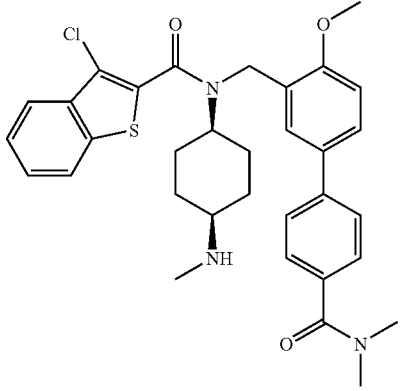 | 317 (R19) | D | D | D | |
| 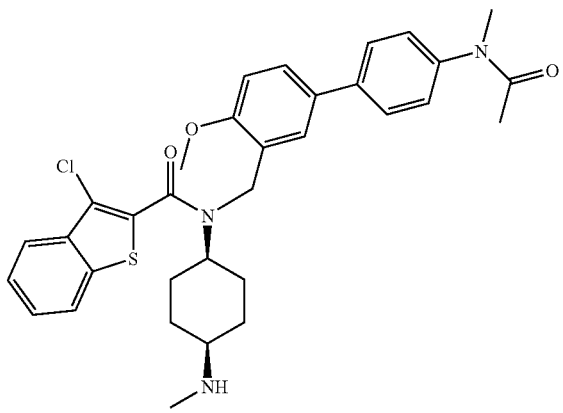 | 318 | D | | D | D |
| 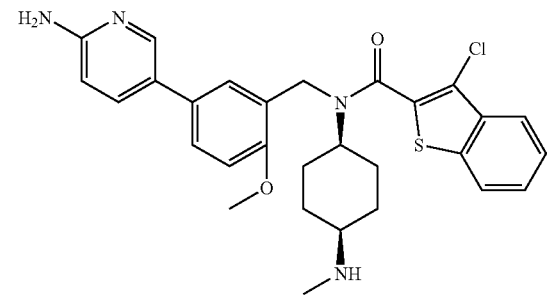 | 319 | D | D | D | |
| 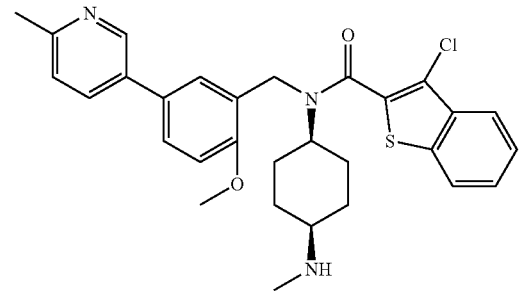 | 320 | D | | D | |

TABLE 1-continued
(2.5 μM > A ≧ 1 μM > B ≧ 250 nM > C ≧ 50 nm > D)
| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 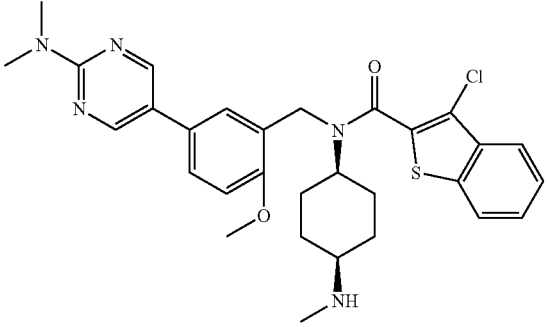 | 321 | A | | | C |
| 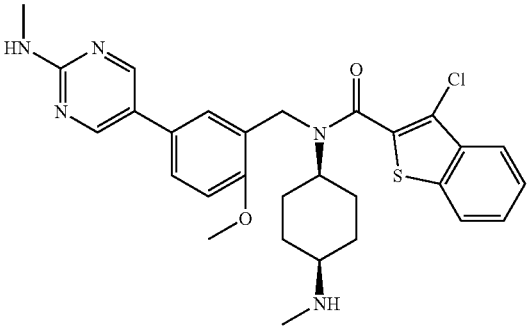 | 322 | B | | | C |
| 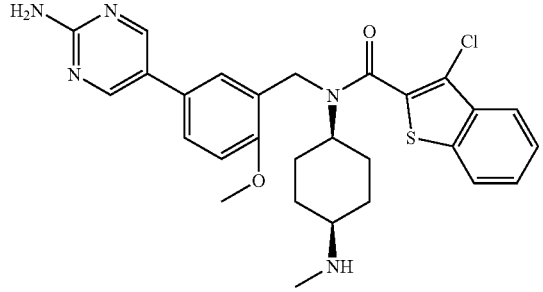 | 323 | C | | | D |
| 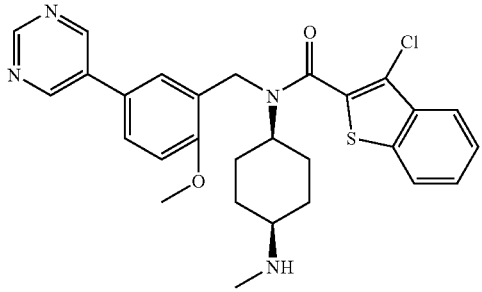 | 324 (R20) | C | | C | D |

TABLE 1-continued (2.5 µM > A ≧ 1 µM > B ≧ 250 nM > C ≧ 50 nm > D)

| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 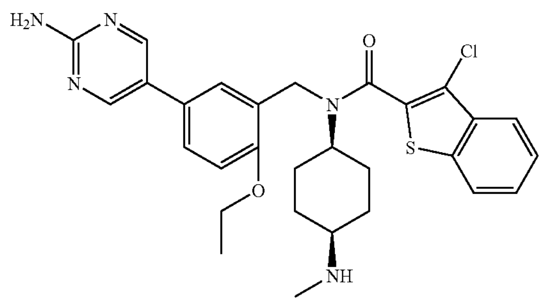 | 325 | B | | C | D |
| 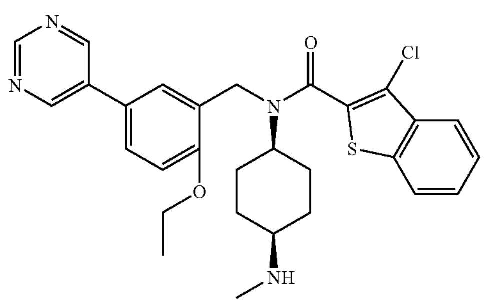 | 326 | C | | C | D |
| 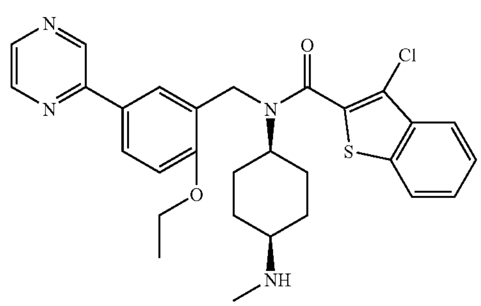 | 327 | B | | B | D |
| 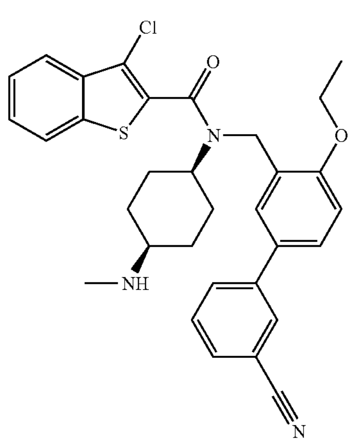 | 328 | D | | C | D |

TABLE 1-continued
(2.5 μM > A ≧ 1 μM > B ≧ 250 nM > C ≧ 50 nm > D)
| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 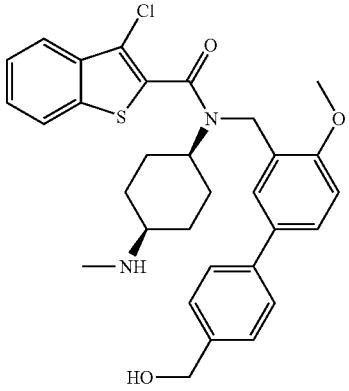 | 329 | D | D | D | |
| 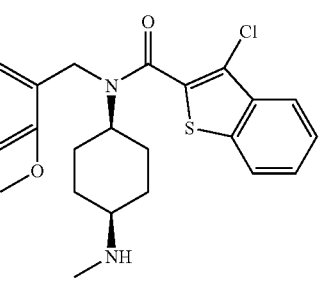 | 330 (R22) | C | | C | D |
| 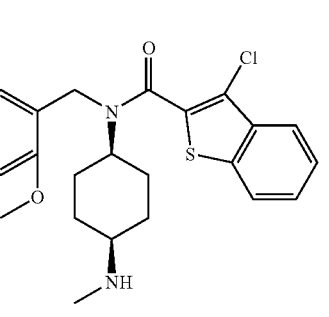 | 331 (R11) | D | | D | |
| 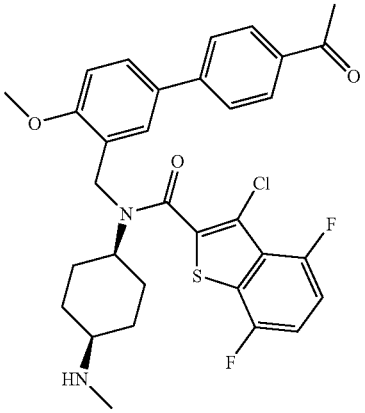 | 332 | D | D | D | D |

TABLE 1-continued (2.5 μM > A ≧ 1 μM > B ≧ 250 nM > C ≧ 50 nm > D)

| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 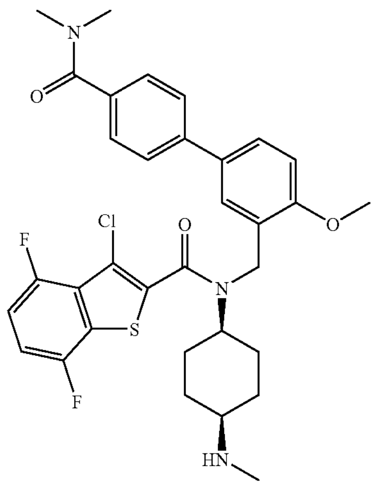 | 333 | D | D | D | D |
| 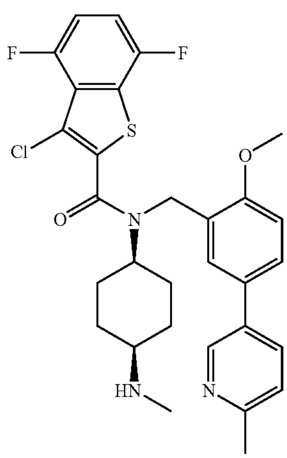 | 334 | D | D | D | D |
| 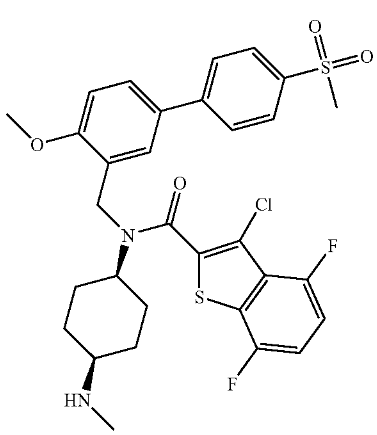 | 335 | D | D | D | D |

TABLE 1-continued (2.5 μM > A ≧ 1 μM > B ≧ 250 nM > C ≧ 50 nm > D)

| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 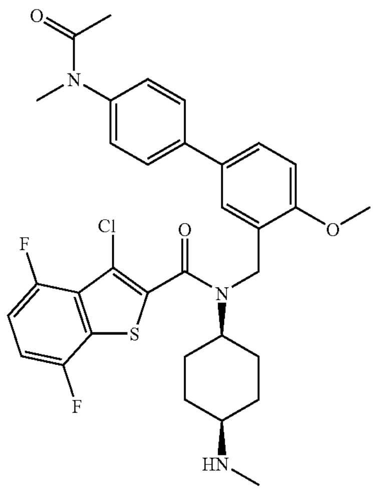 | 336 | D | D | D | D |
| 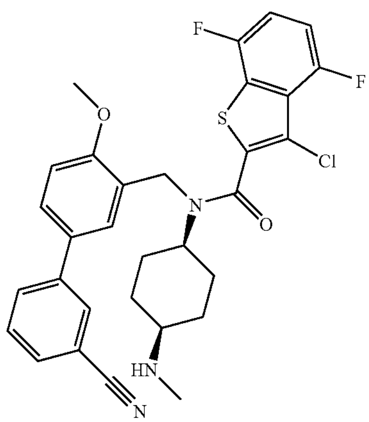 | 337 | D | | D | |
| 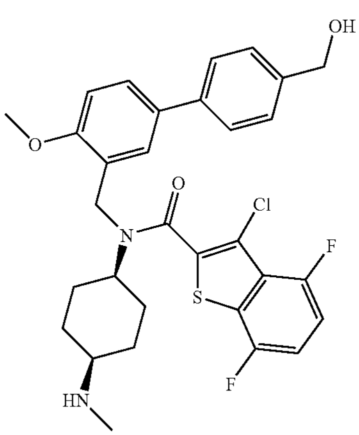 | 338 | D | D | D | D |

TABLE 1-continued (2.5 μM > A ≧ 1 μM > B ≧ 250 nM > C ≧ 50 nm > D)

| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 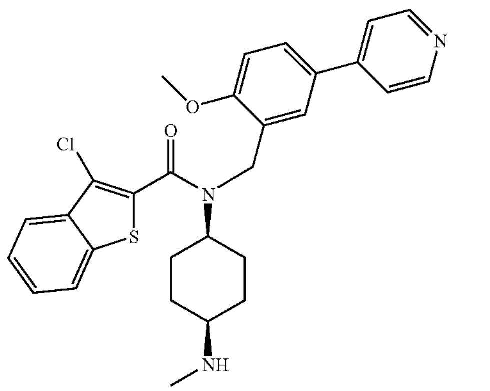 | 339 (R12) | D | | D | |
| 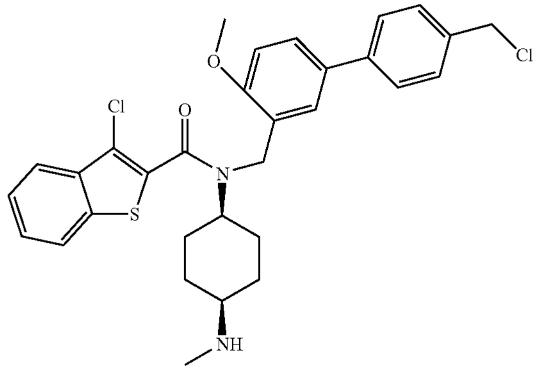 | 340 | D | | D | D |
| 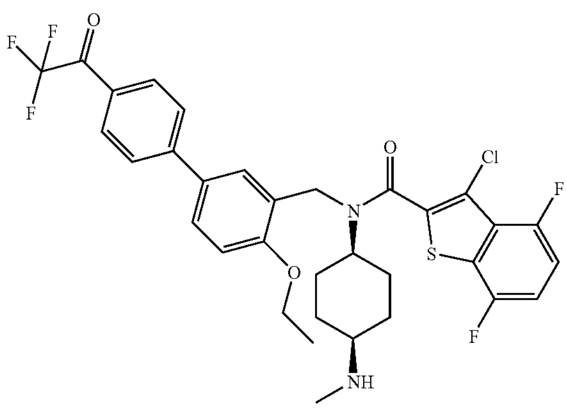 | 341 | D | | C | |
| 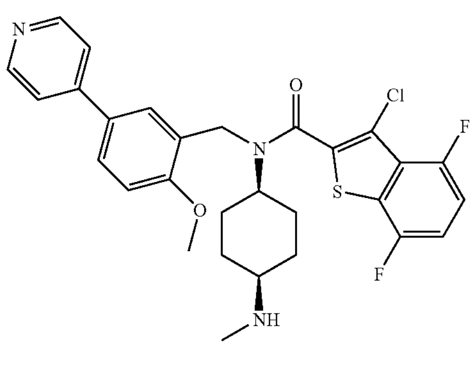 | 342 | D | D | D | D |

TABLE 1-continued

| | | (2.5 µM > A ≧ 1 µM > B ≧ 250 nM > C ≧ 50 nm > D) | | | |
|---|---|---|---|---|---|
| STRUCTURE | COMPOUND | TM3 Avg. EC$_{50}$ | S12 Avg. EC$_{50}$ | HEPM Avg. EC$_{50}$ | Daoy Avg. EC$_{50}$ |
| | 343 (R15) | D | | D | D |
| | 344 (R14) | D | | D | D |
| | 345 | D | | D | D |
| | 346 | D | D | D | D |

TABLE 1-continued
(2.5 μM > A ≧ 1 μM > B ≧ 250 nM > C ≧ 50 nm > D)
| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 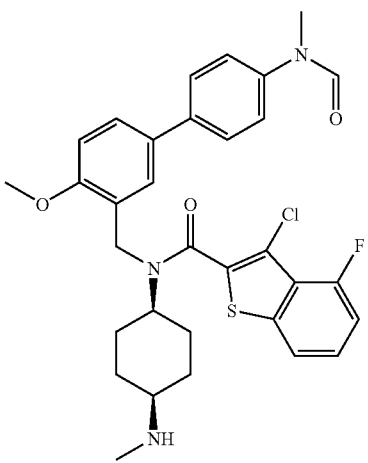 | 347 | D | | D | D |
| 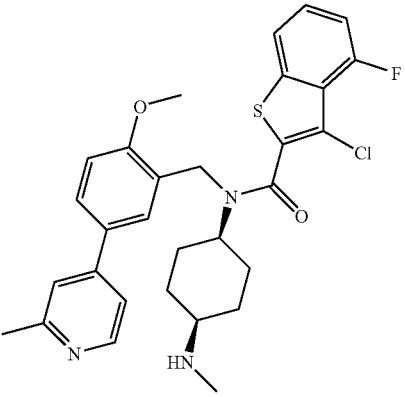 | 348 | D | D | D | D |
| 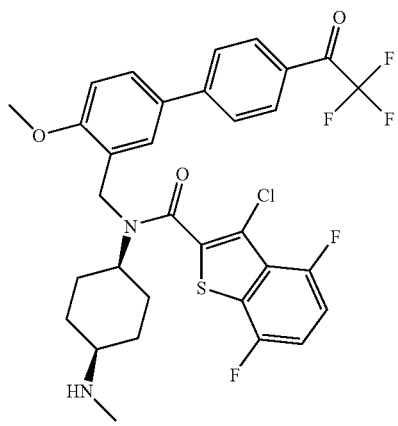 | 349 | D | | D | D |

TABLE 1-continued (2.5 µM > A ≧ 1 µM > B ≧ 250 nM > C ≧ 50 nm > D)

| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 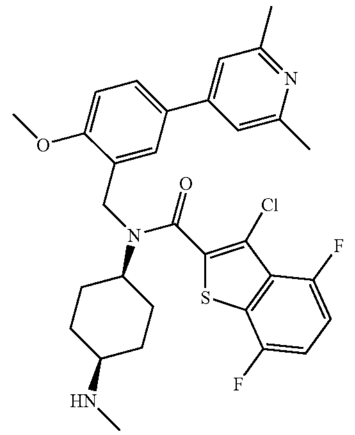 | 350 | D | | C | D |
| 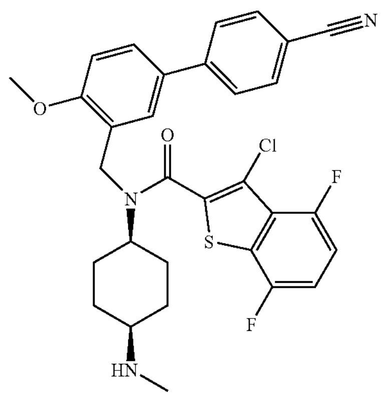 | 351 | D | | D | |
| 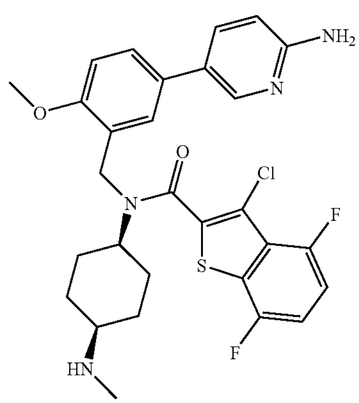 | 352 (R18) | D | | D | D |
| 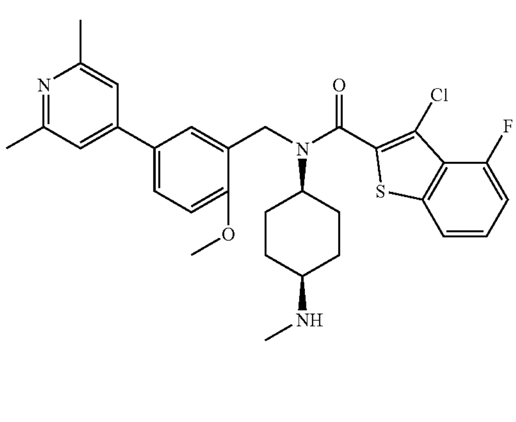 | 353 | D | | C | C |

TABLE 1-continued (2.5 µM > A ≧ 1 µM > B ≧ 250 nM > C ≧ 50 nm > D)

| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 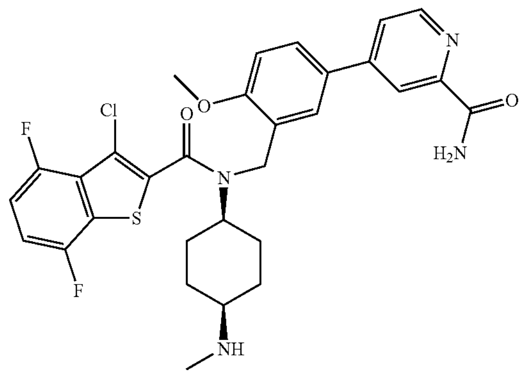 | 354 (R17) | D | D | D | D |
| 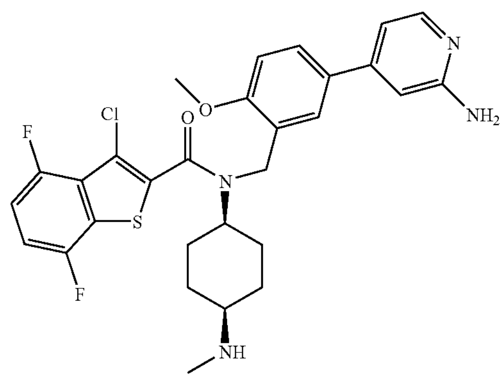 | 355 | D | D | D | |
| 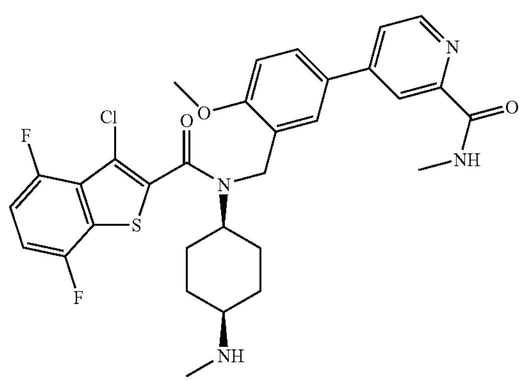 | 356 (R16) | D | | D | D |
| 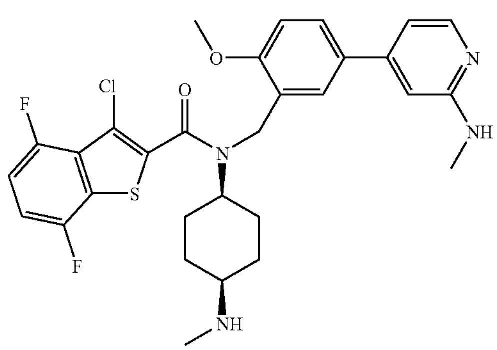 | 357 | D | D | D | D |

TABLE 1-continued

| | | (2.5 μM > A ≧ 1 μM > B ≧ 250 nM > C ≧ 50 nm > D) | | | |
|---|---|---|---|---|---|
| STRUCTURE | COMPOUND | TM3 Avg. EC$_{50}$ | S12 Avg. EC$_{50}$ | HEPM Avg. EC$_{50}$ | Daoy Avg. EC$_{50}$ |
| | 358 | D | | D | D |
| | 359 | D | D | D | D |
| | 360 (R16) | D | D | D | D |

TABLE 1-continued
(2.5 µM > A ≧ 1 µM > B ≧ 250 nM > C ≧ 50 nm > D)
| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 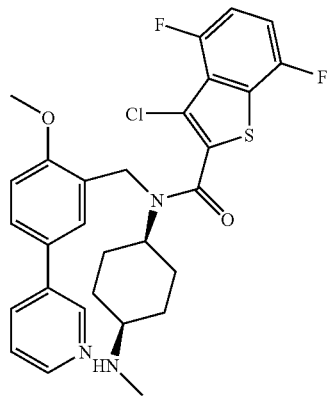 | 361 | D | D | D | D |
| 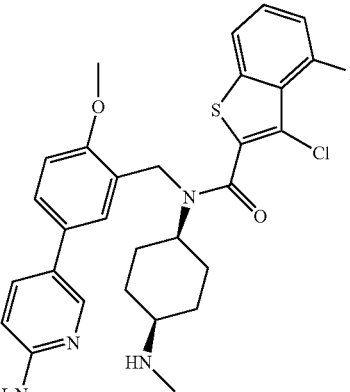 | 362 (R13) | D | D | D | D |
| 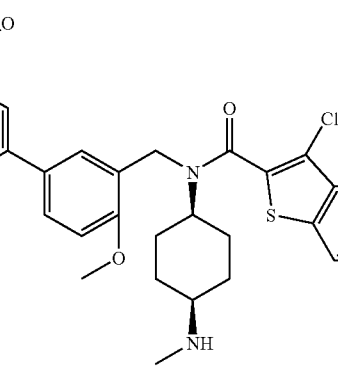 | 363 | D | | D | |
| 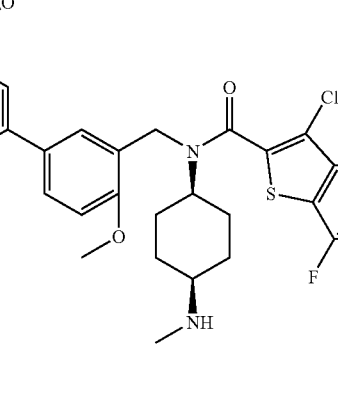 | 364 | D | | D | |

TABLE 1-continued (2.5 μM > A ≧ 1 μM > B ≧ 250 nM > C ≧ 50 nm > D)

| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 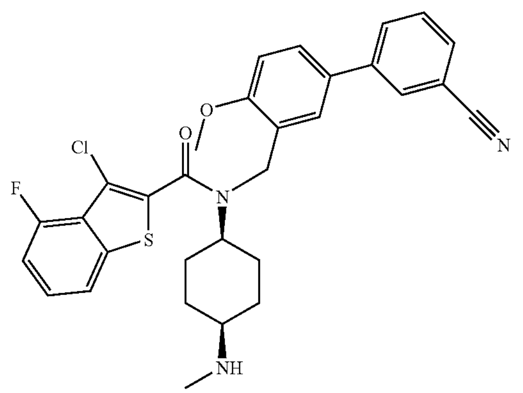 | 365 | D | | | D |
| 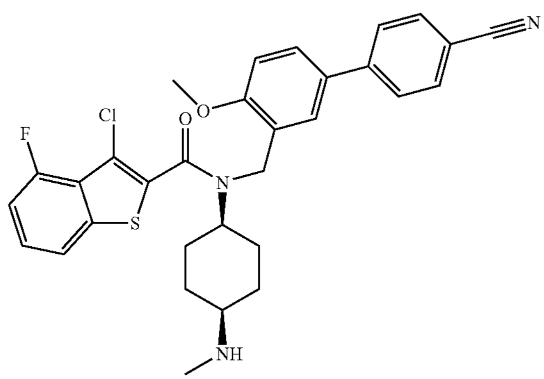 | 366 | D | | | D |
| 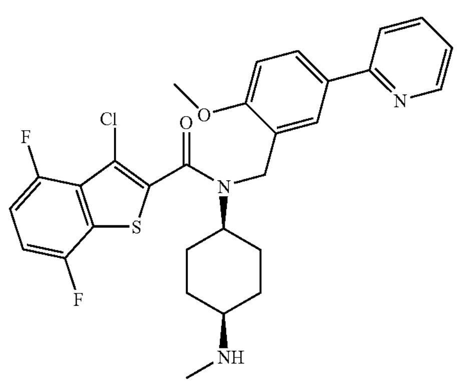 | 367 | D | D | D | D |
| 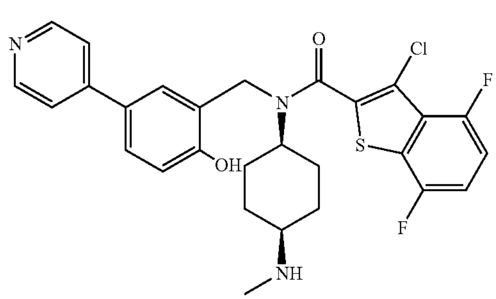 | 368 | | D | D | D |

TABLE 1-continued (2.5 μM > A ≧ 1 μM > B ≧ 250 nM > C ≧ 50 nm > D)

| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 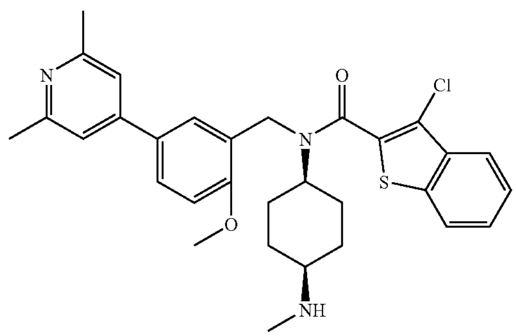 | R1 | D | | C | |
| 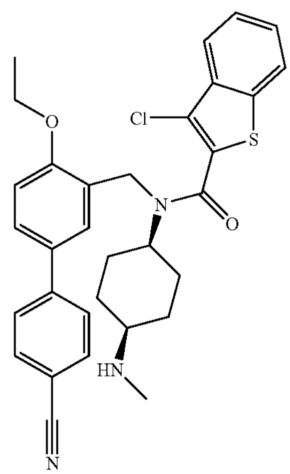 | R2 | C | | C | |
| 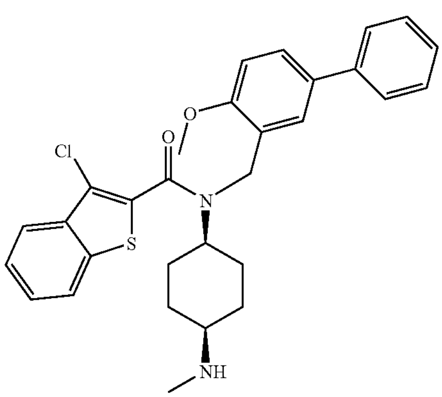 | R3 | D | | C | C |
| 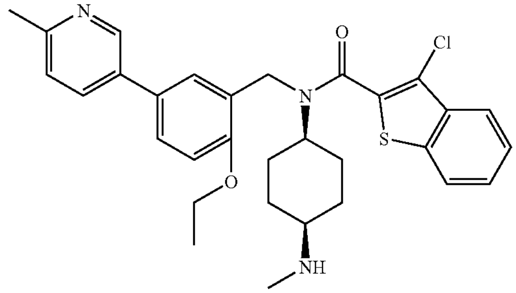 | R4 | C | | C | |

TABLE 1-continued
(2.5 μM > A ≧ 1 μM > B ≧ 250 nM > C ≧ 50 nm > D)
| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 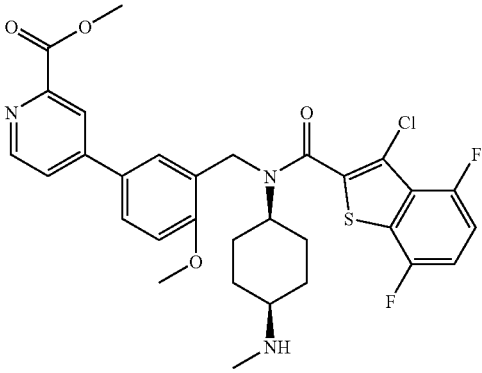 | R5 | D | D | D | D |
| 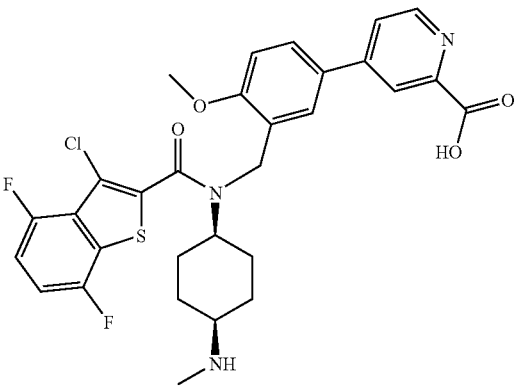 | R6 | C | | C | |
| 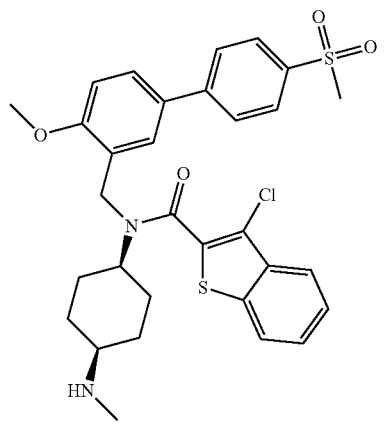 | R7 | D | | D | |

TABLE 1-continued

| | | (2.5 μM > A ≧ 1 μM > B ≧ 250 nM > C ≧ 50 nm > D) | | | |
|---|---|---|---|---|---|
| STRUCTURE | COMPOUND | TM3 Avg. EC$_{50}$ | S12 Avg. EC$_{50}$ | HEPM Avg. EC$_{50}$ | Daoy Avg. EC$_{50}$ |
| | R8 | D | | D | |
| | R9 | D | D | D | D |
| | R10 | D | D | D | |

TABLE 1-continued (2.5 μM > A ≧ 1 μM > B ≧ 250 nM > C ≧ 50 nm > D)

| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 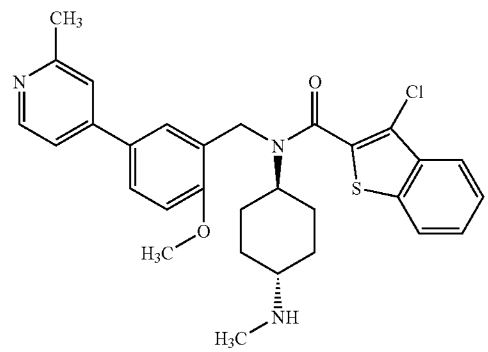 | 331 (R11) | D | | D | |
| 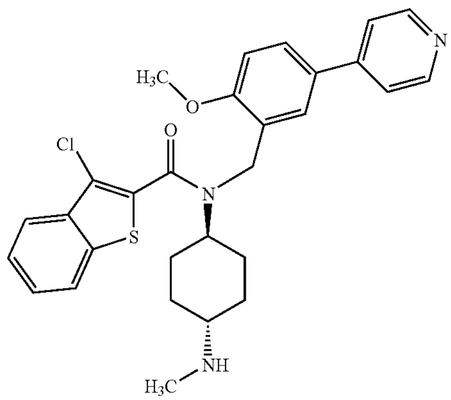 | 339 (R12) | D | | D | |
| 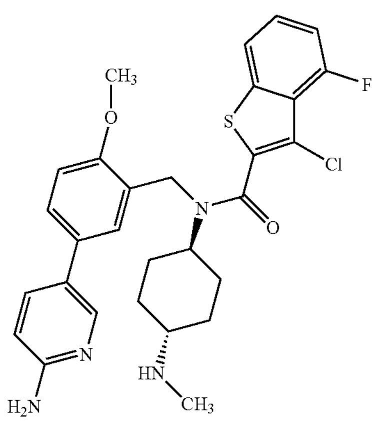 | 362 (R13) | D | D | D | D |
| 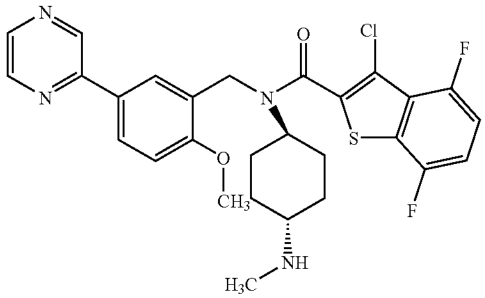 | 344 (R14) | D | | D | D |

TABLE 1-continued (2.5 μM > A ≧ 1 μM > B ≧ 250 nM > C ≧ 50 nm > D)

| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 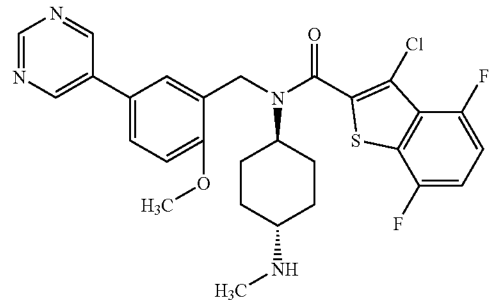 | 343 (R15) | D | | D | D |
| 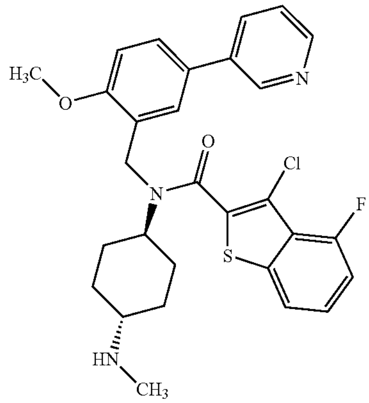 | 360 (R16) | D | D | D | D |
| 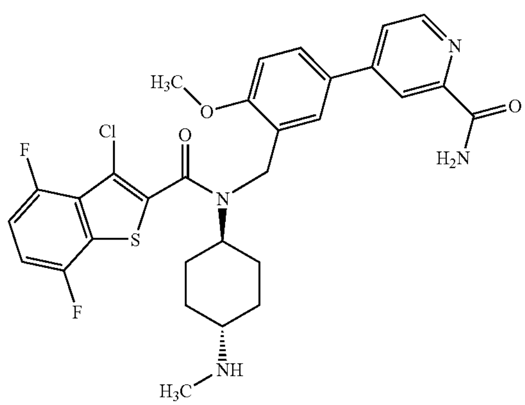 | 354 (R17) | D | D | D | D |
| 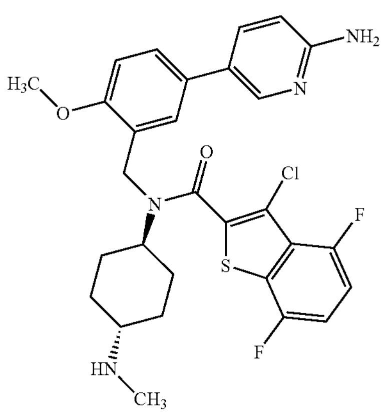 | 352 (R18) | D | | D | D |

TABLE 1-continued
| | | (2.5 μM > A ≧ 1 μM > B ≧ 250 nM > C ≧ 50 nm > D) | | | |
|---|---|---|---|---|---|
| STRUCTURE | COMPOUND | TM3 Avg. EC$_{50}$ | S12 Avg. EC$_{50}$ | HEPM Avg. EC$_{50}$ | Daoy Avg. EC$_{50}$ |
| 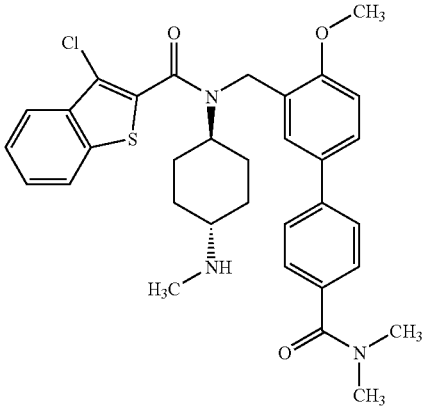 | 317 (R19) | D | D | D | |
| 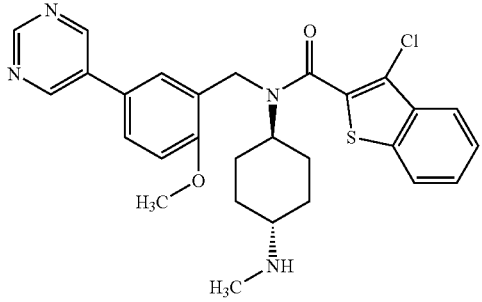 | 324 (R20) | C | | C | D |
| 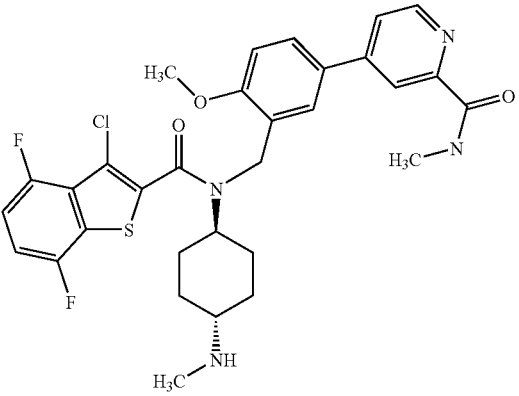 | 356 (R21) | D | | D | D |
| 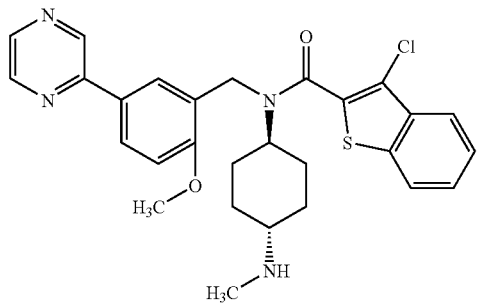 | 330 (R22) | C | | C | D |

TABLE 2
(2.5 μM > A ≧ 1 μM > B ≧ 250 nM > C ≧ 50 nm > D)
| STRUCTURE | COMPOUND | Mouse S12 Avg. EC$_{50}$ (nM) | Human Daoy (Gli-Luc) Avg. EC$_{50}$ (nM) |
|---|---|---|---|
| 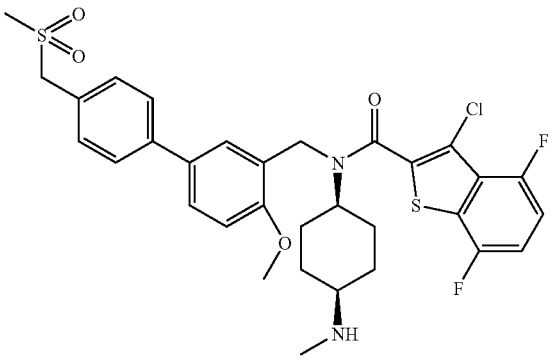 | 369 | D | D |
| 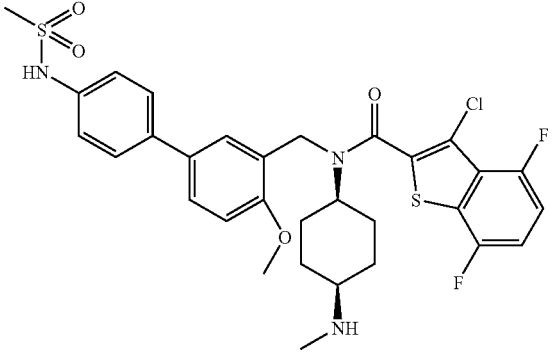 | 370 | D | D |
| 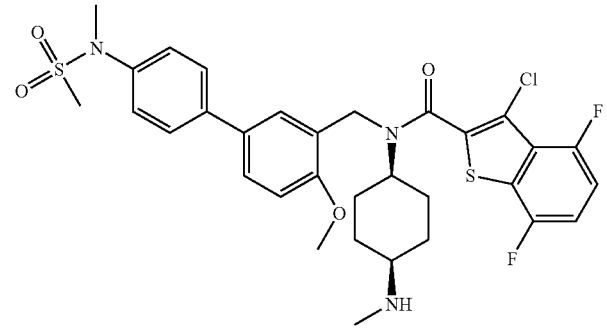 | 371 | D | D |
| 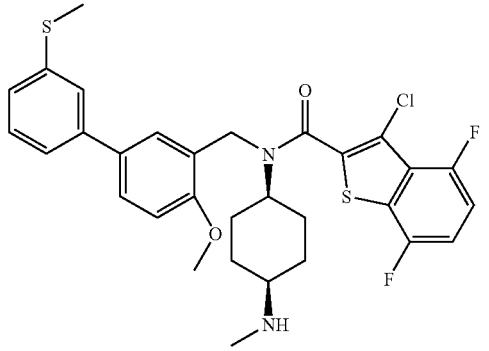 | 372 | D | D |

TABLE 2-continued
(2.5 μM > A ≧ 1 μM > B ≧ 250 nM > C ≧ 50 nm > D)
| STRUCTURE | COMPOUND | Mouse S12 Avg. EC$_{50}$ (nM) | Human Daoy (Gli-Luc) Avg. EC$_{50}$ (nM) |
|---|---|---|---|
| 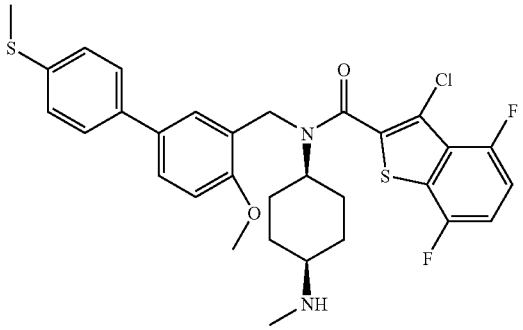 | 373 | D | D |
| 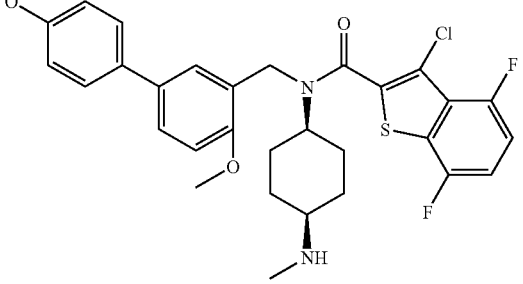 | 374 | D | D |
| 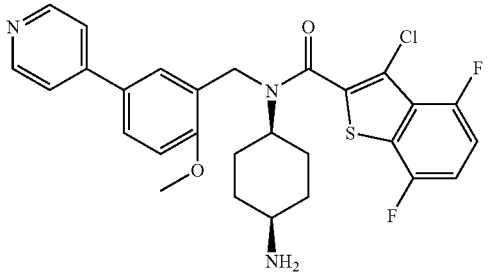 | 375 | D | D |
| 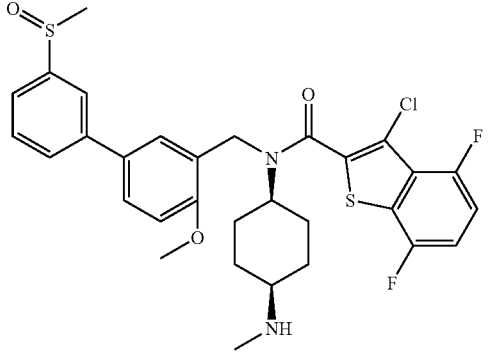 | 376 | D | D |

TABLE 2-continued

| | | | |
|---|---|---|---|
| (2.5 µM > A ≧ 1 µM > B ≧ 250 nM > C ≧ 50 nm > D) | | | |
| STRUCTURE | COMPOUND | Mouse S12 Avg. EC$_{50}$ (nM) | Human Daoy (Gli-Luc) Avg. EC$_{50}$ (nM) |
| | 377 | D | D |
| | 378 | D | D |
| | 379 | D | D |

TABLE 2-continued (2.5 μM > A ≧ 1 μM > B ≧ 250 nM > C ≧ 50 nm > D)

| STRUCTURE | COMPOUND | Mouse S12 Avg. EC$_{50}$ (nM) | Human Daoy (Gli-Luc) Avg. EC$_{50}$ (nM) |
|---|---|---|---|
| 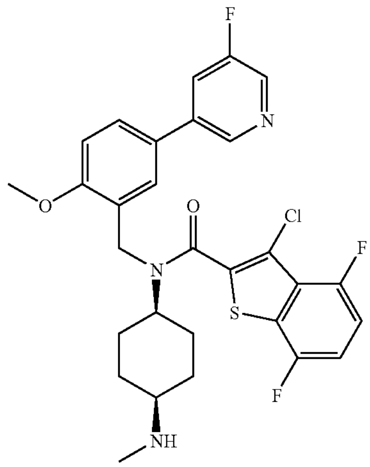 | 380 | D | D |
| 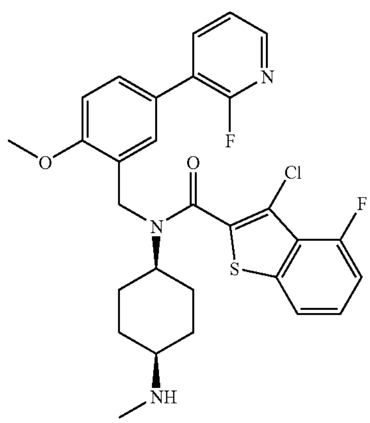 | 381 | D | D |
| 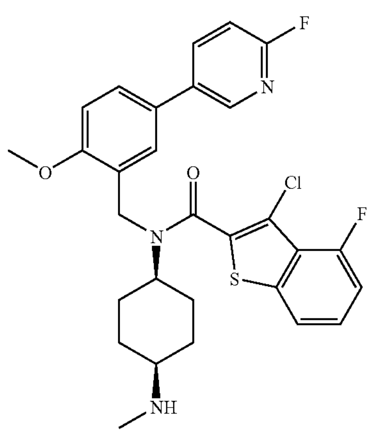 | 382 | D | D |

TABLE 2-continued
(2.5 μM > A ≧ 1 μM > B ≧ 250 nM > C ≧ 50 nm > D)
| STRUCTURE | COMPOUND | Mouse S12 Avg. EC$_{50}$ (nM) | Human Daoy (Gli-Luc) Avg. EC$_{50}$ (nM) |
|---|---|---|---|
| 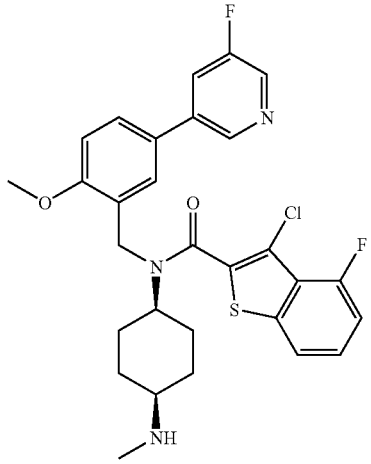 | 383 | D | D |
| 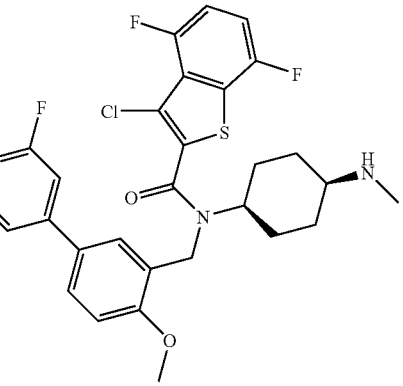 | 384 | D | D |
| 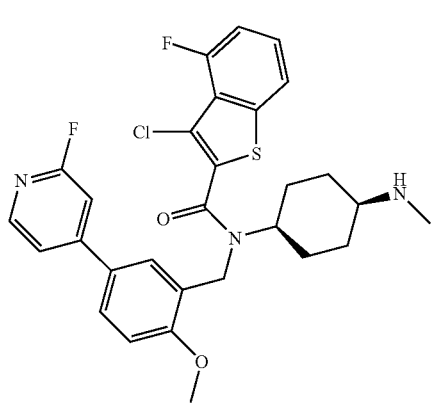 | 385 | D | D |

TABLE 2-continued (2.5 µM > A ≥ 1 µM > B ≥ 250 nM > C ≥ 50 nm > D)

| STRUCTURE | COMPOUND | Mouse S12 Avg. EC$_{50}$ (nM) | Human Daoy (Gli-Luc) Avg. EC$_{50}$ (nM) |
|---|---|---|---|
| 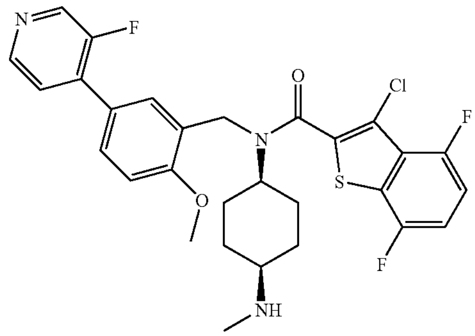 | 386 | D | D |
| 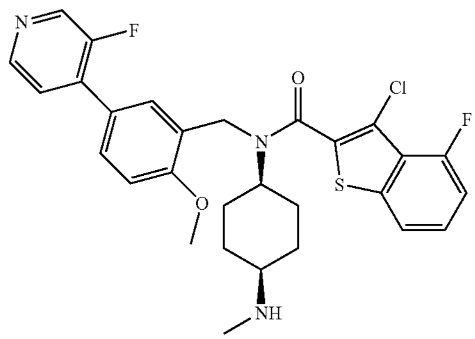 | 387 | D | D |
| 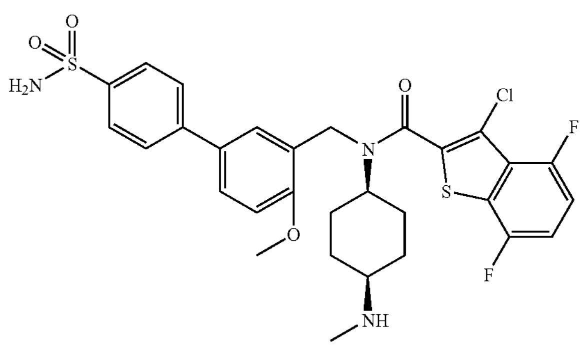 | 388 | D | D |
| 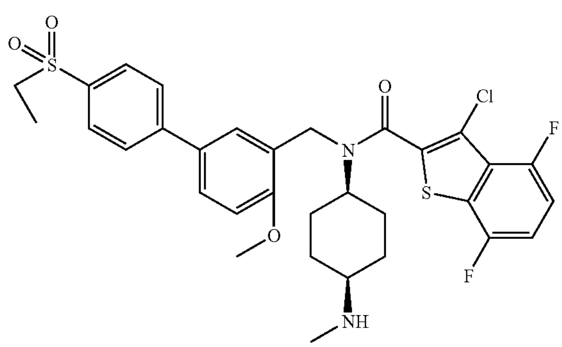 | 389 | D | D |

TABLE 2-continued (2.5 μM > A ≧ 1 μM > B ≧ 250 nM > C ≧ 50 nm > D)

| STRUCTURE | COMPOUND | Mouse S12 Avg. EC$_{50}$ (nM) | Human Daoy (Gli-Luc) Avg. EC$_{50}$ (nM) |
|---|---|---|---|
| 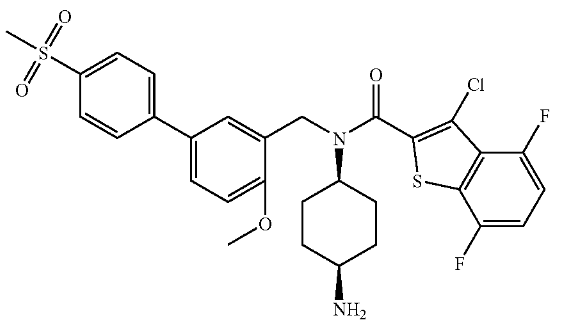 | 390 | D | D |
| 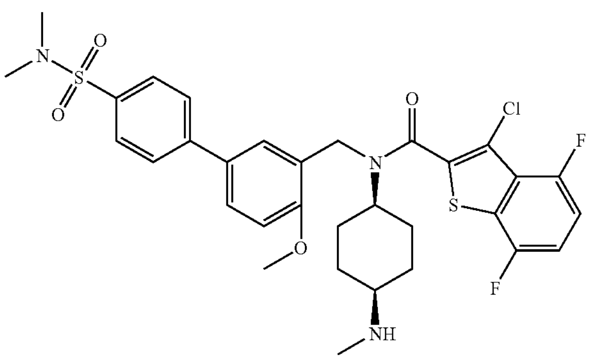 | 391 | D | D |
| 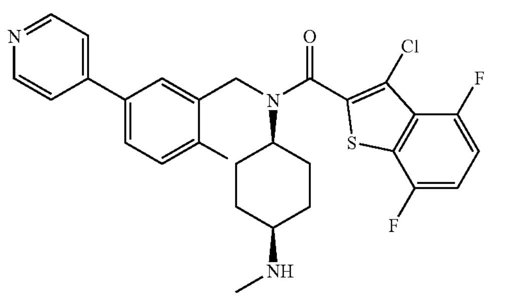 | 392 | D | D |
| 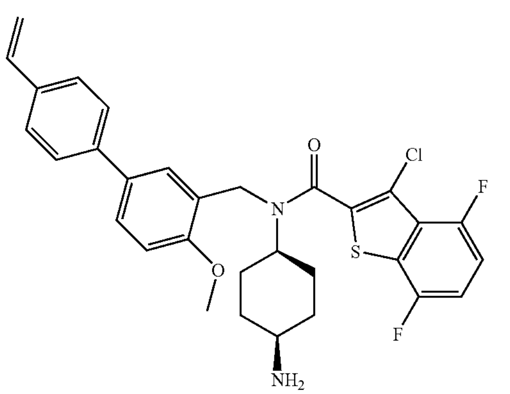 | 393 | C | C |

TABLE 2-continued (2.5 μM > A ≧ 1 μM > B ≧ 250 nM > C ≧ 50 nm > D)

| STRUCTURE | COMPOUND | Mouse S12 Avg. EC$_{50}$ (nM) | Human Daoy (Gli-Luc) Avg. EC$_{50}$ (nM) |
|---|---|---|---|
| 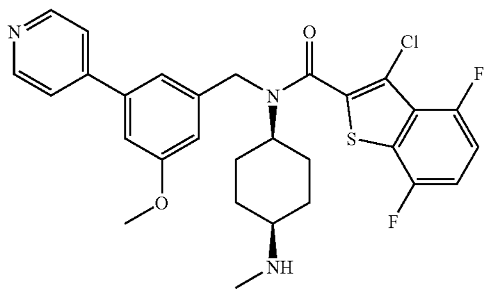 | 394 | D | D |
| 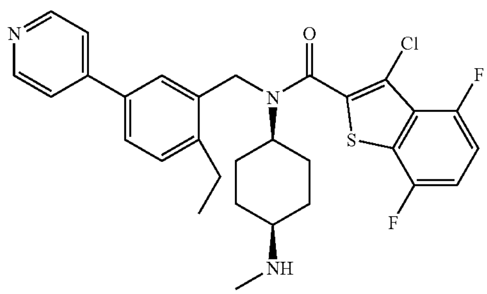 | 395 | C | C |

TABLE 3

(2.5 μM > A ≧ 1 μM > B ≧ 250 nM > C ≧ 50 nm > D)

| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 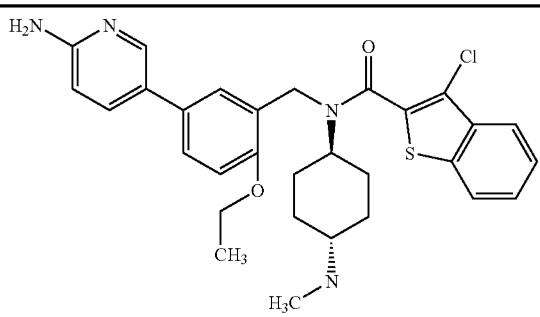 | 396 | B | | | C |
| 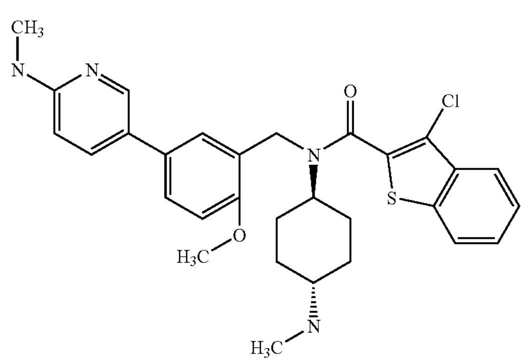 | 397 | B | | | B |

TABLE 3-continued (2.5 μM > A ≧ 1 μM > B ≧ 250 nM > C ≧ 50 nm > D)

| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 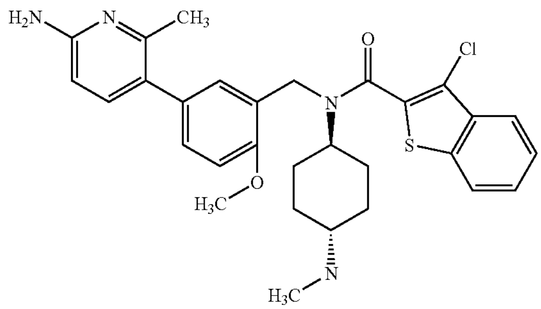 | 398 | A |  | A | B |
| 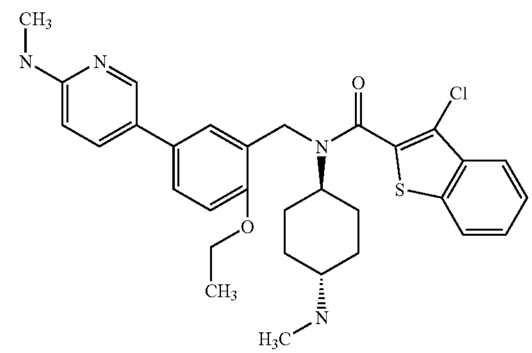 | 399 | A |  | A | B |
| 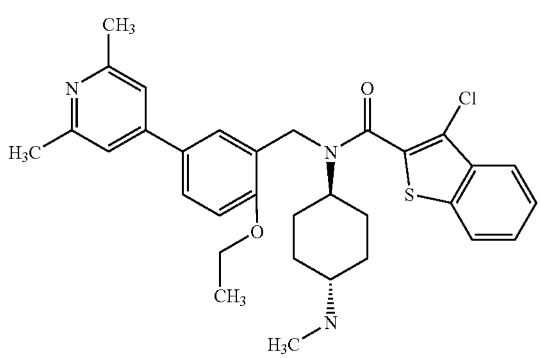 | 400 | B |  | B |  |
| 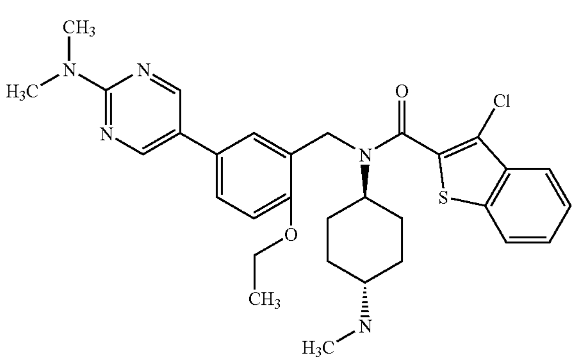 | 401 | A |  |  |  |

TABLE 3-continued (2.5 μM > A ≧ 1 μM > B ≧ 250 nM > C ≧ 50 nm > D)

| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 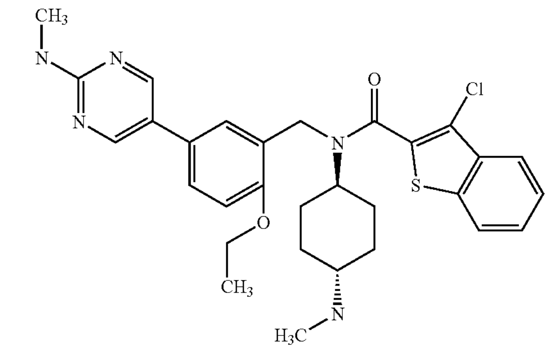 | 402 | A | | B | C |
| 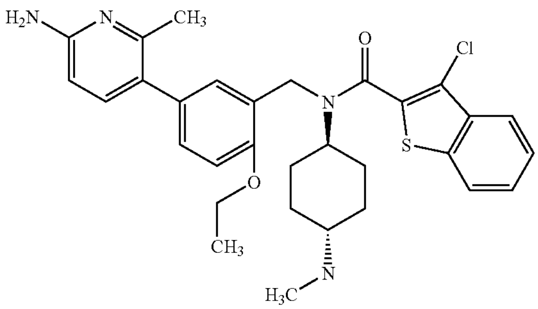 | 403 | A | | B | |
| 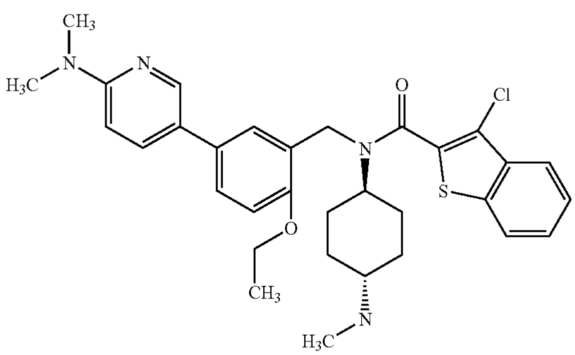 | 404 | A | | B | |
| 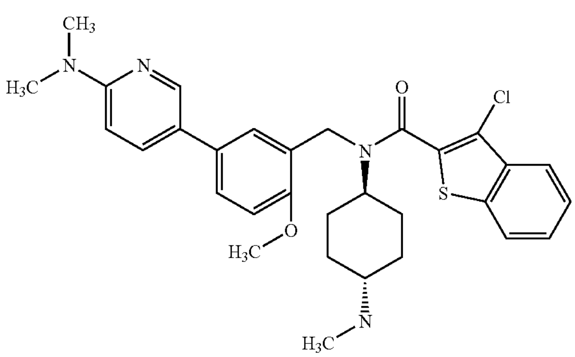 | 405 | A | | B | |

TABLE 3-continued
(2.5 µM > A ≧ 1 µM > B ≧ 250 nM > C ≧ 50 nm > D)
| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 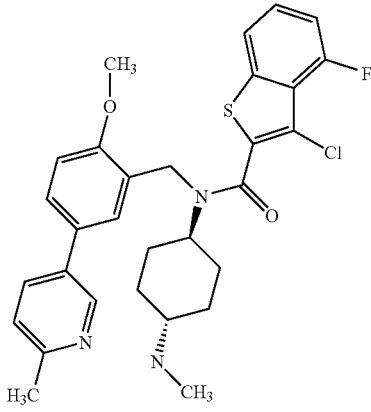 | 406 | D | | C | |
| 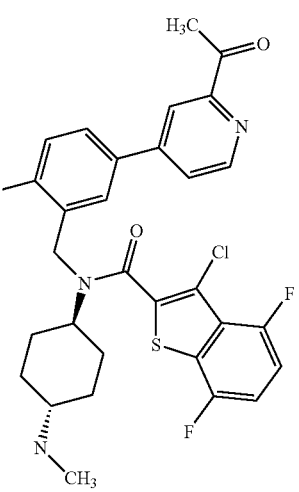 | 407 | D | | | |
| 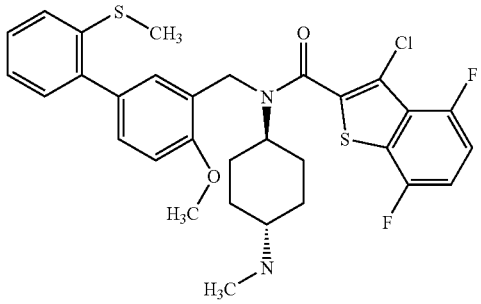 | 408 | B | | | B |

TABLE 3-continued (2.5 μM > A ≧ 1 μM > B ≧ 250 nM > C ≧ 50 nm > D)

| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 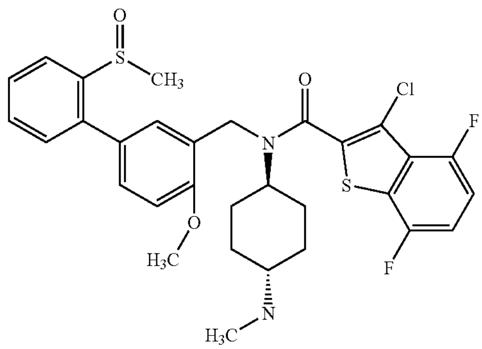 | 409 |  | B |  | A |
| 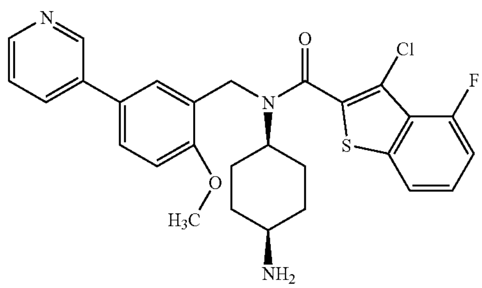 | 410 |  | D |  | D |
| 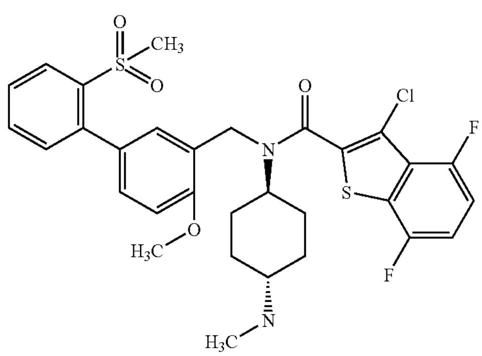 | 411 |  | B |  | A |
| 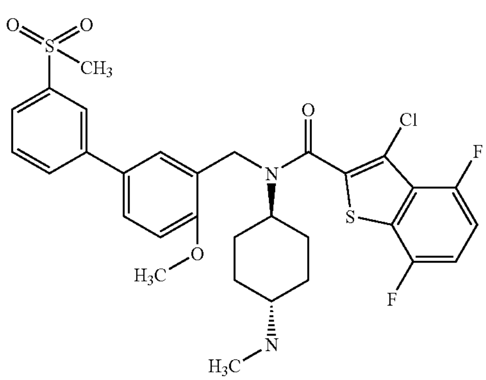 | 412 |  | D |  | D |

TABLE 3-continued
| | | (2.5 μM > A ≧ 1 μM > B ≧ 250 nM > C ≧ 50 nm > D) | | | |
|---|---|---|---|---|---|
| STRUCTURE | COMPOUND | TM3 Avg. EC$_{50}$ | S12 Avg. EC$_{50}$ | HEPM Avg. EC$_{50}$ | Daoy Avg. EC$_{50}$ |
| 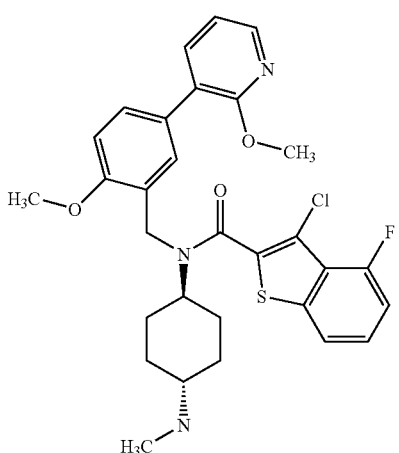 | 413 | | C | | D |
| 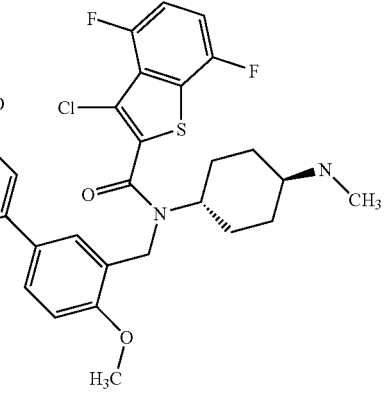 | 414 | | C | | D |
| 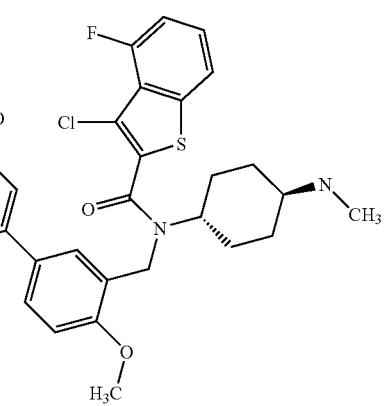 | 415 | | C | | C |

TABLE 3-continued (2.5 μM > A ≧ 1 μM > B ≧ 250 nM > C ≧ 50 nm > D)

| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 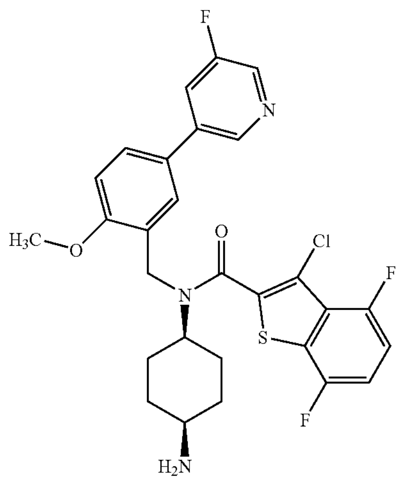 | 416 | | D | | C |
| 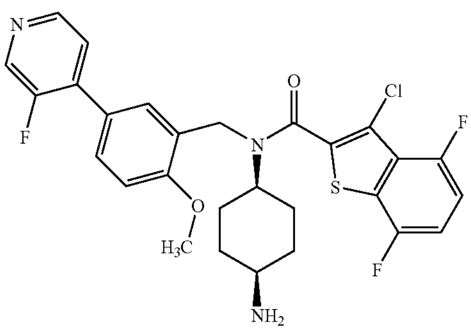 | 417 | | D | | D |
| 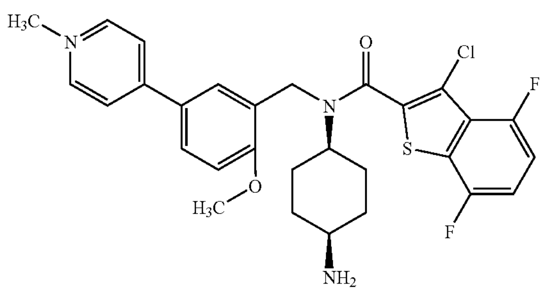 | 418 | | A | | D |
| 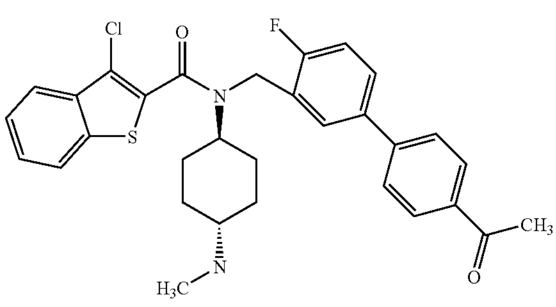 | 419 | D | | B | C |

TABLE 3-continued (2.5 μM > A ≧ 1 μM > B ≧ 250 nM > C ≧ 50 nm > D)

| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 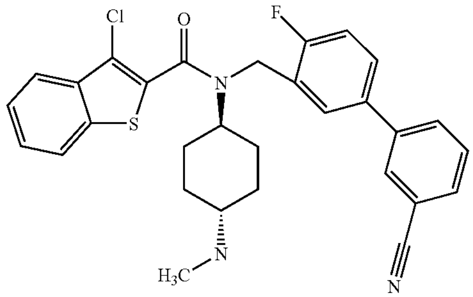 | 420 | C | | | C |
| 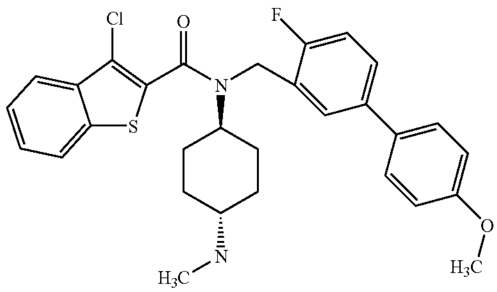 | 421 | B | | | |
| 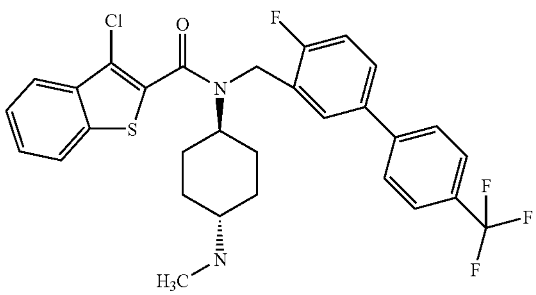 | 422 | B | | | |
| 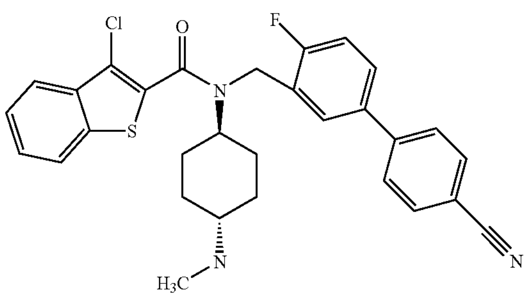 | 423 | B | | | B |
| 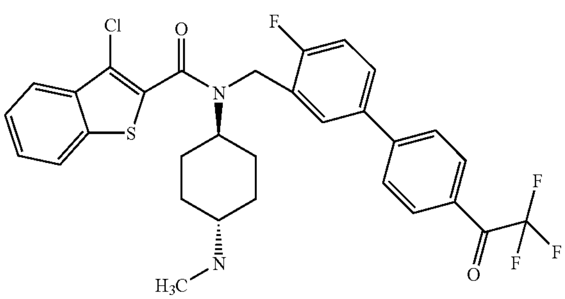 | 424 | D | | B | D |

TABLE 3-continued (2.5 μM > A ≧ 1 μM > B ≧ 250 nM > C ≧ 50 nm > D)

| STRUCTURE | COMPOUND | TM3 Avg. EC$_{50}$ | S12 Avg. EC$_{50}$ | HEPM Avg. EC$_{50}$ | Daoy Avg. EC$_{50}$ |
|---|---|---|---|---|---|
| 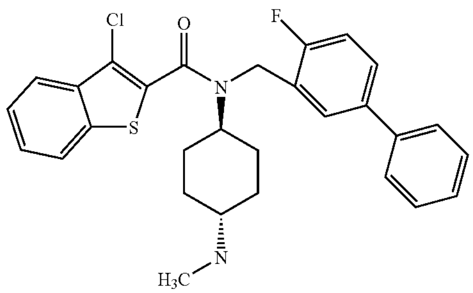 | 425 | D | | | D |
| 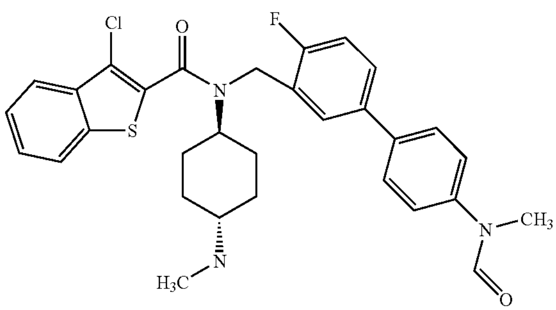 | 426 | D | | | C |
| 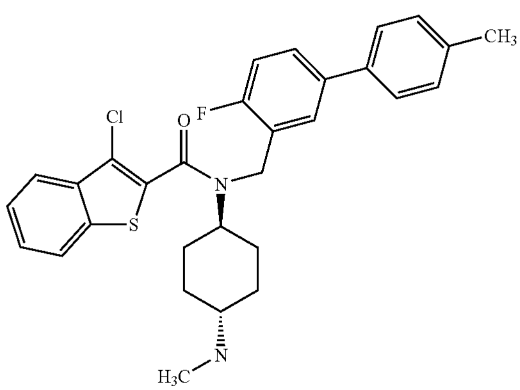 | 427 | B | | | |
| 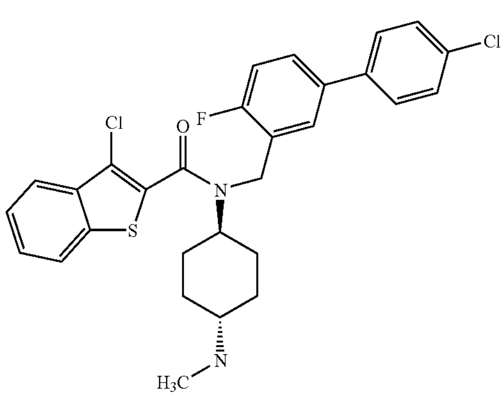 | 428 | B | | | |

TABLE 3-continued

| | (2.5 μM > A ≧ 1 μM > B ≧ 250 nM > C ≧ 50 nm > D) | | | | |
|---|---|---|---|---|---|
| STRUCTURE | COMPOUND | TM3 Avg. EC$_{50}$ | S12 Avg. EC$_{50}$ | HEPM Avg. EC$_{50}$ | Daoy Avg. EC$_{50}$ |
| | 429 | A | | | |
| | 430 | A | | | |
| | 431 | C | | | |

TABLE 3-continued

| | | | (2.5 μM > A ≧ 1 μM > B ≧ 250 nM > C ≧ 50 nm > D) | | | |
|---|---|---|---|---|---|
| STRUCTURE | COMPOUND | TM3 Avg. EC$_{50}$ | S12 Avg. EC$_{50}$ | HEPM Avg. EC$_{50}$ | Daoy Avg. EC$_{50}$ |
| | 432 | B | | | |
| | 433 | D | | | D |
| | 434 | D | | | D |

DHT-Induced Alopecia Experiments

A mouse model of male pattern baldness is used to investigate the effectiveness of the present compounds for growing hair. Agonists for the sonic hedgehog pathway that act by binding and activating Smoothened were tested in a formulation of 50:30:20 PG:EtOH:water or 5:95 DMSO:acetone vehicle. C57BL/6 male mice (48-52 days old on arrival) from Charles River Labs were used on the study. The mice were housed and cared for according to established procedures. Food and water were ad libitum. On Day 0, the mice were shaved on their lower back, an area of ~1.5 inches×~2 inches with Wahl clippers using a surgical blade. On day −3, the mice were anesthetized with isoflurane, their back was rinsed with a pad of 70% ethanol, a placebo pellet or a DHT pellet (2.5 mg 21 day pellet) were implanted subcutaneously between the shoulder blades with a 10 gauge trochar. DHT pellet transplantation results in maintenance of existing hair follicles in the resting (telogen) phase. The hole was stapled with a sterile autoclip and the mice were returned to their cage after awaking. The mice were dosed topically once and visually graded daily, except weekends, for melanogenesis and hair regrowth of fur in the dosed area (Table 4).

TABLE 4

| Compound ID | C57BL/6 Hair Growth | Androgenetic Alopecia |
|---|---|---|
| 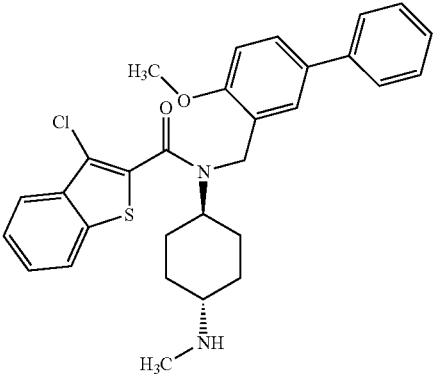 R3 | yes | yes |
| 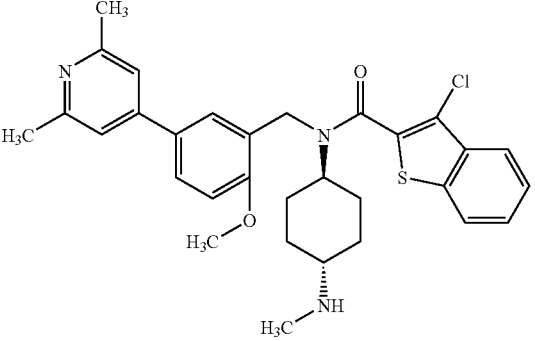 R1 | yes | yes |
| 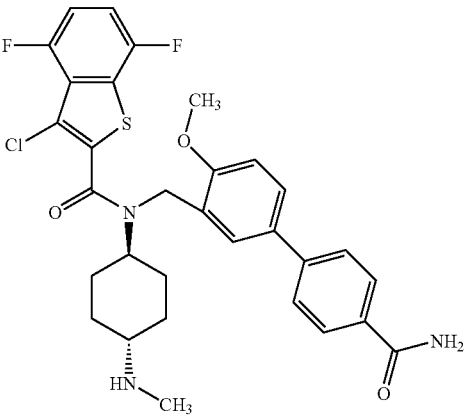 R8 | yes | yes |

TABLE 4-continued
| Compound ID | C57BL/6 Hair Growth | Androgenetic Alopecia |
|---|---|---|
| 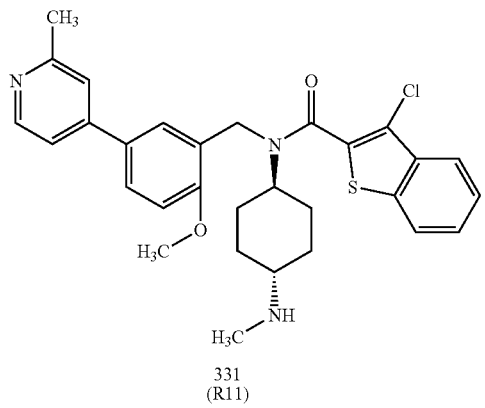 331 (R11) | yes | yes |
| 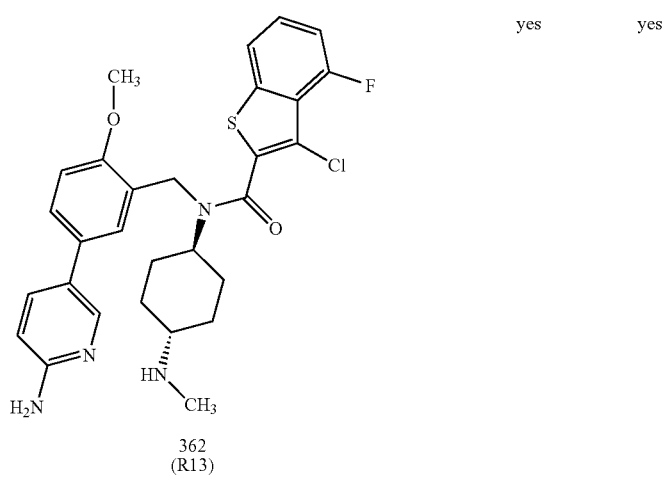 362 (R13) | yes | yes |
| 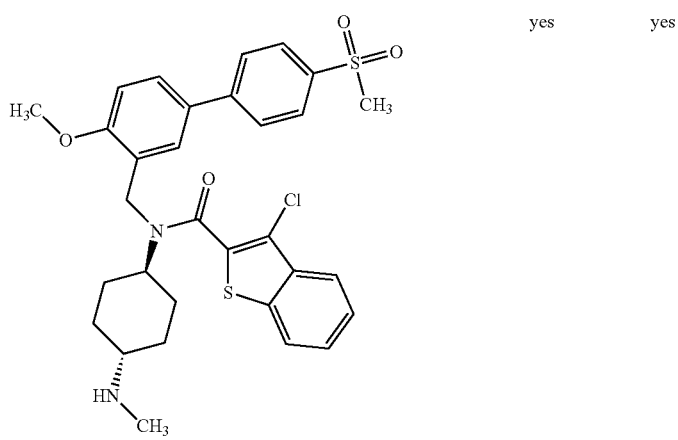 R7 | yes | yes |

TABLE 4-continued
| Compound ID | C57BL/6 Hair Growth | Androgenetic Alopecia |
|---|---|---|
| 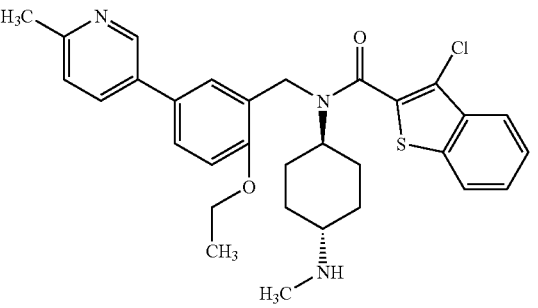 R4 | yes | NA |
| 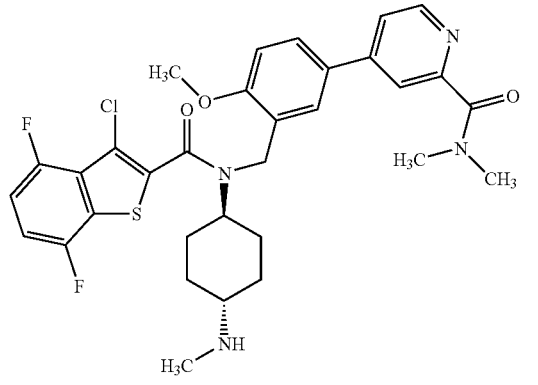 R9 | yes | yes |
| 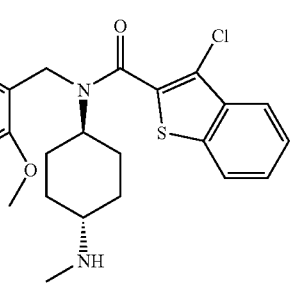 339 (R12) | yes | yes |
| 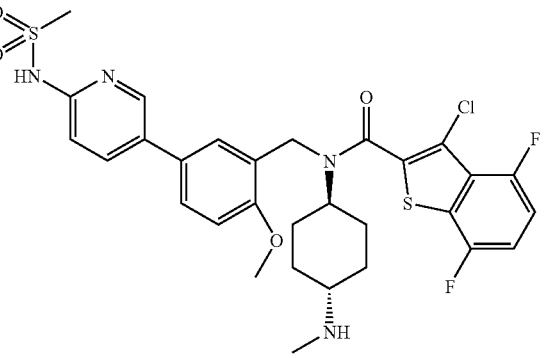 R10 | yes | NA |

TABLE 4-continued

| Compound ID | C57BL/6 Hair Growth | Androgenetic Alopecia |
|---|---|---|
| R2 | yes | NA |
| R5 | yes | yes |
| R6 | no | NA |

The results in Table 4 demonstrate that A single topical administration of a Hedgehog agonist, such as a present compound, may induce anagen in the telogen follicles of mice treated with slow release DHT. In the absence of treatment with the present compounds, the follicles remain in telogen rather than following the normal time course of the mouse hair cycle.

Process Exemplification

A. Overview of an Improved Synthetic Scheme:

An improved synthetic scheme for the preparation of P8a is developed (Scheme P1).

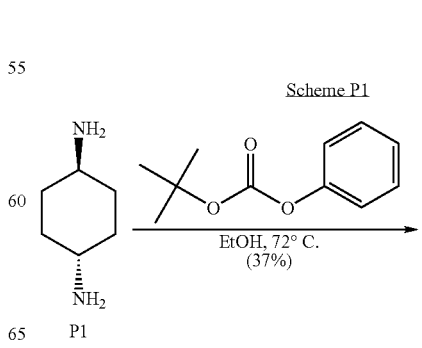

Scheme P1

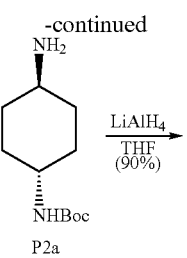

P2a

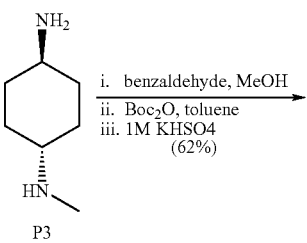

P3

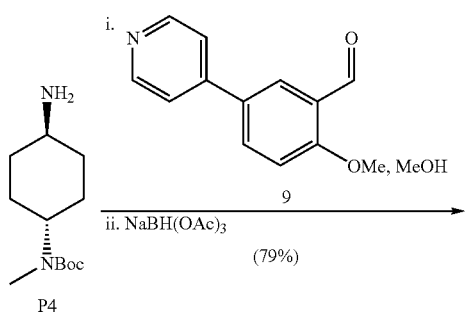

P4

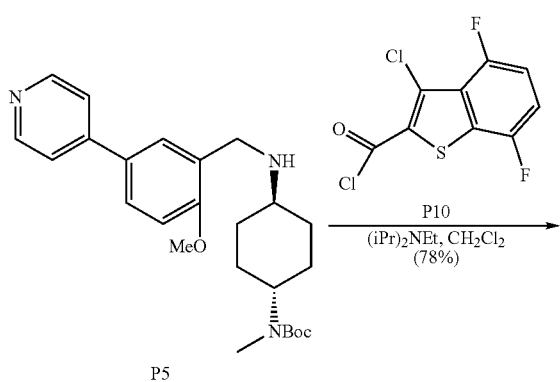

P5

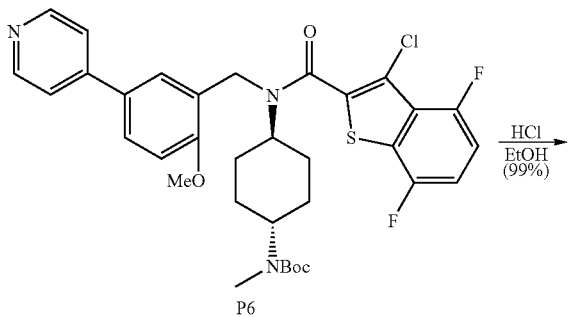

P6

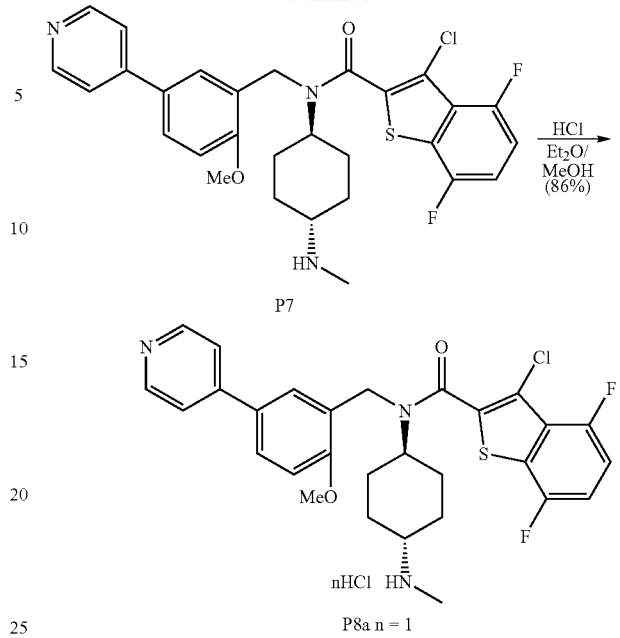

P7

P8a n = 1

TABLE P1

Overall Summary of quantities of intermediates prepared.

| | P2 | P3 | P4 | P5 | P6 | P7 | P8 |
|---|---|---|---|---|---|---|---|
| starting material used | 288.2 g | 198.2 g | 102.9 g | 110.7 g | 134.6 g | 133.8 g | 111.8 g |
| amount obtained | 199.0 g (37%) | 107.2 g (90%) | 115.7 g (62%) | 151.3 g (79%) | 162.5 g (78%) | 112.6 g (99%) | 102.0 g (86%) |

In summary 101.7 g of P8a (monohydrochloride salt) is prepared via a 9-step synthesis (11% overall yield) in two batches (11.14 g; 90.6 g).

B. Discussion

B.1 First Synthetic Scheme

In the first synthetic route, target compound P8b is prepared in 10 steps with an overall yield of 3% (Scheme P2). A sequence in which the order of acylation and Suzuki coupling is reversed is also investigated and gives compound P8b in a comparable overall yield (4%, scheme not shown).

Preparation of the first key intermediate, functionalized diamine P4, is accomplished via a 5-step (3-pot) synthetic sequence. The yield for the monofunctionalization of diamine is calculated based on the amount of amine used in all instances.

Scheme P2

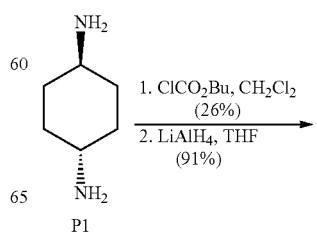

P1

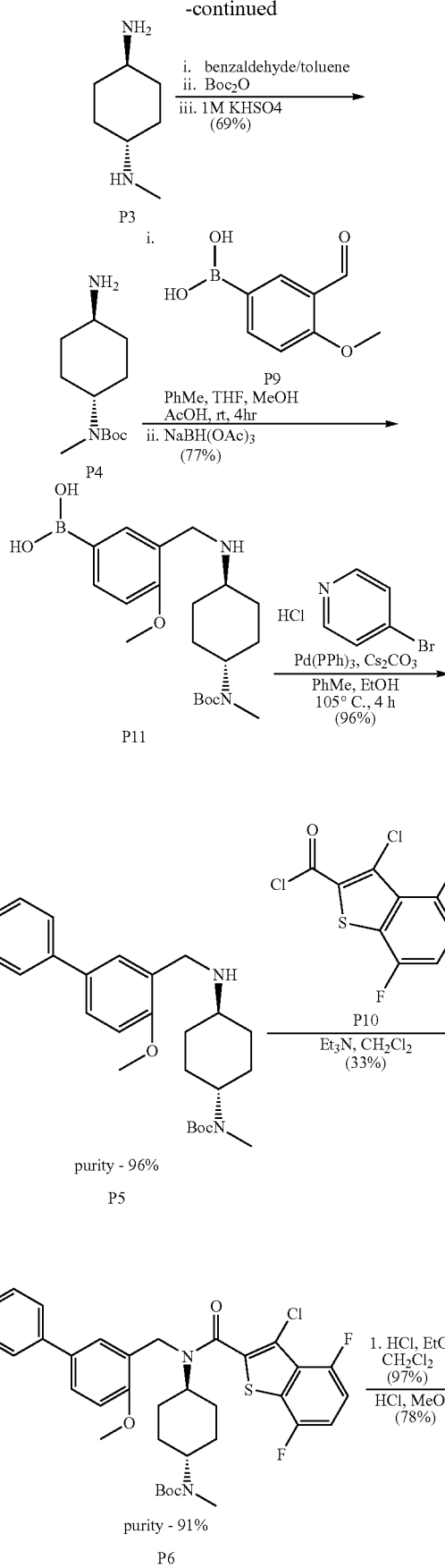
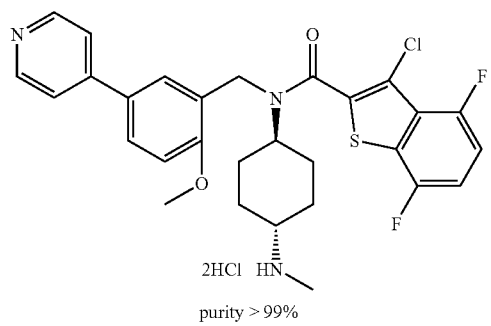
B.2 Modification of the First Synthetic Scheme with a Biaryl Aldehyde
The first synthetic route is modified by incorporating the biaryl aldehyde in one piece as (Scheme P3). Monoacylation of 1,4-cyclohexanediamine produces the desired monocarbamate in 17% yield. The acylated intermediate P6 is isolated in 61% yield.
Scheme P3
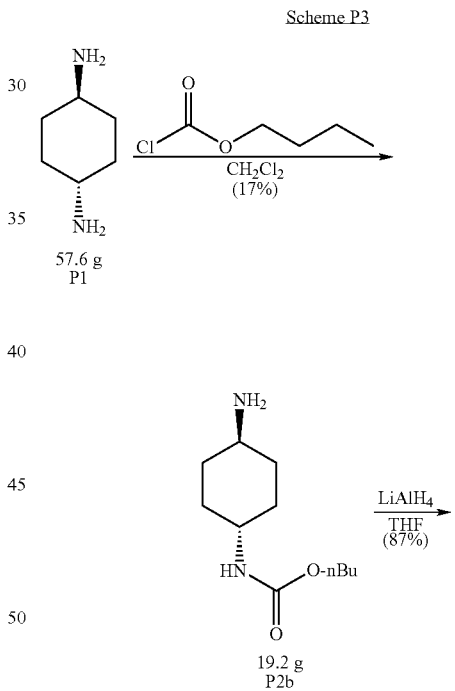
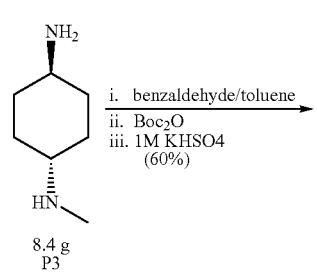

-continued

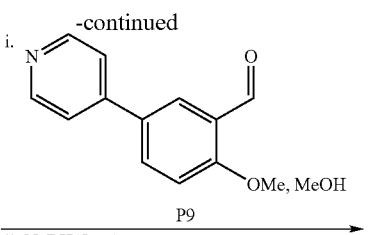

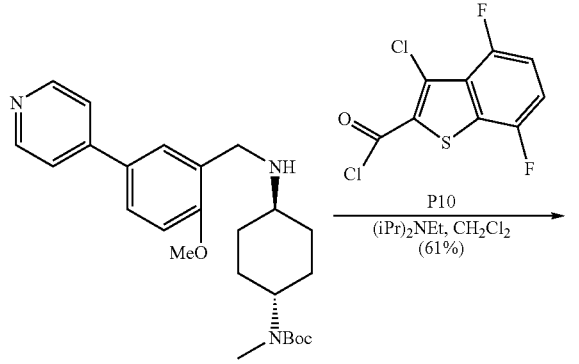

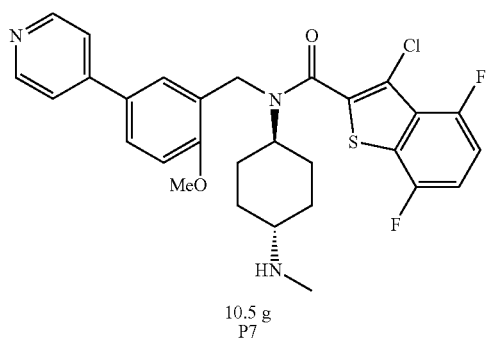

B.3 Early Impurity Profile Analysis

Two main impurities P12 and P13 are identified by LC/MS analysis during the synthesis of P7:

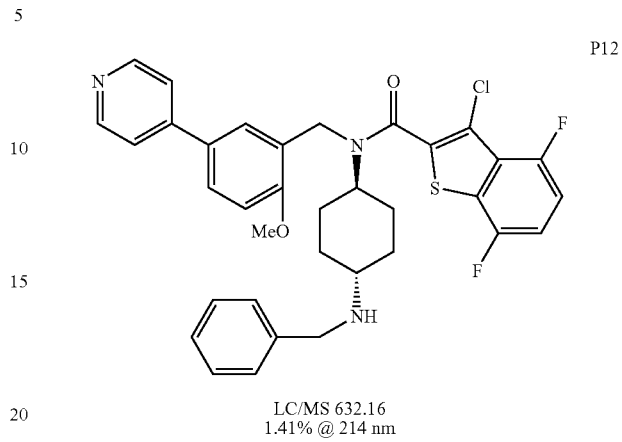

P12

LC/MS 632.16
1.41% @ 214 nm

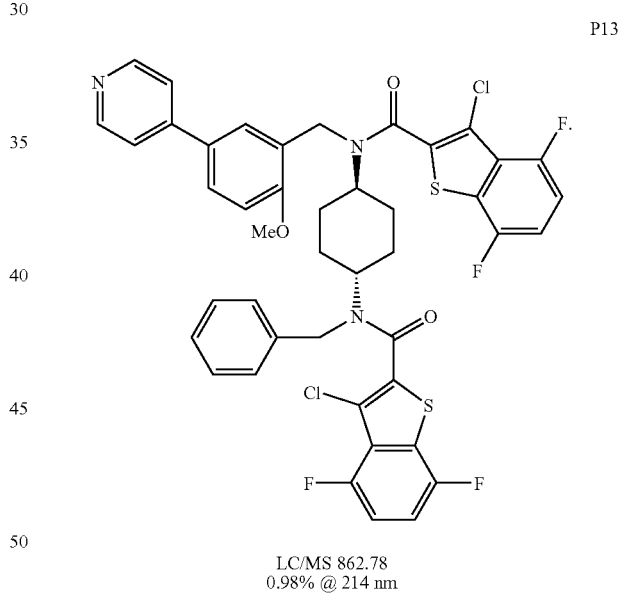

P13

LC/MS 862.78
0.98% @ 214 nm

Both impurities are structural analogs of P7 differing by the presence of a benzyl group in place of the methyl group on the cyclohexane diamine fragment. Notably, the second impurity is an acylated derivative of the first. Not surprisingly, the acylated impurity P13 is eliminated by formation of a HCl salt, however the benzylated impurity P12 remained in appreciable amounts (~1%). Notably, due to the structural interrelation of the two impurities impeding benzylation eliminates or reduces both impurities. In order to identify the origin of the impurity, further LC/MS analysis of upstream intermediates is conducted and reveals that the impurity arose during the reinstallation of the Boc group onto the secondary amine (Scheme P4).

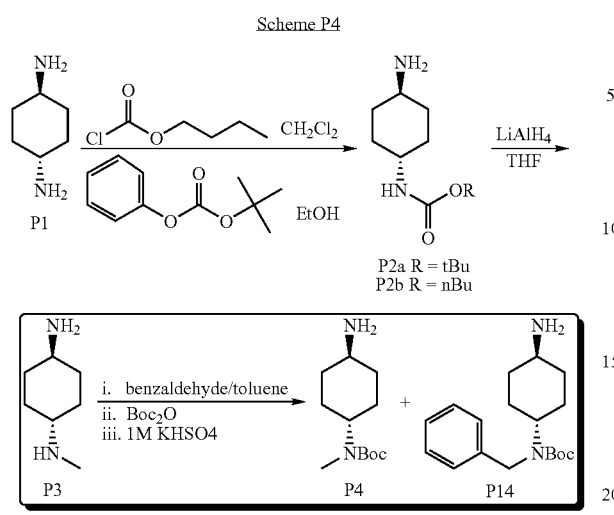

Scheme P4

Likely the impurity is generated during the preparation of the imine in refluxing toluene. Initially alternative solvent systems are investigated in which the imine formation is studied at room temperature (Table P2) While imine formation is observed in all three solvent systems investigated, Boc protection in THF and $CH_2Cl_2$ is sluggish presumably due to solubility problems, which results in a heterogeneous reaction mixture. In methanol, the imine forms smoothly at room temperature and the solvent is readily exchanged for toluene for subsequent Boc protection.

TABLE P2 investigation of alternative solvents for imine formation and Boc protection.

| entry | scale | reaction conditions | reaction outcome |
|---|---|---|---|
| 1 | 513.9 mg | i. benzaldehyde, MeOH<br>ii. Boc$_2$O, toluene<br>iii. KHSO$_4$ | 677 mg (74%) |
| 2 | 500 mg | i. benzaldehyde, THF<br>ii. Boc$_2$O<br>iii. KHSO$_4$ | 430 mg (48%)<br>ppt formation as Boc$_2$O is added, difficult work-up |
| 3 | 500 mg | i. benzaldehyde, CH$_2$Cl$_2$<br>ii. Boc$_2$O<br>iii. KHSO$_4$ | 170 mg (19%)<br>slow imine formation.<br>ppt formation as Boc$_2$O is added |

B.4 Preparation of a Single Crystal

Figure 1B:
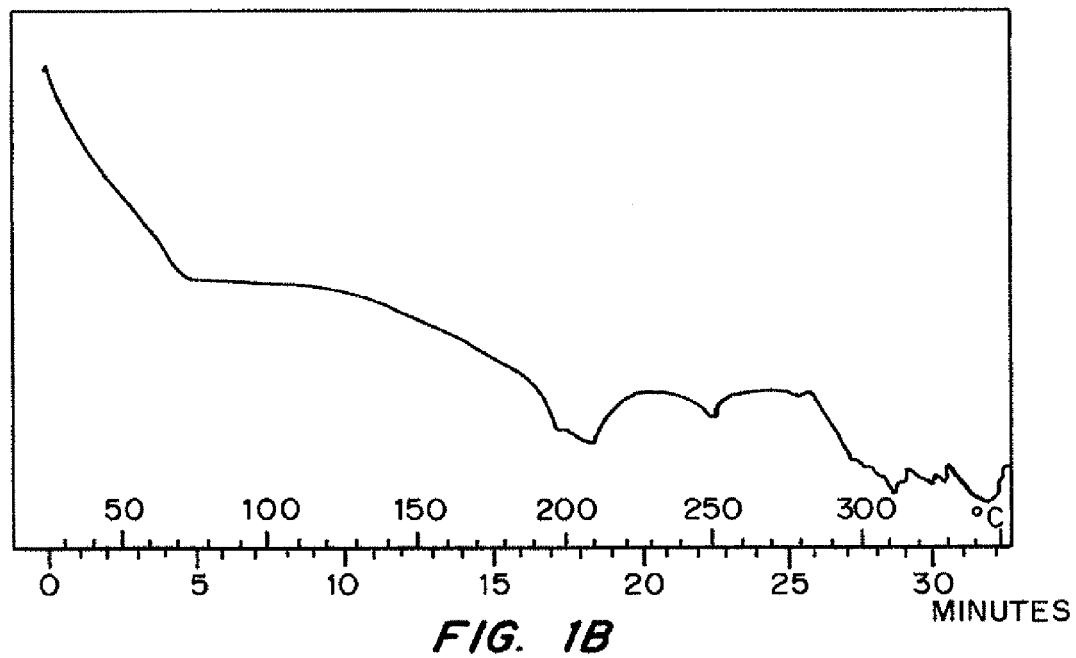

The crystal form of the di- and monohydrochloride salts of P7 are also investigated. While the monohydrochloride had been previously prepared, the salt had not been examined for crystallinity by DSC (differential scanning calorimetry) and the dihydrochloride had been previously shown to be amorphous. The dihydrochloride also proves to be amorphous even after recrystallization, while the monohydrochloride produces a stable single crystal. The DSC data for P8a and P8b are shown in FIGS. 1a and 1b, respectively.

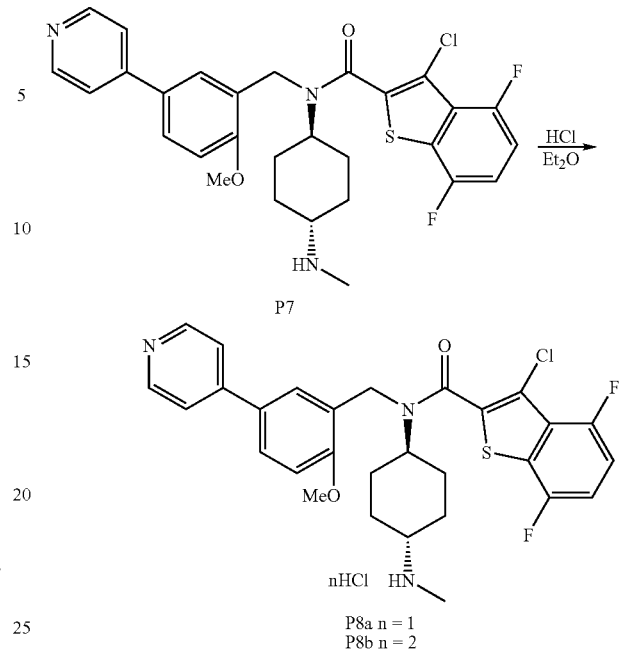

P7

P8a n = 1
P8b n = 2

B.5 Execution of the Improved Synthetic Scheme

Monofunctionalization of 1,4-cyclohexanediamine

A study to monofuctionalize 1,4-cyclohexanediamine is conducted (Table P3). Preparation of the Monocarbamate, Monoamide as Well as Monosulfonaminde is Studied and ultimately the use of t-butyl phenyl carbonate in ethanol (see Pittlekow, M.; Lewinsky, R.; Christensen, J. B. *Synthesis* 2002, 2195-2202) provides a scalable method yielding the mono-Boc protected diamine P8a in an improved 41% yield on a 50 g scale (Table P4, entry 7). The reagents are initially heated to reflux for several hours and once cooled the heterogeneous reaction mixture is vacuum filtered to remove the insoluble bis-carbamate. The reaction mixture is subsequently concentrated to remove the majority of ethanol, and dichloromethane and HCl are added. This results in precipitation of the reaction product as the HCl salt, which may be isolated by filtration. The HCl salt is free-based via a basic extractive work-up. The free-base intermediate requires no further purification.

TABLE P3

Monofunctionalization of 1,4-cyclohexanediamine

| entry | scale | rxn conditions | rxn outcome |
|---|---|---|---|
| 1 | 1.06 g | i. 9BBN, THF[1]<br>ii. 2,4-dinitrobenzenesulfonyl Cl | Bis-sulfonylation Confirmed by LC/MS |

TABLE P3-continued

Monofunctionalization of 1,4-cyclohexanediamine

| 2 | 0.99 g | TsCl, CsOH H$_2$O, DMF, 4Å MS[2] | 1.991 g Bis-Ts confirmed by LCMS |
|---|---|---|---|
| 3 | 1.10 g | i. 9-BBN, THF<br>ii. Cl$_3$CCOCl | Bis-amide<br>LC/MS (Meiyi) |
| 4 | 0.5 g | i. 9-BBN, THF<br>ii. Boc$_2$O | 225.8 mg bis-Boc<br>1.13 g messy mixture by NMR |
| 5 | 2.16 g | Boc$_2$O (0.5 eq), THF, 0 to 22° C. | 0.94 g (48%, based on Boc$_2$O) |
| 6 | 1.03 g | t-butyl phenyl carbonate (3 equiv), THF, 86° C. | 0.49 g (26%) also bis-Boc (1.5 g) |
| 7 | 50.07 g | t-butyl phenyl carbonate (1.0 equiv), EtOH, 85° C. | 38.2 g (41%) |

[1]Zhang, Z.; Yin, Z.; Meanwell, N. A.; Kadow, J. F.; Wang, T. Org. Lett. 2003, 5, 3399-3402.
[2]Salvatore, R. N.; Schmidt, S. E.; Shin, S.; Nagle, A. S.; Worrell, J. H.; Jung, K. W. Tetrahedron Lett. 2000, 41, 9705-9708.

Reduction

Reduction of the carbamate P2a is performed analogously to the above procedure (Scheme P5). For scale-up, a 1M solution of LAH in THF purchased from Aldrich is employed. The reduction is scaled up to 50 g and gives the desired monomethyl diamine in excellent yield. Following filtration the reaction mixture is concentrated and this intermediate is used without further purification

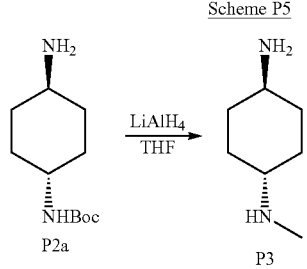

Scheme P5

Boc Protection of the Secondary Amine

During the preparation of initial batches of P7a benzylated impurity is identified (see section B. 3). After a solvent screen, toluene is replaced by methanol in the first part of the reaction sequence, which not only suppresses formation of the undesired impurity but also allows for imine formation at room temperature and reduced reaction time (Scheme P6). Progress of imine formation is monitored by $^1$H NMR and once complete methanol is removed in vacuo. The residue is azeotroped twice with toluene to remove any residual methanol prior to the subsequent Boc-protection. The remainder of the procedure is performed as described above. Following an aqueous work-up the intermediate is used without further purification.

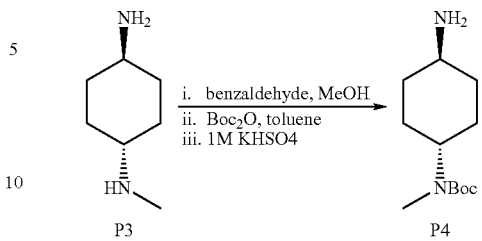

Scheme P6

Suzuki Coupling

The reaction conditions for the Suzuki coupling to prepare P9 are modified from the first procedure (Scheme P7). For scale-up, cost is reduced by replacing Pd(PPh$_3$)$_4$ with Pd(OAc)$_2$ and by utilizing the less expensive 4-chloropyridine hydrochloride. The yield utilizing the modified reaction conditions (93%) compares favorably with the original yield (67%).

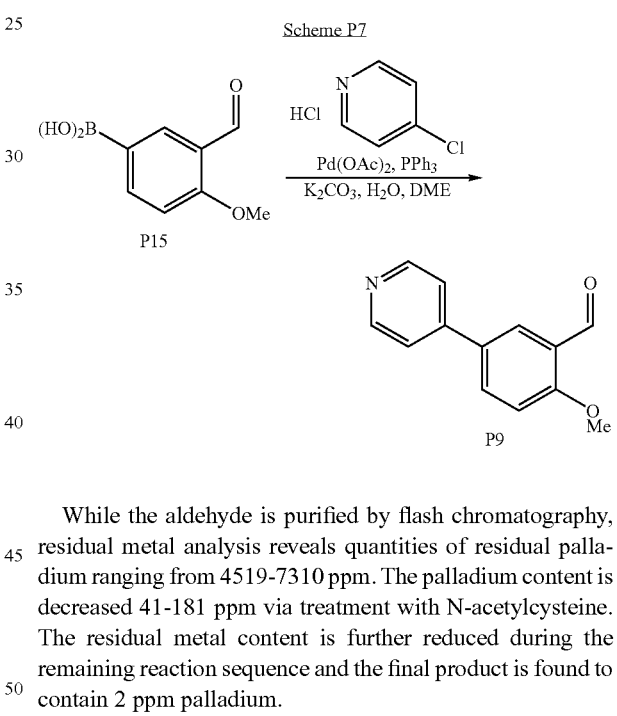

Scheme P7

While the aldehyde is purified by flash chromatography, residual metal analysis reveals quantities of residual palladium ranging from 4519-7310 ppm. The palladium content is decreased 41-181 ppm via treatment with N-acetylcysteine. The residual metal content is further reduced during the remaining reaction sequence and the final product is found to contain 2 ppm palladium.

Reductive Amination

The reaction conditions for the reductive amination are modified from the first experimental procedure, which calls for the use of solvent mixtures and acid additives. Stirring the aldehyde and amine in methanol at room temperature smoothly provides the imine intermediate, which is reduced via treatment with NaBH(OAc)$_3$ (Scheme P8). Interestingly, when using the HCl salt of functionalized diamine P4 the reaction has a less favorable outcome as the imine formation does not go to completion. The intermediate amine P5 is purified by flash chromatography. Notably, intermediate amine P5 is prone to undergo dealkylation (cleavage at the benzylic position leading to loss of the biaryl moiety) in the presence of acid.

Scheme P8

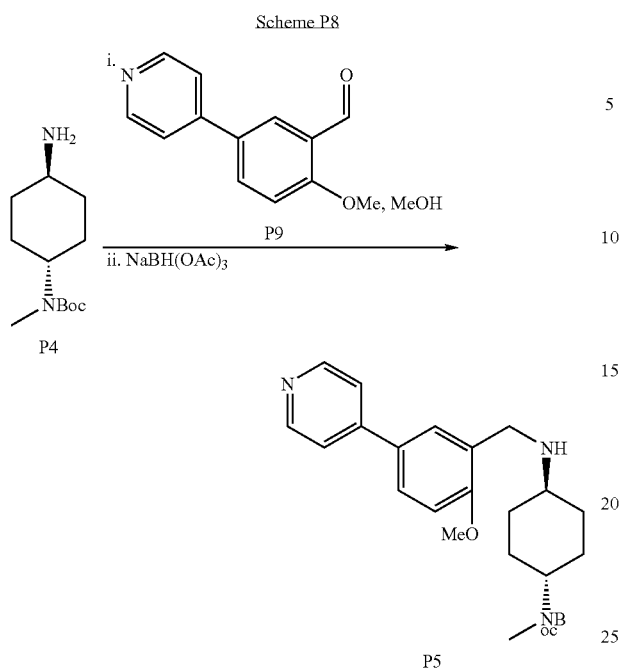

Preparation of 3-chloro-4,7-difluorobenzothiophene-2-carbonyl chloride

The preparation of benzothiophene intermediate P10 is performed in accordance with literature procedures (Scheme P9). The product is purified either via recrystallization or trituration with heptane and ranges in color from a yellow to brown solid. The reaction product retains varying amounts of HCl, which may contribute to the formation of a dealkylated by-product during the acylation step (see next paragraph).

Scheme P9

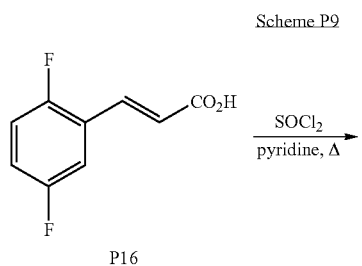

Acylation

The acylation is carried out in analogy to the first procedure (Scheme P10). However, slow addition of a dichloromethane solution of acid chloride reduces the amount of dealkylation observed. While 2.1 equivalents of base are used, dealkylation may be observed by HPLC while monitoring the reaction. Reduction or elimination of the impurity is achieved via careful washing and drying of the acid chloride under vacuum prior to use, alternatively the amount of base used may be increased to compensate for any excess hydrochloric acid.

Scheme P10

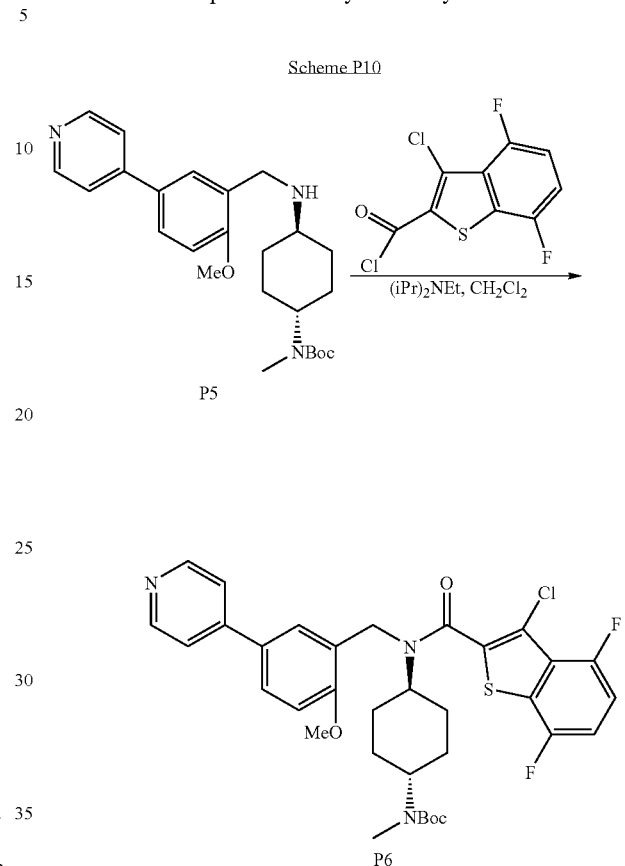

Deprotection

Removal of the Boc protecting group is carried out in ethanol at room temperature in the absence of a co-solvent (Scheme P11, $CH_2Cl_2$ is used in the first procedure). In addition the amount of solvent used is reduced by >50% during scale-up. Once the reaction is complete as indicated by HPLC analysis (2% starting material remained) the solvent is removed in vacuo and the residue is diluted with water and extracted with dichloromethane, which eliminated some of the less polar impurities present. Subsequently, the aqueous layer is cooled and the pH is adjusted to pH 13 with 50% NaOH, which allowed product isolation via extraction.

Scheme P11

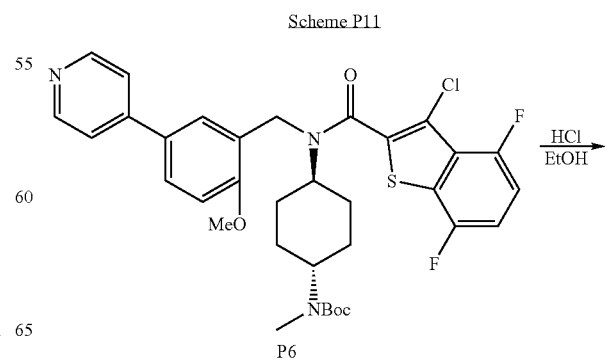

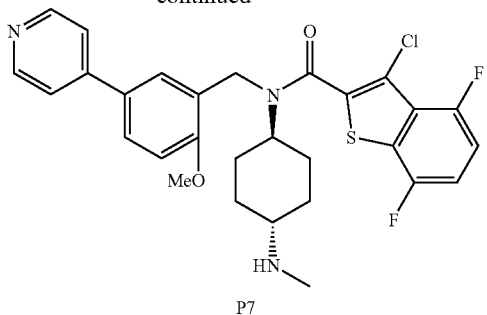

Preparation of the Monohydrochloride Salt

The monohydrochloride P8a is prepared via slow addition of hydrochloric acid (1M in ether) to a solution of n in ether/methanol (Scheme P12). In one run, the substrate (11.32 g) is suspended in 600 mL ether, and methanol (160 mL) is added until a homogeneous solution is obtained. Addition of HCl in this case results in the formation of initially a milky suspension and then a white slurry, which is stirred for 40 minutes and filtered. On larger scale (100.5 g) the amount of solvent is reduced by >50% resulting initially in formation of a gum-like sticky residue on the flask wall. The residue solidifies after scraping the flask wall with a spatula and prolonged stirring. The reduced amount of solvent employed in the large-scale reaction does not adversely affect the crystal form of the hydrochloride salt. The monohydrochloride thus obtained requires no additional purification or recrystallization.

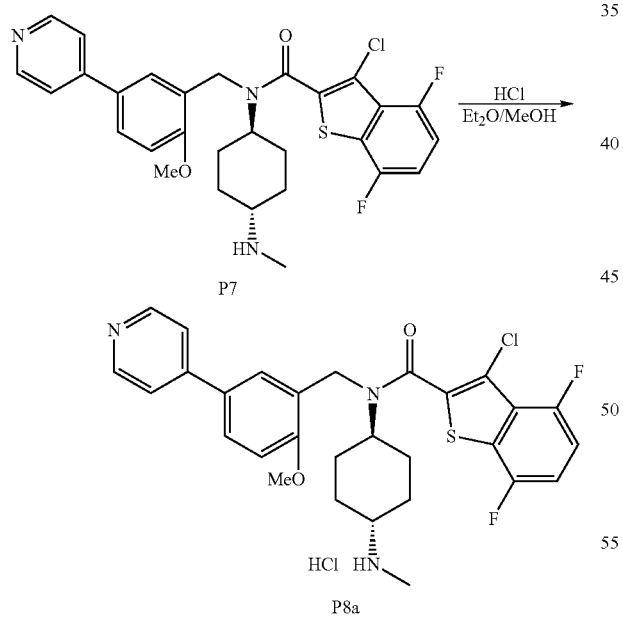

B.6 Investigation of Two Alternative Synthetic Routes

Two alternative reaction routes toward 7 are studied. In the first route, a four step approach to the free base is investigated (Scheme P13). Aminoalcohol P17 is considered as a starting material. Reductive amination installing the biaryl moiety would be followed by oxidation of the alcohol to give aminoketone P19. Acylation would be followed by reductive amination to furnish P7 as the free base.

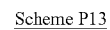
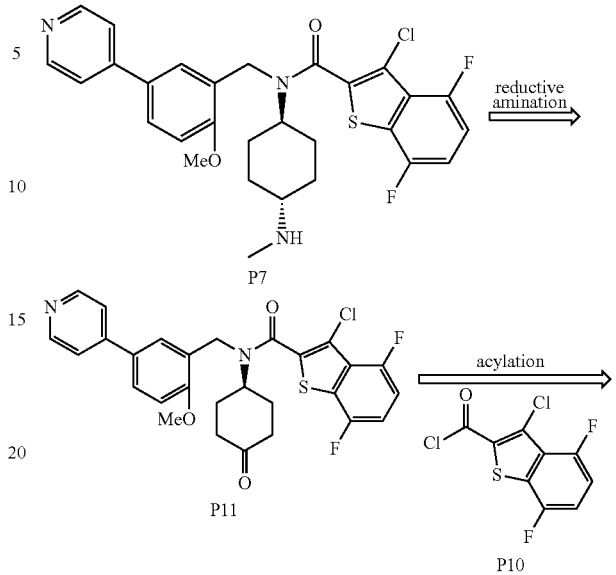
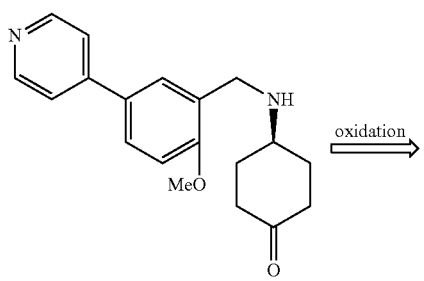
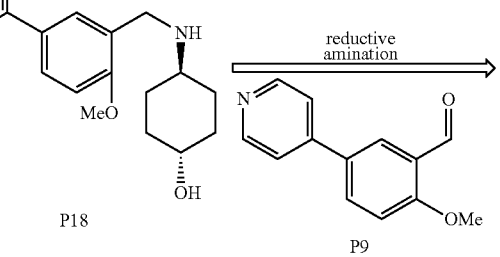
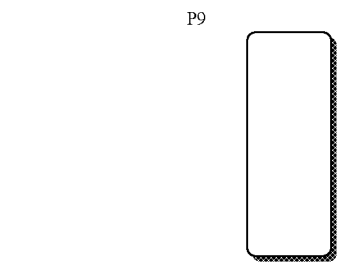

In the forward direction reductive amination produces the desired aminoalcohol P18 in good yield (Scheme P14). However, substrate P18 proves to undergo decomposition (dealkylation) under the oxidation conditions investigated. Swern oxidation gives an unidentified reaction product that is inconsistent with the desired aminoketone P19.

Scheme P14

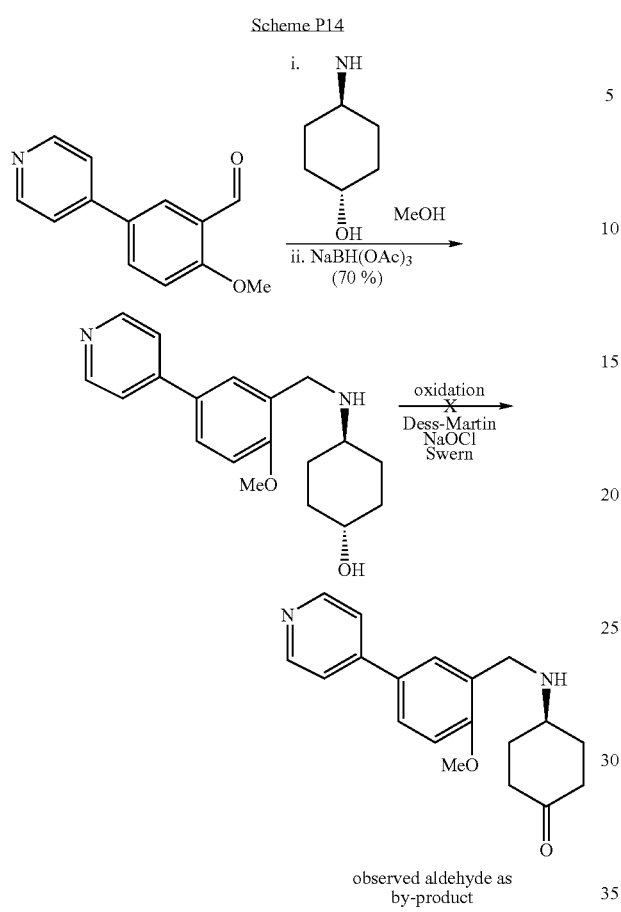

observed aldehyde as by-product

A second alternative route is then considered (Scheme P15). This five-step route would still make use of monofunctionalizing diamine P1 but the N-methyl substituent would be incorporated at a later stage in the synthesis, circumventing five-step sequence used to prepare functionalized diamine P4.

Scheme P15

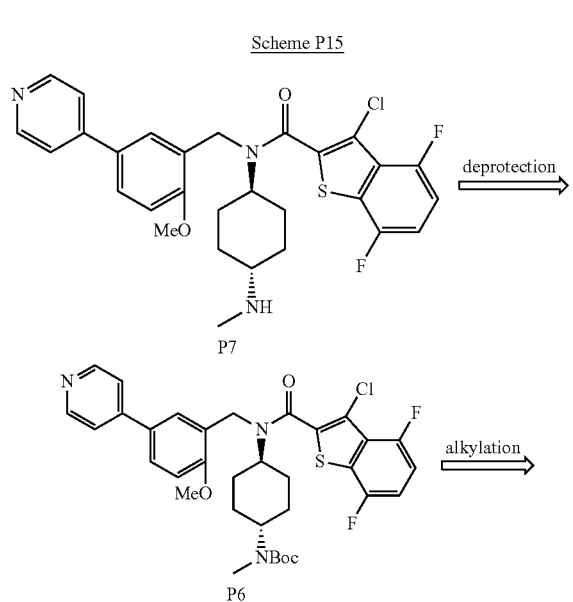

This approach is reduced to practice P7 is prepared via this route (Scheme P16). Notably, reductive amination utilizing the non-methylated diamine proceeds much slower, with reduction of the imine being the rate-determining step. Acylation gives the desired amide P21 in 63% yield after chromatography. The carbamate nitrogen is successfully methylated with methyl iodide in the presence of sodium hydride and the crude product is deprotected to yield P7 (purity 98%). While treatment with sodium hydride and methyl iodide does produce the desired alkylated product, the reaction does not go to completion during a second run.

Scheme P16

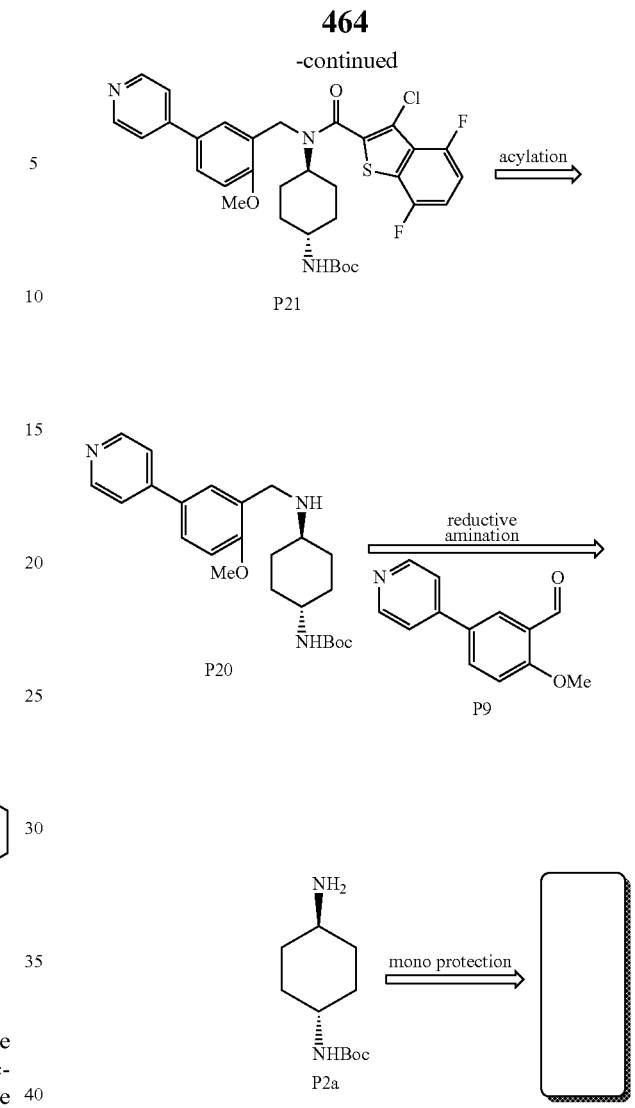

-continued

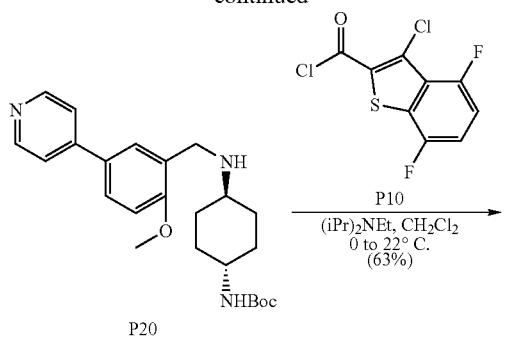

P20

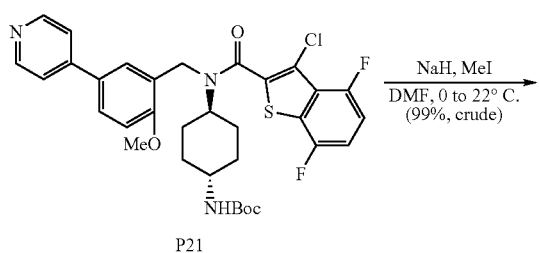

P21

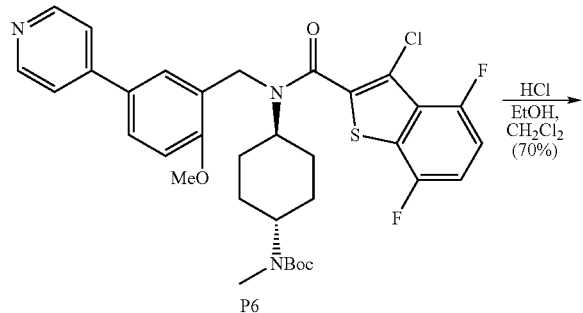

P6

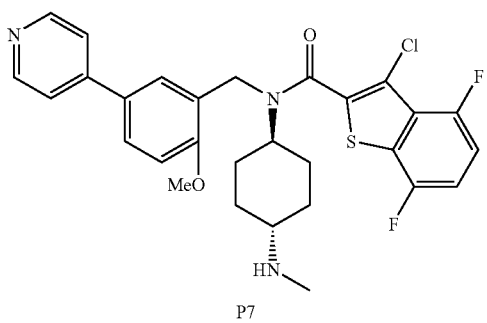

P7

A route to assemble methylated carbamate P4 in two steps from 1,4-cyclohexanediamine is also studied by treating the monocarbamate P2a with methyl iodide in the presence of base (Table P4). Using potassium t-butoxide gives the most promising result and while residual starting material and bis-alkylation are detected by LC/MS, the impurities are not quantified.

TABLE P4

Direct methylation of carbamate P2a.

| entry | scale | reaction conditions | reaction outcome |
|---|---|---|---|
| 1 | 0.2 g | NaH (1.6 equiv), MeI (1.03 equiv), DMF, 0° C. | 0.1 g (45%), mixture of desired product, bis-alkylation and starting material by LC/MS |
| 2 | 0.5 g | KOtBu (1.03 equiv), MeI (1.03 equiv), THF, 0° C. | 0.3 g (53%) desired product (major), sm and bis-alkylated product present by LC/MS |

C. Summary

To increase convergence and in an effort to facilitate isolation and purification of intermediates the synthetic scheme ultimately used during the scale-up is slightly modified (Scheme P1). In addition, reaction conditions for some of the synthetic steps are altered to improve the overall yield and impurity profile. Overall of monohydrochloride P8a is prepared as a stable single crystal form and 102 g P8a is submitted in two batches (11.14 g; 90.6 g). To make most efficient use of 1,4-cyclohexanediamine, an alternative method using t-butyl phenyl carbonate in ethanol is employed to produce monocarbamate P2. Impurity profile analysis results in an investigation of the reaction conditions used during the reinstallation of the Boc group onto the secondary amine. Ultimately, a solvent switch from toluene to methanol gives the desired reaction product with an improved impurity profile and in a shorter reaction time. The reaction yield for the acylation is increased by ensuring purity of the starting material as well as eliminating chromatographic purification.

D. Experimental Procedures for Improved Synthetic Scheme:

Experimental procedures are described below. For some transformations, experimental procedures for different reaction scales are reported.

Monofunctionalization of diamine

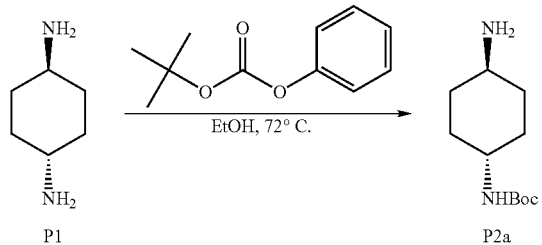

| reagents | MW | Equiv. | mmol | g | d/M | V | S |
|---|---|---|---|---|---|---|---|
| 1,4-diaminocyclohexane | 114.19 | 1 | 1332.9 | 152.2 | | | TCI |
| t-butyl phenyl carbonate | 194.23 | 1.01 | 1351.5 | | 1.05 | 250 mL | Aldrich |
| absolute EtOH | | | | | | 1 L | EMD |

Procedure: To a 3 L 3-neck RB flask equipped with a mechanical stirrer, condenser with $N_2$ inlet and temperature probe is added 1,4-diaminocylcohexane P1 (152.2 g, 1332.9 mmol), EtOH (1 L) and t-butyl phenyl carbonate (250 mL, 1351.5 mmol). The reaction mixture is wrapped with Al foil and heated using a heating mantle (JKem temperature controller >2 L setting, $T_{set}=100°$ C.). A brown solution is obtained and an internal temperature of 73.8° C. is recorded after 2.5 h. After heating for 18 h the now heterogeneous reaction mixture is allowed too cool. The mixture is filtered to remove bis-Boc protected amine, which precipitated as a white solid. The filtrate is concentrated in vacuo to a thick peach colored syrup. The mixture is transferred to an Erlenmeyer flask and the transfer is completed with $CH_2Cl_2$ (50 mL). To the mixture $H_2O$ (100 mL) is added (pH=9) followed by concentrated HCl (180 mL to pH=2) resulting in the precipitation of the (4-aminocyclohexyl)carbamic acid tert-butyl ester as a hydrochloride salt. The mixture is swirled vigorously until a thick slurry is obtained. Additional $CH_2Cl_2$ is added to maximize the amount of precipitate and the slurry is filtered (additional product is obtained from this filtrate #1, as described below). The solid is washed with $Et_2O$ (1.4 L). To free-base the HCl salt $H_2O$ (500 mL) is added followed by NaOH (2.5N, to pH=12). The mixture is extracted with $CH_2Cl_2$ (3×). The combined organic extracts are washed with $H_2O$ (3×400 mL), dried over anhydrous $Na_2SO_4$ and concentrated in vacuo to give (4-aminocyclohexyl)carbamic acid tert-butyl ester P2a (92.89 g) as a white solid.

Additional product is recovered via acid base extraction of filtrate #1: The filtrate is transferred to a separatory funnel and the layers are separated. The $CH_2Cl_2$ layer is washed with $H_2O$ (2×500 mL) and the combined aqueous layers are back-extracted with $CH_2Cl_2$. The pH of the aqueous layer is adjusted to pH=12 with NaOH (50%). The milky suspension is extracted with $CH_2Cl_2$. The combined organic extracts are washed with $H_2O$, dried over anhydrous $Na_2SO_4$ and concentrated in vacuo to give additional (4-aminocyclohexyl)carbamic acid tert-butyl ester P2a (4.6 g). Combined yield 97.2 g, 34%: $^1$H NMR (400 MHz, cdcl$_3$) δ ppm 4.39 (s, 1H), 3.31 (s, 1H), 2.53-2.59 (m, 1H), 1.96-1.91 (m, 2H), 1.75-1.85 (m, 2H), 1.37 (s, 9H), 0.96-1.25 (m, 5H); $^{13}$C NMR (101 MHz, cdcl$_3$) δ ppm 155.20, 78.99, 49.87, 49.19, 35.33, 32.12, 28.35; LRMS (ESI) Calcd for $C_{11}H_{22}N_2O_2$ [M]: 214.1682. Found [M+H]: 215.2.

| reagents | MW | Equiv. | mmol | g | d/M | V | S |
|---|---|---|---|---|---|---|---|
| 1,4-diaminocyclohexane | 114.19 | 1 | 438.5 | 50.07 | | | TCI |
| t-butyl phenyl carbonate | 194.23 | 1.01 | 443.3 | | 1.05 | 82.0 mL | Aldrich |
| absolute EtOH | | | | | | 330 mL | EMD |

Procedure: A mixture of 1,4-diaminocylcohexane P1 (50.07 g, 438.5 mmol) and t-butyl phenyl carbonate (82.0 mL, 443.3 mmol) in EtOH (330 mL) is heated to reflux for 16 h. The heterogeneous reaction mixture is allowed to cool and the precipitated bis-Boc diamine is removed by filtration. The filtrate is concentrated to a thick slurry and $CH_2Cl_2$ is added followed by concentrated HCl to pH=2. The mixture is swirled vigorously and filtered to give t-butyl-4-aminocyclohexylcarbamate hydrochloride (64.07 g). Water (100 mL) and NaOH (2.5N, 280 mL) is added and the slurry is extracted with $CH_2Cl_2$ (2×250 mL). The combined organic extracts are washed with $H_2O$ (2×200 mL) dried over anhydrous $Na_2SO_4$ and concentrated in vacuo to give (4-aminocyclohexyl)carbamic acid tert-butyl ester P2a (38.2 g, 41%) as a white solid.

Reduction
N-methylcyclohexane-1,4-diamine

P2a → (LiAlH4 / THF) → P3

| reagents | MW | Equiv. | mmol | g | d/M | V | S |
|---|---|---|---|---|---|---|---|
| (4-amino-cyclohexyl)carbamic acid tert-butyl ester | 214.30 | 1 | 225.59 | 48.34 | | | L31584-20-3,4 |
| LAH | | 3.3 | 750.0 | | 1 M in THF | 750 mL | Aldrich |
| THF | | | | | | 300 mL | EMD |

Procedure: To a 3 L 3-neck-RB flask equipped with a mechanical stirrer, condenser with $N_2$ inlet and addition funnel is added LAH (750.0 mL, 1M in THF, 750.0 mmol). The addition funnel is rinsed with 20 mL THF and the solution is cooled in an ice bath for 20 minutes. (4-aminocyclohexyl)carbamic acid tert-butyl ester P2a (48.34 g, 225.59 mmol) is dissolved in THF (250 mL) and insoluble material is removed via filtration to give a light yellow solution, which is added to the cooled LAH solution over 1 h 45 minutes via addition funnel. The transfer is completed by rinsing with THF (2×10 mL). After 20 minutes the cold bath is removed and the pink solution is allowed to warm over 45 minutes. The flask is wrapped with Al foil for insulation and the opaque pink mixture is heated (JKem controller 300 mL-2 L setting, $T_{set\ external}$=55° C.). The external temperature setting is gradually increased to 85° C. until the internal temperature reached 64° C. and the solvent started to reflux. Reflux is continued for 3 h and TLC analysis showed no remaining starting material.

The mixture is allowed to cool and stirred overnight at 22° C. The resulting slurry is cooled in an ice bath and $H_2O$ (40 mL) is added carefully via addition funnel (1 drop every 10 seconds) over 2 h while maintaining an internal temperature of 10° C. or below. Subsequently, NaOH (16% wt., 40 mL) is added dropwise over 15 minutes followed by $H_2O$ (100 mL) over 10 minutes. The cold bath is removed and the slurry is stirred for 1 h and filtered through a medium fritted filter funnel. The transfer is completed with THF (2×100 mL) and the filter cake is washed with TBME (2×200 mL) and $CH_2Cl_2$ (4×250 mL). The light yellow filtrate is concentrated in vacuo to give N-methylcyclohexane-1,4-diamine P3 (28.1 g, 97%) as an off-white crystalline solid: $^1$H NMR (400 MHz, cdcl$_3$) δ ppm 2.64-2.56 (m, 1H), 2.36 (s, 3H), 2.33-2.19 (m, 2H), 1.92-1.85 (m, 2H), 1.85-1.78 (m, 2H), 1.12-0.98 (m, 4H); $^{13}$C NMR (101 MHz, cdcl$_3$) δ ppm 58.05, 50.43, 35.33, 35.23, 35.16, 30.25, 33.83, 31.78, 31.73, 30.25; LRMS (ESI) Calcd for $C_7H_{16}N_2$ [M]: 128.217. Found [M+H]: 129.

Selective Boc-protection of secondary amine
(4-aminocyclohexyl)methylcarbamic acid tert-butyl ester P3 → (i. benzaldehyde, MeOH; ii. Boc$_2$O, toluene; iii. 1 M KHSO4) → P4

| reagents | MW | Equiv. | mol | g | d/M | V | S |
|---|---|---|---|---|---|---|---|
| N-methylcyclohexane-1,4-diamine | 128.22 | 1 | 213.69 | 27.4 | | | L31584-27-1 |
| benzaldehyde | 106.12 | 1 | 214.47 | | 1.044 | 21.8 mL | |
| MeOH | | | | | | 800 mL | Aldrich |
| Boc$_2$O | 218.25 | 1.01 | 216.27 | 47.2 g | | | Aldrich |
| toluene | | | | | | 300 mL | Aldrich |
| KHSO$_4$ | | | | | 1 M aq | 900 mL | Aldrich |

Two reactions of similar scale 27.4 g and 29.6 g are run side by side and are combined during the work-up.

Procedure: To a 2 L 3-neck RB flask equipped with a magnetic stirrer, $N_2$ inlet and stopper is added N-methylcyclohexane-1,4-diamine P3 (27.4 g, 213.69 mmol), MeOH (800 mL) and benzaldehyde (21.8 mL, 214.47 mmol). After stirring the mixture for 1.5 h $^1$HMNR analysis of a small aliquot showed that imine formation is complete (aliquot is concentrated and diluted with $d_6$-dmso). The reaction mixture is concentrated and azeotroped twice with toluene (200 mL and 100 mL). The residue is diluted with toluene (300 mL) and cooled in an ice bath. Di-tert-butyldicarboxylate (47.2 g, 216 mmol) is added over 15 minutes and the mixture is stirred for 2 h. The ice bath is removed and the mixture is concentrated in vacuo. To the residue is added an aqueous solution of $KHSO_4$ (1M, 900 mL) and the mixture is stirred at room temperature for 2.5 h. At this stage the reaction mixture is combined with a second run (29.6 g scale). The combined mixture is extracted with methyl tert-butyl ether (3×700 mL) until no UV active material could be extracted. The pH of the aqueous mixture is adjusted to pH 13 with 25% aqueous NaOH and extracted with dichloromethane (3×600 mL). The combined organic layers are dried over anhydrous $Na_2SO_4$, filtered and concentrated in vacuo to give (4-aminocyclohexyl)methylcarbamic acid tert-butyl ester P4 (64.6 g, 64%) as a yellow oil, which is used without further purification.

| reagents | MW | Equiv. | mol | g | d/M | V | S |
|---|---|---|---|---|---|---|---|
| N-methyl-cylco-hexane-1,4-diamine | 128.22 | 1 | 79.55 | 10.2 | | | L31584-27-1 |
| benzaldehyde | 106.12 | 1.01 | 80.67 | | 1.044 | 8.2 mL | |
| MeOH | | | | | | 320 mL | Aldrich |
| $Boc_2O$ | 218.25 | 1.01 | 80.64 | 17.6 g | | | Aldrich |
| toluene | | | | | | 100 mL | Aldrich |
| $KHSO_4$ | | | | | 1M aq | 300 mL | Aldrich |

Procedure: To a 2 L RB flask equipped with a magnetic stirrer, $N_2$ inlet and stopper is added N-methylcyclohexane-1,4-diamine (10.2 g, 79.55 mmol), MeOH (320 mL) and benzaldehyde (8.2 mL, 80.67 mmol). After stirring the mixture for 1.5 h $^1$HMNR analysis of a small aliquot showed that imine formation is complete (aliquot is concentrated and diluted with $d_6$-dmso). The reaction mixture is concentrated and azeotroped twice with toluene (2×50 mL). The residue is diluted with toluene (100 mL) and cooled in an ice bath. Di-tert-butyldicarboxylate (17.6 g, 80.64 mmol) is added over 5 minutes and the mixture is stirred for 2 h. The ice bath is removed and the mixture is concentrated in vacuo. To the residue is added an aqueous solution of $KHSO_4$ (1M, 300 mL) and the mixture is stirred at room temperature for 2 h. The mixture is extracted with methyl tert-butyl ether (3×250 mL). The pH of the aqueous mixture is adjusted to pH 13 with 25% aqueous NaOH and extracted with dichloromethane (3×250 mL). The combined organic layers are dried over anhydrous $Na_2SO_4$, filtered and concentrated in vacuo to a yellow oil, which is used without further purification (12.0 g, 66%). $^1$H NMR (400 MHz, $cdcl_3$) δ ppm 2.65 (s, 3H), 2.60-2.50 (m, 1H), 1.89-1.78 (appd, J=12.6 Hz, 2H), 1365-1.59 (appd, J=11.5, 2H), 1.50-1.40 (m, 1H), 1.40 (s, 9H), 1.25-1.10 (m, 4H); LRMS (ESI) Calcd for $Cl_2H_{24}N_2O_2$ [M]: 228.184. Found [M+H]: 229.2.

---

Suzuki coupling
2-methoxy-5-(pyridin-4-yl)benzaldehyde

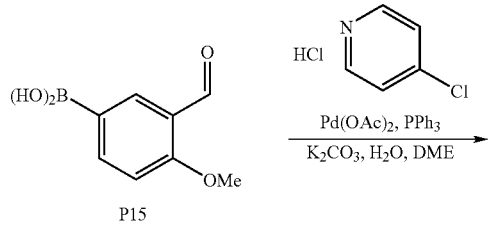

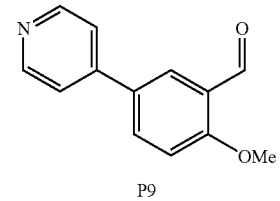

| reagents | MW | equiv. | mmol | g | d/M | V | S |
|---|---|---|---|---|---|---|---|
| 3-formyl-4-methoxy phenylboronic acid | 179.97 | 1 | 276.90 | 49.83 | | | |
| 4-chloropyridine hydrochloride | 150.01 | 1.4 | 396.33 | 59.45 | | | |
| $Pd(OAc)_2$ | 224.49 | 0.037 | 10.16 | 2.28 | | | Ald. |
| $PPh_3$ | 262.29 | 0.15 | 42.13 | 11.05 | | | Ald. |

Suzuki coupling
2-methoxy-5-(pyridin-4-yl)benzaldehyde

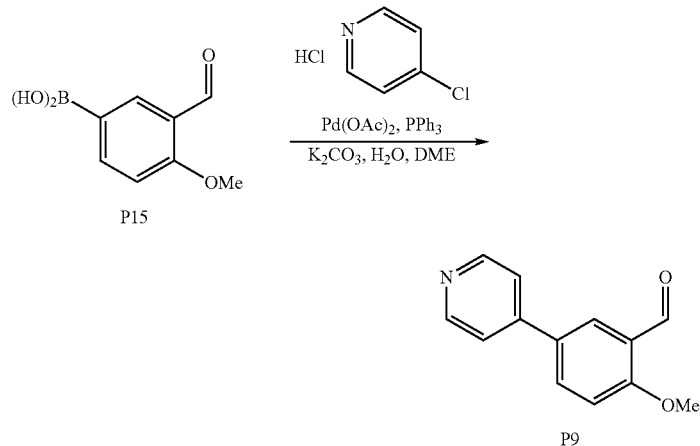

| reagents | MW | equiv. | mmol | g | d/M | V | S |
|---|---|---|---|---|---|---|---|
| K$_2$CO$_3$ | | | | | 2 M aq | 290 mL | |
| DME | | | | | | 280 mL | Ald. |

Procedure: To a 2-L 3-neck RB flask equipped with a mechanical stirrer, condenser with N$_2$ inlet and temperature probe is added 3-formyl-4-methoxyphenylboronic acid P15 (49.83 g, 276.90 mmol), 4-chloropyridine hydrochloride (46.63 g, 310.84 mmol), triphenylphosphine (7.42 g, 28.28 mmol) and dimethoxyethane (280 mL). To the resulting white slurry is added 2M aqueous K$_2$CO$_3$ (290 mL). The resulting mixture is degassed for 20 minutes with N$_2$ and Pd(OAc)$_2$ (1.65 g, 7.36 mmol) is added. Under N$_2$ atmosphere the mixture is heated to 65° C. After 47 h additional 4-chloropyridine hydrochloride (12.82 g, 85.50 mmol), triphenylphosphine (3.63 g, 13.83 mmol) and Pd(OAc)$_2$ (632.3 mg, 2.82 mmol) is added and heating is resumed for an additional 24 h. The reaction mixture is partitioned between EtOAc (300 mL) and H$_2$O (300 mL). The aqueous layer is extracted with EtOAc (4×400 mL) and the combined organic extracts are concentrated to a yellow-orange viscous oil. The crude reaction product is purified by filter chromatography on SiO$_2$ eluting with EtOAc/hexanes (30 to 100%) followed by 3% MeOH/EtOAc. The yellow solid is triturated with 10% Et$_2$O/hexanes and filtered to give 2-methoxy-5-(pyridin-4-yl)benzaldehyde P9 (53.0 g, 90%) as a yellow solid: $^1$H NMR (400 MHz, DMSO-d$_6$) δ ppm 10.39 (s, 1H), 8.61 (d, J=6.10 Hz, 2H), 8.11 (d, J=8.54 Hz, 1H), 8.06 (d, J=2.20 Hz, 1H), 7.70 (d, J=5.12 Hz, 2H), 7.38 (d, J=8.78 Hz, 1H), 3.98 (s, 3H) $^{13}$C NMR (101 MHz, DMSO-d$_6$) δ ppm 189.63, 162.77, 150.92, 146.15, 135.17, 130.03, 126.71, 125.13, 121.34, 114.37, 57.01; LRMS (ESI) Calcd for C$_{13}$H$_{11}$NO$_2$ [M]: 213.079. Found [M+H]: 214.

| reagents | MW | equiv. | mmol | g | d/M | V | S |
|---|---|---|---|---|---|---|---|
| 3-formyl-4-methoxyphenylboronic acid | 179.97 | 1 | 142.38 | 25.62 | | | |
| 4-chloropyridine hydrochloride | 150.01 | 1.4 | 157.66 | 23.65 | | | |
| Pd(OAc)$_2$ | 224.49 | 0.026 | 3.74 | 0.8409 | | | Ald. |
| PPh$_3$ | 262.29 | 0.1 | 14.37 | 3.77 | | | Ald. |
| K$_2$CO$_3$ | | | | | 2M aq | 150 mL | |
| DME | | | | | | 140 mL | Ald. |

Procedure: To a 1 L 3-neck RB flask equipped with a N$_2$ inlet, condenser and temperature probe is added 3-formyl-4-methoxyphenylboronic acid P15 (25.62 g, 142.38 mmol), 4-chloropyridine hydrochloride (23.65 g, 157.66 mmol), triphenylphosphine (3.77 g, 14.37 mmol), diethoxymethane (140 mL), and a solution of K$_2$CO$_3$ (2.7M, 150 mL). The yellow slurry is degassed with N$_2$ for 10 minutes and Pd(OAc)$_2$ (840.9 mg, 3.74 mmol) is added. The mixture is heated to 80° C. for 19 h. The layers are separated and the aqueous layer is extracted with EtOAc. The combined organic extracts are concentrated in vacuo and purified by filter chromatography on SiO$_2$ eluting with EtOAc/hexanes (30 to 100%) followed by 3% MeOH/EtOAc, to give 2-methoxy-5-(pyridin-4-yl)benzaldehyde P9 (29.97 g, 99%) as a yellow solid. (L30464-208, 266146). To remove excess palladium 2-methoxy-5-(pyridin-4-yl)benzaldehyde P9 (28.26 g, 132.53 mmol) in EtOAc (500 mL) is treated with N-acetylcysteine (2.22 g, 13.58 mmol) in H$_2$O (100 mL). The mixture is stirred for 4 h diluted with H$_2$O and the layers are separated. The aqueous layer is extracted with EtOAc (5×200 mL) and the combined organic extracts are concentrated in vacuo and filtered through a Magnesol pad to give 2-methoxy-5-(pyridin-4-yl)benzaldehyde P9 (25.33 g, 90%) as a yellow solid.

Reductive amination
[4-(2-methoxy-5-pyridin-4-yl-benzylamino)
cyclohexyl]methylcarbamic acid t-butyl ester

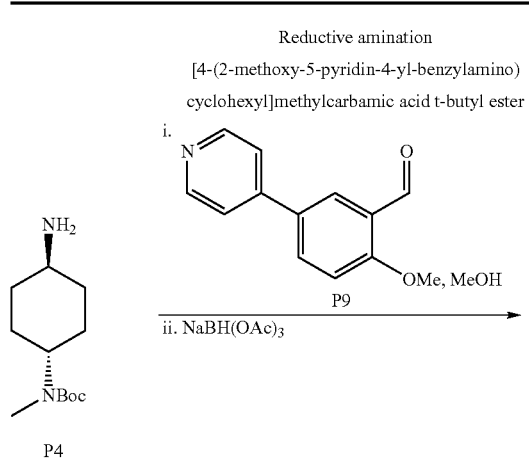

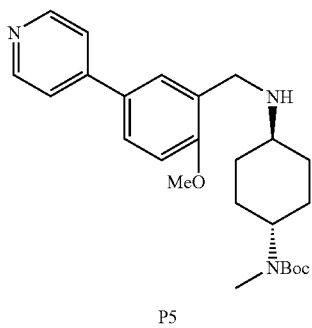

| reagents | MW | equiv. | mmol | g | d/M | V | S |
|---|---|---|---|---|---|---|---|
| (4-aminocyclohexyl) methylcarbamic acid tert-butyl ester | 228.33 | 1.08 | 162.48 | 37.1 | | | |
| 2-methoxy-5-(pyridin-4-yl)benzaldehyde | 213.23 | 1 | 150.12 | 32.01 | | | |
| NaBH(OAc)$_3$ | 211.94 | 2.7 | 404.08 | 85.64 | | | Aldrich |
| MeOH | | | | | | 600 mL | |

Procedure: To a 2 L 3-neck RB flask is added 4-aminocyclcohexyl)methylcarbamic acid t-butyl ester P4 (37.1 g, 162.5 mmol) and MeOH (550 mL). To the resulting light yellow solution is added 2-methoxy-5-(pyridin-4-yl)benzaldehyde P9 (32.01 g, 150.1 mmol) as a solid, and transfer is completed with MeOH (50 mL). After stirring the reaction mixture at room temperature for 1 h, the mixture is cooled in ice and NaBH(OAc) (82.83 g, 390.8 mmol) is added in portions over 1 h. After stirring the yellow slurry for 40 minutes the cold bath is removed and stirring is continued for 1 h at room temperature. Additional NaBH(OAc)$_3$ (2.81 g, 18.0 mmol) is added and stirring is continued for 30 minutes. The reaction mixture is concentrated in vacuo and the residue is diluted with H$_2$O (300 mL) and NaOH (2N and 25%) is added to pH=13. The milky suspension is extracted with dichloromethane (3×400 mL) and the combined organic extracts are dried over anhydrous Na$_2$SO$_4$ and concentrated in vacuo. The residue is purified via filter chromatography on SiO$_2$ eluting with 2M NH$_3$ in MeOH/EtOAc (5-10%) to give [4-(2-methoxy-5-pyridin-4-yl-benzylamino)cyclohexyl]methylcarbamic acid t-butyl ester P5 (45.3 g, 71%) as a light yellow foamy residue: $^1$H NMR (400 MHz, DMSO-d$_6$) δ ppm 8.58 (d, J=8 Hz, 2H), 7.80 (d, J=4 Hz, 1H), 7.68-7.64 (m, 3H), 7.08 (d, J=8 Hz, 1H), 3.84 (s, 3H), 3.75 (s, 2H), 2.62 (s, 3H), 2.32-2.20 (m, 1H), 1.98-1.89 (m, 1H), 1.53-1.38 (m, 4H) 1.38 (s, 9H), 1.25-1.00 (m, 4H); $^{13}$C NMR (101 MHz, DMSO-d$_6$) δ ppm 170.94, 158.67, 155.21, 150.75, 147.53, 130.60, 129.38, 127.62, 126.67, 121.20, 111.69, 78.92, 60.39, 56.21, 55.69, 45.18, 32.83, 28.76; LRMS (ESI) Calcd for C$_{25}$H$_{35}$N$_3$O$_3$ [M]: 425.571. Found [M+H]: 426.2.

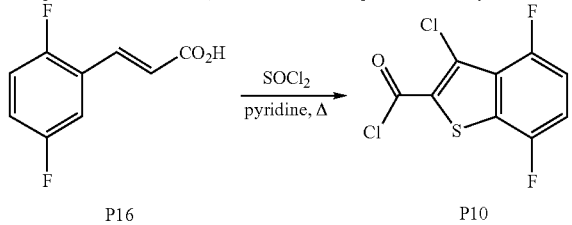

Preparation of 3-chloro-4,7-difluorobenzothiophene-2-carbonyl chloride

| reagents | MW | equiv. | mmol | g | d/M | V | S |
|---|---|---|---|---|---|---|---|
| 2,5-difluorocinnamic acid | 184.14 | 1 | 237.86 | 43.8 | | | |
| thionyl chloride | 118.97 | 3.49 | 830.78 | | 1.631 | 60.6 mL | Aldrich |
| pyridine | 79.10 | 0.28 | 66.39 | | 0.978 | 5.37 mL | Aldrich |

Procedure: To 2,5-difluorocinnamic acid P16 (43.8 g, 237.86 mmol) in thionyl chloride (60.6 mL, 830.78 mmol) is slowly added pyridine (5.37 mL, 66.39 mmol) over 50 minutes and the resulting yellow solution is heated gradually until the internal temperature reached 140° C. After 21 h the reaction mixture is allowed to cool briefly and 300 mL heptane is added. Heating is resumed for 10-15 minutes and the reaction mixture is filtered while hot to remove insoluble impurities. The filtrate is allowed to cool under vacuum for 30 minutes until formation of a precipitate is observed. The precipitate is isolated by filtration and washed with cold heptane. The filtrate is concentrated to a brown solid, which after trituration with hot heptane yields additional crops of the desired product. This is repeated twice and the solids are combined to give 3-chloro-4,7-difluorobenzothiophene-2-carbonyl chloride P10 (39.04 g, 61%) as a yellow-brown solid.

Acylation{4-[(3-chloro-4,7-difluoro-benzo[b]thiophene-2-carbonyl)-(2-methoxy-5-pyridin-4-yl-benzyl)-amino]-cyclohexyl}-methyl-carbamic acid tert-butyl ester

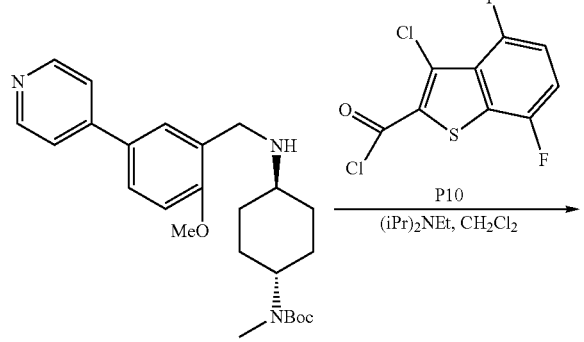

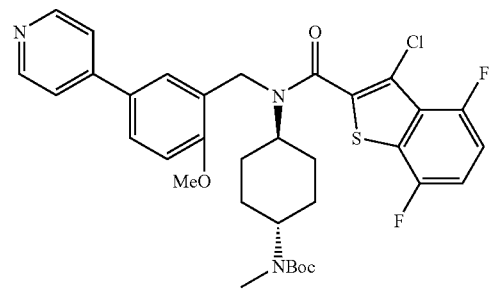

| reagents | MW | equiv. | mmol | g | d/M | V | S |
|---|---|---|---|---|---|---|---|
| [4-(2-methoxy-5-pyridin-4-yl-benzylamino)-cyclohexyl]methylcarbamic acid t-butyl ester | 425.56 | 1 | 118.20 | 50.3 | | | |

Acylation{4-[(3-chloro-4,7-difluoro-benzo[b]thiophene-2-carbonyl)-(2-methoxy-5-pyridin-4-yl-benzyl)-amino]-cyclohexyl}-methyl-carbamic acid tert-butyl ester

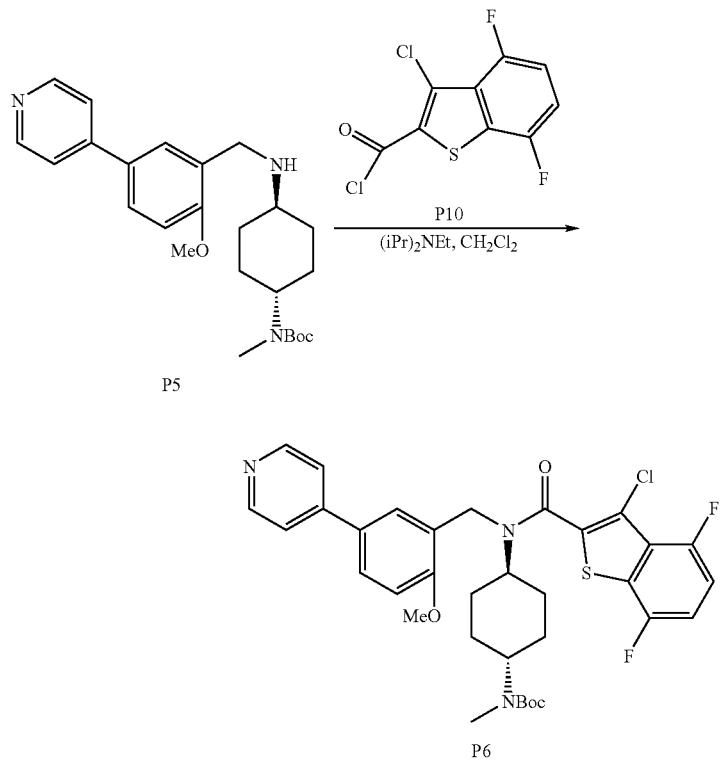

| reagents | MW | equiv. | mmol | g | d/M | V | S |
|---|---|---|---|---|---|---|---|
| 3-chloro-4,7-difluorobenzo-thiophene-2-carbonyl chloride | 267.08 | 1.1 | 129.92 | 34.7 | | | |
| (iPr)₂NEt | 129.25 | 2 | 248.0 | | 0.742 | 43.2 mL | A |
| CH₂Cl₂ | | | | | | 1 L | A |

Procedure: To a 3 L 3-neck RB flask equipped with a mechanical stirrer, $N_2$ inlet and addition funnel is added [4-(2-methoxy-5-pyridin-4-yl-benzylamino)cyclohexyl]methylcarbamic acid t-butyl ester P5 (50.3 g, 118.20 mmol) and $CH_2Cl_2$ (750 mL). The resulting mixture is cooled in an ice bath and 3-chloro-4,7-difluorobenzothiophene-2-carbonyl chloride P10 (34.7 g, 129.92 mmol) in $CH_2Cl_2$ (250 mL) is added over 4 h. The reaction mixture is diluted with $CH_2Cl_2$ and washed with 1N HCl (800 mL), 1N NaOH (800 mL), $H_2O$ (500 mL) and brine (500 mL). The organic layer is dried over anhydrous $Na_2SO_4$ and concentrated in vacuo to an orange-brown solid. The crude product is ground to a fine solid, diluted with EtOAc (450 mL) and the resulting slurry is stirred for 1 h. The mixture is filtered and the filter cake is washed with EtOAc (100 mL), and dried to give {4-[(3-chloro-4,7-difluorobenzothiophene-2-carbonyl)-(2-methoxy-5-pyridin-4-ylbenzyl)amino]cyclohexyl}methylcarbamic acid tert-butyl ester P6 (66.0 g, 85%) as an off-white solid.

Deprotection 3-chloro-4,7-difluoro-benzo[b]thiophene-2-carboxylic acid (2-methoxy-5-pyridin-4-yl-benzyl)-(4-methylaminocyclohexyl)amide

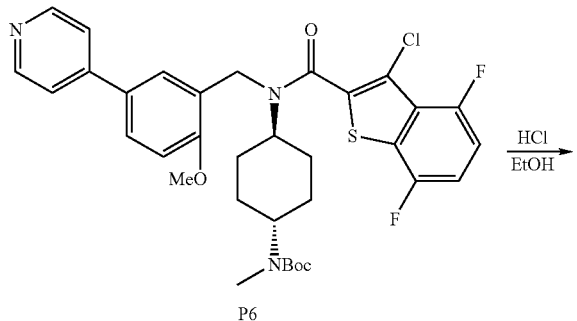

P6

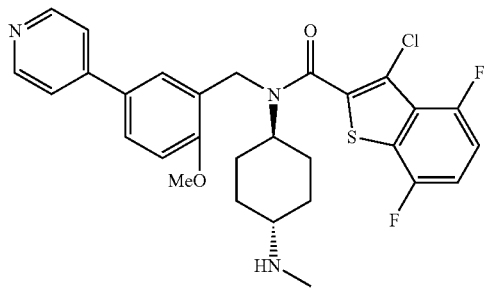

P7

| reagents | MW | equiv. | mmol | g | d/M | V | S |
|---|---|---|---|---|---|---|---|
| {4-[(3-chloro-4,7-difluorobenzo[b]thiophene-2-carbonyl)-(2-methoxy-5-pyridin-4-ylbenzyl)amino]-cyclohexyl}methylcarbamic acid tert-butyl ester | 556.07 | 1 | 83.70 | 54.92 | | | |
| HCl | | | | | 12 | 800 mL | |
| EtOH | | | | | | 1.5 L | |

Procedure: To a 3 L 3-neck RB flask with a mechanical stirrer, addition funnel, temperature probe and $N_2$ inlet is added {4-[(3-chloro-4,7-difluorobenzothiophene-2-carbonyl)-(2-methoxy-5-pyridin-4-ylbenzyl)amino] cyclohexyl}methylcarbamic acid tert-butyl ester P6 (54.92 g, 83.70 mmol) and EtOH (1.5 L). The resulting beige slurry is cooled to 5° C. and concentrated HCl (800 mL) is added over 1 h. The cold bath is removed and the solution is stirred for 4.5 h at room temperature. The reaction mixture is concentrated by removing 1.5 L solvent in vacuo and $H_2O$ (500 mL) is added. The mixture is extracted with $CH_2Cl_2$ (2×350 mL). The aqueous layer is cooled to 2° C. and 50% NaOH (300 mL) is added to pH=13. The mixture is extracted with $CH_2Cl_2$ (3×600 mL) and the combined organic layers are washed with brine, dried over anhydrous $Na_2SO_4$, and concentrated in vacuo to give 3-chloro-4,7-difluoro-benzo[b]thiophene-2-carboxylic acid (2-methoxy-5-pyridin-4-ylbenzyl)-(4-methyl-aminocyclohexyl)amide n (46.5 g, 99%) as a tan foam.

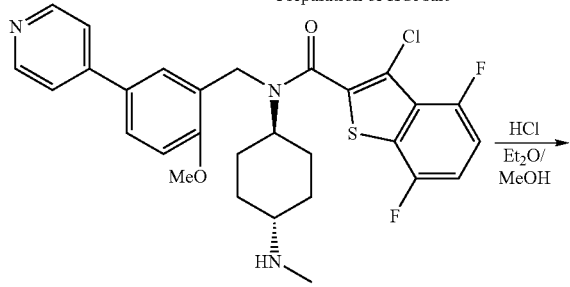

Preparation of HCl salt

P7

HCl
Et₂O/
MeOH
→

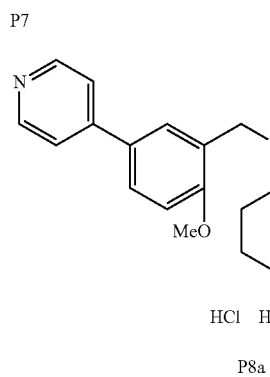

P8a

| reagents | MW | equiv. | mmol | g | d/M | V | S |
|---|---|---|---|---|---|---|---|
| 3-chloro-4,7-difluoro-benzothiophene-2-carboxylic acid (2-methoxy-5-pyridin-4-ylbenzyl)-(4-methyl-aminocyclohexyl)amide | 556.07 | 1 | 180.73 | 100.5 | | | |
| HCl (1 M in Et₂O) | | 0.95 | 172.0 | | 1 M | 172 mL | |
| Et₂O | | | | | | 2.4 L | EMD |
| MeOH | | | | | | 450 mL | Aldrich |

Procedure: To a 5 L 3-neck RB flask is added 3-chloro-4,7-difluoro-benzothiophene-2-carboxylic acid (2-methoxy-5-pyridin-4-ylbenzyl)-(4-methyl-aminocyclohexyl)amide P7 (100.5 g, 180.73 mmol) methanol (450 mL) and Et₂O (1.7 L). A 1.0 M solution of HCl (172 mL, 172 mmol) in Et₂O is added over 20 minutes. The HCl salt initially precipitated as a gum, which solidified after additional Et₂O (700 mL) is added and the flask wall is scratched with a spatula. Stirring is continued for 1 h and the mixture is filtered. The solid is dried under vacuum and N₂ overnight to give 3-chloro-4,7-difluoro-N-[2-methoxy-5-(pyridin-4-yl)benzyl]-N-(4-(methylamino)cyclohexyl)benzothiophene-2-carboxamide hydrochloride P8a (90.6 g, 85%) as an off-white solid.

| reagents | MW | equiv. | mmol | g | d/M | V | S |
|---|---|---|---|---|---|---|---|
| 3-chloro-4,7-difluoro-benzothiophene-2-carboxylic acid (2-methoxy-5-pyridin-4-ylbenzyl)-(4-methyl-amino-cyclohexyl)amide | 556.07 | 1 | 20.36 | 11.32 | | | |
| HCl (1M in Et₂O) | | 1.02 | 20.8 | | 1M | 20.8 mL | |
| Et₂O | | | | | | 600 mL | EMD |
| MeOH | | | | | | 160 mL | Aldrich |

Procedure: To a 2 L RB flask containing 3-chloro-4,7-difluoro-benzothiophene-2-carboxylic acid (2-methoxy-5-pyridin-4-ylbenzyl)-(4-methyl-aminocyclohexyl)amide P7 (11.32 g, 20.36 mmol) is added 600 mL Et₂O. To the white suspension is added MeOH (160 mL) until a homogeneous solution is obtained. A solution of HCl (1M in Et₂O, 20.3 mL) is added dropwise over 17 minutes and the mixture is stirred for 30 minutes. The slurry is filtered through a medium fritted filter funnel and the filter cake is washed with Et₂O (500 mL) and dried under vacuum and N₂ to give 3-chloro-4,7-difluoro-N-[2-methoxy-5-(pyridin-4-yl)benzyl]-N-(4-(methylamino)cyclohexyl)benzothiophene-2-carboxamide hydrochloride P8a (11.41 g, 95%) as an off-white solid.

E. Overview of an Alternate Improved Synthetic Scheme

An alternate improved synthetic scheme for the preparation of P8a is developed (Scheme P17).

Scheme P17
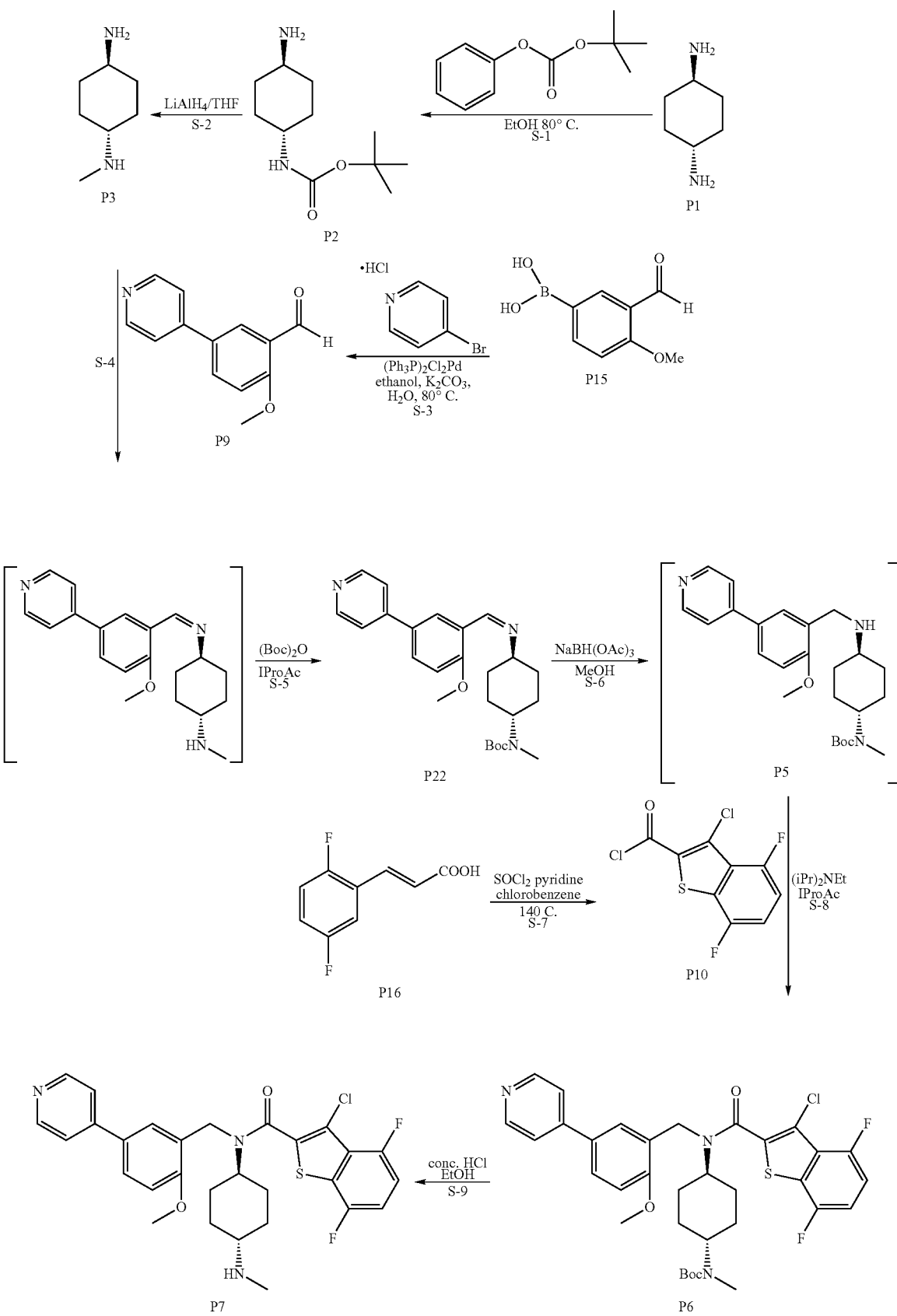

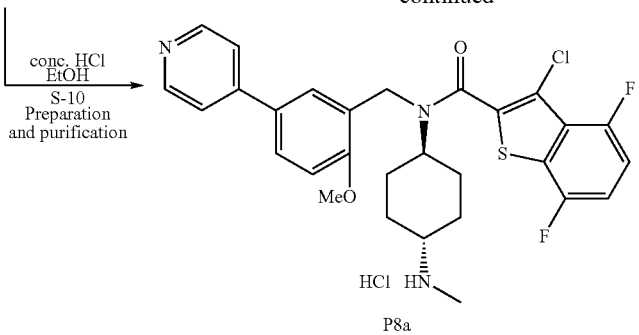

F. Experimental Procedures for Alternate Improved Synthetic Scheme:

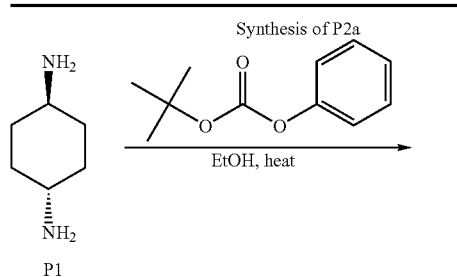

| reagents | MW | equiv | mmol | g | d/M | V |
|---|---|---|---|---|---|---|
| trans-1,4 diaminocyclohexane | 114.19 | | 307.18 | 342 | | |
| t-butylphenyl carbonate | 194.23 | 1 | 308.14 | 550.8 | 1.05 | |
| EtOH | | | | | | 1620 mL |

Procedure: To a 5 L RB flask is added trans-1,4-diaminocyclohexane P1 (342 g, 2.99 mol), EtOH (1620 ml) and t-butyl phenyl carbonate (550.8 g, 2.84 mol). The resulting clear solution is heated for 15-18 h at 85° C. (reflux). Reaction is monitored by GC for the disappearance of t-butyl phenyl carbonate (reaction is complete if all the t-butyl phenyl carbonate is consumed or is ≧1%). The reaction mixture becomes heterogeneous due to the precipitation of bis bocamine. When the reaction is complete by GC, the reaction mixture is allowed to cool to room temperature and the precipitated bis-Boc protected diamine is removed by filtration. The solids are washed with 2×200 ml EtOH (total filtrate 1.75 L). The filtrate is transferred to 5 L RB and EtOH is distilled off atmospherically. Total approx. 1300 ml of Ethanol is distilled off. Heating is discontinued. While hot, 3.5 L of water is added to the residue (pH~10). Cool to room temperature with stirring and then to ~10° C. using an ice water bath. PH is adjusted to ~13 by adding 5N NaOH. (precipitation of light pink solids is observed). The resultant slurry is stirred at room temperature for 2-3 h. (may need longer stirring time to remove major by product phenol, un-reacted diamine also is water soluble). Light pink solids are filtered off through a buchner funnel fitted with polypropylene filter cloth and washed with 2×250 ml water followed by heptane 2×250 ml. The solids are first dried on house vacuum under nitrogen for overnight and then in vacuum oven at 50° C. under nitrogen bleed till the weight is constant. The solids, desired mono-boc carbonate P2a, weighed 226 g, Yield: 35%, GC 94%, phenol 2.8%

| reagents | MW | Equv. | mmol | g |
|---|---|---|---|---|
| P2a | 214 | 1 | 701 | 150 |
| LAH, 1 M | | 3 | 2100 | 2100 mL |
| THF | | | | |
| THF | | | | 1500 mL |
| 15% NaOH | | | | 240 mL |
| Toluene | | | | 800 mL |
| CH$_2$Cl$_2$ | | | | 6000 mL |

Procedure: To slurry of P2a in THF (1500 mL) at 30-40° C. is added 1M LAH (2100 mL) over 1 h. The reaction is exothermic and gas (CO$_2$) evolved. The mixture is heated to reflux and stirred for 3 h. The mixture is cooled to 10-15° C. Then, water (80 mL), 15% NaOH (80 mL), water (240 mL) are added respectively. (Exothermic) The mixture is stirred for 3 h after quench. Then, the solid is filtered off and washed and stirred with THF (3×500 mL).

The solid is washed and stirred again with CH$_2$Cl$_2$ (6×1000 mL). (Only recover ~8% product by this washes. The product has a very limited solubility in organic solvent and soluble in water). The combined organic phases are distillated and chased with toluene (2×400 mL) to dryness to give 66.8 g of P3 as a solid. 74%. GC: 95%

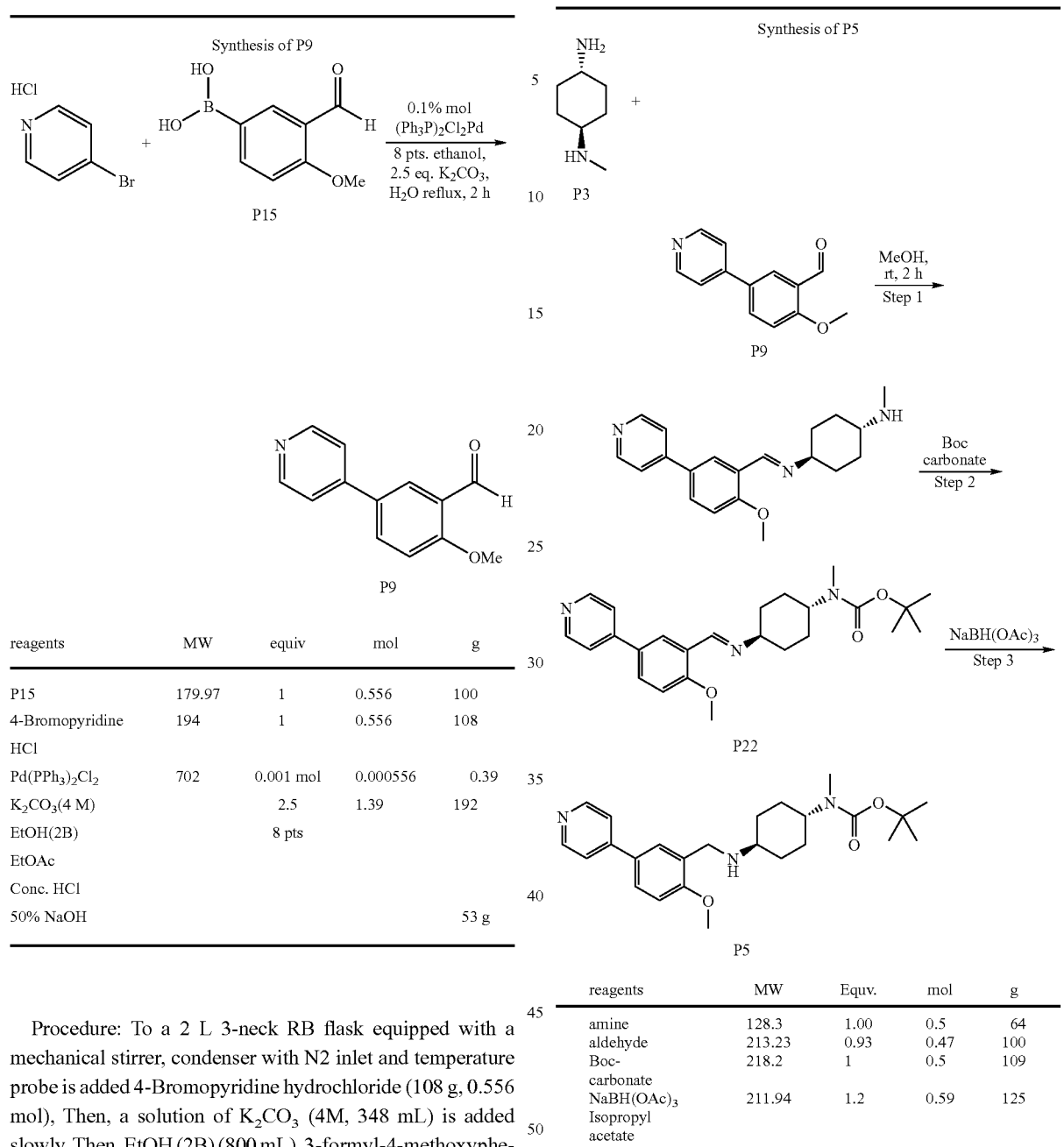

| reagents | MW | equiv | mol | g |
|---|---|---|---|---|
| P15 | 179.97 | 1 | 0.556 | 100 |
| 4-Bromopyridine HCl | 194 | 1 | 0.556 | 108 |
| Pd(PPh₃)₂Cl₂ | 702 | 0.001 mol | 0.000556 | 0.39 |
| K₂CO₃(4 M) | | 2.5 | 1.39 | 192 |
| EtOH(2B) | | 8 pts | | |
| EtOAc | | | | |
| Conc. HCl | | | | |
| 50% NaOH | | | | 53 g |

Procedure: To a 2 L 3-neck RB flask equipped with a mechanical stirrer, condenser with N2 inlet and temperature probe is added 4-Bromopyridine hydrochloride (108 g, 0.556 mol), Then, a solution of $K_2CO_3$ (4M, 348 mL) is added slowly. Then, EtOH (2B) (800 mL), 3-formyl-4-methoxyphenylboronic acid P15 (100 g, 0.556 mol) and Pd(PPh₃)₂Cl₂ (0.39 g) are added. The reaction mixture is heated to 80° C. for 2 h (reflux). The reaction mixture is allowed to cool to 40-50° C. and EtOAc (1200 mL) is added. The solid is filtered. Then, conc. HCl (75 mL) is added to the filtrate to pH 2-3. The solid is stirred for 30 min and filtered and washed with EtOAc (2×200 mL). The solid is dried by air for 2 h. The crude solid is taken into water (1500 mL) and a mixture of 53 g of 50% NaOH and water (70 mL) is added slowly to pH=12-13. The mixture is stirred for 1 h and the solid is filtered and washed with water (2×500 ml) and dried at 40° C. for 24 h to give 113 g of P9 as a solid. (Yield: 96%, Pd: 31 ppm, HPLC: SLI: <0.5%, 98%)

| reagents | MW | Equv. | mol | g |
|---|---|---|---|---|
| amine | 128.3 | 1.00 | 0.5 | 64 |
| aldehyde | 213.23 | 0.93 | 0.47 | 100 |
| Boc-carbonate | 218.2 | 1 | 0.5 | 109 |
| NaBH(OAc)₃ | 211.94 | 1.2 | 0.59 | 125 |
| Isopropyl acetate | | | | |

Procedure: Step 1: Imine Formation: To a 2-L 4-neck RB flask fitted with a mechanical stirrer and thermocouple, is charged 150 mL of Isopropyl acetate. To this is added the N-methyl trans 1,4-diaminocyclohexane P3 (64 g, 0.5 mole). It is warmed to 28-30 C to get a clear solution. An amber solution is obtained. The aldehyde (100 g, 0.47 mole) is added to 350 mL of Isopropyl acetate and warmed 50 C. The clear pale yellow solution is filtered through a carbon pad (Norit, 90 mm diameter) and the pad is rinsed with 2×100 mL of Isopropyl acetate. The aldehyde solution is added to the amine solution in the 2-L flask maintaining temperature between 30-35 C. It is stirred for 2.0-2.5 h at 20-24 C when solids precipitated out. An aliquot is withdrawn, concentrated to dryness and analyzed by NMR. NMR indicated that the reaction is complete. An additional 250 mL of isopropyl acetate is added and the slurry is cooled to 10 C.

Step 2: Boc carbonate (109 g, 0.5 mole) is added drop wise maintaining temperature between 10 to 25 C (Highly exothermic) with stirring. The slurry became thick initially and thinned out upon further addition of the reagent. The reaction mixture is stirred for 16 h (reaction is complete in ~2 h by NMR). The slurry is concentrated to ~450 mL volume in a rotary evaporator at 45 C and 100 torr. 300 mL of n-heptane is added and the slurry is cooled to 10-15 C and stirred for 2 h at 20-22 C. It is filtered through a Buchner funnel and washed with 2×100 mL of n-Heptane. The pale yellow solid (180 g wet, is dried in a vacuum at 40 C for 2 h to give 138 g of product (86% yield). NMR of the product corresponded to the structure of the imine P22.

Step 3: Reduction To a 2 L 3 neck RB flask equipped with mechanical stirrer, N2 inlet and temperature probe, is added P22 (110 g, 0.26 mol), and methanol (850 mL). The reaction mixture is cooled to 2 C. Sodium triacetoxyborohydride (125 g, 0.59 mol) is added portion wise maintaining the temperature between 2-5 C over 1 h. The mixture is stirred for 1 h at 5-15 C. An aliquot is withdrawn and analyzed by HPLC. It is concentrated and analyzed by NMR. The reaction mixture is diluted with cold water (500 mL and 5N NaOH (500 mL, 3-5 C, pH 11-12). It is stirred for 0.5 h and the mixture is extracted with 2×700 mL of isopropyl acetate. The combined organic phase is washed with 2×500 mL of water. The isopropyl acetate extract is concentrated to a volume of 300 mL and this solution is used for the coupling with P10.

washed with 150 mL of heptane. The mixture cooled to −6° C., solids filtered, and washed with 500 mL of cold heptane. The wet cake (138 g) is dried under nitrogen at room temperature. Yield=104.7 g, 48.1% HPLC 98%

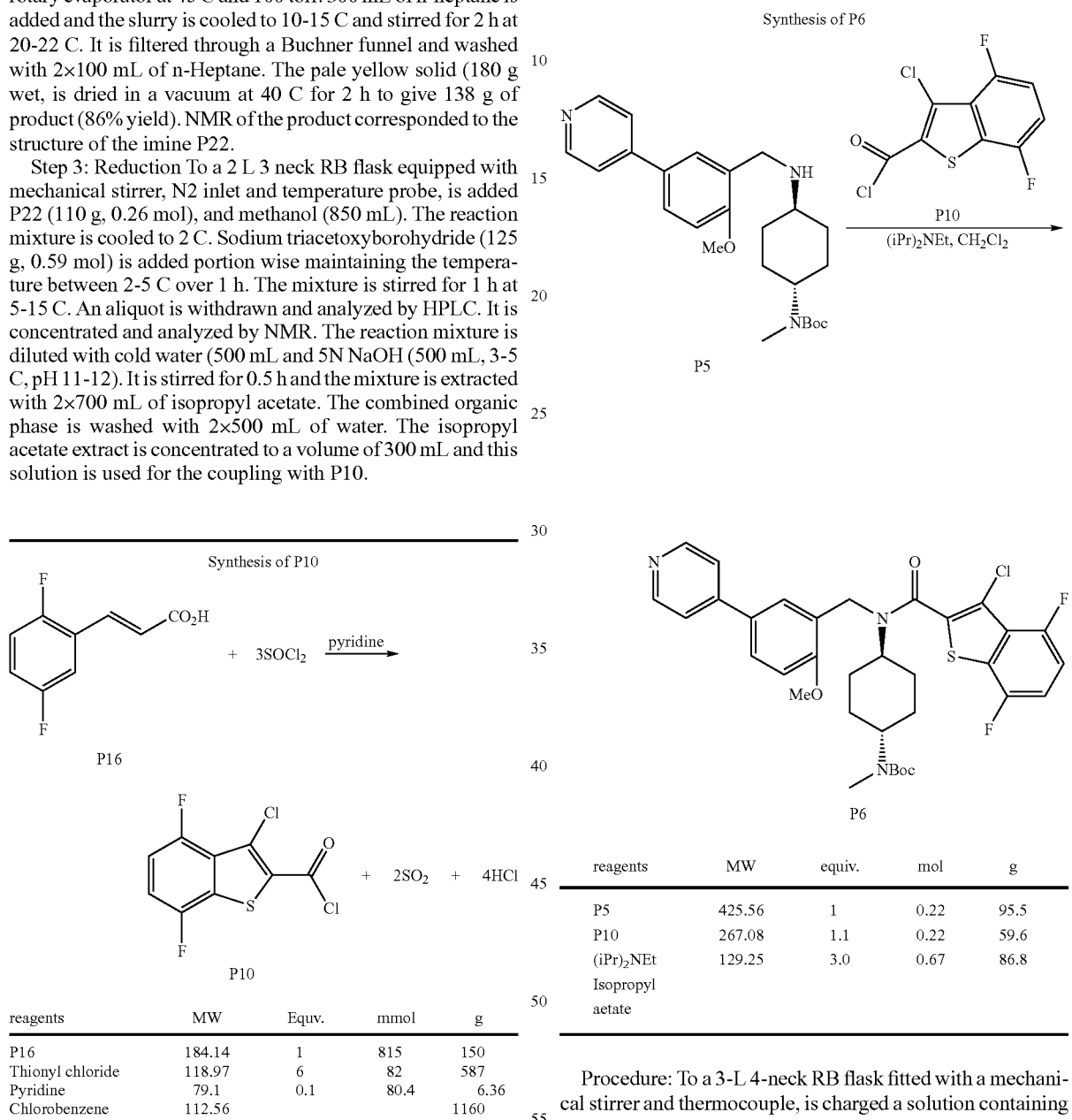

Synthesis of P10

Synthesis of P6

P16

P10

P5

P6

| reagents | MW | Equv. | mmol | g |
|---|---|---|---|---|
| P16 | 184.14 | 1 | 815 | 150 |
| Thionyl chloride | 118.97 | 6 | 82 | 587 |
| Pyridine | 79.1 | 0.1 | 80.4 | 6.36 |
| Chlorobenzene | 112.56 | | | 1160 |

| reagents | MW | equiv. | mol | g |
|---|---|---|---|---|
| P5 | 425.56 | 1 | 0.22 | 95.5 |
| P10 | 267.08 | 1.1 | 0.22 | 59.6 |
| (iPr)₂NEt | 129.25 | 3.0 | 0.67 | 86.8 |
| Isopropyl aetate | | | | |

Procedure: To a 3-L flask under nitrogen and connected to a sodium hydroxide scrubber is charged 150.0 g (0.815 mol) of trans-2,5-difluorocinnamic acid, 500 mL of chlorobenzene and 6.5 mL of pyridine, (0.1 eq.) The mixture is heated to 80° C. and 360 mL (6 eq) of thionyl chloride is added over 2 hours at 75-80° C. The mixture is heated to reflux (117-125° C.) And held for 23 hours. Excess thionyl chloride is atmospherically distilled out with chlorobenzene (125-145° C.), to a residual volume of 300 ml. The residue is cooled to 900 and 750 mL of heptane is added. The mixture is reheated to 95° C. and filtered to remove some yellow solid, 13.6 g. The cake is Procedure: To a 3-L 4-neck RB flask fitted with a mechanical stirrer and thermocouple, is charged a solution containing 95.5 g (0.22 mole) of P5 in 600 mL of isopropy acetate. Diidopropylethylamine (91.8 g, 0.67 mole is added to it. The solution is cooled to −5 C and 59.6 g of P10 (0.22 mol) in 800 mL of isopropyl acetate is added over 2 h maintaining the temperature between −2 to +5° C. with stirring. The reaction mixture is stirred for an additional 0.5 h when solids precipitated out. HPLC indicated that the reaction is complete. The solids are filtered through a buchner lined with polypropylene and washed with 400 mL of 2B EtOH, 400 mL of water and finally 400 mL of isopropyl acetate. It is dried in vacuum at 50° C. for 16 h to give 119.6 g of P6. Yield 81.3%, HPLC 95% by area

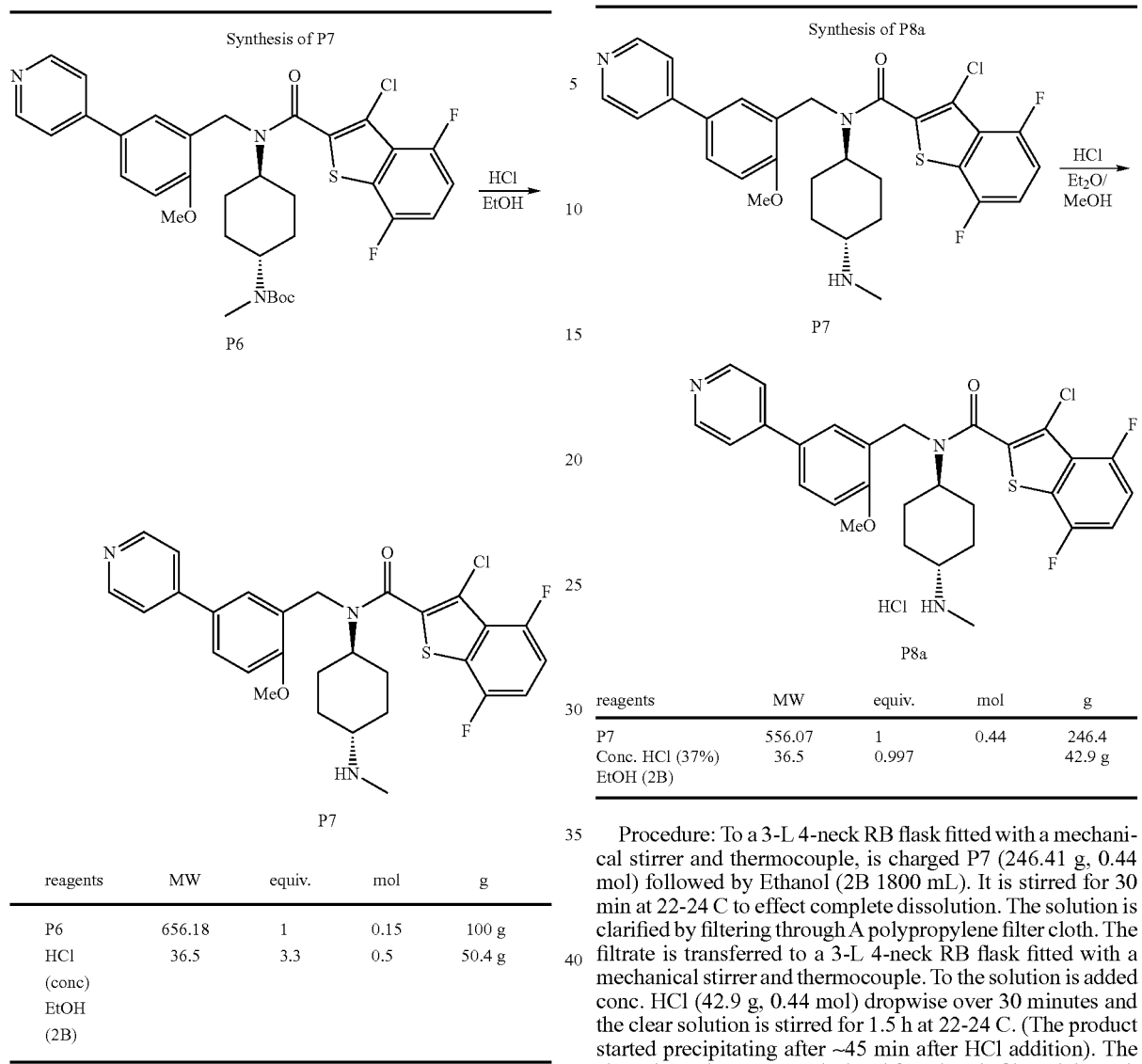

| reagents | MW | equiv. | mol | g |
|---|---|---|---|---|
| P6 | 656.18 | 1 | 0.15 | 100 g |
| HCl (conc) | 36.5 | 3.3 | 0.5 | 50.4 g |
| EtOH (2B) | | | | |

Procedure: To a 3-L 4-neck RB flask fitted with a mechanical stirrer and thermocouple, is charged P6 (100 g, 0.15 mol) followed by 2B-EtOH (750 mL). To the white suspension is added concentrated HCl (42 mL, 0.51 mol) at ambient temperature. The mixture is heated to 70° C. for 2 h when HPLC indicated that the starting material had disappeared. The reaction mixture is cooled to 22-25° C. and water, (750 mL) is added. The solution is extracted with 2×300 mL of methylene chloride and the aq. phase separated. The methylene chloride extract is washed with 300 mL of water containing 15 mL of 37% HCl. The organic phase is discarded and the combined aq. phase basified with 10N NaOH to pH-13. The basic aq. phase is extracted with 2×400 mL of TBME. The phases are separated and the organic phase is washed with 2×400 mL of water. The layers are separated and the organic layer is concentrated to a vol of ~150 mL under vacuum. TBME (20050 mL) is added to the residue and stirred for 2 h at room temperature when solids crystallized out. The solids are filtered and washed with 150 mL of TBME. The cake is dried in vacuum at 40° C. for 24 h to give 70.2 g of P7 85%) as an off-white solid. HPLC 98.2%.

| reagents | MW | equiv. | mol | g |
|---|---|---|---|---|
| P7 | 556.07 | 1 | 0.44 | 246.4 |
| Conc. HCl (37%) | 36.5 | 0.997 | | 42.9 g |
| EtOH (2B) | | | | |

Procedure: To a 3-L 4-neck RB flask fitted with a mechanical stirrer and thermocouple, is charged P7 (246.41 g, 0.44 mol) followed by Ethanol (2B 1800 mL). It is stirred for 30 min at 22-24 C to effect complete dissolution. The solution is clarified by filtering through A polypropylene filter cloth. The filtrate is transferred to a 3-L 4-neck RB flask fitted with a mechanical stirrer and thermocouple. To the solution is added conc. HCl (42.9 g, 0.44 mol) dropwise over 30 minutes and the clear solution is stirred for 1.5 h at 22-24 C. (The product started precipitating after ~45 min after HCl addition). The slurry is cool to 0-4 C and stirred for 1 h. It is filtered through a Buchner funnel lined with polypropylene. The collected solid is washed with cold EtOH (2B, 100 mL, 4-8 C) and dried under vacuum for 24 h at 45 C(N2 flow) to give P8a (225.7 g, Yield: 86%) as a white solid. HPLC purity: 99.62%, single largest=0.11%.

EQUIVALENTS

Those skilled in the art will recognize, or be able to ascertain using no more than routine experimentation, numerous equivalents to the compounds and methods of use thereof described herein. Such equivalents are considered to be within the scope of this invention and are covered by the following claims.

The contents of all references, patents and published patent applications cited throughout this Application, as well as their associated figures are hereby incorporated by reference in entirety.

Stereochemistry

For the purpose of clarity, despite any appearances to the contrary, all of the individual compounds whose structures are depicted above, e.g., in Tables 1-4, all have a cyclohexyl ring with two substituents disposed trans on the ring, with one exception: compound 418 in Table 3 has a cyclohexyl ring with two substituents disposed cis on the ring.

This application incorporates by reference in their entirety U.S. Application entitled Small Organic Molecule Regulators of Cell Proliferation, with first named inventor Shirley Ann Brunton, filed Nov. 2, 2007, Ser. No. 11/982,718; and U.S. Application entitled Small Organic Molecule Regulators of Cell Proliferation, with first named inventor Shirley Ann Brunton, filed Nov. 2, 2007, Ser. No. 11/982,708.

We claim:

1. A compound represented by general formula (V):

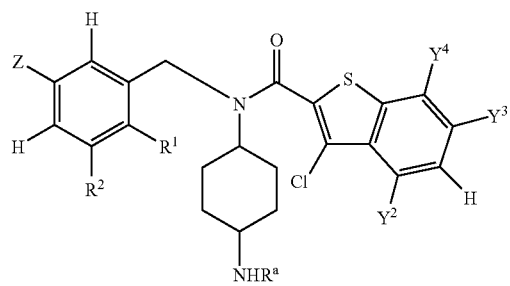

Formula V wherein, as valence and stability permit,

Z is a substituted or unsubstituted aryl or heteroaryl ring, provided that Z is not a substituted or unsubstituted pyridine N-oxide ring or a pyridine ring substituted with one or more halogens;

$R^a$ is methyl;

$R^1$ is halogen, methoxy, or ethoxy;

$R^2$ is H;

$Y^2$ and $Y^4$ are, independently, H or fluoro;

$Y^3$ is H or fluoro;

wherein the two nitrogen atoms bonded to the cyclohexane ring depicted in Formula V are in a trans relationship.

2. A composition comprising a compound of claim 1 and a pharmaceutically acceptable excipient;

wherein the composition is optionally suitable for oral or topical administration.

3. The compound of claim 1, wherein the compound is selected from the following:

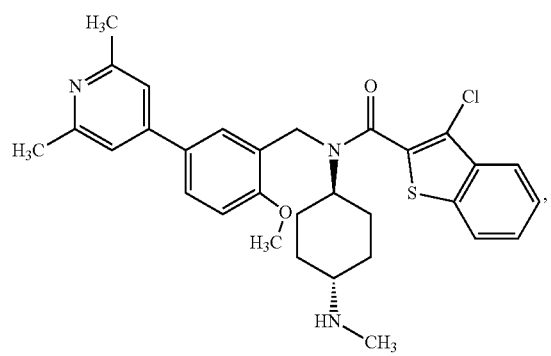

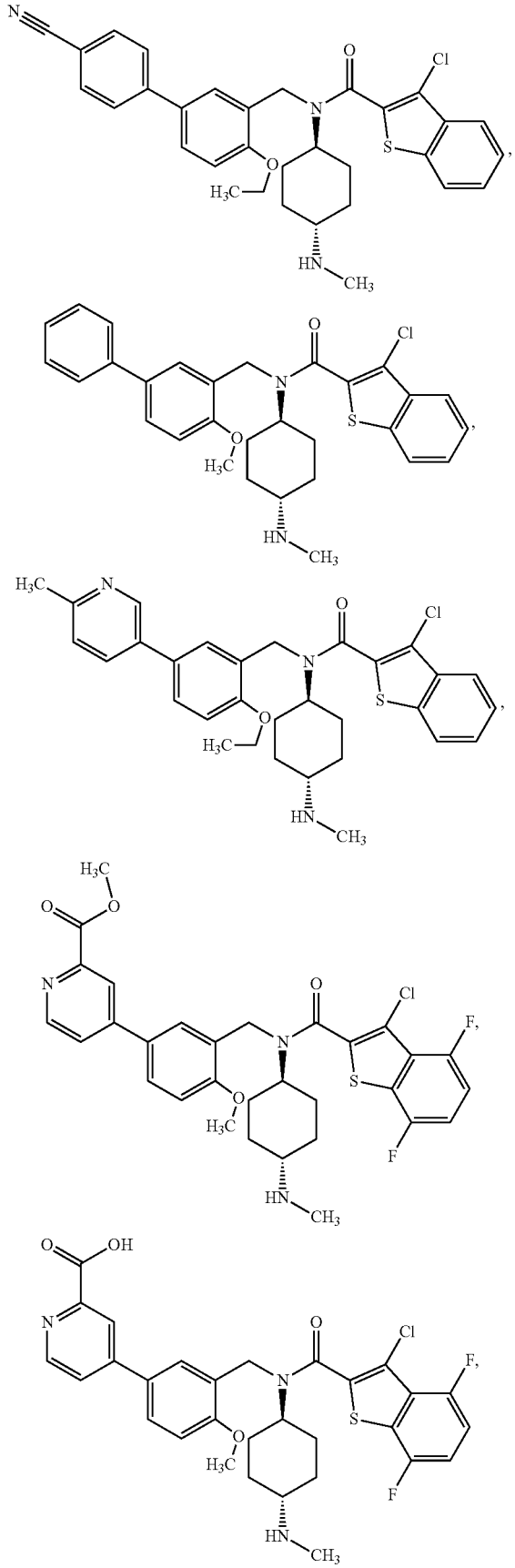

497
-continued
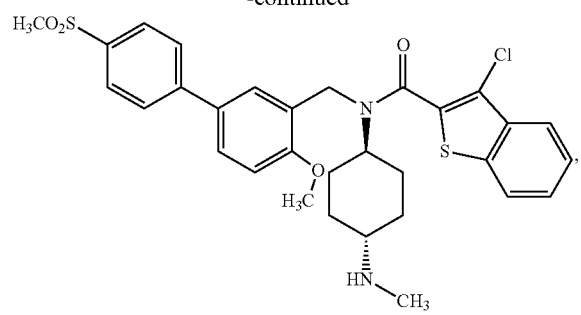
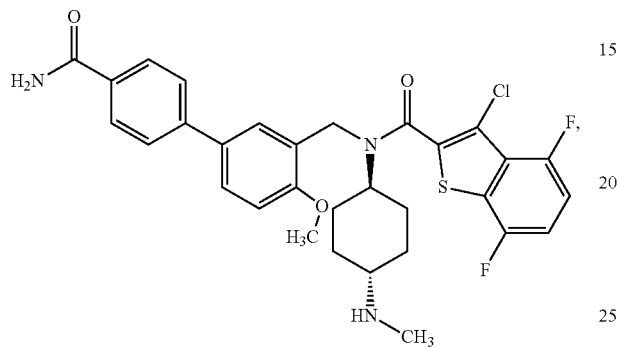
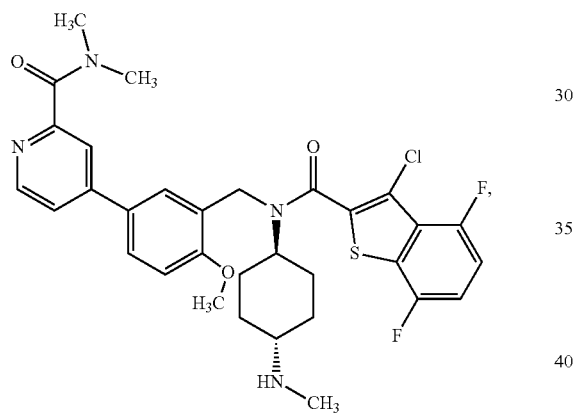
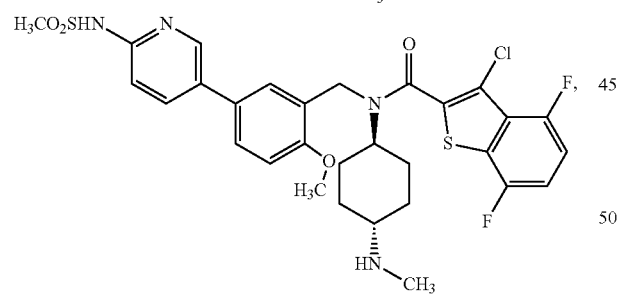
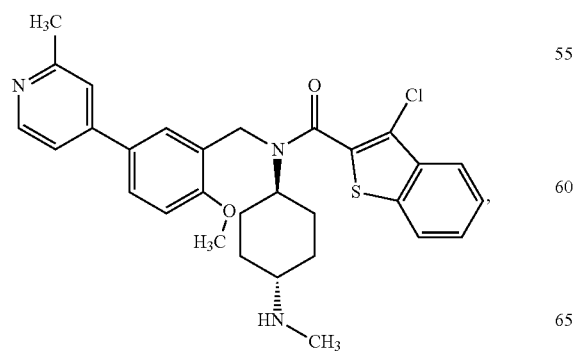
498
-continued
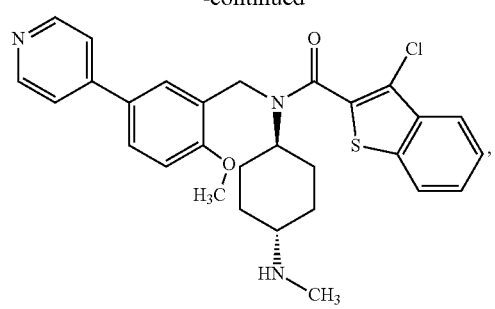
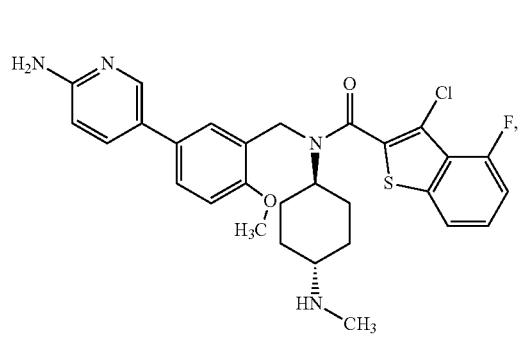
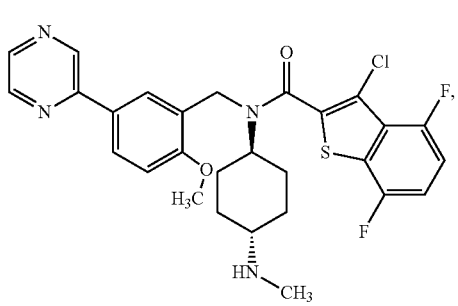
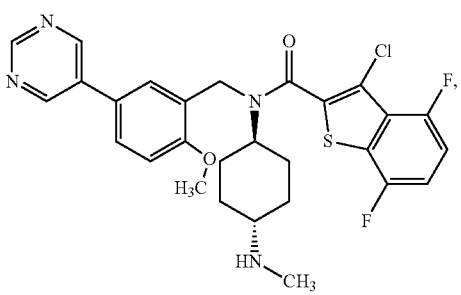
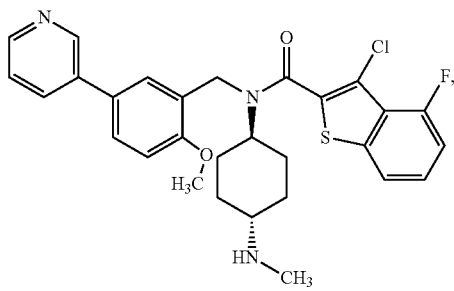

499
-continued
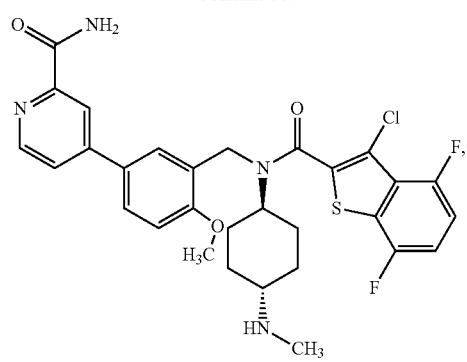
500
-continued
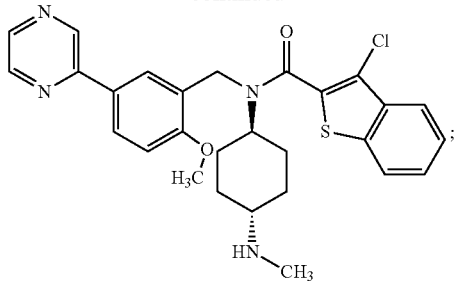
or a pharmaceutically acceptable salt thereof.
4. The compound of claim 3, wherein the compound is
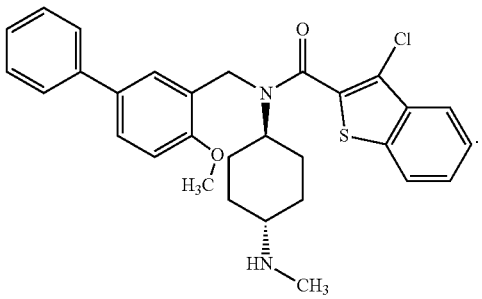
5. The compound of claim 3, wherein the compound is
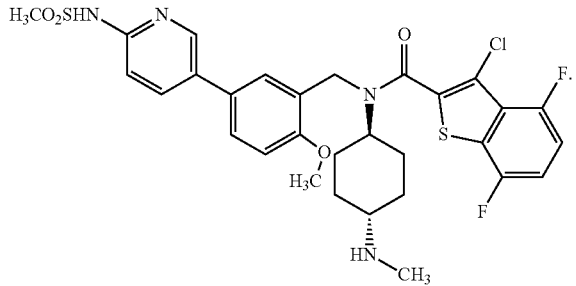
6. The compound of claim 3, wherein the compound is
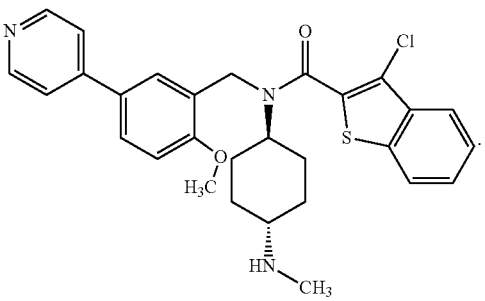

7. The composition of claim 2, wherein the compound is selected from the following:
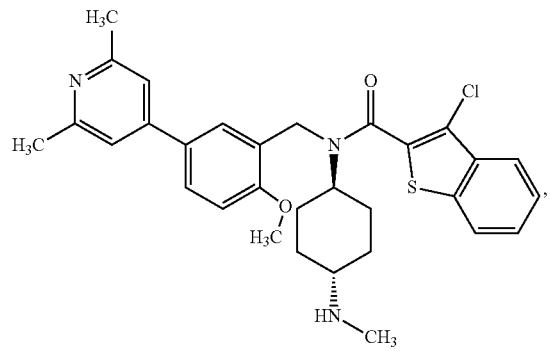
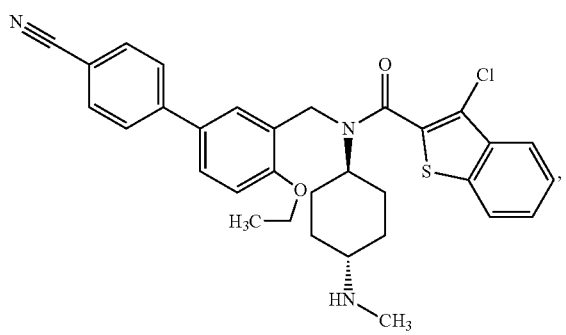
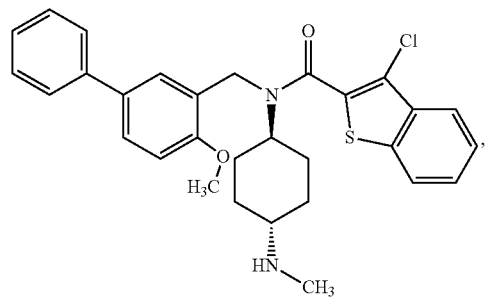
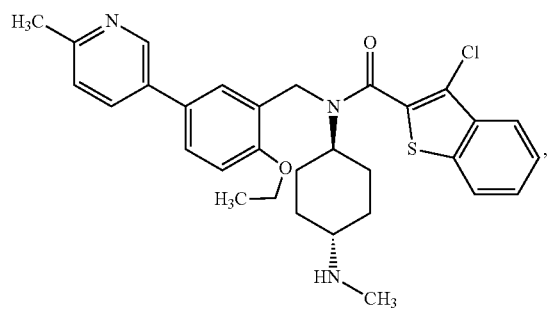
-continued
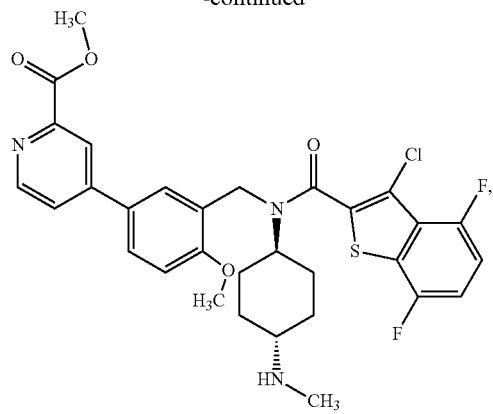
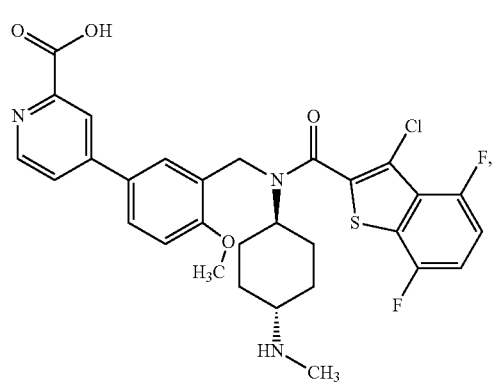
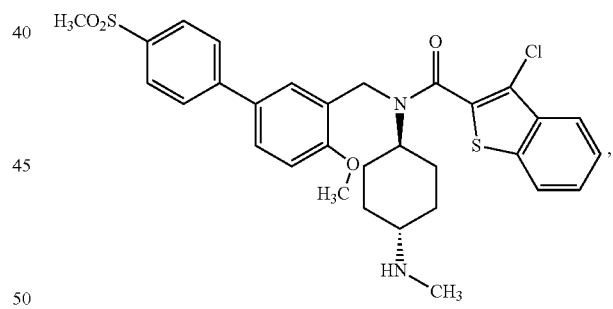
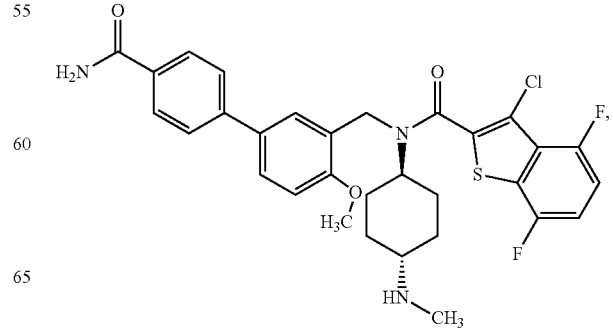

503
-continued
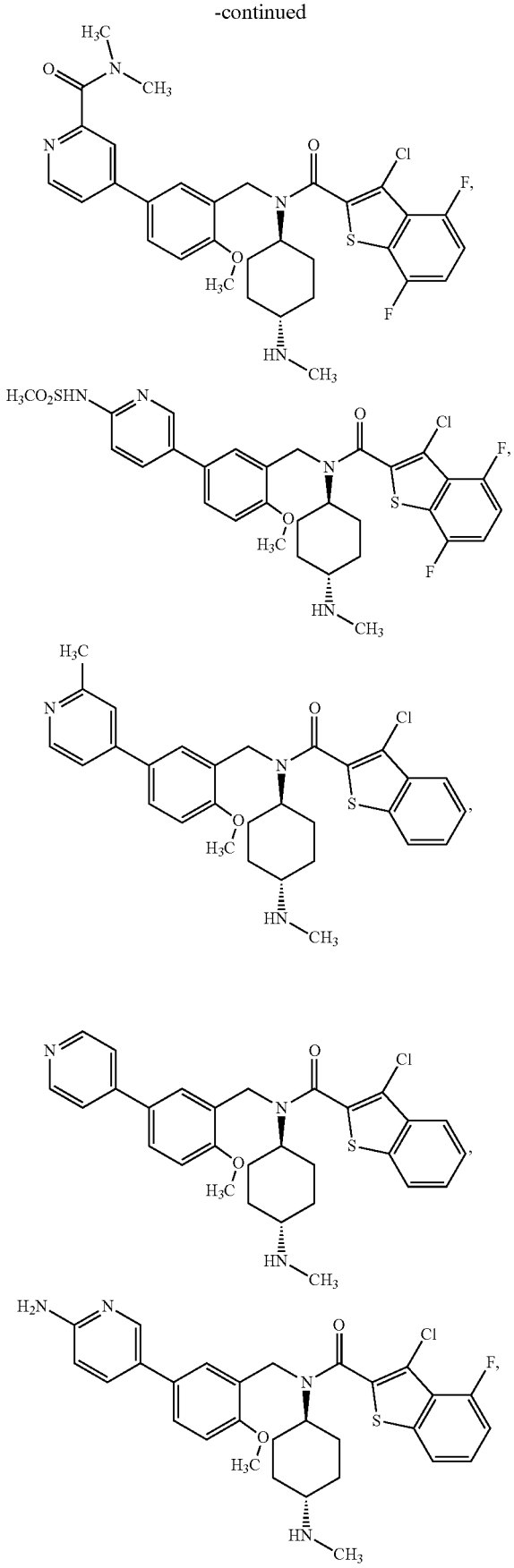
504
-continued
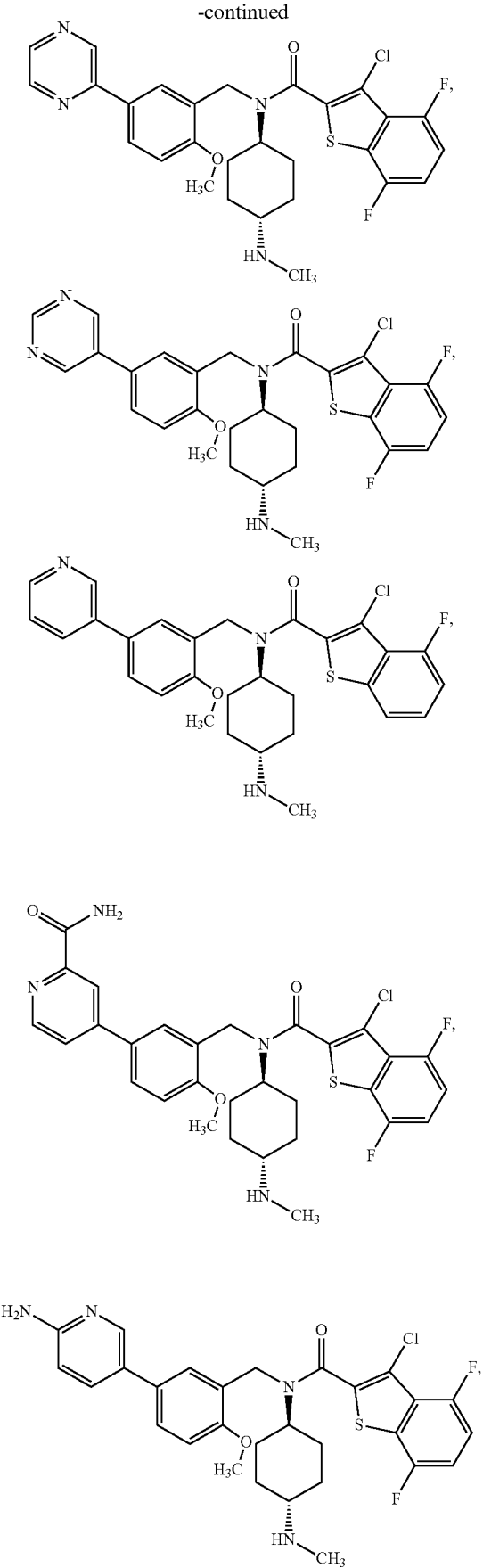

-continued

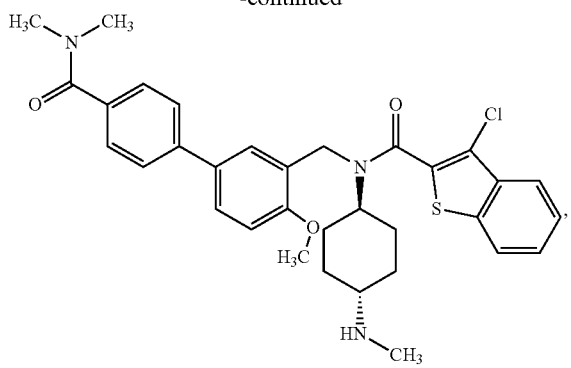

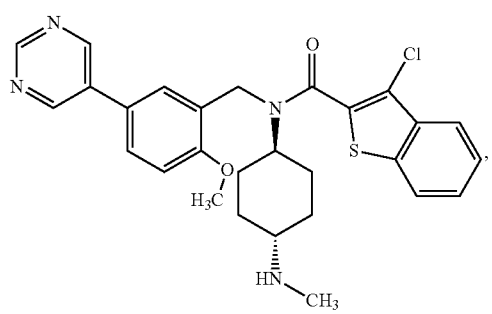

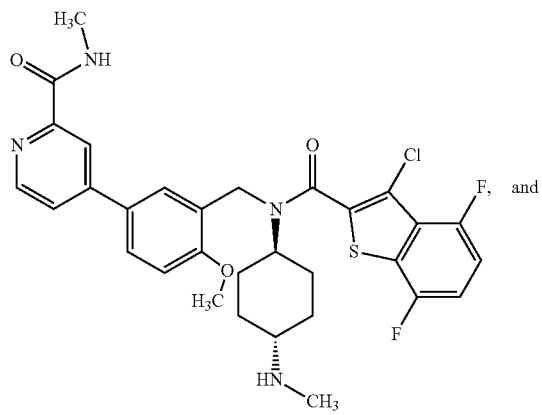

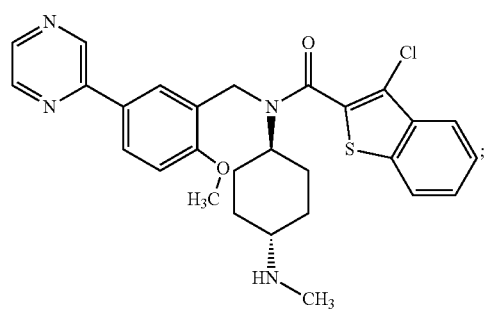

or a pharmaceutically acceptable salt thereof.

8. The composition of claim 7, wherein the compound is

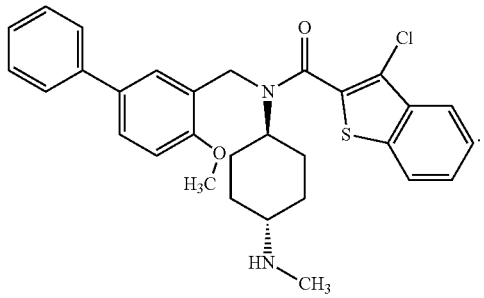

9. The composition of claim 7, wherein the compound is

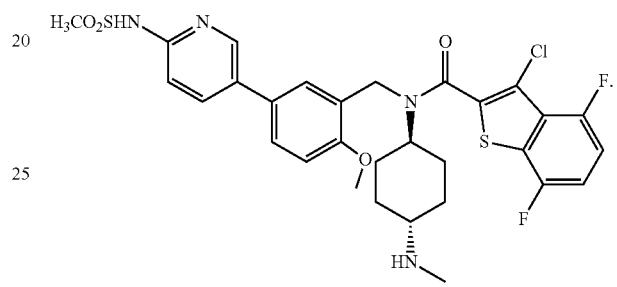

10. The composition of claim 7, wherein the compound is

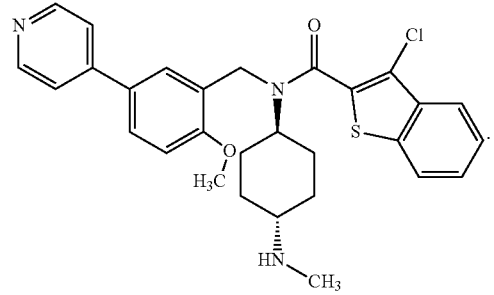

11. A method for promoting the formation or proliferation of hair follicles comprising contacting cells in vitro with an effective amount of a compound of claim 1.

12. The method of claim 11, wherein the compound further comprises a pharmaceutically acceptable excipient.

13. The method of claim 11, wherein the compound is

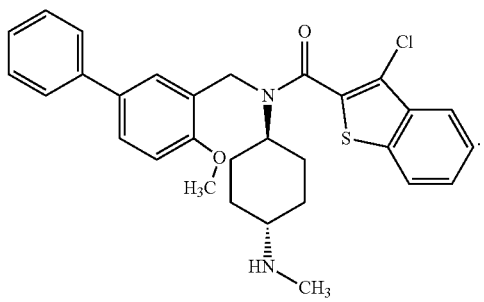

14. The method of claim 11, wherein the compound is

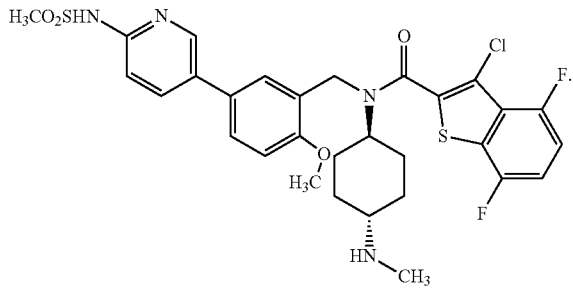

15. The method of claim 11, wherein the compound is

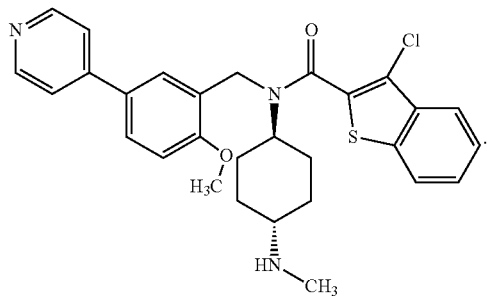

16. The method of claim 11, wherein the compound agonizes hedgehog mediated signal transduction with an $ED_{50}$ of 1 mM or less.

17. The method of claim 11, wherein the compound agonizes hedgehog mediated signal transduction with an $ED_{50}$ of 1 μM or less.

18. The method of claim 11, wherein the compound agonizes hedgehog mediated signal transduction with an $ED_{50}$ of 1 nM or less.

19. The method of claim 11, further comprising implanting the cells in a patient.

20. The method of claim 19, wherein the patient displays male or female pattern baldness.

21. The method of claim 19, wherein the patient has alopecia.

22. The method of claim 21, wherein the amount of cells implanted is suitable for treating alopecia in the patient.

23. The method of claim 11, wherein the cells are contacted with an effective amount of the compound to increase trichogenicity of the cells.

24. The compound of claim 1, wherein the compound is further characterized by one or more of the following:
   $R^1$ is methoxy;
   $R^1$ is fluoro;
   $R^1$ is ethoxy;
   at least one of $Y^2$ or $Y^4$ is F;
   $Y^2$ and $Y^4$ are F;
   $Y^2$ is F and $Y^4$ is H;
   Z is a substituted or unsubstituted aryl ring;
   Z is a substituted or unsubstituted phenyl ring;
   Z is a substituted or unsubstituted heteroaryl ring;
   Z is a substituted or unsubstituted pyridine, pyrimidine, pyrazine, pyridazine, triazine, tetrazine, pyrrole, pyrazole, or imidazole ring;
   Z is a substituted or unsubstituted pyridine, pyrimidine, or pyrazine ring;
   Z is a substituted or unsubstituted pyridine ring;
   Z is a substituted or unsubstituted 4-pyridine ring;
   Z is a substituted or unsubstituted 3-pyridine ring;
   Z is a substituted or unsubstituted 2-pyridine ring;
   Z is a substituted or unsubstituted 5-pyrimidine ring;
   Z is a substituted or unsubstituted 2-pyrimidine ring;
   Z is a substituted or unsubstituted 2-pyrazine ring;
   Z is unsubstituted;
   Z is substituted with one or more electron withdrawing groups;
   Z is substituted with one or more groups selected from halogen, lower alkyl, lower alkenyl, —CN, azido, $NR^XR^X$; —$CO_2OR^X$, —C(O)—$NR^XR^X$, —C(O)—$R^X$, —$NR^X$—C(O)—$R^X$, —$NR^XSO_2R^X$, —$SR^X$, —S(O)$R^X$, —$SO_2R^X$, —$SO_2NR^XR^X$, —$(C(R^X)_2)$—$OR^X$, —$(C(R^X)_2)_n$—, $NR^XR^X$, and —$(C(R^X)_2)_n$—$SO_2R^X$; wherein $R^X$ is, independently for each occurrence, H or lower alkyl; and n is, independently for each occurrence, an integer from 0 to 2;
   Z is substituted with one or more groups selected from halogen, —CN, azido, —$CO_2OR^X$, —C(O)—$NR^XR^X$, and —C(O)—$R^X$; or
   Z is substituted with fluoro.

25. A composition comprising a compound of claim 24 and a pharmaceutically acceptable excipient, wherein the composition is optionally suitable for oral or topical administration.

26. The compound of claim 1, wherein the compound is one of

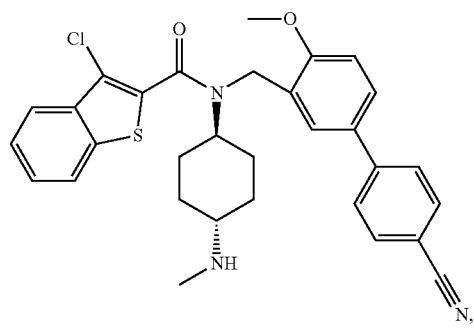

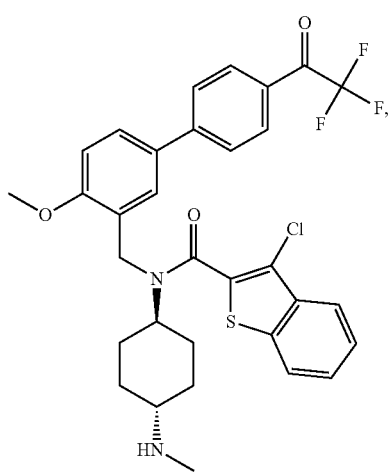

509
-continued
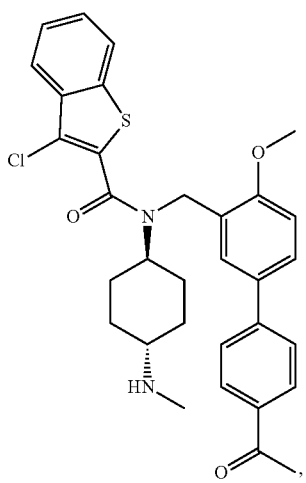
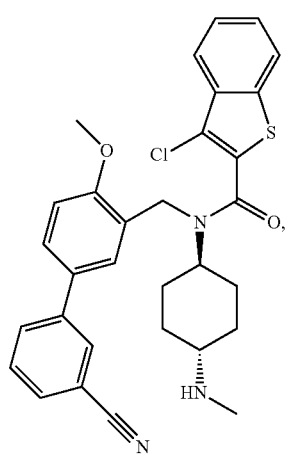
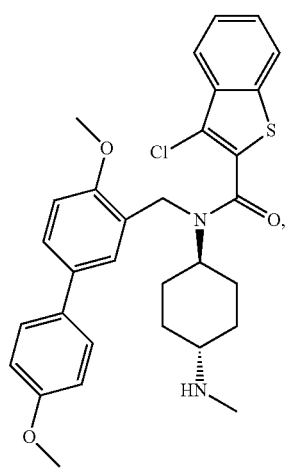
510
-continued
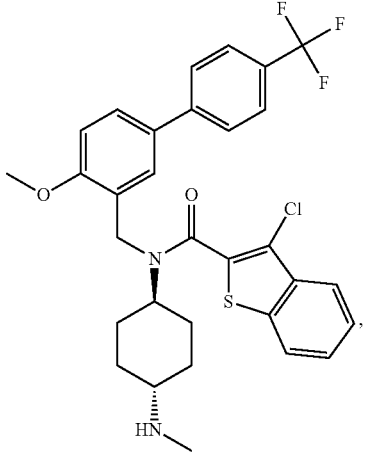
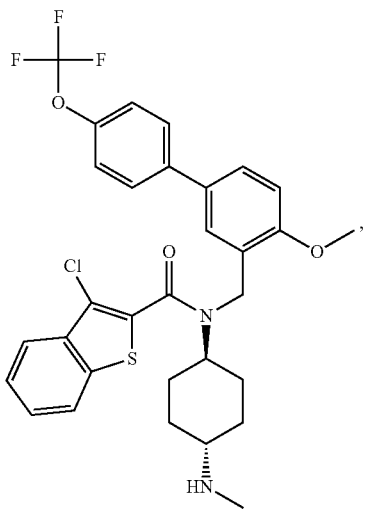
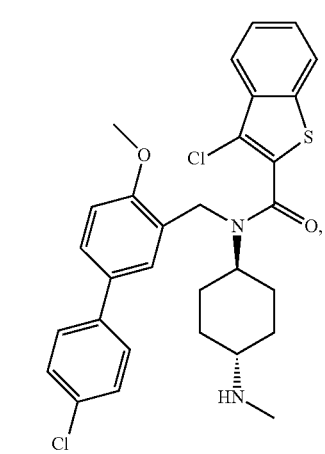

511
-continued
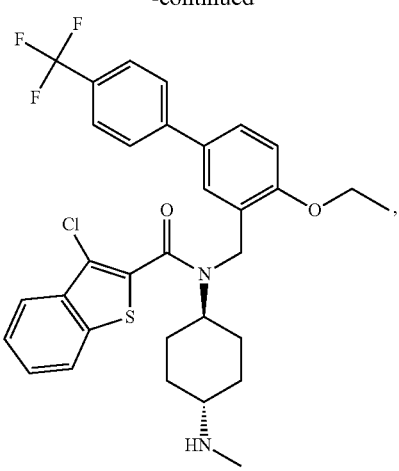
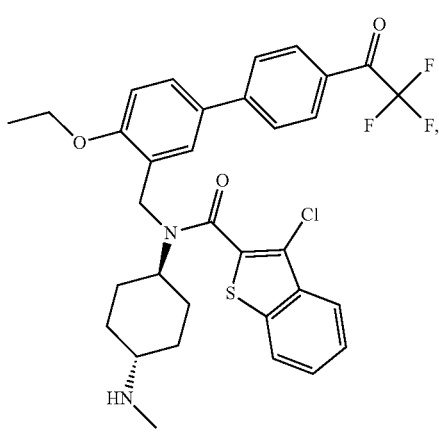
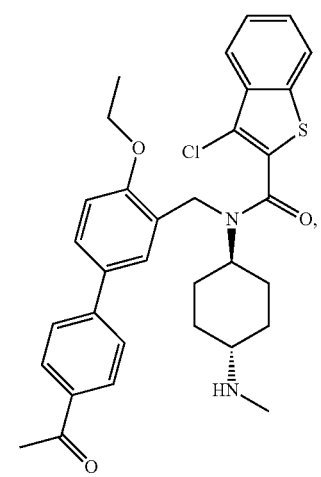
512
-continued
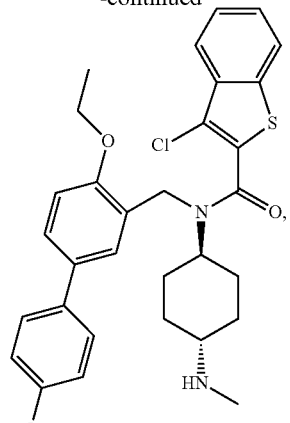
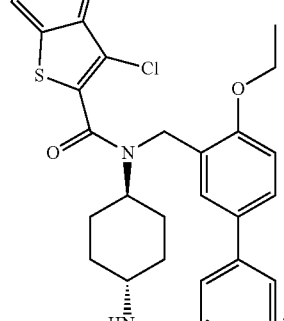
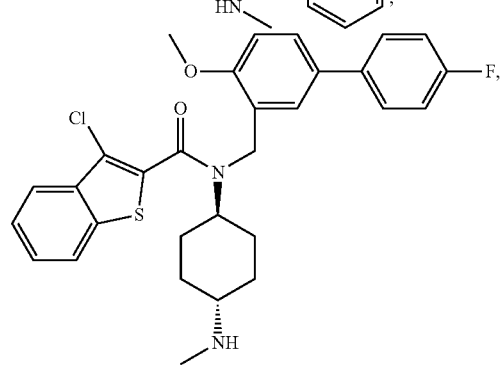
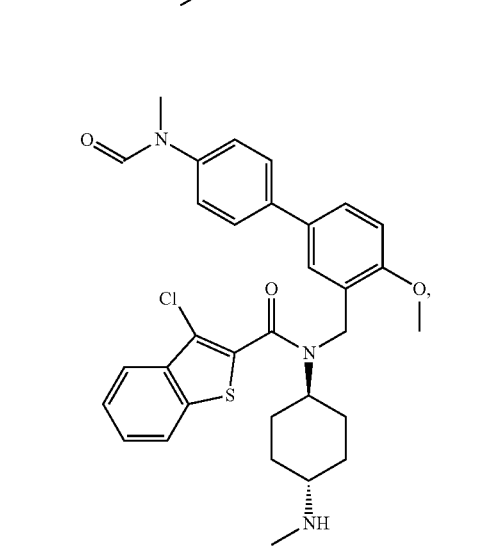

513
-continued
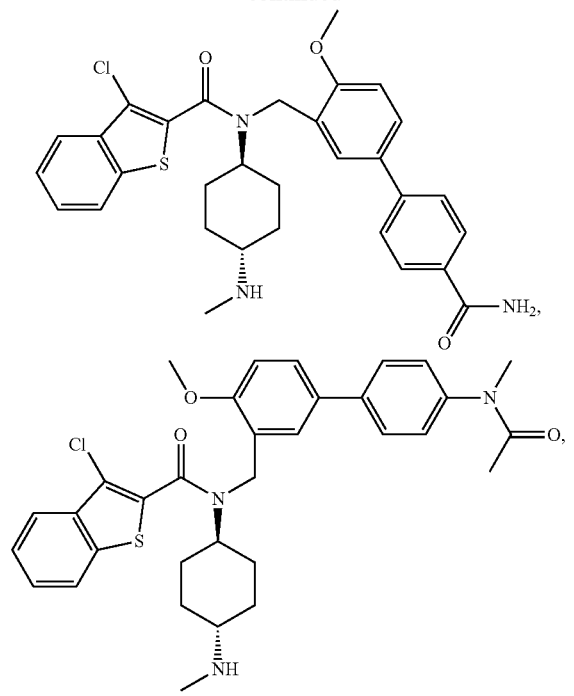
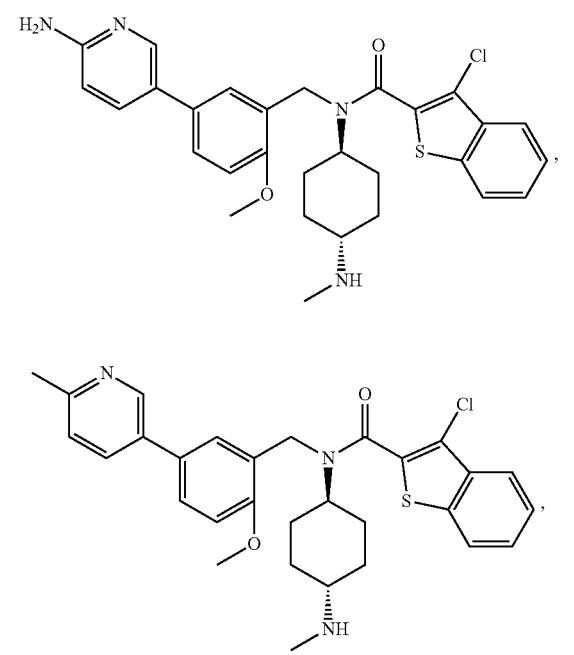
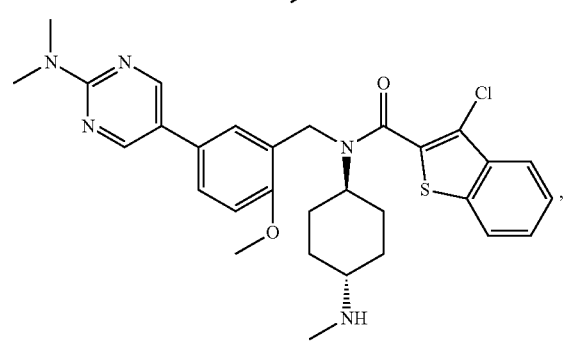
514
-continued
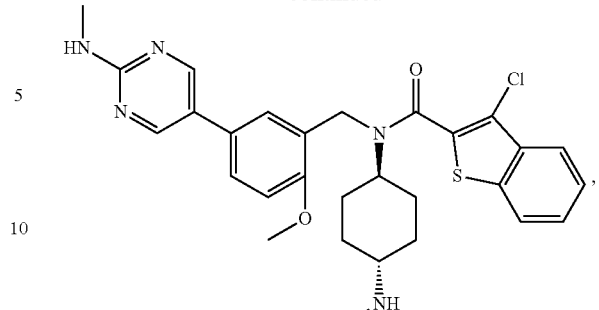
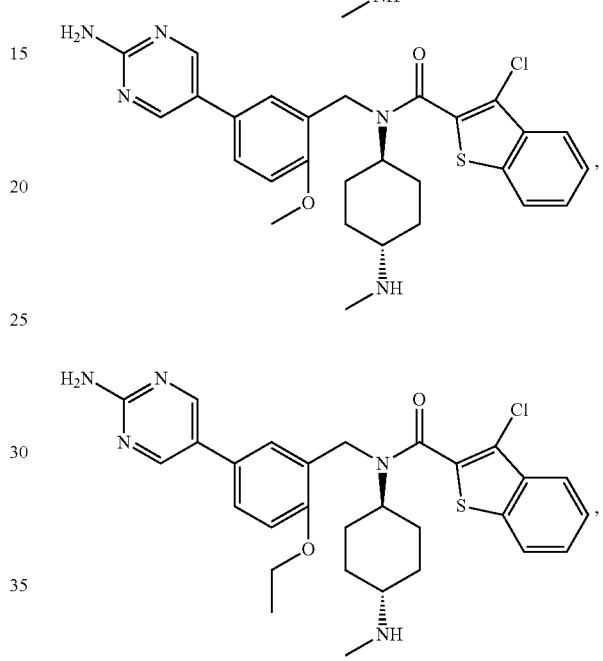
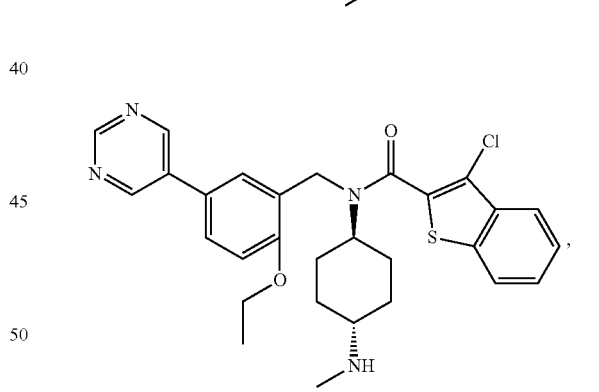
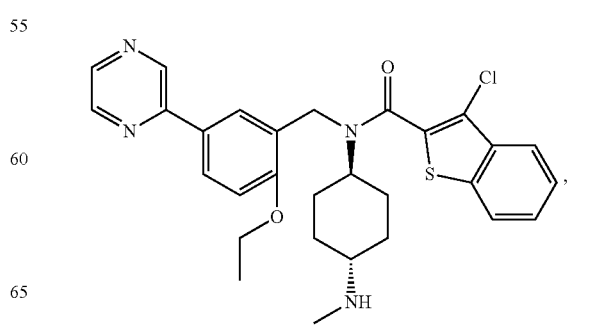

515
-continued
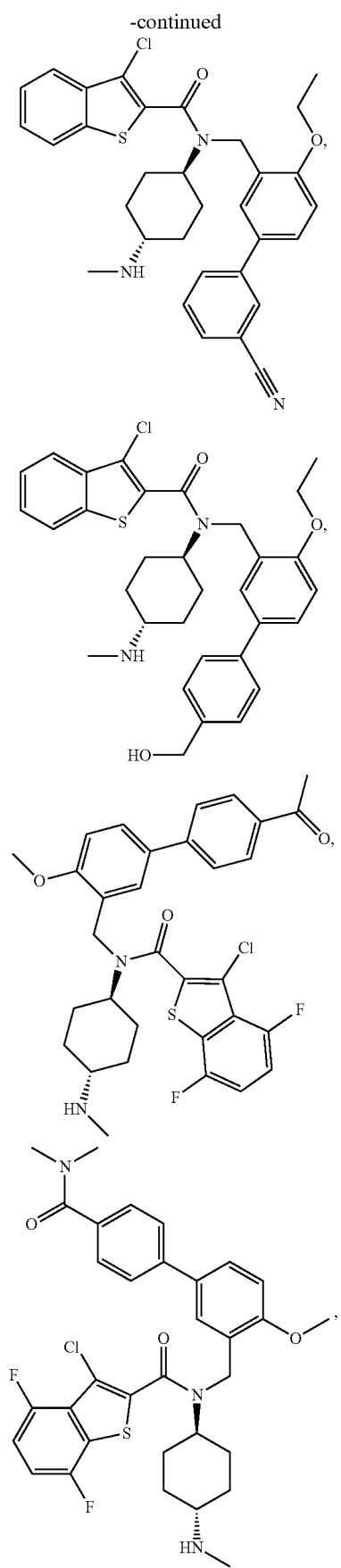
516
-continued
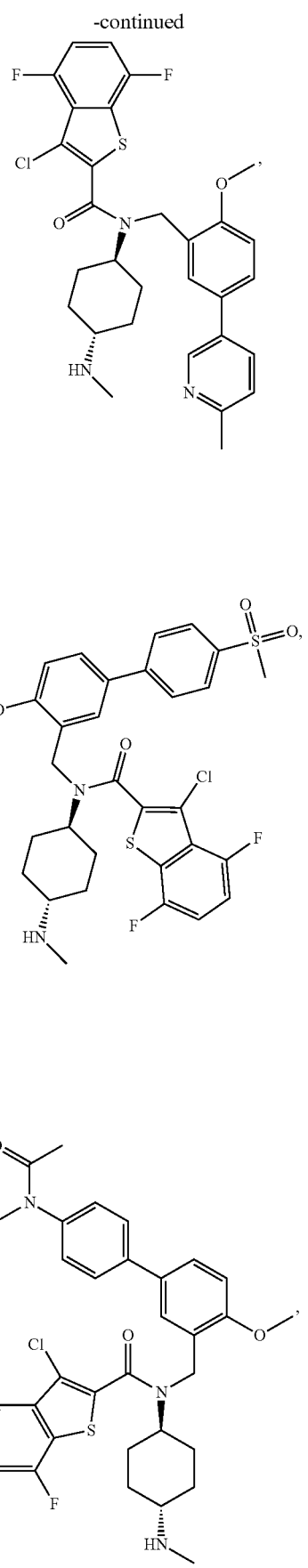

517
-continued
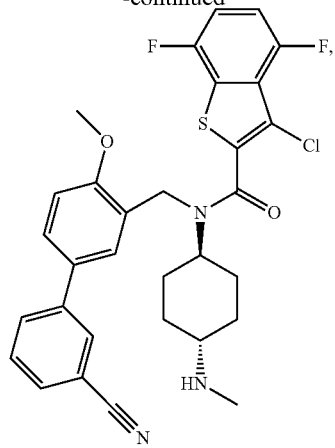
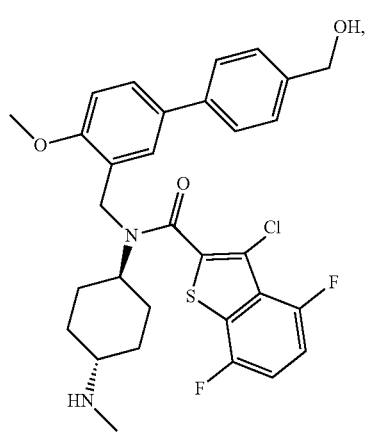
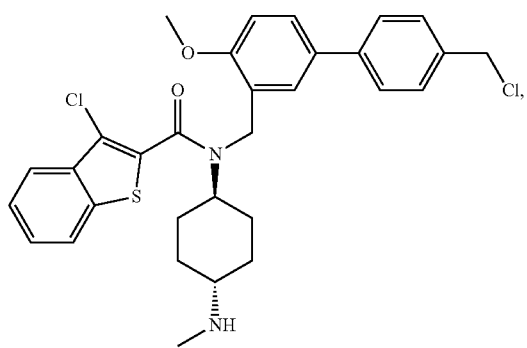
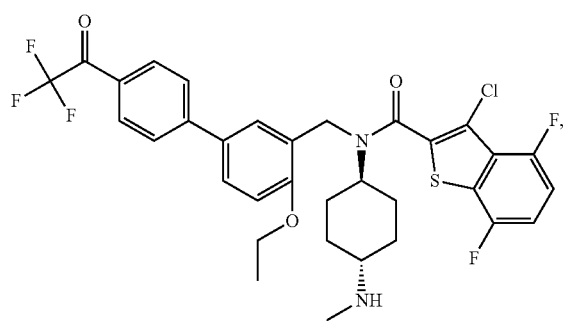
518
-continued
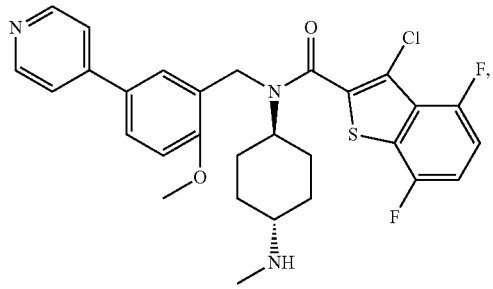
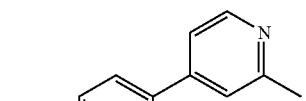
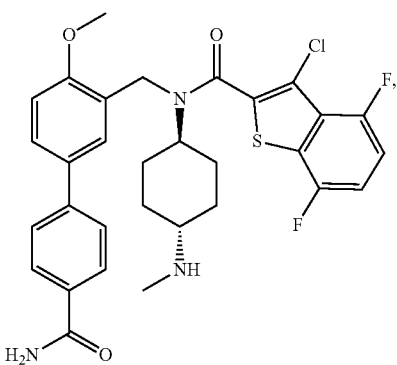
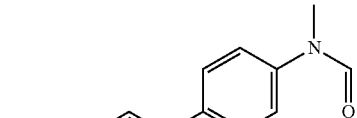
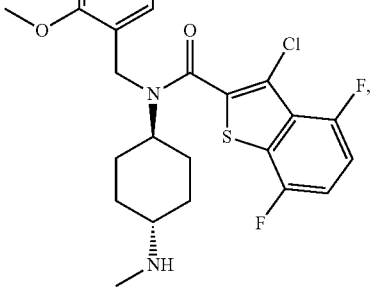

519
-continued
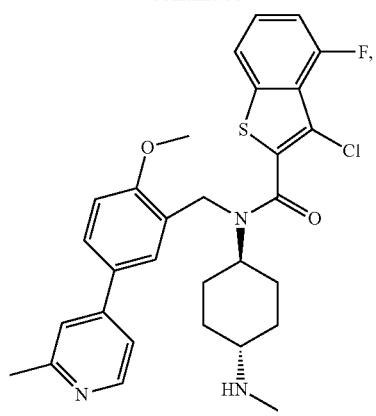
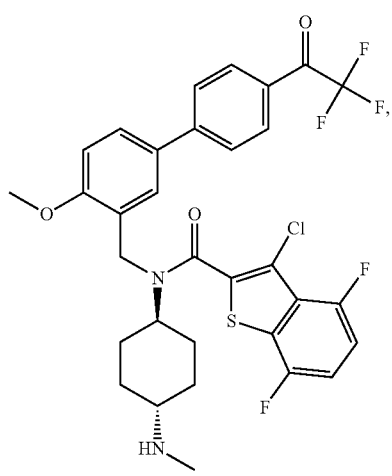
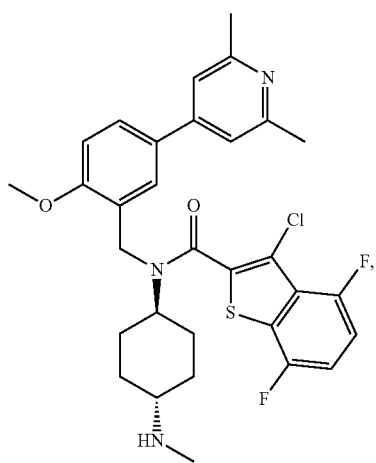
520
-continued
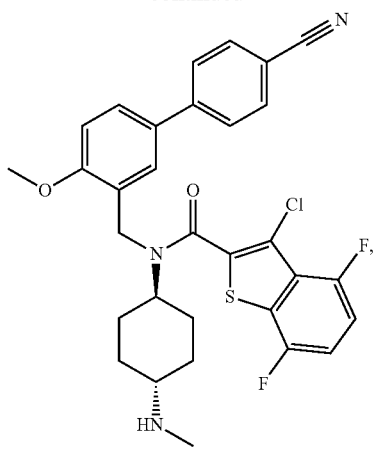
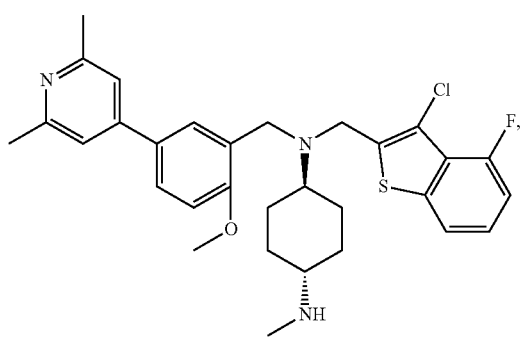
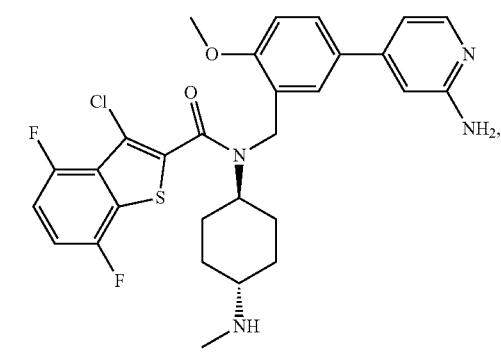
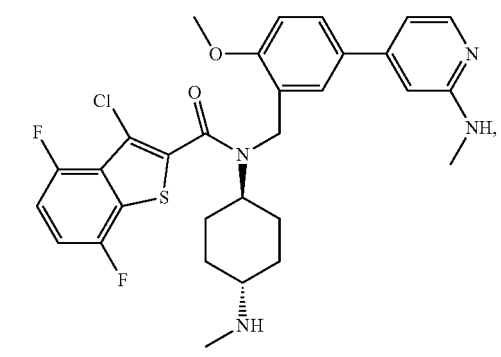

-continued
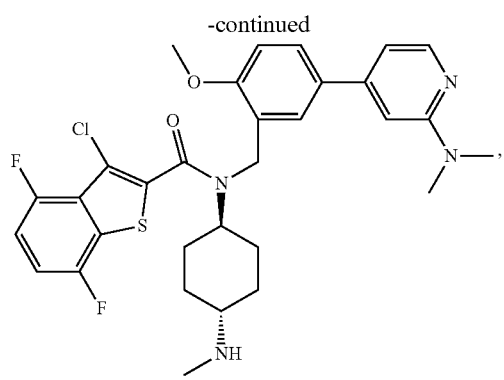
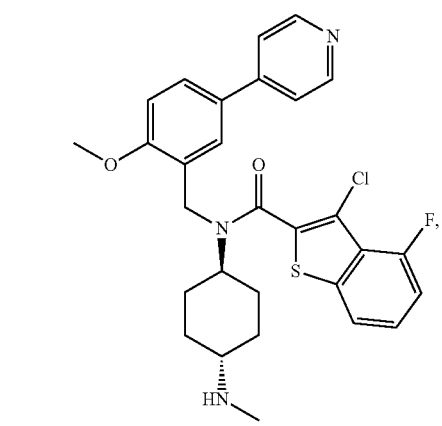
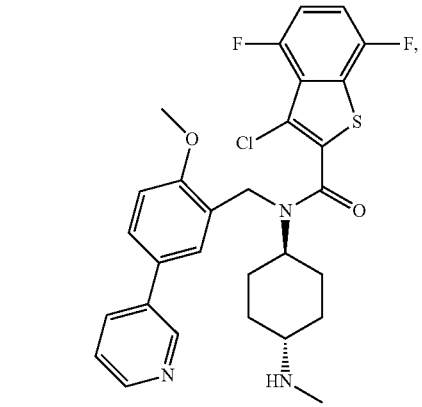
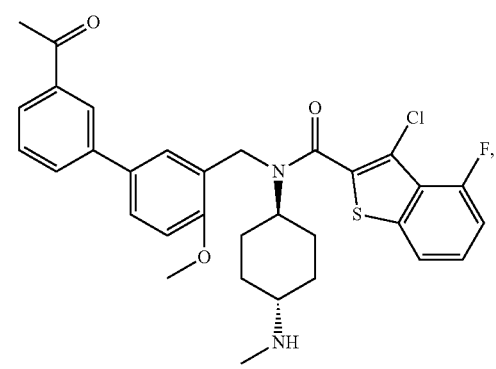
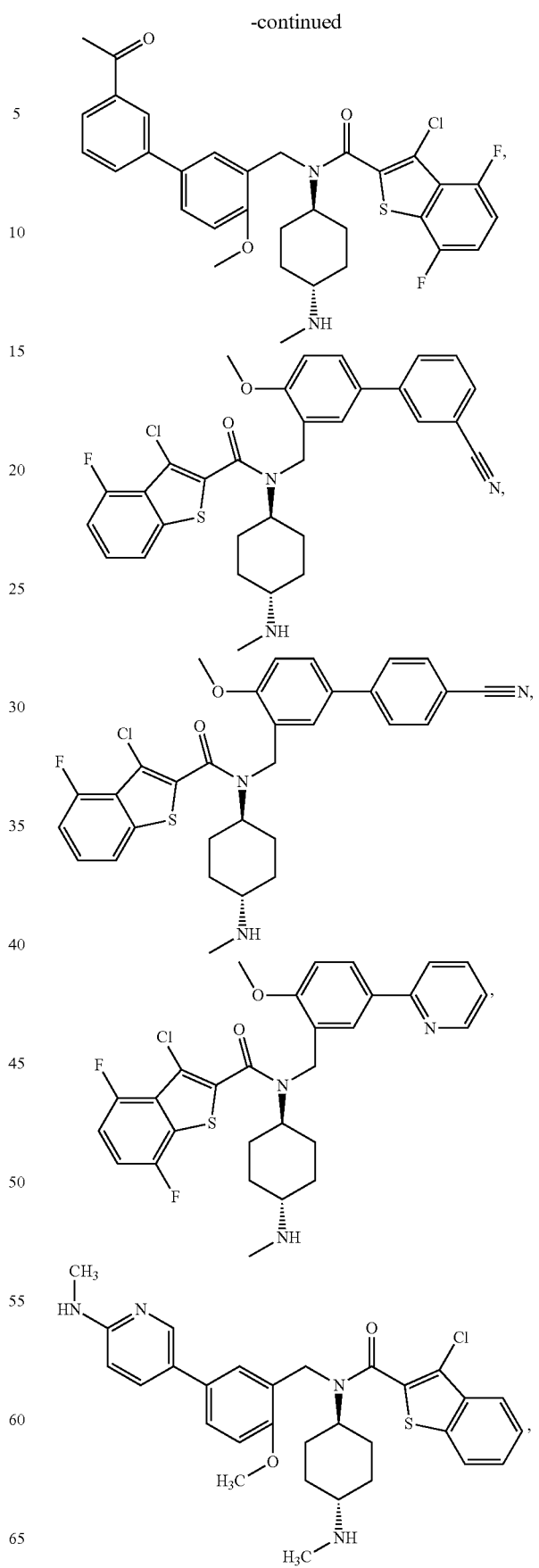

523
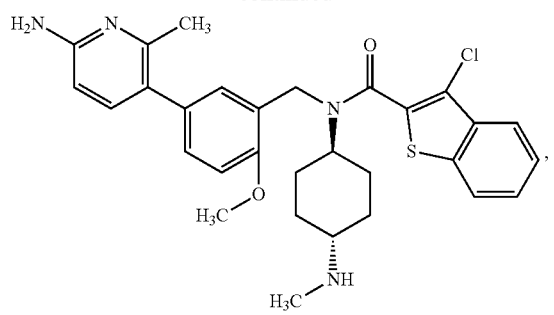
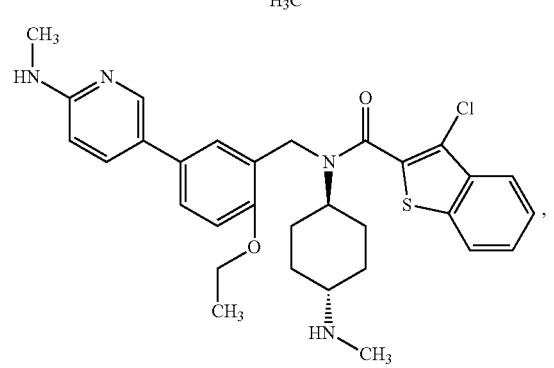
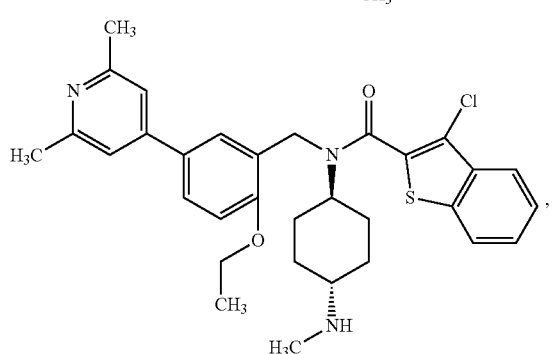
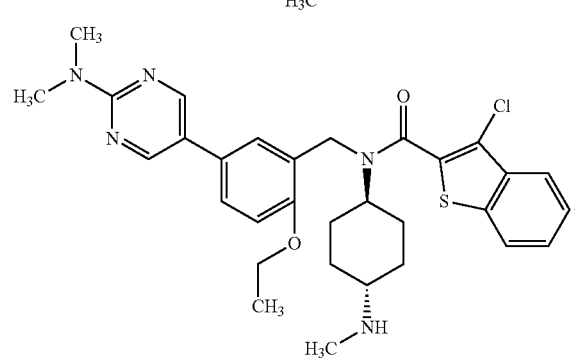
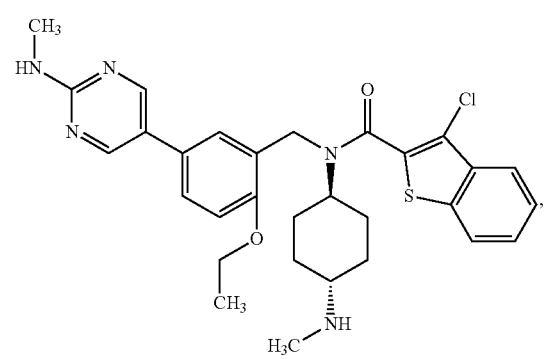
524
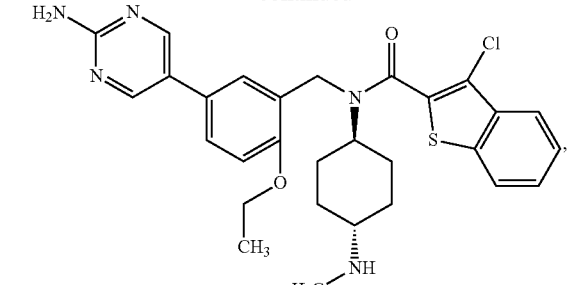
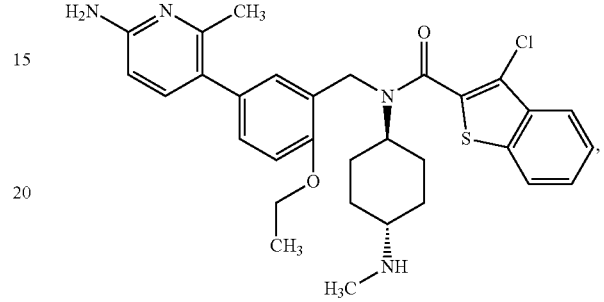
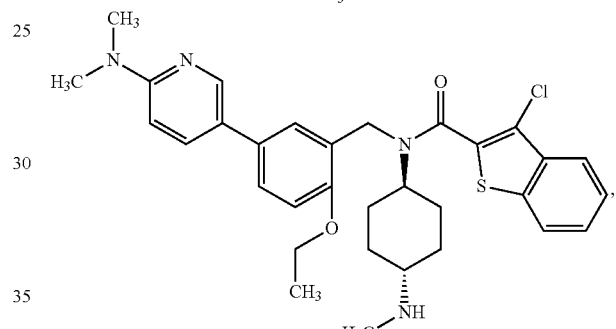
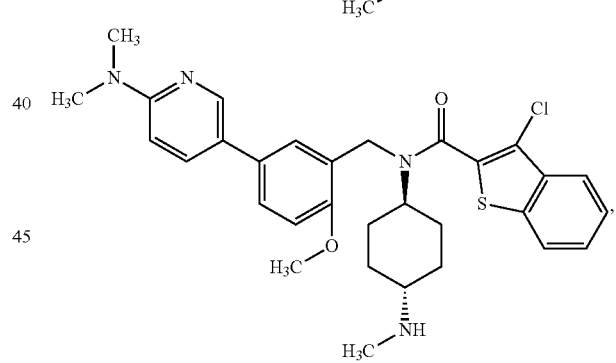
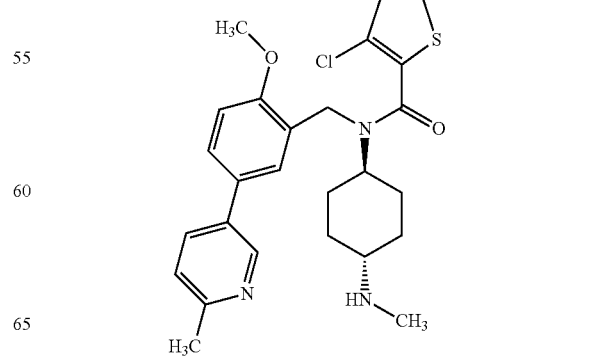

525
-continued
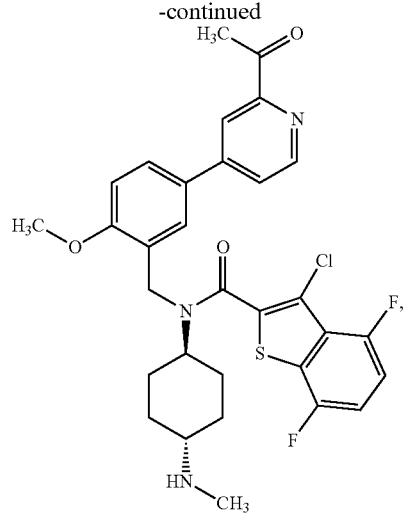
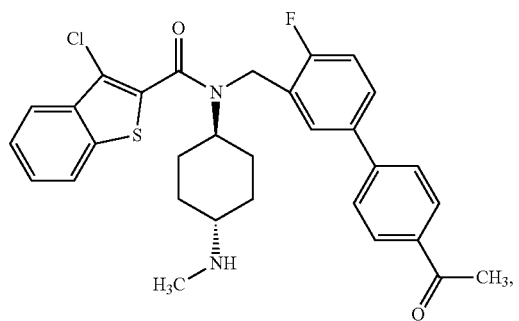
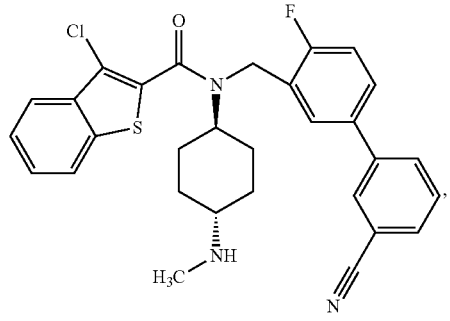
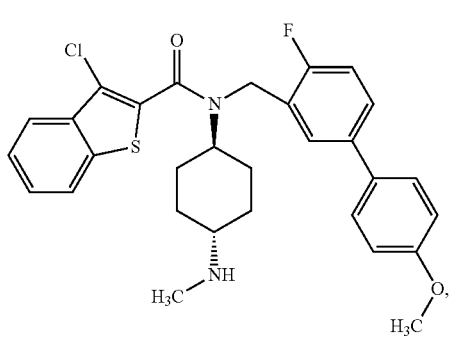
526
-continued
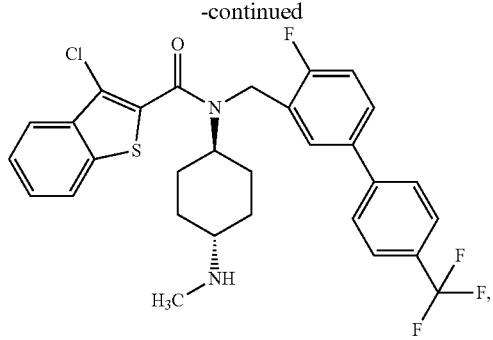
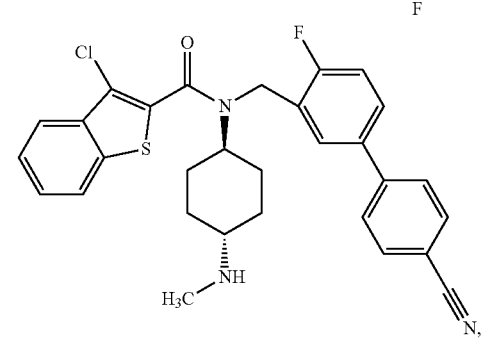
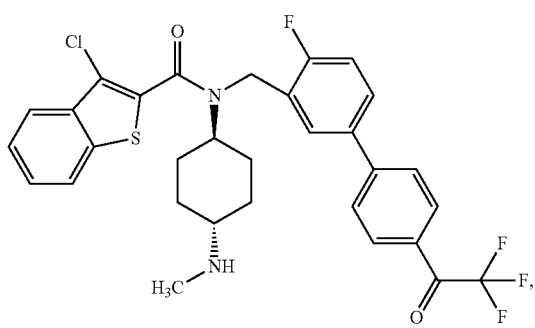
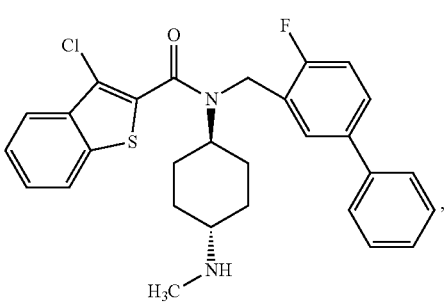

527
-continued
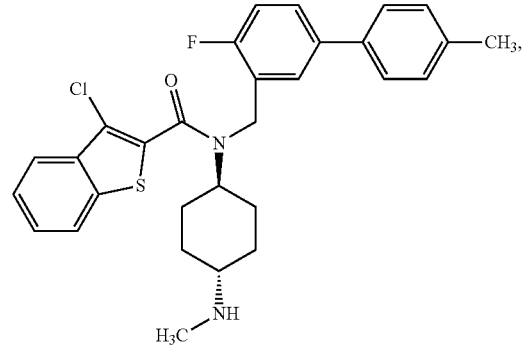
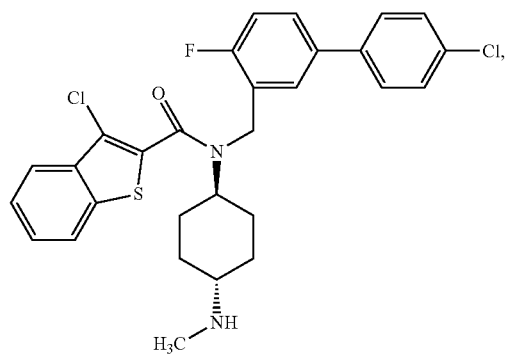
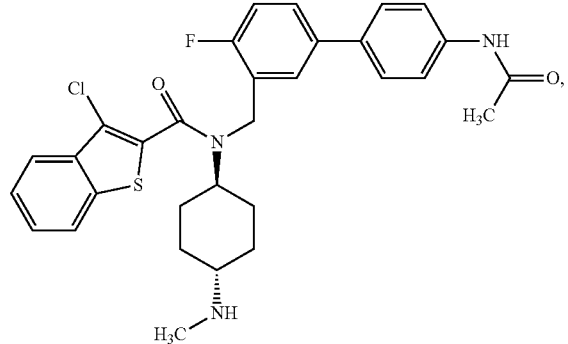
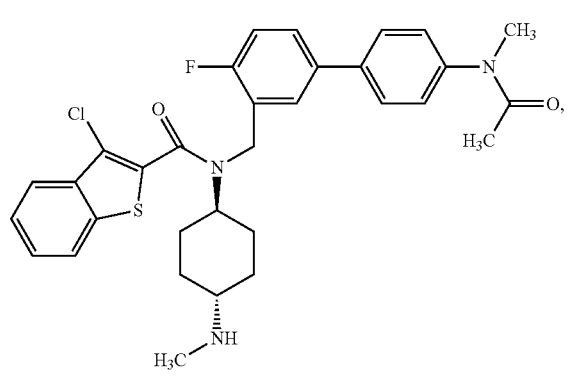
528
-continued
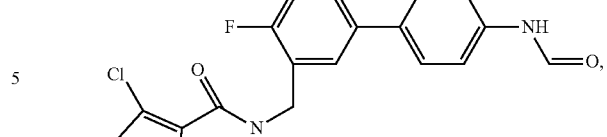
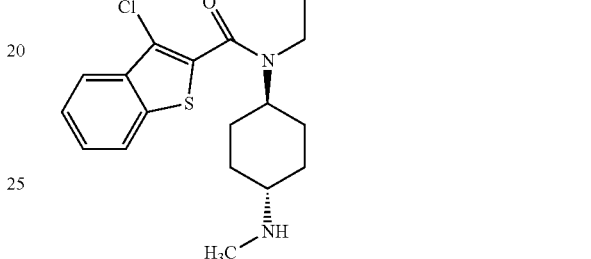
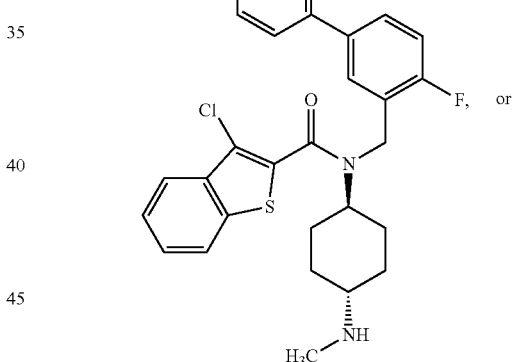, or
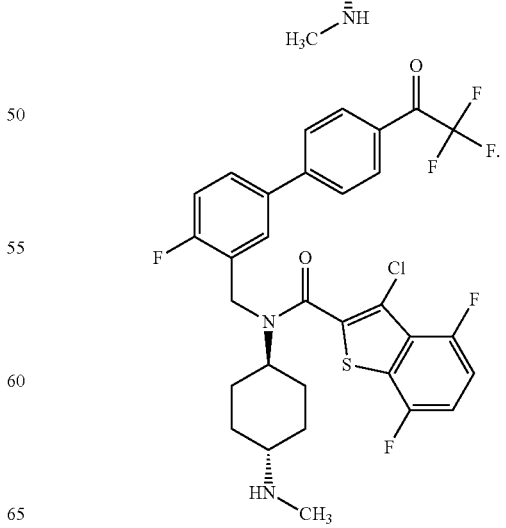

27. A composition comprising a compound of claim 26 and a pharmaceutically acceptable excipient, wherein the composition is optionally suitable for oral or topical administration.

28. A method for promoting the formation or proliferation of hair follicles comprising contacting cells in vitro with an effective amount of a compound of claim 24.

29. A method for promoting the formation or proliferation of hair follicles comprising contacting cells in vitro with an effective amount of a compound of claim 26.

30. The compound of claim 24, wherein $R^1$ is selected from the group consisting of ethoxy and methoxy.

31. The compound of claim 24, wherein Z is a substituted or unsubstituted phenyl ring or a substituted or unsubstituted pyridine ring.

* * * * *

UNITED STATES PATENT AND TRADEMARK OFFICE
CERTIFICATE OF CORRECTION

PATENT NO. : 8,273,747 B2
APPLICATION NO. : 11/982709
DATED : September 25, 2012
INVENTOR(S) : Shirley A. Brunton, Oivin M. Guicherit and Lawrence I. Kruse Page 1 of 2

It is certified that error appears in the above-identified patent and that said Letters Patent is hereby corrected as shown below:

Claim 24, column 508, line 19, replace "-(C(R$^x$)$_2$)-OR$^x$" with --(C(R$^x$)$_2$)$_n$-OR$^x$--.

Claim 26, column 515, lines 20-30 replace:

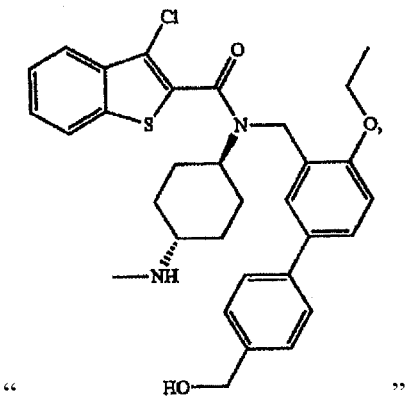

with the structure: -- 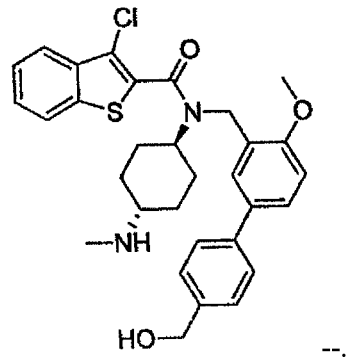 --.

Signed and Sealed this
Nineteenth Day of February, 2013

Teresa Stanek Rea
*Acting Director of the United States Patent and Trademark Office*

CERTIFICATE OF CORRECTION (continued)
U.S. Pat. No. 8,273,747 B2

Claim 26, column 518, lines 35-50 replace the structure:

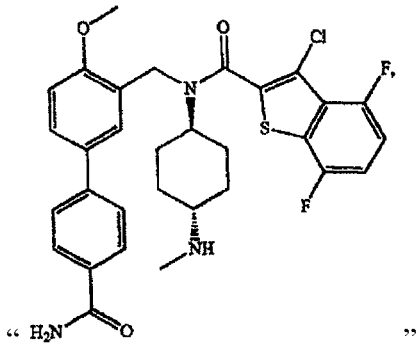

" " with the structure: -- 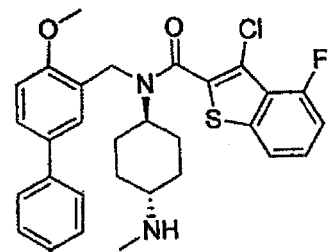 --.

Claim 26, column 518, lines 50-65 replace the structure:

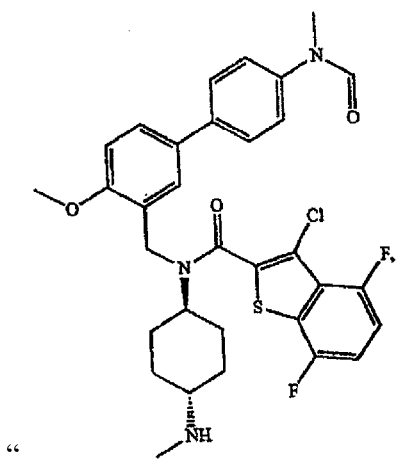

" " with the structure: -- 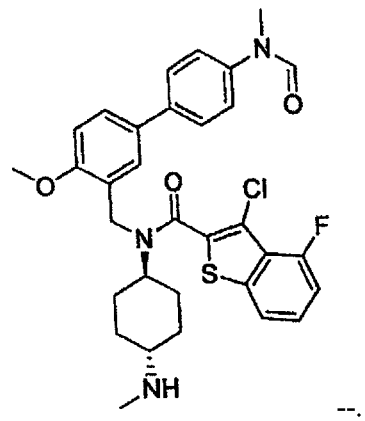 --.